United States Patent
Salceda et al.

(10) Patent No.: US 7,208,267 B2
(45) Date of Patent: Apr. 24, 2007

(54) COMPOSITIONS AND METHODS RELATING TO BREAST SPECIFIC GENES AND PROTEINS

(75) Inventors: Susana Salceda, San Jose, CA (US); Roberto Macina, San Jose, CA (US); Herve E. Recipon, San Francisco, CA (US); Jason Pluta, Mountain View, CA (US); Yongming Sun, San Jose, CA (US); Chenghua Liu, San Jose, CA (US)

(73) Assignee: Diadexus, Inc., South San Francisco, CA (US)

( * ) Notice: Subject to any disclaimer, the term of this patent is extended or adjusted under 35 U.S.C. 154(b) by 231 days.

(21) Appl. No.: 09/989,890

(22) Filed: Nov. 21, 2001

(65) Prior Publication Data
US 2004/0166105 A1   Aug. 26, 2004

Related U.S. Application Data

(60) Provisional application No. 60/252,509, filed on Nov. 22, 2000.

(51) Int. Cl.
| | |
|---|---|
| *C12Q 1/68* | (2006.01) |
| *C12N 15/00* | (2006.01) |
| *C12N 5/00* | (2006.01) |
| *C12N 15/11* | (2006.01) |
| *C12N 15/12* | (2006.01) |
| *C12P 21/02* | (2006.01) |
| *A61K 31/711* | (2006.01) |
| *A61K 31/713* | (2006.01) |

(52) U.S. Cl. .................... 435/6; 435/69.1; 435/320.1; 435/325; 536/23.1; 536/23.5; 514/44

(58) Field of Classification Search .................... None
See application file for complete search history.

(56) References Cited

U.S. PATENT DOCUMENTS

| | | | |
|---|---|---|---|
| 6,218,529 B1 | 4/2001 | An et al. | 536/24.33 |
| 2003/0065156 A1 | 4/2003 | Williams | 536/23.1 |

FOREIGN PATENT DOCUMENTS

| | | |
|---|---|---|
| EP | 1 308 459 A2 | 5/2003 |
| WO | WO 99/33982 | 7/1999 |
| WO | WO-99/38972 A2 * | 8/1999 |
| WO | WO 00/08210 | 2/2000 |
| WO | WO 01/02568 A2 | 1/2001 |
| WO | WO 02/064611 A1 | 8/2002 |
| WO | WO 02/068633 A2 | 9/2002 |
| WO | WO 02/077232 A2 | 10/2002 |
| WO | WO 03/054219 A2 | 7/2003 |

OTHER PUBLICATIONS

Puttikhunt et al, Molec. Gen. Genet. 247: 118 (1995).*
Kennell, Progr. Nucl. Acid Res. Mol. Biol. 11: 259 (1971).*
GenBank® Accession No. AL592304 (Jul. 25, 2001).*
Bouillaud F., "Study of expressed sequences tags in adipose tissue 1995", Apr. 22, 1995 Database accession No. R17114 XP002230461.
Sugano et al., "*Homo sapiens* cDNA:FLJ23313 fis, clone HEP11919" Sep. 29, 2000 Database accession No. AK026966 XP002230460.
Kawai et al., Functional annotation of a full-length mouse cDNA collection, Nature 2001 409(6821):685-690.
Strausberg et al., "Generation and initial analysis of more than 15,000 full-length human and mouse cDNA sequences", Proc. Natl. Acad. Sci. USA 2002 99(26):16899-16903.
NCBI Genbank Accession No. P70339 [gi:3122098] Feb. 1, 1998—Oct. 16, 2001 with Revision History.
NCBI Genbank Accession No. NP_598468 [gi:19526882] Mar. 18, 2002 with Revision History.
NCBI Genbank Accession No. NM_133707 [gi:19526881] Mar. 18, 2002 with Revision History.
NCBI Genbank Accession No. AK091952 [gi:21750433] Jul. 15, 2002 with Revision History.
NCBI Genbank Accession No. NM_152365 [gi:22748786] Sep. 6, 2002 with Revision History.
NCBI Genbank Accession No. AL356390 [gi:7981589] May 18, 2000—Jan. 16, 2002—The Revision History of 21436506 which replaces 7981589 is provided.

* cited by examiner

*Primary Examiner*—James Martinell
(74) *Attorney, Agent, or Firm*—Licata & Tyrrell PC; Nathan P. Letts

(57) ABSTRACT

The present invention relates to newly identified nucleic acids and polypeptides present in normal and neoplastic breast cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating breast cancer and non-cancerous disease states in breast tissue, identifying breast tissue, monitoring and identifying and/or designing agonists and antagonists of polypeptides of the invention. The uses also include gene therapy, production of transgenic animals and cells, and production of engineered breast tissue for treatment and research.

10 Claims, No Drawings

COMPOSITIONS AND METHODS RELATING TO BREAST SPECIFIC GENES AND PROTEINS

This application claims the benefit of priority from U.S. Provisional Application Ser. No. 60/252,509 filed Nov. 22, 2000, which is herein incorporated by reference in its entirety.

FIELD OF THE INVENTION

The present invention relates to newly identified nucleic acid molecules and polypeptides present in normal and neoplastic breast cells, including fragments, variants and derivatives of the nucleic acids and polypeptides. The present invention also relates to antibodies to the polypeptides of the invention, as well as agonists and antagonists of the polypeptides of the invention. The invention also relates to compositions comprising the nucleic acids, polypeptides, antibodies, variants, derivatives, agonists and antagonists of the invention and methods for the use of these compositions. These uses include identifying, diagnosing, monitoring, staging, imaging and treating breast cancer and non-cancerous disease states in breast tissue, identifying breast tissue and monitoring and identifying and/or designing agonists and antagonists of polypeptides of the invention. The uses also include gene therapy, production of transgenic animals and cells, and production of engineered breast tissue for treatment and research.

BACKGROUND OF THE INVENTION

Excluding skin cancer, breast cancer, also called mammary tumor, is the most common cancer among women, accounting for a third of the cancers diagnosed in the United States. One in nine women will develop breast cancer in her lifetime and about 192,000 new cases of breast cancer are diagnosed annually with about 42,000 deaths. Bevers, *Primary Prevention of Breast Cancer*, in BREAST CANCER, 20–54 (Kelly K Hunt et al., ed., 2001); Kochanek et al., 49 Nat'l. Vital Statistics Reports 1, 14 (2001).

In the treatment of breast cancer, there is considerable emphasis on detection and risk assessment because early and accurate staging of breast cancer has a significant impact on survival. For example, breast cancer detected at an early stage (stage T0, discussed below) has a five-year survival rate of 92%. Conversely, if the cancer is not detected until a late stage (i.e., stage T4), the five-year survival rate is reduced to 13%. *AJCC Cancer Staging Handbook* pp. 164–65 (Irvin D. Fleming et al. eds., 5$^{th}$ ed. 1998). Some detection techniques, such as mammography and biopsy, involve increased discomfort, expense, and/or radiation, and are only prescribed only to patients with an increased risk of breast cancer.

Current methods for predicting or detecting breast cancer risk are not optimal. One method for predicting the relative risk of breast cancer is by examining a patient's risk factors and pursuing aggressive diagnostic and treatment regiments for high risk patients. A patient's risk of breast cancer has been positively associated with increasing age, nulliparity, family history of breast cancer, personal history of breast cancer, early menarche, late menopause, late age of first full term pregnancy, prior proliferative breast disease, irradiation of the breast at an early age and a personal history of malignancy. Lifestyle factors such as fat consumption, alcohol consumption, education, and socioeconomic status have also been associated with an increased incidence of breast cancer although a direct cause and effect relationship has not been established. While these risk factors are statistically significant, their weak association with breast cancer limited their usefulness. Most women who develop breast cancer have none of the risk factors listed above, other than the risk that comes with growing older. NIH Publication No. 00-1556 (2000).

Current screening methods for detecting cancer, such as breast self exam, ultrasound, and mammography have drawbacks that reduce their effectiveness or prevent their widespread adoption. Breast self exams, while useful, are unreliable for the detection of breast cancer in the initial stages where the tumor is small and difficult to detect by palpitation. Ultrasound measurements require skilled operators at an increased expense. Mammography, while sensitive, is subject to over diagnosis in the detection of lesions that have questionable malignant potential. There is also the fear of the radiation used in mammography because prior chest radiation is a factor associated with an increase incidence of breast cancer.

At this time, there are no adequate methods of breast cancer prevention. The current methods of breast cancer prevention involve prophylactic mastectomy (mastectomy performed before cancer diagnosis) and chemoprevention (chemotherapy before cancer diagnosis) which are drastic measures that limit their adoption even among women with increased risk of breast cancer. Bevers, supra.

A number of genetic markers have been associated with breast cancer. Examples of these markers include carcinoembryonic antigen (CEA) (Mughal et al., 249 JAMA 1881 (1983)) MUC-1 (Frische and Liu, 22 J. Clin. Ligand 320 (2000)), HER-2/neu (Haris et al., 15 Proc. Am. Soc. Clin. Oncology. A96 (1996)), uPA, PAI-1, LPA, LPC, RAK and BRCA (Esteva and Fritsche, *Serum and Tissue Markers for Breast Cancer*, in BREAST CANCER, 286–308 (2001)). These markers have problems with limited sensitivity, low correlation, and false negatives which limit their use for initial diagnosis. For example, while the BRCA1 gene mutation is useful as an indicator of an increased risk for breast cancer, it has limited use in cancer diagnosis because only 6.2% of breast cancers are BRCA1 positive. Malone et al., 279 JAMA 922 (1998). See also, Mewman et al., 279 JAMA 915 (1998) (correlation of only 3.3%).

Breast cancers are diagnosed into the appropriate stage categories recognizing that different treatments are more effective for different stages of cancer. Stage TX indicates that primary tumor cannot be assessed (i.e., tumor was removed or breast tissue was removed). Stage T0 is characterized by abnormalities such as hyperplasia but with no evidence of primary tumor. Stage Tis is characterized by carcinoma in situ, intraductal carcinoma, lobular carcinoma in situ, or Paget's disease of the nipple with no tumor. Stage T1 is characterized as having a tumor of 2 cm or less in the greatest dimension. Within stage T1, Tmic indicates microinvasion of 0.1 cm or less, T1a indicates a tumor of between 0.1 to 0.5 cm, T1b indicates a tumor of between 0.5 to 1 cm, and T1c indicates tumors of between 1 cm to 2 cm. Stage T2 is characterized by tumors from 2 cm to 5 cm in the greatest dimension. Tumors greater than 5 cm in size are classified as stage T4. Within stage T4, T4a indicates extension of the tumor to the chess wall, T4b indicates edema or ulceration of the skin of the breast or satellite skin nodules confined to the same breast, T4c indicates a combination of T4a and T4b, and T4d indicates inflammatory carcinoma. *AJCC Cancer Staging Handbook* pp. 159–70 (Irvin D. Fleming et al. eds., 5$^{th}$ ed. 1998). In addition to standard staging, breast tumors may be classified according to their estrogen receptor and progesterone receptor protein status. Fisher et al., 7 Breast Cancer Research and Treatment 147 (1986). Additional pathological status, such as HER2/neu status may also be useful. Thor et al., 90 J. Nat'l. Cancer Inst. 1346 (1998); Paik et al., 90 J. Nat'l. Cancer Inst. 1361 (1998); Hutchins et al., 17 Proc.Am.Soc.Clin.Oncology A2 (1998); and Simpson et al., 18 J. Clin. Oncology 2059 (2000).

In addition to the staging of the primary tumor, breast cancer metastases to regional lymph nodes may be staged. Stage NX indicates that the lymph nodes cannot be assessed (e.g., previously removed). Stage N0 indicates no regional lymph node metastasis. Stage N1 indicates metastasis to movable ipsilateral axillary lymph nodes. Stage N2 indicates metastasis to ipsilateral axillary lymph nodes fixed to one another or to other structures. Stage N3 indicates metastasis to ipsilateral internal mammary lymph nodes. Id.

Stage determination has potential prognostic value and provides criteria for designing optimal therapy. Simpson et al., 18 J. Clin. Oncology 2059 (2000). Generally, pathological staging of breast cancer is preferable to clinical staging because the former gives a more accurate prognosis. However, clinical staging would be preferred if it were as accurate as pathological staging because it does not depend on an invasive procedure to obtain tissue for pathological evaluation. Staging of breast cancer would be improved by detecting new markers in cells, tissues, or bodily fluids which could differentiate between different stages of invasion. Progress in this field will allow more rapid and reliable method for treating breast cancer patients.

Treatment of breast cancer is generally decided after an accurate staging of the primary tumor. Primary treatment options include breast conserving therapy (lumpectomy, breast irradiation, and surgical staging of the axilla), and modified radical mastectomy. Additional treatments include chemotherapy, regional irradiation, and, in extreme cases, terminating estrogen production by ovarian ablation.

Until recently, the customary treatment for all breast cancer was mastectomy. Fonseca et al., 127 Annals of Internal Medicine 1013 (1997). However, recent data indicate that less radical procedures may be equally effective, in terms of survival, for early stage breast cancer. Fisher et al., 16 J. of Clinical Oncology 441 (1998). The treatment options for a patient with early stage breast cancer (i.e., stage Tis) may be breast-sparing surgery followed by localized radiation therapy at the breast. Alternatively, mastectomy optionally coupled with radiation or breast reconstruction may be employed. These treatment methods are equally effective in the early stages of breast cancer.

Patients with stage I and stage II breast cancer require surgery with chemotherapy and/or hormonal therapy. Surgery is of limited use in Stage III and stage IV patients. Thus, these patients are better candidates for chemotherapy and radiation therapy with surgery limited to biopsy to permit initial staging or subsequent restaging because cancer is rarely curative at this stage of the disease. *AJCC Cancer Staging Handbook* 84, ¶. 164–65 (Irvin D. Fleming et al. eds., 5$^{th}$ ed. 1998).

In an effort to provide more treatment options to patients, efforts are underway to define an earlier stage of breast cancer with low recurrence which could be treated with lumpectomy without postoperative radiation treatment. While a number of attempts have been made to classify early stage breast cancer, no consensus recommendation on postoperative radiation treatment has been obtained from these studies. Page et al., 75 Cancer 1219 (1995); Fisher et al., 75 Cancer 1223 (1995); Silverstein et al., 77 Cancer 2267 (1996).

As discussed above, each of the methods for diagnosing and staging breast cancer is limited by the technology employed. Accordingly, there is need for sensitive molecular and cellular markers for the detection of breast cancer. There is a need for molecular markers for the accurate staging, including clinical and pathological staging, of breast cancers to optimize treatment methods. Finally, there is a need for sensitive molecular and cellular markers to monitor the progress of cancer treatments, including markers that can detect recurrence of breast cancers following remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

The present invention solves these and other needs in the art by providing nucleic acid molecules and polypeptides as well as antibodies, agonists and antagonists, thereto that may be used to identify, diagnose, monitor, stage, image and treat breast cancer and non-cancerous disease states in breast; identify and monitor breast tissue; and identify and design agonists and antagonists of polypeptides of the invention. The invention also provides gene therapy, methods for producing transgenic animals and cells, and methods for producing engineered breast tissue for treatment and research.

Accordingly, one object of the invention is to provide nucleic acid molecules that are specific to breast cells and/or breast tissue. These breast specific nucleic acids (BSNAs) may be a naturally-occurring cDNA, genomic DNA, RNA, or a fragment of one of these nucleic acids, or may be a non-naturally-occurring nucleic acid molecule. If the BSNA is genomic DNA, then the BSNA is a breast specific gene (BSG). In a preferred embodiment, the nucleic acid molecule encodes a polypeptide that is specific to breast. In a more preferred embodiment, the nucleic acid molecule encodes a polypeptide that comprises an amino acid sequence of SEQ ID NO: 165 through 280. In another highly preferred embodiment, the nucleic acid molecule comprises a nucleic acid sequence of SEQ ID NO: 1 through 164. By nucleic acid molecule, it is also meant to be inclusive of sequences that selectively hybridize or exhibit substantial sequence similarity to a nucleic acid molecule encoding a BSP, or that selectively hybridize or exhibit substantial sequence similarity to a BSNA, as well as allelic variants of a nucleic acid molecule encoding a BSP, and allelic variants of a BSNA. Nucleic acid molecules comprising a part of a nucleic acid sequence that encodes a BSP or that comprises a part of a nucleic acid sequence of a BSNA are also provided.

A related object of the present invention is to provide a nucleic acid molecule comprising one or more expression control sequences controlling the transcription and/or translation of all or a part of a BSNA. In a preferred embodiment, the nucleic acid molecule comprises one or more expression control sequences controlling the transcription and/or translation of a nucleic acid molecule that encodes all or a fragment of a BSP.

Another object of the invention is to provide vectors and/or host cells comprising a nucleic acid molecule of the instant invention. In a preferred embodiment, the nucleic acid molecule encodes all or a fragment of a BSP. In another preferred embodiment, the nucleic acid molecule comprises all or a part of a BSNA.

Another object of the invention is to provided methods for using the vectors and host cells comprising a nucleic acid molecule of the instant invention to recombinantly produce polypeptides of the invention.

Another object of the invention is to provide a polypeptide encoded by a nucleic acid molecule of the invention. In a preferred embodiment, the polypeptide is a BSP. The polypeptide may comprise either a fragment or a full-length protein as well as a mutant protein (mutein), fusion protein, homologous protein or a polypeptide encoded by an allelic variant of a BSP.

Another object of the invention is to provide an antibody that specifically binds to a polypeptide of the instant invention.

Another object of the invention is to provide agonists and antagonists of the nucleic acid molecules and polypeptides of the instant invention.

Another object of the invention is to provide methods for using the nucleic acid molecules to detect or amplify nucleic acid molecules that have similar or identical nucleic acid sequences compared to the nucleic acid molecules described herein. In a preferred embodiment, the invention provides methods of using the nucleic acid molecules of the invention for identifying, diagnosing, monitoring, staging, imaging and treating breast cancer and non-cancerous disease states in breast. In another preferred embodiment, the invention provides methods of using the nucleic acid molecules of the invention for identifying and/or monitoring breast tissue. The nucleic acid molecules of the instant invention may also be used in gene therapy, for producing transgenic animals and cells, and for producing engineered breast tissue for treatment and research.

The polypeptides and/or antibodies of the instant invention may also be used to identify, diagnose, monitor, stage, image and treat breast cancer and non-cancerous disease states in breast. The invention provides methods of using the polypeptides of the invention to identify and/or monitor breast tissue, and to produce engineered breast tissue.

The agonists and antagonists of the instant invention may be used to treat breast cancer and non-cancerous disease states in breast and to produce engineered breast tissue.

Yet another object of the invention is to provide a computer readable means of storing the nucleic acid and amino acid sequences of the invention. The records of the computer readable means can be accessed for reading and displaying of sequences for comparison, alignment and ordering of the sequences of the invention to other sequences.

DETAILED DESCRIPTION OF THE INVENTION

Definitions and General Techniques

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well-known in the art and as described in various general and more specific references that are cited and discussed throughout the present specification unless otherwise indicated. See, e.g., Sambrook et al, *Molecular Cloning: A Laboratory Manual*, 2d ed., Cold Spring Harbor Laboratory Press (1989) and Sambrook et al., *Molecular Cloning: A Laboratory Manual*, 3d ed., Cold Spring Harbor Press (2001); Ausubel et al., *Current Protocols in Molecular Biology*, Greene Publishing Associates (1992, and Supplements to 2000); Ausubel et al., *Short Protocols in Molecular Biology: A Compendium of Methods from Current Protocols in Molecular Biology*—4$^{th}$ Ed., Wiley & Sons (1999); Harlow and Lane, *Antibodies: A Laboratory Manual*, Cold Spring Harbor Laboratory Press (1990); and Harlow and Lane, *Using Antibodies: A Laboratory Manual*, Cold Spring Harbor Laboratory Press (1999); each of which is incorporated herein by reference in its entirety.

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The following terms, unless otherwise indicated, shall be understood to have the following meanings:

A "nucleic acid molecule" of this invention refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." The term "nucleic acid molecule" usually refers to a molecule of at least 10 bases in length, unless otherwise specified. The term includes single- and double-stranded forms of DNA. In addition, a polynucleotide may include either or both naturally-occurring and modified nucleotides linked together by naturally-occurring and/or non-naturally occurring nucleotide linkages.

The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term "nucleic acid molecule" also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

A "gene" is defined as a nucleic acid molecule that comprises a nucleic acid sequence that encodes a polypeptide and the expression control sequences that surround the nucleic acid sequence that encodes the polypeptide. For instance, a gene may comprise a promoter, one or more enhancers, a nucleic acid sequence that encodes a polypeptide, downstream regulatory sequences and, possibly, other nucleic acid sequences involved in regulation of the expression of an RNA. As is well-known in the art, eukaryotic genes usually contain both exons and introns. The term "exon" refers to a nucleic acid sequence found in genomic DNA that is bioinformatically predicted and/or experimentally confirmed to contribute a contiguous sequence to a mature mRNA transcript. The term "intron" refers to a nucleic acid sequence found in genomic DNA that is predicted and/or confirmed to not contribute to a mature mRNA transcript, but rather to be "spliced out" during processing of the transcript.

A nucleic acid molecule or polypeptide is "derived" from a particular species if the nucleic acid molecule or polypeptide has been isolated from the particular species, or if the nucleic acid molecule or polypeptide is homologous to a nucleic acid molecule or polypeptide isolated from a particular species.

An "isolated" or "substantially pure" nucleic acid or polynucleotide (e.g. an RNA, DNA or a mixed polymer) is one which is substantially separated from other cellular components that naturally accompany the native polynucleotide in its natural host cell, e.g., ribosomes, polymerases, or genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, (4) does not occur in nature as part of a larger sequence or (5) includes nucleotides or internucleoside bonds that are not found in nature. The term "isolated" or "substantially pure" also can be used in reference to recombinant or cloned DNA isolates, chemically synthesized polynucleotide analogs, or polynucleotide analogs that are biologically synthesized by heterologous systems. The term "isolated nucleic acid molecule" includes nucleic acid molecules that are integrated into a host cell chromosome at a heterologous site, recombinant fusions of a native fragment to a heterologous sequence, recombinant vectors present as episomes or as integrated into a host cell chromosome.

A "part" of a nucleic acid molecule refers to a nucleic acid molecule that comprises a partial contiguous sequence of at least 10 bases of the reference nucleic acid molecule. Preferably, a part comprises at least 15 to 20 bases of a reference nucleic acid molecule. In theory, a nucleic acid sequence of 17 nucleotides is of sufficient length to occur at random less frequently than once in the three gigabase human genome, and thus to provide a nucleic acid probe that can uniquely identify the reference sequence in a nucleic acid mixture of genomic complexity. A preferred part is one that comprises a nucleic acid sequence that can encode at least 6 contiguous amino acid sequences (fragments of at least 18 nucleotides) because they are useful in directing the expression or synthesis of peptides that are useful in mapping the epitopes of the polypeptide encoded by the reference nucleic acid. See, e.g., Geysen et al., *Proc. Natl. Acad. Sci. USA* 81:3998–4002 (1984); and U.S. Pat. Nos. 4,708,871 and 5,595,915, the disclosures of which are incorporated herein by reference in their entireties. A part may also comprise at least 25, 30, 35 or 40 nucleotides of a reference nucleic acid molecule, or at least 50, 60, 70, 80, 90, 100, 150, 200, 250, 300, 350, 400 or 500 nucleotides of a reference nucleic acid molecule. A part of a nucleic acid molecule may comprise no other nucleic acid sequences. Alternatively, a part of a nucleic acid may comprise other nucleic acid sequences from other nucleic acid molecules.

The term "oligonucleotide" refers to a nucleic acid molecule generally comprising a length of 200 bases or fewer. The term often refers to single-stranded deoxyribonucleotides, but it can refer as well to single- or double-stranded ribonucleotides, RNA:DNA hybrids and double-stranded DNAs, among others. Preferably, oligonucleotides are 10 to 60 bases in length and most preferably 12, 13, 14, 15, 16, 17, 18, 19 or 20 bases in length. Other preferred oligonucleotides are 25, 30, 35, 40, 45, 50, 55 or 60 bases in length. Oligonucleotides may be single-stranded, e.g. for use as probes or primers, or may be double-stranded, e.g. for use in the construction of a mutant gene. Oligonucleotides of the invention can be either sense or antisense oligonucleotides. An oligonucleotide can be derivatized or modified as discussed above for nucleic acid molecules.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP. The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well-known, this reaction can be prevented selectively, where desired, by removing the 5' phosphates of the other polynucleotide(s) prior to ligation.

The term "naturally-occurring nucleotide" referred to herein includes naturally-occurring deoxyribonucleotides and ribonucleotides. The term "modified nucleotides" referred to herein includes nucleotides with modified or substituted sugar groups and the like. The term "nucleotide linkages" referred to herein includes nucleotides linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081–9093 (1986); Stein et al. *Nucl. Acids Res.* 16:3209–3221 (1988); Zon et al. *Anti-Cancer Drug Design* 6:539–568 (1991); Zon et al., in Eckstein (ed.) *Oligonucleotides and Analogues: A Practical Approach*, pp. 87–108, Oxford University Press (1991); U.S. Pat. No. 5,151,510; Uhlmann and Peyman *Chemical Reviews* 90:543 (1990), the disclosures of which are hereby incorporated by reference.

Unless specified otherwise, the left hand end of a polynucleotide sequence in sense orientation is the 5' end and the right hand end of the sequence is the 3' end. In addition, the left hand direction of a polynucleotide sequence in sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

The term "allelic variant" refers to one of two or more alternative naturally-occurring forms of a gene, wherein each gene possesses a unique nucleotide sequence. In a preferred embodiment, different alleles of a given gene have similar or identical biological properties.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Methods Enzymol.* 183: 63–98 (1990); Pearson, *Methods Mol. Biol.* 132: 185–219 (2000); Pearson, *Methods Enzymol.* 266: 227–258 (1996); Pearson, *J. Mol. Biol.* 276: 71–84 (1998); herein incorporated by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

In the molecular biology art, researchers use the terms "percent sequence identity", "percent sequence similarity" and "percent sequence homology" interchangeably. In this application, these terms shall have the same meaning with respect to nucleic acid sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95–98% of the nucleotide bases, as measured by any well-known algorithm of sequence identity, such as FASTA, BLAST or Gap, as discussed above.

Alternatively, substantial similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity, preferably at least about 65%, more preferably at least about 75%, and most preferably at least about 90% sequence identity, over a stretch of at least about 14 nucleotides, more preferably at least 17 nucleotides, even more preferably at least 20, 25, 30, 35, 40, 50, 60, 70, 80, 90 or 100 nucleotides.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook (1989), supra, p. 9.51, hereby incorporated by reference.

The $T_m$ for a particular DNA-DNA hybrid can be estimated by the formula:

$$T_m = 81.5° C. + 16.6(\log_{10}[Na^+]) + 0.41(\text{fraction } G+C) - 0.63(\% \text{ formamide}) - (600/l)$$

where l is the length of the hybrid in base pairs.

The $T_m$ for a particular RNA-RNA hybrid can be estimated by the formula:

$$T_m = 79.8° C. + 18.5(\log_{10}[Na^+]) + 0.58(\text{fraction } G+C) + 11.8(\text{fraction } G+C)^2 - 0.35(\% \text{ formamide}) - (820/l).$$

The $T_m$ for a particular RNA-DNA hybrid can be estimated by the formula:

$$T_m = 79.8° C. + 18.5(\log_{10}[Na^+]) + 0.58(\text{fraction } G+C) + 11.8(\text{fraction } G+C)^2 - 0.35(\% \text{ formamide}) - (820/l).$$

In general, the $T_m$ decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated $T_m$ of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well-known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours and preferably overnight (approximately 16 hours). Another example of stringent hybridization conditions is 6×SSC at 68° C. without formamide for at least ten hours and preferably overnight. An example of moderate stringency hybridization conditions is 6×SSC at 55° C. without formamide for at least ten hours and preferably overnight. An example of low stringency hybridization conditions for hybridization of complementary nucleic acid sequences having more than 100 complementary residues on a filter in a Southern or Northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al. (1989), supra, pages 8.46 and 9.46–9.58, herein incorporated by reference. See also Ausubel (1992), supra, Ausubel (1999), supra, and Sambrook (2001), supra.

Wash conditions also can be altered to change stringency conditions. An example of stringent wash conditions is a 0.2×SSC wash at 65° C. for 15 minutes (see Sambrook (1989), supra, for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acid molecules that do not hybridize to each other under stringent conditions are still substantially similar to one another if they encode polypeptides that are substantially identical to each other. This occurs, for example, when a nucleic acid molecule is created synthetically or recombinantly using high codon degeneracy as permitted by the redundancy of the genetic code.

Hybridization conditions for nucleic acid molecules that are shorter than 100 nucleotides in length (e.g., for oligonucleotide probes) may be calculated by the formula:

$$T_m = 81.5° C. + 16.6(\log_{10}[Na^+]) + 0.41(\text{fraction } G+C) - (600/N),$$

wherein N is change length and the [Na$^+$] is 1 M or less. See Sambrook (1989), supra, p. 11.46. For hybridization of probes shorter than 100 nucleotides, hybridization is usually performed under stringent conditions (5–10° C. below the T$_m$) using high concentrations (0.1–1.0 pmol/ml) of probe. Id. at p. 11.45. Determination of hybridization using mismatched probes, pools of degenerate probes or "guessmers," as well as hybridization solutions and methods for empirically determining hybridization conditions are well-known in the art. See, e.g., Ausubel (1999), supra; Sambrook (1989), supra, pp. 11.45–11.57.

The term "digestion" or "digestion of DNA" refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan. For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well-known methods that are routine for those skilled in the art.

The term "ligation" refers to the process of forming phosphodiester bonds between two or more polynucleotides, which most often are double-stranded DNAS. Techniques for ligation are well-known to the art and protocols for ligation are described in standard laboratory manuals and references, such as, e.g., Sambrook (1989), supra.

Genome-derived "single exon probes," are probes that comprise at least part of an exon ("reference exon") and can hybridize detectably under high stringency conditions to transcript-derived nucleic acids that include the reference exon but do not hybridize detectably under high stringency conditions to nucleic acids that lack the reference exon. Single exon probes typically further comprise, contiguous to a first end of the exon portion, a first intronic and/or intergenic sequence that is identically contiguous to the exon in the genome, and may contain a second intronic and/or intergenic sequence that is identically contiguous to the exon in the genome. The minimum length of genome-derived single exon probes is defined by the requirement that the exonic portion be of sufficient length to hybridize under high stringency conditions to transcript-derived nucleic acids, as discussed above. The maximum length of genome-derived single exon probes is defined by the requirement that the probes contain portions of no more than one exon. The single exon probes may contain priming sequences not found in contiguity with the rest of the probe sequence in the genome, which priming sequences are useful for PCR and other amplification-based technologies.

The term "microarray" or "nucleic acid microarray" refers to a substrate-bound collection of plural nucleic acids, hybridization to each of the plurality of bound nucleic acids being separately detectable. The substrate can be solid or porous, planar or non-planar, unitary or distributed. Microarrays or nucleic acid microarrays include all the devices so called in Schena (ed.), *DNA Microarrays: A Practical Approach (Practical Approach Series)*, Oxford University Press (1999); Nature Genet. 21(1)(suppl.):1-60 (1999); Schena (ed.), *Microarray Biochip: Tools and Technology*, Eaton Publishing Company/BioTechniques Books Division (2000). These microarrays include substrate-bound collections of plural nucleic acids in which the plurality of nucleic acids are disposed on a plurality of beads, rather than on a unitary planar substrate, as is described, inter alia, in Brenner et al., Proc. Natl. Acad. Sci. USA 97(4):1665–1670 (2000).

The term "mutated" when applied to nucleic acid molecules means that nucleotides in the nucleic acid sequence of the nucleic acid molecule may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. In a preferred embodiment, the nucleic acid molecule comprises the wild type nucleic acid sequence encoding a BSP or is a BSNA. The nucleic acid molecule may be mutated by any method known in the art including those mutagenesis techniques described infra.

The term "error-prone PCR" refers to a process for performing PCR under conditions where the copying fidelity of the DNA polymerase is low, such that a high rate of point mutations is obtained along the entire length of the PCR product. See, e.g., Leung et al., *Technique* 1: 11–15 (1989) and Caldwell et al., *PCR Methods Applic.* 2: 28–33 (1992).

The term "oligonucleotide-directed mutagenesis" refers to a process which enables the generation of site-specific mutations in any cloned DNA segment of interest. See, e.g., Reidhaar-Olson et al., *Science* 241: 53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" or "DNA shuffling" refers to a method of error-prone PCR coupled with forced homologous recombination between DNA molecules of different but highly related DNA sequence in vitro, caused by random fragmentation of the DNA molecule based on sequence similarity, followed by fixation of the crossover by primer extension in an error-prone PCR reaction. See, e.g., Stemmer, *Proc. Natl. Acad. Sci. U.S.A.* 91: 10747–10751 (1994). DNA shuffling can be carried out between several related genes ("Family shuffling").

The term "in vivo mutagenesis" refers to a process of generating random mutations in any cloned DNA of interest which involves the propagation of the DNA in a strain of bacteria such as *E. coli* that carries mutations in one or more of the DNA repair pathways. These "mutator" strains have a higher random mutation rate than that of a wild-type parent. Propagating the DNA in a mutator strain will eventually generate random mutations within the DNA.

The term "cassette mutagenesis" refers to any process for replacing a small region of a double-stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. See, e.g., Arkin et al., *Proc. Natl. Acad. Sci. U.S.A.* 89: 7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins. See, e.g., Delegrave et al., *Biotechnology Research* 11: 1548–1552 (1993); Arnold, *Current Opinion in Biotechnology* 4: 450–455 (1993). Each of the references mentioned above are hereby incorporated by reference in its entirety.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include the promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "vector," as used herein, is intended to refer to a nucleic acid molecule capable of transporting another nucleic acid to which it has been linked. One type of vector is a "plasmid", which refers to a circular double-stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome. Viral vectors that infect bacterial cells are referred to as bacteriophages. Certain vectors are capable of autonomous replication in a host cell into which they are introduced (e.g., bacterial vectors having a bacterial origin of replication). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the phrase "open reading frame" and the equivalent acronym "ORF" refer to that portion of a transcript-derived nucleic acid that can be translated in its entirety into a sequence of contiguous amino acids. As so defined, an ORF has length, measured in nucleotides, exactly divisible by 3. As so defined, an ORF need not encode the entirety of a natural protein.

As used herein, the phrase "ORF-encoded peptide" refers to the predicted or actual translation of an ORF.

As used herein, the phrase "degenerate variant" of a reference nucleic acid sequence intends all nucleic acid sequences that can be directly translated, using the standard genetic code, to provide an amino acid sequence identical to that translated from the reference nucleic acid sequence.

The term "polypeptide" encompasses both naturally-occurring and non-naturally-occurring proteins and polypeptides, polypeptide fragments and polypeptide mutants, derivatives and analogs. A polypeptide may be monomeric or polymeric. Further, a polypeptide may comprise a number of different modules within a single polypeptide each of which has one or more distinct activities. A preferred polypeptide in accordance with the invention comprises a BSP encoded by a nucleic acid molecule of the instant invention, as well as a fragment, mutant, analog and derivative thereof.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art.

A protein or polypeptide is "substantially pure," "substantially homogeneous" or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well-known in the art, such as polyacrylamide gel electrophoresis of a protein sample, followed by visualizing a single polypeptide band upon staining the gel with a stain well-known in the art. For certain purposes, higher resolution may be provided by using HPLC or other means well-known in the art for purification.

The term "polypeptide fragment" as used herein refers to a polypeptide of the instant invention that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "derivative" refers to polypeptides or fragments thereof that are substantially similar in primary structural sequence but which include, e.g., in vivo or in vitro chemical and biochemical modifications that are not found in the native polypeptide. Such modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Other modification include, e.g., labeling with radionuclides, and various enzymatic modifications, as will be readily appreciated by those skilled in the art. A variety of methods for labeling polypeptides and of substituents or labels useful for such purposes are well-known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel (1992), supra; Ausubel (1999), supra, herein incorporated by reference.

The term "fusion protein" refers to polypeptides of the instant invention comprising polypeptides or fragments coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "analog" refers to both polypeptide analogs and non-peptide analogs. The term "polypeptide analog" as used herein refers to a polypeptide of the instant invention that is comprised of a segment of at least 25 amino acids that has substantial identity to a portion of an amino acid sequence but which contains non-natural amino acids or non-natural inter-residue bonds. In a preferred embodiment, the analog has the same or similar biological activity as the native polypeptide. Typically, polypeptide analogs comprise a conservative amino acid substitution (or insertion or deletion) with respect to the naturally-occurring sequence. Analogs typically are at least 20 amino acids long, preferably at least 50 amino acids long or longer, and can often be as long as a full-length naturally-occurring polypeptide.

The term "non-peptide analog" refers to a compound with properties that are analogous to those of a reference polypeptide of the instant invention. A non-peptide compound may also be termed a "peptide mimetic" or a "peptidomimetic." Such compounds are often developed with the aid of computerized molecular modeling. Peptide mimetics that are structurally similar to useful peptides may be used to produce an equivalent effect. Generally, peptidomimetics are structurally similar to a paradigm polypeptide (i.e., a polypeptide that has a desired biochemical property or pharmacological activity), but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods well-known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo et al., *Ann. Rev. Biochem.* 61:387–418 (1992), incorporated herein by reference). For example, one may add internal cysteine residues capable of forming intramolecular disulfide bridges which cyclize the peptide.

A "polypeptide mutant" or "mutein" refers to a polypeptide of the instant invention whose sequence contains substitutions, insertions or deletions of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. Further, a mutein may have the same or different biological activity as the naturally-occurring protein. For instance, a mutein may have an increased or decreased biological activity. A mutein has at least 50% sequence similarity to the wild type protein, preferred is 60% sequence similarity, more preferred is 70% sequence similarity. Even more preferred are muteins having 80%, 85% or 90% sequence similarity to the wild type protein. In an even more preferred embodiment, a mutein exhibits 95% sequence identity, even more preferably 97%, even more preferably 98% and even more preferably 99%. Sequence similarity may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs. For example, single or multiple amino acid substitutions (preferably conservative amino acid substitutions) may be made in the naturally-occurring sequence (preferably in the portion of the polypeptide outside the domain(s) forming intermolecular contacts. In a preferred embodiment, the amino acid substitutions are moderately conservative substitutions or conservative substitutions. In a more preferred embodiment, the amino acid substitutions are conservative substitutions. A conservative amino acid substitution should not substantially change the structural characteristics of the parent sequence (e.g., a replacement amino acid should not tend to disrupt a helix that occurs in the parent sequence, or disrupt other types of secondary structure that characterizes the parent sequence). Examples of art-recognized polypeptide secondary and tertiary structures are described in Creighton (ed.), *Proteins, Structures and Molecular Principles*, W. H. Freeman and Company (1984); Branden et al. (ed.), *Introduction to Protein Structure*, Garland Publishing (1991); Thornton et al., *Nature* 354:105–106 (1991), each of which are incorporated herein by reference.

As used herein, the twenty conventional amino acids and their abbreviations follow conventional usage. See Golub et al. (eds.), *Immunology—A Synthesis* 2$^{nd}$ Ed., Sinauer Associates (1991), which is incorporated herein by reference. Stereoisomers (e.g., D-amino acids) of the twenty conventional amino acids, unnatural amino acids such as -, -disubstituted amino acids, N-alkyl amino acids, and other unconventional amino acids may also be suitable components for polypeptides of the present invention. Examples of unconventional amino acids include: 4-hydroxyproline, γ-carboxyglutamate, —N,N,N-trimethyllysine, —N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the right hand direction is the carboxy-terminal direction, in accordance with standard usage and convention.

A protein has "homology" or is "homologous" to a protein from another organism if the encoded amino acid sequence of the protein has a similar sequence to the encoded amino acid sequence of a protein of a different organism and has a similar biological activity or function. Alternatively, a protein may have homology or be homologous to another protein if the two proteins have similar amino acid sequences and have similar biological activities or functions. Although two proteins are said to be "homologous," this does not imply that there is necessarily an evolutionary relationship between the proteins. Instead, the term "homologous" is defined to mean that the two proteins have similar amino acid sequences and similar biological activities or functions. In a preferred embodiment, a homologous protein is one that exhibits 50% sequence similarity to the wild type protein, preferred is 60% sequence similarity, more preferred is 70% sequence similarity. Even more preferred are homologous proteins that exhibit 80%, 85% or 90% sequence similarity to the wild type protein. In a yet more preferred embodiment, a homologous protein exhibits 95%, 97%, 98% or 99% sequence similarity.

When "sequence similarity" is used in reference to proteins or peptides, it is recognized that residue positions that are not identical often differ by conservative amino acid substitutions. In a preferred embodiment, a polypeptide that has "sequence similarity" comprises conservative or moderately conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 24: 307–31 (1994), herein incorporated by reference.

For instance, the following six groups each contain amino acids that are conservative substitutions for one another:
1) Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Alanine (A), Valine (V), and
6) Phenylalanine (F), Tyrosine (Y), Tryptophan (W).

Alternatively, a conservative replacement is any change having a positive value in the PAM250 log-likelihood matrix disclosed in Gonnet et al., *Science* 256: 1443–45 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Other programs include FASTA, discussed supra.

A preferred algorithm when comparing a sequence of the invention to a database containing a large number of sequences from different organisms is the computer program BLAST, especially blastp or tblastn. See, e.g., Altschul et al., *J. Mol. Biol.* 215: 403–410 (1990); Altschul et al., *Nucleic Acids Res.* 25:3389–402 (1997); herein incorporated by reference. Preferred parameters for blastp are:

Expectation value: 10 (default)
Filter: seg (default)
Cost to open a gap: 11 (default)
Cost to extend a gap: 1 (default
Max. alignments: 100 (default)
Word size: 11 (default)
No. of descriptions: 100 (default)
Penalty Matrix: BLOSUM62

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

Database searching using amino acid sequences can be measured by algorithms other than blastp are known in the art. For instance, polypeptide sequences can be compared using FASTA, a program in GCG Version 6.1. FASTA (e.g., FASTA2 and FASTA3) provides alignments and percent sequence identity of the regions of the best overlap between the query and search sequences (Pearson (1990), supra; Pearson (2000), supra. For example, percent sequence identity between amino acid sequences can be determined using FASTA with its default or recommended parameters (a word size of 2 and the PAM250 scoring matrix), as provided in GCG Version 6.1, herein incorporated by reference.

An "antibody" refers to an intact immunoglobulin, or to an antigen-binding portion thereof that competes with the intact antibody for specific binding to a molecular species, e.g., a polypeptide of the instant invention. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH1 domains; an F(ab')$_2$ fragment is a bivalent fragment comprising two Fab fragments linked by a disulfide bridge at the hinge region; an Fd fragment consists of the VH and CH1 domains; an Fv fragment consists of the VL and VH domains of a single arm of an antibody; and a dAb fragment consists of a VH domain. See, e.g., Ward et al., *Nature* 341: 544–546 (1989).

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

A single-chain antibody (scFv) is an antibody in which a VL and VH region are paired to form a monovalent molecule via a synthetic linker that enables them to be made as a single protein chain. See, e.g., Bird et al., *Science* 242: 423–426 (1988); Huston et al., *Proc. Natl. Acad. Sci. USA* 85: 5879–5883 (1988). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. See e.g., Holliger et al., *Proc. Natl. Acad. Sci. USA* 90: 6444–6448 (1993); Poljak et al., *Structure* 2: 1121–1123 (1994). One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. It is known that purified proteins, including purified antibodies, may be stabilized with non-naturally-associated components. The non-naturally-associated component may be a protein, such as albumin (e.g., BSA) or a chemical such as polyethylene glycol (PEG).

A "neutralizing antibody" or "an inhibitory antibody" is an antibody that inhibits the activity of a polypeptide or blocks the binding of a polypeptide to a ligand that normally binds to it. An "activating antibody" is an antibody that increases the activity of a polypeptide.

The term "epitope" includes any protein determinant capable of specifically binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the dissociation constant is less than 1 μM, preferably less than 100 nM and most preferably less than 10 nM.

The term "patient" as used herein includes human and veterinary subjects.

Throughout this specification and claims, the word "comprise," or variations such as "comprises" or "comprising," will be understood to imply the inclusion of a stated integer or group of integers but not the exclusion of any other integer or group of integers.

The term "breast specific" refers to a nucleic acid molecule or polypeptide that is expressed predominantly in the breast as compared to other tissues in the body. In a preferred embodiment, a "breast specific" nucleic acid molecule or polypeptide is expressed at a level that is 5-fold higher than any other tissue in the body. In a more preferred embodiment, the "breast specific" nucleic acid molecule or polypeptide is expressed at a level that is 10-fold higher than any other tissue in the body, more preferably at least 15-fold, 20-fold, 25-fold, 50-fold or 100-fold higher than any other tissue in the body. Nucleic acid molecule levels may be measured by nucleic acid hybridization, such as Northern blot hybridization, or quantitative PCR. Polypeptide levels may be measured by any method known to accurately quantitate protein levels, such as Western blot analysis.

Nucleic Acid Molecules, Regulatory Sequences, Vectors, Host Cells and Recombinant Methods of Making Polypeptides Nucleic Acid Molecules One aspect of the invention provides isolated nucleic acid molecules that are specific to the breast or to breast cells or tissue or that are derived from such nucleic acid molecules. These isolated breast specific nucleic acids (BSNAs) may comprise a cDNA, a genomic DNA, RNA, or a fragment of one of these nucleic acids, or may be a non-naturally-occurring nucleic acid molecule. In a preferred embodiment, the nucleic acid molecule encodes a polypeptide that is specific to breast, a breast-specific polypeptide (BSP). In a more preferred embodiment, the nucleic acid molecule encodes a polypeptide that comprises an amino acid sequence of SEQ ID NO: 165 through 280. In another highly preferred embodiment, the nucleic acid molecule comprises a nucleic acid sequence of SEQ ID NO: 1 through 164.

A BSNA may be derived from a human or from another animal. In a preferred embodiment, the BSNA is derived from a human or other mammal. In a more preferred embodiment, the BSNA is derived from a human or other primate. In an even more preferred embodiment, the BSNA is derived from a human.

By "nucleic acid molecule" for purposes of the present invention, it is also meant to be inclusive of nucleic acid sequences that selectively hybridize to a nucleic acid molecule encoding a BSNA or a complement thereof. The hybridizing nucleic acid molecule may or may not encode a polypeptide or may not encode a BSP. However, in a preferred embodiment, the hybridizing nucleic acid molecule encodes a BSP. In a more preferred embodiment, the invention provides a nucleic acid molecule that selectively hybridizes to a nucleic acid molecule that encodes a polypeptide comprising an amino acid sequence of SEQ ID NO: 165 through 280. In an even more preferred embodiment, the invention provides a nucleic acid molecule that selectively hybridizes to a nucleic acid molecule comprising the nucleic acid sequence of SEQ ID NO: 1 through 164.

In a preferred embodiment, the nucleic acid molecule selectively hybridizes to a nucleic acid molecule encoding a BSP under low stringency conditions. In a more preferred embodiment, the nucleic acid molecule selectively hybridizes to a nucleic acid molecule encoding a BSP under moderate stringency conditions. In a more preferred embodiment, the nucleic acid molecule selectively hybridizes to a nucleic acid molecule encoding a BSP under high stringency conditions. In an even more preferred embodiment, the nucleic acid molecule hybridizes under low, moderate or high stringency conditions to a nucleic acid molecule encoding a polypeptide comprising an amino acid sequence of SEQ ID NO: 165 through 280. In a yet more preferred embodiment, the nucleic acid molecule hybridizes under low, moderate or high stringency conditions to a nucleic acid molecule comprising a nucleic acid sequence selected from SEQ ID NO: 1 through 164. In a preferred embodiment of the invention, the hybridizing nucleic acid molecule may be used to express recombinantly a polypeptide of the invention.

By "nucleic acid molecule" as used herein it is also meant to be inclusive of sequences that exhibits substantial sequence similarity to a nucleic acid encoding a BSP or a complement of the encoding nucleic acid molecule. In a preferred embodiment, the nucleic acid molecule exhibits substantial sequence similarity to a nucleic acid molecule encoding human BSP. In a more preferred embodiment, the nucleic acid molecule exhibits substantial sequence similarity to a nucleic acid molecule encoding a polypeptide having an amino acid sequence of SEQ ID NO: 165 through 280. In a preferred embodiment, the similar nucleic acid molecule is one that has at least 60% sequence identity with a nucleic acid molecule encoding a BSP, such as a polypeptide having an amino acid sequence of SEQ ID NO: 165 through 280, more preferably at least 70%, even more preferably at least 80% and even more preferably at least 85%. In a more preferred embodiment, the similar nucleic acid molecule is one that has at least 90% sequence identity with a nucleic acid molecule encoding a BSP, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a nucleic acid molecule encoding a BSP.

In another preferred embodiment, the nucleic acid molecule exhibits substantial sequence similarity to a BSNA or its complement. In a more preferred embodiment, the nucleic acid molecule exhibits substantial sequence similarity to a nucleic acid molecule comprising a nucleic acid sequence of SEQ ID NO: 1 through 164. In a preferred embodiment, the nucleic acid molecule is one that has at least 60% sequence identity with a BSNA, such as one having a nucleic acid sequence of SEQ ID NO: 1 through 164, more preferably at least 70%, even more preferably at least 80% and even more preferably at least 85%. In a more preferred embodiment, the nucleic acid molecule is one that has at least 90% sequence identity with a BSNA, more preferably at least 95%, more preferably at least 97%, even more preferably at least 98%, and still more preferably at least 99%. In another highly preferred embodiment, the nucleic acid molecule is one that has at least 99.5%, 99.6%, 99.7%, 99.8% or 99.9% sequence identity with a BSNA.

A nucleic acid molecule that exhibits substantial sequence similarity may be one that exhibits sequence identity over its entire length to a BSNA or to a nucleic acid molecule encoding a BSP, or may be one that is similar over only a part of its length. In this case, the part is at least 50 nucleotides of the BSNA or the nucleic acid molecule encoding a BSP, preferably at least 100 nucleotides, more preferably at least 150 or 200 nucleotides, even more preferably at least 250 or 300 nucleotides, still more preferably at least 400 or 500 nucleotides.

The substantially similar nucleic acid molecule may be a naturally-occurring one that is derived from another species, especially one derived from another primate, wherein the similar nucleic acid molecule encodes an amino acid sequence that exhibits significant sequence identity to that of SEQ ID NO: 165 through 280 or demonstrates significant sequence identity to the nucleotide sequence of SEQ ID NO: 1 through 164. The similar nucleic acid molecule may also be a naturally-occurring nucleic acid molecule from a human, when the BSNA is a member of a gene family. The similar nucleic acid molecule may also be a naturally-occurring nucleic acid molecule derived from a non-primate, mammalian species, including without limitation, domesticated species, e.g., dog, cat, mouse, rat, rabbit, hamster, cow, horse and pig; and wild animals, e.g., monkey, fox, lions, tigers, bears, giraffes, zebras, etc. The substantially similar nucleic acid molecule may also be a naturally-occurring nucleic acid molecule derived from a non-mammalian species, such as birds or reptiles. The naturally-occurring substantially similar nucleic acid molecule may be isolated directly from humans or other species. In another embodiment, the substantially similar nucleic acid molecule may be one that is experimentally produced by random mutation of a nucleic acid molecule. In another embodiment, the substantially similar nucleic acid molecule may be one that is experimentally produced by directed mutation of a BSNA. Further, the substantially similar nucleic acid molecule may or may not be a BSNA. However, in a preferred embodiment, the substantially similar nucleic acid molecule is a BSNA.

By "nucleic acid molecule" it is also meant to be inclusive of allelic variants of a BSNA or a nucleic acid encoding a BSP. For instance, single nucleotide polymorphisms (SNPs) occur frequently in eukaryotic genomes. In fact, more than 1.4 million SNPs have already identified in the human genome, International Human Genome Sequencing Consortium, Nature 409: 860–921 (2001). Thus, the sequence determined from one individual of a species may differ from other allelic forms present within the population. Additionally, small deletions and insertions, rather than single nucleotide polymorphisms, are not uncommon in the general population, and often do not alter the function of the protein. Further, amino acid substitutions occur frequently among natural allelic variants, and often do not substantially change protein function.

In a preferred embodiment, the nucleic acid molecule comprising an allelic variant is a variant of a gene, wherein the gene is transcribed into an mRNA that encodes a BSP. In a more preferred embodiment, the gene is transcribed into an mRNA that encodes a BSP comprising an amino acid sequence of SEQ ID NO: 165 through 280. In another preferred embodiment, the allelic variant is a variant of a gene, wherein the gene is transcribed into an mRNA that is a BSNA. In a more preferred embodiment, the gene is transcribed into an mRNA that comprises the nucleic acid sequence of SEQ ID NO: 1 through 164. In a preferred embodiment, the allelic variant is a naturally-occurring allelic variant in the species of interest. In a more preferred embodiment, the species of interest is human.

By "nucleic acid molecule" it is also meant to be inclusive of a part of a nucleic acid sequence of the instant invention. The part may or may not encode a polypeptide, and may or may not encode a polypeptide that is a BSP. However, in a preferred embodiment, the part encodes a BSP. In one aspect, the invention comprises a part of a BSNA. In a second aspect, the invention comprises a part of a nucleic acid molecule that hybridizes or exhibits substantial sequence similarity to a BSNA. In a third aspect, the invention comprises a part of a nucleic acid molecule that is an allelic variant of a BSNA. In a fourth aspect, the invention comprises a part of a nucleic acid molecule that encodes a BSP. A part comprises at least 10 nucleotides, more preferably at least 15, 17, 18, 20, 25, 30, 35, 40, 50, 60, 70, 80, 90, 100, 150, 200, 250, 300, 350, 400 or 500 nucleotides. The maximum size of a nucleic acid part is one nucleotide shorter than the sequence of the nucleic acid molecule encoding the full-length protein.

By "nucleic acid molecule" it is also meant to be inclusive of sequence that encoding a fusion protein, a homologous protein, a polypeptide fragment, a mutein or a polypeptide analog, as described below.

Nucleotide sequences of the instantly-described nucleic acids were determined by sequencing a DNA molecule that had resulted, directly or indirectly, from at least one enzymatic polymerization reaction (e.g., reverse transcription and/or polymerase chain reaction) using an automated sequencer (such as the MegaBACE™ 1000, Molecular Dynamics, Sunnyvale, Calif., USA). Further, all amino acid sequences of the polypeptides of the present invention were predicted by translation from the nucleic acid sequences so determined, unless otherwise specified.

In a preferred embodiment of the invention, the nucleic acid molecule contains modifications of the native nucleic acid molecule. These modifications include normative internucleoside bonds, post-synthetic modifications or altered nucleotide analogues. One having ordinary skill in the art would recognize that the type of modification that can be made will depend upon the intended use of the nucleic acid molecule. For instance, when the nucleic acid molecule is used as a hybridization probe, the range of such modifications will be limited to those that permit sequence-discriminating base pairing of the resulting nucleic acid. When used to direct expression of RNA or protein in vitro or in vivo, the range of such modifications will be limited to those that permit the nucleic acid to function properly as a polymerization substrate. When the isolated nucleic acid is used as a therapeutic agent, the modifications will be limited to those that do not confer toxicity upon the isolated nucleic acid.

In a preferred embodiment, isolated nucleic acid molecules can include nucleotide analogues that incorporate labels that are directly detectable, such as radiolabels or fluorophores, or nucleotide analogues that incorporate labels that can be visualized in a subsequent reaction, such as biotin or various haptens. In a more preferred embodiment, the labeled nucleic acid molecule may be used as a hybridization probe.

Common radiolabeled analogues include those labeled with $^{33}$P, $^{32}$P, and $^{35}$S, such as -$^{32}$P-dATP, -$^{32}$P-dCTP, -$^{32}$P-dGTP, -$^{32}$P-dTTP, -$^{32}$P-3'ATP, -$^{32}$P-ATP, -$^{32}$P-CTP, -$^{32}$P-GTP, -$^{32}$P-UTP, -$^{35}$S-dATP, $\alpha$-$^{35}$S-GTP, $\alpha$-$^{33}$P-dATP, and the like.

Commercially available fluorescent nucleotide analogues readily incorporated into the nucleic acids of the present invention include Cy3-dCTP, Cy3-dUTP, Cy5-dCTP, Cy3-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® TMR-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). One may also custom synthesize nucleotides having other fluorophores. See Henegariu et al., *Nature Biotechnol.* 18: 345–348 (2000), the disclosure of which is incorporated herein by reference in its entirety.

Haptens that are commonly conjugated to nucleotides for subsequent labeling include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-1-dUTP, Molecular Probes, Inc., Eugene, Oreg., USA).

Nucleic acid molecules can be labeled by incorporation of labeled nucleotide analogues into the nucleic acid. Such analogues can be incorporated by enzymatic polymerization, such as by nick translation, random priming, polymerase chain reaction (PCR), terminal transferase tailing, and end-filling of overhangs, for DNA molecules, and in vitro transcription driven, e.g., from phage promoters, such as T7, T3, and SP6, for RNA molecules. Commercial kits are readily available for each such labeling approach. Analogues can also be incorporated during automated solid phase chemical synthesis. Labels can also be incorporated after nucleic acid synthesis, with the 5' phosphate and 3' hydroxyl providing convenient sites for post-synthetic covalent attachment of detectable labels.

Other post-synthetic approaches also permit internal labeling of nucleic acids. For example, fluorophores can be attached using a cisplatin reagent that reacts with the N7 of guanine residues (and, to a lesser extent, adenine bases) in DNA, RNA, and PNA to provide a stable coordination complex between the nucleic acid and fluorophore label (Universal Linkage System) (available from Molecular Probes, Inc., Eugene, Oreg., USA and Amersham Pharmacia Biotech, Piscataway, N.J., USA); see Alers et al., *Genes, Chromosomes & Cancer* 25: 301–305 (1999); Jelsma et al., *J NIH Res.* 5: 82 (1994); Van Belkum et al., *BioTechniques* 16: 148–153 (1994), incorporated herein by reference. As another example, nucleic acids can be labeled using a disulfide-containing linker (FastTag™ Reagent, Vector Laboratories, Inc., Burlingame, Calif., USA) that is photo- or thermally-coupled to the target nucleic acid using aryl azide chemistry; after reduction, a free thiol is available for coupling to a hapten, fluorophore, sugar, affinity ligand, or other marker.

One or more independent or interacting labels can be incorporated into the nucleic acid molecules of the present invention. For example, both a fluorophore and a moiety that in proximity thereto acts to quench fluorescence can be included to report specific hybridization through release of fluorescence quenching or to report exonucleotidic excision. See, e.g., Tyagi et al, *Nature Biotechnol.* 14: 303–308 (1996); Tyagi et al., *Nature Biotechnol.* 16: 49–53 (1998); Sokol et al., *Proc. Natl. Acad. Sci. USA* 95: 11538–11543 (1998); Kostrikis et al., *Science* 279: 1228–1229 (1998); Marras et al., *Genet. Anal.* 14: 151–156 (1999); U.S. Pat. Nos. 5,846,726; 5,925,517; 5,925,517; 5,723,591 and 5,538,848; Holland et al., *Proc. Natl. Acad. Sci. USA* 88: 7276–7280 (1991); Heid et al., *Genome Res.* 6(10): 986–94 (1996); Kuimelis et al., *Nucleic Acids Symp. Ser.* (37): 255–6 (1997); the disclosures of which are incorporated herein by reference in their entireties.

Nucleic acid molecules of the invention may be modified by altering one or more native phosphodiester internucleoside bonds to more nuclease-resistant, internucleoside bonds. See Hartmann et al. (eds.), *Manual of Antisense Methodology: Perspectives in Antisense Science*, Kluwer Law International (1999); Stein et al. (eds.), *Applied Antisense Oligonucleotide Technology*, Wiley-Liss (1998); Chadwick et al. (eds.), *Oligonucleotides as Therapeutic Agents—Symposium No. 209*, John Wiley & Son Ltd (1997); the disclosures of which are incorporated herein by reference in their entireties. Such altered internucleoside bonds are often desired for antisense techniques or for targeted gene correction. See Gamper et al., *Nucl. Acids Res.* 28(21): 4332–4339 (2000), the disclosure of which is incorporated herein by reference in its entirety.

Modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, the disclosures of which are incorporated herein by reference in their entireties. In a preferred embodiment, the modified internucleoside linkages may be used for antisense techniques.

Other modified oligonucleotide backbones do not include a phosphorus atom, but have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above backbones include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437 and 5,677,439; the disclosures of which are incorporated herein by reference in their entireties.

In other preferred oligonucleotide mimetics, both the sugar and the internucleoside linkage are replaced with novel groups, such as peptide nucleic acids (PNA). In PNA compounds, the phosphodiester backbone of the nucleic acid is replaced with an amide-containing backbone, in particular by repeating N-(2-aminoethyl) glycine units linked by amide bonds. Nucleobases are bound directly or indirectly to aza nitrogen atoms of the amide portion of the backbone, typically by methylene carbonyl linkages. PNA can be synthesized using a modified peptide synthesis protocol. PNA oligomers can be synthesized by both Fmoc and tBoc methods. Representative U.S. patents that teach the preparation of PNA compounds include, but are not limited to, U.S. Pat. Nos. 5,539,082; 5,714,331; and 5,719,262, each of which is herein incorporated by reference. Automated PNA synthesis is readily achievable on commercial synthesizers (see, e.g., "PNA User's Guide," Rev. 2, February 1998, Perseptive Biosystems Part No. 60138, Applied Biosystems, Inc., Foster City, Calif.).

PNA molecules are advantageous for a number of reasons. First, because the PNA backbone is uncharged, PNA/DNA and PNA/RNA duplexes have a higher thermal stability than is found in DNA/DNA and DNA/RNA duplexes. The Tm of a PNA/DNA or PNA/RNA duplex is generally 1° C. higher per base pair than the Tm of the corresponding DNA/DNA or DNA/RNA duplex (in 100 mM NaCl). Second, PNA molecules can also form stable PNA/DNA complexes at low ionic strength, under conditions in which DNA/DNA duplex formation does not occur. Third, PNA also demonstrates greater specificity in binding to complementary DNA because a PNA/DNA mismatch is more destabilizing than DNA/DNA mismatch. A single mismatch in mixed a PNA/DNA 15-mer lowers the Tm by 8–20° C. (15° C. on average). In the corresponding DNA/DNA duplexes, a single mismatch lowers the Tm by 4–16° C. (11° C. on average). Because PNA probes can be significantly shorter than DNA probes, their specificity is greater. Fourth, PNA oligomers are resistant to degradation by enzymes, and the lifetime of these compounds is extended both in vivo and in vitro because nucleases and proteases do not recognize the PNA polyamide backbone with nucleobase sidechains. See, e.g., Ray et al., *FASEB J.* 14(9): 1041–60 (2000); Nielsen et al., *Pharmacol Toxicol.* 86(1): 3–7 (2000); Larsen et al., *Biochim Biophys. Acta.* 1489(1): 159–66 (1999); Nielsen, *Curr. Opin. Struct. Biol.* 9(3): 353–7 (1999), and Nielsen, *Curr. Opin. Biotechnol.* 10(1): 71–5 (1999), the disclosures of which are incorporated herein by reference in their entireties.

Nucleic acid molecules may be modified compared to their native structure throughout the length of the nucleic acid molecule or can be localized to discrete portions thereof. As an example of the latter, chimeric nucleic acids can be synthesized that have discrete DNA and RNA domains and that can be used for targeted gene repair and modified PCR reactions, as further described in U.S. Pat. Nos. 5,760,012 and 5,731,181, Misra et al., *Biochem.* 37: 1917–1925 (1998); and Finn et al., *Nucl. Acids Res.* 24: 3357–3363 (1996), the disclosures of which are incorporated herein by reference in their entireties.

Unless otherwise specified, nucleic acids of the present invention can include any topological conformation appropriate to the desired use; the term thus explicitly comprehends, among others, single-stranded, double-stranded, triplexed, quadruplexed, partially double-stranded, partially-triplexed, partially-quadruplexed, branched, hairpinned, circular, and padlocked conformations. Padlock conformations and their utilities are further described in Baner et al., *Curr. Opin. Biotechnol.* 12: 11–15 (2001); Escude et al., *Proc. Natl. Acad. Sci. USA* 14: 96(19):10603–7 (1999); Nilsson et al., *Science* 265(5181): 2085–8 (1994), the disclosures of which are incorporated herein by reference in their entireties. Triplex and quadruplex conformations, and their utilities, are reviewed in Praseuth et al., *Biochim. Biophys. Acta.* 1489(1): 181–206 (1999); Fox, *Curr. Med. Chem.* 7(1): 17–37 (2000); Kochetkova et al., *Methods Mol. Biol.* 130: 189–201 (2000); Chan et al., *J. Mol. Med.* 75(4): 267–82 (1997), the disclosures of which are incorporated herein by reference in their entireties.

Methods for Using Nucleic Acid Molecules as Probes and Primers

The isolated nucleic acid molecules of the present invention can be used as hybridization probes to detect, characterize, and quantify hybridizing nucleic acids in, and isolate hybridizing nucleic acids from, both genomic and transcript-derived nucleic acid samples. When free in solution, such probes are typically, but not invariably, detectably labeled; bound to a substrate, as in a microarray, such probes are typically, but not invariably unlabeled.

In one embodiment, the isolated nucleic acids of the present invention can be used as probes to detect and characterize gross alterations in the gene of a BSNA, such as deletions, insertions, translocations, and duplications of the BSNA genomic locus through fluorescence in situ hybridization (FISH) to chromosome spreads. See, e.g., Andreeff et al. (eds.), *Introduction to Fluorescence In Situ Hybridization: Principles and Clinical Applications*, John Wiley & Sons (1999), the disclosure of which is incorporated herein by reference in its entirety. The isolated nucleic acids of the present invention can be used as probes to assess smaller genomic alterations using, e.g., Southern blot detection of restriction fragment length polymorphisms. The isolated nucleic acid molecules of the present invention can be used as probes to isolate genomic clones that include the nucleic acid molecules of the present invention, which thereafter can be restriction mapped and sequenced to identify deletions, insertions, translocations, and substitutions (single nucleotide polymorphisms, SNPs) at the sequence level.

In another embodiment, the isolated nucleic acid molecules of the present invention can be used as probes to detect, characterize, and quantify BSNA in, and isolate BSNA from, transcript-derived nucleic acid samples. In one aspect, the isolated nucleic acid molecules of the present invention can be used as hybridization probes to detect, characterize by length, and quantify mRNA by Northern blot of total or poly-A$^+$-selected RNA samples. In another aspect, the isolated nucleic acid molecules of the present invention can be used as hybridization probes to detect, characterize by location, and quantify mRNA by in situ hybridization to tissue sections. See, e.g., Schwarchzacher et al., *In Situ Hybridization*, Springer-Verlag New York (2000), the disclosure of which is incorporated herein by reference in its entirety. In another preferred embodiment, the isolated nucleic acid molecules of the present invention can be used as hybridization probes to measure the representation of clones in a cDNA library or to isolate hybridizing nucleic acid molecules acids from cDNA libraries, permitting sequence level characterization of mRNAs that hybridize to BSNAs, including, without limitations, identification of deletions, insertions, substitutions, truncations, alternatively spliced forms and single nucleotide polymorphisms. In yet another preferred embodiment, the nucleic acid molecules of the instant invention may be used in microarrays.

All of the aforementioned probe techniques are well within the skill in the art, and are described at greater length in standard texts such as Sambrook (2001), supra; Ausubel (1999), supra; and Walker et al. (eds.), *The Nucleic Acids Protocols Handbook*, Humana Press (2000), the disclosures of which are incorporated herein by reference in their entirety.

Thus, in one embodiment, a nucleic acid molecule of the invention may be used as a probe or primer to identify or amplify a second nucleic acid molecule that selectively hybridizes to the nucleic acid molecule of the invention. In a preferred embodiment, the probe or primer is derived from a nucleic acid molecule encoding a BSP. In a more preferred embodiment, the probe or primer is derived from a nucleic acid molecule encoding a polypeptide having an amino acid sequence of SEQ ID NO: 165 through 280. In another preferred embodiment, the probe or primer is derived from a BSNA. In a more preferred embodiment, the probe or primer is derived from a nucleic acid molecule having a nucleotide sequence of SEQ ID NO: 1 through 164.

In general, a probe or primer is at least 10 nucleotides in length, more preferably at least 12, more preferably at least 14 and even more preferably at least 16 or 17 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well-known in the art. See, e.g., Sambrook et al., 1989, supra, Chapter 11 and pp. 11.31–11.32 and 11.40–11.44, which describes radiolabeling of short probes, and pp. 11.45–11.53, which describe hybridization conditions for oligonucleotide probes, including specific conditions for probe hybridization (pp. 11.50–11.51).

Methods of performing primer-directed amplification are also well-known in the art. Methods for performing the polymerase chain reaction (PCR) are compiled, inter alia, in McPherson, *PCR Basics: From Background to Bench*, Springer Verlag (2000); Innis et al. (eds.), *PCR Applications: Protocols for Functional Genomics*, Academic Press (1999); Gelfand et al. (eds.), *PCR Strategies*, Academic Press (1998); Newton et al., *PCR*, Springer-Verlag New York (1997); Burke (ed.), *PCR: Essential Techniques*, John Wiley & Son Ltd (1996); White (ed.), *PCR Cloning Protocols: From Molecular Cloning to Genetic Engineering*, Vol. 67, Humana Press (1996); McPherson et al. (eds.), *PCR 2: A Practical Approach*, Oxford University Press, Inc. (1995); the disclosures of which are incorporated herein by reference in their entireties. Methods for performing RT-PCR are collected, e.g., in Siebert et al. (eds.), *Gene Cloning and Analysis by RT-PCR*, Eaton Publishing Company/Bio Techniques Books Division, 1998; Siebert (ed.), *PCR Technique: RT-PCR*, Eaton Publishing Company/BioTechniques Books (1995); the disclosure of which is incorporated herein by reference in its entirety.

PCR and hybridization methods may be used to identify and/or isolate allelic variants, homologous nucleic acid molecules and fragments of the nucleic acid molecules of the invention. PCR and hybridization methods may also be used to identify, amplify and/or isolate nucleic acid molecules that encode homologous proteins, analogs, fusion protein or muteins of the invention. The nucleic acid primers of the present invention can be used to prime amplification of nucleic acid molecules of the invention, using transcript-derived or genomic DNA as template.

The nucleic acid primers of the present invention can also be used, for example, to prime single base extension (SBE) for SNP detection (See, e.g., U.S. Pat. No. 6,004,744, the disclosure of which is incorporated herein by reference in its entirety).

Isothermal amplification approaches, such as rolling circle amplification, are also now well-described. See, e.g., Schweitzer et al., *Curr. Opin. Biotechnol.* 12(1): 21–7 (2001); U.S. Pat. Nos. 5,854,033 and 5,714,320; and international patent publications WO 97/19193 and WO 00/15779, the disclosures of which are incorporated herein by reference in their entireties. Rolling circle amplification can be combined with other techniques to facilitate SNP detection. See, e.g., Lizardi et al., *Nature Genet.* 19(3): 225–32 (1998).

Nucleic acid molecules of the present invention may be bound to a substrate either covalently or noncovalently. The substrate can be porous or solid, planar or non-planar, unitary or distributed. The bound nucleic acid molecules may be used as hybridization probes, and may be labeled or unlabeled. In a preferred embodiment, the bound nucleic acid molecules are unlabeled.

In one embodiment, the nucleic acid molecule of the present invention is bound to a porous substrate, e.g., a membrane, typically comprising nitrocellulose, nylon, or positively-charged derivatized nylon. The nucleic acid molecule of the present invention can be used to detect a hybridizing nucleic acid molecule that is present within a labeled nucleic acid sample, e.g., a sample of transcript-derived nucleic acids. In another embodiment, the nucleic acid molecule is bound to a solid substrate, including, without limitation, glass, amorphous silicon, crystalline silicon or plastics. Examples of plastics include, without limitation, polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. The solid substrate may be any shape, including rectangular, disk-like and spherical. In a preferred embodiment, the solid substrate is a microscope slide or slide-shaped substrate.

The nucleic acid molecule of the present invention can be attached covalently to a surface of the support substrate or applied to a derivatized surface in a chaotropic agent that facilitates denaturation and adherence by presumed noncovalent interactions, or some combination thereof. The nucleic acid molecule of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that include the nucleic acids of the present invention.

Expression Vectors, Host Cells and Recombinant Methods of Producing Polypeptides Another aspect of the present invention relates to vectors that comprise one or more of the isolated nucleic acid molecules of the present invention, and host cells in which such vectors have been introduced.

The vectors can be used, inter alia, for propagating the nucleic acids of the present invention in host cells (cloning vectors), for shuttling the nucleic acids of the present invention between host cells derived from disparate organisms (shuttle vectors), for inserting the nucleic acids of the present invention into host cell chromosomes (insertion vectors), for expressing sense or antisense RNA transcripts of the nucleic acids of the present invention in vitro or within a host cell, and for expressing polypeptides encoded by the nucleic acids of the present invention, alone or as fusions to heterologous polypeptides (expression vectors). Vectors of the present invention will often be suitable for several such uses.

Vectors are by now well-known in the art, and are described, inter alia, in Jones et al. (eds.), *Vectors: Cloning Applications: Essential Techniques* (Essential Techniques Series), John Wiley & Son Ltd. (1998); Jones et al. (eds.), *Vectors: Expression Systems: Essential Techniques* (Essential Techniques Series), John Wiley & Son Ltd. (1998); Gacesa et al., *Vectors: Essential Data*, John Wiley & Sons Ltd. (1995); Cid-Arregui (eds.), *Viral Vectors: Basic Science and Gene Therapy*, Eaton Publishing Co. (2000); Sambrook (2001), supra; Ausubel (1999), supra; the disclosures of which are incorporated herein by reference in their entireties. Furthermore, an enormous variety of vectors are available commercially. Use of existing vectors and modifications thereof being well within the skill in the art, only basic features need be described here.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences.

In one embodiment, prokaryotic cells may be used with an appropriate vector. Prokaryotic host cells are often used for cloning and expression. In a preferred embodiment, prokaryotic host cells include *E. coli, Pseudomonas, Bacillus* and *Streptomyces*. In a preferred embodiment, bacterial host cells are used to express the nucleic acid molecules of the instant invention. Useful expression vectors for bacterial hosts include bacterial plasmids, such as those from *E. coli, Bacillus* or *Streptomyces*, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, λGT10 and λGT11, and other phages, e.g., M13 and filamentous single-stranded phage DNA. Where *E. coli* is used as host, selectable markers are, analogously, chosen for selectivity in gram negative bacteria: e.g., typical markers confer resistance to antibiotics, such as ampicillin, tetracycline, chloramphenicol, kanamycin, streptomycin and zeocin; auxotrophic markers can also be used.

In other embodiments, eukaryotic host cells, such as yeast, insect, mammalian or plant cells, may be used. Yeast cells, typically *S. cerevisiae*, are useful for eukaryotic genetic studies, due to the ease of targeting genetic changes by homologous recombination and the ability to easily complement genetic defects using recombinantly expressed proteins. Yeast cells are useful for identifying interacting protein components, e.g. through use of a two-hybrid system. In a preferred embodiment, yeast cells are useful for protein expression. Vectors of the present invention for use in yeast will typically, but not invariably, contain an origin of replication suitable for use in yeast and a selectable marker that is functional in yeast. Yeast vectors include Yeast Integrating plasmids (e.g., YIp5) and Yeast Replicating plasmids (the YRp and YEp series plasmids), Yeast Centromere plasmids (the YCp series plasmids), Yeast Artificial Chromosomes (YACs) which are based on yeast linear plasmids, denoted YLp, pGPD-2, 2μ plasmids and derivatives thereof, and improved shuttle vectors such as those described in Gietz et al., *Gene,* 74: 527–34 (1988) (YIplac, YEplac and YCplac). Selectable markers in yeast vectors include a variety of auxotrophic markers, the most common of which are (in *Saccharomyces cerevisiae*) URA3, HIS3, LEU2, TRP1 and LYS2, which complement specific auxotrophic mutations, such as ura3-52, his3-D1, leu2-D1, trp1-D1 and lys2-201.

Insect cells are often chosen for high efficiency protein expression. Where the host cells are from *Spodoptera frugiperda*, e.g., Sf9 and Sf21 cell lines, and expresSF™ cells (Protein Sciences Corp., Meriden, Conn., USA)), the vector replicative strategy is typically based upon the baculovirus life cycle. Typically, baculovirus transfer vectors are used to replace the wild-type AcMNPV polyhedrin gene with a heterologous gene of interest. Sequences that flank the polyhedrin gene in the wild-type genome are positioned 5' and 3' of the expression cassette on the transfer vectors. Following co-transfection with AcMNPV DNA, a homologous recombination event occurs between these sequences resulting in a recombinant virus carrying the gene of interest and the polyhedrin or p10 promoter. Selection can be based upon visual screening for lacZ fusion activity.

In another embodiment, the host cells may be mammalian cells, which are particularly useful for expression of proteins intended as pharmaceutical agents, and for screening of potential agonists and antagonists of a protein or a physiological pathway. Mammalian vectors intended for autonomous extrachromosomal replication will typically include a viral origin, such as the SV40 origin (for replication in cell lines expressing the large T-antigen, such as COS1 and COS7 cells), the papillomavirus origin, or the EBV origin for long term episomal replication (for use, e.g., in 293-EBNA cells, which constitutively express the EBV EBNA-1 gene product and adenovirus E1A). Vectors intended for integration, and thus replication as part of the mammalian chromosome, can, but need not, include an origin of replication functional in mammalian cells, such as the SV40 origin. Vectors based upon viruses, such as adenovirus, adeno-associated virus, vaccinia virus, and various mammalian retroviruses, will typically replicate according to the viral replicative strategy. Selectable markers for use in mammalian cells include resistance to neomycin (G418), blasticidin, hygromycin and to zeocin, and selection based upon the purine salvage pathway using HAT medium.

Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Plant cells can also be used for expression, with the vector replicon typically derived from a plant virus (e.g., cauliflower mosaic virus, CaMV; tobacco mosaic virus, TMV) and selectable markers chosen for suitability in plants.

It is known that codon usage of different host cells may be different. For example, a plant cell and a human cell may exhibit a difference in codon preference for encoding a particular amino acid. As a result, human mRNA may not be efficiently translated in a plant, bacteria or insect host cell. Therefore, another embodiment of this invention is directed to codon optimization. The codons of the nucleic acid molecules of the invention may be modified to resemble, as much as possible, genes naturally contained within the host cell without altering the amino acid sequence encoded by the nucleic acid molecule.

Any of a wide variety of expression control sequences may be used in these vectors to express the DNA sequences of this invention. Such useful expression control sequences include the expression control sequences associated with structural genes of the foregoing expression vectors. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation.

Examples of useful expression control sequences for a prokaryote, e.g., *E. coli*, will include a promoter, often a phage promoter, such as phage lambda pL promoter, the trc promoter, a hybrid derived from the trp and lac promoters, the bacteriophage T7 promoter (in *E. coli* cells engineered to express the T7 polymerase), the TAC or TRC system, the major operator and promoter regions of phage lambda, the control regions of fd coat protein, or the araBAD operon. Prokaryotic expression vectors may further include transcription terminators, such as the aspA terminator, and elements that facilitate translation, such as a consensus ribosome binding site and translation termination codon, Schomer et al., *Proc. Natl. Acad. Sci. USA* 83: 8506–8510 (1986).

Expression control sequences for yeast cells, typically *S. cerevisiae*, will include a yeast promoter, such as the CYC1 promoter, the GAL1 promoter, the GAL10 promoter, ADH1 promoter, the promoters of the yeast_-mating system, or the GPD promoter, and will typically have elements that facilitate transcription termination, such as the transcription termination signals from the CYC1 or ADH1 gene.

Expression vectors useful for expressing proteins in mammalian cells will include a promoter active in mammalian cells. These promoters include those derived from mammalian viruses, such as the enhancer-promoter sequences from the immediate early gene of the human cytomegalovirus (CMV), the enhancer-promoter sequences from the Rous sarcoma virus long terminal repeat (RSV LTR), the enhancer-promoter from SV40 or the early and late promoters of adenovirus. Other expression control sequences include the promoter for 3-phosphoglycerate kinase or other glycolytic enzymes, the promoters of acid phosphatase. Other expression control sequences include those from the gene comprising the BSNA of interest. Often, expression is enhanced by incorporation of polyadenylation sites, such as the late SV40 polyadenylation site and the polyadenylation signal and transcription termination sequences from the bovine growth hormone (BGH) gene, and ribosome binding sites. Furthermore, vectors can include introns, such as intron II of rabbit β-globin gene and the SV40 splice elements.

Preferred nucleic acid vectors also include a selectable or amplifiable marker gene and means for amplifying the copy number of the gene of interest. Such marker genes are well-known in the art. Nucleic acid vectors may also comprise stabilizing sequences (e.g., ori- or ARS-like sequences and telomere-like sequences), or may alternatively be designed to favor directed or non-directed integration into the host cell genome. In a preferred embodiment, nucleic acid sequences of this invention are inserted in frame into an expression vector that allows high level expression of an RNA which encodes a protein comprising the encoded nucleic acid sequence of interest. Nucleic acid cloning and sequencing methods are well-known to those of skill in the art and are described in an assortment of laboratory manuals, including Sambrook (1989), supra, Sambrook (2000), supra; and Ausubel (1992), supra, Ausubel (1999), supra. Product information from manufacturers of biological, chemical and immunological reagents also provide useful information.

Expression vectors may be either constitutive or inducible. Inducible vectors include either naturally inducible promoters, such as the trc promoter, which is regulated by the lac operon, and the pL promoter, which is regulated by tryptophan, the MMTV-LTR promoter, which is inducible by dexamethasone, or can contain synthetic promoters and/or additional elements that confer inducible control on adjacent promoters. Examples of inducible synthetic promoters are the hybrid Plac/ara-1 promoter and the PLtetO-1 promoter. The PltetO-1 promoter takes advantage of the high expression levels from the PL promoter of phage lambda, but replaces the lambda repressor sites with two copies of operator 2 of the Tn10 tetracycline resistance operon, causing this promoter to be tightly repressed by the Tet repressor protein and induced in response to tetracycline (Tc) and Tc derivatives such as anhydrotetracycline. Vectors may also be inducible because they contain hormone response elements, such as the glucocorticoid response element (GRE) and the estrogen response element (ERE), which can confer hormone inducibility where vectors are used for expression in cells having the respective hormone receptors. To reduce background levels of expression, elements responsive to ecdysone, an insect hormone, can be used instead, with coexpression of the ecdysone receptor.

In one aspect of the invention, expression vectors can be designed to fuse the expressed polypeptide to small protein tags that facilitate purification and/or visualization. Tags that facilitate purification include a polyhistidine tag that facilitates purification of the fusion protein by immobilized metal affinity chromatography, for example using NiNTA resin (Qiagen Inc., Valencia, Calif., USA) or TALON™ resin (cobalt immobilized affinity chromatography medium, Clontech Labs, Palo Alto, Calif., USA). The fusion protein can include a chitin-binding tag and self-excising intein, permitting chitin-based purification with self-removal of the fused tag (IMPACT™ system, New England Biolabs, Inc., Beverley, Mass., USA). Alternatively, the fusion protein can include a calmodulin-binding peptide tag, permitting purification by calmodulin affinity resin (Stratagene, La Jolla, Calif., USA), or a specifically excisable fragment of the biotin carboxylase carrier protein, permitting purification of in vivo biotinylated protein using an avidin resin and subsequent tag removal (Promega, Madison, Wis., USA). As another useful alternative, the proteins of the present invention can be expressed as a fusion protein with glutathione-S-transferase, the affinity and specificity of binding to glutathione permitting purification using glutathione affinity resins, such as Glutathione-Superflow Resin (Clontech Laboratories, Palo Alto, Calif., USA), with subsequent elution with free glutathione. Other tags include, for example, the Xpress epitope, detectable by anti-Xpress antibody (Invitrogen, Carlsbad, Calif., USA), a myc tag, detectable by anti-myc tag antibody, the V5 epitope, detectable by anti-V5 antibody (Invitrogen, Carlsbad, Calif., USA), FLAG® epitope, detectable by anti-FLAG® antibody (Stratagene, La Jolla, Calif., USA), and the HA epitope.

For secretion of expressed proteins, vectors can include appropriate sequences that encode secretion signals, such as leader peptides. For example, the pSecTag2 vectors (Invitrogen, Carlsbad, Calif., USA) are 5.2 kb mammalian expression vectors that carry the secretion signal from the V-J2-C region of the mouse Ig kappa-chain for efficient secretion of recombinant proteins from a variety of mammalian cell lines.

Expression vectors can also be designed to fuse proteins encoded by the heterologous nucleic acid insert to polypeptides that are larger than purification and/or identification tags. Useful fusion proteins include those that permit display of the encoded protein on the surface of a phage or cell, fusion to intrinsically fluorescent proteins, such as those that have a green fluorescent protein (GFP)-like chromophore, fusions to the IgG Fc region, and fusion proteins for use in two hybrid systems.

Vectors for phage display fuse the encoded polypeptide to, e.g., the gene III protein (pIII) or gene VIII protein (PVIII) for display on the surface of filamentous phage, such as M13. See Barbas et al., *Phage Display: A Laboratory Manual*, Cold Spring Harbor Laboratory Press (2001); Kay et al. (eds.), *Phage Display of Peptides and Proteins: A Laboratory Manual*, Academic Press, Inc., (1996); Abelson et al. (eds.), *Combinatorial Chemistry* (Methods in Enzymology, Vol. 267) Academic Press (1996). Vectors for yeast display, e.g. the pYD1 yeast display vector (Invitrogen, Carlsbad, Calif., USA), use the -agglutinin yeast adhesion receptor to display recombinant protein on the surface of *S. cerevisiae*. Vectors for mammalian display, e.g., the pDisplay™ vector (Invitrogen, Carlsbad, Calif., USA), target recombinant proteins using an N-terminal cell surface targeting signal and a C-terminal transmembrane anchoring domain of platelet derived growth factor receptor.

A wide variety of vectors now exist that fuse proteins encoded by heterologous nucleic acids to the chromophore of the substrate-independent, intrinsically fluorescent green fluorescent protein from *Aequorea victoria* ("GFP") and its variants. The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422), and need include only so much of the native protein as is needed to retain the chromophore's intrinsic fluorescence. Methods for determining the minimal domain required for fluorescence are known in the art. See Li et al., *J. Biol. Chem.* 272: 28545-28549 (1997). Alternatively, the GFP-like chromophore can be selected from GFP-like chromophores modified from those found in nature. The methods for engineering such modified GFP-like chromophores and testing them for fluorescence activity, both alone and as part of protein fusions, are well-known in the art. See Heim et al., *Curr. Biol.* 6: 178–182 (1996) and Palm et al., *Methods Enzymol.* 302: 378–394 (1999), incorporated herein by reference in its entirety. A variety of such modified chromophores are now commercially available and can readily be used in the fusion proteins of the present invention. These include EGFP ("enhanced GFP"), EBFP ("enhanced blue fluorescent protein"), BFP2, EYFP ("enhanced yellow fluorescent protein"), ECFP ("enhanced cyan fluorescent protein") or Citrine. EGFP (see, e.g, Cormack et al., *Gene* 173: 33–38 (1996); U.S. Pat. Nos. 6,090,919 and 5,804,387) is found on a variety of vectors, both plasmid and viral, which are available commercially (Clontech Labs, Palo Alto, Calif., USA); EBFP is optimized for expression in mammalian cells whereas BFP2, which retains the original jellyfish codons, can be expressed in bacteria (see, e.g, Heim et al., *Curr. Biol.* 6: 178–182 (1996) and Cormack et al., Gene 173: 33–38 (1996)). Vectors containing these blue-shifted variants are available from Clontech Labs (Palo Alto, Calif., USA). Vectors containing EYFP, ECFP (see, e.g., Heim et al., *Curr. Biol.* 6: 178–182 (1996); Miyawaki et al., *Nature* 388: 882–887 (1997)) and Citrine (see, e.g., Heikal et al., *Proc. Natl. Acad. Sci. USA* 97: 11996–12001 (2000)) are also available from Clontech Labs. The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties. See also Conn (ed.), *Green Fluorescent Protein* (Methods in Enzymology, Vol. 302), Academic Press, Inc. (1999). The GFP-like chromophore of each of these GFP variants can usefully be included in the fusion proteins of the present invention.

Fusions to the IgG Fc region increase serum half life of protein pharmaceutical products through interaction with the FcRn receptor (also denominated the FcRp receptor and the Brambell receptor, FcRb), further described in International Patent Application Nos. WO 97/43316, WO 97/34631, WO 96/32478, WO 96/18412.

For long-term, high-yield recombinant production of the proteins, protein fusions, and protein fragments of the present invention, stable expression is preferred. Stable expression is readily achieved by integration into the host cell genome of vectors having selectable markers, followed by selection of these integrants. Vectors such as pUB6/V5-His A, B, and C (Invitrogen, Carlsbad, Calif., USA) are designed for high-level stable expression of heterologous proteins in a wide range of mammalian tissue types and cell lines. pUB6/V5-His uses the promoter/enhancer sequence from the human ubiquitin C gene to drive expression of recombinant proteins: expression levels in 293, CHO, and NIH3T3 cells are comparable to levels from the CMV and human EF-1 a promoters. The bsd gene permits rapid selection of stably transfected mammalian cells with the potent antibiotic blasticidin.

Replication incompetent retroviral vectors, typically derived from Moloney murine leukemia virus, also are useful for creating stable transfectants having integrated provirus. The highly efficient transduction machinery of retroviruses, coupled with the availability of a variety of packaging cell lines such as RetroPack™ PT 67, Eco-Pack2™-293, AmphoPack-293, and GP2-293 cell lines (all available from Clontech Laboratories, Palo Alto, Calif., USA), allow a wide host range to be infected with high efficiency; varying the multiplicity of infection readily adjusts the copy number of the integrated provirus.

Of course, not all vectors and expression control sequences will function equally well to express the nucleic acid sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must be replicated in it. The vector's copy number, the ability to control that copy number, the ability to control integration, if any, and the expression of any other proteins encoded by the vector, such as antibiotic or other selection markers, should also be considered. The present invention further includes host cells comprising the vectors of the present invention, either present episomally within the cell or integrated, in whole or in part, into the host cell chromosome. Among other considerations, some of which are described above, a host cell strain may be chosen for its ability to process the expressed protein in the desired fashion. Such post-translational modifications of the polypeptide include, but are not limited to, acetylation, carboxylation, glycosylation, phosphorylation, lipidation, and acylation, and it is an aspect of the present invention to provide BSPs with such post-translational modifications.

Polypeptides of the invention may be post-translationally modified. Post-translational modifications include phosphorylation of amino acid residues serine, threonine and/or tyrosine, N-linked and/or O-linked glycosylation, methylation, acetylation, prenylation, methylation, acetylation, arginylation, ubiquination and racemization. One may determine whether a polypeptide of the invention is likely to be post-translationally modified by analyzing the sequence of the polypeptide to determine if there are peptide motifs indicative of sites for post-translational modification. There are a number of computer programs that permit prediction of post-translational modifications. See, e.g., www.expasy.org (accessed Aug. 31, 2001), which includes PSORT, for prediction of protein sorting signals and localization sites, SignalP, for prediction of signal peptide cleavage sites, MITOPROT and Predotar, for prediction of mitochondrial targeting sequences, NetOGlyc, for prediction of type O-glycosylation sites in mammalian proteins, big-PI Predictor and DGPI, for prediction of prenylation-anchor and cleavage sites, and NetPhos, for prediction of Ser, Thr and Tyr phosphorylation sites in eukaryotic proteins. Other computer programs, such as those included in GCG, also may be used to determine post-translational modification peptide motifs.

General examples of types of post-translational modifications may be found in web sites such as the Delta Mass database http://www.abrf.org/ABRF/Research Committees/deltamass/deltamass.html (accessed Oct. 19, 2001); "GlycoSuiteDB: a new curated relational database of glycoprotein glycan structures and their biological sources" Cooper et al. Nucleic Acids Res. 29; 332–335 (2001) and http://www.glycosuite.com/ (accessed Oct. 19, 2001); "O-GLYCBASE version 4.0: a revised database of O-glycosylated proteins" Gupta et al. Nucleic Acids Research, 27: 370–372 (1999) and http://www.cbs.dtu.dk/databases/OGLYCBASE/ (accessed Oct. 19, 2001); "PhosphoBase, a database of phosphorylation sites: release 2.0.", Kreegipuu et al. Nucleic Acids Res 27(1):237–239 (1999) and http://www.cbs.dtu.dk/databases/PhosphoBase/ (accessed Oct. 19, 2001); or http://pir.georgetown.edu/pirwww/search/textresid.html (accessed Oct. 19, 2001).

Tumorigenesis is often accompanied by alterations in the post-translational modifications of proteins. Thus, in another embodiment, the invention provides polypeptides from cancerous cells or tissues that have altered post-translational modifications compared to the post-translational modifications of polypeptides from normal cells or tissues. A number of altered post-translational modifications are known. One common alteration is a change in phosphorylation state, wherein the polypeptide from the cancerous cell or tissue is hyperphosphorylated or hypophosphorylated compared to the polypeptide from a normal tissue, or wherein the polypeptide is phosphorylated on different residues than the polypeptide from a normal cell. Another common alteration is a change in glycosylation state, wherein the polypeptide from the cancerous cell or tissue has more or less glycosylation than the polypeptide from a normal tissue, and/or wherein the polypeptide from the cancerous cell or tissue has a different type of glycosylation than the polypeptide from a noncancerous cell or tissue. Changes in glycosylation may be critical because carbohydrate-protein and carbohydrate-carbohydrate interactions are important in cancer cell progression, dissemination and invasion. See, e.g., Barchi, Curr. Pharm. Des. 6: 485–501 (2000), Verma, Cancer Biochem. Biophys. 14: 151–162 (1994) and Dennis et al., Bioessays 5: 412–421 (1999).

Another post-translational modification that may be altered in cancer cells is prenylation. Prenylation is the covalent attachment of a hydrophobic prenyl group (either farnesyl or geranylgeranyl) to a polypeptide. Prenylation is required for localizing a protein to a cell membrane and is often required for polypeptide function. For instance, the Ras superfamily of GTPase signaling proteins must be prenylated for function in a cell. See, e.g., Prendergast et al., Semin. Cancer Biol. 10: 443–452 (2000) and Khwaja et al., Lancet 355: 741–744 (2000).

Other post-translation modifications that may be altered in cancer cells include, without limitation, polypeptide methylation, acetylation, arginylation or racemization of amino acid residues. In these cases, the polypeptide from the cancerous cell may exhibit either increased or decreased amounts of the post-translational modification compared to the corresponding polypeptides from noncancerous cells.

Other polypeptide alterations in cancer cells include abnormal polypeptide cleavage of proteins and aberrant protein-protein interactions. Abnormal polypeptide cleavage may be cleavage of a polypeptide in a cancerous cell that does not usually occur in a normal cell, or a lack of cleavage in a cancerous cell, wherein the polypeptide is cleaved in a normal cell. Aberrant protein-protein interactions may be either covalent cross-linking or non-covalent binding between proteins that do not normally bind to each other. Alternatively, in a cancerous cell, a protein may fail to bind to another protein to which it is bound in a noncancerous cell. Alterations in cleavage or in protein-protein interactions may be due to over- or underproduction of a polypeptide in a cancerous cell compared to that in a normal cell, or may be due to alterations in post-translational modifications (see above) of one or more proteins in the cancerous cell. See, e.g., Henschen-Edman, Ann. N.Y. Acad. Sci. 936: 580–593 (2001).

Alterations in polypeptide post-translational modifications, as well as changes in polypeptide cleavage and protein-protein interactions, may be determined by any method known in the art. For instance, alterations in phosphorylation may be determined by using anti-phosphoserine, anti-phosphothreonine or anti-phosphotyrosine antibodies or by amino acid analysis. Glycosylation alterations may be determined using antibodies specific for different sugar residues, by carbohydrate sequencing, or by alterations in the size of the glycoprotein, which can be determined by, e.g., SDS polyacrylamide gel electrophoresis (PAGE). Other alterations of post-translational modifications, such as prenylation, racemization, methylation, acetylation and arginylation, may be determined by chemical analysis, protein sequencing, amino acid analysis, or by using antibodies specific for the particular post-translational modifications. Changes in protein-protein interactions and in polypeptide cleavage may be analyzed by any method known in the art including, without limitation, non-denaturing PAGE (for non-covalent protein-protein interactions), SDS PAGE (for covalent protein-protein interactions and protein cleavage), chemical cleavage, protein sequencing or immunoassays.

In another embodiment, the invention provides polypeptides that have been post-translationally modified. In one embodiment, polypeptides may be modified enzymatically or chemically, by addition or removal of a post-translational modification. For example, a polypeptide may be glycosylated or deglycosylated enzymatically. Similarly, polypeptides may be phosphorylated using a purified kinase, such as a MAP kinase (e.g, p38, ERK, or JNK) or a tyrosine kinase (e.g., Src or erbB2). A polypeptide may also be modified through synthetic chemistry. Alternatively, one may isolate the polypeptide of interest from a cell or tissue that expresses the polypeptide with the desired post-translational modification. In another embodiment, a nucleic acid molecule encoding the polypeptide of interest is introduced into a host cell that is capable of post-translationally modifying the encoded polypeptide in the desired fashion. If the polypeptide does not contain a motif for a desired post-translational modification, one may alter the post-translational modification by mutating the nucleic acid sequence of a nucleic acid molecule encoding the polypeptide so that it contains a site for the desired post-translational modification. Amino acid sequences that may be post-translationally modified are known in the art. See, e.g., the programs described above on the website www.expasy.org. The nucleic acid molecule is then be introduced into a host cell that is capable of post-translationally modifying the encoded polypeptide. Similarly, one may delete sites that are post-translationally modified by either mutating the nucleic acid sequence so that the encoded polypeptide does not contain the post-translational modification motif, or by introducing the native nucleic acid molecule into a host cell that is not capable of post-translationally modifying the encoded polypeptide.

In selecting an expression control sequence, a variety of factors should also be considered. These include, for example, the relative strength of the sequence, its controllability, and its compatibility with the nucleic acid sequence of this invention, particularly with regard to potential secondary structures. Unicellular hosts should be selected by consideration of their compatibility with the chosen vector, the toxicity of the product coded for by the nucleic acid sequences of this invention, their secretion characteristics, their ability to fold the polypeptide correctly, their fermentation or culture requirements, and the ease of purification from them of the products coded for by the nucleic acid sequences of this invention.

The recombinant nucleic acid molecules and more particularly, the expression vectors of this invention may be used to express the polypeptides of this invention as recombinant polypeptides in a heterologous host cell. The polypeptides of this invention may be full-length or less than full-length polypeptide fragments recombinantly expressed from the nucleic acid sequences according to this invention. Such polypeptides include analogs, derivatives and muteins that may or may not have biological activity.

Vectors of the present invention will also often include elements that permit in vitro transcription of RNA from the inserted heterologous nucleic acid. Such vectors typically include a phage promoter, such as that from T7, T3, or SP6, flanking the nucleic acid insert. Often two different such promoters flank the inserted nucleic acid, permitting separate in vitro production of both sense and antisense strands.

Transformation and other methods of introducing nucleic acids into a host cell (e.g., conjugation, protoplast transformation or fusion, transfection, electroporation, liposome delivery, membrane fusion techniques, high velocity DNA-coated pellets, viral infection and protoplast fusion) can be accomplished by a variety of methods which are well-known in the art (See, for instance, Ausubel, supra, and Sambrook et al., supra). Bacterial, yeast, plant or mammalian cells are transformed or transfected with an expression vector, such as a plasmid, a cosmid, or the like, wherein the expression vector comprises the nucleic acid of interest. Alternatively, the cells may be infected by a viral expression vector comprising the nucleic acid of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

A wide variety of unicellular host cells are useful in expressing the DNA sequences of this invention. These hosts may include well-known eukaryotic and prokaryotic hosts, such as strains of, fungi, yeast, insect cells such as *Spodoptera frugiperda* (SF9), animal cells such as CHO, as well as plant cells in tissue culture. Representative examples of appropriate host cells include, but are not limited to, bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from Spodoptera frugiperda, e.g., Sf9 and Sf21 cell lines, and expresSF™ cells (Protein Sciences Corp., Meriden, Conn., USA), *Drosophila* S2 cells, and *Trichoplusia ni* High Five® Cells (Invitrogen, Carlsbad, Calif., USA); and mammalian cells. Typical mammalian cells include BHK cells, BSC 1 cells, BSC 40 cells, BMT 10 cells, VERO cells, COS1 cells, COS7 cells, Chinese hamster ovary (CHO) cells, 3T3 cells, NIH 3T3 cells, 293 cells, HEPG2 cells, HeLa cells, L cells, MDCK cells, HEK293 cells, WI38 cells, murine ES cell lines (e.g., from strains 129/SV, C57/BL6, DBA-1, 129/SVJ), K562 cells, Jurkat cells, and BW5147 cells. Other mammalian cell lines are well-known and readily available from the American Type Culture Collection (ATCC) (Manassas, Va., USA) and the National Institute of General Medical Sciences (NIGMS) Human Genetic Cell Repository at the Coriell Cell Repositories (Camden, N.J., USA). Cells or cell lines derived from breast are particularly preferred because they may provide a more native post-translational processing. Particularly preferred are human breast cells.

Particular details of the transfection, expression and purification of recombinant proteins are well documented and are understood by those of skill in the art. Further details on the various technical aspects of each of the steps used in recombinant production of foreign genes in bacterial cell expression systems can be found in a number of texts and laboratory manuals in the art. See, e.g., Ausubel (1992), supra, Ausubel (1999), supra, Sambrook (1989), supra, and Sambrook (2001), supra, herein incorporated by reference.

Methods for introducing the vectors and nucleic acids of the present invention into the host cells are well-known in the art; the choice of technique will depend primarily upon the specific vector to be introduced and the host cell chosen.

Nucleic acid molecules and vectors may be introduced into prokaryotes, such as *E. coli*, in a number of ways. For instance, phage lambda vectors will typically be packaged using a packaging extract (e.g., Gigapack® packaging extract, Stratagene, La Jolla, Calif., USA), and the packaged virus used to infect *E. coli*.

Plasmid vectors will typically be introduced into chemically competent or electrocompetent bacterial cells. *E. coli* cells can be rendered chemically competent by treatment, e.g., with $CaCl_2$, or a solution of $Mg^{2+}$, $Mn^{2+}$, $Ca^{2+}$, $Rb^+$ or $K^+$, dimethyl sulfoxide, dithiothreitol, and hexamine cobalt (III), Hanahan, *J. Mol. Biol.* 166(4):557–80 (1983), and vectors introduced by heat shock. A wide variety of chemically competent strains are also available commercially (e.g., *Epicurian Coli*® XL10-Gold® Ultracompetent Cells (Stratagene, La Jolla, Calif., USA); DH5 competent cells (Clontech Laboratories, Palo Alto, Calif., USA); and TOP10 Chemically Competent *E. coli* Kit (Invitrogen, Carlsbad, Calif., USA)). Bacterial cells can be rendered electrocompetent, that is, competent to take up exogenous DNA by electroporation, by various pre-pulse treatments; vectors are introduced by electroporation followed by subsequent outgrowth in selected media. An extensive series of protocols is provided online in *Electroprotocols* (BioRad, Richmond, Calif., USA) (http://www.biorad.com/LifeScience/pdf/New_Gene_Pulser.pdf).

Vectors can be introduced into yeast cells by spheroplasting, treatment with lithium salts, electroporation, or protoplast fusion. Spheroplasts are prepared by the action of hydrolytic enzymes such as snail-gut extract, usually denoted Glusulase, or Zymolyase, an enzyme from *Arthrobacter luteus*, to remove portions of the cell wall in the presence of osmotic stabilizers, typically 1 M sorbitol. DNA is added to the spheroplasts, and the mixture is co-precipitated with a solution of polyethylene glycol (PEG) and $Ca^{2+}$. Subsequently, the cells are resuspended in a solution of sorbitol, mixed with molten agar and then layered on the surface of a selective plate containing sorbitol.

For lithium-mediated transformation, yeast cells are treated with lithium acetate, which apparently permeabilizes the cell wall, DNA is added and the cells are co-precipitated with PEG. The cells are exposed to a brief heat shock, washed free of PEG and lithium acetate, and subsequently spread on plates containing ordinary selective medium. Increased frequencies of transformation are obtained by using specially-prepared single-stranded carrier DNA and certain organic solvents. Schiestl et al., *Curr. Genet.* 16(5–6): 339–46 (1989).

For electroporation, freshly-grown yeast cultures are typically washed, suspended in an osmotic protectant, such as sorbitol, mixed with DNA, and the cell suspension pulsed in an electroporation device. Subsequently, the cells are spread on the surface of plates containing selective media. Becker et al., *Methods Enzymol.* 194: 182–187 (1991). The efficiency of transformation by electroporation can be increased over 100-fold by using PEG, single-stranded carrier DNA and cells that are in late log-phase of growth. Larger constructs, such as YACs, can be introduced by protoplast fusion.

Mammalian and insect cells can be directly infected by packaged viral vectors, or transfected by chemical or electrical means. For chemical transfection, DNA can be coprecipitated with $CaPO_4$ or introduced using liposomal and nonliposomal lipid-based agents. Commercial kits are available for $CaPO_4$ transfection (CalPhos™ Mammalian Transfection Kit, Clontech Laboratories, Palo Alto, Calif., USA), and lipid-mediated transfection can be practiced using commercial reagents, such as LIPOFECTAMINE™ 2000, LIPOFECTAMINE™ Reagent, CELLFECTIN® Reagent, and LIPOFECTIN® Reagent (Invitrogen, Carlsbad, Calif., USA), DOTAP Liposomal Transfection Reagent, FuGENE 6, X-tremeGENE Q2, DOSPER, (Roche Molecular Biochemicals, Indianapolis, Ind. USA), Effectene™, PolyFect®, Superfect® (Qiagen, Inc., Valencia, Calif., USA). Protocols for electroporating mammalian cells can be found online in Electroprotocols (Bio-Rad, Richmond, Calif., USA) (http://www.bio-rad.com/LifeScience/pdf/New_Gene_Pulser.pdf); Norton et al. (eds.), *Gene Transfer Methods: Introducing DNA into Living Cells and Organisms*, BioTechniques Books, Eaton Publishing Co. (2000); incorporated herein by reference in its entirety. Other transfection techniques include transfection by particle bombardment and microinjection. See, e.g., Cheng et al., *Proc. Natl. Acad. Sci. USA* 90(10): 4455–9 (1993); Yang et al., *Proc. Natl. Acad. Sci. USA* 87(24): 9568–72 (1990).

Production of the recombinantly produced proteins of the present invention can optionally be followed by purification.

Purification of recombinantly expressed proteins is now well by those skilled in the art. See, e.g., Thorner et al. (eds.), *Applications of Chimeric Genes and Hybrid Proteins, Part A: Gene Expression and Protein Purification* (Methods in Enzymology, Vol. 326), Academic Press (2000); Harbin (ed.), *Cloning, Gene Expression and Protein Purification: Experimental Procedures and Process Rationale*, Oxford Univ. Press (2001); Marshak et al., *Strategies for Protein Purification and Characterization: A Laboratory Course Manual*, Cold Spring Harbor Laboratory Press (1996); and Roe (ed.), *Protein Purification Applications*, Oxford University Press (2001); the disclosures of which are incorporated herein by reference in their entireties, and thus need not be detailed here.

Briefly, however, if purification tags have been fused through use of an expression vector that appends such tags, purification can be effected, at least in part, by means appropriate to the tag, such as use of immobilized metal affinity chromatography for polyhistidine tags. Other techniques common in the art include ammonium sulfate fractionation, immunoprecipitation, fast protein liquid chromatography (FPLC), high performance liquid chromatography (HPLC), and preparative gel electrophoresis.

Polypeptides

Another object of the invention is to provide polypeptides encoded by the nucleic acid molecules of the instant invention. In a preferred embodiment, the polypeptide is a breast specific polypeptide (BSP). In an even more preferred embodiment, the polypeptide is derived from a polypeptide comprising the amino acid sequence of SEQ ID NO: 165 through 280. A polypeptide as defined herein may be produced recombinantly, as discussed supra, may be isolated from a cell that naturally expresses the protein, or may be chemically synthesized following the teachings of the specification and using methods well-known to those having ordinary skill in the art.

In another aspect, the polypeptide may comprise a fragment of a polypeptide, wherein the fragment is as defined herein. In a preferred embodiment, the polypeptide fragment is a fragment of a BSP. In a more preferred embodiment, the fragment is derived from a polypeptide comprising the amino acid sequence of SEQ ID NO: 165 through 280. A polypeptide that comprises only a fragment of an entire BSP may or may not be a polypeptide that is also a BSP. For instance, a full-length polypeptide may be breast-specific, while a fragment thereof may be found in other tissues as well as in breast. A polypeptide that is not a BSP, whether it is a fragment, analog, mutein, homologous protein or derivative, is nevertheless useful, especially for immunizing animals to prepare anti-BSP antibodies. However, in a preferred embodiment, the part or fragment is a BSP. Methods of determining whether a polypeptide is a BSP are described infra.

Fragments of at least 6 contiguous amino acids are useful in mapping B cell and T cell epitopes of the reference protein. See, e.g., Geysen et al., *Proc. Natl. Acad. Sci. USA* 81: 3998–4002 (1984) and U.S. Pat. Nos. 4,708,871 and 5,595,915, the disclosures of which are incorporated herein by reference in their entireties. Because the fragment need not itself be immunogenic, part of an immunodominant epitope, nor even recognized by native antibody, to be useful in such epitope mapping, all fragments of at least 6 amino acids of the proteins of the present invention have utility in such a study.

Fragments of at least 8 contiguous amino acids, often at least 15 contiguous amino acids, are useful as immunogens for raising antibodies that recognize the proteins of the present invention. See, e.g., Lemer, *Nature* 299: 592–596 (1982); Shinnick et al., *Annu. Rev. Microbiol.* 37: 425–46 (1983); Sutcliffe et al., *Science* 219: 660–6 (1983), the disclosures of which are incorporated herein by reference in their entireties. As further described in the above-cited references, virtually all 8-mers, conjugated to a carrier, such as a protein, prove immunogenic, meaning that they are capable of eliciting antibody for the conjugated peptide; accordingly, all fragments of at least 8 amino acids of the proteins of the present invention have utility as immunogens.

Fragments of at least 8, 9, 10 or 12 contiguous amino acids are also useful as competitive inhibitors of binding of the entire protein, or a portion thereof, to antibodies (as in epitope mapping), and to natural binding partners, such as subunits in a multimeric complex or to receptors or ligands of the subject protein; this competitive inhibition permits identification and separation of molecules that bind specifically to the protein of interest, U.S. Pat. Nos. 5,539,084 and 5,783,674, incorporated herein by reference in their entireties.

The protein, or protein fragment, of the present invention is thus at least 6 amino acids in length, typically at least 8, 9, 10 or 12 amino acids in length, and often at least 15 amino acids in length. Often, the protein of the present invention, or fragment thereof, is at least 20 amino acids in length, even 25 amino acids, 30 amino acids, 35 amino acids, or 50 amino acids or more in length. Of course, larger fragments having at least 75 amino acids, 100 amino acids, or even 150 amino acids are also useful, and at times preferred.

One having ordinary skill in the art can produce fragments of a polypeptide by truncating the nucleic acid molecule, e.g., a BSNA, encoding the polypeptide and then expressing it recombinantly. Alternatively, one can produce a fragment by chemically synthesizing a portion of the full-length polypeptide. One may also produce a fragment by enzymatically cleaving either a recombinant polypeptide or an isolated naturally-occurring polypeptide. Methods of producing polypeptide fragments are well-known in the art. See, e.g., Sambrook (1989), supra; Sambrook (2001), supra; Ausubel (1992), supra; and Ausubel (1999), supra. In one embodiment, a polypeptide comprising only a fragment of polypeptide of the invention, preferably a BSP, may be produced by chemical or enzymatic cleavage of a polypeptide. In a preferred embodiment, a polypeptide fragment is produced by expressing a nucleic acid molecule encoding a fragment of the polypeptide, preferably a BSP, in a host cell.

By "polypeptides" as used herein it is also meant to be inclusive of mutants, fusion proteins, homologous proteins and allelic variants of the polypeptides specifically exemplified.

A mutant protein, or mutein, may have the same or different properties compared to a naturally-occurring polypeptide and comprises at least one amino acid insertion, duplication, deletion, rearrangement or substitution compared to the amino acid sequence of a native protein. Small deletions and insertions can often be found that do not alter the function of the protein. In one embodiment, the mutein may or may not be breast-specific. In a preferred embodiment, the mutein is breast-specific. In a preferred embodiment, the mutein is a polypeptide that comprises at least one amino acid insertion, duplication, deletion, rearrangement or substitution compared to the amino acid sequence of SEQ ID NO: 164 through 280. In a more preferred embodiment, the mutein is one that exhibits at least 50% sequence identity, more preferably at least 60% sequence identity, even more preferably at least 70%, yet more preferably at least 80% sequence identity to a BSP comprising an amino acid sequence of SEQ ID NO: 165 through 280. In yet a more preferred embodiment, the mutein exhibits at least 85%, more preferably 90%, even more preferably 95% or 96%, and yet more preferably at least 97%, 98%, 99% or 99.5% sequence identity to a BSP comprising an amino acid sequence of SEQ ID NO: 165 through 280.

A mutein may be produced by isolation from a naturally-occurring mutant cell, tissue or organism. A mutein may be produced by isolation from a cell, tissue or organism that has been experimentally mutagenized. Alternatively, a mutein may be produced by chemical manipulation of a polypeptide, such as by altering the amino acid residue to another amino acid residue using synthetic or semi-synthetic chemical techniques. In a preferred embodiment, a mutein may be produced from a host cell comprising an altered nucleic acid molecule compared to the naturally-occurring nucleic acid molecule. For instance, one may produce a mutein of a polypeptide by introducing one or more mutations into a nucleic acid sequence of the invention and then expressing it recombinantly. These mutations may be targeted, in which particular encoded amino acids are altered, or may be untargeted, in which random encoded amino acids within the polypeptide are altered. Muteins with random amino acid alterations can be screened for a particular biological activity or property, particularly whether the polypeptide is breast-specific, as described below. Multiple random mutations can be introduced into the gene by methods well-known to the art, e.g., by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis and site-specific mutagenesis. Methods of producing muteins with targeted or random amino acid alterations are well-known in the art. See, e.g., Sambrook (1989), supra; Sambrook (2001), supra; Ausubel (1992), supra; and Ausubel (1999), U.S. Pat. No. 5,223,408, and the references discussed supra, each herein incorporated by reference.

By "polypeptide" as used herein it is also meant to be inclusive of polypeptides homologous to those polypeptides exemplified herein. In a preferred embodiment, the polypeptide is homologous to a BSP. In an even more preferred embodiment, the polypeptide is homologous to a BSP selected from the group having an amino acid sequence of SEQ ID NO: 165 through 280. In a preferred embodiment, the homologous polypeptide is one that exhibits significant sequence identity to a BSP. In a more preferred embodiment, the polypeptide is one that exhibits significant sequence identity to an comprising an amino acid sequence of SEQ ID NO: 165 through 280. In an even more preferred embodiment, the homologous polypeptide is one that exhibits at least 50% sequence identity, more preferably at least 60% sequence identity, even more preferably at least 70%, yet more preferably at least 80% sequence identity to a BSP comprising an amino acid sequence of SEQ ID NO: 165 through 280. In a yet more preferred embodiment, the homologous polypeptide is one that exhibits at least 85%, more preferably 90%, even more preferably 95% or 96%, and yet more preferably at least 97% or 98% sequence identity to a BSP comprising an amino acid sequence of SEQ ID NO: 165 through 280. In another preferred embodiment, the homologous polypeptide is one that exhibits at least 99%, more preferably 99.5%, even more preferably 99.6%, 99.7%, 99.8% or 99.9% sequence identity to a BSP comprising an amino acid sequence of SEQ ID NO: 165 through 280. In a preferred embodiment, the amino acid substitutions are conservative amino acid substitutions as discussed above.

In another embodiment, the homologous polypeptide is one that is encoded by a nucleic acid molecule that selectively hybridizes to a BSNA. In a preferred embodiment, the homologous polypeptide is encoded by a nucleic acid molecule that hybridizes to a BSNA under low stringency, moderate stringency or high stringency conditions, as defined herein. In a more preferred embodiment, the BSNA is selected from the group consisting of SEQ ID NO: 1 through 164. In another preferred embodiment, the homologous polypeptide is encoded by a nucleic acid molecule that hybridizes to a nucleic acid molecule that encodes a BSP under low stringency, moderate stringency or high stringency conditions, as defined herein. In a more preferred embodiment, the BSP is selected from the group consisting of SEQ ID NO: 165 through 280.

The homologous polypeptide may be a naturally-occurring one that is derived from another species, especially one derived from another primate, such as chimpanzee, gorilla, rhesus macaque, baboon or gorilla, wherein the homologous polypeptide comprises an amino acid sequence that exhibits significant sequence identity to that of SEQ ID NO: 165 through 280. The homologous polypeptide may also be a naturally-occurring polypeptide from a human, when the BSP is a member of a family of polypeptides. The homologous polypeptide may also be a naturally-occurring polypeptide derived from a non-primate, mammalian species, including without limitation, domesticated species, e.g., dog, cat, mouse, rat, rabbit, guinea pig, hamster, cow, horse, goat or pig. The homologous polypeptide may also be a naturally-occurring polypeptide derived from a non-mammalian species, such as birds or reptiles. The naturally-occurring homologous protein may be isolated directly from humans or other species. Alternatively, the nucleic acid molecule encoding the naturally-occurring homologous polypeptide may be isolated and used to express the homologous polypeptide recombinantly. In another embodiment, the homologous polypeptide may be one that is experimentally produced by random mutation of a nucleic acid molecule and subsequent expression of the nucleic acid molecule. In another embodiment, the homologous polypeptide may be one that is experimentally produced by directed mutation of one or more codons to alter the encoded amino acid of a BSP. Further, the homologous protein may or may not encode polypeptide that is a BSP. However, in a preferred embodiment, the homologous polypeptide encodes a polypeptide that is a BSP.

Relatedness of proteins can also be characterized using a second functional test, the ability of a first protein competitively to inhibit the binding of a second protein to an antibody. It is, therefore, another aspect of the present invention to provide isolated proteins not only identical in sequence to those described with particularity herein, but also to provide isolated proteins ("cross-reactive proteins") that competitively inhibit the binding of antibodies to all or to a portion of various of the isolated polypeptides of the present invention. Such competitive inhibition can readily be determined using immunoassays well-known in the art.

As discussed above, single nucleotide polymorphisms (SNPs) occur frequently in eukaryotic genomes, and the sequence determined from one individual of a species may differ from other allelic forms present within the population. Thus, by "polypeptide" as used herein it is also meant to be inclusive of polypeptides encoded by an allelic variant of a nucleic acid molecule encoding a BSP. In a preferred embodiment, the polypeptide is encoded by an allelic variant of a gene that encodes a polypeptide having the amino acid sequence selected from the group consisting of SEQ ID NO: 165 through 280. In a yet more preferred embodiment, the polypeptide is encoded by an allelic variant of a gene that has the nucleic acid sequence selected from the group consisting of SEQ ID NO: 1 through 164.

In another embodiment, the invention provides polypeptides which comprise derivatives of a polypeptide encoded by a nucleic acid molecule according to the instant invention. In a preferred embodiment, the polypeptide is a BSP. In a preferred embodiment, the polypeptide has an amino acid sequence selected from the group consisting of SEQ ID NO: 165 through 280, or is a mutein, allelic variant, homologous protein or fragment thereof. In a preferred embodiment, the derivative has been acetylated, carboxylated, phosphorylated, glycosylated or ubiquitinated. In another preferred embodiment, the derivative has been labeled with, e.g., radioactive isotopes such as $^{125}$I, $^{32}$P, $^{35}$S, and $^{3}$H. In another preferred embodiment, the derivative has been labeled with fluorophores, chemiluminescent agents, enzymes, and antiligands that can serve as specific binding pair members for a labeled ligand.

Polypeptide modifications are well-known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance Creighton, *Protein Structure and Molecular Properties,* 2nd ed., W. H. Freeman and Company (1993). Many detailed reviews are available on this subject, such as, for example, those provided by Wold, in Johnson (ed.), *Posttranslational Covalent Modification of Proteins,* pgs. 1–12, Academic Press (1983); Seifter et al., *Meth. Enzymol.* 182: 626–646 (1990) and Rattan et al., *Ann. N.Y. Acad. Sci.* 663: 48–62 (1992).

It will be appreciated, as is well-known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

Useful post-synthetic (and post-translational) modifications include conjugation to detectable labels, such as fluorophores. A wide variety of amine-reactive and thiol-reactive fluorophore derivatives have been synthesized that react under nondenaturing conditions with N-terminal amino groups and epsilon amino groups of lysine residues, on the one hand, and with free thiol groups of cysteine residues, on the other.

Kits are available commercially that permit conjugation of proteins to a variety of amine-reactive or thiol-reactive fluorophores: Molecular Probes, Inc. (Eugene, Oreg., USA), e.g., offers kits for conjugating proteins to Alexa Fluor 350, Alexa Fluor 430, Fluorescein-EX, Alexa Fluor 488, Oregon Green 488, Alexa Fluor 532, Alexa Fluor 546, Alexa Fluor 546, Alexa Fluor 568, Alexa Fluor 594, and Texas Red-X.

A wide variety of other amine-reactive and thiol-reactive fluorophores are available commercially (Molecular Probes, Inc., Eugene, Oreg., USA), including Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA).

The polypeptides of the present invention can also be conjugated to fluorophores, other proteins, and other macromolecules, using bifunctional linking reagents. Common homobifunctional reagents include, e.g., APG, AEDP, BASED, BMB, BMDB, BMH, BMOE, BM[PEO]3, BM[PEO]4, BS3, BSOCOES, DFDNB, DMA, DMP, DMS, DPDPB, DSG, DSP (Lomant's Reagent), DSS, DST, DTBP, DTME, DTSSP, EGS, HBVS, Sulfo-BSOCOES, Sulfo-DST, Sulfo-EGS (all available from Pierce, Rockford, Ill., USA); common heterobifunctional cross-linkers include ABH, AMAS, ANB-NOS, APDP, ASBA, BMPA, BMPH, BMPS, EDC, EMCA, EMCH, EMCS, KMUA, KMUH, GMBS, LC-SMCC, LC-SPDP, MBS, M2C2H, MPBH, MSA, NHS-ASA, PDPH, PMPI, SADP, SAED, SAND, SANPAH, SASD, SATP, SBAP, SFAD, SIA, SIAB, SMCC, SMPB, SMPH, SMPT, SPDP, Sulfo-EMCS, Sulfo-GMBS, Sulfo-HSAB, Sulfo-KMUS, Sulfo-LC-SPDP, Sulfo-MBS, Sulfo-NHS-LC-ASA, Sulfo-SADP, Sulfo-SANPAH, Sulfo-SIAB, Sulfo-SMCC, Sulfo-SMPB, Sulfo-LC-SMPT, SVSB, TFCS (all available Pierce, Rockford, Ill., USA).

The polypeptides, fragments, and fusion proteins of the present invention can be conjugated, using such cross-linking reagents, to fluorophores that are not amine- or thiol-reactive. Other labels that usefully can be conjugated to the polypeptides, fragments, and fusion proteins of the present invention include radioactive labels, echosonographic contrast reagents, and MRI contrast agents.

The polypeptides, fragments, and fusion proteins of the present invention can also usefully be conjugated using cross-linking agents to carrier proteins, such as KLH, bovine thyroglobulin, and even bovine serum albumin (BSA), to increase immunogenicity for raising anti-BSP antibodies.

The polypeptides, fragments, and fusion proteins of the present invention can also usefully be conjugated to polyethylene glycol (PEG); PEGylation increases the serum half-life of proteins administered intravenously for replacement therapy. Delgado et al., *Crit. Rev. Ther. Drug Carrier Syst.* 9(3–4): 249–304 (1992); Scott et al., *Curr. Pharm. Des.* 4(6): 423–38 (1998); DeSantis et al., *Curr. Opin. Biotechnol.* 10(4): 324–30 (1999), incorporated herein by reference in their entireties. PEG monomers can be attached to the protein directly or through a linker, with PEGylation using PEG monomers activated with tresyl chloride (2,2,2-trifluoroethanesulphonyl chloride) permitting direct attachment under mild conditions.

In yet another embodiment, the invention provides analogs of a polypeptide encoded by a nucleic acid molecule according to the instant invention. In a preferred embodiment, the polypeptide is a BSP. In a more preferred embodiment, the analog is derived from a polypeptide having part or all of the amino acid sequence of SEQ ID NO: 165 through 280. In a preferred embodiment, the analog is one that comprises one or more substitutions of non-natural amino acids or non-native inter-residue bonds compared to the naturally-occurring polypeptide. In general, the non-peptide analog is structurally similar to a BSP, but one or more peptide linkages is replaced by a linkage selected from the group consisting of —$CH_2NH$—, —$CH_2S$—, —$CH_2$—$CH_2$—, —CH═CH—(cis and trans), —$COCH_2$—, —CH(OH)$CH_2$— and —$CH_2SO$—. In another embodiment, the non-peptide analog comprises substitution of one or more amino acids of a BSP with a D-amino acid of the same type or other non-natural amino acid in order to generate more stable peptides. D-amino acids can readily be incorporated during chemical peptide synthesis: peptides assembled from D-amino acids are more resistant to proteolytic attack; incorporation of D-amino acids can also be used to confer specific three-dimensional conformations on the peptide. Other amino acid analogues commonly added during chemical synthesis include ornithine, norleucine, phosphorylated amino acids (typically phosphoserine, phosphothreonine, phosphotyrosine), L-malonyltyrosine, a non-hydrolyzable analog of phosphotyrosine (see, e.g., Kole et al., *Biochem. Biophys. Res. Com.* 209: 817–821 (1995)), and various halogenated phenylalanine derivatives.

Non-natural amino acids can be incorporated during solid phase chemical synthesis or by recombinant techniques, although the former is typically more common. Solid phase chemical synthesis of peptides is well established in the art. Procedures are described, inter alia, in Chan et al. (eds.), *Fmoc Solid Phase Peptide Synthesis: A Practical Approach* (Practical Approach Series), Oxford Univ. Press (March 2000); Jones, *Amino Acid and Peptide Synthesis* (Oxford Chemistry Primers, No 7), Oxford Univ. Press (1992); and Bodanszky, *Principles of Peptide Synthesis* (Springer Laboratory), Springer Verlag (1993); the disclosures of which are incorporated herein by reference in their entireties.

Amino acid analogues having detectable labels are also usefully incorporated during synthesis to provide derivatives and analogs. Biotin, for example can be added using biotinoyl-(9-fluorenylmethoxycarbonyl)-L-lysine (FMOC biocytin) (Molecular Probes, Eugene, Oreg., USA). Biotin can also be added enzymatically by incorporation into a fusion protein of a E. coli BirA substrate peptide. The FMOC and tBOC derivatives of dabcyl-L-lysine (Molecular Probes, Inc., Eugene, Oreg., USA) can be used to incorporate the dabcyl chromophore at selected sites in the peptide sequence during synthesis. The aminonaphthalene derivative EDANS, the most common fluorophore for pairing with the dabcyl quencher in fluorescence resonance energy transfer (FRET) systems, can be introduced during automated synthesis of peptides by using EDANS-FMOC-L-glutamic acid or the corresponding tBOC derivative (both from Molecular Probes, Inc., Eugene, Oreg., USA). Tetramethylrhodamine fluorophores can be incorporated during automated FMOC synthesis of peptides using (FMOC)-TMR-L-lysine (Molecular Probes, Inc. Eugene, Oreg., USA).

Other useful amino acid analogues that can be incorporated during chemical synthesis include aspartic acid, glutamic acid, lysine, and tyrosine analogues having allyl side-chain protection (Applied Biosystems, Inc., Foster City, Calif., USA); the allyl side chain permits synthesis of cyclic, branched-chain, sulfonated, glycosylated, and phosphorylated peptides.

A large number of other FMOC-protected non-natural amino acid analogues capable of incorporation during chemical synthesis are available commercially, including, e.g., Fmoc-2-aminobicyclo[2.2.1]heptane-2-carboxylic acid, Fmoc-3-endo-aminobicyclo[2.2.1]heptane-2-endo-carboxylic acid, Fmoc-3-exo-aminobicyclo[2.2.1]heptane-2-exo-carboxylic acid, Fmoc-3-endo-amino-bicyclo[2.2.1]hept-5-ene-2-endo-carboxylic acid, Fmoc-3-exo-amino-bicyclo[2.2.1]hept-5-ene-2-exo-carboxylic acid, Fmoc-cis-2-amino-1-cyclohexanecarboxylic acid, Fmoc-trans-2-amino-1-cyclohexanecarboxylic acid, Fmoc-1-amino-1-cyclopentanecarboxylic acid, Fmoc-cis-2-amino-1-cyclopentanecarboxylic acid, Fmoc-1-amino-1-cyclopropanecarboxylic acid, Fmoc-D-2-amino-4-(ethylthio)butyric acid, Fmoc-L-2-amino-4-(ethylthio)butyric acid, Fmoc-L-buthionine, Fmoc-S-methyl-L-Cysteine, Fmoc-2-aminobenzoic acid(anthranillic acid), Fmoc-3-aminobenzoic acid, Fmoc-4-aminobenzoic acid, Fmoc-2-aminobenzophenone-2'-carboxylic acid, Fmoc-N-(4-aminobenzoyl)-≠-alanine, Fmoc-2-amino-4,5-dimethoxybenzoic acid, Fmoc-4-aminohippuric acid, Fmoc-2-amino-3-hydroxybenzoic acid, Fmoc-2-amino-5-hydroxybenzoic acid, Fmoc-3-amino-4-hydroxybenzoic acid, Fmoc-4-amino-3-hydroxybenzoic acid, Fmoc-4-amino-2-hydroxybenzoic acid, Fmoc-5-amino-2-hydroxybenzoic acid, Fmoc-2-amino-3-methoxybenzoic acid, Fmoc-4-amino-3-methoxybenzoic acid, Fmoc-2-amino-3-methylbenzoic acid, Fmoc-2-amino-5-methylbenzoic acid, Fmoc-2-amino-6-methylbenzoic acid, Fmoc-3-amino-2-methylbenzoic acid, Fmoc-3-amino-4-methylbenzoic acid, Fmoc-4-amino-3-methylbenzoic acid, Fmoc-3-amino-2-naphtoic acid, Fmoc-D,L-3-amino-3-phenylpropionic acid, Fmoc-L-Methyldopa, Fmoc-2-amino-4,6-dimethyl-3-pyridinecarboxylic acid, Fmoc-D,L-amino-2-thiophenacetic acid, Fmoc-4-(carboxymethyl)piperazine, Fmoc-4-carboxypiperazine, Fmoc-4-(carboxymethyl)homopiperazine, Fmoc-4-phenyl-4-piperidinecarboxylic acid, Fmoc-L-1,2,3,4-tetrahydronorharman-3-carboxylic acid, Fmoc-L-thiazolidine-4-carboxylic acid, all available from The Peptide Laboratory (Richmond, Calif., USA).

Non-natural residues can also be added biosynthetically by engineering a suppressor tRNA, typically one that recognizes the UAG stop codon, by chemical aminoacylation with the desired unnatural amino acid. Conventional site-directed mutagenesis is used to introduce the chosen stop codon UAG at the site of interest in the protein gene. When the acylated suppressor tRNA and the mutant gene are combined in an in vitro transcription/translation system, the unnatural amino acid is incorporated in response to the UAG codon to give a protein containing that amino acid at the specified position. Liu et al., *Proc. Natl. Acad. Sci.* USA 96(9): 4780–5 (1999); Wang et al., *Science* 292(5516): 498–500 (2001).

Fusion Proteins

The present invention further provides fusions of each of the polypeptides and fragments of the present invention to heterologous polypeptides. In a preferred embodiment, the polypeptide is a BSP. In a more preferred embodiment, the polypeptide that is fused to the heterologous polypeptide comprises part or all of the amino acid sequence of SEQ ID NO: 165 through 280, or is a mutein, homologous polypeptide, analog or derivative thereof. In an even more preferred embodiment, the nucleic acid molecule encoding the fusion protein comprises all or part of the nucleic acid sequence of SEQ ID NO: 1 through 164, or comprises all or part of a nucleic acid sequence that selectively hybridizes or is homologous to a nucleic acid molecule comprising a nucleic acid sequence of SEQ ID NO: 1 through 164.

The fusion proteins of the present invention will include at least one fragment of the protein of the present invention, which fragment is at least 6, typically at least 8, often at least 15, and usefully at least 16, 17, 18, 19, or 20 amino acids long. The fragment of the protein of the present to be included in the fusion can usefully be at least 25 amino acids long, at least 50 amino acids long, and can be at least 75, 100, or even 150 amino acids long. Fusions that include the entirety of the proteins of the present invention have particular utility.

The heterologous polypeptide included within the fusion protein of the present invention is at least 6 amino acids in length, often at least 8 amino acids in length, and usefully at least 15, 20, and 25 amino acids in length. Fusions that include larger polypeptides, such as the IgG Fc region, and even entire proteins (such as GFP chromophore-containing proteins) are particular useful.

As described above in the description of vectors and expression vectors of the present invention, which discussion is incorporated here by reference in its entirety, heterologous polypeptides to be included in the fusion proteins of the present invention can usefully include those designed to facilitate purification and/or visualization of recombinantly-expressed proteins. See, e.g., Ausubel, Chapter 16, (1992), supra. Although purification tags can also be incorporated into fusions that are chemically synthesized, chemical synthesis typically provides sufficient purity that further purification by HPLC suffices; however, visualization tags as above described retain their utility even when the protein is produced by chemical synthesis, and when so included render the fusion proteins of the present invention useful as directly detectable markers of the presence of a polypeptide of the invention.

As also discussed above, heterologous polypeptides to be included in the fusion proteins of the present invention can usefully include those that facilitate secretion of recombinantly expressed proteins—into the periplasmic space or extracellular milieu for prokaryotic hosts, into the culture medium for eukaryotic cells—through incorporation of secretion signals and/or leader sequences. For example, a His$^6$ tagged protein can be purified on a Ni affinity column and a GST fusion protein can be purified on a glutathione affinity column. Similarly, a fusion protein comprising the Fc domain of IgG can be purified on a Protein A or Protein G column and a fusion protein comprising an epitope tag such as myc can be purified using an immunoaffinity column containing an anti-c-myc antibody. It is preferable that the epitope tag be separated from the protein encoded by the essential gene by an enzymatic cleavage site that can be cleaved after purification. See also the discussion of nucleic acid molecules encoding fusion proteins that may be expressed on the surface of a cell. Other useful protein fusions of the present invention include those that permit use of the protein of the present invention as bait in a yeast two-hybrid system. See Bartel et al. (eds.), *The Yeast Two-Hybrid System*, Oxford University Press (1997); Zhu et al., *Yeast Hybrid Technologies*, Eaton Publishing (2000); Fields et al., *Trends Genet.* 10(8): 286–92 (1994); Mendelsohn et al., *Curr. Opin. Biotechnol.* 5(5): 482–6 (1994); Luban et al., *Curr. Opin. Biotechnol.* 6(1): 59–64 (1995); Allen et al., *Trends Biochem. Sci.* 20(12): 511–6 (1995); Drees, *Curr. Opin. Chem. Biol.* 3(1): 64–70 (1999); Topcu et. al., *Pharm. Res.* 17(9): 1049–55 (2000); Fashena et al., *Gene* 250 (1–2): 1–(2000);;Colas et al., (1996) Genetic selection of peptide aptamers that recognize and inhibit cyclin-dependent kinase 2. *Nature* 380, 548–550; Norman, T. et al., (1999) Genetic selection of peptide inhibitors of biological pathways. *Science* 285, 591–595, Fabbrizio et al., (1999) Inhibition of mammalian cell proliferation by genetically selected peptide aptamers that functionally antagonize E2F activity. *Oncogene* 18, 4357–4363; Xu et al., (1997) Cells that register logical relationships among proteins. *Proc Natl Acad Sci USA*. 94, 12473–12478; Yang, et al., (1995) Protein-peptide interactions analyzed with the yeast two-hybrid system. *Nuc. Acids Res.* 23, 1152–1156; Kolonin et al., (1998) Targeting cyclin-dependent kinases in Drosophila with peptide aptamers. *Proc Natl Acad Sci USA* 95, 14266–14271; Cohen et al., (1998) An artificial cell-cycle inhibitor isolated from a combinatorial library. *Proc Natl Acad Sci USA* 95, 14272–14277; Uetz, P.; Giot, L.; al, e.; Fields, S.; Rothberg, J. M. (2000) A comprehensive analysis of protein-protein interactions in Saccharomyces cerevisiae. *Nature* 403, 623–627; Ito, et al., (2001) A comprehensive two-hybrid analysis to explore the yeast protein interactome. *Proc Natl Acad Sci USA* 98, 4569–4574, the disclosures of which are incorporated herein by reference in their entireties. Typically, such fusion is to either *E. coli* LexA or yeast GAL4 DNA binding domains. Related bait plasmids are available that express the bait fused to a nuclear localization signal.

Other useful fusion proteins include those that permit display of the encoded protein on the surface of a phage or cell, fusions to intrinsically fluorescent proteins, such as green fluorescent protein (GFP), and fusions to the IgG Fc region, as described above, which discussion is incorporated here by reference in its entirety.

The polypeptides and fragments of the present invention can also usefully be fused to protein toxins, such as Pseudomonas exotoxin A, diphtheria toxin, shiga toxin A, anthrax toxin lethal factor, ricin, in order to effect ablation of cells that bind or take up the proteins of the present invention.

Fusion partners include, inter alia, myc, hemagglutinin (HA), GST, immunoglobulins, β-galactosidase, biotin trpE, protein A, β-lactamase, -amylase, maltose binding protein, alcohol dehydrogenase, polyhistidine (for example, six histidine at the amino and/or carboxyl terminus of the polypeptide), lacZ, green fluorescent protein (GFP), yeast_mating factor, GAL4 transcription activation or DNA binding domain, luciferase, and serum proteins such as ovalbumin, albumin and the constant domain of IgG. See, e.g., Ausubel (1992), supra and Ausubel (1999), supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques well-known in the art (e.g., a Merrifield synthesis), or produced by chemical cross-linking.

Another advantage of fusion proteins is that the epitope tag can be used to bind the fusion protein to a plate or column through an affinity linkage for screening binding proteins or other molecules that bind to the BSP.

As further described below, the isolated polypeptides, muteins, fusion proteins, homologous proteins or allelic variants of the present invention can readily be used as specific immunogens to raise antibodies that specifically recognize BSPs, their allelic variants and homologues. The antibodies, in turn, can be used, inter alia, specifically to assay for the polypeptides of the present invention, particularly BSPs, e.g. by ELISA for detection of protein fluid samples, such as serum, by immunohistochemistry or laser scanning cytometry, for detection of protein in tissue samples, or by flow cytometry, for detection of intracellular protein in cell suspensions, for specific antibody-mediated isolation and/or purification of BSPs, as for example by immunoprecipitation, and for use as specific agonists or antagonists of BSPs.

One may determine whether polypeptides including muteins, fusion proteins, homologous proteins or allelic variants are functional by methods known in the art. For instance, residues that are tolerant of change while retaining function can be identified by altering the protein at known residues using methods known in the art, such as alanine scanning mutagenesis, Cunningham et al., *Science* 244 (4908): 1081–5 (1989); transposon linker scanning mutagenesis, Chen et al., *Gene* 263(1–2): 39–48 (2001); combinations of homolog- and alanine-scanning mutagenesis, Jin et al., *J. Mol. Biol.* 226(3): 851–65 (1992); combinatorial alanine scanning, Weiss et al., *Proc. Natl. Acad. Sci USA* 97(16): 8950–4 (2000), followed by functional assay. Transposon linker scanning kits are available commercially (New England Biolabs, Beverly, Mass., USA, catalog. no. E7-102S; EZ::TN™ In-Frame Linker Insertion Kit, catalogue no. EZI04KN, Epicentre Technologies Corporation, Madison, Wis., USA).

Purification of the polypeptides including fragments, homologous polypeptides, muteins, analogs, derivatives and fusion proteins is well-known and within the skill of one having ordinary skill in the art. See, e.g., Scopes, *Protein Purification*, 2d ed. (1987). Purification of recombinantly expressed polypeptides is described above. Purification of chemically-synthesized peptides can readily be effected, e.g., by HPLC.

Accordingly, it is an aspect of the present invention to provide the isolated proteins of the present invention in pure or substantially pure form in the presence of absence of a stabilizing agent. Stabilizing agents include both proteinaceous or non-proteinaceous material and are well-known in the art. Stabilizing agents, such as albumin and polyethylene glycol (PEG) are known and are commercially available.

Although high levels of purity are preferred when the isolated proteins of the present invention are used as therapeutic agents, such as in vaccines and as replacement therapy, the isolated proteins of the present invention are also useful at lower purity. For example, partially purified proteins of the present invention can be used as immunogens to raise antibodies in laboratory animals.

In preferred embodiments, the purified and substantially purified proteins of the present invention are in compositions that lack detectable ampholytes, acrylamide monomers, bis-acrylamide monomers, and polyacrylamide.

The polypeptides, fragments, analogs, derivatives and fusions of the present invention can usefully be attached to a substrate. The substrate can be porous or solid, planar or non-planar; the bond can be covalent or noncovalent.

For example, the polypeptides, fragments, analogs, derivatives and fusions of the present invention can usefully be bound to a porous substrate, commonly a membrane, typically comprising nitrocellulose, polyvinylidene fluoride (PVDF), or cationically derivatized, hydrophilic PVDF; so bound, the proteins, fragments, and fusions of the present invention can be used to detect and quantify antibodies, e.g. in serum, that bind specifically to the immobilized protein of the present invention.

As another example, the polypeptides, fragments, analogs, derivatives and fusions of the present invention can usefully be bound to a substantially nonporous substrate, such as plastic, to detect and quantify antibodies, e.g. in serum, that bind specifically to the immobilized protein of the present invention. Such plastics include polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof; when the assay is performed in a standard microtiter dish, the plastic is typically polystyrene.

The polypeptides, fragments, analogs, derivatives and fusions of the present invention can also be attached to a substrate suitable for use as a surface enhanced laser desorption ionization source; so attached, the protein, fragment, or fusion of the present invention is useful for binding and then detecting secondary proteins that bind with sufficient affinity or avidity to the surface-bound protein to indicate biologic interaction there between. The proteins, fragments, and fusions of the present invention can also be attached to a substrate suitable for use in surface plasmon resonance detection; so attached, the protein, fragment, or fusion of the present invention is useful for binding and then detecting secondary proteins that bind with sufficient affinity or avidity to the surface-bound protein to indicate biological interaction there between.

Antibodies

In another aspect, the invention provides antibodies, including fragments and derivatives thereof, that bind specifically to polypeptides encoded by the nucleic acid molecules of the invention, as well as antibodies that bind to fragments, muteins, derivatives and analogs of the polypeptides. In a preferred embodiment, the antibodies are specific for a polypeptide that is a BSP, or a fragment, mutein, derivative, analog or fusion protein thereof. In a more preferred embodiment, the antibodies are specific for a polypeptide that comprises SEQ ID NO: 165 through 280, or a fragment, mutein, derivative, analog or fusion protein thereof.

The antibodies of the present invention can be specific for linear epitopes, discontinuous epitopes, or conformational epitopes of such proteins or protein fragments, either as present on the protein in its native conformation or, in some cases, as present on the proteins as denatured, as, e.g., by solubilization in SDS. New epitopes may be also due to a difference in post translational modifications (PTMs) in disease versus normal tissue. For example, a particular site on a BSP may be glycosylated in cancerous cells, but not glycosylated in normal cells or visa versa. In addition, alternative splice forms of a BSP may be indicative of cancer. Differential degradation of the C or N-terminus of a BSP may also be a marker or target for anticancer therapy. For example, a BSP may be N-terminal degraded in cancer cells exposing new epitopes to which antibodies may selectively bind for diagnostic or therapeutic uses.

As is well-known in the art, the degree to which an antibody can discriminate as among molecular species in a mixture will depend, in part, upon the conformational relatedness of the species in the mixture; typically, the antibodies of the present invention will discriminate over adventitious binding to non-BSP polypeptides by at least 2-fold, more typically by at least 5-fold, typically by more than 10-fold, 25-fold, 50-fold, 75-fold, and often by more than 100-fold, and on occasion by more than 500-fold or 1000-fold. When used to detect the proteins or protein fragments of the present invention, the antibody of the present invention is sufficiently specific when it can be used to determine the presence of the protein of the present invention in samples derived from human breast.

Typically, the affinity or avidity of an antibody (or antibody multimer, as in the case of an IgM pentamer) of the present invention for a protein or protein fragment of the present invention will be at least about $1 \times 10^{-6}$ molar (M), typically at least about $5 \times 10^{-7}$ M, $1 \times 10^{-7}$ M, with affinities and avidities of at least $1 \times 10^{-8}$ M, $5 \times 10^{-9}$ M, $1 \times 10^{-10}$ M and up to $1 \times 10^{-13}$ M proving especially useful.

The antibodies of the present invention can be naturally-occurring forms, such as IgG, IgM, IgD, IgE, IgY, and IgA, from any avian, reptilian, or mammalian species.

Human antibodies can, but will infrequently, be drawn directly from human donors or human cells. In this case, antibodies to the proteins of the present invention will typically have resulted from fortuitous immunization, such as autoimmune immunization, with the protein or protein fragments of the present invention. Such antibodies will typically, but will not invariably, be polyclonal. In addition, individual polyclonal antibodies may be isolated and cloned to generate monoclonals.

Human antibodies are more frequently obtained using transgenic animals that express human immunoglobulin genes, which transgenic animals can be affirmatively immunized with the protein immunogen of the present invention. Human Ig-transgenic mice capable of producing human antibodies and methods of producing human antibodies therefrom upon specific immunization are described, inter alia, in U.S. Pat. Nos. 6,162,963; 6,150,584; 6,114,598; 6,075,181; 5,939,598; 5,877,397; 5,874,299; 5,814,318; 5,789,650; 5,770,429; 5,661,016; 5,633,425; 5,625,126; 5,569,825; 5,545,807; 5,545,806, and 5,591,669, the disclosures of which are incorporated herein by reference in their entireties. Such antibodies are typically monoclonal, and are typically produced using techniques developed for production of murine antibodies.

Human antibodies are particularly useful, and often preferred, when the antibodies of the present invention are to be administered to human beings as in vivo diagnostic or therapeutic agents, since recipient immune response to the administered antibody will often be substantially less than that occasioned by administration of an antibody derived from another species, such as mouse.

IgG, IgM, IgD, IgE, IgY, and IgA antibodies of the present invention can also be obtained from other species, including mammals such as rodents (typically mouse, but also rat, guinea pig, and hamster) lagomorphs, typically rabbits, and also larger mammals, such as sheep, goats, cows, and horses, and other egg laying birds or reptiles such as chickens or alligators. For example, avian antibodies may be generated using techniques described in WO 00/29444, published 25 May 2000, the contents of which are hereby incorporated in their entirety. In such cases, as with the transgenic human-antibody-producing non-human mammals, fortuitous immunization is not required, and the non-human mammal is typically affirmatively immunized, according to standard immunization protocols, with the protein or protein fragment of the present invention.

As discussed above, virtually all fragments of 8 or more contiguous amino acids of the proteins of the present invention can be used effectively as immunogens when conjugated to a carrier, typically a protein such as bovine thyroglobulin, keyhole limpet hemocyanin, or bovine serum albumin, conveniently using a bifunctional linker such as those described elsewhere above, which discussion is incorporated by reference here.

Immunogenicity can also be conferred by fusion of the polypeptide and fragments of the present invention to other moieties. For example, peptides of the present invention can be produced by solid phase synthesis on a branched polylysine core matrix; these multiple antigenic peptides (MAPs) provide high purity, increased avidity, accurate chemical definition and improved safety in vaccine development. Tam et al., *Proc. Natl. Acad. Sci. USA* 85: 5409–5413 (1988); Posnett et al., *J. Biol. Chem.* 263: 1719–1725 (1988).

Protocols for immunizing non-human mammals or avian species are well-established in the art. See Harlow et al. (eds.), *Using Antibodies: A Laboratory Manual*, Cold Spring Harbor Laboratory (1998); Coligan et al. (eds.), *Current Protocols in Immunology*, John Wiley & Sons, Inc. (2001); Zola, *Monoclonal Antibodies: Preparation and Use of Monoclonal Antibodies and Engineered Antibody Derivatives (Basics: From Background to Bench)*, Springer Verlag (2000); Gross M, Speck *J.Dtsch. Tierarztl. Wochenschr.* 103: 417–422 (1996), the disclosures of which are incorporated herein by reference. Immunization protocols often include multiple immunizations, either with or without adjuvants such as Freund's complete adjuvant and Freund's incomplete adjuvant, and may include naked DNA immunization (Moss, *Semin. Immunol.* 2: 317–327 (1990).

Antibodies from non-human mammals and avian species can be polyclonal or monoclonal, with polyclonal antibodies having certain advantages in immunohistochemical detection of the proteins of the present invention and monoclonal antibodies having advantages in identifying and distinguishing particular epitopes of the proteins of the present invention. Antibodies from avian species may have particular advantage in detection of the proteins of the present invention, in human serum or tissues (Vikinge et al., *Biosens. Bioelectron.* 13: 1257–1262 (1998).

Following immunization, the antibodies of the present invention can be produced using any art-accepted technique. Such techniques are well-known in the art, Coligan, supra; Zola, supra; Howard et al. (eds.), *Basic Methods in Antibody Production and Characterization*, CRC Press (2000); Harlow, supra; Davis (ed.), *Monoclonal Antibody Protocols*, Vol. 45, Humana Press (1995); Delves (ed.), *Antibody Production: Essential Techniques*, John Wiley & Son Ltd (1997); Kenney, *Antibody Solution: An Antibody Methods Manual*, Chapman & Hall (1997), incorporated herein by reference in their entireties, and thus need not be detailed here.

Briefly, however, such techniques include, inter alia, production of monoclonal antibodies by hybridomas and expression of antibodies or fragments or derivatives thereof from host cells engineered to express immunoglobulin genes or fragments thereof. These two methods of production are not mutually exclusive: genes encoding antibodies specific for the proteins or protein fragments of the present invention can be cloned from hybridomas and thereafter expressed in other host cells. Nor need the two necessarily be performed together: e.g., genes encoding antibodies specific for the proteins and protein fragments of the present invention can be cloned directly from B cells known to be specific for the desired protein, as further described in U.S. Pat. No. 5,627,052, the disclosure of which is incorporated herein by reference in its entirety, or from antibody-displaying phage.

Recombinant expression in host cells is particularly useful when fragments or derivatives of the antibodies of the present invention are desired.

Host cells for recombinant production of either whole antibodies, antibody fragments, or antibody derivatives can be prokaryotic or eukaryotic.

Prokaryotic hosts are particularly useful for producing phage displayed antibodies of the present invention.

The technology of phage-displayed antibodies, in which antibody variable region fragments are fused, for example, to the gene III protein (pIII) or gene VIII protein (pVIII) for display on the surface of filamentous phage, such as M13, is by now well-established. See, e.g., Sidhu, *Curr. Opin. Biotechnol.* 11(6): 610–6 (2000); Griffiths et al., *Curr. Opin. Biotechnol.* 9(1): 102–8 (1998); Hoogenboom et al., *Immunotechnology*, 4(1): 1–20 (1998); Rader et al., *Current Opinion in Biotechnology* 8: 503–508 (1997); Aujame et al., *Human Antibodies* 8: 155–168 (1997); Hoogenboom, *Trends in Biotechnol.* 15: 62–70 (1997); de Kruif et al., 17: 453–455 (1996); Barbas et al., *Trends in Biotechnol.* 14: 230–234 (1996); Winter et al., *Ann. Rev. Immunol.* 433–455 (1994). Techniques and protocols required to generate, propagate, screen (pan), and use the antibody fragments from such libraries have recently been compiled. See, e.g., Barbas (2001), supra; Kay, supra; Abelson, supra, the disclosures of which are incorporated herein by reference in their entireties.

Typically, phage-displayed antibody fragments are scFv fragments or Fab fragments; when desired, full length antibodies can be produced by cloning the variable regions from the displaying phage into a complete antibody and expressing the full length antibody in a further prokaryotic or a eukaryotic host cell.

Eukaryotic cells are also useful for expression of the antibodies, antibody fragments, and antibody derivatives of the present invention.

For example, antibody fragments of the present invention can be produced in *Pichia pastoris* and in *Saccharomyces cerevisiae*. See, e.g., Takahashi et al., *Biosci. Biotechnol. Biochem.* 64(10): 2138–44 (2000); Freyre et al., *J. Biotechnol.* 76(2–3):1 57–63 (2000); Fischer et al., *Biotechnol. Appl. Biochem.* 30 (Pt 2): 117–20 (1999); Pennell et al., *Res. Immunol.* 149(6): 599–603 (1998); Eldin et al., *J. Immunol. Methods.* 201(1): 67–75 (1997);, Frenken et al., *Res. Immunol.* 149(6): 589–99 (1998); Shus *Nature Biotechnol.* 16(8): 773–7 (1998), the disclosures of which are incorporated herein by reference in their entireties.

Antibodies, including antibody fragments and derivatives, of the present invention can also be produced in insect cells. See, e.g., Li et al., *Protein Expr. Purif.* 21(1): 121–8 (2001); Ailor et al., *Biotechnol. Bioeng.* 58(2–3): 196–203 (1998 *Biotechnol. Prog.* 13(1): 96–104 (1997); Edelman et al., *Immunology* 91(1): 13–9 (1997); and Nesbit et al., *J. Immunol. Methods* 151(1–2): 201–8 (1992), the disclosures of which are incorporated herein by reference in their entireties.

Antibodies and fragments and derivatives thereof of the present invention can also be produced in plant cells, particularly maize or tobacco, Giddings et al., *Nature Biotechnol.* 18(11): 1151–5 (2000); Gavilondo et al., *Biotechniques* 29(1): 128–38 (2000); Fischer et al., *J. Biol. Regul. Homeost. Agents* 14(2): 83–92 (2000); Fischer et al., *Biotechnol. Appl. Biochem.* 30 (Pt 2): 113–6 (1999); Fischer et al., *Biol. Chem.* 380(7–8): 825–39 (1999); Russell, *Curr. Top. Microbiol. Immunol.* 240: 119–38 (1999); and Ma et al., *Plant Physiol.* 109(2): 341–6 (1995), the disclosures of which are incorporated herein by reference in their entireties.

Antibodies, including antibody fragments and derivatives, of the present invention can also be produced in transgenic, non-human, mammalian milk. See, e.g. Pollock et al., *J. Immunol Methods.* 231: 147–57 (1999); Young et al., *Res. Immunol.* 149: 609–10 (1998); Limonta et al., *Immunotechnology* 1: 107–13 (1995), the disclosures of which are incorporated herein by reference in their entireties.

Mammalian cells useful for recombinant expression of antibodies, antibody fragments, and antibody derivatives of the present invention include CHO cells, COS cells, 293 cells, and myeloma cells.

Verma et al., *J. Immunol. Methods* 216(1–2):165–81 (1998), herein incorporated by reference, review and compare bacterial, yeast, insect and mammalian expression systems for expression of antibodies.

Antibodies of the present invention can also be prepared by cell free translation, as further described in Merk et al., *J. Biochem.* (Tokyo) 125(2): 328–33 (1999) and Ryabova et al., *Nature Biotechnol.* 15(1): 79–84 (1997), and in the milk of transgenic animals, as further described in Pollock et al., *J. Immunol. Methods* 231(1–2): 147–57 (1999), the disclosures of which are incorporated herein by reference in their entireties.

The invention further provides antibody fragments that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful fragments are Fab, Fab', Fv, F(ab)'$_2$, and single chain Fv (scFv) fragments. Other useful fragments are described in Hudson, *Curr. Opin. Biotechnol.* 9(4): 395–402 (1998).

It is also an aspect of the present invention to provide antibody derivatives that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

Among such useful derivatives are chimeric, primatized, and humanized antibodies; such derivatives are less immunogenic in human beings, and thus more suitable for in vivo administration, than are unmodified antibodies from non-human mammalian species. Another useful derivative is PEGylation to increase the serum half life of the antibodies.

Chimeric antibodies typically include heavy and/or light chain variable regions (including both CDR and framework residues) of immunoglobulins of one species, typically mouse, fused to constant regions of another species, typically human. See, e.g., U.S. Pat. No. 5,807,715; Morrison et al., *Proc. Natl. Acad. Sci USA.* 81(21): 6851–5 (1984); Sharon et al., *Nature* 309(5966): 364–7 (1984); Takeda et al., *Nature* 314(6010): 452–4 (1985), the disclosures of which are incorporated herein by reference in their entireties. Primatized and humanized antibodies typically include heavy and/or light chain CDRs from a murine antibody grafted into a non-human primate or human antibody V region framework, usually further comprising a human constant region, Riechmann et al., *Nature* 332(6162): 323–7 (1988); Co et al., *Nature* 351(6326): 501–2 (1991); U.S. Pat. Nos. 6,054,297; 5,821,337; 5,770,196; 5,766,886; 5,821,123; 5,869,619; 6,180,377; 6,013,256; 5,693,761; and 6,180,370, the disclosures of which are incorporated herein by reference in their entireties.

Other useful antibody derivatives of the invention include heteromeric antibody complexes and antibody fusions, such as diabodies (bispecific antibodies), single-chain diabodies, and intrabodies.

It is contemplated that the nucleic acids encoding the antibodies of the present invention can be operably joined to other nucleic acids forming a recombinant vector for cloning or for expression of the antibodies of the invention. The present invention includes any recombinant vector containing the coding sequences, or part thereof, whether for eukaryotic transduction, transfection or gene therapy. Such vectors may be prepared using conventional molecular biology techniques, known to those with skill in the art, and would comprise DNA encoding sequences for the immunoglobulin V-regions including framework and CDRs or parts thereof, and a suitable promoter either with or without a signal sequence for intracellular transport. Such vectors may be transduced or transfected into eukaryotic cells or used for gene therapy (Marasco et al., *Proc. Natl. Acad. Sci.* (*USA*) 90: 7889–7893 (1993); Duan et al., *Proc. Natl. Acad. Sci.* (*USA*) 91: 5075–5079 (1994), by conventional techniques, known to those with skill in the art.

The antibodies of the present invention, including fragments and derivatives thereof, can usefully be labeled. It is, therefore, another aspect of the present invention to provide labeled antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

The choice of label depends, in part, upon the desired use.

For example, when the antibodies of the present invention are used for immunohistochemical staining of tissue samples, the label is preferably an enzyme that catalyzes production and local deposition of a detectable product.

Enzymes typically conjugated to antibodies to permit their immunohistochemical visualization are well-known, and include alkaline phosphatase, β-galactosidase, glucose oxidase, horseradish peroxidase (HRP), and urease. Typical substrates for production and deposition of visually detectable products include o-nitrophenyl-beta-D-galactopyranoside (ONPG); o-phenylenediamine dihydrochloride (OPD); p-nitrophenyl phosphate (PNPP); p-nitrophenyl-beta-D-galactopryanoside (PNPG); 3',3'-diaminobenzidine (DAB); 3-amino-9-ethylcarbazole (AEC); 4-chloro-1-naphthol (CN); 5-bromo-4-chloro-3-indolyl-phosphate (BCIP); ABTS®; BluoGal; iodonitrotetrazolium (INT); nitroblue tetrazolium chloride (NBT); phenazine methosulfate (PMS); phenolphthalein monophosphate (PMP); tetramethyl benzidine (TMB); tetranitroblue tetrazolium (TNBT); X-Gal; X-Gluc; and X-Glucoside.

Other substrates can be used to produce products for local deposition that are luminescent. For example, in the presence of hydrogen peroxide ($H_2O_2$), horseradish peroxidase (HRP) can catalyze the oxidation of cyclic diacylhydrazides, such as luminol. Immediately following the oxidation, the luminol is in an excited state (intermediate reaction product), which decays to the ground state by emitting light. Strong enhancement of the light emission is produced by enhancers, such as phenolic compounds. Advantages include high sensitivity, high resolution, and rapid detection without radioactivity and requiring only small amounts of antibody. See, e.g., Thorpe et al., *Methods Enzymol.* 133: 331–53 (1986); Kricka et al., *J. Immunoassay* 17(1): 67–83 (1996); and Lundqvist et al., *J. Biolumin. Chemilumin.* 10(6): 353–9 (1995), the disclosures of which are incorporated herein by reference in their entireties. Kits for such enhanced chemiluminescent detection (ECL) are available commercially.

The antibodies can also be labeled using colloidal gold.

As another example, when the antibodies of the present invention are used, e.g., for flow cytometric detection, for scanning laser cytometric detection, or for fluorescent immunoassay, they can usefully be labeled with fluorophores.

There are a wide variety of fluorophore labels that can usefully be attached to the antibodies of the present invention.

For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCP-Cy5.5, PE-Cy5, PE-Cy5.5, PE-Cy7, PE-Texas Red, and APC-Cy7.

Other fluorophores include, inter alia, Alexa Fluor® 350, Alexa Fluor® 488, Alexa Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7, all of which are also useful for fluorescently labeling the antibodies of the present invention.

For secondary detection using labeled avidin, streptavidin, captavidin or neutravidin, the antibodies of the present invention can usefully be labeled with biotin.

When the antibodies of the present invention are used, e.g., for Western blotting applications, they can usefully be labeled with radioisotopes, such as $^{33}P$, $^{32}P$, $^{35}S$, $^{3}H$, and $^{125}I$.

As another example, when the antibodies of the present invention are used for radioimmunotherapy, the label can usefully be $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{9}Sr$, $^{88}Y$, $^{72}Se$, $^{67}CU$, or $^{47}Sc$.

As another example, when the antibodies of the present invention are to be used for in vivo diagnostic use, they can be rendered detectable by conjugation to MRI contrast agents, such as gadolinium diethylenetriaminepentaacetic acid (DTPA), Lauffer et al., *Radiology* 207(2): 529–38 (1998), or by radioisotopic labeling.

As would be understood, use of the labels described above is not restricted to the application for which they are mentioned.

The antibodies of the present invention, including fragments and derivatives thereof, can also be conjugated to toxins, in order to target the toxin's ablative action to cells that display and/or express the proteins of the present invention. Commonly, the antibody in such immunotoxins is conjugated to Pseudomonas exotoxin A, diphtheria toxin, shiga toxin A, anthrax toxin lethal factor, or ricin. See Hall (ed.), *Immunotoxin Methods and Protocols* (Methods in Molecular Biology, vol. 166), Humana Press (2000); and Frankel et al. (eds.), *Clinical Applications of Immunotoxins*, Springer-Verlag (1998), the disclosures of which are incorporated herein by reference in their entireties.

The antibodies of the present invention can usefully be attached to a substrate, and it is, therefore, another aspect of the invention to provide antibodies that bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention, attached to a substrate.

Substrates can be porous or nonporous, planar or nonplanar.

For example, the antibodies of the present invention can usefully be conjugated to filtration media, such as NHS-activated Sepharose or CNBr-activated Sepharose for purposes of immunoaffinity chromatography.

For example, the antibodies of the present invention can usefully be attached to paramagnetic microspheres, typically by biotin-streptavidin interaction, which microspheres can then be used for isolation of cells that express or display the proteins of the present invention. As another example, the antibodies of the present invention can usefully be attached to the surface of a microtiter plate for ELISA.

As noted above, the antibodies of the present invention can be produced in prokaryotic and eukaryotic cells. It is, therefore, another aspect of the present invention to provide cells that express the antibodies of the present invention, including hybridoma cells, B cells, plasma cells, and host cells recombinantly modified to express the antibodies of the present invention.

In yet a further aspect, the present invention provides aptamers evolved to bind specifically to one or more of the proteins and protein fragments of the present invention, to one or more of the proteins and protein fragments encoded by the isolated nucleic acids of the present invention, or the binding of which can be competitively inhibited by one or more of the proteins and protein fragments of the present invention or one or more of the proteins and protein fragments encoded by the isolated nucleic acids of the present invention.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

Transgenic Animals and Cells

In another aspect, the invention provides transgenic cells and non-human organisms comprising nucleic acid molecules of the invention. In a preferred embodiment, the transgenic cells and non-human organisms comprise a nucleic acid molecule encoding a BSP. In a preferred embodiment, the BSP comprises an amino acid sequence selected from SEQ ID NO: 165 through 280, or a fragment, mutein, homologous protein or allelic variant thereof. In another preferred embodiment, the transgenic cells and non-human organism comprise a BSNA of the invention, preferably a BSNA comprising a nucleotide sequence selected from the group consisting of SEQ ID NO: 1 through 164, or a part, substantially similar nucleic acid molecule, allelic variant or hybridizing nucleic acid molecule thereof.

In another embodiment, the transgenic cells and non-human organisms have a targeted disruption or replacement of the endogenous orthologue of the human BSG. The transgenic cells can be embryonic stem cells or somatic cells. The transgenic non-human organisms can be chimeric, nonchimeric heterozygotes, and nonchimeric homozygotes. Methods of producing transgenic animals are well-known in the art. See, e.g., Hogan et al., *Manipulating the Mouse Embryo: A Laboratory Manual*, 2d ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999).

Any technique known in the art may be used to introduce a nucleic acid molecule of the invention into an animal to produce the founder lines of transgenic animals. Such techniques include, but are not limited to, pronuclear microinjection. (see, e.g., Paterson et al., Appl. *Microbiol. Biotechnol.* 40: 691–698 (1994); Carver et al., *Biotechnology* 11: 1263–1270 (1993); Wright et al., *Biotechnology* 9: 830–834 (1991); and U.S. Pat. No. 4,873,191 (1989 retrovirus-mediated gene transfer into germ lines, blastocysts or embryos (see, e.g., Van der Putten et al., *Proc. Natl. Acad. Sci., USA* 82: 6148–6152 (1985)); gene targeting in embryonic stem cells (see, e.g., Thompson et al., *Cell* 56: 313–321 (1989)); electroporation of cells or embryos (see, e.g., Lo, 1983, *Mol. Cell. Biol.* 3: 1803–1814 (1983)); introduction using a gene gun (see, e.g., Ulmer et al., *Science* 259: 1745–49 (1993); introducing nucleic acid constructs into embryonic pleuripotent stem cells and transferring the stem cells back into the blastocyst; and sperm-mediated gene transfer (see, e.g., Lavitrano et al., *Cell* 57: 717–723 (1989)).

Other techniques include, for example, nuclear transfer into enucleated oocytes of nuclei from cultured embryonic, fetal, or adult cells induced to quiescence (see, e.g., Campell et al., *Nature* 380: 64–66 (1996); Wilmut et al., *Nature* 385: 810–813 (1997)). The present invention provides for transgenic animals that carry the transgene (i.e., a nucleic acid molecule of the invention) in all their cells, as well as animals which carry the transgene in some, but not all their cells, i.e., mosaic animals or chimeric animals.

The transgene may be integrated as a single transgene or as multiple copies, such as in concatamers, e.g., head-to-head tandems or head-to-tail tandems. The transgene may also be selectively introduced into and activated in a particular cell type by following, e.g., the teaching of Lasko et al., *Proc. Natl. Acad. Sci. USA* 89: 6232–6236 (1992). The regulatory sequences required for such a cell-type specific activation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Methods for creating a transgenic animal with a disruption of a targeted gene are also well-known in the art. In general, a vector is designed to comprise some nucleotide sequences homologous to the endogenous targeted gene. The vector is introduced into a cell so that it may integrate, via homologous recombination with chromosomal sequences, into the endogenous gene, thereby disrupting the function of the endogenous gene. The transgene may also be selectively introduced into a particular cell type, thus inactivating the endogenous gene in only that cell type. See, e.g., Gu et al., *Science* 265: 103–106 (1994). The regulatory sequences required for such a cell-type specific inactivation will depend upon the particular cell type of interest, and will be apparent to those of skill in the art. See, e.g., Smithies et al., *Nature* 317: 230–234 (1985); Thomas et al., *Cell* 51: 503–512 (1987); Thompson et al., *Cell* 5: 313–321 (1989).

In one embodiment, a mutant, non-functional nucleic acid molecule of the invention (or a completely unrelated DNA sequence) flanked by DNA homologous to the endogenous nucleic acid sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene. See, e.g., Thomas, supra and Thompson, supra. However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from an animal or patient or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. See, e.g., U.S. Pat. Nos. 5,399,349 and 5,460,959, each of which is incorporated by reference herein in its entirety.

When the cells to be administered are non-autologous or non-MHC compatible cells, they can be administered using well-known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Computer Readable Means

A further aspect of the invention relates to a computer readable means for storing the nucleic acid and amino acid sequences of the instant invention. In a preferred embodiment, the invention provides a computer readable means for storing SEQ ID NO: 1 through 164 and SEQ ID NO: 165 through 280 as described herein, as the complete set of sequences or in any combination. The records of the computer readable means can be accessed for reading and display and for interface with a computer system for the application of programs allowing for the location of data upon a query for data meeting certain criteria, the comparison of sequences, the alignment or ordering of sequences meeting a set of criteria, and the like.

The nucleic acid and amino acid sequences of the invention are particularly useful as components in databases useful for search analyses as well as in sequence analysis algorithms. As used herein, the terms "nucleic acid sequences of the invention" and "amino acid sequences of the invention" mean any detectable chemical or physical characteristic of a polynucleotide or polypeptide of the invention that is or may be reduced to or stored in a computer readable form. These include, without limitation, chromatographic scan data or peak data, photographic data or scan data therefrom, and mass spectrographic data.

This invention provides computer readable media having stored thereon sequences of the invention. A computer readable medium may comprise one or more of the following: a nucleic acid sequence comprising a sequence of a nucleic acid sequence of the invention; an amino acid sequence comprising an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of one or more nucleic acid sequences of the invention; a data set representing a nucleic acid sequence encoding an amino acid sequence comprising the sequence of an amino acid sequence of the invention; a set of nucleic acid sequences wherein at least one of said sequences comprises the sequence of a nucleic acid sequence of the invention; a set of amino acid sequences wherein at least one of said sequences comprises the sequence of an amino acid sequence of the invention; a data set representing a nucleic acid sequence comprising the sequence of a nucleic acid sequence of the invention; a data set representing a nucleic acid sequence encoding an amino acid sequence comprising the sequence of an amino acid sequence of the invention. The computer readable medium can be any composition of matter used to store information or data, including, for example, commercially available floppy disks, tapes, hard drives, compact disks, and video disks.

Also provided by the invention are methods for the analysis of character sequences, particularly genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, and sequencing chromatogram peak analysis.

A computer-based method is provided for performing nucleic acid sequence identity or similarity identification. This method comprises the steps of providing a nucleic acid sequence comprising the sequence of a nucleic acid of the invention in a computer readable medium; and comparing said nucleic acid sequence to at least one nucleic acid or amino acid sequence to identify sequence identity or similarity.

A computer-based method is also provided for performing amino acid homology identification, said method comprising the steps of: providing an amino acid sequence comprising the sequence of an amino acid of the invention in a computer readable medium; and comparing said an amino acid sequence to at least one nucleic acid or an amino acid sequence to identify homology.

A computer-based method is still further provided for assembly of overlapping nucleic acid sequences into a single nucleic acid sequence, said method comprising the steps of: providing a first nucleic acid sequence comprising the sequence of a nucleic acid of the invention in a computer readable medium; and screening for at least one overlapping region between said first nucleic acid sequence and a second nucleic acid sequence.

Diagnostic Methods for Breast Cancer

The present invention also relates to quantitative and qualitative diagnostic assays and methods for detecting, diagnosing, monitoring, staging and predicting cancers by comparing expression of a BSNA or a BSP in a human patient that has or may have breast cancer, or who is at risk of developing breast cancer, with the expression of a BSNA or a BSP in a normal human control. For purposes of the present invention, "expression of a BSNA" or "BSNA expression" means the quantity of BSG mRNA that can be measured by any method known in the art or the level of transcription that can be measured by any method known in the art in a cell, tissue, organ or whole patient. Similarly, the term "expression of a BSP" or "BSP expression" means the amount of BSP that can be measured by any method known in the art or the level of translation of a BSG BSNA that can be measured by any method known in the art.

The present invention provides methods for diagnosing breast cancer in a patient, in particular squamous cell carcinoma, by analyzing for changes in levels of BSNA or BSP in cells, tissues, organs or bodily fluids compared with levels of BSNA or BSP in cells, tissues, organs or bodily fluids of preferably the same type from a normal human control, wherein an increase, or decrease in certain cases, in levels of a BSNA or BSP in the patient versus the normal human control is associated with the presence of breast cancer or with a predilection to the disease. In another preferred embodiment, the present invention provides methods for diagnosing breast cancer in a patient by analyzing changes in the structure of the mRNA of a BSG compared to the mRNA from a normal control. These changes include, without limitation, aberrant splicing, alterations in polyadenylation and/or alterations in 5' nucleotide capping. In yet another preferred embodiment, the present invention provides methods for diagnosing breast cancer in a patient by analyzing changes in a BSP compared to a BSP from a normal control. These changes include, e.g., alterations in glycosylation and/or phosphorylation of the BSP or subcellular BSP localization.

In a preferred embodiment, the expression of a BSNA is measured by determining the amount of an mRNA that encodes an amino acid sequence selected from SEQ ID NO: 165 through 280, a homolog, an allelic variant, or a fragment thereof. In a more preferred embodiment, the BSNA expression that is measured is the level of expression of a BSNA mRNA selected from SEQ ID NO: 1 through 164, or a hybridizing nucleic acid, homologous nucleic acid or allelic variant thereof, or a part of any of these nucleic acids. BSNA expression may be measured by any method known in the art, such as those described supra, including measuring mRNA expression by Northern blot, quantitative or qualitative reverse transcriptase PCR (RT-PCR), microarray, dot or slot blots or in situ hybridization. See, e.g., Ausubel (1992), supra; Ausubel (1999), supra; Sambrook (1989), supra; and Sambrook (2001), supra. BSNA transcription may be measured by any method known in the art including using a reporter gene hooked up to the promoter of a BSG of interest or doing nuclear run-off assays. Alterations in mRNA structure, e.g., aberrant splicing variants, may be determined by any method known in the art, including, RT-PCR followed by sequencing or restriction analysis. As necessary, BSNA expression may be compared to a known control, such as normal breast nucleic acid, to detect a change in expression.

In another preferred embodiment, the expression of a BSP is measured by determining the level of a BSP having an amino acid sequence selected from the group consisting of SEQ ID NO: 165 through 280, a homolog, an allelic variant, or a fragment thereof. Such levels are preferably determined in at least one of cells, tissues, organs and/or bodily fluids, including determination of normal and abnormal levels. Thus, for instance, a diagnostic assay in accordance with the invention for diagnosing over- or underexpression of BSNA or BSP compared to normal control bodily fluids, cells, or tissue samples may be used to diagnose the presence of breast cancer. The expression level of a BSP may be determined by any method known in the art, such as those described supra. In a preferred embodiment, the BSP expression level may be determined by radioimmunoassays, competitive-binding assays, ELISA, Western blot, FACS, immunohistochemistry, immunoprecipitation, proteomic approaches: two-dimensional gel electrophoresis (2D electrophoresis) and non-gel-based approaches such as mass spectrometry or protein interaction profiling. See, e.g, Harlow (1999), supra; Ausubel (1992), supra; and Ausubel (1999), supra. Alterations in the BSP structure may be determined by any method known in the art, including, e.g., using antibodies that specifically recognize phosphoserine, phosphothreonine or phosphotyrosine residues, two-dimensional polyacrylamide gel electrophoresis (2D PAGE) and/or chemical analysis of amino acid residues of the protein. Id.

In a preferred embodiment, a radioimmunoassay (RIA) or an ELISA is used. An antibody specific to a BSP is prepared if one is not already available. In a preferred embodiment, the antibody is a monoclonal antibody. The anti-BSP antibody is bound to a solid support and any free protein binding sites on the solid support are blocked with a protein such as bovine serum albumin. A sample of interest is incubated with the antibody on the solid support under conditions in which the BSP will bind to the anti-BSP antibody. The sample is removed, the solid support is washed to remove unbound material, and an anti-BSP antibody that is linked to a detectable reagent (a radioactive substance for RIA and an enzyme for ELISA) is added to the solid support and incubated under conditions in which binding of the BSP to the labeled antibody will occur. After binding, the unbound labeled antibody is removed by washing. For an ELISA, one or more substrates are added to produce a colored reaction product that is based upon the amount of a BSP in the sample. For an RIA, the solid support is counted for radioactive decay signals by any method known in the art. Quantitative results for both RIA and ELISA typically are obtained by reference to a standard curve.

Other methods to measure BSP levels are known in the art. For instance, a competition assay may be employed wherein an anti-BSP antibody is attached to a solid support and an allocated amount of a labeled BSP and a sample of interest are incubated with the solid support. The amount of labeled BSP detected which is attached to the solid support can be correlated to the quantity of a BSP in the sample.

Of the proteomic approaches, 2D PAGE is a well-known technique. Isolation of individual proteins from a sample such as serum is accomplished using sequential separation of proteins by isoelectric point and molecular weight. Typically, polypeptides are first separated by isoelectric point (the first dimension) and then separated by size using an electric current (the second dimension). In general, the second dimension is perpendicular to the first dimension. Because no two proteins with different sequences are identical on the basis of both size and charge, the result of 2D PAGE is a roughly square gel in which each protein occupies a unique spot. Analysis of the spots with chemical or antibody probes, or subsequent protein microsequencing can reveal the relative abundance of a given protein and the identity of the proteins in the sample.

Expression levels of a BSNA can be determined by any method known in the art, including PCR and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction.

Hybridization to specific DNA molecules (e.g., oligonucleotides) arrayed on a solid support can be used to both detect the expression of and quantitate the level of expression of one or more BSNAs of interest. In this approach, all or a portion of one or more BSNAs is fixed to a substrate. A sample of interest, which may comprise RNA, e.g., total RNA or polyA-selected mRNA, or a complementary DNA (cDNA) copy of the RNA is incubated with the solid support under conditions in which hybridization will occur between the DNA on the solid support and the nucleic acid molecules in the sample of interest. Hybridization between the substrate-bound DNA and the nucleic acid molecules in the sample can be detected and quantitated by several means, including, without limitation, radioactive labeling or fluorescent labeling of the nucleic acid molecule or a secondary molecule designed to detect the hybrid.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood. In a preferred embodiment, the specimen tested for expression of BSNA or BSP includes, without limitation, breast tissue, fluid obtained by bronchial alveolar lavage (BAL), sputum, breast cells grown in cell culture, blood, serum, lymph node tissue and lymphatic fluid. In another preferred embodiment, especially when metastasis of a primary breast cancer is known or suspected, specimens include, without limitation, tissues from brain, bone, bone marrow, liver, adrenal glands and colon. In general, the tissues may be sampled by biopsy, including, without limitation, needle biopsy, e.g., transthoracic needle aspiration, cervical mediatinoscopy, endoscopic lymph node biopsy, video-assisted thoracoscopy, exploratory thoracotomy, bone marrow biopsy and bone marrow aspiration. See Scott, supra and Franklin, pp. 529–570, in Kane, supra. For early and inexpensive detection, assaying for changes in BSNAs or BSPs in cells in sputum samples may be particularly useful. Methods of obtaining and analyzing sputum samples is disclosed in Franklin, supra.

All the methods of the present invention may optionally include determining the expression levels of one or more other cancer markers in addition to determining the expression level of a BSNA or BSP. In many cases, the use of another cancer marker will decrease the likelihood of false positives or false negatives. In one embodiment, the one or more other cancer markers include other BSNA or BSPs as disclosed herein. Other cancer markers useful in the present invention will depend on the cancer being tested and are known to those of skill in the art. In a preferred embodiment, at least one other cancer marker in addition to a particular BSNA or BSP is measured. In a more preferred embodiment, at least two other additional cancer markers are used. In an even more preferred embodiment, at least three, more preferably at least five, even more preferably at least ten additional cancer markers are used.

Diagnosing

In one aspect, the invention provides a method for determining the expression levels and/or structural alterations of one or more BSNAs and/or BSPs in a sample from a patient suspected of having breast cancer. In general, the method comprises the steps of obtaining the sample from the patient, determining the expression level or structural alterations of a BSNA and/or BSP and then ascertaining whether the patient has breast cancer from the expression level of the BSNA or BSP. In general, if high expression relative to a control of a BSNA or BSP is indicative of breast cancer, a diagnostic assay is considered positive if the level of expression of the BSNA or BSP is at least two times higher, and more preferably are at least five times higher, even more preferably at least ten times higher, than in preferably the same cells, tissues or bodily fluid of a normal human control. In contrast, if low expression relative to a control of a BSNA or BSP is indicative of breast cancer, a diagnostic assay is considered positive if the level of expression of the BSNA or BSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

The present invention also provides a method of determining whether breast cancer has metastasized in a patient. One may identify whether the breast cancer has metastasized by measuring the expression levels and/or structural alterations of one or more BSNAs and/or BSPs in a variety of tissues. The presence of a BSNA or BSP in a certain tissue at levels higher than that of corresponding noncancerous tissue (e.g., the same tissue from another individual) is indicative of metastasis if high level expression of a BSNA or BSP is associated with breast cancer. Similarly, the presence of a BSNA or BSP in a tissue at levels lower than that of corresponding noncancerous tissue is indicative of metastasis if low level expression of a BSNA or BSP is associated with breast cancer. Further, the presence of a structurally altered BSNA or BSP that is associated with breast cancer is also indicative of metastasis.

In general, if high expression relative to a control of a BSNA or BSP is indicative of metastasis, an assay for metastasis is considered positive if the level of expression of the BSNA or BSP is at least two times higher, and more preferably are at least five times higher, even more preferably at least ten times higher, than in preferably the same cells, tissues or bodily fluid of a normal human control. In contrast, if low expression relative to a control of a BSNA or BSP is indicative of metastasis, an assay for metastasis is considered positive if the level of expression of the BSNA or BSP is at least two times lower, more preferably are at least five times lower, even more preferably at least ten times lower than in preferably the same cells, tissues or bodily fluid of a normal human control.

The BSNA or BSP of this invention may be used as element in an array or a multi-analyte test to recognize expression patterns associated with breast cancers or other breast related disorders. In addition, the sequences of either the nucleic acids or proteins may be used as elements in a computer program for pattern recognition of breast disorders.

Staging

The invention also provides a method of staging breast cancer in a human patient. The method comprises identifying a human patient having breast cancer and analyzing cells, tissues or bodily fluids from such human patient for expression levels and/or structural alterations of one or more BSNAs or BSPs. First, one or more tumors from a variety of patients are staged according to procedures well-known in the art, and the expression level of one or more BSNAs or BSPs is determined for each stage to obtain a standard expression level for each BSNA and BSP. Then, the BSNA or BSP expression levels are determined in a biological sample from a patient whose stage of cancer is not known. The BSNA or BSP expression levels from the patient are then compared to the standard expression level. By comparing the expression level of the BSNAs and BSPs from the patient to the standard expression levels, one may determine the stage of the tumor. The same procedure may be followed using structural alterations of a BSNA or BSP to determine the stage of a breast cancer.

Monitoring

Further provided is a method of monitoring breast cancer in a human patient. One may monitor a human patient to determine whether there has been metastasis and, if there has been, when metastasis began to occur. One may also monitor a human patient to determine whether a preneoplastic lesion has become cancerous. One may also monitor a human patient to determine whether a therapy, e.g., chemotherapy, radiotherapy or surgery, has decreased or eliminated the breast cancer. The method comprises identifying a human patient that one wants to monitor for breast cancer, periodically analyzing cells, tissues or bodily fluids from such human patient for expression levels of one or more BSNAs or BSPs, and comparing the BSNA or BSP levels over time to those BSNA or BSP expression levels obtained previously. Patients may also be monitored by measuring one or more structural alterations in a BSNA or BSP that are associated with breast cancer.

If increased expression of a BSNA or BSP is associated with metastasis, treatment failure, or conversion of a preneoplastic lesion to a cancerous lesion, then detecting an increase in the expression level of a BSNA or BSP indicates that the tumor is metastasizing, that treatment has failed or that the lesion is cancerous, respectively. One having ordinary skill in the art would recognize that if this were the case, then a decreased expression level would be indicative of no metastasis, effective therapy or failure to progress to a neoplastic lesion. If decreased expression of a BSNA or BSP is associated with metastasis, treatment failure, or conversion of a preneoplastic lesion to a cancerous lesion, then detecting an decrease in the expression level of a BSNA or BSP indicates that the tumor is metastasizing, that treatment has failed or that the lesion is cancerous, respectively. In a preferred embodiment, the levels of BSNAs or BSPs are determined from the same cell type, tissue or bodily fluid as prior patient samples. Monitoring a patient for onset of breast cancer metastasis is periodic and preferably is done on a quarterly basis, but may be done more or less frequently.

The methods described herein can further be utilized as prognostic assays to identify subjects having or at risk of developing a disease or disorder associated with increased or decreased expression levels of a BSNA and/or BSP. The present invention provides a method in which a test sample is obtained from a human patient and one or more BSNAs and/or BSPs are detected. The presence of higher (or lower) BSNA or BSP levels as compared to normal human controls is diagnostic for the human patient being at risk for developing cancer, particularly breast cancer. The effectiveness of therapeutic agents to decrease (or increase) expression or activity of one or more BSNAs and/or BSPs of the invention can also be monitored by analyzing levels of expression of the BSNAs and/or BSPs in a human patient in clinical trials or in in vitro screening assays such as in human cells. In this way, the gene expression pattern can serve as a marker, indicative of the physiological response of the human patient or cells, as the case may be, to the agent being tested.

Detection of Genetic Lesions or Mutations

The methods of the present invention can also be used to detect genetic lesions or mutations in a BSG, thereby determining if a human with the genetic lesion is susceptible to developing breast cancer or to determine what genetic lesions are responsible, or are partly responsible, for a person's existing breast cancer. Genetic lesions can be detected, for example, by ascertaining the existence of a deletion, insertion and/or substitution of one or more nucleotides from the BSGs of this invention, a chromosomal rearrangement of BSG, an aberrant modification of BSG (such as of the methylation pattern of the genomic DNA), or allelic loss of a BSG. Methods to detect such lesions in the BSG of this invention are known to those having ordinary skill in the art following the teachings of the specification.

Methods of Detecting Noncancerous Breast Diseases

The invention also provides a method for determining the expression levels and/or structural alterations of one or more BSNAs and/or BSPs in a sample from a patient suspected of having or known to have a noncancerous breast disease. In general, the method comprises the steps of obtaining a sample from the patient, determining the expression level or structural alterations of a BSNA and/or BSP, comparing the expression level or structural alteration of the BSNA or BSP to a normal breast control, and then ascertaining whether the patient has a noncancerous breast disease. In general, if high expression relative to a control of a BSNA or BSP is indicative of a particular noncancerous breast disease, a diagnostic assay is considered positive if the level of expression of the BSNA or BSP is at least two times higher, and more preferably at least five times higher, even more preferably at least ten times higher, than in preferably the same cells, tissues or bodily fluid of a normal human control. In contrast, if low expression relative to a control of a BSNA or BSP is indicative of a noncancerous breast disease, a diagnostic assay is considered positive if the level of expression of the BSNA or BSP is at least two times lower, more preferably are at least five times lower, even more preferably at least ten times lower than in preferably the same cells, tissues or bodily fluid of a normal human control. The normal human control may be from a different patient or from uninvolved tissue of the same patient.

One having ordinary skill in the art may determine whether a BSNA and/or BSP is associated with a particular noncancerous breast disease by obtaining breast tissue from a patient having a noncancerous breast disease of interest and determining which BSNAs and/or BSPs are expressed in the tissue at either a higher or a lower level than in normal breast tissue. In another embodiment, one may determine whether a BSNA or BSP exhibits structural alterations in a particular noncancerous breast disease state by obtaining breast tissue from a patient having a noncancerous breast disease of interest and determining the structural alterations in one or more BSNAs and/or BSPs relative to normal breast tissue.

Methods for Identifying Breast Tissue

In another aspect, the invention provides methods for identifying breast tissue. These methods are particularly useful in, e.g., forensic science, breast cell differentiation and development, and in tissue engineering.

In one embodiment, the invention provides a method for determining whether a sample is breast tissue or has breast tissue-like characteristics. The method comprises the steps of providing a sample suspected of comprising breast tissue or having breast tissue-like characteristics, determining whether the sample expresses one or more BSNAs and/or BSPs, and, if the sample expresses one or more BSNAs and/or BSPs, concluding that the sample comprises breast tissue. In a preferred embodiment, the BSNA encodes a polypeptide having an amino acid sequence selected from SEQ ID NO: 165 through 280, or a homolog, allelic variant or fragment thereof. In a more preferred embodiment, the BSNA has a nucleotide sequence selected from SEQ ID NO: 1 through 164, or a hybridizing nucleic acid, an allelic variant or a part thereof. Determining whether a sample expresses a BSNA can be accomplished by any method known in the art. Preferred methods include hybridization to microarrays, Northern blot hybridization, and quantitative or qualitative RT-PCR. In another preferred embodiment, the method can be practiced by determining whether a BSP is expressed. Determining whether a sample expresses a BSP can be accomplished by any method known in the art. Preferred methods include Western blot, ELISA, RIA and 2D PAGE. In one embodiment, the BSP has an amino acid sequence selected from SEQ ID NO: 165 through 280, or a homolog, allelic variant or fragment thereof. In another preferred embodiment, the expression of at least two BSNAs and/or BSPs is determined. In a more preferred embodiment, the expression of at least three, more preferably four and even more preferably five BSNAs and/or BSPs are determined.

In one embodiment, the method can be used to determine whether an unknown tissue is breast tissue. This is particularly useful in forensic science, in which small, damaged pieces of tissues that are not identifiable by microscopic or other means are recovered from a crime or accident scene. In another embodiment, the method can be used to determine whether a tissue is differentiating or developing into breast tissue. This is important in monitoring the effects of the addition of various agents to cell or tissue culture, e.g., in producing new breast tissue by tissue engineering. These agents include, e.g., growth and differentiation factors, extracellular matrix proteins and culture medium. Other factors that may be measured for effects on tissue development and differentiation include gene transfer into the cells or tissues, alterations in pH, aqueous:air interface and various other culture conditions.

Methods for Producing and Modifying Breast Tissue

In another aspect, the invention provides methods for producing engineered breast tissue or cells. In one embodiment, the method comprises the steps of providing cells, introducing a BSNA or a BSG into the cells, and growing the cells under conditions in which they exhibit one or more properties of breast tissue cells. In a preferred embodiment, the cells are pluripotent. As is well-known in the art, normal breast tissue comprises a large number of different cell types. Thus, in one embodiment, the engineered breast tissue or cells comprises one of these cell types. In another embodiment, the engineered breast tissue or cells comprises more than one breast cell type. Further, the culture conditions of the cells or tissue may require manipulation in order to achieve full differentiation and development of the breast cell tissue. Methods for manipulating culture conditions are well-known in the art.

Nucleic acid molecules encoding one or more BSPs are introduced into cells, preferably pluripotent cells. In a preferred embodiment, the nucleic acid molecules encode BSPs having amino acid sequences selected from SEQ ID NO: 165 through 280, or homologous proteins, analogs, allelic variants or fragments thereof. In a more preferred embodiment, the nucleic acid molecules have a nucleotide sequence selected from SEQ ID NO: 1 through 164, or hybridizing nucleic acids, allelic variants or parts thereof. In another highly preferred embodiment, a BSG is introduced into the cells. Expression vectors and methods of introducing nucleic acid molecules into cells are well-known in the art and are described in detail, supra.

Artificial breast tissue may be used to treat patients who have lost some or all of their breast function.

Pharmaceutical Compositions

In another aspect, the invention provides pharmaceutical compositions comprising the nucleic acid molecules, polypeptides, antibodies, antibody derivatives, antibody fragments, agonists, antagonists, and inhibitors of the present invention. In a preferred embodiment, the pharmaceutical composition comprises a BSNA or part thereof. In a more preferred embodiment, the BSNA has a nucleotide sequence selected from the group consisting of SEQ ID NO: 1 through 164, a nucleic acid that hybridizes thereto, an allelic variant thereof, or a nucleic acid that has substantial sequence identity thereto. In another preferred embodiment, the pharmaceutical composition comprises a BSP or fragment thereof. In a more preferred embodiment, the BSP having an amino acid sequence that is selected from the group consisting of SEQ ID NO: 165 through 280, a polypeptide that is homologous thereto, a fusion protein comprising all or a portion of the polypeptide, or an analog or derivative thereof. In another preferred embodiment, the pharmaceutical composition comprises an anti-BSP antibody, preferably an antibody that specifically binds to a BSP having an amino acid that is selected from the group consisting of SEQ ID NO: 165 through 280, or an antibody that binds to a polypeptide that is homologous thereto, a fusion protein comprising all or a portion of the polypeptide, or an analog or derivative thereof.

Such a composition typically contains from about 0.1 to 90% by weight of a therapeutic agent of the invention formulated in and/or with a pharmaceutically acceptable carrier or excipient.

Pharmaceutical formulation is a well-established art, and is further described in Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins (1999); and Kibbe (ed.), *Handbook of Pharmaceutical Excipients* American Pharmaceutical Association, 3$^{rd}$ ed. (2000), the disclosures of which are incorporated herein by reference in their entireties, and thus need not be described in detail herein.

Briefly, formulation of the pharmaceutical compositions of the present invention will depend upon the route chosen for administration. The pharmaceutical compositions utilized in this invention can be administered by various routes including both enteral and parenteral routes, including oral, intravenous, intramuscular, subcutaneous, inhalation, topical, sublingual, rectal, intra-arterial, intramedullary, intrathecal, intraventricular, transmucosal, transdermal, intranasal, intraperitoneal, intrapulmonary, and intrauterine.

Oral dosage forms can be formulated as tablets, pills, dragees, capsules, liquids, gels, syrups, slurries, suspensions, and the like, for ingestion by the patient.

Solid formulations of the compositions for oral administration can contain suitable carriers or excipients, such as carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, sodium carboxymethylcellulose, or microcrystalline cellulose; gums including arabic and tragacanth; proteins such as gelatin and collagen; inorganics, such as kaolin, calcium carbonate, dicalcium phosphate, sodium chloride; and other agents such as acacia and alginic acid.

Agents that facilitate disintegration and/or solubilization can be added, such as the cross-linked polyvinyl pyrrolidone, agar, alginic acid, or a salt thereof, such as sodium alginate, microcrystalline cellulose, corn starch, sodium starch glycolate, and alginic acid.

Tablet binders that can be used include acacia, methylcellulose, sodium carboxymethylcellulose, polyvinylpyrrolidone (Povidone™), hydroxypropyl methylcellulose, sucrose, starch and ethylcellulose.

Lubricants that can be used include magnesium stearates, stearic acid, silicone fluid, talc, waxes, oils, and colloidal silica.

Fillers, agents that facilitate disintegration and/or solubilization, tablet binders and lubricants, including the aforementioned, can be used singly or in combination.

Solid oral dosage forms need not be uniform throughout. For example, dragee cores can be used in conjunction with suitable coatings, such as concentrated sugar solutions, which can also contain gum arabic, talc, polyvinylpyrrolidone, carbopol gel, polyethylene glycol, and/or titanium dioxide, lacquer solutions, and suitable organic solvents or solvent mixtures.

Oral dosage forms of the present invention include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Additionally, dyestuffs or pigments can be added to the tablets or dragee coatings for product identification or to characterize the quantity of active compound, i.e., dosage.

Liquid formulations of the pharmaceutical compositions for oral (enteral) administration are prepared in water or other aqueous vehicles and can contain various suspending agents such as methylcellulose, alginates, tragacanth, pectin, kelgin, carrageenan, acacia, polyvinylpyrrolidone, and polyvinyl alcohol. The liquid formulations can also include solutions, emulsions, syrups and elixirs containing, together with the active compound(s), wetting agents, sweeteners, and coloring and flavoring agents.

The pharmaceutical compositions of the present invention can also be formulated for parenteral administration. Formulations for parenteral administration can be in the form of aqueous or non-aqueous isotonic sterile injection solutions or suspensions.

For intravenous injection, water soluble versions of the compounds of the present invention are formulated in, or if provided as a lyophilate, mixed with, a physiologically acceptable fluid vehicle, such as 5% dextrose ("D5"), physiologically buffered saline, 0.9% saline, Hanks' solution, or Ringer's solution. Intravenous formulations may include carriers, excipients or stabilizers including, without limitation, calcium, human serum albumin, citrate, acetate, calcium chloride, carbonate, and other salts.

Intramuscular preparations, e.g. a sterile formulation of a suitable soluble salt form of the compounds of the present invention, can be dissolved and administered in a pharmaceutical excipient such as Water-for-Injection, 0.9% saline, or 5% glucose solution. Alternatively, a suitable insoluble form of the compound can be prepared and administered as a suspension in an aqueous base or a pharmaceutically acceptable oil base, such as an ester of a long chain fatty acid (e.g., ethyl oleate), fatty oils such as sesame oil, triglycerides, or liposomes.

Parenteral formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like).

Aqueous injection suspensions can also contain substances that increase the viscosity of the suspension, such as sodium carboxymethyl cellulose, sorbitol, or dextran. Non-lipid polycationic amino polymers can also be used for delivery. Optionally, the suspension can also contain suitable stabilizers or agents that increase the solubility of the compounds to allow for the preparation of highly concentrated solutions.

Pharmaceutical compositions of the present invention can also be formulated to permit injectable, long-term, deposition. Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in microemulsions that are compatible with body tissues.

The pharmaceutical compositions of the present invention can be administered topically.

For topical use the compounds of the present invention can also be prepared in suitable forms to be applied to the skin, or mucus membranes of the nose and throat, and can take the form of lotions, creams, ointments, liquid sprays or inhalants, drops, tinctures, lozenges, or throat paints. Such topical formulations further can include chemical compounds such as dimethylsulfoxide (DMSO) to facilitate surface penetration of the active ingredient. In other transdermal formulations, typically in patch-delivered formulations, the pharmaceutically active compound is formulated with one or more skin penetrants, such as 2-N-methyl-pyrrolidone (NMP) or Azone. A topical semi-solid ointment formulation typically contains a concentration of the active ingredient from about 1 to 20%, e.g., 5 to 10%, in a carrier such as a pharmaceutical cream base.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Inhalation formulations can also readily be formulated. For inhalation, various powder and liquid formulations can be prepared. For aerosol preparations, a sterile formulation of the compound or salt form of the compound may be used in inhalers, such as metered dose inhalers, and nebulizers. Aerosolized forms may be especially useful for treating respiratory disorders.

Alternatively, the compounds of the present invention can be in powder form for reconstitution in the appropriate pharmaceutically acceptable carrier at the time of delivery.

The pharmaceutically active compound in the pharmaceutical compositions of the present invention can be provided as the salt of a variety of acids, including but not limited to hydrochloric, sulfuric, acetic, lactic, tartaric, malic, and succinic acid. Salts tend to be more soluble in aqueous or other protonic solvents than are the corresponding free base forms.

After pharmaceutical compositions have been prepared, they are packaged in an appropriate container and labeled for treatment of an indicated condition.

The active compound will be present in an amount effective to achieve the intended purpose. The determination of an effective dose is well within the capability of those skilled in the art.

A "therapeutically effective dose" refers to that amount of active ingredient, for example BSP polypeptide, fusion protein, or fragments thereof, antibodies specific for BSP, agonists, antagonists or inhibitors of BSP, which ameliorates the signs or symptoms of the disease or prevents progression thereof; as would be understood in the medical arts, cure, although desired, is not required.

The therapeutically effective dose of the pharmaceutical agents of the present invention can be estimated initially by in vitro tests, such as cell culture assays, followed by assay in model animals, usually mice, rats, rabbits, dogs, or pigs. The animal model can also be used to determine an initial preferred concentration range and route of administration.

For example, the ED50 (the dose therapeutically effective in 50% of the population) and LD50 (the dose lethal to 50% of the population) can be determined in one or more cell culture of animal model systems. The dose ratio of toxic to therapeutic effects is the therapeutic index, which can be expressed as LD50/ED50. Pharmaceutical compositions that exhibit large therapeutic indices are preferred.

The data obtained from cell culture assays and animal studies are used in formulating an initial dosage range for human use, and preferably provide a range of circulating concentrations that includes the ED50 with little or no toxicity. After administration, or between successive administrations, the circulating concentration of active agent varies within this range depending upon pharmacokinetic factors well-known in the art, such as the dosage form employed, sensitivity of the patient, and the route of administration.

The exact dosage will be determined by the practitioner, in light of factors specific to the subject requiring treatment. Factors that can be taken into account by the practitioner include the severity of the disease state, general health of the subject, age, weight, gender of the subject, diet, time and frequency of administration, drug combination(s), reaction sensitivities, and tolerance/response to therapy. Long-acting pharmaceutical compositions can be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Where the therapeutic agent is a protein or antibody of the present invention, the therapeutic protein or antibody agent typically is administered at a daily dosage of 0.01 mg to 30 mg/kg of body weight of the patient (e.g., 1 mg/kg to 5 mg/kg). The pharmaceutical formulation can be administered in multiple doses per day, if desired, to achieve the total desired daily dose.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions.

Therapeutic Methods

The present invention further provides methods of treating subjects having defects in a gene of the invention, e.g., in expression, activity, distribution, localization, and/or solubility, which can manifest as a disorder of breast function. As used herein, "treating" includes all medically-acceptable types of therapeutic intervention, including palliation and prophylaxis (prevention) of disease. The term "treating" encompasses any improvement of a disease, including minor improvements. These methods are discussed below.

Gene Therapy and Vaccines

The isolated nucleic acids of the present invention can also be used to drive in vivo expression of the polypeptides of the present invention. In vivo expression can be driven from a vector, typically a viral vector, often a vector based upon a replication incompetent retrovirus, an adenovirus, or an adeno-associated virus (AAV), for purpose of gene therapy. In vivo expression can also be driven from signals endogenous to the nucleic acid or from a vector, often a plasmid vector, such as pVAX1 (Invitrogen, Carlsbad, Calif., USA), for purpose of "naked" nucleic acid vaccination, as further described in U.S. Pat. Nos. 5,589,466; 5,679,647; 5,804,566; 5,830,877; 5,843,913; 5,880,104; 5,958,891; 5,985,847; 6,017,897; 6,110,898; and 6,204,250, the disclosures of which are incorporated herein by reference in their entireties. For cancer therapy, it is preferred that the vector also be tumor-selective. See, e.g., Doronin et al., *J. Virol.* 75: 3314–24 (2001).

In another embodiment of the therapeutic methods of the present invention, a therapeutically effective amount of a pharmaceutical composition comprising a nucleic acid of the present invention is administered. The nucleic acid can be delivered in a vector that drives expression of a BSP, fusion protein, or fragment thereof, or without such vector. Nucleic acid compositions that can drive expression of a BSP are administered, for example, to complement a deficiency in the native BSP, or as DNA vaccines. Expression vectors derived from virus, replication deficient retroviruses, adenovirus, adeno-associated (AAV) virus, herpes virus, or vaccinia virus can be used as can plasmids. See, e.g., Cid-Arregui, supra. In a preferred embodiment, the nucleic acid molecule encodes a BSP having the amino acid sequence of SEQ ID NO: 165 through 280, or a fragment, fusion protein, allelic variant or homolog thereof.

In still other therapeutic methods of the present invention, pharmaceutical compositions comprising host cells that express a BSP, fusions, or fragments thereof can be administered. In such cases, the cells are typically autologous, so as to circumvent xenogeneic or allotypic rejection, and are administered to complement defects in BSP production or activity. In a preferred embodiment, the nucleic acid molecules in the cells encode a BSP having the amino acid sequence of SEQ ID NO: 165 through 280, or a fragment, fusion protein, allelic variant or homolog thereof.

Antisense Administration

Antisense nucleic acid compositions, or vectors that drive expression of a BSG antisense nucleic acid, are administered to downregulate transcription and/or translation of a BSG in circumstances in which excessive production, or production of aberrant protein, is the pathophysiologic basis of disease.

Antisense compositions useful in therapy can have a sequence that is complementary to coding or to noncoding regions of a BSG. For example, oligonucleotides derived from the transcription initiation site, e.g., between positions −10 and +10 from the start site, are preferred.

Catalytic antisense compositions, such as ribozymes, that are capable of sequence-specific hybridization to BSG transcripts, are also useful in therapy. See, e.g., Phylactou, *Adv. Drug Deliv. Rev.* 44(2–3): 97–108 (2000); Phylactou et al., *Hum. Mol. Genet.* 7(10): 1649–53 (1998); Rossi, *Ciba Found. Symp.* 209: 195–204 (1997); and Sigurdsson et al., *Trends Biotechnol.* 13(8): 286–9 (1995), the disclosures of which are incorporated herein by reference in their entireties.

Other nucleic acids useful in the therapeutic methods of the present invention are those that are capable of triplex helix formation in or near the BSG genomic locus. Such triplexing oligonucleotides are able to inhibit transcription. See, e.g., Intody et al., *Nucleic Acids Res.* 28(21): 4283–90 (2000); McGuffie et al., *Cancer Res.* 60(14): 3790–9(2000), the disclosures of which are incorporated herein by reference. Pharmaceutical compositions comprising such triplex forming oligos (TFOs) are administered in circumstances in which excessive production, or production of aberrant protein, is a pathophysiologic basis of disease.

In a preferred embodiment, the antisense molecule is derived from a nucleic acid molecule encoding a BSP, preferably a BSP comprising an amino acid sequence of SEQ ID NO: 165 through 280, or a fragment, allelic variant or homolog thereof. In a more preferred embodiment, the antisense molecule is derived from a nucleic acid molecule having a nucleotide sequence of SEQ ID NO: 1 through 164, or a part, allelic variant, substantially similar or hybridizing nucleic acid thereof.

Polypeptide Administration

In one embodiment of the therapeutic methods of the present invention, a therapeutically effective amount of a pharmaceutical composition comprising a BSP, a fusion protein, fragment, analog or derivative thereof is administered to a subject with a clinically-significant BSP defect.

Protein compositions are administered, for example, to complement a deficiency in native BSP. In other embodiments, protein compositions are administered as a vaccine to elicit a humoral and/or cellular immune response to BSP. The immune response can be used to modulate activity of BSP or, depending on the immunogen, to immunize against aberrant or aberrantly expressed forms, such as mutant or inappropriately expressed isoforms. In yet other embodiments, protein fusions having a toxic moiety are administered to ablate cells that aberrantly accumulate BSP.

In a preferred embodiment, the polypeptide is a BSP comprising an amino acid sequence of SEQ ID NO: 165 through 280, or a fusion protein, allelic variant, homolog, analog or derivative thereof. In a more preferred embodiment, the polypeptide is encoded by a nucleic acid molecule having a nucleotide sequence of SEQ ID NO: 1 through 164, or a part, allelic variant, substantially similar or hybridizing nucleic acid thereof.

Antibody, Agonist and Antagonist Administration

In another embodiment of the therapeutic methods of the present invention, a therapeutically effective amount of a pharmaceutical composition comprising an antibody (including fragment or derivative thereof) of the present invention is administered. As is well-known, antibody compositions are administered, for example, to antagonize activity of BSP, or to target therapeutic agents to sites of BSP presence and/or accumulation. In a preferred embodiment, the antibody specifically binds to a BSP comprising an amino acid sequence of SEQ ID NO: 165 through 280, or a fusion protein, allelic variant, homolog, analog or derivative thereof. In a more preferred embodiment, the antibody specifically binds to a BSP encoded by a nucleic acid molecule having a nucleotide sequence of SEQ ID NO: 1 through 164, or a part, allelic variant, substantially similar or hybridizing nucleic acid thereof.

The present invention also provides methods for identifying modulators which bind to a BSP or have a modulatory effect on the expression or activity of a BSP. Modulators which decrease the expression or activity of BSP (antagonists) are believed to be useful in treating breast cancer. Such screening assays are known to those of skill in the art and include, without limitation, cell-based assays and cell-free assays. Small molecules predicted via computer imaging to specifically bind to regions of a BSP can also be designed, synthesized and tested for use in the imaging and treatment of breast cancer. Further, libraries of molecules can be screened for potential anticancer agents by assessing the ability of the molecule to bind to the BSPs identified herein. Molecules identified in the library as being capable of binding to a BSP are key candidates for further evaluation for use in the treatment of breast cancer. In a preferred embodiment, these molecules will downregulate expression and/or activity of a BSP in cells.

In another embodiment of the therapeutic methods of the present invention, a pharmaceutical composition comprising a non-antibody antagonist of BSP is administered. Antagonists of BSP can be produced using methods generally known in the art. In particular, purified BSP can be used to screen libraries of pharmaceutical agents, often combinatorial libraries of small molecules, to identify those that specifically bind and antagonize at least one activity of a BSP.

In other embodiments a pharmaceutical composition comprising an agonist of a BSP is administered. Agonists can be identified using methods analogous to those used to identify antagonists.

In a preferred embodiment, the antagonist or agonist specifically binds to and antagonizes or agonizes, respectively, a BSP comprising an amino acid sequence of SEQ ID NO: 165 through 280, or a fusion protein, allelic variant, homolog, analog or derivative thereof. In a more preferred embodiment, the antagonist or agonist specifically binds to and antagonizes or agonizes, respectively, a BSP encoded by a nucleic acid molecule having a nucleotide sequence of SEQ ID NO: 1 through 164, or a part, allelic variant, substantially similar or hybridizing nucleic acid thereof.

Targeting Breast Tissue

The invention also provides a method in which a polypeptide of the invention, or an antibody thereto, is linked to a therapeutic agent such that it can be delivered to the breast or to specific cells in the breast. In a preferred embodiment, an anti-BSP antibody is linked to a therapeutic agent and is administered to a patient in need of such therapeutic agent. The therapeutic agent may be a toxin, if breast tissue needs to be selectively destroyed. This would be useful for targeting and killing breast cancer cells.

In another embodiment, the therapeutic agent may be a growth or differentiation factor, which would be useful for promoting breast cell function.

In another embodiment, an anti-BSP antibody may be linked to an imaging agent that can be detected using, e.g., magnetic resonance imaging, CT or PET. This would be useful for determining and monitoring breast function, identifying breast cancer tumors, and identifying noncancerous breast diseases.

EXAMPLES

Example 1

Gene Expression Analysis

BSGs were identified by mRNA subtraction analysis using standard methods. The sequences were extended using GeneBank sequences, Incyte's proprietary database. From the nucleotide sequences, predicted amino acid sequences were prepared. DEX0287_1, DEX0287_2 correspond to SEQ ID NO.1, 2 etc. DEX0131 was the parent sequence found in the mRNA subtractions.

| | | |
|---|---|---|
| DEX0287_1 | DEX0131_1 | DEX0287_165 |
| DEX0287_2 | flex DEX0131_1 | |
| DEX0287_3 | DEX0131_2 | DEX0287_166 |
| DEX0287_4 | flex DEX0131_2 | |

-continued

| | | |
|---|---|---|
| DEX0287_5 | DEX0131_3 | DEX0287_167 |
| DEX0287_6 | flex DEX0131_3 | DEX0287_168 |
| DEX0287_7 | DEX0131_4 | DEX0287_169 |
| DEX0287_8 | flex DEX0131_4 | |
| DEX0287_9 | DEX0131_5 | |
| DEX0287_10 | DEX0131_6 | DEX0287_170 |
| DEX0287_11 | flex DEX0131_6 | |
| DEX0287_12 | DEX0131_7 | DEX0287_171 |
| DEX0287_13 | flex DEX0131_7 | |
| DEX0287_14 | DEX0131_8 | DEX0287_172 |
| DEX0287_15 | DEX0131_9 | DEX0287_173 |
| DEX0287_16 | flex DEX0131_9 | |
| DEX0287_17 | DEX0131_10 | DEX0287_174 |
| DEX0287_18 | flex DEX0131_10 | DEX0287_175 |
| DEX0287_19 | DEX0131_11 | DEX0287_176 |
| DEX0287_20 | flex DEX0131_11 | DEX0287_177 |
| DEX0287_21 | DEX0131_12 | DEX0287_178 |
| DEX0287_22 | flex DEX0131_12 | |
| DEX0287_23 | DEX0131_13 | DEX0287_179 |
| DEX0287_24 | flex DEX0131_13 | DEX0287_180 |
| DEX0287_25 | DEX0131_14 | DEX0287_181 |
| DEX0287_26 | flex DEX0131_14 | DEX0287_182 |
| DEX0287_27 | DEX0131_15 | DEX0287_183 |
| DEX0287_28 | flex DEX0131_15 | DEX0287_184 |
| DEX0287_29 | DEX0131_16 | DEX0287_185 |
| DEX0287_30 | DEX0131_17 | DEX0287_186 |
| DEX0287_31 | flex DEX0131_17 | DEX0287_187 |
| DEX0287_32 | DEX0131_18 | DEX0287_188 |
| DEX0287_33 | flex DEX0131_18 | DEX0287_189 |
| DEX0287_34 | DEX0131_19 | DEX0287_190 |
| DEX0287_35 | DEX0131_20 | DEX0287_191 |
| DEX0287_36 | flex DEX0131_20 | |
| DEX0287_37 | DEX0131_21 | DEX0287_192 |
| DEX0287_38 | DEX0131_22 | DEX0287_193 |
| DEX0287_39 | flex DEX0131_22 | |
| DEX0287_40 | DEX0131_23 | DEX0287_194 |
| DEX0287_41 | flex DEX0131_23 | DEX0287_195 |
| DEX0287_42 | DEX0131_24 | DEX0287_196 |
| DEX0287_43 | flex DEX0131_24 | |
| DEX0287_44 | DEX0131_25 | DEX0287_197 |
| DEX0287_45 | flex DEX0131_25 | DEX0287_198 |
| DEX0287_46 | DEX0131_26 | DEX0287_199 |
| DEX0287_47 | flex DEX0131_26 | DEX0287_200 |
| DEX0287_48 | DEX0131_27 | DEX0287_201 |
| DEX0287_49 | flex DEX0131_27 | |
| DEX0287_50 | DEX0131_28 | DEX0287_202 |
| DEX0287_51 | flex DEX0131_28 | |
| DEX0287_52 | DEX0131_30 | DEX0287_203 |
| DEX0287_53 | flex DEX0131_30 | |
| DEX0287_54 | DEX0131_31 | DEX0287_204 |
| DEX0287_55 | DEX0131_32 | DEX0287_205 |
| DEX0287_56 | flex DEX0131_32 | DEX0287_206 |
| DEX0287_57 | DEX0131_33 | DEX0287_207 |
| DEX0287_58 | flex DEX0131_33 | |
| DEX0287_59 | DEX0131_34 | DEX0287_208 |
| DEX0287_60 | flex DEX0131_34 | |
| DEX0287_61 | DEX0131_35 | DEX0287_209 |
| DEX0287_62 | flex DEX0131_35 | |
| DEX0287_63 | DEX0131_36 | DEX0287_210 |
| DEX0287_64 | DEX0131_38 | DEX0287_211 |
| DEX0287_65 | flex DEX0131_38 | |
| DEX0287_66 | DEX0131_39 | DEX0287_212 |
| DEX0287_67 | flex DEX0131_39 | DEX0287_213 |
| DEX0287_68 | DEX0131_40 | DEX0287_214 |
| DEX0287_69 | flex DEX0131_40 | |
| DEX0287_70 | DEX0131_41 | DEX0287_215 |
| DEX0287_71 | DEX0131_42 | DEX0287_216 |
| DEX0287_72 | DEX0131_43 | DEX0287_217 |
| DEX0287_73 | DEX0131_44 | DEX0287_218 |
| DEX0287_74 | flex DEX0131_44 | DEX0287_219 |
| DEX0287_75 | DEX0131_45 | DEX0287_220 |
| DEX0287_76 | flex DEX0131_45 | |
| DEX0287_77 | DEX0131_46 | DEX0287_221 |
| DEX0287_78 | flex DEX0131_46 | |
| DEX0287_79 | DEX0131_47 | |
| DEX0287_80 | flex DEX0131_47 | |
| DEX0287_81 | DEX0131_48 | DEX0287_222 |
| DEX0287_82 | flex DEX0131_48 | |
| DEX0287_83 | DEX0131_49 | DEX0287_223 |

-continued

| | | |
|---|---|---|
| DEX0287_84 | flex DEX0131_49 | |
| DEX0287_85 | DEX0131_50 | DEX0287_224 |
| DEX0287_86 | flex DEX0131_50 | DEX0287_225 |
| DEX0287_87 | DEX0131_51 | DEX0287_226 |
| DEX0287_88 | flex DEX0131_51 | |
| DEX0287_89 | DEX0131_52 | DEX0287_227 |
| DEX0287_90 | flex DEX0131_52 | |
| DEX0287_91 | DEX0131_53 | DEX0287_228 |
| DEX0287_92 | flex DEX0131_53 | |
| DEX0287_93 | DEX0131_54 | DEX0287_229 |
| DEX0287_94 | flex DEX0131_54 | |
| DEX0287_95 | DEX0131_55 | DEX0287_230 |
| DEX0287_96 | flex DEX0131_55 | DEX0287_231 |
| DEX0287_97 | DEX0131_56 | DEX0287_232 |
| DEX0287_98 | flex DEX0131_56 | DEX0287_233 |
| DEX0287_99 | DEX0131_58 | DEX0287_234 |
| DEX0287_100 | flex DEX0131_58 | |
| DEX0287_101 | DEX0131_59 | DEX0287_235 |
| DEX0287_102 | flex DEX0131_59 | |
| DEX0287_103 | DEX0131_61 | DEX0287_236 |
| DEX0287_104 | DEX0131_62 | DEX0287_237 |
| DEX0287_105 | flex DEX0131_62 | DEX0287_238 |
| DEX0287_106 | DEX0131_63 | DEX0287_239 |
| DEX0287_107 | flex DEX0131_63 | DEX0287_240 |
| DEX0287_108 | DEX0131_64 | DEX0287_241 |
| DEX0287_109 | DEX0131_65 | DEX0287_242 |
| DEX0287_110 | flex DEX0131_65 | |
| DEX0287_111 | DEX0131_66 | DEX0287_243 |
| DEX0287_112 | flex DEX0131_66 | DEX0287_244 |
| DEX0287_113 | DEX0131_68 | DEX0287_245 |
| DEX0287_114 | DEX0131_69 | DEX0287_246 |
| DEX0287_115 | flex DEX0131_69 | |
| DEX0287_116 | DEX0131_70 | DEX0287_247 |
| DEX0287_117 | flex DEX0131_70 | |
| DEX0287_118 | DEX0131_71 | DEX0287_248 |
| DEX0287_119 | DEX0131_72 | DEX0287_249 |
| DEX0287_120 | flex DEX0131_72 | |
| DEX0287_121 | DEX0131_73 | DEX0287_250 |
| DEX0287_122 | flex DEX0131_73 | |
| DEX0287_123 | DEX0131_74 | DEX0287_251 |
| DEX0287_124 | DEX0131_75 | DEX0287_252 |
| DEX0287_125 | DEX0131_77 | DEX0287_254 |
| DEX0287_126 | DEX0131_78 | DEX0287_255 |
| DEX0287_127 | flex DEX0131_78 | |
| DEX0287_128 | DEX0131_79 | DEX0287_256 |
| DEX0287_129 | flex DEX0131_79 | |
| DEX0287_130 | DEX0131_80 | DEX0287_257 |
| DEX0287_131 | flex DEX0131_80 | |
| DEX0287_132 | DEX0131_81 | DEX0287_258 |
| DEX0287_133 | flex DEX0131_81 | DEX0287_259 |
| DEX0287_134 | DEX0131_82 | DEX0287_260 |
| DEX0287_135 | flex DEX0131_82 | |
| DEX0287_136 | DEX0131_84 | DEX0287_261 |
| DEX0287_137 | flex DEX0131_84 | DEX0287_262 |
| DEX0287_138 | DEX0131_85 | DEX0287_263 |
| DEX0287_139 | DEX0131_86 | DEX0287_264 |
| DEX0287_140 | flex DEX0131_86 | DEX0287_265 |
| DEX0287_141 | DEX0131_87 | DEX0287_266 |
| DEX0287_142 | flex DEX0131_87 | DEX0287_267 |
| DEX0287_143 | DEX0131_88 | DEX0287_268 |
| DEX0287_144 | flex DEX0131_88 | |
| DEX0287_145 | DEX0131_89 | DEX0287_269 |
| DEX0287_146 | flex DEX0131_89 | |
| DEX0287_147 | DEX0131_90 | DEX0287_270 |
| DEX0287_148 | flex DEX0131_90 | |
| DEX0287_149 | DEX0131_91 | DEX0287_271 |
| DEX0287_150 | DEX0131_92 | DEX0287_272 |
| DEX0287_151 | DEX0131_93 | DEX0287_273 |
| DEX0287_152 | flex DEX0131_93 | |
| DEX0287_153 | DEX0131_94 | DEX0287_274 |
| DEX0287_154 | flex DEX0131_94 | |
| DEX0287_155 | DEX0131_95 | DEX0287_275 |
| DEX0287_156 | flex DEX0131_95 | |
| DEX0287_157 | DEX0131_96 | DEX0287_276 |
| DEX0287_158 | flex DEX0131_96 | DEX0287_277 |
| DEX0287_159 | DEX0131_97 | DEX0287_278 |
| DEX0287_160 | flex DEX0131_97 | |
| DEX0287_161 | DEX0131_98 | DEX0287_279 |
| DEX0287_162 | flex DEX0131_98 | |
| DEX0287_163 | DEX0131_99 | DEX0287_280 |
| DEX0287_164 | flex DEX0131_99 | |

The expression levels from the Incyte LifeSeq database are listed below:

| | | | | | | | | | |
|---|---|---|---|---|---|---|---|---|---|
| DEX0287_1 | SEQ ID NO: 1 | THR | .0023 | FTS | .0038 | BRN | .0063 | BLD | .008 |
| DEX0287_10 | SEQ ID NO: 10 | CRD | .0023 | PAN | .0035 | ESO | .0051 | | |
| DEX0287_100 | SEQ ID NO: 100 | INL | .0006 | | | | | | |
| DEX0287_101 | SEQ ID NO: 101 | NOS | .0073 | STO | .0081 | ESO | .0102 | | |
| DEX0287_102 | SEQ ID NO: 102 | NOS | .0073 | STO | .0081 | ESO | .0102 | | |
| DEX0287_104 | SEQ ID NO: 104 | LNG | .0006 | OVR | .001 | PRO | .0017 | BLD | .0048 |
| DEX0287_105 | SEQ ID NO: 105 | LNG | .0006 | OVR | .001 | PRO | .0017 | BLD | .0048 |
| DEX0287_106 | SEQ ID NO: 106 | PAN | .0012 | | | | | | |
| DEX0287_111 | SEQ ID NO: 111 | CON | .0113 | LIV | .0189 | ADR | .0209 | | |
| DEX0287_116 | SEQ ID NO: 116 | BLV | .0016 | BLV | .0016 | INL | .0019 | INL | .0019 |
| DEX0287_117 | SEQ ID NO: 117 | BLV | .0016 | BLV | .0016 | INL | .0019 | INL | .0019 |
| DEX0287_121 | SEQ ID NO: 121 | LMN | .0083 | UNC | .012 | | | | |
| DEX0287_122 | SEQ ID NO: 122 | LMN | .0083 | UNC | .012 | | | | |
| DEX0287_124 | SEQ ID NO: 124 | OVR | .0133 | ADR | .0164 | FAL | .0189 | TON | .0299 |
| DEX0287_126 | SEQ ID NO: 126 | THR | .0091 | UTR | .0132 | TON | .0299 | | |
| DEX0287_127 | SEQ ID NO: 127 | THR | .0091 | UTR | .0132 | TON | .0299 | | |
| DEX0287_130 | SEQ ID NO: 130 | LNG | .0039 | ESO | .0051 | BON | .0056 | PNS | .007 |
| DEX0287_131 | SEQ ID NO: 131 | LNG | .0039 | ESO | .0051 | BON | .0056 | PNS | .007 |
| DEX0287_132 | SEQ ID NO: 132 | FTS | .0035 | CRD | .0045 | PNS | .0187 | | |
| DEX0287_133 | SEQ ID NO: 133 | FTS | .0035 | CRD | .0045 | PNS | .0187 | | |
| DEX0287_136 | SEQ ID NO: 136 | UTR | .0013 | URE | .0225 | | | | |
| DEX0287_138 | SEQ ID NO: 138 | PNS | .0023 | THR | .0023 | MAM | .0033 | CRD | .0068 |
| DEX0287_141 | SEQ ID NO: 141 | PAN | .0353 | LMN | .0416 | OVR | .0503 | INT | .1052 |
| DEX0287_142 | SEQ ID NO: 142 | PAN | .0353 | LMN | .0416 | OVR | .0503 | INT | .1052 |
| DEX0287_15 | SEQ ID NO: 15 | INS | .0038 | ADR | .006 | CRD | .0068 | | |
| DEX0287_150 | SEQ ID NO: 150 | BRN | .0001 | FTS | .0001 | TST | .0011 | MAM | .0081 |
| DEX0287_151 | SEQ ID NO: 151 | BRN | .0017 | UTR | .0019 | PAN | .0035 | LIV | .0038 |
| DEX0287_152 | SEQ ID NO: 152 | BRN | .0017 | UTR | .0019 | PAN | .0035 | LIV | .0038 |
| DEX0287_153 | SEQ ID NO: 153 | MAM | .0005 | ADR | .0015 | CON | .0023 | | |

-continued

| | | | | | | | | | |
|---|---|---|---|---|---|---|---|---|---|
| DEX0287_155 | SEQ ID NO: 155 | MAM | .0033 | LNG | .0034 | THR | .0045 | PNS | .0047 |
| DEX0287_156 | SEQ ID NO: 156 | MAM | .0033 | LNG | .0034 | THR | .0045 | PNS | .0047 |
| DEX0287_157 | SEQ ID NO: 157 | BON | .0169 | | | | | | |
| DEX0287_16 | SEQ ID NO: 16 | INS | .0038 | ADR | .006 | CRD | .0068 | | |
| DEX0287_161 | SEQ ID NO: 161 | PRO | .0102 | KID | .0128 | NOS | .022 | FAL | .0503 |
| DEX0287_163 | SEQ ID NO: 163 | LIV | .0057 | PNS | .007 | GLB | .0093 | ADR | .0149 |
| DEX0287_164 | SEQ ID NO: 164 | LIV | .0057 | PNS | .007 | GLB | .0093 | ADR | .0149 |
| DEX0287_17 | SEQ ID NO: 17 | PRO | .0006 | | | | | | |
| DEX0287_18 | SEQ ID NO: 18 | PRO | .0006 | | | | | | |
| DEX0287_19 | SEQ ID NO: 19 | BLD | .0016 | BMR | .0064 | | | | |
| DEX0287_2 | SEQ ID NO: 2 | THR | .0023 | FTS | .0038 | BRN | .0063 | BLD | .008 |
| DEX0287_21 | SEQ ID NO: 21 | UTR | .0006 | PAN | .0012 | KID | .0013 | | |
| DEX0287_22 | SEQ ID NO: 22 | UTR | .0006 | PAN | .0012 | KID | .0013 | | |
| DEX0287_23 | SEQ ID NO: 23 | INL | .0013 | MAM | .0024 | THR | .0045 | LNG | .0078 |
| DEX0287_24 | SEQ ID NO: 24 | INL | .0013 | MAM | .0024 | THR | .0045 | LNG | .0078 |
| DEX0287_25 | SEQ ID NO: 25 | INL | .0006 | BON | .0056 | | | | |
| DEX0287_26 | SEQ ID NO: 26 | PAN | .0024 | | | | | | |
| DEX0287_27 | SEQ ID NO: 27 | KID | .0013 | | | | | | |
| DEX0287_3 | SEQ ID NO: 3 | INS | .001 | INS | .001 | UTR | .0013 | BLV | .0016 |
| DEX0287_30 | SEQ ID NO: 30 | BRN | .0078 | KID | .0128 | ADR | .0134 | LNG | .0134 |
| DEX0287_31 | SEQ ID NO: 31 | BRN | .0078 | KID | .0128 | ADR | .0134 | LNG | .0134 |
| DEX0287_33 | SEQ ID NO: 33 | INS | .0048 | PNS | .007 | BON | .0112 | URE | .0225 |
| DEX0287_34 | SEQ ID NO: 34 | UTR | .0013 | ESO | .0051 | BON | .0056 | | |
| DEX0287_35 | SEQ ID NO: 35 | BRN | .0031 | THR | .0045 | | | | |
| DEX0287_36 | SEQ ID NO: 36 | BRN | .0031 | THR | .0045 | | | | |
| DEX0287_38 | SEQ ID NO: 38 | PAN | .0071 | NOS | .0073 | LMN | .0083 | PRO | .0119 |
| DEX0287_39 | SEQ ID NO: 39 | PAN | .0071 | NOS | .0073 | LMN | .0083 | PRO | .0119 |
| DEX0287_4 | SEQ ID NO: 4 | INS | .001 | INS | .001 | UTR | .0013 | BLV | .0016 |
| DEX0287_40 | SEQ ID NO: 40 | KID | .0013 | BLD | .0032 | | | | |
| DEX0287_42 | SEQ ID NO: 42 | MAM | .0047 | | | | | | |
| DEX0287_43 | SEQ ID NO: 43 | MAM | .0047 | | | | | | |
| DEX0287_44 | SEQ ID NO: 44 | SPL | .0042 | MAM | .0043 | ESO | .0051 | PNS | .007 |
| DEX0287_45 | SEQ ID NO: 45 | THR | .0045 | BRN | .0048 | UNC | .008 | ADR | .0089 |
| DEX0287_46 | SEQ ID NO: 46 | URE | .0225 | PLE | .0449 | | | | |
| DEX0287_47 | SEQ ID NO: 47 | URE | .0225 | PLE | .0449 | | | | |
| DEX0287_52 | SEQ ID NO: 52 | THY | .002 | | | | | | |
| DEX0287_53 | SEQ ID NO: 53 | THY | .002 | | | | | | |
| DEX0287_55 | SEQ ID NO: 55 | PAN | .0012 | LMN | .0028 | INS | .0038 | GLB | .0046 |
| DEX0287_56 | SEQ ID NO: 56 | PAN | .0012 | LMN | .0028 | INS | .0038 | GLB | .0046 |
| DEX0287_57 | SEQ ID NO: 57 | BLD | .0032 | NOS | .0073 | | | | |
| DEX0287_58 | SEQ ID NO: 58 | BLD | .0032 | NOS | .0073 | | | | |
| DEX0287_59 | SEQ ID NO: 59 | UTR | .01 | | | | | | |
| DEX0287_60 | SEQ ID NO: 60 | UTR | .01 | | | | | | |
| DEX0287_61 | SEQ ID NO: 61 | INS | .001 | KID | .0013 | BLD | .0032 | INL | .0032 |
| DEX0287_62 | SEQ ID NO: 62 | INS | .001 | KID | .0013 | BLD | .0032 | INL | .0032 |
| DEX0287_64 | SEQ ID NO: 64 | SAG | .0593 | TON | .0896 | CTL | .1252 | PAN | .1422 |
| DEX0287_65 | SEQ ID NO: 65 | SAG | .0593 | TON | .0896 | CTL | .1252 | PAN | .1422 |
| DEX0287_66 | SEQ ID NO: 66 | INL | .0013 | MAM | .0024 | THR | .0045 | LNG | .0078 |
| DEX0287_67 | SEQ ID NO: 67 | INL | .0013 | MAM | .0024 | THR | .0045 | LNG | .0078 |
| DEX0287_7 | SEQ ID NO: 7 | UTR | .0075 | PLE | .0449 | | | | |
| DEX0287_73 | SEQ ID NO: 73 | THR | .0045 | PAN | .0059 | OVR | .0123 | MAM | .0255 |
| DEX0287_75 | SEQ ID NO: 75 | PNS | .0117 | UTR | .0176 | LMN | .0222 | | |
| DEX0287_77 | SEQ ID NO: 77 | BRN | .0004 | KID | .0006 | ADR | .0013 | ADR | .0015 |
| DEX0287_78 | SEQ ID NO: 78 | BRN | .0004 | KID | .0006 | ADR | .0013 | ADR | .0015 |
| DEX0287_85 | SEQ ID NO: 85 | INS | .0019 | TON | .0299 | | | | |
| DEX0287_90 | SEQ ID NO: 90 | BRN | .0002 | BRN | .0006 | KID | .0006 | LNG | .0006 |
| DEX0287_91 | SEQ ID NO: 91 | LNG | .0017 | | | | | | |
| DEX0287_92 | SEQ ID NO: 92 | LNG | .0017 | | | | | | |
| DEX0287_93 | SEQ ID NO: 93 | LNG | .0335 | | | | | | |
| DEX0287_94 | SEQ ID NO: 94 | LNG | .0335 | | | | | | |
| DEX0287_95 | SEQ ID NO: 95 | SKN | .0015 | BLD | .0016 | TNS | .0016 | SPL | .002 |
| DEX0287_97 | SEQ ID NO: 97 | BRN | .0006 | MAM | .0009 | UTR | .0013 | INL | .0013 |
| DEX0287_99 | SEQ ID NO: 99 | INL | .0006 | | | | | | |

Abbreviation for tissues:
BLO Blood;
BRN Brain;
CON Connective Tissue;
CRD Heart;
FTS Fetus;
INL Intestine, Large;
INS Intestine, Small;
KID Kidney;
LIV Liver;
LNG Lung;
MAM Breast;
MSL Muscles;
NRV Nervous Tissue;
OVR Ovary;

-continued

PRO Prostate;
STo Stomach;
THR Thyroid Gland;
TNS Tonsil/Adenoids;
UTR Uterus

Example 2

Relative Quantitation of Gene Expression

Real-Time quantitative PCR with fluorescent Taqman probes is a quantitation detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA). Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene are evaluated for every sample in normal and cancer tissues. Total RNA is extracted from normal tissues, cancer tissues, and from cancers and the corresponding matched adjacent tissues. Subsequently, first strand cDNA is prepared with reverse transcriptase and the polymerase chain reaction is done using primers and Taqman probes specific to each target gene. The results are analyzed using the ABI PRISM 7700 Sequence Detector. The absolute numbers are relative levels of expression of the target gene in a particular tissue compared to the calibrator tissue.

One of ordinary skill can design appropriate primers. The relative levels of expression of the BSNA versus normal tissues and other cancer tissues can then be determined. All the values are compared to a normal tissue (calibrator). These RNA samples are commercially available pools, originated by pooling samples of a particular tissue from different individuals.

The relative levels of expression of the BSNA in pairs of matching samples and 1 cancer and 1 normal/normal adjacent of tissue may also be determined. All the values are compared to a normal tissue (calibrator). A matching pair is formed by mRNA from the cancer sample for a particular tissue and mRNA from the normal adjacent sample for that same tissue from the same individual.

In the analysis of matching samples, BSNAs show a high degree of tissue specificity for the tissue of interest. These results confirm the tissue specificity results obtained with normal pooled samples.

Further, the level of mRNA expression in cancer samples and the isogenic normal adjacent tissue from the same individual are compared. This comparison provides an indication of specificity for the cancer stage (e.g. higher levels of mRNA expression in the cancer sample compared to the normal adjacent). Altogether, the high level of tissue specificity, plus the mRNA overexpression in matching samples tested are indicative of SEQ ID NO: 1 through 81 being diagnostic markers for cancer.

DEX0131_24 (sqmam047); DEX0289_43 (SEQ ID NO: 43)

Semi-quantitative PCR was done using the following primers:

| Primer | DexSeqID | From | To | Primer Length |
|---|---|---|---|---|
| sqmam047F | DEX0289_43 | 172 | 193 | 22 |
| sqmam047R | DEX0289_43 | 413 | 390 | 24 |

TABLE 1

The absolute numbers are relative levels of expression of sqmam047 in 12 normal samples from 12 different tissues. These RNA samples are from single individual or are commercially available pools, originated by pooling samples of a particular tissue from different individuals . . . Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| TISSUE | NORMAL |
|---|---|
| Breast | 100 |
| Colon | 10 |
| Endometrium | 100 |
| Kidney | 1000 |
| Liver | 10 |
| Lung | 10 |
| Ovary | 100 |
| Prostate | 10 |
| Small Intestine | 10 |
| Stomach | 1 |
| Testis | 1000 |
| Uterus | 1 |

Relative levels of expression in Table 1 show that all the normal tissues have a different degree of expression with normal kidney and testis having the highest expression of sqmam047.

TABLE 2

The absolute numbers are relative levels of expression of sqmam047 in 12 cancer samples from 12 different tissues . . . Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| TISSUE | CANCER |
|---|---|
| Bladder | 10 |
| Breast | 10 |
| Colon | 1000 |
| Kidney | 100 |
| Liver | 100 |
| Lung | 100 |
| Ovary | 100 |
| Pancreas | 10 |
| Prostate | 100 |
| Stomach | 1000 |
| Testes | 100 |
| Uterus | 100 |

Relative levels of expression in Table 2 show that sqmam047. is expressed in most of the carcinomas tested.

TABLE 3

The absolute numbers are relative levels of expression of sqmam047 in 6 mammary gland cancer matching samples. A matching pair is formed by mRNA from the cancer sample for a particular tissue and mRNA from the normal adjacent sample for that same tissue from the same individual.
Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

| SAMPLE ID | TISSUE | CANCER | NORMAL ADJACENT TISSUE |
|---|---|---|---|
| S99522A/B | mammary gland 1 | 1000 | 1 |
| 4005724A2/B3 | mammary gland 2 | 100 | 10 |
| 4005599A4/B2 | mammary gland 3 | 1000 | 1 |
| 4005629A2/B2 | mammary gland 4 | 10 | 1000 |
| S9822245A/B | mammary gland 5 | 1000 | 100 |
| S9819997A/B | mammary gland 6 | 1000 | 100 |

Relative levels of expression in Table 2 shows that sqmam047 is expressed in all six mammary gland cancer samples and matching normal adjacent tissue (NAT). This assay shows that sqmam047 is upregulated in 5 out of 6 (83%) of the matching samples analyzed.

Experiments are underway to design and test primers and probe for quantitative PCR. The chromosomal locations were determined for several of the sequences. Specifically:

| | |
|---|---|
| DEX0287_2 | chromosome 1 |
| DEX0287_6 | chromosome 8 |
| DEX0287_8 | chromosome 2 |
| DEX0287_11 | chromosome 1 |
| DEX0287_12 | chromosome 9 |
| DEX0287_13 | chromosome 9 |
| DEX0287_17 | chromosome 12 |
| DEX0287_18 | chromosome 12 |
| DEX0287_20 | chromosome 3 |
| DEX0287_24 | chromosome 1 |
| DEX0287_26 | chromosome 11 |
| DEX0287_28 | chromosome 19 |
| DEX0287_30 | chromosome 16 |
| DEX0287_38 | chromosome 7 |
| DEX0287_39 | chromosome 7 |
| DEX0287_41 | chromosome 19 |
| DEX0287_44 | chromosome 8 |
| DEX0287_45 | chromosome 4 |
| DEX0287_47 | chromosome 3 |
| DEX0287_48 | chromosome 2 |
| DEX0287_51 | chromosome 1 |
| DEX0287_52 | chromosome 8 |
| DEX0287_53 | chromosome 8 |
| DEX0287_54 | chromosome 8 |
| DEX0287_56 | chromosome 5 |
| DEX0287_58 | chromosome 7 |
| DEX0287_62 | chromosome 8 |
| DEX0287_63 | chromosome 3 |
| DEX0287_65 | chromosome 4 |
| DEX0287_68 | chromosome 10 |
| DEX0287_69 | chromosome 13 |
| DEX0287_70 | chromosome 8 |
| DEX0287_71 | chromosome 9 |
| DEX0287_72 | chromosome 6 |
| DEX0287_74 | chromosome 16 |
| DEX0287_77 | chromosome Un |
| DEX0287_78 | chromosome Un |
| DEX0287_80 | chromosome 2 |
| DEX0287_82 | chromosome 3 |
| DEX0287_86 | chromosome 16 |
| DEX0287_88 | chromosome 2 |
| DEX0287_89 | chromosome 8 |
| DEX0287_90 | chromosome 8 |
| DEX0287_94 | chromosome 16 |
| DEX0287_103 | chromosome 16 |
| DEX0287_107 | chromosome 18 |
| DEX0287_108 | chromosome 8 |
| DEX0287_109 | chromosome 4 |
| DEX0287_110 | chromosome 4 |
| DEX0287_112 | chromosome 2 |
| DEX0287_114 | chromosome 6 |
| DEX0287_115 | chromosome 6 |
| DEX0287_116 | chromosome 11 |
| DEX0287_117 | chromosome 12 |
| DEX0287_119 | chromosome Un |
| DEX0287_122 | chromosome 1 |
| DEX0287_123 | chromosome 17 |
| DEX0287_124 | chromosome 8 |
| DEX0287_131 | chromosome 5 |
| DEX0287_132 | chromosome 5 |
| DEX0287_133 | chromosome 5 |
| DEX0287_137 | chromosome 15 |
| DEX0287_139 | chromosome 2 |
| DEX0287_140 | chromosome 2 |
| DEX0287_149 | chromosome 6 |
| DEX0287_151 | chromosome 7 |
| DEX0287_152 | chromosome 7 |
| DEX0287_153 | chromosome 8 |
| DEX0287_154 | chromosome 8 |
| DEX0287_156 | chromosome 1 |
| DEX0287_157 | chromosome 10 |
| DEX0287_158 | chromosome 10 |

Example 3

Protein Expression

The BSNA is amplified by polymerase chain reaction (PCR) and the amplified DNA fragment encoding the BSNA is subcloned in pET-21d for expression in *E. coli*. In addition to the BSNA coding sequence, codons for two amino acids, Met-Ala, flanking the $NH_2$-terminus of the coding sequence of BSNA, and six histidines, flanking the COOH-terminus of the coding sequence of BSNA, are incorporated to serve as initiating Met/restriction site and purification tag, respectively.

An over-expressed protein band of the appropriate molecular weight may be observed on a Coomassie blue stained polyacrylamide gel. This protein band is confirmed by Western blot analysis using monoclonal antibody against 6× Histidine tag.

Large-scale purification of BSP was achieved using cell paste generated from 6-liter bacterial cultures, and purified using immobilized metal affinity chromatography (IMAC). Soluble fractions that had been separated from total cell lysate were incubated with a nickle chelating resin. The column was packed and washed with five column volumes of wash buffer. BSP was eluted stepwise with various concentration imidazole buffers.

Example 4

Protein Fusions

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 2, is ligated into this BamHI site. Note that the polynucleotide is cloned without a stop codon, otherwise a fusion protein will not be produced. If the naturally occurring signal sequence is used to produce the secreted protein, pC4 does not need a second signal peptide. Alternatively, if the naturally occurring signal sequence is not used, the vector can be modified to include a heterologous signal sequence. See, e.g., WO 96/34891.

Example 5

Production of an Antibody from a Polypeptide

In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100, μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al., *Gastroenterology* 80: 225–232 (1981).

The hybridoma cells obtained through such a selection are then assayed to identify clones which secrete antibodies capable of binding the polypeptide. Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein specific antibody and can be used to immunize an animal to induce formation of further protein-specific antibodies. Using the Jameson-Wolf methods the following epitopes were predicted. (Jameson and Wolf, CABIOS, 4(1), 181–186, 1988, the contents of which are incorporated by reference).

The predicted antigenicity for the amino acid sequences is as follows:

| positions | AI avg | length |
|---|---|---|
| DEX0287__165 Antigenicity Index(Jameson-Wolf) | | |
| 14–33 | 1.17 | 20 |
| DEX0287__166 Antigenicity Index(Jameson-Wolf) | | |
| 5–22 | 1.08 | 18 |
| DEX0287__167 Antigenicity Index(Jameson-Wolf) | | |
| 6–15 | 1.06 | 10 |
| DEX0287__168 Antigenicity Index(Jameson-Wolf) | | |
| 177–188 | 1.06 | 12 |
| 88–107 | 1.03 | 20 |
| DEX0287__169 Antigenicity Index(Jameson-Wolf) | | |
| 2–12 | 1.05 | 11 |
| DEX0287__171 Antigenicity Index(Jameson-Wolf) | | |
| 12–25 | 1.06 | 14 |
| 49–67 | 1.02 | 19 |
| DEX0287__173 Antigenicity Index(Jameson-Wolf) | | |
| 9–29 | 1.37 | 21 |
| DEX0287__176 Antigenicity Index(Jameson-Wolf) | | |
| 34–47 | 1.11 | 14 |
| DEX0287__177 Antigenicity Index(Jameson-Wolf) | | |
| 191–202 | 1.19 | 12 |
| 113–149 | 1.05 | 37 |
| 246–259 | 1.04 | 14 |
| DEX0287__179 Antigenicity Index(Jameson-Wolf) | | |
| 63–84 | 1.22 | 22 |
| 30–39 | 1.08 | 10 |
| DEX0287__180 Antigenicity Index(Jameson-Wolf) | | |
| 60–81 | 1.23 | 22 |
| 27–36 | 1.08 | 10 |
| DEX0287__182 Antigenicity Index(Jameson-Wolf) | | |
| 710–723 | 1.17 | 14 |
| 150–166 | 1.11 | 17 |
| 320–335 | 1.09 | 16 |
| 40–55 | 1.04 | 16 |
| 177–237 | 1.01 | 61 |
| DEX0287__184 Antigenicity Index(Jameson-Wolf) | | |
| 1405–1417 | 1.14 | 13 |
| 717–779 | 1.13 | 63 |
| 794–824 | 1.11 | 31 |
| 1141–1157 | 1.10 | 17 |
| 839–874 | 1.09 | 36 |
| 1419–1433 | 1.05 | 15 |
| 1278–1287 | 1.03 | 10 |

| positions | AI avg | length |
|---|---|---|
| 1036–1052 | 1.02 | 17 |
| 1292–1327 | 1.01 | 36 |
| 1480–1503 | 1.01 | 24 |
| 1230–1255 | 1.01 | 26 |
| 1000–1030 | 1.00 | 31 |
| DEX0287__189 Antigenicity Index(Jameson-Wolf) | | |
| 389–398 | 1.26 | 10 |
| 349–382 | 1.22 | 34 |
| 59–73 | 1.20 | 15 |
| DEX0287__194 Antigenicity Index(Jameson-Wolf) | | |
| 43–63 | 1.24 | 21 |
| DEX0287__195 Antigenicity Index(Jameson-Wolf) | | |
| 75–85 | 1.04 | 11 |
| 42–51 | 1.03 | 10 |
| DEX0287__197 Antigenicity Index(Jameson-Wolf) | | |
| 41–57 | 1.07 | 17 |
| DEX0287__198 Antigenicity Index(Jameson-Wolf) | | |
| 814–826 | 1.25 | 13 |
| 736–753 | 1.15 | 18 |
| 462–471 | 1.15 | 10 |
| 649–690 | 1.14 | 42 |
| 781–807 | 1.11 | 27 |
| 633–643 | 1.09 | 11 |
| 124–138 | 1.08 | 15 |
| 861–872 | 1.05 | 12 |
| 52–87 | 1.04 | 36 |
| 395–405 | 1.03 | 11 |
| 91–118 | 1.03 | 28 |
| DEX0287__200 Antigenicity Index(Jameson-Wolf) | | |
| 158–189 | 1.12 | 32 |
| 259–272 | 1.06 | 14 |
| 61–100 | 1.00 | 40 |
| DEX0287__205 Antigenicity Index(Jameson-Wolf) | | |
| 63–72 | 1.16 | 10 |
| DEX0287__206 Antigenicity Index(Jameson-Wolf) | | |
| 90–101 | 1.08 | 12 |
| DEX0287__207 Antigenicity Index(Jameson-Wolf) | | |
| 22–34 | 1.27 | 13 |
| DEX0287__209 Antigenicity Index(Jameson-Wolf) | | |
| 17–55 | 1.02 | 39 |
| DEX0287__212 Antigenicity Index(Jameson-Wolf) | | |
| 19–32 | 1.10 | 14 |
| DEX0287__213 Antigenicity Index(Jameson-Wolf) | | |
| 51–72 | 1.23 | 22 |
| 18–27 | 1.08 | 10 |
| DEX0287__214 Antigenicity Index(Jameson-Wolf) | | |
| 28–38 | 1.12 | 11 |
| DEX0287__218 Antigenicity Index(Jameson-Wolf) | | |
| 2–25 | 1.18 | 24 |
| DEX0287__219 Antigenicity Index(Jameson-Wolf) | | |
| 502–511 | 1.36 | 10 |
| 546–587 | 1.15 | 42 |
| 153–191 | 1.05 | 39 |
| 193–213 | 1.03 | 21 |
| DEX0287__223 Antigenicity Index(Jameson-Wolf) | | |
| 18–33 | 1.14 | 16 |
| DEX0287__226 Antigenicity Index(Jameson-Wolf) | | |
| 11–21 | 1.07 | 11 |
| DEX0287__227 Antigenicity Index(Jameson-Wolf) | | |
| 39–66 | 1.17 | 28 |
| DEX0287__230 Antigenicity Index(Jameson-Wolf) | | |
| 68–78 | 1.00 | 11 |
| DEX0287__231 Antigenicity Index(Jameson-Wolf) | | |
| 153–190 | 1.16 | 38 |
| 205–231 | 1.06 | 27 |
| 21–37 | 1.00 | 17 |
| DEX0287__232 Antigenicity Index(Jameson-Wolf) | | |
| 30–41 | 1.02 | 12 |
| DEX0287__233 Antigenicity Index(Jameson-Wolf) | | |
| 239–249 | 1.13 | 11 |
| DEX0287__234 Antigenicity Index(Jameson-Wolf) | | |
| 35–46 | 1.25 | 12 |
| DEX0287__238 Antigenicity Index(Jameson-Wolf) | | |
| 91–100 | 1.19 | 10 |
| 140–150 | 1.04 | 11 |
| DEX0287__244 Antigenicity Index(Jameson-Wolf) | | |
| 662–694 | 1.20 | 33 |
| 36–61 | 1.12 | 26 |
| 98–118 | 1.10 | 21 |
| 283–334 | 1.02 | 52 |
| 699–740 | 1.01 | 42 |
| DEX0287__245 Antigenicity Index(Jameson-Wolf) | | |
| 7–16 | 1.09 | 10 |
| DEX0287__251 Antigenicity Index(Jameson-Wolf) | | |
| 2–61 | 1.05 | 60 |
| DEX0287__262 Antigenicity Index(Jameson-Wolf) | | |
| 51–98 | 1.28 | 48 |
| 154–164 | 1.13 | 11 |
| 236–265 | 1.08 | 30 |
| 179–220 | 1.08 | 42 |
| 334–363 | 1.04 | 30 |
| 290–312 | 1.02 | 23 |
| DEX0287__263 Antigenicity Index(Jameson-Wolf) | | |
| 4–24 | 1.03 | 21 |
| DEX0287__265 Antigenicity Index(Jameson-Wolf) | | |
| 8–17 | 1.05 | 10 |
| DEX0287__273 Antigenicity Index(Jameson-Wolf) | | |
| 7–22 | 1.11 | 16 |
| DEX0287__279 Antigenicity Index(Jameson-Wolf) | | |
| 10–21 | 1.15 | 12 |

The predicted helicity for the amino acid sequences is listed below:

| | | |
|---|---|---|
| DEX0287__166 | PredHel = 1 | Topology = i21-41o |
| DEX0287__171 | PredHel = 1 | Topology = o26-48i |
| DEX0287__174 | PredHel = 1 | Topology = o22-44i |
| DEX0287__176 | PredHel = 1 | Topology = o15-32i |
| DEX0287__179 | PredHel = 1 | Topology = o40-62i |
| DEX0287__180 | PredHel = 1 | Topology = o37-59i |
| DEX0287__181 | PredHel = 1 | Topology = i12-34o |
| DEX0287__183 | PredHel = 1 | Topology = o10-32i |
| DEX0287__186 | PredHel = 2 | Topology = i34-56o60-82i |
| DEX0287__187 | PredHel = 3 | Topology = o20-39i46-68o73-92i |
| DEX0287__189 | PredHel = 1 | Topology = i200-222o |
| DEX0287__190 | PredHel = 1 | Topology = o20-42i |

| | | |
|---|---|---|
| DEX0287_191 | PredHel = 1 | Topology = o10-32i |
| DEX0287_202 | PredHel = 2 | Topology = i5-27o67-89i |
| DEX0287_203 | PredHel = 1 | Topology = o65-87i |
| DEX0287_208 | PredHel = 1 | Topology = o15-37i |
| DEX0287_209 | PredHel = 1 | Topology = o51-73i |
| DEX0287_213 | PredHel = 1 | Topology = o28-50i |
| DEX0287_217 | PredHel = 1 | Topology = o22-44i |
| DEX0287_222 | PredHel = 1 | Topology = i7-24o |
| DEX0287_224 | PredHel = 1 | Topology = o15-37i |
| DEX0287_227 | PredHel = 2 | Topology = i2-21o68-85i |
| DEX0287_234 | PredHel = 1 | Topology = i48-70o |
| DEX0287_235 | PredHel = 1 | Topology = i20-42o |
| DEX0287_236 | PredHel = 1 | Topology = o10-32i |
| DEX0287_244 | PredHel = 1 | Topology = o616-638i |
| DEX0287_248 | PredHel = 1 | Topology = i7-26o |
| DEX0287_252 | PredHel = 2 | Topology = i5-27o42-64i |
| DEX0287_258 | PredHel = 1 | Topology = o37-59i |
| DEX0287_260 | PredHel = 1 | Topology = o15-32i |
| DEX0287_263 | PredHel = 1 | Topology = i23-45o |
| DEX0287_265 | PredHel = 3 | Topology = o15-37i74-96o169-191i |
| DEX0287_271 | PredHel = 3 | Topology = i5-22o32-54i61-83o |
| DEX0287_274 | PredHel = 1 | Topology = o62-84i |
| DEX0287_280 | PredHel = 2 | Topology = i7-29o33-55i |

Examples of post-translational modifications (PTMs) of the BSPs of this invention are listed below. In addition, antibodies that specifically bind such post-translational modifications may be useful as a diagnostic or as therapeutic. Using the ProSite database (Bairoch et al., Nucleic Acids Res. 25(1):217–221 (1997), the contents of which are incorporated by reference), the following PTMs were predicted for the LSPs of the invention (http://npsa-pbil.ibcp.fr/cgi-bin/npsa_automat.pl?page=npsa_prosite.html most recently accessed Oct. 23, 2001). For full definitions of the PTMs see http://www.expasy.org/cgi-bin/prosite-list.pl most recently accessed Oct. 23, 2001.

| | |
|---|---|
| DEX0287_165 | Ck2_Phospho_Site 50–53; 73–76; Myristyl 46–51; Pkc_Phospho_Site 13–15; 73–75; Tyr_Phospho_Site 14–21; 15–21; |
| DEX0287_166 | Ck2_Phospho_Site 43–46; Pkc_Phospho_Site 6–8; 17–19; |
| DEX0287_167 | Pkc_Phospho_Site 42–44; Tyr_Phospho_Site 28–34; |
| DEX0287_168 | Atp_Gtp_A 40–47; Ck2_Phospho_Site 7–10; 127–130; Myristyl 17–22; Pkc_Phospho_Site 50–52; 178–180; 201–203; |
| DEX0287_169 | Myristyl 26–31; 47–52; 51–56; |
| DEX0287_170 | Asn_Glycosylation 31–34; Ck2_Phospho_Site 10–13; |
| DEX0287_171 | Myristyl 9–14; Pkc_Phospho_Site 13–15; 14–16; |
| DEX0287_172 | Pkc_Phospho_Site 29–31; |
| DEX0287_173 | Asn_Glycosylation 23–26; |
| DEX0287_174 | Prokar_Lipoprotein 23–33; |
| DEX0287_175 | Camp_Phospho_Site 3–6; Myristyl 31–36; 90–95; |
| DEX0287_176 | Asn_Glycosylation 44–47; |
| DEX0287_177 | Asn_Glycosylation 55–58; Ck2_Phospho_Site 91–94; 193–196; Myristyl 141–146; 199–204; 200–205; 223–228; Pkc_Phospho_Site 26–28; 34–36; 91–93; 95–97; 115–117; 121–123; 252–254; 253–255; |
| DEX0287_178 | Ck2_Phospho_Site 43–46; |
| DEX0287_179 | Asn_Glycosylation 4–7; Myristyl 2–7; 3–8; 16–21; 47–52; Pkc_Phospho_Site 7–9; 12–14; 64–66; |
| DEX0287_180 | Myristyl 13–18; 44–49; Pkc_Phospho_Site 4–6; 9–11; 61–63; 96–98; |
| DEX0287_181 | Asn_Glycosylation 37–40; Pkc_Phospho_Site 49–51; 54–56; |
| DEX0287_182 | Asn_Glycosylation 7–10; 70–73; 336–339; 408–411; 519–522; Camp_Phospho_Site 561–564; Ck2_Phospho_Site 65–68; 176–179; 181–184; 186–189; 191–194; 200–203; 201–204; 217–220; 229–232; 231–234; 247–250; 317–320; 321–324; 322–325; 359–362; 365–368; 410–413; 416–419; 457–460; 484–487; 510–513; 521–524; 569–572; 627–630; 631–634; 636–639; 661–664; 718–721; Cpsase_2 618–625; Myristyl 130–135; 291–296; 332–337; 458–463; 604–609; 680–685; Pkc_Phospho_Site 44–46; 150–152; 181–183; 214–216; 397–399; 450–452; 713–715; Tyr_Phospho_Site 578–585; Uch_2_2 281–298; |
| DEX0287_183 | Amidation 22–25; |
| DEX0287_184 | Asn_Glycosylation 61–64; 154–157; 241–244; 345–348; Camp_Phospho_Site 3–6; Ck2_Phospho_Site 56–59; 621–624; 839–842; 851–854; Myristyl 32–37; 37–42; 38–43; 39–44; 40–45; 41–46; 42–47; 89–94; 94–99; 96–101; 165–170; 169–174; 172–177; 173–178; 257–262; 258–263; 267–272; 271–276; 324–329; 444–449; 456–461; 484–489; 513–518; 629–634; 926–931; 952–957; Pkc_Phospho_Site 316–318; 844–846; |
| DEX0287_185 | Pkc_Phospho_Site 20–22; |
| DEX0287_186 | Asn_Glycosylation 10–13; 75–78; Myristyl 28–33; Pkc_Phospho_Site 82–84; Prokar_Lipoprotein 8–18; 19–29; |
| DEX0287_187 | Asn_Glycosylation 19–22; 84–87; Myristyl 37–42; Pkc_Phospho_Site 91–93; Prokar_Lipoprotein 17–27; 28–38; |
| DEX0287_188 | Asn_Glycosylation 42–45; Pkc_Phospho_Site 13–15; Tyr_Phospho_Site 30–36; |
| DEX0287_189 | Asn_Glycosylation 52–55; 131–134; 145–148; 343–346; Camp_Phospho_Site 240–243; Ck2_Phospho_Site 57–60; 68–71; 119–122; 363–366; Myristyl 102–107; 178–183; 231–236; 353–358; Pkc_Phospho_Site 61–63; 68–70; 119–121; 238–240; 243–245; 254–256; 374–376; |
| DEX0287_190 | Amidation 6–9; |
| DEX0287_192 | Asn_Glycosylation 34–37; Ck2_Phospho_Site 15–18; 27–30; |
| DEX0287_193 | Myristyl 42–47; 72–77; 76–81; Pkc_Phospho_Site 53–55; |
| DEX0287_194 | Ck2_Phospho_Site 57–60; Myristyl 55–60; 72–77; |
| DEX0287_195 | Camp_Phospho_Site 36–39; Ck2_Phospho_Site 75–78; |
| DEX0287_197 | Asn_Glycosylation 20–23; Camp_Phospho_Site 26–29; Ck2_Phospho_Site 38–41; 43–46; Myristyl 16–21; 63–68; |
| DEX0287_198 | Amidation 653–656; Asn_Glycosylation 75–78; 673–676; Camp_Phospho_Site 126–129; Ck2_Phospho_Site 13–16; 66–69; 76–79; 77–80; 97–100; 99–102; 129–132; 225–228; 400–403; |

| | |
|---|---|
| | 434–437; 461–464; 481–484; 547–550; 603–606; 610–613; 801–804; 814–817; 818–821; 834–837; 865–868; 917–920; 919–922; Glycosaminoglycan 854–857; Myristyl 72–77; 155–160; 173–178; 326–331; 440–445; 507–512; 508–513; 576–581; 639–644; 740–745; 741–746; 744–749; 806–811; 855–860; Pkc_Phospho_Site 31–33; 61–63; 66–68; 163–165; 177–179; 400–402; 441–443; 465–467; 466–468; 495–497; 586–588; 648–650; 801–803; 904–906; |
| DEX0287_199 | Ck2_Phospho_Site 7–10; Pkc_Phospho_Site 13–15; |
| DEX0287_200 | Amidation 44–47; 93–96; Asn_Glycosylation 172–175; Camp_Phospho_Site 108–111; 158–161; Ck2_Phospho_Site 33–36; 260–263; 290–293; Glycosaminoglycan 78–81; Myristyl 10–15; 73–78; 100–105; 112–117; 177–182; 227–232; 288–293; Pkc_Phospho_Site 126–128; 164–166; 245–247; 260–262; |
| DEX0287_201 | Asn_Glycosylation 82–85; Ck2_Phospho_Site 58–61; 91–94; Myristyl 8–13; 16–21; 23–28; 55–60; Pkc_Phospho_Site 28–30; 75–77; 79–81; 96–98; |
| DEX0287_202 | Ck2_Phospho_Site 26–29; 47–50; |
| DEX0287_203 | Ck2_Phospho_Site 17–20; Myristyl 55–60; Pkc_Phospho_Site 59–61; |
| DEX0287_204 | Ck2_Phospho_Site 21–24; 35–38; Myristyl 8–13; Pkc_Phospho_Site 12–14; |
| DEX0287_205 | Pkc_Phospho_Site 16–18; 75–77; |
| DEX0287_206 | Ck2_Phospho_Site 90–93; Myristyl 21–26; 58–63; |
| DEX0287_207 | Asn_Glycosylation 22–25; 41–44; 45–48; Myristyl 23–28; Pkc_Phospho_Site 50–52; |
| DEX0287_210 | Pkc_Phospho_Site 22–24; |
| DEX0287_211 | Ck2_Phospho_Site 36–39; Myristyl 2–7; 94–99; |
| DEX0287_212 | Asn_Glycosylation 17–20; 42–45; Ck2_Phospho_Site 20–23; Myristyl 21–26; Pkc_Phospho_Site 12–14; 29–31; |
| DEX0287_213 | Asn_Glycosylation 101–104; Myristyl 4–9; 35–40; Pkc_Phospho_Site 52–54; 87–89; |
| DEX0287_214 | Pkc_Phospho_Site 31–33; 34–36; |
| DEX0287_215 | Asn_Glycosylation 47–50; Pkc_Phospho_Site 28–30; 38–40; Tyr_Phospho_Site 29–36; 30–36; |
| DEX0287_216 | Camp_Phospho_Site 40–43; 59–62; Ck2_Phospho_Site 17–20; 48–51; 106–109; Pkc_Phospho_Site 28–30; 29–31; 45–47; 53–55; 124–126; |
| DEX0287_218 | Amidation 109–112; Asn_Glycosylation 59–62; Camp_Phospho_Site 68–71; Myristyl 19–24; 83–88; Pkc_Phospho_Site 58–60; 76–78; 92–94; |
| DEX0287_219 | Amidation 523–526; Asn_Glycosylation 60–63; 395–398; 455–458; Camp_Phospho_Site 44–47; 346–349; 507–510; 549–552; Ck2_Phospho_Site 11–14; 48–51; 165–168; 191–194; 216–219; 226–229; 231–234; 256–259; 313–316; 314–317; 349–352; 356–359; 376–379; 397–400; 401–404; 402–405; 403–406; 444–447; 457–460; 458–461; 463–466; 472–475; 484–487; Myristyl 85–90; 243–248; 250–255; 288–293; 369–374; Pkc_Phospho_Site 47–49; 48–50; 77–79; 88–90; 134–136; 184–186; 233–235; 282–284; 318–320; 329–331; 438–440; 499–501; 503–505; 554–556; 576–578; |
| DEX0287_220 | Myristyl 36–41; Pkc_Phospho_Site 5–7; 40–42; Tyr_Phospho_Site 26–32; |
| DEX0287_223 | Myristyl 24–29; |
| DEX0287_225 | Asn_Glycosylation 297–300; Camp_Phospho_Site 266–269; Ck2_Phospho_Site 37–40; 77–80; 107–110; Myristyl 8–13; 53–58; 57–62; 125–130; 177–182; Pkc_Phospho_Site 12–14; 93–95; 107–109; 250–252; 265–267; 299–301; 308–310; Prokar_Lipoprotein 177–187; Thiol_Protease_His 255–265; |
| DEX0287_226 | Pkc_Phospho_Site 4–6; 12–14; |
| DEX0287_227 | Amidation 30–33; Pkc_Phospho_Site 65–67; Prokar_Lipoprotein 2–12; |
| DEX0287_228 | Pkc_Phospho_Site 18–20; |
| DEX0287_229 | Asn_Glycosylation 37–40; Ck2_Phospho_Site 10–13; Myristyl 3–8; Pkc_Phospho_Site 36–38; |
| DEX0287_230 | Camp_Phospho_Site 45–48; Ck2_Phospho_Site 9–12; |
| DEX0287_231 | Amidation 25–28; Camp_Phospho_Site 156–159; Glycosaminoglycan 15–18; Myristyl 11–16; 12–17; 18–23; 22–27; 38–43; 78–83; 82–87; 83–88; 90–95; 101–106; 111–116; 115–120; 123–128; 166–171; 231–236; 232–237; 246–251; 263–268; Pkc_Phospho_Site 93–95; 251–253; Prokar_Lipoprotein 7–17; |
| DEX0287_232 | Asn_Glycosylation 86–89; Ck2_Phospho_Site 21–24; Myristyl 96–101; Pkc_Phospho_Site 18–20; |
| DEX0287_233 | Amidation 72–75; Asn_Glycosylation 119–122; 120–123; Camp_Phospho_Site 107–110; 216–219; Ck2_Phospho_Site 28–31; 43–46; 63–66; 160–163; 169–172; 187–190; Myristyl 69–74; 158–163; Pkc_Phospho_Site 17–19; 24–26; 35–37; 52–54; 59–61; 106–108; 122–124; 184–186; Prokar_Lipoprotein 248–258; |
| DEX0287_234 | Asn_Glycosylation 43–46; Myristyl 56–61; |
| DEX0287_236 | Leucine_Zipper 12–33; |
| DEX0287_237 | Camp_Phospho_Site 6–9; Myristyl 54–59; |
| DEX0287_238 | Ck2_Phospho_Site 66–69; 96–99; Glycosaminoglycan 50–53; Myristyl 47–52; 49–54; 53–58; 62–67; 111–116; 112–117; Pkc_Phospho_Site 12–14; 131–133; 191–193; 209–211; |
| DEX0287_239 | Asn_Glycosylation 2–5; Ck2_Phospho_Site 54–57; Pkc_Phospho_Site 54–56; |
| DEX0287_240 | Amidation 53–56; Asn_Glycosylation 107–110; Camp_Phospho_Site 32–35; 60–63; Pkc_Phospho_Site 4–6; 35–37; 63–65; 70–72; 71–73; 84–86; 123–125; |
| DEX0287_241 | Asn_Glycosylation 37–40; Camp_Phospho_Site 14–17; Ck2_Phospho_Site 7–10; Pkc_Phospho_Site 13–15; |
| DEX0287_242 | Ck2_Phospho_Site 18–21; Myristyl 12–17; |
| DEX0287_243 | Pkc_Phospho_Site 30–32; |
| DEX0287_244 | Asn_Glycosylation 72–75; 261–264; 370–373; 474–477; 516–519; Camp_Phospho_Site 224–227; 366–369; Ck2_Phospho_Site 36–39; 180–183; 253–256; 333–336; 380–383; 457–460; 778–781; Myristyl 177–182; 217–222; 266–271; 319–324; 368–373; 381–386; 384–389; 393–398; 482–487; 575–580; 585–590; 649–654; 731–736; 732–737; Pkc_Phospho_Site 50–52; 151–153; 315–317; 475–477; 507–509; 513–515; 637–639; 653–655; 694–696; Tyr_Phospho_Site 193–200; 290–296; 681–688; |
| DEX0287_245 | Ck2_Phospho_Site 9–12; 27–30; 29–32; Myristyl 16–21; Pkc_Phospho_Site 5–7; 21–23; 24–26; |
| DEX0287_246 | Glycosaminoglycan 25–28; Myristyl 24–29; |
| DEX0287_248 | Asn_Glycosylation 34–37; Ck2_Phospho_Site 36–39; |

-continued

| | |
|---|---|
| DEX0287_249 | Asn_Glycosylation 43–46; 51–54; Ck2_Phospho_Site 34–37; Pkc_Phospho_Site 70–72; |
| DEX0287_250 | Asn_Glycosylation 35–38; Ck2_Phospho_Site 37–40; Myristyl 3–8; Pkc_Phospho_Site 57–59; |
| DEX0287_251 | Amidation 28–31; 75–78; 101–104; Camp_Phospho_Site 7–10; Ck2_Phospho_Site 19–22; 48–51; 111–114; Myristyl 16–21; 83–88; 84–89; 96–101; Pkc_Phospho_Site 3–5; 10–12; 26–28; |
| DEX0287_252 | Myristyl 33–38; 52–57; |
| DEX0287_253 | Pkc_Phospho_Site 16–18; |
| DEX0287_254 | Myristyl 14–19; Prokar_Lipoprotein 8–18; |
| DEX0287_255 | Asn_Glycosylation 42–45; Camp_Phospho_Site 12–15; Myristyl 4–9; |
| DEX0287_256 | Asn_Glycosylation 8–11; |
| DEX0287_257 | Pkc_Phospho_Site 11–13; |
| DEX0287_258 | Pkc_Phospho_Site 23–25; |
| DEX0287_259 | Myristyl 19–24; Pkc_Phospho_Site 12–14; |
| DEX0287_260 | Amidation 10–13; Myristyl 18–23; |
| DEX0287_262 | Asn_Glycosylation 53–56; 76–79; Camp_Phospho_Site 64–67; Ck2_Phospho_Site 179–182; 190–193; 216–219; 253–256; 338–341; Dnaj_1 168–187; Glycosaminoglycan 67–70; 83–86; 85–88; 300–303; Myristyl 54–59; 84–89; 99–104; 163–168; 172–177; 227–232; 232–237; 301–306; N6_Mtase 288–294; Pkc_Phospho_Site 42–44; 122–124; 305–307; Rgd 261–263; Tyr_Phospho_Site 337–343; |
| DEX0287_263 | Camp_Phospho_Site 47–50; Myristyl 4–9; Pkc_Phospho_Site 8–10; 19–21; |
| DEX0287_264 | Ck2_Phospho_Site 7–10; Myristyl 3–8; Pkc_Phospho_Site 17–19; |
| DEX0287_265 | Ck2_Phospho_Site 10–13; 144–147; Myristyl 17–22; 157–162; Pkc_Phospho_Site 114–116; 199–201; Prokar_Lipoprotein 15–25; |
| DEX0287_266 | Pkc_Phospho_Site 3–5; 8–10; |
| DEX0287_267 | Ck2_Phospho_Site 58–61; 80–83; 84–87; Pkc_Phospho_Site 28–30; |
| DEX0287_271 | Myristyl 27–32; 141–146; 144–149; Pkc_Phospho_Site 17–19; 55–57; 90–92; 111–113; |
| DEX0287_272 | Myristyl 3–8; |
| DEX0287_273 | Asn_Glycosylation 82–85; Ck2_Phospho_Site 63–66; Myristyl 9–14; 79–84; |
| DEX0287_274 | Asn_Glycosylation 30–33; Pkc_Phospho_Site 31–33; |
| DEX0287_276 | Asn_Glycosylation 11–14; 12–15; |
| DEX0287_277 | Myristyl 4–9; 41–46; Pkc_Phospho_Site 15–17; 21–23; 68–70; |
| DEX0287_278 | Asn_Glycosylation 12–15; Tyr_Phospho_Site 29–36; |
| DEX0287_279 | Myristyl 12–17; Pkc_Phospho_Site 32–34; |

Example 6

Method of Determining Alterations in a Gene Corresponding to a Polynucleotide

RNA is isolated from individual patients or from a family of individuals that have a phenotype of interest. cDNA is then generated from these RNA samples using protocols known in the art. See, Sambrook (2001), supra. The cDNA is then used as a template for PCR, employing primers surrounding regions of interest in SEQ ID NO: 1 through 164. Suggested PCR conditions consist of 35 cycles at 95° C. for 30 seconds; 60–120 seconds at 52–58° C.; and 60–120 seconds at 70° C., using buffer solutions described in Sidransky et al., *Science* 252(5006): 706–9 (1991). See also Sidransky et al., *Science* 278(5340): 1054–9 (1997).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations are then cloned and sequenced to validate the results of the direct sequencing. PCR products is cloned into T-tailed vectors as described in Holton et al., *Nucleic Acids Res.*, 19: 1156 (1991) and sequenced with T7 polymerase (United States Biochemical). Affected individuals are identified by mutations not present in unaffected individuals.

Genomic rearrangements may also be determined. Genomic clones are nick-translated with digoxigenin deoxyuridine 5' triphosphate (Boehringer Manheim), and FISH is performed as described in Johnson et al., *Methods Cell Biol.* 35: 73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C-and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. Id. Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 7

Method of Detecting Abnormal Levels of a Polypeptide in a Biological Sample

Antibody-sandwich ELISAs are used to detect polypeptides in a sample, preferably a biological sample. Wells of a microtiter plate are coated with specific antibodies, at a final concentration of 0.2 to 10 µg/ml. The antibodies are either monoclonal or polyclonal and are produced by the method described above. The wells are blocked so that non-specific binding of the polypeptide to the well is reduced. The coated wells are then incubated for >2 hours at RT with a sample containing the polypeptide. Preferably, serial dilutions of the sample should be used to validate results. The plates are then washed three times with deionized or distilled water to remove unbound polypeptide. Next, 50 µl of specific antibody-alkaline phosphatase conjugate, at a concentration of 25–400 ng, is added and incubated for 2 hours at room temperature. The plates are again washed three times with deionized or distilled water to remove unbound conjugate. 75 μl of 4-methylumbelliferyl phosphate (MUP) or p-nitrophenyl phosphate (NPP) substrate solution are added to each well and incubated 1 hour at room temperature.

The reaction is measured by a microtiter plate reader. A standard curve is prepared, using serial dilutions of a control sample, and polypeptide concentrations are plotted on the X-axis (log scale) and fluorescence or absorbance on the Y-axis (linear scale). The concentration of the polypeptide in the sample is calculated using the standard curve.

Example 8

Formulating a Polypeptide

The secreted polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of secreted polypeptide administered parenterally per dose will be in the range of about 1, μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the secreted polypeptide is typically administered at a dose rate of about 1 μg/kg/hour to about 50 mg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the secreted protein of the invention are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The secreted polypeptide is also suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22: 547–556 (1983)), poly (2-hydroxyethyl methacrylate) (R. Langer et al., J. Biomed. Mater. Res. 15: 167–277 (1981), and R. Langer, Chem. Tech. 12: 98–105 (1982)), ethylene vinyl acetate (R. Langer et al.) or poly-D-(−)-3-hydroxybutyric acid (EP 133,988). Sustained-release compositions also include liposomally entrapped polypeptides. Liposomes containing the secreted polypeptide are prepared by methods known per se: DE Epstein et al., Proc. Natl. Acad. Sci. USA 82: 3688–3692 (1985); Hwang et al., Proc. Natl. Acad. Sci. USA 77: 4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the secreted polypeptide is formulated generally by mixing it at the desired degree of purity, in a unit dosage injectable form (solution, suspension, or emulsion), with a pharmaceutically acceptable carrier, I.e., one that is non-toxic to recipients at the dosages and concentrations employed and is compatible with other ingredients of the formulation.

For example, the formulation preferably does not include oxidizing agents and other compounds that are known to be deleterious to polypeptides. Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The secreted polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

Polypeptides ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Example 9

Method of Treating Decreased Levels of the Polypeptide

It will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 μg/kg of the polypeptide for six consecutive days. Preferably, the polypeptide is in the secreted form. The exact details of the dosing scheme, based on administration and formulation, are provided above.

Example 10

Method of Treating Increased Levels of the Polypeptide

Antisense technology is used to inhibit production of a polypeptide of the present invention. This technology is one example of a method of decreasing levels of a polypeptide, preferably a secreted form, due to a variety of etiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided above.

Example 11

Method of Treatment Using Gene Therapy

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7: 219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB 101, which are then plated onto agar containing kanamycin for the purpose of confirming that the vector has the gene of interest properly inserted.

The amphotropic pA317 or GP+aml2 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media.

If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 12

Method of Treatment Using Gene Therapy-In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide.

The polynucleotide of the present invention may be operatively linked to a promoter or any other genetic elements necessary for the expression of the polypeptide by the target tissue. Such gene therapy and delivery techniques and methods are known in the art, see, for example, WO 90/11092, WO 98/11779; U.S. Pat. Nos. 5,693,622; 5,705, 151; 5,580,859; Tabata H. et al. (1997) Cardiovasc. Res. 35 (3): 470–479, Chao J et al. (1997) Pharmacol. Res. 35 (6): 517–522, Wolff J. A. (1997) Neuromuscul. Disord. 7 (5): 314–318, Schwartz B. et al. (1996) Gene Ther. 3 (5):

405–411, Tsurumi Y. et al. (1996) Circulation 94 (12): 3281–3290 (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772: 126–139 and Abdallah B. et al. (1995) Biol. Cell 85 (1): 1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 μg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice.

The results of the above experimentation in mice can be use to extrapolate proper dosages and other treatment parameters in humans and other animals using naked DNA.

Example 13

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40: 691–698 (1994); Carver et al., Biotechnology (NY) 11: 1263–1270 (1993); Wright et al., Biotechnology (NY) 9: 830–834 (1991); and Hoppe et al., U.S. Pat. No. 4,873,191 (1989)); retrovirus mediated gene transfer into germ lines (Van der Putten et al., Proc. Natl. Acad. Sci., USA 82: 6148–6152 (1985)), blastocysts or embryos; gene targeting in embryonic stem cells (Thompson et al., Cell 56: 313–321 (1989)); electroporation of cells or embryos (Lo, 1983, Mol Cell. Biol. 3: 1803–1814 (1983)); introduction of the polynucleotides of the invention using a gene gun (see, e.g., Ulmer et al., Science 259: 1745 (1993); introducing nucleic acid constructs into embryonic pleuripotent stem cells and transferring the stem cells back into the blastocyst; and sperm mediated gene transfer (Lavitrano et al., Cell 57: 717–723 (1989); etc. For a review of such techniques, see Gordon, "Transgenic Animals," Intl. Rev. Cytol. 115: 171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380: 64–66 (1996); Wilmut et al., Nature 385: 810813 (1997)).

The present invention provides for transgenic animals that carry the transgene in all their cells, as well as animals which carry the transgene in some, but not all their cells, I. e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89: 6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265: 103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

Example 14

Knock-Out Animals

Endogenous gene expression can also be reduced by inactivating or "knocking out" the gene and/or its promoter using targeted homologous recombination. (E. g., see Smithies et al., Nature 317: 230–234 (1985); Thomas & Capecchi, Cell 51: 503512 (1987); Thompson et al., Cell 5: 313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (I.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc.

The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying conditions and/or disorders associated with aberrant expression, and in screening for compounds effective in ameliorating such conditions and/or disorders.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

We claim:

1. An isolated nucleic acid molecule comprising
   (a) a nucleic acid molecule comprising a nucleic acid sequence that encodes SEQ ID NO: 238;
   (b) a nucleic acid molecule comprising SEQ ID NO: 105;
   (c) a nucleic acid molecule having at least 70% sequence identity to the nucleic acid molecule of (a) or (b).

2. The nucleic acid molecule according to claim 1, wherein the nucleic acid molecule is a cDNA.

3. The nucleic acid molecule according to claim 1, wherein the nucleic acid molecule is genomic DNA.

4. The nucleic acid molecule according to claim 1, wherein the nucleic acid molecule is a mammalian nucleic acid molecule.

5. The nucleic acid molecule according to claim 4, wherein the nucleic acid molecule is a human nucleic acid molecule.

6. A method for determining the presence of a breast specific nucleic acid (BSNA) in a sample, comprising the steps of:
   (a) contacting the sample with the nucleic acid molecule according to claim 1 under conditions in which the nucleic acid molecule will selectively hybridize to a breast specific nucleic acid; and
   (b) detecting hybridizatioin of the nucleic acid molecule to a BSNA in the sample, wherein the detection of the hybridization indicates the presence of a BSNA in the sample.

7. A vector comprising the nucleic acid molecule of claim 1.

8. A host cell comprising the vector according to claim 7.

9. A method for producing a polypeptide encoded by the nucleic acid molecule according to claim 1, comprising the steps of (a) providing a host cell comprising the nucleic acid molecule operably linked to one or more expression control sequences, and (b) incubating the host cell under conditions in which the polypeptide is produced.

10. A vaccine comprising the nucleic acid encoding the polypeptide of claim 1.

* * * * *

SEQUENCE LISTING

<160> NUMBER OF SEQ ID NOS: 280

<210> SEQ ID NO 1
<211> LENGTH: 598
<212> TYPE: DNA
<213> ORGANISM: Homo sapien

<400> SEQUENCE: 1

```
cgaggtactc tgctgggtta caggatttca gtaggtattt gtgtccacct gagaattctg      60
tttattacct ttcatttgac agtgtctttc ccttctgcag ttgattttgc tagagaggca     120
attcataagg tgaggtcctg ttcatagtat gacttgcttt ctcaatatct ccttcaattt     180
ttagtaactc ttggtctatt tggtgtcttt aaaaaaaata acctagtaat aaagacttct     240
tttaatgtgg aaatgtggtc tggtagtaag ttatttcttt ccacatgtaa ctgacccaat     300
ctggtttcca aatgagaagt gtgcaggccc cagaggttga gaagccatat ttcaactgtg     360
aaaaaaatct gcttcctgca tctgttgaaa tatagttgtt catacttgcc atcccttatc     420
tttcttgtaa caatttgcac agttcttgcc agaataaatg ccattatctg tatgtttcag     480
ggagttcccc aatttgatca tttttgtgtg tgtgtggtgt gtgtgtgaga gagagagata     540
ctgcagtaaa acatttctaa aggatgaaag ctcttgtatg gcatagatat gaattcct      598
```

<210> SEQ ID NO 2
<211> LENGTH: 2563
<212> TYPE: DNA
<213> ORGANISM: Homo sapien

<400> SEQUENCE: 2

```
gagtcttagt tttcctgcat aagacctcct ttatgaatag aataaaagac tgtcaaagta      60
ggctgggctt gggcccaggc taatctatga aggaagcaag ctcgtgttcc ttacctatcc     120 tttttggtgtc cattggattg tgccccgaag tggccttttac ccttgagccg tccccagcca     180
tggtgctcac acataggctt ttgagctcct tggagctatc cagatcctgc tcacttttcc     240
ttcctgaggt cagaacaaat caccccctta ctcccactcc aaacaaggcc ttgatgataa     300
actaatcctt cctaaaatgc tggtaggtaa acaagcaatg atgaagcatt gaacacaggt     360
taactcctga ctttttgtacc attgtctatt ccattacaca ttaacatgac tctgaatgcc     420
```

```
agatccaaac ctttgcccac catctgcttg tcgtgcaaca gttgaggcag taaccagggg    480
agattcactt cctgtcttgt ccttccccag ggatcacccc cctgctgccc tctagcagcc    540
aagctcagat gagttccatt gttaccctag gtgtgcccat ctctttggta gggaaggaga    600
aaggtaagaa tagccatcaa tgaggaagga ttcttggagc gaggagccac tgtggttttt    660
cctgctattt aagatgttga gaccggataa ctttagaaag atacctgcac aaacccataa    720
atactgcttt tataaagttt agttcaccgg aacctgagtt cagtatttga cattagcttt    780
ttgtccaaag agttgaagcc tgctggaggt ctttgctcaa ataataaata ccacatattt    840
ccaagtgtgt tcaggtatag cactaggta ctgtctgttt acttcatgtt aggcacatta    900
catgcattgg ctaatcaaat cctcatcaat tacatatgta ataatctaaa cttgcctcct    960
tgtattataa atggaaataa tcctgtttat ttaaacgggt tttcatgtac ctgtagggat   1020
taggaaactc aaatggcctt tttaatacct ttccctagtt tgagctccct gttctcttta   1080
acagataaaa caacatattt gcttcagcct ggaatctgtt tttggtgctt tggtgcagag   1140
acaggaaatg ggcactcaga gtcacactgg tagttgcaca ctgtatctac agagggcgtg   1200
tctcatctgt actctgctgg gttacaggat ttcagtaggt atttgtgtcc acctgagaat   1260
tctgtttatt acctttcatt tgacagtgtc tttcctttct gcagttgatt ttgctagaga   1320
ggcaattcat aaggtgaggt cctgttcata gtatgacttg cttctcaat atctccttca    1380 attttagta actcttggtc tatttggtgt ctttaaaaaa aataacctag taataaagac    1440
ttcttttaat gtggaaatgt ggtctggtag taagttattt cttccacat gtaactgacc    1500 caatctggtt tccaaatgag aagtgtgcag gccccagagg ttgagaagcc atatttcaac   1560
tgtgaaaaaa atctgcttcc tgcatctgtt gaaatatagt tgttcatact tgccatccct   1620
tatctttctt gtaacaattt gcacagttct tgccagaata aatgccatta tctgtatgtt   1680
tcagggagtt ccccaatttg atcattttg tgtgtgtgtg gtgtgtgtgt gagagagaga    1740
gatactgcag taaaacattt ctaaaggatg aaagctcttg tatggcatag atatgaattc   1800
cttcctctgg taataattag gttattccca gaagcacagt gtcattcttt aaataaaagc   1860
tttcctgttt aaagcttttc aaaggagcag accaccttga agattccccc tagggttgat   1920
atgtgtctaa ttcattttat aaaaattatt cttgtcttca ttttaaagct ttggctatat   1980
agtcagaaat gtcctaaata acaaactatt ttgtatttaa tttagggaag actaaaggga   2040
agaaaaatga aaactcagtc tttatgtaag ctccaaggat attagggctt aaagggcttt   2100
tctagtttta tgagaatttg tactactgat ttttatatat tcctgttttt gagatgaaca   2160
gatctctggg gaaattgttg agttacaatg gcatttcact gtgatccctc tcaagctcag   2220
atcagttcta taacccaatg acaacctgtc tctttggttt actgtcctgt gaaatgtcag   2280
ctcaagtttc ccagaagtcg tgtgtttatg atgagtcaga gtgcttttcc tcggtgggac   2340
agttgctggc cctcttaatt ttggtgtatg tgcttccaag tatctaaacc tccagtctga   2400
tctgtatatg ctatcctaac tgttaattgt attattgatt atgttgatta tcttgcttga   2460
aggttcatac ttttcaattt gatagaaata aagttttttt ctgcttatag ctagcgaaaa   2520
aaaaaaaaaa aaaaaaaaa aaaaaaaaa aaaaactcgg cgc                       2563
```

<210> SEQ ID NO 3
<211> LENGTH: 870
<212> TYPE: DNA
<213> ORGANISM: Homo sapien

<400> SEQUENCE: 3

-continued

```
acagtctgtt tcctccttca cccccagaac aaaaatcgaa cttctggttg dacagcgtca    60
gatgtcactg aggtgacccc agcctgtttg cagttccaag tcttccgtgt aggcgtcact   120
gctactggaa ctttgtagat gaggagcctg tatgatgatg tcctgaacat ttctatcctt   180
tcctcacaca gagggaagct acagaatgaa ggggctggaa aacgttggtc tggttccttt   240
tagagctgat tccccattgg atactgcctg gaggccttgg ggatgaatga aagttctgc    300
agtttggatc agtagcagaa gcaggtaaca catcagggaa ccggtcagcc ttttagggtc   360
tcagcttcct catctggaaa attagaacaa aatatctacc tcacaatggt cacctgtgga   420
tttaatgaga aatatgtgta agatgcttag aacattttcc agatatataa cagatgtgaa   480
ataaatattt ttattggtgt tatcgagtgg ttctagatta actttggggc ttggaactct   540
gcacataagc tctgagccag ttaattatcc cttttacttt tcgccaagtg acaggttttt   600
ctcccatcca tttcttcctt caaaagagcc ctaaagtaac accgggccaa gggctatatg   660
acacatatac aaagcgaaga tgcctattta aatctgttgt ctaacccaa cttttagtaa    720
acttaaaagc acagcatatt ccttctccca tttgggaaga ttttaacgtc tcttatactc   780
tggatttgtt accgctcatc ctttggaaaa agttttttcg ttttatactt cccttgatgt   840
cccatctaac atccacttct cggtttcttg                                    870

<210> SEQ ID NO 4
<211> LENGTH: 1000
<212> TYPE: DNA
<213> ORGANISM: Homo sapien

<400> SEQUENCE: 4
gcccgcactt tttttttttt ttttttttag acaagaaatt attttagtcc tttagtacag    60
tctgtttcct ccttcacccc cagaacaaaa atcgaacttc tggttggaca gcgtcagatg   120
tcactgaggt gaccccagcc tgtttgcagt tccaagtctt ccgtgtaggc gtcactgcta   180
ctggaacttt gtagatgagg agcctgtatg atgatgtcct gaacatttct atcctttcct   240
cacacagagg gaagctacag aatgaagggg ctggaaaacg ttggtctggt tcctttttaga   300
gctgattccc cattggatac tgcctggagg ccttggggat gaatgagaag ttctgcagtt   360
tggatcagta gcagaagcag gtaacacatc agggaaccgg tcagcctttt agggtctcag   420
cttcctcatc tggaaaatta gaacaaaata tctacctcac aatggtcacc tgtggattta   480
atgagaaata tgtgtaagat gcttagaaca ttttccagat atataacaga tgtgaaataa   540
atatttttat tggtgttatc gagtggttct agattaactt tggggcttgg aactctgcac   600
ataagctctg agccagttaa ttatcccttt tactttcgcc aagtgacagg ttttctccca   660
tccatttctc cttcaaagag ccctaaggta acgggcaaa gggctaatga cacataacaa    720
aggaagatgc ctattaaaat ctgttgttct aaacacaact tttagtaaac attagaaagc   780
aacaggatat ttccttcctc atttggagag aattttaaag tcctgtgaat acattgagga   840
tgtggattac agactagaa tcctaggaaa agaaagtatc tctgccgttg tcaattacct    900
gtccccagct aagactgctc cacaactaaa aacaatccaa actttcagta gggaatatct   960
agttagaagc ttcaaattgg caagttaatg gaccaactct                         1000

<210> SEQ ID NO 5
<211> LENGTH: 319
<212> TYPE: DNA
<213> ORGANISM: Homo sapien
```

```
<400> SEQUENCE: 5
agtagatcca tggggccgtg tcccagatct gccgagcggc gcagtgtgat ggattttcta    60
aagtggggga agaaagttta tagactttcc aagcacattt atggtttttt attactatta   120
ttatggtttt aaaagagta acttttatttc tttttgtaag gaattaagta atatccttta   180
caggttctgt gaaaggactt attttttaac tgtaatattt attagtttta aaatatttgt   240
atctcatttg taacaatttg ttttaatttt ttatatatat gttttttattt ttaaaaaaca   300 taccagttga atggggtta                                                319

<210> SEQ ID NO 6
<211> LENGTH: 4261
<212> TYPE: DNA
<213> ORGANISM: Homo sapien

<400> SEQUENCE: 6
gcttcctcca gagggcggga accttggacg tggcggggct gggtcagtca gggcgctggg    60
cccagcctct ctgcaggctg gccttccgcg ctgccgtgaa gccccgaca ggtcccacgc    120 ctgcctaggt agaccggcgc cagcccgagt gacgcctggc gtgtggccgc gggcaggcgg   180
ctccgtgcgg cggggcgggc gggtgccaca cctgtgcggg caagggcggg gcgggaaggt   240
gcgcaggcgc gctcggggct ggtgggcggt ggctcctggg aagttgcgca gccgaactgg   300
ccggctgggc gcgcgctctt gcggtggcgt aatctctcag cctttctgtg tctcctttcc   360
tccgcctcag tttggggcgg gtcggggaa tggctgagga gatggagtcg tcgctcgagg   420
caagcttttc gtccagcggg gcagtgtcag gggcctcagg gttttttgcct cctgcccgct   480 cccgcatctt caagataatc gtgatcggcg actccaatgt gggcaagaca tgcctgacct   540
accgcttctg cgctggccgc ttccccgacc gcaccgaggc cacgatagg gtggatttcc    600 gagaacgagc ggtggagatt gatgggagc gcatcaagat ccagctatgg gacacagcag   660
gacaagaacg attcagaaag agcatggttc agcactacta cagaaatgta catgctgttg   720
tcttcgtgta tgatatgacc aacatggcta gttttcatag cctaccatct tggatagaag   780
aatgcaaaca acatttgcta gccaatgata taccacggat tcttgttgga aataaatgtg   840
acttgagaag tgccatacag gtacccacag acttggcaca aaatttgct gacacacaca   900 gtatgccttt gtttgaaacg tctgctaaaa accccaatga taatgaccat gtggaagcta   960 tattatgac cttggctcat aagcttaaga gccacaaacc attaatgctt agtcagcccc   1020
ctgataatgg aattatcctg aagcctgaac caaagcctgc aatgacgtgc tggtgctaaa   1080
taacagtctt tattatatta tctaattttg actaaagaaa acttttgaa gtatgacagt   1140 attaagtcat aagatttaat ctcaactata atgggtcatc ttgacacttt gctgtttgtc   1200
attgtcacgc ttttgtattt tgtatctact taagtttgtc actgtgacaa cacaggaaaa   1260
gttggttttc aggtgagatt gaaaatgaag caaagatagg atgaatctga acatctctcc   1320
atctagagcc caatgaagga agcttcaaat gagaacatga tggaatcagt aaccattcaa   1380
tcttttgtcc taggattgga aaaaaatgtt aaaggtttag dacacaccta atagtatgtc   1440
ctttgaatgg gaagtgttct taataggata aaaactggta tttgcctctc cccagagtac   1500
tttttttgtt ttttcataga gacggggtct tgctatgttg tccaggctgg ccttgagctc   1560
ctgggctcaa gcaatcctcc cacctcagcc tccccagtac tgggactgta ggtactcacc   1620
actgcatctg gcctttcttt gttttattaa catatttagt tttgttatta ttggtatgtt   1680
ttagagccaa gactttagtt ccagtgggat aagaaggcat agaatgtttt ctggttccca   1740
```

-continued

```
gtccataaag aatgactttt ccaagagttc tagatgtttg attttctaat taatacttat    1800
cagatctaca aaaatcatta ttattttaaa agagttattt gagtttcttt ctttcttttt    1860
tttttttttt tttttttgaga tggagtctcg ctctgtctcc aggctggagt gcagtggcgt    1920
catctcggct cactgcaacc tccgcctccc aggttcaagt gattctcctg cctcagcctc    1980
ccgagtagct gggattacag gcgtgcacta ccacacccag ctgattttg tattttagt       2040
atagatgggg tttcaccatg ttggccagga tggtctcgat ctcttgacct catgatccac    2100
ccgcctcagc ttcccaaagt gctgggatta caggtgtgag tcactgcacc cagccgagtt    2160
gctttcttac taaatcctat taaaatatgc aaaaataagt cagattttaa ggcaaataaa    2220
gtgacataag gtgctttata ttttattttg gtatatttaa acagtgaaaa actaactgaa    2280
agcacatgaa gagttgtaac ttgggggaaa ataggtaaac atagcttcta gctaacacag    2340
gagacctatt cttagccttt actaatttca agcagtgtat cccatatggt atctcttgct    2400
cttccttcaa ctccaataaa tttaatgact aaatgccaag ttaacaaatc aacttccatt    2460
tggattgtag gtgtgaaggc acaactctaa ttgctattag tctacatgta tttctgtaat    2520
agtattgtgt catatcaatt tttaagatgt ctaaatttta tggtcacaag ttatccctcc    2580
tcagtatgaa aaataaatta gatattgaaa aatgtctaaa cttcagtgat ggaaagaata    2640
tttcaagaag tttttttaacc taaatacttt tattttgaat ttaagtcttt gcacataaaa    2700
tatagcaagc ttacatatta aactatttac gtaaatggaa tgtaagccat gactttaact    2760
gaagtgttca cattcactaa ttttgataga ttgctgtcct taataatttt ggaggaaatt    2820
aagccaaatg attattgtac tacagtattt tcagaatatg ggaaatcaat taaaaatgta    2880
atctaatcta gtttaagatt tttgtttaat catcatggtg gtcctacctg gataatttaa    2940
ctataaagac aaagtaattc tattaaatga actaactgaa ataataatt ataggaagtg      3000
attattccat tttaagtatt agagctcaaa ttggctttat ttgcatttag ggagatcatg    3060
ttttcttaat catgctggaa tttaaaaatt gttttacttg tatcgaaatt aaccttgatt    3120
tataactatt tttgtaataa aacaatgaca gctgtagtaa ctatgatggg tgtaacaaca    3180
ttttttttaaa gaagggaatc tgtttatcgc ttttcaaaat attttctaaa gtgggggaag    3240
aaagtttata gactttccaa gcacatttat ggttttttat tactattatt atggttttaa    3300
aaagagtaac tttatttctt tttgtaagga attaagtaat atcctttaca gttctgtgaa    3360
aggacttatt ttttaactgt aatatttatt agttttaaaa tatttgtatc tcatttgtaa    3420
caatttgttt taatttttta tatatatgtt tttattttta aaaaacatac cagttgaatg    3480
gggttaaagc tttcaatatc ttaaaatatt tataaaacat ttcactgttg caaaatcact    3540
tccaaaatga tagctatcta acaactaatt actaattttt aaagaacaaa tcacacattt    3600
aaaaaatctg tagaatttat tttaactatg acctttaatt gaaaataaat aattaaaata    3660
tcagacatgt tttggaaaag tcttaatttg agaacaccaa aggaaactac cccagaatct    3720
aatgtagttc gctattaata acaatgcatt attgaaagta tattgcaaat acatgtttcc    3780
tcatgaaatc taagtaattt tgttgtggaa tagtgtcact gttacatttc ccccatgaag    3840
ttcaataaac cagcttagcc acaaaaaaat tacttagatt tcatgaggaa acatgtattt    3900
gcaatatact ttcaataatg cattgttatt aatagctaac tacattagat tctgggtag     3960
tttcctttgg tgttctctaa ttaagacttt tccaaaacat gtctgatatt ttaattattt    4020
attttcaatt aaaggtcata gttaaaataa ataattacaa tatcagacat gttttggaaa    4080
```

```
agtcttaatt tgagaacacc aaaggaaact accccagaat ctaatgtagt tagctattaa      4140
taacaatgca ttattgaaag tatattgcaa atacatgttt cctcatgaaa tctaagtaat      4200
tttgttgtgg aatagtgtca ctgttacatt tcccccatga agttcaataa accagcttag      4260
c                                                                       4261

<210> SEQ ID NO 7
<211> LENGTH: 539
<212> TYPE: DNA
<213> ORGANISM: Homo sapien

<400> SEQUENCE: 7
actaaagagc acagctgctc aaagtaaagc ctgagcagtg ttctcagtaa tgtatttgaa        60
ggaaaaatac cctgatttga aaccaacagc agatgttgca aactttcata ccactgctgg       120
ccatggaagc ctcttaacaa cacactgtca tttaaggctg tgcttgtgct ttatacaaag       180
agaaagaggt ggtcttaagg ggatgcttcc agggggtga gttcatgcct ctcctgtatt        240
ttccagcaag tggggtataa gtggtggttt gttttttaga ggggcataat aatccaggat       300
tctaagcata tggctcagct attttaaaga ggaaattaaa tattataaaa gaaatagtaa       360
agataagtta tcctcactta ggcaaaagca caggtccttt ccatatcaag tttagcctac       420
cagggttgtt ttttgtttta accctgctta ataatgttgg tgttttagaa gtagatacag       480
gcactgctct gaaaacctgg ctagccaagg atattctcag aatgttatca cctgtttgt        539

<210> SEQ ID NO 8
<211> LENGTH: 3262
<212> TYPE: DNA
<213> ORGANISM: Homo sapien

<400> SEQUENCE: 8
atccaacaac aatactgaga tgatctaaga aggttataac aaaatgctct tcagaaatac        60
ctaagtgctg agaattttta gtactaaaga gcacagctgc tcaaagtaaa gcctgagcag       120
tgttctcagt aatgtatttg aaggaaaaat accctgattt gaaaccaaca gcagatgttg       180
caaactttca taccactgct ggccatggaa gcctcttaac aacacactgt catttaaggc       240
tgtgcttgtg ctttatacaa agagaaagag gtggtcttaa ggggatgctt ccagggggt        300 gagttcatgc ctctcctgta ttttccagca agtggggtat gtgtggtggt ttgttttttta       360 gaggggcata ataatccagg attctaagca tatgctcagc tattttaaag aggaaattaa       420
atattataaa agaaatagta agataagtt atcctcactt aggcaaaagc acaggtcctt        480
tccatatcaa gtttagccta ccagggttgt ttttgtttt aaccctgctt aataatgttg        540
gtgttttaga gtagataca ggcactgctc tgaaaacctg gctagccaag gatattctca        600
gaatgttatc acctgtttgt caaagcttgt ttaaattata aaacttttt aattatatat        660 atgaggcaaa gaactaaga cttttttcaa actaaattag aaaggagtgt cattatttga        720
ctgttaaacc aaaatatttt tggtgggtct ttttatggaa gtttaaagaa aggacatcat       780
catagatatg atctaacagt atttctaact atatttgatc attaaaagcc tcttggaatt       840
tgaagcgtga cgtgtttcta atgcccttg agaggtgaaa ataccacat aatgatcagt        900 atgctgtgcc agcttcattt ggggagaaat aactagtaga agttctgggg tgtgaggtgt       960
acagcagtct aggtggcata gtgatgaaga aagggatcag agtctgactg tcactcagaa       1020
tcctgggctc agttgcttga caaccttggg aaaattgttt tatctttgtg cgtctgtttg      1080
ctgatcttca gcgtgggaat aataacagta cctacttgaa aggatcattg tgcggattaa       1140
```

```
aagaaataat atatgtaaag cactttaaca cagcaccagg cccacggaaa gtggctaatg      1200
ttagctacta tgaatggtgc cagtgaagac actgaaaaat aagtgatttc agtaaccttc      1260
tggaaagcta tcagtttcaa ataatatttt ctctgtagta tgagatgaaa ttaaaagtgg      1320
atagctttca ggaaagataa agagaacatg cttagaatgt aagctaaaca gatttttct       1380 gttgctcttt gaaaactatg agccctggcc agcttaacct ggtctgaggt gagactaaac      1440
acaaaaacag tagataaatc tctccctaaa agatggattc ccccacatac ccatgctact      1500
agtttctctg tctattcaca catatgtaca aatacatgaa cacagcctgt ctgtgctcag      1560
acatagagaa gtactacctg acttgagtca atgcacccaa gaagaaaagc ttggagtaga      1620
gcagaaggga gggcttggga ctcctgtctt ccagcatgc cctggggtgc agtggtcagc       1680
cacctgaaga gagagccaat agcatgggt ttacaaggca aagatagtca ttcattcaac       1740
acatattcat agagctcctt ctctgtgcca gacactgttc tggaagatag ctagatgaaa      1800
atctttgcac tcacagagct acatgccag tgagtgaaga tcgatgataa ataaagcaaa       1860
tgcatcatat gttcacattt gataagtata tgccaaaaaa tgaagccggg aaggaggaca      1920
aggcccatgg gtgggtgttg aggttttaa agtgtggtca ggaaaggccc cactgataag       1980
gtaacatttg agcaagtctg aaaaaggcaa ggggatcttt gggctaact tcggatccc        2040 tgcactttat gtaagaatgt aaacctggag tctcatttaa gaatgatcag caatacgttt     2100
agaacatatg aactgaatga aatggacatt ttttcttaat ttacgtataa atccatatga      2160
ttatacataa agttctgatg cattaataaa agcagccaaa tagggccaaa gagaaaaata     2220
acaggactct gtactggacc taactttatc attaattagg taatatttc ctcatttctt      2280 tactgctgcc atttcctca ccagtattcc agagatggtc atagctcatt actctaccac     2340
caagaaccta aaaggaatta gaatacagca gaattggcct cagtgaagag ctaaaattg     2400 ttctcctcgt agaactggac tattgatcat taccacgtga cgttggctct attactttct    2460
gttcccaatg tccttctagt ggtttgaaaa tgttaaaaca tccctaaaat ctaaatcata    2520
taatcagaat tctatagtgt cccactctat ctgtaaagat catttggaag actttagact    2580
ctattaattt taaaggaat atttattagc catatgcaga atttctaatg atgatattgt     2640
acagcttcta attcactttt cagatcagtg tttgaaatgg caattatcag tgttggattt    2700
agttccaact acttgattta caaaaatgta catttagaga aggttaaaag aaacagtgag    2760
aaatgtaaac attcaaaatg ataattgaat ctctcagttg tgggaataat tatcagagac    2820
atgcaactga aaatgtctca cctttcatct ttttttctta attcataaag ttatcttgta    2880
gaatttgatg agaccctcct agtcattctc aactggggcg gtgctgtcac cgaaatggtg    2940
gtttgacagt gttggggcta ggcacatttt ttggttgtca cagccaccgg gtggcattgc    3000
tgccgtgcat gattgtacat tatgaatgcc gcacgtgtgc tcagtaagtc tccctccaag    3060
gccgcccggg gtcagccgta tccagacttg gagcacgtgg cggtacctgt gtcgggtctg    3120 accctggcc atgtgaactc gttctcacaa aaaagggg caataccggg cactctcctt        3180
ttaagccatg agttaaaacg gggaatagaa aagtttaacc ttgttgaccc actacttttg    3240
ttctcgtata taaacaacat ct                                              3262
```

<210> SEQ ID NO 9
<211> LENGTH: 505
<212> TYPE: DNA
<213> ORGANISM: Homo sapien
<220> FEATURE:

<221> NAME/KEY: misc_feature
<222> LOCATION: (170)..(171)
<223> OTHER INFORMATION: a, c, g or t
<221> NAME/KEY: misc_feature
<222> LOCATION: (179)..(180)
<223> OTHER INFORMATION: a, c, g or t
<221> NAME/KEY: misc_feature
<222> LOCATION: (187)..(188)
<223> OTHER INFORMATION: a, c, g or t
<221> NAME/KEY: misc_feature
<222> LOCATION: (194)..(194)
<223> OTHER INFORMATION: a, c, g or t
<221> NAME/KEY: misc_feature
<222> LOCATION: (197)..(197)
<223> OTHER INFORMATION: a, c, g or t
<221> NAME/KEY: misc_feature
<222> LOCATION: (201)..(202)
<223> OTHER INFORMATION: a, c, g or t
<221> NAME/KEY: misc_feature
<222> LOCATION: (307)..(307)
<223> OTHER INFORMATION: a, c, g or t
<221> NAME/KEY: misc_feature
<222> LOCATION: (326)..(326)
<223> OTHER INFORMATION: a, c, g or t
<221> NAME/KEY: misc_feature
<222> LOCATION: (355)..(355)
<223> OTHER INFORMATION: a, c, g or t
<221> NAME/KEY: misc_feature
<222> LOCATION: (365)..(365)
<223> OTHER INFORMATION: a, c, g or t
<221> NAME/KEY: misc_feature
<222> LOCATION: (430)..(430)
<223> OTHER INFORMATION: a, c, g or t
<221> NAME/KEY: misc_feature
<222> LOCATION: (448)..(448)
<223> OTHER INFORMATION: a, c, g or t
<221> NAME/KEY: misc_feature
<222> LOCATION: (451)..(451)
<223> OTHER INFORMATION: a, c, g or t
<221> NAME/KEY: misc_feature
<222> LOCATION: (456)..(456)
<223> OTHER INFORMATION: a, c, g or t

<400> SEQUENCE: 9

| | | | | | |
|---|---|---|---|---|---|
| acacatctat | ctttcctttg | ggtagggtca | cccaactgct | ctgccacttc | cagctgtgaa | 60 |
| aggcatctat | gtgacagacc | cctctgcagt | ttgaaactgt | gtgacaatct | ttaacaccca | 120 |
| actcagcatc | tgcatgcggt | ttctgagaat | tacctatatc | ttttgtgggn | ngtctcttnn | 180 |
| tgctganntt | ctcntgnttt | nncattaaaa | aaaaaaaga | gtgacctcgg | ggatctccct | 240 |
| gtgagttccc | tatattatat | acgccaaaat | tttatactct | cactatagct | ataaagaaaa | 300 |
| cacgggntat | ttatacaaat | gtgacnaaaa | ccctatagaa | acagcatatg | tatangcgcc | 360 |
| gaggnctctc | ctacattaca | gggaactctc | catgtgacag | gggactgtgc | ggtgaattgt | 420 |
| gccctattan | acacagagcg | tctctttntc | naccanaaaa | ggacggggga | aatttctgtg | 480 |
| tggaacaccc | tttgtgtgaa | ccccg | | | | 505 |

<210> SEQ ID NO 10
<211> LENGTH: 626
<212> TYPE: DNA
<213> ORGANISM: Homo sapien

<400> SEQUENCE: 10

| | | | | | |
|---|---|---|---|---|---|
| gcgtggtcgc | ggcgaggtac | ataatttcta | ttatgagatt | tagaaggtta | aatagttttt | 60 |
| ttttttcagg | cctaccaagt | tgatagacca | aaagtatata | gtagaacagc | acagtagaaa | 120 |
| aaatttaaaa | gtgaatttct | tatggtccaa | aaggatggat | agtcacagtc | cataacccttt | 180 |
| cataatatat | gctggaatgg | gaatctctgg | tcatctggct | tggctctgaa | ttttagaact | 240 |

| agaagtgtgc atgtatgtca aaagattatg cagagctatt ttcttggcta acaagtgtaa | 300 |
|---|---|
| acattgtgca ccccatgaat gggactttat aatctggaag tgagcctaag gttgcgtata | 360 |
| ctgaagtcat gttttaacaa gttaaggttg acttaaacat atacaaggct gtattttaat | 420 |
| ggtaactaga aatcatttac tatgcataca gaacctcatg tatcttatca tggaatttgt | 480 |
| gaattaatgg gccttgccga attcaagggt aagggaaact ggtaacaact gtgttttaaa | 540 |
| tcaacatact ataagctccg tgcttgcttg actcaagtgg gtttgaaaat ctgaattaaa | 600 |
| caggatctca tgtgtcagga aacatc | 626 |

<210> SEQ ID NO 11
<211> LENGTH: 2758
<212> TYPE: DNA
<213> ORGANISM: Homo sapien

<400> SEQUENCE: 11

| atcttgaaga gaaggagaaa aaagatctga gtttggctct cccatcttaa gtgcagcttt | 60 |
|---|---|
| tagttgtttt atagtcatag acgctattgc actggacagc atgcatcctg atgtaaaaca | 120 |
| atgcggaaaa atcaatggag tgaccatctt ggggtcagtg gtgttgcata aagcaccagt | 180 |
| ggtgtgctgt tctgtgtcag tttcctctgc gccacgtgct ttcacagttt gaattaccag | 240 |
| catctctgtg gtggcttcag tacattctcc attgtgcttc aacctggaag cacattctgc | 300 |
| cgttcagaaa gactgattcc aatcatgtaa tgggaccaca cgagatccat gctccaatta | 360 |
| tatgaatagc agaaggtcca tttgactctt gtagttcaag agctgtttct aagtaaacag | 420 |
| actttccaga gctcgatgaa gtgaagaagc ccttctttca attcctgggc agaattcagt | 480 |
| ggttttcata tcatctgaac ctgctgtgct gctgtttatt ctatcactgt cagccttgaa | 540 |
| aggaaaaaag gaataatctt accctcctgc ccttcttatt ttatatcttc catcttatcc | 600 |
| atctatatcc atgtagtcat tccttccgag ttccctggtt ttaatccaaa agactctgtt | 660 |
| taacagcaat gtcttggcag accaggtgcc gcttccgtgc catttgaggg ctctgagtct | 720 |
| ttgcttcgtc ttaggaagat aaagataatt tggcagaaag tcagagatgg aaatagcagt | 780 |
| ttgggatgat aaaagatggg tcctgttttg ctgacattct tttactttgg ttcttggtgc | 840 |
| gtgtcctttg ggattcattt cttgctagca tgaataggac atgcttttcg ttaggtgctt | 900 |
| ttctttttg gagaacatga agtgtttcta acaaaactga atgagctaga aagaattcta | 960 |
| ttttgagaca tctgtagttg atgcaaagta tttctgtaat cctcaatgac agtacttaca | 1020 |
| tatttgcata gaattttttt tttaattttt gaggaaacct ctctggagtc tgtatttata | 1080 |
| ggagcatcct gaaagtccct attatgtagc tggtgggagc gagagaggga cagccacact | 1140 |
| cgtgctgtga gcagagcaca acttcaggca gagtgaatgc cttctgagtt ctcattggaa | 1200 |
| gctttctgtt gctcagcctc tggcagattt cagaaccttc tacttaagcc aggtgtggtg | 1260 |
| gtgcgtgctc ctaggcacag cgactcgggg ggctgaggca gaaggattgc ttgagcccaa | 1320 |
| agtttgagac cagcctgggc aacatagcga ggcctgtctc cttaaaaaat aaataaataa | 1380 |
| ataataaata aataaataaa taaaaacctt gtccttgact attgtgctgt ctgctgcccc | 1440 |
| tttgtaggga tggggttggg gtcagaataa gcatgtgcat gaatggcgga aagctttggt | 1500 |
| ggtgtttgtt tgtttgtttg tttttttgaga ggtgggggag tcagcagtga acctttctgg | 1560 |
| ttaaagaaca acgtacataa tttctattat gagatttaga aggttaaata ctttttttt | 1620 |
| tcaggcctac caagttgata gaccaaaagt atatagtaga acagcacagt agaaaaaatt | 1680 |
| taaaagtgaa tttcttatgg tccaaaagga tggatagtca cagtccataa cctttcataa | 1740 |

```
tatatgctgg aattggaatc tcttgtcatc ttgctttgct ctgaatttta gaactagaag    1800
tgtgcacgta tgtcaaaaga ttatgcagag ctattttctt tgctaacaat gtaaacattt    1860 gcacccatg aatgggactt tataatctgg aagtgagcct aaggttgcgt atactgaagt     1920
catgttttaa aagttaaggt tgacttaaac atatacaagg ctgtatttta attgtaacta    1980
gaaatcattt actatgcata cagaacctca tgtatcttat catggaattt gtgaattaat    2040
gggccttgcc gaattcaagg gtaagggaaa ctggtaacaa cttgttttaa atcaacatac    2100
tataagctcc tgcttgcttg actcaagttg tttgaaaatc tgaattaaac aggatctcat    2160
tgtcaggaaa catcttctaa gcttgacatc tacgtttaag aagggaacgt ggaagagaag    2220
gtgagacatg aaactaaaac agctgggagg gtaggatcag actgcacctg atttttggac    2280
caaagtttca tataggaata ataaaaagg aggaccactt gtgagccaac ctaggaagga    2340
cttgccagaa agtagcagct cctgctgcaa aatacagtgc cttcaaaatg attctctgtg    2400
tgaattgcat gcaatttcat gtaaccataa agtgtaacct gtatgtgcat gacatgtgtc    2460
tagaatgtgt aaagttagga ttcagcagga aggggcctgg ccctgtcact gtggtggatc    2520
agtggacctg ctgaagtcac tggactcatg tgacttaggt ttgcagcatc agacccctgt    2580
gtttgcatta agtggccaca tcgttgaaat cggatcaatc tctccctcag ctttctttcc    2640
tactttgcag ctttgctggt tttaactgct tcattcttct gcttcttggt atccttttt    2700 cttttgaaat aaaaacatga aatacttaat tcaaaaaaaa aaaaaaaaaa ttgcggcc     2758

<210> SEQ ID NO 12
<211> LENGTH: 744
<212> TYPE: DNA
<213> ORGANISM: Homo sapien

<400> SEQUENCE: 12
actgtttatt ttagtattga tcaaaaactt tattttaat tctagaacag tcaaaatgag    60
ttctaaaaaa ataagatatc ggtgagctta ctaaggcaag actcttattc aaatagaagt    120 aactttcta aaaccaacct taaccatttta taaaaaataa ccatattaaa ataatgtaac    180
agtatgtaga ctcaaatta caacaaaatc aaaaagaaa ttgcttcctt ctcataccc     240 aagatgcctt tggtctatat tttttaaatg aagtggtccc aaaatggtat gttgtaaata    300
attttcccta ttttttttt tttacagggg gggcagaaac gggaaaagaa actctgaatc    360
cgaccagtgt aggtgattac tttagcccctt tgaagtcaac acaaagttta aaacttccag    420
gatttggcac aagttgtata ttatttaatg gctgggcaac tgctaaacta tgcagttttc    480
tcttgaagga actaaaagca actagctccc taatggtcta taatttatat tcctttgggc    540
ttaaagtgac aacacgaaga attagagaat ccccgcagaa tccaggggct ggtctactat    600
ccatacttct tatcactttta gttttctcat cagtcaataa aattatttta ctcttccaaa    660
aaaaaaaaca aaaaaaaggg gtggggtacc ctgggccaaa agcgttcccg gggtggaatt    720
tgtttccgcc aatcaaacca aaag                                          744

<210> SEQ ID NO 13
<211> LENGTH: 799
<212> TYPE: DNA
<213> ORGANISM: Homo sapien

<400> SEQUENCE: 13
atcaaatttc taatgctaat gtgagcaaaa cgcaacagaa cttgaattat aaattgaatt    60
```

```
acccaaaagg taatgaactg aattactaaa tttgctgatc atatggaaca aatttaagtg    120
tactgtttat tttagtattg atcaaaaact ttattttaa ttctagaaca gtcaaaatga    180
gttctaaaaa aataagatat cggtgagctt actaaggcaa gactcttatt caaatagaag    240
taacttttct aaaaccaacc ttaaccattt ataaaaata accatattaa aataatgtag    300
cagtatgtag actcaaattt acaacaaaat caaaaagaa attgcttcct tctcataccc    360
caagatgcct ttggtctata ttttttaaat gaagtggtcc caaaatggta tgttgtaaat    420
aattttccct attttttttt tttttacagg gtggcagaaa agggaaaaga aactctgaat    480
ccgaccagtg taggtgatta cattagcctt tgaagtcaac acaaagttta aaacttccag    540
gattttgcaa agttgtatat atttaatgct gtgcaactgc taaactatgc agttttttgtt    600 gaaggaacta aaagcaacta gctccctaat ggtctataat tttatttctt ttggcttaaa    660
gtgaaaaaga agaaatagag aattccagca gaattcagtg gttgtctact atccatactt    720
cttatcactt tagtttttca tcagtcaata aaattaattt actcttccaa aaaaaaaaa    780 aaaaaaaaaa ttggcggcc                                                 799

<210> SEQ ID NO 14
<211> LENGTH: 456
<212> TYPE: DNA
<213> ORGANISM: Homo sapien

<400> SEQUENCE: 14
atctctttaa ataattagca agaagggaga caagatgcag gagttcactt ggctctttga     60
aaaggaaaac tttaaagtca gtggttggac tgagtcccat gaagccagat cacttctgac    120
tgcaaggagc ttggaaaagc aagtatctgg atcttttacc agctaaattg ggaggaacta    180
taaaatgaga aaagattgat gaatattaag tagaagagtg agatggtcat ctttgcattt    240
aaaaaagatc atttgctgta gttgtatgga aaatgaattg gagcaggcga tgaggcttcc    300
tctttgaaga tcacaggtga aagattaggt gctttctca gaagcccagc aacctgatgg    360
gagtgtggag tgagcaagac ccaaatcgga gcttcatccc tgcatggttc attttgctta    420
tttggcaaac ttgccctgca gaatctactc aagctt                              456

<210> SEQ ID NO 15
<211> LENGTH: 282
<212> TYPE: DNA
<213> ORGANISM: Homo sapien

<400> SEQUENCE: 15
acattctgga cagccagtta cctgggatga gttgggaggg aggagaataa ggacaaaaga     60
ccatctgggc aaaaatcacg aagggtatg tgtgtcatgc aaaggtgtgc catgatagtt    120
attcatattg ctattgtaat attaatatat agtaattaac tacacatgac acagctttac    180
atgaccttaa gtagttatca acattaccat aatagtaata ttaataacta caataagagc    240
cattattatt cacttgaggc acttgttcaa aatagatttt ac                       282

<210> SEQ ID NO 16
<211> LENGTH: 2658
<212> TYPE: DNA
<213> ORGANISM: Homo sapien

<400> SEQUENCE: 16
ggccgcatat ttttttttt tttttttt tgtaaaatct attttgaaca agtgcctcaa     60
gactgcttcc ctaacagact gtttctcctg aaaatgcagg agctattctt tctgttctgg    120
```

```
ttatatagtt tccattcatg gcttcttgtc ctgttgtttt ttgtgtcgag tacactatat      180
aaattatctc cttatacata tttctcaggc aagcacagag ttatactgaa cttttctaaa      240
gatgctttgc atcaagaagc aaagggaaat acagaattaa aatgtttctt tccatttgc       300 tttgttttc  tatatcgatc tagactttgt aggaaaatgc aaagcgtata tttaagaaaa      360
cctaaataag aatagattca tttactcatt ttcatttatt cattcatgaa gaatttattg      420
aatgcctact atgtgccagg aatattgcta tattttgaa  atttaaggat aaaatatggc      480
ccaatctatc aagaaaggaa agtgaaagac aaatgtaaga cataattaca acattctgtg      540
ggagcacaaa gtaggggact cagttcttag agaagtcttt tggtcttaga gttcatcaag      600
cagagaaggg gaaggacatg gtccaggaaa ataaatcagc acacaaagag atggggtctt      660
gagggtgcat agtacattct ggacagccag ttacctggga tgagttggga gggaggagaa      720
taaggacaaa agaccatctg ggcaaaaatc acgaaggggt atgtgtgtca tgtaaaggtg      780
tgccatgata gttattcata ttgctattgt aatattaata tatagtaatt aactacacat      840
gacacagctt tacatgacct taagtagtta tcaacattac cataatagta atattaataa      900
ctacaataag agccattatt attcacttga ggcacttgtt caaaatagat tttacaaaag      960
aaaaaaaaaa aagaagcaac atgagtaaaa ttagatccat tggctactga ctccctctcc     1020
aacagtttta aagctactag ataagagaag catcaagtct taaaggaaga gaatggtatg     1080
atcagatgtg tgttttccaa agactattag aaacagcatg gttaaggata gggtggatat     1140
ttacttgcac aggtgactga atgaacatct gtttatacat caaggaaaaa tgattcattt     1200
tatatcctgg atattttacc ataagtatga gcataaagct gggatgtctg gcattggaat     1260
tttatgtcac tctcaaggct aattagtctt tcagatcctt tggtagggag gaaagaagag     1320
ttgcttcagc attttgacta acatttcttc caaatttctt ctccctgata tttccagcca     1380
cgccaaggca aagactccc  agctctgtct caggttaggt taaagaagg  cataggatgg     1440 aagagggtgg tctgtggtag gcctagcaaa tgaaagagat gaataaacaa gagtgtctag     1500
tctaactagt gcctgaggaa tagacatcag tcctctgaga ttacccagct ggaaaactgc     1560
ccagatggag ctttacatgc aaagctccag tgaagtctag tgctgtataa tgctttaaat     1620
ccacaatcaa gccttgttg  atgcaaatgt tagtcgccca aagcagaatg ggttaacgaa     1680
ttactgcagt ggttttaggt gcatgggttt gacccatgta aatcatttta ataagtaaaa     1740
ttgaatcttt gatacatatt tgttgaggag cttgtcagat cactaccttt cactgaacag     1800
taaaacatgg atcatttatt tcacctcatt ttgcacttca atgcaatttc actctttagg     1860
tggttgtact tggacagtta aatgaagact gtctttaagg gtgcagggat ggagaacaca     1920
gcgtatatga gaggtgggag ggcagagacg ccttgcgatt cctgtgagga gggacttacc     1980
gtctcctcca aaacagaaat tcagtgctgc agagacggta gcaaagtgca gttctcttgt     2040
taaaacacag gctaaaagca gtgactgctt aacttattaa gcagagaaaa ccaaaatgtc     2100
attttcaacc aaaattgagt gttagagttt atggtctctg ttatgatact tttcaagacc     2160
tgggaaatat ttgtatcctt tagtgaaaag gggaagaatc aattactgaa agccataagc     2220
ttacagtaac ggagccaatt aatcctttgt catctttgtt gagtttagtt ttcttctgtt     2280
cttagcacgt cagctagtag atctttgatg aactgttgct cctcttttaaa tgtttctttt    2340 attatattga tgatgtgcac tcattcagta ttcttatttt aagctgcagt aatcactgta     2400
catttgattg ccatctgtac ttcccttgaa gcagctttgc ttattacagc cacacctgca     2460
```

| | |
|---|---:|
| tctgttttga ctagcccaca taacctacac attttttcatc caaagctatc ccattacctt | 2520 |
| atttatgtcc atttattttc atatatagta tctgccaaaa tagtagcaaa agttttatca | 2580 |
| atgtgtagat ttcaatcaga aaacctaag caaaagggga aaaaagtgat attctaaaag | 2640 |
| gcacacttct tttatcac | 2658 |

<210> SEQ ID NO 17
<211> LENGTH: 493
<212> TYPE: DNA
<213> ORGANISM: Homo sapien

<400> SEQUENCE: 17

| | |
|---|---:|
| gcggccgccg ggcaggtctt cgatctcccg gggtgctggg attacaggtg tgagccacag | 60 |
| cacctagcct taccttcaaa ttctaaacca agctatttaa atagccactg tttgattatt | 120 |
| tgaattaaca tggagcatct tctgggatat tgttcaggga aatatgagta gatcaaggta | 180 |
| ttttggggat gtaaaccctc atgtttgata aaataaatga tattttgagc tactgtttgc | 240 |
| tgggaacaga aagtaagaag ggaaaaggag cgaccataca ggaaagtaaa aataataaaa | 300 |
| gaaaatttag aaaactagag gaaaaggtat gaaaggataa atcctccatc ccatactgat | 360 |
| aatggccttt gagcatcact aagccccttt gcttctccca ttaagcaaag gatgatgact | 420 |
| gaggaggaac aaacaaaaat agacatcatt ataaaaaata cccaagactt ttagatgttt | 480 |
| ctctaacatt tgg | 493 |

<210> SEQ ID NO 18
<211> LENGTH: 1412
<212> TYPE: DNA
<213> ORGANISM: Homo sapien

<400> SEQUENCE: 18

| | |
|---|---:|
| tgaattagcc atacaaaaaa aataaaaaat tactgttagt caccctacag tgcaaggtaa | 60 |
| cactagaatt tatcttttcca tctagtaacc actgtttttt aaagagacag agtatctccc | 120 |
| tgttgcccca gctggagtgc agtggcacaa tcatagttca ccacccctg gaactcctgg | 180 |
| gctaagggat cctccttagc ctcagcctcc caagtagcta ggtatacagg catgtgctac | 240 |
| catgcctggc taattaaaaa agatttttt agagatgagg tcttgctgtg ttgcccaggc | 300 |
| tggtctcaaa ctcctgggct caaacaatcc tcccaccttg gcctcccaaa gtgctgggat | 360 |
| tacaggtgtg agccacagca cctagcctta ccttcaaatt ctaaaccaag ctatttaaat | 420 |
| agccactgtt tgattatttg aattaacatg gagcatcttc tgggatattg ttcagggaaa | 480 |
| tatgagtaga tcaaggtatt ttggggatgt aaaccctcat gtttgataaa ataaatgata | 540 |
| ttttgagcta gtgtttgctg ggaacagaaa gtaagaaggg aaaaggagcg accatacagg | 600 |
| aaagtaaaaa taataaaaga aaatttagaa aactagagga aaaggtatga aaggataaat | 660 |
| cctccatccc atactgataa tggcctttga gcatcactaa gccccttttgc ttctcccatt | 720 |
| aagcaaagga tgatgactga ggaggaacaa acaaaaatag acatcattag aaaaaatacc | 780 |
| caagactttt agatgtttct ctaacatttt ggggtcattt tcagattacc agtgttcatt | 840 |
| tgctgaggta tattaacgga tatttgtact taatttgaaa aatagcagga tccaaaccag | 900 |
| aggtctgtat aagagcaggc ggcatgcgtg tctggagagc tgctgcctcc acaagtattc | 960 |
| tgacagcact gggctgctag tgagacctgg atggccaccc tccccatgtc atggccatgg | 1020 |
| gttttcggga accgtttcct ccttttactg catcacagtt gcaaactcgt ctatttattt | 1080 |
| ttctctcttgat taacaactgc actctgacat tgcagcagtg ttgatgaaga caatttaact | 1140 |

```
catgttttg ttaacataat aattgtctgt cgtaactaaa atataagttt cttgaaagct    1200
ataatcaggt atagagaaaa tctttgttat gcacaatacc agggcaggta atatctgtaa    1260
tatgtattaa cagcaattca ctaaacattg aatgtctctg tatgctggca cctgtgctaa    1320
agatttgctg tataaagata aataggaaat tgcctcttct cccacgaaac tcaaaacatt    1380
tattgaatga ataataata ggtgaattaa ta    1412
```

<210> SEQ ID NO 19
<211> LENGTH: 383
<212> TYPE: DNA
<213> ORGANISM: Homo sapien

<400> SEQUENCE: 19

```
cgagcggcgc ccgggcaggt acttggagaa ctaacttctt gcaatagatt tttaagcact    60
attagaagca tatgacttaa acagttttta aaagtcagga agtaagtatg cttaaataaa    120
atacaatctg tgaaacaaat ctctgaatta ttatcacttc actggacact ctaacttgac    180
catatttctg actttaatgt aactcactct tattccgtag tcacatgttt gctgctcatg    240
gttcacatta catttattca gcatctgctt gagccaaggc actgtaacta catgttttt    300 ttagttacct actttgtaag gtcctgtttc ttggctacat ctgattacag taaacatagg    360
aagtttaata aaacaatttt cac    383
```

<210> SEQ ID NO 20
<211> LENGTH: 1804
<212> TYPE: DNA
<213> ORGANISM: Homo sapien

<400> SEQUENCE: 20

```
ccagtctgct gccactgggc tgtatgtaag gcggttcttc tgtccacccc accgctactg    60
gactctcttc cctgtagaca gggtctcacg ctagttgccc aggttcggag tacagtggca    120
caatcagggc ctacactgac aagcctatga ctttaccagg ttcaaacaat accacctgcc    180
tcagcctcac aagtagctgg gactacaggc atgtgcaacc acaccgtgc taattatata    240 ttgaattcct agtggagaca aggtctcatt atgttgccca ggctggtctt gaactcctta    300
gcttaagcaa tcctcctgcc tcagcaatcc caaagtgctg ggattatggg cgtgagccaa    360
catgcctggc aatatctacc ctatctcgaa ggctgaaata acattccatg atggtcctag    420
aacaattgga gattcatacg cacacaaaga acctcaaccc ttacctcaca ccagacacaa    480
aagctaccct caaataaatc ataggcctaa cttgaagagc taaaaccatg caactccaga    540 aagttttgt cagaaagaaa atacaggaga aaatcttagt gaccttgggg taggcaaaga    600
tttcttaaga cacaaaagc atgaagtata aggggaaaa atcgctaaa ttggatttca    660 tccaagttaa aaacttttaa tctttgaaag ataccttaa gaaatgaaa aagtacgcct    720 tgggctggga gaaatatttt gcagaacgtg tgtctgacag aggatgtgta tctagaagat    780
ataaagaatt gtaactcaag aattgaaaga caaccccata agaaaagggg gaaacaattt    840
gaataaagtt catcaaagaa tataaatggc aaataagcac atgaaaagat gcccaaagtc    900
gtaagtcatt agggaaatat aaatttaaac cataatgaga taccactgca tactccctag    960
aatggctgta atgaatagga ttagtcacat ggtgacaaga atggaggatc atctggaact    1020
ctcatacact gacgataga atgtgaaatg gatcaactac tttggaagac aattgggcag    1080 tttcttcaa agtaaatgtg aagatgccat acgattcatc cattccattt ctaattattc    1140
```

```
aagagaaatg aaactgtata tccacaaaaa agacttgtac acaaacattc acagcagcta   1200
ttatttattg gtaatagcta aaaactgtaa acagctccca tatccatcaa gtgtatggat   1260
aaacaaattt ggtgtattta tacaatggaa tactactcgg caataaaaag aacagttgat   1320
actctcaaca acctagatgg acctcaaaat aattcggttt aatgaatgaa gccaaactta   1380
agaagagtac attgtatgta cttggagaac taacttcttg caatagattt ttaagcacta   1440
ttaggagcat atgacttaaa cagttttaa aagtcaggga gtaagtatgc ttaaataaaa    1500
tacaatctgt gaaacaaatc tctgaattat tatcacttca ctggacactc taacttgacc   1560
atatttctga ctttaatgta actcactctt attccgtagt cacatgtttg cttgctcatt   1620
ggttcacatt acatttattc agcatctgct tgagccaagg cactgtaact acatgttttt   1680
tttagttacc tacttttgta aggtcctgtt tctttggcta catctgatta cagtaaacat   1740
aggaagttta ataaaacaat tttcatgacc gaaaaaaaaa aaaaaaaaa aaaaattgc     1800 ggcc                                                                1804

<210> SEQ ID NO 21
<211> LENGTH: 252
<212> TYPE: DNA
<213> ORGANISM: Homo sapien

<400> SEQUENCE: 21
gcggcgccgg gcagtgtacc agtttaataa ttttgatgta aatttgctgt gtgtgttttt    60
acttgttcat gtagtgattt tataaattac tcttttaatt ttctatcaat gaatatcctg   120
ggataaaccc ctcatgatca taatgaataa tgatgtgtgg agagtgggga gggtttacat   180
atgaaaaatg tagaaaatac aaaaagtgtc tatatataca aaatgtaagt gttaacattt   240
ttatatttgc tt                                                       252

<210> SEQ ID NO 22
<211> LENGTH: 1595
<212> TYPE: DNA
<213> ORGANISM: Homo sapien

<400> SEQUENCE: 22
gaaaagaaga aacctgagtg agtcagcatg accaaatatt aaaacatctt ataaagctac    60
ataattaaaa acaatgtggt gctgatatgt ggagggtcaa tggaacaaga tgaaatggcc   120
aaaaataaat ttaaaataca tgttgaaatg tattaacagc atatgttaaa gttaagttat   180 gttaactta tatgttaaat tcaagttaat tggggaaaga tggattattc aatatatgat    240
gaacaactct gtcacccagc taaaaaaaat taagctgggg ccatatgcca gactagatac   300
caaaataaat tccaggagga ccaagttttt aaaagtaaaa atatgaaatc atggaagtgc   360
atgaagaaga agtagcactt aaaaaaataa taatctcagc atgggaagg tctaagtatg     420 gccctcaatc agaaaccagg aaggaaaata ttaactattt taaacaaaat tatctctgta   480
ccaaaaacag cataaaaggt caagaaacaa cacactggaa aaagaattgc aatgaatatc   540
acagccaaat agttaatttc ttattttcaa aaaatagctt ctacaaatcg aagagaaaaa   600
ttctaaggtc tcaaaggaaa aatgagcaaa ggatttgaca ggtggtagaa tacagaaaaa   660
gaatttaaaa tagctcctaa agatatgaaa acattactca tgatagcaga agtatcaatt   720
gacaaaatta ctcagattgg taacaaactt aagggggaa agcacttcca tgcattgctg    780
taaattggta catcttctac tgagaacaat ccggcagtag ttaacaaaat tgtgaatgca   840
tatatctctt tctctagaaa tttctctttt gggaatttat tctacatata tattcaaaca   900
```

```
tgtgtgaaat acttctatac aggtgattga atttcacttt attcctaaga gcagaagact    960
gcaaaatagt aaatatatac ccaaaagggt ctaatggatt agttttttggc atatcagcac   1020 atgataatac tatgaagcca taaaaaagag agatctctat atgtattgat gggggaccat   1080
ctttaagata tactgtggtg ttgaacaaaa caacatgctg aaaatgtctc ttattctttt   1140
agaatcaata taagtctgtg cttgtaaatg cagtaagtat ctttggaagt atacctaaaa   1200
attggtaata gtgtttgact ccagggaaga acagatgggt gccagagtga aaaaagata    1260 gcttttgctt tttatgactt ttggattctg taccacgtaa aattttgat gtaaattttg    1320 ctgtgtgtgt ttttacttgt tcatgtagtg attttataaa ttactctttt aattttctat   1380
caatgaatat cctgggataa accctcatg atcataatga ataatgatgt gtggagagtg    1440
gggagggttt acatatgaaa aatgtagaaa atacaaaaag tgtctatata tacaaaaatg   1500
taagtgttaa catttttata tttgcttcaa gcttttttt taaataaaag aaatgcaata    1560
ttgcaattaa aaaaaaaaa aaaaaaaagg cggcc                               1595

<210> SEQ ID NO 23
<211> LENGTH: 297
<212> TYPE: DNA
<213> ORGANISM: Homo sapien

<400> SEQUENCE: 23
gtcgtgctat gaccggactt tttcttggaa ggggatgaca gcatgggagg caatggctcc     60
acatgtaaac ccgacactga agacaaggc actctctcca cagcagcccc aacaactagc    120
cctgcaccct gtctctctaa ccaccacaac aaaaaacatt taatccttgc cttttgtgct   180
ggggttctac tgacactgct gctgatagcc tttatcttcc tcatcataaa gagctacaga   240
aaatatcact ccaagcccca ggccccagat cctcactcag atcctccagc caagctt      297

<210> SEQ ID NO 24
<211> LENGTH: 900
<212> TYPE: DNA
<213> ORGANISM: Homo sapien

<400> SEQUENCE: 24
agtttagtaa gatctttgct acacacaatg tgatgctggc agtggcaggg gcagtaatct     60
ttatttcgtc attttgaaa catagaagcc gtaacggaag caagtgaaat gctcagtctt    120
agacgactgc gtcgtgctat gaccggactt tttcttggaa ggggatgaca gcatgggagg    180
caatggctcc acatgtaaac ccgacactga agacaaggc actctctcca cagcagcccc    240
aacaactagc cctgcaccct gtctctctaa ccaccacaac aaaaaacatt taatccttgc    300
cttttgtgct ggggttctac tgacactgct gctgatagcc tttatcttcc tcatcataaa   360
gagctacaga aaatatcact ccaagcccca ggccccagat cctcactca gatcctccag   420 ccaagctttc atccatccca ggggaatcac ttacctatgc cagcacaact ttcaaactct   480
cagaagatgc tcaaattaaa gtaacaaact aactcagctt ttccaatgag gcttgaatcc    540
atttcctctc atctcagccc tatcttcaca catcactttc acttttttac aaattttgga   600 ccacccctg tgtgaaactg cagtcggagt tgtttagatg tgatctggca atgctatcca    660
gcatctttgg agaccaatgg tcagtctttt cctggccaga ggaaagattg atggccctcc    720
cacttgaact gacagcctgt gagccccttg ggggcataga ctgccttcct tggacccttc    780
caaagtgtgt ggtacagagc tcagtgcaca gagtattcac ccagcatcat gaatcaactt    840
```

| | |
|---|---|
| gggaggagtc aaccaaatga acaatctacc aaaaatttca aataaagtca aaccccccac | 900 |

<210> SEQ ID NO 25
<211> LENGTH: 908
<212> TYPE: DNA
<213> ORGANISM: Homo sapien

<400> SEQUENCE: 25

| | |
|---|---|
| gacccacccc ccacacaccc ccaccaaaga gatcgacata taggcatggt gactaatgct | 60 |
| gctcgagcgg cgccatgtga tggatgccga ggtccaaaga ttacacttgt gttctacaca | 120 |
| gcaaaccatt tttctttcat gaaaataata tattattaac atgaatatat tattttgcta | 180 |
| ttaatgtgaa agttgtctct taatatttt taattttcaa actcatactt tattttcatt | 240 |
| tgaaatgttt ttcacacctt ttgcattaca taataatttt gtggaagcat tttgcccttt | 300 |
| agaataaata ttagattgat atagctgaaa tgtgacttcc agttctttga tattcccctt | 360 |
| gttattcaaa tagaaatatg gaaatgcttt atatattact gttaaatttc ttagtgcaga | 420 |
| aataacatta ttaatagagt attgttttca aaacagatga ttaatttcaa gaggtttaac | 480 |
| agtgaaattg tgtcaatatt ttgcatttaa aatgaattta attgaccgat attttctgta | 540 |
| gttaaattta gtcacaatat cacatatgtt cttcaagaaa cacatgaaat tattaataaa | 600 |
| gtaattaaaa aattttaat gtataacaga attgaccaat aggccagttt tctggtaact | 660 |
| tatgatagta gattgtttct ttagaaactg ggcagaagct ctgcattctc acttgtactt | 720 |
| tgatttctta tttcttggtc aggcacttcg aggaacgaag aactggctgg gggaatatat | 780 |
| atgtttcgtt cttagggaaa acgtctgaga aatgaattaa agcctgagta ctaaaaaaaa | 840 |
| caaaaaaaaa cacactctgg gcgacccgcc tcacgtcctt gtaaatgtcc gcccacatcc | 900 |
| aataaaag | 908 |

<210> SEQ ID NO 26
<211> LENGTH: 5574
<212> TYPE: DNA
<213> ORGANISM: Homo sapien

<400> SEQUENCE: 26

| | |
|---|---|
| agtgatcact ataggcctg gttatctaat gctgctcgag cgcgcgcagt gtgctggaaa | 60 |
| gcgcggctgg gcgcctcggc catgactgcg gagctgcagc aggacgacgc ggccggcgcg | 120 |
| gcagacggcc acggctcgag ctgccaaatg ctgttaaatc aactgagaga aatcacaggc | 180 |
| attcaggacc cttcctttct ccatgaagct ctgaaggcca gtaatggtga cattactcag | 240 |
| gcagtcagcc ttctcactga tgagagagtt aaggagccca gtcaagacac tgttgctaca | 300 |
| gaaccatctg aagtagaggg gagtgctgcc aacaaggaag tattagcaaa agttatagac | 360 |
| cttactcatg ataacaaaga tgatcttcag gctgccattg ctttgagtct actggagtct | 420 |
| cccaaaattc aagctgatgg aagagatctt aacaggatgc atgaagcaac ctctgcagaa | 480 |
| actaaacgct caaagagaaa acgctgtgaa gtctggggag aaaacccaa tcccaatgac | 540 |
| tggaggagag ttgatggttg gccagttggg ctgaaaaatg ttggcaatac atgttggttt | 600 |
| agtgctgtta ttcagtctct ctttcaattg cctgaatttc gaagacttgt tctcagttat | 660 |
| agtctgccac aaaatgtact tgaaaattgt cgaagtcata cagaaagag aaatatcatg | 720 |
| tttatgcaag agcttcagta tttgtttgct ctaatgatgg gatcaaatag aaaatttgta | 780 |
| gacccgtctg cagccctgga tctattaaag ggagcattcc gatcatctga ggaacagcag | 840 |
| caagatgtga gtgaattcac acacaagctc ctggattggc tagaggacgc attccagcta | 900 |

```
gctgttaatg ttaacagtcc caggaacaaa tctgaaaatc caatggtgca gctgttctat     960
ggtactttcc tgactgaagg ggttcgtgaa ggaaaaccct tttgtaacaa tgagaccttc    1020
ggccagtatc ctcttcaggt aaacggttat cgcaacttag acgagtgttt ggaaggggcc    1080
atggtggagg gtgatgttga gcttcttccc tccgatcact cggtgaagta tggacaagag    1140
cgttggttta caaagctacc tccagtgttg acctttgaac tctcaagatt tgagtttaat    1200
cagtcccttg ggcagccaga gaaaattcac aataagctgg aatttcctca gattatttat    1260
atggacaggt acatgtacag gagcaaggag cttattcgaa ataagagaga gtgtattcga    1320
aagttgaagg aggaaataaa aattctgcag caaaaattgg aaaggtatgt gaaatatggc    1380
tcaggcccag ctcggttccc gctcccggac atgctgaaat atgttattga atttgctagt    1440
acaaaacctg cctcagaaag ctgtccacct gaaagtgaca cacatatgac attaccactt    1500
tcttcagtgc actgctcggt ttctgaccag acatccaagg aaagtacaag tacagaaagc    1560
tcttctcagg atgttgaaag tacctttttct tctcctgaag attctttacc caagtctaaa    1620
ccactgacat cttctcggtc ttccatggaa atgccttcac agccagctcc acgaacagtc    1680
acagatgagg agataaattt tgttaagacc tgtcttcaga gatggaggag tgagattgaa    1740
caagatatac aagatttaaa gacttgtatt gcaagtacta ctcagactat tgaacagatg    1800
tactgcgatc ctctccttcg tcaggtgcct tatcgcttgc atgcagttct tgttcatgaa    1860
ggacaagcaa atgctggaca ctattgggcc tatatctata tcaacccccg acagagctgg    1920
ctcaagtaca atgacatctc tgttactgaa tcttcctggg aagaagttga aagagattcc    1980
tatggaggcc tgagaaatgt tagtgcttac tgtctgatgt acattaatga caaactaccc    2040
tacttcaatg cagaggcagc cccaactgaa tcagatcaaa tgtcagaagt ggaagcccta    2100
tctgtggaac tcaagcatta cattcaggag gataactggc ggtttgagca ggaagtagag    2160
gagtgggaag aagagcagtc ttgcaaaatc cctcaaatgg agtcctccac caactcctca    2220
tcacaggact actctacatc acaagagcct tcagtagcct cttctcatgg ggttcgctgc    2280
ttgtcatctg agcatgctgt gattgtaaag gagcaaactg cccaggctat tgcaaacaca    2340
gcccgtgcct atgagaagag cggtgtagaa gcggcactga gtgaggcatt ccatgaagaa    2400
tactccaggc tctatcagct tgccaaagag acccccacct ctcacagtga tcctcgactt    2460
cagcatgtcc ttgtctactt tttccaaaat gaagcaccca aagggtagt agaacgaacc    2520
cttctggaac agtttgcaga taaaaatctt agctatgatg aaagatcaat cagcattatg    2580
aaggtggctc aagcgaaact gaaggaaatt ggtccagatg acatgaatat ggaagagtac    2640
aagaagtggc atgaagatta tagtttgttc cgaaaagtgt ctgtgtatct cctaacaggc    2700
ctagaactct atcaaaaagg aaagtaccaa gaggcacttt cctacctggt atatgcctac    2760
cagagcaatg ctgccctgct gatgaagggg ccccgccggg gggtcaaaga atccgtgatt    2820
gctttatacc gaagaaaatg ccttctggag ctgaatgcca aagcagcttc tcttttttgaa    2880
acaaatgatg atcactccgt aactgagggc attaatgtga tgaatgaact gatcatcccc    2940
tgcattcacc ttatcattaa taatgacatt tccaaggatg atctggatgc cattgaggtc    3000
atgagaaacc attggtgctc ttaccttggg caagatattg cagaaaatct gcagctgtgc    3060
ctagggagt ttctacccag acttctagat ccttctgcag aaatcatcgt cttgaaagag    3120
cctccaacta ttcgacccaa ttctccctat gacctatgta gccgatttgc agctgtcatg    3180
gagtcaattc agggagtttc aactgtgaca gtgaaataag ctcccacatg ttcaaggccc    3240
```

-continued

```
attctggttc ctggctgcct gcctcttgca cagaagttcg ttgtcatagt gctcaccttg    3300
ggaaaaggat taggtgggca cataagattc cgatcagacc ccaaccatgc tgcatgtgta    3360
aagaaggatt gaaataaaa ttgcactttt taggtacaaa atcataaaag ctgtttcact     3420
agaaaaggca gaaagcagtg tattaaggtg ttgaattacg ccagaagacc tgaaatgcct    3480
tgtacctaca acaatgctta ggcttttcta agcctcttgc cacttttaaa attatccttc    3540
aggcataaat atttttgaca gcagaataga agaatgattc atgagaacct gaaccagatg    3600
aacagctact agttatttta tcaaatacag atgacattta aaaattctta actacaagag    3660
attagaaata taaaccttgc ctggctcttg ccaggagata acaaaatggg ttgctgatga    3720
actgcaccct tttacatgtg ggtagaatat aagctcacat ggcagtgaga tgttgaaaag    3780
tcaaaagaga cctgtctctc cctttctttt tctatcttta aaccagaaaa cctcatactc    3840
agtcctcagt gaaagaaagt aaagtattaa ggactttaga cagaagagca ttgtgtaact    3900
tgactgaaga tcatccatta atagttatta ggcatttagg taaaattttc taatacctaa    3960
aaattgtcaa aaacagtcaa tagggctact gctggcccaa agaccattta ggtccacctc    4020 ctctttttg ctcttttttt ttttctgtga cagtttcact gtgttgccca ggctggagta     4080
cagtggcgcg atctcagctc actgcaagct ccgcctccca agttcactcc attctcctgc    4140
ctcagcctcc ggagtagctg ggactgcagg cgcctgccac cacgcctggc taattttttg    4200
tatttttagt ggagacggat tttcaccgtg ttagccagga tggtctcaat ctcctgacct    4260
cgtgatccac ccgccttggc ctcccaaagt gctgggatta caggcgtgag ccaccgtgcc    4320
tggccgacat ttttaaaaaa gttttatttt gcacggctct aaacctccat gttatttcc     4380 agtggtgtag aaggtaccag ctaaagtgaa ccactatgta atattaggcc attctaaagg    4440
aaagatgttc catgtcatca gagatggtaa aataggcagg gaaaaaaaa tctttggtac     4500 caaagattac acttgtgttt ctacacagca aaccattttt ctttcatgaa aataatatat    4560
tattaacatg aatatattat tttgctatta atgtgaaagt tgtctctaaa tatttttaa     4620 ttttcaaact catactttat tttcatttga aatgttttc acaccttttg cattacataa     4680
taattttgtg gaagcatttt gccctttaga ataaatatta gattgatata gctgaaatgt    4740
gacttccagt tctttgatat tccccttgtt attcaaatag aaatatgaa atgctttata     4800 tattactgtt aaatttctta gtgcagaaat aacattatta atagagtatt gttttcaaaa    4860
cagatgatta atttcaagag gtttaacagt gaaattgtgt caatattttg catttaaaat    4920
gaatttaatt gaccgatatt ttctgtagtt aaatttagtc acaatatcac atatgttctt    4980
caagaaacac atgaaattat taataaagta attaaaaaat ttttaatgta aacagaatt     5040 gaccaatagg ccagttttct ggtaacttat gatagtagat tgtttcttta gaaactgggc    5100
agaagctctg cattctcact tgtactttga tttcttattt cttggtcagg caatttgagg    5160
aaagaagaaa tggcatgggg aatatatatg ttttgtttct tagggaaaac agtctgagaa    5220
atgaataaaa agcatgaagt acgtgtgtgt gtgtgtgtgt gtgtgttacc atggaaaagg    5280
atattcccag tagtccagtt ctcaatattt ttaattagat gtcatatttt tttaatatag    5340 taaaccttg ggatatagaa tattccatct tttgagaatg tatgtgtctc taagtaagta     5400
aaatttaatg cgtataggag actgatagct aaaaatgaat ggacccttaa tgtactttta    5460
taattaaccc tcttatctat cagaaattgt aagagaatag atacatgttt tgaatgtaaa    5520
gttgaaaagt ctggtttact gaataaattg aaagtgattt ataaaaaaaa aaaa          5574
```

<210> SEQ ID NO 27
<211> LENGTH: 444
<212> TYPE: DNA
<213> ORGANISM: Homo sapien

<400> SEQUENCE: 27

| | | | | | |
|---|---|---|---|---|---|
| actcaagcat | tttcttatga | atgtattatc | tgtggggagg | tgttcatggt | ttttctgcta | 60 |
| ttttgcattt | cagatatgta | ttattttagc | ttgatagcca | ttgagattgc | tatagattat | 120 |
| ttgatttgta | tataatgatg | tatgtatgta | tatttcacta | tattttttcta | tttttctata | 180 |
| actgggtttt | aaatatttttt | ggtagaaaaa | taattatact | ttcattgcta | aaaataaata | 240 |
| tgcataacct | accoctctat | attgcttata | acattttgat | gatgtagcca | gtgaatatgt | 300 |
| gctaatttaa | ataacttta | tataaaatta | agccaactgc | cgtattataa | ctggtttctt | 360 |
| tttaacttaa | tagggtattg | ttttataata | ttaaatcata | tgtttaagct | cattctcttt | 420 |
| aaaaataaac | aataagcaat | ttcc | | | | 444 |

<210> SEQ ID NO 28
<211> LENGTH: 6850
<212> TYPE: DNA
<213> ORGANISM: Homo sapien

<400> SEQUENCE: 28

| | | | | | |
|---|---|---|---|---|---|
| tttttttttt | ttatagaaat | tgtttattgt | ttattttaa | agaaaatgag | cttaaacata | 60 |
| tgatttaata | ttataaaaca | atatcctatt | aagttaaaaa | gaaaccagtt | ataatacggc | 120 |
| agttggctta | atttatata | aaagttattt | aaattagcac | atattcactg | gctacatcat | 180 |
| caaaatgtta | taagcaatat | agaggggtag | gttatgcata | tttatttta | gcaatgaaag | 240 |
| tataattatt | tttctaccaa | aaatatttaa | aacccagtta | tagaaaaata | gaaaatata | 300 |
| gtgaaatatg | catacataca | tcattatata | caaatcaaat | aatctatagc | aatctcaatg | 360 |
| gctatcaagc | taaataata | catatctgaa | atgcaaaaat | agcagaaaaa | ccatgaacac | 420 |
| ctcccaacaa | gataatacat | tcataagaaa | atgcttgagt | actgaccgta | ggatagtttc | 480 |
| tgtcagttgt | ctgacctgct | gtgtgacagt | atctgtatat | acactttgt | gcattcttgc | 540 |
| aaaattacaa | accttgtaca | gggaccaggc | atcttataag | tagaatccta | agcaaactct | 600 |
| aataaaacac | tgattttcat | ttgtggaaac | aaattttagt | ggtcctttgt | aattcactta | 660 |
| ttagtaagta | ataacattac | tagtaagtac | ttgtaagtaa | tgctgattgg | tccaaaagta | 720 |
| aaaatccaca | gaactgtgca | ttgtttacta | aaggaaacca | aaaataatta | atttttggat | 780 |
| ctgcccatgc | caaatctgaa | ggcaatgaat | acattaatag | cttctgtgtc | ccctgattat | 840 |
| ggctaccttc | tccacttaag | ccaagtacac | atacacactt | cctgcccact | tgttttatat | 900 |
| tacgtactta | cttcttatgg | ttattataag | aatgcaggca | ggaggaggat | accaatttgc | 960 |
| tggttgatac | agatcctgtc | tctgaattca | gaggcaaaag | atgaatgaat | tatgtagtat | 1020 |
| cttctatttt | tgtttttcag | gtttcatgtg | ccaaacaggg | cttgagtgtt | atttttttttc | 1080 |
| tttaaaaatt | tgtatttttt | tttttctttc | agacagtctt | gctctgtcat | caaggctgga | 1140 |
| ttacagtggt | gcagttgtag | ctcactgcag | cctcaaactc | ctgggctcca | gtgatcctct | 1200 |
| cacctcagcc | tcccaagtag | ctaagaccac | aggcacatgc | tgccacccct | gactaattt | 1260 |
| tcttttttaa | aattttttttc | tcactgcgtt | gcccaggctg | gtctcaaact | ctttggctca | 1320 |
| agccatccat | cctcctacct | cagcctccca | aagtgctgag | attacaagcg | tgaaccacca | 1380 |
| tgccaggagg | gaatgttctt | tcttgaacgt | ggctgccctg | tcacctcagc | attctttgcg | 1440 |

```
gcagctgtgg cctaagcgta gccccttgct aacctcagct cttcttcc cacctttccc      1500
ggcctgcagc tccatgtgca agaagctttc cggcaaccac ctgaacccag agcccaacca    1560
gccggccccc agtgtggacc tagacttcct ggaagatgac atcctgggct tcctgcgac     1620
aggggcggc ggcgggggca gtgggggcgc tgaccagccc tgtgacatcc tccagcagag     1680
cctccaagag gccaacatca cggagcagac gctggaggcc gaggctgagc tggacctggg    1740
tcccttccag ctgcccaccc tgcagcctgc ggatggcggg gcaggcccga cgggcgctgg    1800
aggggcagcg gccgtggctg cggggcccca agccctcttc ccaggcagca ctgacctgct    1860
ggggctgcag ggcccgccca ccgtgctgac ccaccaggcc ctggtgccgc cccaggacgt    1920
ggtcaacaag gccctgagtg tgcagcccct cctgcagcct gtgggcctgg caatgtgac    1980
actgcagccc atcccgggcc tccaaggcct gcccaatggc agccctgggg gtgccacggc   2040
ggccacgctg ggcctggcgc ccatccaggt ggtgggccag cccgtcatgg cgctcaacac   2100
gcccacctcc cagctcctgg ccaagcaggt gcccgtcagc ggctacctgg cctcggcggc   2160
tggcccctcg gagcccgtga cgctggcgtc ggccggtgtc tcgccacagg gggctggcct   2220
ggtcatccaa aagaacctct cggccgctgt ggccaccacg ctcaatggga actctgtgtt   2280
cggaggcgcg ggggccgcct cggctcccac cgggacgccc tcgggacagc cgctggcggt   2340
ggccccaggc ctcggctcgt cgccactggt ccggcgcccc aacgtgatcc tgcatcgcac   2400
acccacgccc atccagccca gcccgcgggg ggtgctgccg cccaagctct accagctgac   2460
gcccaagccg tttgcgcccg cgggcgccac gctcaccatc cagggcgagc cggggcgct   2520
cccgcagcag cccaaggccc cgcagaacct gacgttcatg gcggcgggga aggcgggcca   2580
gaacgtggtg ctgtcgggct tccccgcgcc tgcgctgcaa cgaacgtctc tcaagcagcc   2640
accggccacc accaccggag cggccccgcc gcagcccccc ggggccctga gcaaacccat   2700
gagcgtccac ctcctgaacc aaggcagcag catcgtcatc cccgcccagc acatgctgcc   2760
gggccagaac cagttcctac tgcctggcgc cccggcggtc cagctcccgc agcagctctc   2820
agccctgccg gccaacgtgg gcgggcagat cctggcggcc gctgccccc acacaggtgg   2880
acagctcatc gcgaacccca tcctcacaaa ccagaacctg gcgggccac tgagcctggg   2940
ccccgtgttg gccccccact ccggggccca cagcgcgcac atcctctccg ccgctcccat   3000
ccaggtgggc cagcctgcgc tcttccagat gcccgtgtcg ctggcggcgg gcagcctgcc   3060
cacgcagagc cagccagcgc ccgcggggcc ggccgccacc actgtcctcc agggggtcac   3120
cctgccccc agcgccgtgg ccatgctcaa caccccgac ggcctggtgc agccggccac    3180
ccctgccgct gccaccgggg aggccgcgcc tgtcctcacg gtgcagcctg cccccaggc    3240
gcccccgcg gtcagcacac ccctgcccct gggcctccag cagccgcagg cgcagcagcc   3300
cccgcaggcc cccaccccac aggcgccgcc cccgcctcag ccaccaccc ccagcccag    3360
ccctggcctg gcgtctagcc cggagaagat cgtcctgggg cagccgccct ctgccacccc   3420
cacggccatc ctcactcagg actccctgca gatgttcctg cccaggaga ggagccagca   3480
gcccctctcc gcagagggcc cccacctctc cgtgcctgcc tcggtcatag tcagcgcccc   3540
gcctcccgcc caagacccag ccccagccac ccccgtcgcc aaaggagctg gcctcggccc   3600
tcaggccccc gacagccagg cttccccggc tccggccccc cagatcccgg cagcggctcc   3660
gctgaagggc ccaggcccct cttcgtcccc gtcactacct caccaggccc ctctggggga   3720
cagcccccac ctgccctccc cacacccac ccggccccct tccgcccac cctcccggcc    3780
acagagtgtg tcccgccctc cctcagagcc acccttgcac ccttgccccc cacccagg    3840
```

-continued

```
cccccccaact ctgcctggca tctttgtcat ccaaaaccag ctaggcgttc cccgcctgc    3900
cagcaacccg gccccctactg ccccaggccc gccgcagccg cctctccgcc cccagtccca   3960
gccgcctgag ggaccgctgc ccccagcccc ccacctccct ccatcctcca cctcctctgc   4020
tgtggcctcc tcctctgaga cgtcctccag gttgccagcc cctacgccat ccgacttcca   4080
gctccagttc ccacccagcc agggggcccca caagtccccc actcccccctc caaccctcca  4140
cctggtccct gagccggcag caccccccccc accgcctcct cggaccttcc agatggtgac   4200
cacccccttc ccagcgctgc cccagccgaa ggctcttctc gagagatttc accaggtgcc   4260
gtccggaatc atcctccaga caaggctggg ggggcccct gccgccccgc agacctccac    4320
cagcctgggg cccctcacca gcccgctgc gtctgtgctg gtcagtgggc aggcccatc     4380
tgggaccccc actgcccca gccacgcccc cgccccggca ccatgcccg ccacaggcct    4440
cctcctctg cttccagccg agaacaaggc ttttgccagc aacctcccga ccctgaatgt    4500
ggccaaggcc gcttcctccg ggccagggaa gccctccggg ctgcagtatg agagcaaact   4560
gagtggcctg aagaagcccc ccacgcttca gcccagcaag gaagcctgtt tcctggagca   4620
tttgcacaaa caccagggct ccgtcctgca ccccgactac aagacggcct tcccctcctt   4680
tgaggacgcc ctgcatcgcc tcctgcccta ccatgtctac cagggcgccc tcccctcccc   4740
cagtgactac cacaaagtgg acgaggagtt tgagacggtc tccacgcagc tgctgaaacg   4800
cacccaggcc atgctcaata aatatcggct cctgctcctg gaggagtccc ggagggtgag   4860
cccctcagcg gagatggtaa tgatcgaccg aatgttcatt caggaggaga agaccaccct   4920
tgccttggat aaacagctgg ccaaggagaa gccggacgag tacgtgtctt cctcccgctc   4980
gctcggcctc cccatcgcag cctcttccga gggtcatcgg cttcccggcc acggcccct    5040
gtcgtcttca gctcccgggg cctccaccca gccccctcca cacctgccca ccaagcttgt   5100
gatccggcac ggcggggcag gcggctcccc ttcggtcacc tgggcccggg cgtcctcctc   5160
cctgtcctcc tcttcctcct cctcctctgc cgcctcctcc ttggacgccg acgaggacgg   5220
ccccatgccc tcccgcaacc gccgccccat caagacctac gaggcccgga gccgcatcgg   5280
gctcaagctc aagatcaagc aggaagccgg gctcagcaag gtcgtgcaca cacggccct    5340
ggaccccgtg caccagcccc cgccaccccc cgctaccctc aaggtggccg agccccccgcc  5400
acggccgcca ccaccaccgc cgcccacggg ccagatgaac ggcacggtgg accacccgcc   5460
gcctgccgcc cccgagcgca agccctgg caccgccccg cactgcccgc gcctgccact     5520
gcgcaagacc taccgcgaga cgtgggggg cctggcgcg ccggagggga cgcccgcagg    5580
cagggcacgg ggaggcagcc cggcgccgct gcccgcaaaa gtggacgagg ccaccagcgg   5640
gctcatccgc gagctggcgg ccgtggagga cgagctgtac cagcgtatgc tgaagggccc   5700
cccgccagag cccgcagcca gcgccgccca aggcaccggg gaccccgact gggaggcgcc   5760
cgggctgccc cctgccaagc ggcgcaagtc cgagtcgccc gacgtggacc aggccagctt   5820
ctccagcgac agcccgcagg atgacacgct caccgagcac ctgcagagcg ccatcgacag   5880
catcctgaac ctgcagcagg ccccccggccg gacgcccgcg ccctcgtacc ccacgctgc   5940
ctcggccggc accccccgcat ccccgccgcc cctgcacagg cccgaggcct acccacctc   6000
cagtcacaac ggtggcctcg gcgccaggac gttgaccaga taacaccggg ccgcctcccc   6060
ttccccgtcc cctcctcccg aagacgccgg gacagtcggg tgtccgccct cagcctcctg   6120
gggactcgag ccggggatcc cctgacggtt tttcttgcct aagttatttg agtcacaaag   6180
```

| | |
|---|---:|
| gcctccttcc ctgccgcctg cttcagctgg gttgctgggg ggtgggcgtg gatttaggga | 6240 |
| gggggctgtg atgtaaaacg tctcccctgc caaggaggg gcaaagtgct gtgtcagttc | 6300 |
| ctgtttcttc ccatttcctg gcacactctg cccctctgtc cggggacac gcgcatgtgt | 6360 |
| ttgccaggga tggggccacc gggttgatgc caacgctccg ggtgcctgtc ttgtctgtgt | 6420 |
| ggcttctcag atggtggagg gtgctggag ctggcaggt ccttccagac agtctcagcc | 6480 |
| tctcccgcc gcccccaaca ggctgtcaaa caaaaccgga gaggggtgg gggagccagc | 6540 |
| ctcccagcgt gctgtgcccg caggcacccg tgtgacatcc gcacgtccag ctccgtgacc | 6600 |
| tgtgtgtgtg tgtgtgtgca caagtgagtg agagatttcg aacgcccacc cctcgacttt | 6660 |
| gaaatctgag caaaacaaga aactggggtc ttcctctccc ccgaacctct ccccagctag | 6720 |
| tcttccctct gttcttcctg cctccagccg cccgcgccag attttgaaat ctcggagaca | 6780 |
| aaactagtac tgtaagataa atttttttgt actgtattta ttgtgtataa cgatttttttt | 6840 |
| aaaggagaat | 6850 |

<210> SEQ ID NO 29
<211> LENGTH: 477
<212> TYPE: DNA
<213> ORGANISM: Homo sapien

<400> SEQUENCE: 29

| | |
|---|---:|
| gcgtggtcgc ggcgaggtac aaaaataaca gcatttagtt gcagattaga aacagatgtg | 60 |
| aagggcgaaa aagcaccata gggaaggaca taagaggtcc ctggagtcag acttgggaga | 120 |
| tgtgagtttt atcagtttgc cattaggtag ttgtgtgcac ccttgggcat atagcacttt | 180 |
| tttggtaatt ctattttcgc acttttcaaa tgagatgcaa ttagattaga gactgtaaag | 240 |
| taaaagctgc catgcttcat ttttttaaaa ccaattaaac gccattttta tacggaagtt | 300 |
| tggacaaaca aaaacaacaa aaaaacaaca acaaaacagc ttgggcggct acttcggtgg | 360 |
| ctcattacgc ggtttccctg gtggtggaca ttgggtttct ccgctccaca attccccaga | 420 |
| caacttaggg acgcaagaaa ccccgatcac aaaagcactc ccacaaccac acacaca | 477 |

<210> SEQ ID NO 30
<211> LENGTH: 662
<212> TYPE: DNA
<213> ORGANISM: Homo sapien

<400> SEQUENCE: 30

| | |
|---|---:|
| gcatgatgct gggacaggac agcatcctca atcaatccaa cagcatattc ggttgcatct | 60 |
| tctacacact acagctattg ttaggttgcc tgcggacacg ctgggcctct gtcctgatac | 120 |
| tgctgagctc cctggtgtct ctcgctggtt ctgtctacct ggcctggatc ctgttcttcg | 180 |
| tgctctatga tttctgcatt gtttgtatca ccacctatgc tatcaacgtg agcctgatgt | 240 |
| ggctcagttt ccggaaggtc caagaacccc agggcaaggc taagaggcac tgagccctca | 300 |
| acccaagcca ggctgacctc atctgctttg ctttggcatg tgagccttgc taagggggc | 360 |
| atatctgggt ccctagaagg ccctagatgt ggggcttcta gattacccc tcctcctgcc | 420 |
| atacccgcac atgacaatgg accaaatgtg ccacacgctc gctctttttt acacccagtg | 480 |
| cctctgactc tgtcccccatg ggctggtctc caaagctctt tccattgccc agggaggaa | 540 |
| ggttctgagc aataaagttt cttagatcaa tcgaaaaaaa aacaaaaaaa aaaaaaggt | 600 |
| gggggaaccg gggcaagggt ccgggggaat tgttcgccca accaaaaata aaaaaaaag | 660 |
| gc | 662 |

-continued

<210> SEQ ID NO 31
<211> LENGTH: 780
<212> TYPE: DNA
<213> ORGANISM: Homo sapien

<400> SEQUENCE: 31

| tcgttaaaga | ggataaccag | gtggctcatg | gtagtcacct | ttctcgggca | gtgatcaagg | 60 |
| cacatggggt | tgacagatcc | taaccatgga | ttcaaccccca | cacccaccac | ctctgccagg | 120 |
| atggggcaga | ggtatcgggc | tggtggagca | tgtgctggga | caggacagca | tcctcaatca | 180 |
| atccaacagc | atattcggtt | gcatcttcta | cacactacag | ctattgttag | gttgcctgcg | 240 |
| gacacgctgg | gcctctgtcc | tgatgctgct | gagctccctg | gtgtctctcg | ctggttctgt | 300 |
| ctacctggcc | tggatcctgt | tcttcgtgct | ctatgatttc | tgcattgttt | gtatcaccac | 360 |
| ctatgctatc | aacgtgagcc | tgatgtggct | cagtttccgg | aaggtccaag | aaccccaggg | 420 |
| caaggctaag | aggcactgag | ccctcaaccc | aagccaggct | gacctcatct | gctttgcttt | 480 |
| ggcatgtgag | ccttgcctaa | gggggcatat | ctgggtccct | agaaggccct | agatgtgggg | 540 |
| cttctagatt | accccctcct | cctgccatac | ccgcacatga | caatggacca | aatgtgccac | 600 |
| acgctcgctc | ttttttacac | ccagtgcctc | tgactctgtc | cccatgggct | ggtctccaaa | 660 |
| gctctttcca | ttgcccaggg | agggaaggtt | ctgagcaata | aagtttctta | gatcaatcaa | 720 |
| aaaaaaaaaa | aaaaaaaaaa | aaaaaaaaaa | aaaaaaaaaa | aaaaaaaaaa | aatcgcggcc | 780 |

<210> SEQ ID NO 32
<211> LENGTH: 597
<212> TYPE: DNA
<213> ORGANISM: Homo sapien

<400> SEQUENCE: 32

| actctaatat | aaaggacagg | tggtgtttct | aaataattgg | ctgctatggt | tctgtaaaaa | 60 |
| ccagttaatt | ctatttttca | aggttttttgg | caaagcacat | caatgttaga | ctagttgaag | 120 |
| tggaattgta | taattcaatt | cgataattga | tctcatgggc | tttccctggg | aggaaaggtt | 180 |
| ttttttgtgg | tgttttttttt | aagaacttga | aacttgtaaa | ctgaagatgt | ctgtgagctt | 240 |
| ttttgcccat | ctgtaggtgt | actgtgaaga | tttcaaaacc | tgagagcact | ttttcttgtg | 300 |
| tgttagaatt | atgagaaagt | ggctagatga | ctttaggatt | tgcgattttt | ccctttattg | 360 |
| gctcatttct | ttgtgacgcc | tttgtttggg | gagggaaatc | tgtttattt | ttcctacaaa | 420 |
| taacaagagc | gtaaaggaat | cttaaaaaaa | gaaacaacaa | aaaatgacat | gaagacaaaa | 480 |
| caagagaaaa | aaaaaaacaa | acaacgaccg | tgggggtgct | taaccgcggg | ccaacagttg | 540 |
| tgcatcccgt | gggagacaga | tgttgctcgc | ccgacaaatc | cccacaaaaa | tgggagg | 597 |

<210> SEQ ID NO 33
<211> LENGTH: 2328
<212> TYPE: DNA
<213> ORGANISM: Homo sapien

<400> SEQUENCE: 33

| gcggcccgac | ccgcctcagt | cttccagggc | ggcggtgggt | gtccgcttct | ctctgctctt | 60 |
| cgactgcacc | gcactcgcgc | gtgaccctga | ctcccccctag | tcagctcagc | ggtgctgcca | 120 |
| tggcgtggcg | gcggcgcgaa | gccggcgtcg | gggctcgcgg | cgtgttggct | ctggcgttgc | 180 |
| tcgccctggc | cctgtgcgtg | cccggggccc | ggggccgggc | tctcgagtgg | ttctcggccg | 240 |

-continued

```
tggtaaacat cgagtacgtg gacccgcaga ccaacctgac ggtgtggagc gtctcggaga      300
gtggccgctt cggcgacagc tcgcccaagg agggctgcgc atggcctggt gggcgtcccg      360
tgggcgcccg gcggagacct cgagggctgc gcgcccgaca cgcgcttctt cgtgcccgag      420
cccggcggcc gaggggccgc gccctgggtc gccctggtgg ctcgtggggg ctgcaccttc      480
aaggacaagg tgctggtggc ggcgcggagg aacgcctcgg ccgtcgtcct ctacaatgag      540
gagcgctacg ggaacatcac cttgcccatg tctcacgcgg gaacaggaaa tatagtggtc      600
attatgatta gctatccaaa aggaagagaa attttggagc tggtgcaaaa aggaattcca      660
gtaacgatga ccatagggt tggcacccgg catgtacagg agttcatcag cggtcagtct      720
gtggtgtttg tggccattgc cttcatcacc atgatgatta tctcgttagc ctggctaata      780
ttttactata tacagcgttt cctatatact ggctctcaga ttggaagtca gagccataga      840
aaagaaacta agaaagttat tggccagctt ctacttcata ctgtaaagca tggagaaaag      900
ggaattgatg ttgatgctga aaattgtgca gtgtgtattg aaaatttcaa agtaaaggat      960
attattagaa ttctgccatg caagcatatt tttcatagaa tatgcattga cccatggctt     1020
ttggatcacc gaacatgtcc aatgtgtaaa cttgatgtca tcaaagccct aggatattgg     1080
ggagagcctg gggatgtaca ggagatgcct gctccagaat ctcctcctgg aagggatcca     1140
gctgcaaatt tgagtctagc tttaccagat gatgacggaa gtgatgagag cagtccacca     1200
tcagcctccc ctgctgaatc tgagccacag tgtgatccca gctttaaagg agatgcagga     1260
gaaaatacgg cattgctaga agccggcagg agtgactctc ggcatggagg acccatctcc     1320
tagcacacgt gcccactgaa gtggcaccaa cagaagtttg gcttgaacta aaggacattt     1380
tattttttt actttagcac ataatttgta tatttgaaaa taatgtatat tattttacct     1440
attagattct gatttgatat acaaaggact aagatatttt cttcttgaag agacttttcg     1500
attagtcctc atatatttat ctactaaaat agagtgttta ccatgaacag tgtgttgctt     1560
cagactatta caaagacaac tggggcaggt actctaatat aaaggacagg tggtgtttct     1620
aaataattgg ctgctatggt tctgtaaaaa ccagttaatt ctattttca aggttttgg     1680
caaagcacat caatgttaga ctagttgaag tggaattgta taattcaatt cgataattga     1740
tctcatgggc tttccctgga ggaaaggttt tttttgttgt ttttttttta agaacttgaa     1800
acttgtaaac tgagatgtct gtagcttttt tgcccatctg tagtgtatgt gaagatttca     1860
aaacctgaga gcacttttc tttgtttaga attatgagaa aggcactaga tgactttagg     1920
atttgcattt ttccctttat tgcctcattt cttgtgacgc cttgttgggg agggaaatct     1980
gtttattttt tcctacaaat aaaaagctaa gattctatat cgcaaaaaaa aaaaaaaaaa     2040
aaaaaaaaac aaattgtttg gtgggcgggc cttgggccct gtgagaaaag gtttttaaac     2100
acaattcggt tggggcgcgc ggggcccgag agtaggcgat aggtcgaaca gtgggccata     2160
agggtgttcc tagggaaacc ggggcaaaac acatgcgcct gtgatttcac ccagataaaa     2220
aaacccgggg ggggaccccg gggcttttg gacaaatcca agagggtt ccaagggca     2280
taccgggggtt ctacacacgg ggttccagag ggccgatttt atttccag                 2328
```

<210> SEQ ID NO 34
<211> LENGTH: 737
<212> TYPE: DNA
<213> ORGANISM: Homo sapien

<400> SEQUENCE: 34

```
gtgatcgata tatagcgcaa tgttcctcta atgctgctcg agcggcgcgt gtgatggatg       60
```

```
cgtggtcgcg gcgaggtaca tcttcagagt ttcagtcggc aatttcttgg acatggatgt      120
agaacctaca gataaggtga gccaactgca ttaggaaata actctaataa ttctgttaat      180
tcttagagag gaaaactttc aaaatcttcc tcaggtattt attacaactg cctttaccat      240
tttagttgta acacagttta aattgttatg ataacaagta aataagagca agaatttat       300 ttcttaattc aaaactatac gtttgaattc aatatggtat aacttaaagt ggtataatac      360
atacaatgca tgaatcataa tggattcttt tataagttat taatttttat ggtttaatca      420
gtctaattgt tttgactgtt atagaaacca aatattttac tgtttctttt aaggactaat      480
attgtcaaaa actgctgtta ttaacttcac ttgagttgtt taacttcctt ctgttttaag      540
attgtacatt aaaaattact attttgttat atggaatggt taattttttac ctaataaaaa      600 catagatgaa atacattgga aaaaaaaaaa aaacaaaaaa aaaaaaaaaa aagcttgggg      660
gacccggggc caaagcgggg tccccggggg aaatttttttt cccggcccca attcccccat      720
ttccaaacaa aaaatca                                                     737

<210> SEQ ID NO 35
<211> LENGTH: 215
<212> TYPE: DNA
<213> ORGANISM: Homo sapien

<400> SEQUENCE: 35
cgtggtcgcg gcgaggtaca agtttccaat aaacagacag acagaagcaa aacccccaaat      60 gagaaagaat acattggtaa cctaaatcat aggcatttgt gggtatgttc atacaatcta     120
cctatttctt tgtaatttac tatagcactg atgacaaagc atagacatac aatgagaaag     180
agcaaatcag catatcagtg tgactgtgca accac                                 215

<210> SEQ ID NO 36
<211> LENGTH: 1065
<212> TYPE: DNA
<213> ORGANISM: Homo sapien

<400> SEQUENCE: 36
gccgatcttt tttttttttt tttttttttt tttttttttt tttttttttt tttacatgaa      60
aacatgttta ttgcctgaat aataaaaactt agctaaggag ttattagaat taggattccc     120
cctacttgaa gtacaagttt ccaataaaca gacagacaga agcaaaaccc caaatgagaa     180
agaatacatt ggtaacctaa atcataggca tttgtgggta tgttcataca atctacctat     240
ttctttgtaa tttactatag cactgatgac aaagcataga catacaatga aagagcaa       300 atcagcatat cagtgtgact gtgcaaccac tacaaagctt ggccttctta aatgtggcca     360
ctttaactta cacacaccca cagaggcatc agaaatctcc ctgcaaacac gatttgccta     420
tagttttgtg gcaatactgt tacatagaac aaaaacaact ctcagaccat ggttaataaa     480
taagagagaa aagaagtaag aaacaacttc catgggttgg caggcatgca aagcagcacc     540
ttgaacctca tttgaaaaac aggcaactgg gatagctttt ggagcccagg agtgaaggct     600
agaggctgaa aggagctatg cactattatc tttgggtatt tccacataat ctgcaggatg     660
gggaagttta attccgcacc acataaactg tgctctttta gatgtggctg aaacgggtgt     720
ctctgcagaa ttagaaaccc atctagaaat gacattgctt aaaattgttc tttccaggtg     780
acaattccat aacaatcaca taataatgt acaaaaacaa aactaaaaac aaagtcactc      840
aagtgtccaa ttttttctctt ttgaaagatg accttagatg tattctcaaa gtgcaaatcg     900
```

| | |
|---|---:|
| ggatataaaa aaatagtagg tatgggggaa atgtagcmcm atcttctgtc ccccaccctc | 960 |
| caaaacgggg ctgatttgat tccctctttc tagcatttgt atccttccac ctatacttta | 1020 |
| agataatcat ttttcagccg acctagtsgg gtcccatggc tccta | 1065 |

<210> SEQ ID NO 37
<211> LENGTH: 872
<212> TYPE: DNA
<213> ORGANISM: Homo sapien

<400> SEQUENCE: 37

| | |
|---|---:|
| gtggtcgcgg ccgaggtaca ttgtagaaga aaaattccac aagactctca ctaaaattgg | 60 |
| tatagaatga gaccaaggcc ttggaacagc tgccagtgca atccctacta agagagcttc | 120 |
| tgctgttagt gtatagcagc ttcactgacc aaaccagcac aaccacctca tagagaaaag | 180 |
| gcttctagaa ttctctgctg gatgaaatat gattaaaatg tgggactagt agggttagtc | 240 |
| ttctaagaat tttgaggtaa taattatgga aaatatatct tttacagatt tcttttggga | 300 |
| aaacataaag ctgccattga agtatataat gaagcagcta aactcaacca gaaagattgg | 360 |
| gtaagtagag aacttacagt tctttcttat tagtaaactt gctaatggtt ccatttaaag | 420 |
| aaaaaaacac aaaacaacaa aaaacaacag cgcaggacgg gaaacacagg gacaaaccca | 480 |
| gaaccacggg agaaaacaag aaaaaccgca cagagatcca acaaaaaaac ccgaaacaaa | 540 |
| gagaaacaca accacaacag agaggagaaa aaaaaaaagc aaaataagaa cagaaaaaaa | 600 |
| gaagagaaga aaaagacaga aaaaaagcag acaagcaaaa aagaaaaaca aacagaagaa | 660 |
| gagaagaaaa gaagcagaga agagaacaga agcaagaaaa gcgaaaagaa gagaaaaaaa | 720 |
| acgagacacg accacaaaag cgaaaagaaa gagagaatag cacaacgata aagaaaaca | 780 |
| agagccgaaa agaaaagaga aaaaaagca agagaaggac aaggagaaga gagggcgaag | 840 |
| gagaagaata gagcagaaac aacaaaagac ga | 872 |

<210> SEQ ID NO 38
<211> LENGTH: 751
<212> TYPE: DNA
<213> ORGANISM: Homo sapien

<400> SEQUENCE: 38

| | |
|---|---:|
| cggccgcccg ggcggtacgg ggagaacata tcaaaagggg gaaggatgga ttcccttgat | 60 |
| gcccaggatt acagggcacc taaagcacat tttttttttt ctgagccaac cagctaaagg | 120 |
| atcactgcag ctaatacag atagagaagc aacaaaaggc ccaaggccaa atacccatca | 180 |
| gagacagtga caagagcagc tgggggcacg ggggaggcgg aaggaagaga agaaggggga | 240 |
| ggagcctcca gagtcccagc cccaaccccc tctgccattg ctacccttg ctccccaaaa | 300 |
| atccctgggg ttgaagtgag gaggactaca ggctggggtg aaaatacaca aggacagccc | 360 |
| aacaaaatac aacaaggact agcatcagtc tccccttac tccaccccca agaaaaatac | 420 |
| ccttattgtg actagtattt atgaaaatct gtaagagact attctatgta gtggctctaa | 480 |
| tcccatatac acagcagctg cctgtgttgg gaacttttca aatcagtgat ttgcgggaac | 540 |
| aaacagtatt ttcagcttct tacggtgcca tgcaggcttt accaagacct tggttaagtc | 600 |
| ccaagtcaca tgtactttct gtcttacatc tgaagagggt gagggaaagg aggggagggg | 660 |
| agaaaggtgc ctcgggtgct aggtaaagct tggcgtatca tggtcctagc tgtccctgtg | 720 |
| tgaatgtttc gctccatcaa aaaaaaacca c | 751 |

<210> SEQ ID NO 39
<211> LENGTH: 2299
<212> TYPE: DNA
<213> ORGANISM: Homo sapien
<220> FEATURE:
<221> NAME/KEY: misc_feature
<222> LOCATION: (275)..(275)
<223> OTHER INFORMATION: a, c, g or t

<400> SEQUENCE: 39

| | | | | | | |
|---|---|---|---|---|---|---|
| gtcaggcgct | gatgtcgggt | gccccgaggg | tttttgattg | ggcggctgtc | tctctttggg | 60 |
| cccgccgttg | tttgtcttct | tgggccctgt | ggacggtggg | tgattgtggc | ccctgggttt | 120 |
| cttcgcgccc | gctgttggtg | ttgtgtcttt | gctggctcgc | cgcacacctg | gtccccca | 180 |
| cggggcgtcc | cctgcgctcg | cgccactctg | tgtgaaccc | gtccggttgt | agcctttccg | 240 |
| ttgaccccgg | gcaatgattc | gcgcaactcc | agatntaggc | ccttacagtt | ccgcctgtat | 300 |
| gccagacatg | ctctgcccta | tggcaggtcc | aaggagagga | ttgtccactt | gaaagtgggc | 360 |
| accacttaaa | tggatgacca | gacacacctg | gaccccacag | acccagagcc | atttcttcta | 420 |
| agcgcgctgg | agtagctcga | ggaatggaag | agggaaattt | ggaagcaggg | tcccttttcg | 480 |
| atcttcatgt | gaagagaccc | agcctcttca | agggtatcca | agataaactt | ccgttcccca | 540 |
| agcccaccaa | tccctgtcca | gttcctttgc | ttcctgccct | cccaaatagg | acattctcct | 600 |
| ttgtgcccag | cccccctttg | cacagatcct | ccaaggggag | tccccatgat | ccacaaggca | 660 |
| gagaccttca | tagcagaggg | cagggcaggt | acacactatc | ctctccctta | tgcatggctg | 720 |
| gacactgact | gaggccctgc | atcacaagaa | tcgccaatac | ccactgggag | ccataacaat | 780 |
| aaatctggaa | gtacggggag | aacatatcaa | aagggggaag | gatggattcc | cttgatgccc | 840 |
| aggattacag | ggcacctaaa | gcacattttt | tttttctga | gccaaccagc | taaggatca | 900 |
| ctgcagctaa | atacagatag | agaagcaaca | agccaggca | ataccccatc | agagacagtg | 960 |
| acaagagcag | ctgggggcac | gggggaggcg | gaaggaagag | aaagaagggg | aggagcctcc | 1020 |
| agagtcccag | ccccaacccc | ctctgccatt | ggctaccctt | gctccccaaa | aatccctggg | 1080 |
| gttgaagtga | ggaggactac | aggctggggt | gaaaatacac | aaggacagcc | caacaaaata | 1140 |
| caacaaggac | tagcatcagt | ctccccctta | ctccaccccc | aagaaaaata | cccttattgt | 1200 |
| gactagtatt | tatgaaaatc | tgtaagagac | tattctatgt | agtggctcta | atcccatata | 1260 |
| cacagcagct | gcctgtgttg | ggaacttttc | aaatcagtga | ttgcgggaac | aaacagtatt | 1320 |
| ttcagcttct | tacggtgcca | tgcaggcttt | accaagacct | tggttaagtc | ccagtcacat | 1380 |
| ttactttctg | tcttacatct | agaaagggt | gaggaaagag | gggaggggag | aaaggtgctc | 1440 |
| aggtgctagg | taaagcttac | tgatcagcag | cctagactcc | accactgttc | cttctctttg | 1500 |
| gtctgtctag | aacagtgact | ataaattagg | aaaaacaaaa | ttatgctggc | ctgtgggaaa | 1560 |
| taatggggga | aggaaggcag | ggaggaaaag | ggcattggga | agccctgctt | caagactgaa | 1620 |
| gacagacaaa | tagacaacca | cccagactgc | ttaagtgtca | cagacagccc | ccaccccaag | 1680 |
| ctcccttcca | ggtatcccca | taatcattt | gggcacactc | cctcttggaa | ttgcaatttc | 1740 |
| catcttccac | ttatccctaa | ggagctggcc | ctgtggagag | gtgtgttggt | tgttttgttt | 1800 |
| ttgccaaagg | ccctcgctct | agtgctcct | gtaaaggtac | cttggcccc | tgatacggga | 1860 |
| tgaatggatg | aacgaagccc | cagatgctcc | agtgccaagg | aggtcagacc | gggaacaggc | 1920 |
| ccccactccc | acaccctggg | atcggagctt | gcttggttct | tgccatcttg | caggatgact | 1980 |
| tcgagtctgg | agggagatac | acagtgcctc | tccatccctg | gggtgggggg | aagggattct | 2040 |

```
gctgggactc ttgagtgggg aagggggaga tgggagcagg gtctaaaccc tcaggctccc    2100
atgaaggtct gtctctgtcc cagatgaact gctatcagag tccatttctg cattctcatt    2160
atggagcctc tccagcataa ttttgttttt cctaatttat agtcactgtt ctagacagac    2220
catagagaag gaacagtggt ggagtctagg ctgctgatca gtaagcttta cctagcacct    2280
gagcaccttt ctcccctcc                                                  2299

<210> SEQ ID NO 40
<211> LENGTH: 301
<212> TYPE: DNA
<213> ORGANISM: Homo sapien

<400> SEQUENCE: 40
acttctaagt gccctgcag atgggcagag ggatgcatgg ggatgcaggt cccttgcatt      60
tcttggtatc tctcagcttt tcctcttgca gctcccccta ccaggggtcg ctttctcctg    120
gattgcaaat gcctcttcag tttggactca gctctgacag cccctcctcc aggaaggcct    180
tccaggactt cctcctctgg gtcctctagc tctgacccta tagggactcc agatctcaac    240
ctgttccctg gaagtagggc ctgctctcca tcccagtgaa ataaacatgt attagacacc    300
t                                                                     301

<210> SEQ ID NO 41
<211> LENGTH: 1035
<212> TYPE: DNA
<213> ORGANISM: Homo sapien

<400> SEQUENCE: 41
gcgtgggtcg acccacgcgt ccgggggcat aagcctaggc cccacccagt gcccgactat      60
gagctaagga ggcccaagtt gcagcccggg tttggaggga gtttgagatg aagcgaatgg    120
tgagtcttgc atcccacagc ttggtcttgc acccctgaga cttctgtgag gctgggggtgc   180 ctgtgcccag tttctttttt ttttctttct tttgagacag aatctcgctc tgtcacccag    240 gcggagtgc agtggtatga tctcagctca ctgcaacctc agcgtcccgg gttcaagcgg    300
ttctcctgcc tcagctggga tcacaggcgc ccaccaccgt gcctggcaaa ttttggtatt    360
gtagtagaga tgggggtttca ccatgttggc caggctggtc tcgaactcct gacctcaagt    420
gatccgccca cctcggcctc ccagactgct gggattacag gcatgagcca ccttgcccgg    480
ctcacccggt cgcctgtgcc cagtttcaag gagagaaaat tgaggctcgg agaatgaaag    540
gcagagagtt aagcagcttg aaggccacag ggcagactgc tgcaaagact tccgggtctc    600
gccctgccta ggatcctggc ttcctggaca gcaggctcg ctgccactac ctgaagggta     660
aactgaggca tctcaagact cagatccaga aattcgatga ccaaggagac agcgagggct    720
ccgtgtactt ctaagtgccc ctgcagatgg gcagagggat gcatgggat gcaggtccct    780 tgcatttctt ggtatctctc agcttttcct cttgcagctc cccctaccag gggtcgcttt    840
ctcctggatt gcaaatgcct cttcagtttg gactcagctc tgacagcccc tcctccagga    900
aggccttcca ggacttcctc ctctgggtcc tctagtctg accctacagg gactccagat    960
ctcaacctgt tccctggaag tagggcctgc tctccatccc agtgaaataa acatgtatta    1020
gacacctaaa aaaaa                                                      1035

<210> SEQ ID NO 42
<211> LENGTH: 368
<212> TYPE: DNA
<213> ORGANISM: Homo sapien
```

<400> SEQUENCE: 42

| aaaaaacaaa | agtgtttcca | ttgctaggct | atgtaactgt | cggaggcgcg | agttgtagga | 60 |
| ctgtgcgcgg | cgggcgacga | tagtctccag | gtccgcgtcg | ccccggtcc | cccggcgctg | 120 |
| cctcgtcctt | gaagatctcc | agtgctacct | tttgttgaac | atctcgaata | gtatcatgtt | 180 |
| ctagatagac | ggctagaggg | ggaaattctc | tgaaggaact | aaggagggc | tggaagggaa | 240 |
| ggaagtgttt | ttaaaactac | gtgaggcatc | agaatccgaa | agccacttta | gttcttagca | 300 |
| aatgtgtttg | taggtgtttg | agcttttact | tagaaacctc | attccttttt | cttgccttct | 360 |
| tttacgtt | | | | | | 368 |

<210> SEQ ID NO 43
<211> LENGTH: 549
<212> TYPE: DNA
<213> ORGANISM: Homo sapien

<400> SEQUENCE: 43

| tcatttcttc | ttccggtccg | aggtcgccgg | gatcccggcc | agctcccgcg | catgagacgt | 60 |
| gaagcccgcg | cagacgtcgc | gcgtcggtgt | ggttacagcc | ggcagccacg | gcacctcctt | 120 |
| ccggccgact | agtctccagg | tcccgcggtc | tggcccctgg | tcaccccgcg | ctgtccctcg | 180 |
| ttccttgaag | atctccagtg | ctaccttttg | ttgaacatct | cgaatagtat | catgttctag | 240 |
| atagacggct | agagggggaa | attctctgaa | ggaactaagg | aggggctgga | agggaaggaa | 300 |
| gtgtttttaa | aactacgtga | ggcatcagaa | tccgaaagcc | actttagtct | tagcaaatgt | 360 |
| gtttgtaggt | gtttgagctt | ttacttagaa | acctcattcc | ttttcttgc | cttcttttac | 420 |
| gttaagcttg | aatgtcatgt | gttatcttgc | tctgatgttg | aaactatata | agaacattca | 480 |
| ttttctttt | tttttaagaa | cattaatttt | ttctagtcag | agaaggctaa | ttttttgaag | 540 |
| tttttttcta | | | | | | 549 |

<210> SEQ ID NO 44
<211> LENGTH: 463
<212> TYPE: DNA
<213> ORGANISM: Homo sapien

<400> SEQUENCE: 44

| acaaacaaac | aaacaaacaa | aaacaagtgg | ccagtctgtg | agctatagtt | cccaacacct | 60 |
| ggtctagact | cttctgccct | tgctctgcag | cttctttcct | gttgattggg | cattcaggga | 120 |
| aggagtttaa | aaagtgacac | tcatggctca | tgacaaatga | gatactttgg | gagtgtggaa | 180 |
| acatggcttg | atatttgcct | tcagatattt | ttgcttatat | aagttctaaa | tggaagtgat | 240 |
| aagttcattc | ttagggtcca | agttgaaagg | cggtggttct | tttgtgaaca | ccactaacta | 300 |
| cattcgaaaa | gcctctccaa | ttccacattc | caagtctata | acagctttgg | aaatgagtaa | 360 |
| caatgacctc | tcatgtagta | gattaaagca | gaggccttgc | catatgattg | ttcttggctt | 420 |
| aaatgtttgt | ggcccggtac | tgtatacttt | ggttccagat | cct | | 463 |

<210> SEQ ID NO 45
<211> LENGTH: 5969
<212> TYPE: DNA
<213> ORGANISM: Homo sapien

<400> SEQUENCE: 45

| tttttttttt | gagaaatttt | tttattgtat | ttgttttcaa | gtgattctgg | taaccaaagt | 60 |

```
attacagtta caggggcaagc aaacatttaa gccaaaaaac aatcatatgg caaaggcctt    120
tgctttaatc tactacatga gaggtcattg ttactcattt cccaaagctg ttatagactt    180
ggaatgtgga attggagagg cttttcgaat gtagttagtg gtgttcacaa agaaccact     240 gcctttcaac ttggaccccta agaatgaact tatcacttcc atttagaact tatataagca    300
aaaatatctg aaggcaaata tcaagccatg tttccacact cccaaagtat ctcatttgtc    360
atgagccatg agtgtcactt tttaaactcc ttccctgaat gcccaatcaa caggaaagaa    420
gctgcagagc aagggcagaa gagtctagac caggtgttgg gaactatagc tcacagactg    480
gccacttgtt tttgtttgtt tgtttgtttg tttgttttg  agacagtctt actctatcgc    540
ccaggctgga gtgcaatggc atgatctcgg ctcactgcaa cctccacctc ccgggttcaa    600
gtgattctcc tgcctcagcc tcccaggtag ctgggactcc aggcacccac cgtcatgcct    660
ggctaatttt tgtatttta gtagagatgg ggtttcacca tgttggccag gctggtcttg    720
aactcctgac ctcaagtgat ccacccacct cggcctccca aagtgctggg attacaggcg    780
tgagccaccg cacccggcct tttattttt tttttaatat aatttctttt tttgtagaga    840
tggtgtctct ctgtgttgcc cagcctagtc ttgaactcct gggctcagga agttgagca    900 gattgttcag agaactctca tctataccac cccccatgca gagtttcctc tattattaac    960
atcttactat ggtggttcca ggaaagaaat cactgaacac tgggaatggc ttgagcaaaa    1020
tctcttgcag acactctcca tctttgaaaa tgagaatgat atcaccacat tgtgagagg    1080 aaaaatacag ggcatcattg cagaatacaa caaaatcaat gatgtaaagg aagatgatga    1140
cacggagaag tttaagaag ccattgtgaa atttcatagg ctgtttggga tgccagagga    1200
agagaaactc gtcaactatt actcttgcag ctattggaag gggaaggtcc cccgtcaggg    1260
ttggatgtac ctcagcatta accacctttg ctttattct tttcttatgg aagggaagc     1320 gaaactggtc atccggtggg tagacatcac tcagcttgag aagaatgcca ccctgcttct    1380
gcctgatgtg atcaaagtga gcacacggtc cagtgagcat ttcttctctg tattcctcaa    1440
catcaacgag accttcaagt taatggagca gcttgccaac atagccatga ggcaactctt    1500
agacaatgag ggatttgaac aagatcgatc cctgcccaaa ctcaaaagga aatctcctaa    1560
aaaagtgtct gctctaaaac gtgatcttga tgccagggca aagagtgaga gataccgtgc    1620
acttttccgg ctgcccaaag atgaaaaatt agatggccac acagactgca ctctctggac    1680
tccatttaac aaaatgcaca ttttggggca gatgtttgtg tccacaaatt acatctgttt    1740
taccagcaag gaggagaact tatgtagcct cattatcccg ctccgtgagg tgacaattgt    1800
ggaaaaggca gacagctcca gtgtgctccc cagtcccta  tccatcagca cccgaaacag    1860
gatgaccttc ctatttgcca acttgaaaga tagagacttt ctagtgcaga ggatctcaga    1920
tttcctgcaa cagactactt ccaaaatata ttctgacaag gagtttgcag gaagttacaa    1980
cagttcagat gatgaggtgt actctcgacc cagcagcct  gtctcctcca gcccccagag    2040
aagcacgagc tctgatgctg atggagagcg ccagtttaac ctaaatggca acagcgtccc    2100
cacagccaca cagaccctga tgaccatgta tcggcggcgg tctcccgagg agttcaaccc    2160
gaaattggcc aaagagtttc tgaaagagca agcctggaag attcacttttg ctgagtatgg    2220 gcaagggatc tgcatgtacc gcacagagaa acgcgggact ctggtgttga agggcatccc    2280
ggagagcatg cgtggggagc tctggctgct gctgtcaggt gccatcaatg agaaggccac    2340
acatcctggg tactatgaag acctagtgga gaagtccatg gggaagtata atctcgccac    2400
ggaggagatt gagagggatt tacaccgctc ccttccagaa cacccagctt ttcagaatga    2460
```

-continued

```
aatgggcatt gctgcactaa ggagagtctt aacagcttat gcttttcgaa atcccaacat    2520
agggtattgc caggccatga atattgtcac ttcagtgctg ctgctttatg ccaaagagga    2580
ggaagctttc tggctgcttg tggctttgtg tgagcgcatg ctcccagatt actacaacac    2640
cagagttgtg ggtgcactgg tggaccaagg tgtctttgag gagctagcac gagactacgt    2700
cccacagctg tacgactgca tgcaagacct gggcgtgatt ccaccatct ccctgtcttg     2760
gttcctcaca ctatttctca gtgtgatgcc ttttgagagt gcagttgtgg ttgttgactg    2820
tttcttctat gaaggaatta aagtgatatt ccagttggcc ctagctgtgc tggatgcaaa    2880
tgtggacaaa ctgttgaact gcaaggatga tggggaggcc atgaccgttt gggaaggta    2940
tttagacagt gtgaccaata agacagcac actgcctccc attcctcacc tccactcctt    3000
gctcagcgat gatgtggaac cttaccctga gtagacatc tttagactca tcagaacttc     3060
ctacgagaaa ttcggaacta tccgggcaga tttgattgaa cagatgagat tcaaacagag    3120
actgaaagtg atccagacgc tggaggatac tacgaaacgc aacgtggtac gaaccattgt    3180
gacagaaact tcctttacca ttgatgagct ggaagaactt tatgctctttt tcaaggtgag   3240
ttgcaaggca gaacatctca ccagctgcta ctggggcggg agcagcaacg cgctggaccg    3300
gcatgacccc agcctgccct acctggaaca gtatcgcatt gacttcgagc agttcaaggg    3360
aatgtttgct cttctctttc cttgggcatg tggaactcac tctgacgttc tggcctcccg    3420
cttgttccag ttattagatg aaaatggaga ctctttgatt aacttccggg agtttgtctc    3480
tgggctaagt gctgcatgcc atgggggcct cacagagaag ctcaaactcc tgtacaaaat    3540
gcacgtcttg cctgagccat cctctgatca agatgaacca gattctgctt tgaagcaac    3600
tcagtacttc tttgaagata ttaccccaga atgtacacat gttgttggat tggatagcag    3660
aagcaaacag ggtgcagatg atggctttgt tacggtgagc ctaaagccag acaaagggaa    3720
gagagcaaat tcccaagaaa atcgtaatta tttgagactg tggactccag aaaataaatc    3780
taagtcaaag aatgcaaagg atttacccaa attaaatcag gggcagttca ttgaactgtg    3840
taagacaatg tataacatgt tcagcgaaga ccccaatgag caggagctgt accatgccac    3900
ggcagcagtg accagcctcc tgctggagat tgggaggtc ggcaagttgt tcgtggccca     3960
gcctgcaaag gagggcggga gcggaggcag tgggccgtcc tgccaccagg gcatcccagg    4020
cgtgctcttc cccaagaaag ggccaggcca gccttacgtg gtggagtctg ttgagcccct    4080
gccgccagc ctggccccg acagcgagga acactcccctt ggaggacaaa tggaggacat    4140
caagctggag gactcctcgc cccgggacaa cggggcctgc tcctccatgc tgatctctga    4200
cgacgacacc aaggacgaca gctccatgtc ctcatactcg gtgctgagtg ccggctccca    4260
cgaggaggac aagctgcact gcgaggacat cggagaggac acggtcctgg tgcggagcgg    4320
ccagggcacg gcggcactgc cccggagcac cagcctggac cgggactggg ccatcacctt    4380
cgagcagttc ctggcctccc tcttaactga gcctgccctg gtcaagtact tgacaagcc    4440
cgtgtgcatg atggccagga ttaccagtgc aaaaaacatc cggatgatgg gcaagccccct   4500
cacctcggcc agtgactatg aaatctcggc catgtccggc tgacacgggc gccttcccgg    4560
gggagtggga ggagggag gggagggatt ttttatgttc ttctgtgttg agttttttct      4620
ttctttcttt taaattaaat atttattagt acctggcttg aagcctagtg ttttcataat    4680
gtaattcaat gaaaactgtt ggagaaatat ttaaacacct caatgtaggt acattacact    4740
cttgttgcgg ggagggggatt taccagaata cagtttattt cgtgaattct aaaaaacaaa   4800
```

```
aagatgaatc tgtcagtgat atgtgtgtat tataacttat taatcttgct gttgagctgt    4860
atacatggtt taaaaatag tactgtttaa tgctaagtaa ggcagcagtc atttgtgtat     4920
tcaggctttt taaataaaat tagagctgta aggaaaatga aaagccacaa atgcaagact    4980
gttcttaaat ggaaggcata gtcagcgagg gtaaatccta taccacttta ggaagtatta   5040
aaaatatttt taagatttga aatatatttc atagaagtcc tctattcaaa atcatattcc   5100
acagatgttc cccttcaaag ggaaaacatt tgggttcta aacagttatg aaagtaagtg    5160 attttttacat gattccagaa taacacttgt attgaccaat ttagacagat accagaccaa  5220
ttttgcattt aagaaattgt tctgattatt tacgtcaact cattgaattt cagtgaaaag   5280
taacagtctt ttgtcacaga gaatctgaaa gtagcagcaa agacagaggg ctcatgacag   5340
gtttttgctt ttgctttgct tttgtttttg aaagagtaaa agtactgatg cttctgatac   5400
tggatgttta gcttcttact gcaaaaacat aagtaaaaca gtcaacttta ccatttccgt   5460
attctccata gattgaagaa atttatacca catatcgcat atgaccatct ttccatcaaa   5520
tcaatgtaga gataatgtaa actgaaaaaa aatctgcaag ataatgtaac tgaatgtttt   5580
aaaaacagaa cttgtcactt tatataaaag aatagtatgc tctatttcct gaatggatgt   5640
ggaaatgaaa gctagcgcac ctgcactttg aattcttgct tcttttttat tactgttatg   5700
attttgcttt ttacagatgt tggacgattt tttcttctga ttgttgaatt cataatcatg   5760
gtctcatttc ctttgcttct ttggaatatt tctttcaaca cattcccttta ttttattata  5820 cattgtgtcc ttttttttagc tattgctgct gttgttttt attctatta caggatgatt    5880 tttaaactgt caaatgaagt agtgttaacc tcaaataggc taaatgtgaa caaataaaat   5940
acagcaaata ctcagataca aaaaaaaa                                      5969

<210> SEQ ID NO 46
<211> LENGTH: 337
<212> TYPE: DNA
<213> ORGANISM: Homo sapien

<400> SEQUENCE: 46
gatcgactca tatgggcgaa tgggtcacat agatgcatgt cgagcggcgc agtgtgatgg     60
atgcatggtc gcggcgaggt gcaggaaaat atacagatat taaagatcag atttaattct    120
ttggtataag catgaaactg ttactgatag cttctccatgg cgagcataaa ccatgaagca   180
actcaagaag catgagagac aacaatgaaa tctagtatac aatgcagggc aggccaagaa    240
cgatgtctgc tttacaggaa aagtcaacac taacaatcta ctcctgagaa actaacacct    300
atttagatgt ttttaacata atggcaaact aaaatgt                             337

<210> SEQ ID NO 47
<211> LENGTH: 3443
<212> TYPE: DNA
<213> ORGANISM: Homo sapien

<400> SEQUENCE: 47
gcgcgagtgg gaggtggcag gcctgcgact ccggccttgt ccgcgcccgc tctcggcgcg     60
acgtctccag ccatgaaccg gtttggtacc cggttggtgg agccacggc gacttcttcg     120 ccgccgccga aggcccgcag caatgaaaac ctcgacaaaa tagatatgtc tttggatgat    180
atcatcaagt tgaatcgaaa ggaagggaag aagcagaatt ttccaagact aaatagaaga    240
ctcctccagc aaagtggtgc ccagcaattc aggatgagag tgcgatgggg aatccaacag    300
aattctggtt ttggtaagac tagtctgaat catagaggaa gagtaatgcc tggaaagaga    360
```

-continued

```
cgtcctaatg gagttatcac tggccttgca gctaggaaaa cgactggaat tcgaaaagga    420
attagtccta tgaatcgtcc acctctaagt gacaagaata tagaacaata ttttccagtg    480
ttaaaagga aggcaaacct tctgagacaa aatgaagggc agaggaaacc agtagcagtt    540
ctcaagagac ctagccagct aagcagaaaa aataacattc cagctaattt taccaggagt    600
ggaaataaat taaatcatca gaaagatact cgtcaggcaa cttttctttt cagaagaggc    660
ctgaaggtgc aggcccagtt gaatacagaa caactgctag acgatgtagt agcaaagaga    720
actcgtcaat ggcggacttc caccacaaat ggagggattt tgactgtatc tattgacaat    780
cctggagcag tgcaatgccc agtaactcag aaaccacgat taactcgtac tgctgtacct    840
tcatttttaa caaagcggga gcaaagtgac gtcaagaaag ttcctaaagg tgttcccctg    900
cagtttgaca taaacagtgt cggaaaacag acagggatga cgttgaatga gcggtttggg    960
atcctgaagg aacaaagagc cactctcaca tacaacaaag ggggaagccg ctttgtcacc   1020
gtgggatagg tcccatgtca aggaactttt gagtgatga ctctgagaag ttgaattgct   1080
tgaagagttc atcacggaaa ttcaagaaac tttacttcaa atattcaca aggctaaata   1140
actcttattt ttattttttga aggttttttt ttttaaaaaa aaaaaacgta taaaataatg   1200
ccctgaaaga ataataggga ttatacctgt ctgttcttaa agatttcatg gttggctcag   1260
acagaacaat catctgtttg acttctttgg ttcctcatgc agcagaagga agacagaagg   1320
atagaaattg attattttta tgatagcggt attcaggatc tcatcaccttt tgcccgtgtt   1380
ttagactttg tcatggtaaa tcctggtctt cataaacatg agtaggtccc ttggttgctg   1440
tcacttgccc tttaatagtg ttgatgtagt cagtgccgtt gccttttctt cattagagac   1500
acagaacaat gtattagaat ttccagctgt gggtttgaag acttagggg acatccagaa   1560
cgtgcttcct ctttcagacg gtgtaaagtc ccctggaatt acacagcttt agtgctgagc   1620
ttttaacagg aaatgtggcc ctaggtatta gtcttagttt aaaatgttgg tgtttagaga   1680
ctgtaaatgc atattcacaa agttatctga tagggccttg gaggagaagg tccagtttta   1740
aaaaatgaca gtttgtgttt aataaatgaa ggcatgagag gaagtaagta gcaagttgaa   1800
ggacaggtag ttgagatgaa acacttcaaa accctggtta tagatgtact gtttggatgt   1860
agcatagtct tgagtctagc gtccacaaag aattattcaa atgatattta gaagaattat   1920
aactattaca ttgaatggag tcccttggat attttgatag taaaattaat agccataaag   1980
tcctagactt cttatttgaa gttaaaattt cttatttgaa aagttgaaat ttatgagctt   2040
tgaagattgc taaattaaat aatttatagc tccaaaaaca aaaatatact tgtatatgtc   2100
acagagaaaa aaaatgcaaa atttataata gagttacatt aaccttgttg tttacctttc   2160
actgatttct tatatggtat aaattaaagt tcaggcattt atggggagaa aaggccctcc   2220
ccaccgaccc gccacctgcc acctctgacg gagtgggaga agttagtctg tgctaagata   2280
gtactgagtc cccagatgtt gtatactgta aattacagta taatgccaaa tgcagcaaaa   2340
tcttccagct gtacgttaca agtttggtca ttttgaagct tgacatttta gtttgccatt   2400
atgttaaaaa catctaaata ggtgttagtt tctcaggagt agattgttag tgttgacttt   2460
tcctgtaaag cagacatcgt tcttggcctg ccctgcattg tatactagat ttcattgttg   2520
tctctcatgc ttcttgagtt gcttcatggt ttatgctcgc catggaaagc tatcagtaac   2580
agtttcatgc ttataccaaa gaattaaatc tgatctttaa tatctgatat tttcctggta   2640
ctcgtactga taagggatta ttggaagtca gtcacagaat ttggaaataa attctagtct   2700
```

-continued

```
ctccttagct atttgatgct tttcatatag gccaagaact cattgcaaaa cattttttgca    2760 aggatgaatg cctgtatttg gtctaggaac agtacatttt agtctgattt agaattactg    2820
gtagcttatt ttaaagcaag gaaaagcagc tgagctcaag tttgctgtct ttagaatggt    2880
ttgtgaaaat atggtataaa ggtgttttca ttttcctgtt cttacctatt attgtataga    2940
gctattcatg ccatttttg ggaaaacttt aaaaattgcc ccaaatactg acattgagtg    3000
cattaaataa caaattatct ttgatacatt aaactttat tcttcatgca tctgtaattt    3060
aattttaagt ataatgtttt gcctttggta caactaaatt aaaactcttg gtggtcacat    3120
attgtatata aacaaaacaa tatgctttgt tgaaggaaaa ttttctttat tggaatgtgg    3180
tgtaatcctt gttcagttct taagtttcgg tttttttaa aaacaggatg caacttaaac    3240
ttttctttgc atcaaggtat atgcaaaaca ttggtgccgt gcatcaccaa atgaaagttt    3300
gtatttaacg aggaggtgct ttacactgta cttttggtg tttttggaa aagttacatt    3360 tagatctatt ctgaagctgt tcatttttaa caaataaat gttacaggtt tcacatgatt    3420
tattctcagc tctaaaaaaa aaa    3443
```

<210> SEQ ID NO 48
<211> LENGTH: 670
<212> TYPE: DNA
<213> ORGANISM: Homo sapien

<400> SEQUENCE: 48

```
gcgtggcgcg gccgaggtac tccagcctgg gagacagagt gagactccat atcaaaaaaa     60 taaaaataa aaaataaaag taataatcag gaaaagggga aaggaattct tgcaagaaca    120
tgacagcgta aatagaaaaa ttaatacatt tgaaagataa agttgaaata tccctataat    180
gtggaacaga atgacaaagg gacatgataa tgaaccaaag gtgataggag ataaaaaaaa    240
ttagaatatt aagtcaaaag atgtaatatc taactaataa tagaaaacag aagagaagaa    300
taaaagaaat aataaagaa aatttccccg aactgaaggc atgtctgtag tttgaaagga    360
cccaatgatt aaaaaaagat taataggcat atttgtgaat tttagaaaag gcatattcgt    420
taatctctac ggacaatcaa tcacaacaaa caagcacaca aacacacaac aaagaaccgc    480
cttcggcgag aaaccacacg gggccaaaga acgaaaggga ccaccggggg gcgagacatc    540
tggtgatacc acaccaggca caaacaatca tcaccagcaa aaactatcag cgaagcaaac    600
gaagaagaac aaaacacaga caaaaacaa aagaacaaga acgaagaca caaaaaaaaa    660 caacaaacag                                                           670
```

<210> SEQ ID NO 49
<211> LENGTH: 973
<212> TYPE: DNA
<213> ORGANISM: Homo sapien
<220> FEATURE:
<221> NAME/KEY: misc_feature
<222> LOCATION: (234)..(398)
<223> OTHER INFORMATION: a, c, g or t

<400> SEQUENCE: 49

```
ggtttatttg ctggcaagaa ggatgaatat aaaatggagt gaccatggtt tatttcagtt     60
aaggtttggt ggcattgaag accaccaaac caagaaaagg tcgaggaagt catttattct    120
ttgagactga tgctagaata acaacagtag aagtgattat ttctgataat ggggattaga    180
atgtgtaatc ttcctgggga aaatacttgg ctaggttggt tgtaggcaat ggtnnnnnnn    240
nnnnnnnnnn nnnnnnnnnn nnnnnnnnnn nnnnnnnnnn nnnnnnnnnn nnnnnnnnnn    300
```

```
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnag ggaaaggaat tcttgcaaga       420
acatgacagc gtaaatagaa aaattaatac atttgaaaga taaagttgaa atatccctat       480
aatgtggaac agaatgacaa agggacatga taatgaacca aaggtgatag gagataaaaa       540
aaattagaat attaagtcaa aagatgtaat atctaactaa taatagaaaa cagaagagaa       600
gaataaaaga aataataaaa gaaaatttcc ccgaactgaa ggcatgtctg tagtttgaaa       660
ggacccaatg attaaaaaaa gattaatagg catatttgtg aattttagaa aaggcatatt       720
cgttaatctc tacggacaat caatcacaac aaacaagcac acaaacacac aacaaagaac       780
cgccttcggc gagaaaccac acggggccaa agaacgaaag ggaccaccgg ggggcgagac       840
atctggtgat accacaccag gcacaaacaa tcatcaccag caaaaactat cagcgaagca       900
aacgaagaag aacaaaacac agacaaaaaa caaaagaaca agaaacgaag acacaaaaaa       960
aaacaacaaa cag                                                          973

<210> SEQ ID NO 50
<211> LENGTH: 1019
<212> TYPE: DNA
<213> ORGANISM: Homo sapien

<400> SEQUENCE: 50
ataggaatgg ctctaatcat gctgagcggc gcaggtgatg gatcgcggcg aggtacaagt        60
ttagagcagc ctagctcgag tcctcaaccc cagtcctctt agaagtgaac tgattgcact       120
ggatccctaa acccacaatg ttgaggacac atgtgatgac tccacttgct caggccagct       180
ggcctcttgc actttccoct gcccaccact tgtaactacc acttaattat cttgtgttaa       240
ttgctttgtt gtgttgggtc tgtattttg tggtcagtgc ctgcaggcag aaatgtgaaa       300
gcatttggta tgttgaagat acttgcttct ttttaataa aattaaaagt gcagcacgta       360
agtatgatac tgtgtagttt tttgacacaa ccatgagata caataagcag ctttgactta       420
gtgtcccaaa aagtggttct tggtctacag cagggcaaac atatatgtgg caagttctga       480
tcacatactt ttagacagaa agaataaaaa attcatatcg catggctttg tagcctaaga       540
gcacagaatc atacacgtgt gttaggagaa acattcattc tcacgcatat aaactggctc       600
ctggcagagt agggcagtaa gtgggatcaa agtgaattc accttatttt cagttggtag       660
agtatggaca atatatcact tatttgaaaa tacctgaatg gaaacccagc ctctactact       720
gtacttaaca ctgggcagtt acttgttctt cctgagccct caaattttc tttctctgtt       780 agaatgggat ttatgccacc tacggggttg cagtgcttac aggggctggg cagccacgga       840
agtcgagttg ttgagacctc ggttacgggg cctggtcgcg aggcagcctt gtaccatttt       900
tttctcaacg ccgagtttag ttttaactc cttagttggg ggccttgctg ctcccagctt       960
tattaggagg gaggctaatg ggagggccc cggtcagtgg cgtgtcgtgc cccataaat       1019

<210> SEQ ID NO 51
<211> LENGTH: 2169
<212> TYPE: DNA
<213> ORGANISM: Homo sapien

<400> SEQUENCE: 51
atagaattcg gcacgaggcg tgaacccggg aggcggactt gcaggaggc ggacttgcag         60 cgagccgaga tagtgccact gcagtggggc ctgggccaaa gagtgagact ccatctcaaa       120
```

```
aaaaaaaaaa aagaaagaaa tgtgttgctg gtatcagata tcagaccaag aacacttcag        180
tctctctaag gatgccctga gctacctcac tgttaaagga cgacatcaac acagaatgca        240
ctaaacagga aataagctgt aatctagaga atttccatta tgtgttactt tttggtgact        300
aacatggaat gttgaaaagg aagagctgga aagctcagtt gttttccttg ttcctctgac        360
attgtccagg caagagggca tcctgatcag atgagtagat ttggctgaga aaaaccctag        420
agtaaggcag gcactttgtg gaggtggatg atgatggctc ataaaaacgt ttgttctcag        480
tccagttcag ggctctgcca gcagtctttc agatttgaac tgcttaaaca aaccctacag        540
ataaattggc actctgattt gtaattctgt ttgtacaagt ttagagcagc ctagctcgag        600
tcctcaaccc cagtcctctt agaagtgaac tgattgcact ggatccctaa acccacaatg        660
ttgaggacac atgtgatgac tccacttgct cagccagctg gcctcttgca ctttcccctg        720
cccaccactt gtaactacca cttaattatc ttgtgttaat tgcttttgtt gtgttgggtc        780 tgtattttg tggtcagtgc ctgcaggcag aaatgtgaaa gcatttggta tgttgaagat        840
acttgcttct tttttaataa aattaaaagt gcagcacgta agtatgatac tgtgtagttt        900
tttgacacaa ccatgagata caataagcag ctttgactta gtgtcccaaa agtggttct        960 tggtctacag cagggcaaac atatatgtgg caagttctga tcacatactt ttagacagaa       1020
agaataaaaa attcatatcg catggctttt gtagcctaag agcacagaat catacacgtg       1080
tgttaggaga acattcatt ctcacgcata taaactggct cctggcagag tagagcagta       1140
agtgggatca aaggtgaatt caccttattt tcagttggta gagtatggaa aaatgtatca       1200
cttatttgaa atacctgaat ggaaacccag cctctactac tgtaacttaa cactgggcag       1260
ttacttgttc ttcctgagcc tcaaattttc tttctctgta agaatgggaa ttaatgccca       1320
cctacgggtt gcaagtgctt acaggagctg ggcaagcaac gaaggtaaga gttgtagaga       1380
cttcggtaaa ctggagcaca tgattcctgg gaagcaggcc tagtgtaaac aatttatttt       1440
tctagaaaag acagaagttt agagtatatg aaatctaatt tttaagtatt ggttggcaac       1500
taattgacta tcgtctacca taaggttata tgataattat tagggcagga gagtgaatgc       1560
atcttaatat gcatggcaga actgtgtgtt tccttccatc tggattttca taaagctttc       1620
tgatttatca gtaacgatct gaaaaatgta ctgtggcatg taacatcttt tattcatttt       1680
attaggcatt agaggaagaa tattctgtag tcctgcttta ttctgccatc tttacctgga       1740
aatccatttt tataaaattt ttgtaataaa aattcacttg atcacttgcc tgctttcttt       1800
taaacagtgc caagcgtaat gccccttgat aatttacata tatgtgaacg tggctgtgat       1860
agctgctgat gttcacacat aggccatctt acatgtaatg attccatgtt tggacttaaa       1920
cagcttcaca catttattgt acagttaggt gtcacatgct tttacttttt attttataat       1980
ctgtatttct gtgaggtaga cattattggc tccatgttat atacattgat agcccggagc       2040
tagagattga acccaggcca tcctccccac tgcctttcat catcaacaca accaccacca       2100
acagtatttt aaaagtgtta aatattggca gacgtgtcat tgttctgagc actaggacta       2160
gggcttatg                                                               2169

<210> SEQ ID NO 52
<211> LENGTH: 919
<212> TYPE: DNA
<213> ORGANISM: Homo sapien

<400> SEQUENCE: 52
acttaatttg tgcaagagac tgggctatgt gctgggggtg aggtggaaat acaaaaacac         60
```

```
caagatgcaa tccctctcaa gaactgtata atctagtaag agcacataca gagatggtgc    120
ctgcaggtaa aaactgctct gaaaccatgg ggagagaaga gtttacttcc ttccagaggg    180
tgaagtcggg acccatttaa atttggtagt atgggtgagg aaggtcataa cacgctaagt    240
aaactggtgt ctaagcatgt gacggcaaca gctaatggtc tagttcctcc atggctttaa    300
atgcatgaaa gggaaaagag tattcaaagg tattttttatt ttatctcatt gttagcccag    360
tataaggcag gatgacaaaa aataaataaa agtatgaaga ggcaagaaca tagattgaaa    420
actccatttc ctagttttag tgtaaaactca atcccttgtg catatacatc tagttcctga    480
agtccacact gccaaagggg aaaacaaga aaaccagcc ctagcagtgc cctgtcatca     540
tggcagagca ctgtctcttc tgtgggactg aaacagctag ctttggctac tgccggtagt    600
ggaccaatat ggcacatgga aattaaaaag tcccataaaa cgtgccctcc taacacgaga    660
ataagaaagg tggctgaagt agataatttc agtgacggag ggggatgaaa tattttttggt   720 ttatttgatg tatgatgacc cactatgctt attcctattt taaaaaccag atgagcagtc    780
tctgacaatt tctggtggtt acttcctcaa tgatttgggc tttctcccct cccgtttgct    840
tccttccctg tttttgttct ggcttcctta cagctccttt ccccactgag ggggttttct    900
gagaacttct cccttccta                                                 919

<210> SEQ ID NO 53
<211> LENGTH: 1611
<212> TYPE: DNA
<213> ORGANISM: Homo sapien

<400> SEQUENCE: 53
ccccgttacc tataccaccc cccttttca acccccgct ttttgtgacc cccttccccg      60
tcttggacct gccttctttc attgcccccc cccacatgtt taaaattttt cgcccgcccc   120
caattttttt tttttttttt ttttagacat gaccaattta ttcagagaat tcaaatttcg    180
tttggcaaag tatatccggg gcagagagtt tgggataatt atgtcattgg aagcaatcac    240
attatctaca gcaaattgcc tggggtagta tctgaaggaa aggcaaaact tttaaaaaca    300
atttagtatg tgggggggtg ataatcataa atatttgcaa aggtaacaaa acaaacaacc    360
agcttataca accaaggcac aaaatatgct aatgctaata atcctttatt caatttagct    420
caacacacat taagtactta atttgtgcaa gagactgggc tatgtgctgg gggtgaggtg    480
gaaatacaaa acaccaaga tgcaatccct ctcaagaact gtataatcta gtaagagcac     540
atacagagat ggtgcttgca ggtaaaaact gctctgaaac catggggaga aagagtttta    600
cttccttcca gagggtgaag tcgggaccca tttaaatttg gtagtatggg tgaggaaggt    660
cataacacgc taagtaaact ggtgtctaag catgtgacgg caacagctaa tggtctagtt    720
cctccatggc tttaaatgca tgaaagggaa aagtattc aaaggtattt ttattttatc      780
tcattgttag cccagtataa ggcaggatga caaaaaataa ataaaagtat gaagaggcaa    840
gaacatagat tgaaaactcc atttcctagt tttagtgtaa actcaatccc ttgtgcatat    900
acatctagtt cctgaagtcc acactgccaa agggaaaaa caagaaaaac cagccctagc    960
agtgccctgt catcatggca gagcactgtc tcttctgtgg gactgaaaca gctagctttg   1020
gctactgccg gtagtggaca atatggcaca tggaaattaa aaagtccata acgtgccct    1080 cctaacacga gaataagaaa ggtggctgaa atagataatt tcagtgacgg aggggatgaa   1140
atattttttg gttaattgat gtaatgatga ctcactatgc cttattttcct attttttaaaa 1200
```

| | |
|---|---|
| acacagaatg agcaagtcat tcctgaacaa aaatttactg tgtgtataac atacacctca | 1260 |
| aaatgaattt taagggaaca tattactaat caaataacac agtttatgct ttttcaattt | 1320 |
| ccacaaattg ttaattatga tacttaaggg aaccettaca atatataaca agtcatttca | 1380 |
| atattattca tcatccttaa cttctgaaag tttggtttat gttatcttat ctagaaagaa | 1440 |
| aactacttac aaatctcatt ttcccacaaa attaattcaa catccaatcc ttaaaaataa | 1500 |
| ataaagcttt gccaatggta aattggaatg catatacttg ccaggctttg atgaaataaa | 1560 |
| aataaacgat ttacataagc agtacctggt aaaaccaaaa cctccttttg a | 1611 |

<210> SEQ ID NO 54
<211> LENGTH: 859
<212> TYPE: DNA
<213> ORGANISM: Homo sapien

<400> SEQUENCE: 54

| | |
|---|---|
| actcctcact cagaaacaag aacagcgaca gcccttctcg agcgagatga cacgagctag | 60 |
| tccacgtctg acagtgctta acgcactaac gtgctaactc gttgccctgg tctctcctag | 120 |
| caaggtggag gacagacaca ggagaaataa acagagatg atgctcgcta ggaatccttc | 180 |
| ttataaaata ttcaacatgt tattattatc ctcgtccccc agagggtggt ttgatccatg | 240 |
| gatagaccta aagaagaaaa gaacatcaat ccagcatata aactccatag aatagtcaaa | 300 |
| ggtcaggtgg gacgcgaaaa ccgatcaaat cgcacctagg ttacgcccac ggccgatcag | 360 |
| cccaacctcc acctctggag ggtcccccag agaccctcgc ccgacgctag acccggagga | 420 |
| gcctcagcta agggcgcccg tgcagaagaa tcggctatgt cttcgattga tggagagcag | 480 |
| gagagatcgg cagagtatat ggttcggcta ggtgaagtag tttatcttca tatcccactt | 540 |
| aagatccgta tagcttacta aagctctgta gtaatccccg acaaagggaa aaacaagaa | 600 |
| aaaacagcct ctgggcgagt gcccctggc atcatggcga tgaccgcgt gtcatacttc | 660 |
| gtgttgccgc actgaaacag cctcacgctt agctttcccc cgcccccgag tattgggacc | 720 |
| attattggca catgggaaat ttaaaaagtc cataaaccgt gccctcccta acacgagaat | 780 |
| aagaaaggtg gctgaagtag ataattccag tgacggaagg gggatgaaat attttgggta | 840 |
| tgaaggtatg atgactcca | 859 |

<210> SEQ ID NO 55
<211> LENGTH: 748
<212> TYPE: DNA
<213> ORGANISM: Homo sapien

<400> SEQUENCE: 55

| | |
|---|---|
| acggacagcc acgtgctgac tgcgatgcgg ccgcccggcg ccaggtacat agtctctgac | 60 |
| gtaacaatat attcacactc ggcaaggcta gaatattgaa attatggcca acattgctta | 120 |
| ctttaagatt gtttacttta taagaagct agagtagttg tgcaactaga acagatgttt | 180 |
| ttaaaatgtt tgccattcaa agataggctt ggtgggacaa aactaatatg catactacat | 240 |
| acatatattt cttgtcttct ttactgtcaa tctttcagaa cagtaacatg acattacaaa | 300 |
| cacctcaaat tcccacttca aaatgaacag aaaaatggaa aaacattatt tcccatttca | 360 |
| taaaattaaa aatcaagtca gaagagaagt aaaactcatt tttatgcatt taacttaaaa | 420 |
| gcctgaatac acgactcctc ctagagagaa ggaagccaga acttcagaag tagccagtgg | 480 |
| tccaaagaat aaatgccccc atgaccttct ctatggttca tgacttactg agggctgatg | 540 |
| caaactctgg caagttattt ttcatgattt ccaaggatct gggatatgta aacgaaatga | 600 |

| | |
|---|---:|
| ttaaaagaca tttctctgaa tttgcaagaa gacgactgaa gaatcagaac aaagatccaa | 660 |
| cggcctttca cgtggctaca tgttcaccat acaccacaa ctcaaaaccc acaggcgagc | 720 |
| tttctctcaa atacacattc caaatggt | 748 |

<210> SEQ ID NO 56
<211> LENGTH: 2408
<212> TYPE: DNA
<213> ORGANISM: Homo sapien

<400> SEQUENCE: 56

| | |
|---|---:|
| gggaaatgtg atagaagatt attcagagca aaataagtag acaaaataac aatagacagg | 60 |
| aaaataagtc tctatgaatc cttattaatc atttgaaatt atgctataat atttttaaa | 120 |
| actcacctgt ttggttctgg gtgaagcagt tcctgaagga gtgttttgtc agaatatatt | 180 |
| gttaggtgaa tagagggttc tgtggccaag taagtttggg aaatagtggg ttagacaaag | 240 |
| ttgagttact gttggccttt cagacctttg atacgctaat gtgcatttta aatctccaag | 300 |
| aagcacctct attttataca tcatttccct aatttatttt aatatggatt tcttgttttt | 360 |
| gttttcttga gacggagtct tggtcttgtc acccaggctg gagtgcagtg gcacgatctc | 420 |
| ggctcactac aacctccgcc tcccaggttc aagcgattct cctggcctca gcctcccaat | 480 |
| ttactgggat tacaggcacc tgccaccacg cccagctaat ttttgtattt ttagtagaga | 540 |
| tgggttttca ccatgttgac caggctgatt ttgaactcct gacctcaggt gattctgccc | 600 |
| gcctcaccct cccacagtgc tggaattata ggtatgagcc actgtccccg ccagattttt | 660 |
| tttaaaagta ggtatcttgt gggatttatg ttctgagaga tacacctaag gaatgctgc | 720 |
| cctacagtgt ttttgctagt tcatactcat tacaaaggtt tcttgttgtt gggtgccct | 780 |
| ctagccagtg gtagtaaaat gggaagagac aggtcaagac tcccttggac catggcattg | 840 |
| agagagggat ggctgtcggc atagatatgt tggttattta ggcatttgtg agggaggccc | 900 |
| ctggctcttc cagcctgttt ccttaggatc ccagttggcc gggaacagct gtacaagggt | 960 |
| ctgctgaact ggtggtttca gcagactacc cagttcctaa gcatccatga gacagaggga | 1020 |
| accaacttgt atttccagaa caattttcca aacctttct ggctgtactt taaaagtgcc | 1080 |
| aaaaaggcaa tgggtgttta tgacactaaa gtcacataca agctagtatg atacatacat | 1140 |
| catagaaagc ttatagttgc tcagtgacaa agcaaaggaa gtttaatatt ttccagtttt | 1200 |
| gttcattacc gaagacagtc tacggttcat agttttcact aaattctaag cagattctat | 1260 |
| atcctaaaac atttaaacct cactaggcct gcaattttga gagggttagc taaatatgtt | 1320 |
| tggtatcact tcagagtcta aaaccagatt actaatcgtg tgtaaggagg cattttgtgt | 1380 |
| gtctttgcaa tgtatacaat tggattattt ggaacaccat tttgaatgtg tatttgagag | 1440 |
| aaagctcgcc tgtgggtttt gagttgtggt gtaatggtga acatgtagcc acgtgaaagg | 1500 |
| ccgttggatc tttgttctga ttcttcagtc gtcttcttgc aaattcagag aaatgtcttt | 1560 |
| taatcatttc gtttacatat cccagatcct tggaaatcat gaaaaataac ttgccagagt | 1620 |
| ttgcatcagc cctcagtaag tcatgaacca tagagaaggt catggggcca tttattcttt | 1680 |
| ggaccactgg ctacttctga agttctggct tccttctctc taggaggagt cgtgtattca | 1740 |
| agcttttaag ttaaatgcat aaaaatgagt tttacttctc ttctgacttg atttttaatt | 1800 |
| ttatgaaatg ggaataatg ttttccatt tttctgttca ttttgaagtg ggaatttgag | 1860 |
| gtgtttgtaa tgtcatgtta ctgttctgaa agattgacag taaagaagac aagaaatata | 1920 |

```
tgtatgtagt atgcatatta gttttgtccc accaagccta tctttgaatg gcaaacattt    1980
taaaaacatc tgttctagtt gcacaactac tctagcttct ttataaagta aacaatctta    2040
aagtaagcaa tgttggccat aatttcaata ttctagcctt gccgagtgtg aatatatttt    2100
actcagagac tatgtacaaa tacactaaag tggtgatggt gatcaatatt gtaaagaatt    2160
tattctgata aatgagaaac tggatataat gtcaaaatag ctattttctc aataaaaatc    2220
tcaaatctcc tgaaaaaaaa tcagaaataa caagaagaat ggggggcac gggctataaa     2280 tttttaaaca cttttttgggg ggggcccaag gggtggacac gggttgttcc agagactggg   2340
ccaaagggtg ggttcccaaa aaacgggggc gaggcgcaac cggggggggg gcttcaaaag   2400
aagaggtg                                                             2408

<210> SEQ ID NO 57
<211> LENGTH: 892
<212> TYPE: DNA
<213> ORGANISM: Homo sapien

<400> SEQUENCE: 57
cgtgttacgt cactataggc cctcgctgat ctagatgctg ctcgagccgc gccatttgtg     60
atggatccgc ccgggcaggt acaaaaacag catagaattt gagaaaacta aaactgctat    120
gagatagcta tgagaaaact aaaactgcta tgagatagaa atgatgtaaa attatgtgga    180
aagttttccc tcatatactc acatacagcc tttgaagggc tctggctctg accggttgat    240
ggccttgagc gagatgaaat catgaaattg agtcaaatca atttgacatt gaatgacaa     300 gaggaaactc ttaaatacat aaaaacaagc tctcatttgc ctaggataga tactgtctta    360
aaaataaaga ctgaacctag atgttctgag cactagcaac aaggtatttt aacaagttta    420
aaggaattct ctgaaaaagt tataaaatta ttctaggaaa cataaccata atagtgtttt    480
aagggacttt cacctgggga ttttatattc atgaacagag tgtattctgt atttaaaatg    540
tctcatttgt gggaattgga tgacatgttt tttgataaat ttattcgcaa tataaattga    600 cttttttattc taggaccatg tgaatcatgg gttccattgc acaaatacaa atattttaat   660
agcttcttag gcagtggtgt agacatcttg gatataatca ttgtagatct tgtatatttg    720 atttttttaag aaacctaaat aaacagagag gcataaacat atcttagagt caagtggtag   780
tgtttagcat tggatataac tactggtgtt ttcaacacac aaaaaaaaaa aaaagcgggg    840
gaccctgcca tccttcctgg tgaatttttcc ccccaccaaa aacaaaacag tt            892

<210> SEQ ID NO 58
<211> LENGTH: 3788
<212> TYPE: DNA
<213> ORGANISM: Homo sapien

<400> SEQUENCE: 58
tttgaggtca ctcattgtgt tttccgcaca cggtagtttg ctcgcaaatt aatgctgttc     60
ttttcgcgct ctgaaatcac aggcctgaca taggagcaag gcctcgatat atagccgccg    120 tgttttttgta aggaatcgtt cgcacaaact ttatagaatt tccccccattt gtagagaaag   180 aatcgcgtag gaaaaccatc agctacagga ttaaaataag ataaaatgtg taatcacaat    240
tcattactac aagatgtgag ttactactac cagcacacta gtatacatat tctttgggag    300
aagggcatcc agacctgcta acctcatata gatcccattg gacaactgga tgtacaccag    360
gttttttaat aaaaatgggc caaccactgt cttttcagaa tcaaatgcag acaatggaaa    420
aattatggta ttaaccttca caagtttgag cctcccccaa ttatgccacc agttttacaa    480
```

-continued

| | |
|---|---|
| ttttaacagc ccttctacat acactccatc ttctctatct tagttccaag ttttagtttt | 540 |
| caatccccat tatacccatt ccatgtgtta ttttaagaaa aaaccttccc agttagttgt | 600 |
| cagaaactat gatttagctt accccctcca ctacccagcc aactacagag aggatggagt | 660 |
| gtaatatgag ccgtacagag tcttaatgcc attcatgagg accacttagt ccttacatga | 720 |
| atctggttgc taacatttct attatattgt gaccatgact cccgactgtt attctctgtg | 780 |
| agaaatgggg ggagtaaatt cttaataaaa gacaccaggt accaagccac ctttctcaca | 840 |
| gagaataaca gtcgggagtc attgtcacaa tataatagaa atgttagcaa ccagattcat | 900 |
| gtaaggacta agtggtcctc atgaattgca ttaagactct gtactgctca tattacactc | 960 |
| catcctctct gtagtttgct gggtagtgga gggggtaagc taaatcatag tttctgacaa | 1020 |
| taactgggaa ggttttttct taaaataaca atggaattgg tataattggg attgaaaact | 1080 |
| aaaacttgga actaagatag agaagatgga gtgtatgtag aagggctgtt aaaaatgtaa | 1140 |
| aacttggttg cattatttgt ggaggctcaa acttgtgaag gttaatacca taattttttcc | 1200 |
| atttgttctg cattttgatt ctgaaaagaa agctggcttt gcccatttct tattaaaaaa | 1260 |
| acttgttgta aatccagttg tctaatggga tctatatgaa gttagccatg tctgtatgcc | 1320 |
| cttctcccac aaaatactgt ataactagtg tgcttgtagt agttaactcc accatctttg | 1380 |
| taagctaatg aaattgtgag tcacccattt atatcttaat tttaatcat gtcagttctt | 1440 |
| gaatgggtat ctccttagcc tgctgatttc tttttctttc taaagaaagt gggtggagaa | 1500 |
| attaatttag acgtttgttt gcaataaaaa gaattcattt tactcttgtt ttgggattct | 1560 |
| cgccatcaag gttcaaaatc cctttatata actcccaaga ggagaaattt attaagtgtg | 1620 |
| tgctttctgg acagcttatt ctttactctg catagaacat ttaggtttta aaacttaaa | 1680 |
| tgtatactga caattgatac ataattatga agtaaagttg aattcttccc ttcccctccc | 1740 |
| ccccagacaa ctttttaacat atttaatgag gggaaaaggt actggctggg agaagttaac | 1800 |
| actgagttta tcatctttac agaatgctaa tgctgtcctc aactgattat tttatataca | 1860 |
| tatatatgat acatgaaact ctgggatcag atgcttttag aagccatcat gcaagccagt | 1920 |
| cattgatgtc actgctacac aacactgcta acttgactgt agctatgtaa taacattaga | 1980 |
| tccccctaatt gtaattatat tgggtttgca cagaacactt taatcttccc ctcaccaatg | 2040 |
| tgaagtgagg aatcaggagt caaactgtag aactaaaatt tgacttcagt ctagcgtttc | 2100 |
| cttggtgttt ttaggttgct ttggtaagtt taggtttgct atatttctga ttgcttagaa | 2160 |
| ttttgtttta gcccttaaa atcagatcat aaatatgaat tcatacttct aaggaatttt | 2220 |
| cttgctataa gctggagttt aggtgatgta taggttcagt tgagacattt ttggaacagg | 2280 |
| caaatcctta gttaacataa gatatttaac agttgaagat agtgtcatgg attttatct | 2340 |
| ttttagcaa gtaatgctaa gaaccactgg cctgagctac tactcttcag tatacattat | 2400 |
| taggattgca tagacttact agaggaacag tttcaggttt tgatgctaat cagtgttgtg | 2460 |
| tcctaaagtt gtccttttgtg cctttaaaaa gttttggata tatcttctag tttaaaattg | 2520 |
| cttattaagg aattcatttt ataattgcag tgggaaagta atggtcaagt aacactaggt | 2580 |
| agactatcat gcctgtttag cccagagaat tggggggag agagaataga taaaaatggc | 2640 |
| acccagaaaa atgttaaaat ctttagtcaa gactagaatt aatacaattg tctacacttg | 2700 |
| tatggcagaa ataaccttat aaagtgttta aggaattcag agaagggaat gtaccaaata | 2760 |
| agcaacaggg agaaaattag gtaagaagta agatacgaac gagaaacctg atttattgct | 2820 |

-continued

```
catccttccc ttgcctccct aatggcaagc aaaactctga acatctgaaa aggatgtagt      2880
tctggacaaa tcctgactac ccagaggaaa ctcactgtga gattgctgtt gatttgaagg      2940
gtgctttcac taaggttata ttttaaagta gaataacaca tgctgagtgt aaactggctt      3000
tggattggtc agctgcagta gtacaaaaac agcatagaat ttgagaaaac taaaactgct      3060
atgagatagc tatgagaaaa ctaaaactgc tatgagatag aaatgatgta aaattatgtg      3120
gaaagttttc cctcatatac tcacatacag cctttgaagg gctctggctc tgaccggttg      3180
atggccttga gcgagatgaa atcatgaaat tgagtcaaat caatttgaca ttgaaatgac      3240
aagaggaaac tcttaaatac ataaaaacaa gctctcattt gcctaggata gatactgtct      3300
taaaaataaa gactgaacct agatgttctg agcactagca acaaggtatt ttaacaagtt      3360
taaaggaatt ctctgaaaaa gttataaaat tattctagga aacataacca taatagtgtt      3420
ttaagggact ttcacctggg gatttttatat tcatgaacag agtgtattct gtatttaaaa      3480
tgtctcattt gtgggaattg gatgacatgt ttttgataa atttattcac aatataaatt       3540 gacttttat tctaggacca tgtgaataat gggttccatt gcacaaatac aaatatttta      3600
atagcttctt aggcagtggt gtagacatct tggatataaa taattgtaga tcttgtatat      3660 ttgatttta aaaaactaga ataaacagag aggcataaac atatcttaga gtccaagtgg       3720
tagtgtttag cattggatat aataaatgga tgttttacaa aaaaaaaaa aaaaaaaaa        3780 aactcggc                                                              3788
```

<210> SEQ ID NO 59
<211> LENGTH: 432
<212> TYPE: DNA
<213> ORGANISM: Homo sapien

<400> SEQUENCE: 59

```
gtgactgact catatggcga atggtgcact gatgctgccg agcggcgcag tgtgatggat       60
cgagcggccc ccgggcaggt actaaataat agaaaatatt tatattcttt gagtgtgagc      120
tttgaataga tggcattatc actttattgt tttttttaaca aaaactttttt ctcaattatt    180 ctattgcaat gttattctga gcaagtccta tgccaaatat cttgtataat gtttgtatgg     240
aagattaaat tttactcttg tatggtaaga ctatttcagt tactgatttt atagttggaa     300
tttgatattc cagcacaaag tccacagtgt attcagaaat ccaagttggt gtcatacatt     360
tcattttgat gtgaactttt ctttgctttc ctttgttcta agactccatt ttgcaataaa     420
cgttttgaca gt                                                         432
```

<210> SEQ ID NO 60
<211> LENGTH: 1123
<212> TYPE: DNA
<213> ORGANISM: Homo sapien

<400> SEQUENCE: 60

```
caagtgtccc atggattaag attaggtcgg gaggtttagg agtgatccag aatgacctcc       60
cagaattact gtgcgtacaa ctttattttt cagagttttc atggaatggt aagagttta      120 tgaaagacag ttttaaaact tattctgagt taaatattaa tactttaaaa aattattgta     180
ctagacttat cgcagccttt tgaaagtagc agagtttcat cataccacat atataacaga     240
gcataaattt tctataatca ggcaccttttt gctgcttttg agtaagactg ttttcctgtt    300
taagtgttaa gcatcgccag acataaaaat ctattctctc ctctcgattg tagcatagcc     360
tgacagctct agatacagca tttctatgat gaaaaatgag tatccatcag gaaatctaga     420
```

```
agactagccg tgttttctca gactccacct ttgtttgcac tctgttgcct gtgaggagct    480
ttctggcatg tgattattta cttcaaaact agagttccaa gcacctacat taattatttt    540
atattgtgtg cagaatagta tatcttttaa tgtcagatat gatacactgc acatattgct    600
tttgcactct taaaatttt gtactaaata atagaaaata tttatattct ttgagtgtga     660
gctttgaata gatggcatta tcactttatt gttttttta caaaaacttt ttctcaatta     720
ttctattgca atgttattct gagcaagtcc tatgccaaat atcttgtata atgtttgtat    780
ggaagattaa attttactct tgtgtggtaa gactatttca gttactgatt ttatagttgg    840
aatttgatat tccagcacaa agtccacagt gtattcagaa atccaagttg gtgtcataca    900
tttcattttg atgtgaactt ttcttgctt cctttgttc taagactcca ttttgcaata     960
aacgttttga cagtaaaaaa aaaaaaaaaa caaaaaaaaa caacaaaaaa aaaaaaccaa   1020
cgaaaaaacc gaggaaaaaa ggagagaagg aaacagaaag acagaaagcg gcgaagagag   1080
aaggcaaggc aggcggagga aagaaggga gaggcgcagc agg                     1123

<210> SEQ ID NO 61
<211> LENGTH: 676
<212> TYPE: DNA
<213> ORGANISM: Homo sapien

<400> SEQUENCE: 61
ggtggcgagg gaggaagaag cgcgaagagc cgttagtcat gccggtgtgg tggcggcggc     60
ggagactgcg ggcccgtagc tgggctctgc gaggtgcaag aaagcctttg aggtgaaggt    120
gtatgaaagt catcataaca gatgttttcc aaaaacttgt agaaggttgt gaaaaaacta    180
ctaggatcac gcggcatgta ttgagcatat aggttgctgt agatgaatgt tcttagctgt    240 catgttttaaa aatacttctg cttcgttacc tcaagtgtgg catgcagcat tttggaagga    300
aaattgaaga cgtgttcaag aaaacatgaa cagaagcaaa tgatgaaaat gagcatttta    360
cttgatgttg ataacatcac aataaattat ggagacaaaa tacatatttg gctaactttt    420
aattgctgaa caataaagtg ttttctttta agatcaacaa caagaagaac atgaaaacat    480
cgaaaataat gaaaacataa caggcttgtg gggtactcca gtggcacata gggtgtttcc    540
cgtgtgtgtg gcaagttggt ttctccgggc tccagttccc ccacaattct cgcggcacac    600 aggggaagg gtaccttgat acaatccccg acatcggtag acaaccgtac agcatcagtc    660
gggacattga actagt                                                    676

<210> SEQ ID NO 62
<211> LENGTH: 883
<212> TYPE: DNA
<213> ORGANISM: Homo sapien
<220> FEATURE:
<221> NAME/KEY: misc_feature
<222> LOCATION: (870)..(870)
<223> OTHER INFORMATION: a, c, g or t

<400> SEQUENCE: 62
cgaccggcga gggaggaaga agcgcgaaga gccgttagtc atgccggtgt ggtggcggcg     60
gcggagactg cgggcccgta gctgggctct gcgaggtgca agaaagcctt tgaggtgaag    120
gtgtatgaaa gtcatcataa cagatgtttt ccaaaaactt gtagaaggtt gtgaaaaaac    180
tactaggatc acgcggcatg tattgagcat ataggttgct gtagatgaat gttcttagct    240
gtcatgttta aaaatacttc tgcttcgtta cctcaagagg tgtggcatgc agcattttgg    300
```

-continued

| | |
|---|---|
| aaggaaaatt gaagacgtgt tcaagaaaac atgaacagaa gcaaatgatg aaaatgagca | 360 |
| ttttacttga tgttgataac atcacaataa attatggaga aaaatacata tttggctaac | 420 |
| ttttaattgc tgaacaataa agtgttttct tttaaatcaa ctctaaatag ctccattctc | 480 |
| atagtcacta gtcagacctg ttttgaacat attcgaaaga ttataatctt gtcaataatt | 540 |
| agcttattta tgggtggtga ttctcattga ggctgacagc tggggagaca ttgcttgtac | 600 |
| ctctaggttc cctgtctggc ttccccttca gagcctgctg ttgtaccagg tggttgaatc | 660 |
| ttaaaactct ttaataccaa atagcaatca aattcccect tacagataaa ggtttcacct | 720 |
| tttttattca gtttgctttc atctttgtga acaaaaaagt catcctaata ctagtacatg | 780 |
| taataactaa gcaatatgct atgttaagag aaatgactga gcagaccagt ctgtctagga | 840 |
| ctaaattggc aagaattcta aagctgaatn tatatctggg tga | 883 |

<210> SEQ ID NO 63
<211> LENGTH: 795
<212> TYPE: DNA
<213> ORGANISM: Homo sapien

<400> SEQUENCE: 63

| | |
|---|---|
| actaacgaca ttgtgcccag ctgggactct tgggctctgg tgcctgaggg aaaatgtttc | 60 |
| acaactagtg gctgcccaat tgctgctgac cagttgtctt agaaatggtc aattggattc | 120 |
| aactttagtc ctctccttcc ccctaaaagc gaatgtttgt gtgtgcagac aatcttagca | 180 |
| tgaaaatggt ttaaataggc tggtccctac atgtattagg ttctttcaag tttgactggg | 240 |
| aggtcacctt tttctgattt acaagtccta attgttggag ctcagtaaag gtaggaggaa | 300 |
| ggtggctggt tggtcctccc ttccccctgt ttgtgacctg aatttacagg aagtgtttca | 360 |
| acttgtctta tgcatcttat ctggcatgtc ctgggagatg gatgggcaag aactggcctg | 420 |
| agcagggatt tttgccttga ttttaagtca ctgggttcca ttgtcctggc acctccattt | 480 |
| ccttagtttc tgtaagcctg ttaacagaaa gtagaggcta ttcaaggtta tcaagaaagt | 540 |
| gccctgtgct aatgatgaga cagtgaattt ttttttttcg agatgggagt ttcactctta | 600 |
| ttgcccaggc tagagtgcaa tggtgcgatc taggctcacg aactctgcct tccaggttca | 660 |
| agtgattgag acagtgaaat tttttatgga tactgcccta ttaacacatg caatctgtta | 720 |
| gcggcctgac ggatttataa aaccagggga gccaaaaaaa aaaaggcgg ggccggcaaa | 780 |
| cggccgggaa tgtcc | 795 |

<210> SEQ ID NO 64
<211> LENGTH: 951
<212> TYPE: DNA
<213> ORGANISM: Homo sapien

<400> SEQUENCE: 64

| | |
|---|---|
| tcttaatctg tcacggcgca gtgtgatgga ttggtcgcgg cgaggtactg taaatgtgat | 60 |
| ggaaaacatt gatgagaatt tattggcagt tcagattgtg ttttcccaac ttaggctctt | 120 |
| tattaattgg ttaaggtttt ctccaaaaag ggcatttcaa caatgggaat tattttaaat | 180 |
| tggttaaacc agtgggcaca gattacttat cttccttctc tgctttgtga ctcaccagca | 240 |
| gtaacacaca caatccacat cttgtgcacc tcaaatgaac agacttggtt tccttgcttt | 300 |
| cttgacattt ccatgactgt ttcacataca aactattggg tgaggttttt cagctgttac | 360 |
| cgacccacgt cctgctgtct ctgtgtggtc ctacaaaaac tgtccattcc cacccctttg | 420 |
| cttttgccatt tgcaagagtc tggaattgtc aggtctcagc ttcgaaaagt cctggttcca | 480 |

```
ctgacaggac acattcttta gtgggaatta agacctacaa agtctagttt gtatgtaggt      540
atgaagggaa ttttttaaat aaattgaaaa gctgtgaaca gcattagaac tttgtctatt      600
tcttaatttt aaaatatgct gatatgcctt aaactgtagt tgtagatcct tgtccatttg      660
ctgtttgaaa ataaccaatg tgttttctaa aactgtcgtg taatctactt tcattgttaa      720
tgcagaattg tcatatatgt aagccgcatg ttagacattt gtctttttta aactaaagta      780
attgtattga tgtgaagcat atcatttttt caaatatgaa agtgatcact tagcaacatg      840
cttggtaatt tggcatctgt taaggtagga gagtggtgaa cagataatct atgcatatat      900
cactagtgcc aagacataaa gcggggggaaa atatattttt acccaaacat t              951

<210> SEQ ID NO 65
<211> LENGTH: 1666
<212> TYPE: DNA
<213> ORGANISM: Homo sapien

<400> SEQUENCE: 65
ctgggtgatg aagtgagact ctccaaaaaa aaaagaaat tattaatccc tgcctgtgct        60
ctacatagcc tcatgggcat cattggatag ctcagagggc ccttgattct ggcaaggcaa      120
ataaagccag aatgagaaat taccatcttc tactagagaa aaccaagaga aaaatttta       180 tgctaggatg cctttatgac cacttaattt tttaatctta gtttaatggt ctctccctgg      240
tgctaactgc tgacagtggc cacctctttt ttggggattg aggggcctac ataactagct      300
ggccttaccc catatctttt gttcaaacat aataccatct ttttgcttct tctgaacttt      360
agatctccat aacacatgta ctgtagaatg tgatggaaaa gcattgatga gaatttattg      420
gcagttcaga ttgtgttttc ccaacttagg ctctttatta attggttaag gttttctcca      480
aaaagggcat ttcaacaatg ggaattattt aatgtaacag tgggcacaga ttacttatct      540
tccttctctg ctttgtgact caccagcagt aacacacaca atccacatct tgtgcacctc      600
aaatgaacag acttggtttc cttgctttct tgacatttcc atgactgttt cacatacaaa      660
ctattgggtg aggtttttca gctgttaccg acccacgtcc tgctgtctct gtgtggtcct      720
acaaaaactg tccattccca ccccttttgct ttgccatttg caagagtctg gaattgtcag      780
gtctcagctt cgaaaagtcc tggttccact gacaggacac attctttagt gggaattaag      840
acctacaaag tctagtttgt atgtaggtat gaagggaatt ttttaaataa attgaaaagc      900
tgtgaacagc attagaactt tgtctatttc ttaattttaa aatatgctga tatgccttaa      960
actgtagttg tagatccttg tcattttgct gtttgaaaat aaccaatgtg ttttctaaaa     1020
ctgtcgtgta atctactttc attgttaatg cagaattgtc atatatgtaa gctgcatgtt     1080
agacatttgt cttttttaaa ctaaagtaat tgtattgatg tgaagcatat catttttca      1140 aatatgaaag tgatcactta gcaacatgct tggtaatttg gcatctgtta aggtaggaga     1200
gtggtgaaca gataatctat gcatatatca ctagtgccaa gacataaagc ggggggaaaat     1260 atatttttac ccaaacatta aaaaaaaaa aaaaaaaaa aaaaaaaaa caactgtgtt        1320 cggcgcgctt gtggccccgg aagaagagtc ttctcgtaga accatcgtgg tttgggccca     1380
gcggggcccc aggaggtagg gtgccacacg ggccaaaagc gtgtcccagg agacacccgg     1440
gggcactaga acaacttagg gtgtgtgagg aatatttcg ctcacccccat gttacaaaaa     1500 caaccgcgca gagggggcaa acagcaacag ggtttctgtg aaacaacaac ccccaaatgg     1560
agggaagtcc tcgagaagga catacaggga aagcctaata caacagaggg aagatcccaa     1620
```

```
ggaaaagcac tatcatataa ataattatcg ccgccggctg tgcggg              1666
```

<210> SEQ ID NO 66
<211> LENGTH: 425
<212> TYPE: DNA
<213> ORGANISM: Homo sapien

<400> SEQUENCE: 66

```
accacacact ttggaagggt ccaaggaagg cagtctatgc ccccaagggg ctcacaggct    60
gtcagttcaa gtgggagggc catcaatctt tcctctggcc aggaaaagac tgaccattgg   120
tctccaaaga tgctggatag cattgccaga tcacatctaa acaactccga ctgcagtttc   180
acacaggtgg tggtccaaaa tttgtaaaaa agtgaaagtg atgtgtgaag atagggctga   240
gatgagagga aatggattca agcctcattg gaaaagctgg gttagtttgt tactttaatt   300
tgagcataga caatggggtc aaagtctgca gaatggttct cagccaagta attgctcttt   360
tcttctgaga gtttgaaagt tgtgctggca taggtaagtg attcccctgg gatggatgaa   420
agctt                                                              425
```

<210> SEQ ID NO 67
<211> LENGTH: 1342
<212> TYPE: DNA
<213> ORGANISM: Homo sapien

<400> SEQUENCE: 67

```
gggggaacca cagagacctg cctggccctc caaatctgag taaagggtgt ctctgctcaa    60
tatcaaacta ggtgggtcct gctcccctat ttgtggtgta ggcattggga aaaccactgt   120
ggctgttttg gctaggcact gctaatagct gctctgcaaa agggcaaac ataaaagggc    180
agcagtttca aggtcaaatt ccccaaggac tttgggaagc attgttgttt ctccctagct   240
gggagatgct ttccttaggc cagagggagc atatctcttc aggagttcct attaaaatct   300
ttgaggagag caacatatga gatttttttt tttaatcaaa ggaacactag gcttgtattt   360
catgtatgta gttgattttt aagttctatt tttcatttaa aagtactggg aatctaaaaa   420
acaatgttct ctcattttgg taagagtgca gccccatcct taatttccac tggttgcttg   480
ggtagaatgg ggcacctggg gaacttaag ctggaagggt atcatgaaaa gtgacagata    540
cactaattcc tttggtggtt ttctttgtag aaagacaagg cactctctcc acagcagccc   600
caacaactag ccctgcaccc tgtctctcta accaccacaa caaaaaacat ttaatccttg   660
cctttgtgc tggggttcta ctgacactgc tgctgatagc ctttatcttc ctcatcataa    720
agagctacag aaaatatcac tccaagcccc aggccccaga tcctcactca gatcctccag   780
ccaagctttc atccatccca ggggaatcac ttacctatgc cagcacaact ttcaaactct   840
cagaagaaaa gagcaatcac ttggctgaga accattctgc agactttgac cccattgtct   900
atgctcaaat taaagtaaca aactaactca gcttttccaa tgaggcttga atccatttcc   960
tctcatctca gccctatctt cacacatcac tttcactttt ttacaaattt tggaccacca  1020
cctgtgtgaa actgcagtcg gagttgttta gatgtgatct ggcaatgcta tccagcatct  1080
ttggagacca atggtcagtc ttttcctggc cagaggaaag attgatggcc ctcccacttg  1140
aactgacagc ctgtgagccc cttggggca tagactgcct tccttggacc cttccaaagt   1200
gtgtggtaca gagctcagtg cacagagtat tcacccagca tcatgaatca acttgggagg  1260
agtcaaccaa atgaacaatc taccaaaaat ttcaaataaa gtcaaacccc ccacaaaaaa  1320
aaaaaaaaaa aaatgagcgg cc                                          1342
```

<210> SEQ ID NO 68
<211> LENGTH: 567
<212> TYPE: DNA
<213> ORGANISM: Homo sapien

<400> SEQUENCE: 68

```
acccttcaca gctgctttct tctgggaagg cttcctagct tatattcaag gctgggaaca      60
aagagaagag attcttactg tttctgttgt ctcccatatc taaagatact taagtgacta     120
attctattag tccttgttga ctgtgattct attaatggca aaatatgacc cattttcatt     180
ggattattta tggcaatcca ttttctacag aatttgaatt ctaaggccat ttgaggtggg     240
aagtaagtaa atagagctaa gaatgcctgg aaacctcagg cacttagaat tttttttatca     300
tcgggtagtg aggtacaggg atggtgcaaa ataaatattt aaagtagagg aaattccatt     360
atgttataat aacattttc ataattttat gttgttttat cactactgag gatcaaacta       420
tatgattcca cagaacaact gtgtaaactt ttaaataaat ttaagctggg ctcaaaaaaa     480
aaaacaacaa aaaaacaaaa ccgtggcgga accggggca aaaggagccc ccggtggaga       540
atggctcccg cccaattccc aaaaaag                                          567
```

<210> SEQ ID NO 69
<211> LENGTH: 1007
<212> TYPE: DNA
<213> ORGANISM: Homo sapien

<400> SEQUENCE: 69

```
cacagctgga agtggcagag cagttgggtg accctaccca aaggaaagat agatgtgttc      60
ctggccagtg caggggtgag atgtgagcac agctgcatgg ccatgctgct gtcttgggtc     120
tttgtcggag gggattcaga agtttagaca gaggtcattg cccagatcag ttccagtgct     180
acatgatgct ggtggtcatg acttgcaagg gtggttcctg ggccatcagt gagaataaca     240
cagggagttc cctctctagg tctcagtgag agaacagtct ctgaggccct ggcttctgag     300
ccggatattc ctgatgggta cccttcacag ctgctttctt ctgggaaggc ttcctagtta     360
tattcaaggc tgggaacaaa gagaagagat tcttattgtt tctgttgtct cccatatcta     420
aagatactta agtgactaat tctattagtc cttgttgact gtgattctat taatggcaaa     480
atatgaccca ttttcattgg attatttatg gcaatccatt ttctacagaa tttgaattct     540
aaggccattt gaggtgggaa gtaagtaaat agagctaaga atgcctggaa acctcaggca     600
ctttgaattt tttttttttt ggtagtgagg tcagggatgg tgcaaaataa atatttaaag     660
tagaggaaat tccattatgt tataataaca tttttcataa ttttatgttg ttttatcact     720
actgaggatc aaactatatg attcccagaa caacttgtaa acttttaaat aaatttaagc     780
tgggctttaa cagttctgtc attgcagtga caaaactatt aatgaaacta agtggggaa      840
attcaggta ggtgtggaaa actgtgagta gatacaggac ttaaagggtg gaagatgggg      900
aagtatagga aggcagttga aaactaaatt gtaaaggctt tgagtgtgag gttaagaaa      960
ttggaactta attgcttagg ccatttgaag gtcgataaag tagttaa                  1007
```

<210> SEQ ID NO 70
<211> LENGTH: 568
<212> TYPE: DNA
<213> ORGANISM: Homo sapien

<400> SEQUENCE: 70

| | |
|---|---|
| agatgctgcc gagcggcgca gtgtgatgga tagtccaaaa aaaaaaagta ttaaaatgtg | 60 |
| attgatgtaa tttaccatgt ttactttatg catgcatttt attggggagg ggacgtgtca | 120 |
| gaataataca cccaaatcta gtggtctaat ttcatagtgc taatctggtt tatattggca | 180 |
| ttaaacgata ctgcgaagga gctagatcat tttacaagag ttgtaggttt gtcttatgtt | 240 |
| ggaaaagcag tcctctatta atatcatgtg tgaagagtat ctgttcacaa gatttatgag | 300 |
| attatgacgt gtttcagaga atgtctacta gtatatcttt acagtatttg cctgttgaac | 360 |
| tccctgcaca aactggaatt actttccaga agacttaggg aatgcaaata tgttactcat | 420 |
| aagatgcatt ggagtatggt aaataaaaca aaccattttg gattggttta aattggctcg | 480 |
| ttacagttct cttgtgggga gggactttgt cagtcatttt ggcatcttaa gctagactaa | 540 |
| acttttttgtt gttgtttttcc taaaacca | 568 |

<210> SEQ ID NO 71
<211> LENGTH: 879
<212> TYPE: DNA
<213> ORGANISM: Homo sapien

<400> SEQUENCE: 71

| | |
|---|---|
| gcgtggtcgc ggcgaggtgc ctcaagcagt cctctcgatc ctcccacctt ggaccctcct | 60 |
| aaagtgctga gattacaggt gtgagccact gcatctggct tacttatttg tctatgtctg | 120 |
| ttccactagt atgtaaagtc ttacgagagc aagaattttt gtttatttct ttctcttcct | 180 |
| cctttccttt cttcctctttt tacttcgttc actactgtat tccacataaa atatatttgg | 240 |
| catatagtag gtgttcaata tgttgaagga atgaaagaat ttatagactt gagttgcaat | 300 |
| ataaaatgta ttttttttttt actgtgagtt atggcaaaaa aagttttgaa agccgcttct | 360 |
| aaataatgca gatgtcagtg ctttgacccct ggaataaaaa ctgaaatgac ttagaaaaaa | 420 |
| aaacaaaaaa acaaacaaac aaaaagcttg ggggataacc tgggcccaca gcgggtcccc | 480 |
| gggggggacaa atggtttccc ggccccacaa tcccccaaa aaatacgcgg cgagcaaaac | 540 |
| gtgctgcgac gacgaggcac ggacgagcac caccacaaga aggcacgaag cgccacagaa | 600 |
| cggggagaga cggaagacga ggacacgcaa aaccaggaac gaagagacag aacgaacgcc | 660 |
| acacagacga cagacccgcg accggaagaa acaggagacg atggtcccgc accgggccga | 720 |
| gacgaggagc gcagcgcagc gagagcaaag cacagaagca aacagccgca gcacgcagtc | 780 |
| gaaggcccct cagctgcgca caccgacgac gcaagaagca gaaagagaaa gcaacacccca | 840 |
| cactcacgca acacaggcca cggagcggag gacacggcc | 879 |

<210> SEQ ID NO 72
<211> LENGTH: 260
<212> TYPE: DNA
<213> ORGANISM: Homo sapien

<400> SEQUENCE: 72

| | |
|---|---|
| acaataaaat aaagtaaata aataaatgtt cactactggg tgatcattta ataggtgttt | 60 |
| ttttaatcaa gaaattatct tttttcagccc agtatatcgt gtgaataaaa ttatgaagaa | 120 |
| tctaaaaaaa caaaaaaaaa acacaaaagg aaaaaaaaca aaacaaaaaa aaaaagacag | 180 |
| ctggggcgac actcgcgggg gcacaagggg tgacccgggg tggaacggtg ggttcgcgcc | 240 |
| catccccccg atctgggaac | 260 |

<210> SEQ ID NO 73
<211> LENGTH: 826

```
<212> TYPE: DNA
<213> ORGANISM: Homo sapien

<400> SEQUENCE: 73
accgaggctc gctgacacag agaaacccca acgcgaggaa aggaatggcc agccacacct      60
tcgcgaaacc tgtggtggcc caccagtcct aacgggacag gacagagaga cagagcagcc     120
ctgcactgtt ttccctccac cacagccatc ctgtccctca ttggctctgt gctttccact     180
atacacagtc acctgtccca atgagaaaca agaaggagca ccctccacat ggactcccac     240
ctgcaagtgg acagcgacat tcagtcctgc actgctcacc tgggtttact gatgactcct     300
ggctgcccca ccatcctctc tgatctgtga gaaacagcta agctgctggt gacttccctt     360
taggacaatt ttgtgtaaat cttttgaagga cacaccgaag accttttatac tgtgatcttt    420 taccccttttc actcttggct ttcttatgtt gctttcatga atggaatgga aaaagatga      480 ctcagttaag gcaccagcaa aaaaaaaaaa aaaggctggg gcgtacccag ggccaaagcg      540
gttcccggtg tcgaatggtc atcccgccca cattcccaca caataccgcg acaacgaccc      600
acacacacca ccaccacaca gcccacccca gcgcacacac gcacaccacc aatagaagcg      660
caggtcggga ccgacctcgc aagcagactg aacccgcaca gaccagcaag caccacacta      720
acggacaaca cgacaccaca gcacaaggaa cccacaagca cgactccacc tggcccaccc      780
ccccaccgcg cagctaccca cacggccggc gctccccacc cacacc                     826

<210> SEQ ID NO 74
<211> LENGTH: 3009
<212> TYPE: DNA
<213> ORGANISM: Homo sapien

<400> SEQUENCE: 74 gttttttttcc agatttataa tttaatggct gtgcagatcc cagtccctca tttctgtcgc      60
tcacgtgccc actggtctgg ggtcagggtt ttctgttcaa aggcatggat gtgcgggagc     120
tcttctgcta ggcacgcgtt caccagcctg tgtctctgaa gcagcggttt cccctcgaac     180
ttgtgcgaca caccaggact cggaagctac aggagcaacg gttgagggtc gtgtcctcca     240
gctccacatg ctccgcctcc aggtcccgct gcagcttctc gcggaggtat tcggcgctga     300
gttccatggc ggcagtccag ctggaacggc agccagtcca gccttgcccc ggcgccctga     360
cctgacgccc tggcctgacg ccctgcttcg tcgcctcctt tctctcccag gtgctgaacc     420
agggactgag cgtcccccgg agagggtccg gtgtgacccc gacaagaagc agaaatgggg     480
aagaaactgg atctttccaa gctcactgat gaagaggccc agcatgtctt ggaagttgtt     540
caacgagatt ttgacctccg aaggaaagaa gaggaacggc tagaggcgtt gaagggcaag     600
attaagaagg aaagctccaa gagggagctg ctttccgaca ctgcccatct gaacgagacc     660
cactgcgccc gctgcctgca gccctaccag ctgcttgtga atagcaaaag gcagtgcctg     720
gaatgtggcc tcttcacctg caaaagctgt ggccgcgtcc accggaggga gcagggctgg     780
atctgtgacc cctgccatct ggccagagtc gtgaagatcg gctcactgga gtggtactat     840
gagcatgtga agcccgcttc aagaggttc ggaagtgcca aggtcatccg gtccctccac      900
gggcggctgc agggtggagc tgggcctgaa ctgatatctg aagagagaag tggagacagc      960
gaccagacag atgaggatgg agaacctggc tcagaggccc aggcccaggc ccagcccttt     1020
ggcagcaaaa aaaagcgcct cctctccgtc cacgacttcg acttcgaggg agactcagat     1080
gactccactc agcctcaagg tcactccctg cacctgtcct cagtccctga ggccagggac     1140
```

-continued

```
agcccacagt ccctcacaga tgagtcctgc tcagagaagg cagccctca caaggctgag    1200 ggcctggagg aggctgatac tggggcctct gggtgccact cccatccgga agagcagccg    1260
accagcatct caccttccag acacggcgcc ctggctgagc tctgcccgcc tggaggctcc    1320
cacaggatgg ccctggggac tgctgctgca ctcgggtcga atgtcatcag gaatgagcag    1380
ctgcccctgc agtacttggc cgatgtggac acctctgatg aggaaagcat ccgggctcac    1440
gtgatggcct cccaccattc caagcggaga ggccgggcgt cttctgagag tcagatcttt    1500
gagctgaata gcgtatttc agctgtggaa tgcctgctga cctacctgga aacacagtt    1560 gtgcctccct tggccaaggg tctaggtgct ggagtgcgca cggaggccga tgtagaggag    1620
gaggccctga ggaggaagct ggaggagctg accagcaacg tcagtgacca ggagacctcg    1680
tccgaggagg aggaagccaa ggacgaaaag gcagagccca acaggacaa atcagttggg    1740 cctctccccc aggcggaccc ggaggtgggc acggctgccc atcaaaccaa cagacaggaa    1800
aaaagccccc aggaccctgg ggaccccgtc cagtacaaca ggaccacaga tgaggagctg    1860
tcagagctgg aggacagagt ggcagtgacg gcctcagaag tccagcaggc agagagcgag    1920
gtttcagaca ttgaatccag gattgcagcc ctgagggccg cagggctcac ggtgaagccc    1980
tcgggaaagc cccggaggaa gtcaaacctc ccgatatttc tccctcgagt ggctgggaaa    2040
cttggcaaga gaccgaggaa cccaaatgca gaccttcaa gtgaggccaa ggcaatggct    2100
gtgccctatc ttctgagaag aaagttcagt aattccctga aagtcaagg taaagatgat    2160 gattcttttg atcggaaatc agtgtaccga ggctcgctga cacagagaaa ccccaacgcg    2220
aggaaaggaa tggccagcca caccttcgcg aaacctgtgg tgcccacca gtcctaacgg    2280 gacaggacag agagacagag cagccctgca ctgttttccc tccaccacag ccatcctgtc    2340
cctcattggc tctgtgcttt ccactataca cagtcaccgt cccaatgaga aacaagaagg    2400
agcaccctcc acatggactc ccacctgcaa gtggacagcg acattcagtc ctgcactgct    2460
cacctgggtt tactgatgac tcctggctgc cccaccatcc tctctgatct gtgagaaaca    2520
gctaagctgc tgtgacttcc ctttaggaca atgttgtgta aatctttgaa ggacacaccg    2580 aagacctta tactgtgatc tttacccct ttcactcttg ctttcttat gttgctttca    2640 tgaatggaat ggaaaaaga tgactcagtt aaggcaccag caaaaaaaaa aaaaaaggc    2700 tgggcgtacc cagggccaaa gcggttcccg gtgtcgaatg gtcatcccgc ccacattccc    2760
acacaatacc gcgacaacga cccacacaca ccaccaccac acagcccacc ccagcgcaca    2820
cacgcacacc accaatagaa gcgcaggtcg ggaccgacct cgcaagcaga ctgaacccgc    2880
acagaccagc aagcaccaca ctaacggaca acacgacacc acagcacaag gaacccacaa    2940
gcacgactcc acctggccca cccccccacc gcgcagctac ccacacggcc ggcgctcccc    3000
acccacacc                                                           3009
```

<210> SEQ ID NO 75
<211> LENGTH: 605
<212> TYPE: DNA
<213> ORGANISM: Homo sapien

<400> SEQUENCE: 75

```
actgctttat gtttattttc tctctacttc aaccaaaatc agatctttga ggttttgctg     60
acattgttgg tggttttgcg catgttcttt ctaattggat ttatgaatag ttctatgggt    120
tttcaaagat gaatcatgct aagaacactt ctgcttttg atccactgtt tgcagcagaa    180
ttatatatat gtataggaaa atccactttt gaataatcca tgttttgtat ttggaaattg    240
```

| | |
|---|---|
| ttttttaaaaa taaaaaggaa aggaaatata taaagctgtt atttattctg catttcttac | 300 |
| atatctatcg cttgtcagta tacccgtttt ggtatatatt gcctctgcac atctacattt | 360 |
| gtatatgcaa acagtgagct ttatatctac ataaactgta ataatccctt tctgtgaaag | 420 |
| gatcatcata tcaagatgat accaaaagta tgtaaaaaga cacctgcatt atttgtaatt | 480 |
| atttctatat aagatatttc catggtaaga ttagcagtca ataaagttac ttttttggct | 540 |
| tcaaaaaaaa aaaaaaaaaa agcttggggt acccgggcca agcgttcccg gggaaatgtt | 600 |
| tcgca | 605 |

<210> SEQ ID NO 76
<211> LENGTH: 1836
<212> TYPE: DNA
<213> ORGANISM: Homo sapien

<400> SEQUENCE: 76

| | |
|---|---|
| gcacaatgtc tttctataag atatttttaa tgatttagta ttttacaaca tttgtttacc | 60 |
| atattttgat ataccatttt tttttatctg cccagttttta ttaaaaaaac tatatattat | 120 |
| tttctaaaga aacaatcata tttttataca aaattatgtt ttcaggtaat gaaatagatg | 180 |
| tagggtacag tggaacataa gcagtgttac ccctggctgg gagtcagtat tatacaacaa | 240 |
| atggtgagct ggaacatgcc ctgtctgtgc tgtccctcct gtgctgggtc gcggatgtgt | 300 |
| aggcaacatt gccttatcac gctaggttca cctgacactt taaaggaaa aaaagttcca | 360 |
| tagagttctg tggtcacaaa attgttttgc ttttatcaaa tactttaata gaaccaaagt | 420 |
| tgcagatatt ggaatgtatg gaagtatctc agtctctgca taagaggatt aaagtatgaa | 480 |
| aggatcattt aatgactgtt ttacttataa gtcattaagt aatccaccat ttcttatgga | 540 |
| tgatgcttaa gcctggtgag gtttgtactc taaggagccc agatcataat gcagtgcatt | 600 |
| tcctagccc ttagagtttc ttgcaaacat taaaaaaag acatatttaa gaaagaaaga | 660 |
| taaagaaaaa acatatttaa ttactgtaaa caggtactgc tttatgttta ttttctctct | 720 |
| acttcaacca aaatcagatc tttgaggttt tgctgacatt gttggtggtt ttgcacatgt | 780 |
| tctttctaat tggatttatg aatagttcta tgggttttca aagatgaatc atgctaagaa | 840 |
| cacttctgct ttttgatcca ctgtttgcag cagaattata tatatgtata ggaaaaatcc | 900 |
| actttgaata atccatgttt tgtatttgga aattgttttt aaaaataaaa aggaaaggaa | 960 |
| atatataaag ctgttatttta ttctgcattt cttacatatc tatcgcttgt cagtataccc | 1020 |
| gttttggtat atattgcctc tgcacatcta catttgtata tgcaacagtg agctttatat | 1080 |
| ctacataaac tgtaaataat cctttctgtg aaaggatcat catatcaaga tgataccaaa | 1140 |
| agtatgtaaa aagaaacctg cattattttg taattatttc ttatagatat ttcatggtaa | 1200 |
| gattagcagt caataaagtt actttttttgc ctttaaaaaa aaaaaaaaa aaaaaaaaa | 1260 |
| aaaaaaaaa aaaaaaaaa aaaaaaaggg ggggggggc aaacctatta ctcccccctgg | 1320 |
| ggggcccca attcgcttca ccccgtccct ccccgttatt gttgtagatg agaaaaaaag | 1380 |
| ggggggcgcac cacattatgg aggaggtagt agtatttatt aacgccaagg gacgcgcgcg | 1440 |
| cggcaagtat taaacaaagg actgctgacc agaaggggca aaaccgctgg gctagcgtgg | 1500 |
| gctaaccact tggtgaagcg aggacaccct atcaccactc tggaggagag ggtgggacag | 1560 |
| aacctagcat gctgtgcgga gccaaaatca cagctctcat ccatgctcgt acgtagacaa | 1620 |
| tttatattaa cagacctctt gcttgggga gtacacaagt ctaataaata cactttgtta | 1680 |

```
cgacggcgtg tgtaagatat agcgtgggtg ataaaccacc gacaatggag caaggcaatt    1740
tgttgcctag gtgggaaggc gacatgtaag aaaattttt tgcgcaccaa ccacgtggga     1800 tattttcga tattactgga aagacaatct tctac                               1836
```

<210> SEQ ID NO 77
<211> LENGTH: 791
<212> TYPE: DNA
<213> ORGANISM: Homo sapien

<400> SEQUENCE: 77

```
tggtctatgg taatttttta tagcagtccc agccaagaca gtgcgctcat ttactacata    60
ccatttatat tattatatag gctcctttca gaaacccatg ttcaaataag agataagata   120
ctgaaacaca taacaccttc actagttttt agtatacaaa tattgagaaa tagttgttat   180
taactatctc atccaagaaa tgcagattca tgttgtttct aaattttta tatatattga    240 ccaaaatgaa gaaacttaac accatcctag atttagctg cccaagaat gaaaagaatg     300 aaaaaaaat cttgtgaaaa cccacaagtg atatggatct aatttatggt taaatagata    360
tagataacaa acagaatacg cctgtttaaa actgttaaaa tgacattggt tctaattata   420
cttttattta aattgaaaga caaggcattt atatggtatc tctaaccatc acaactttgg   480
tgtgacaaaa agaaattatc accaaaatac acctccttaa gtaagtgtct gatttcacac   540
ttccagaaaa agtgctcttt ctggtcaagg ccagcaagaa ttgagaaaga ttaagaaagt   600
gcttcaaaga tgtttattac aaagttgtca taaaaactgt gaagtagatg tagacatcaa   660
gcataccaaa taaagtaaaa actgtcctcc ggcaaaacaa caacccaaaa aaaaaagcgg   720 ggggggacc ggggccaaaa cgggtcccgg ggggaatggt tccgccaatc accccaacaa    780
aaaaaaaagg a                                                        791
```

<210> SEQ ID NO 78
<211> LENGTH: 1523
<212> TYPE: DNA
<213> ORGANISM: Homo sapien

<400> SEQUENCE: 78

```
gggagatgct gccacctagg ttacttgtag gaccctatac ggcaacctcc tttgccagga    60
actatttata aacatcctgc aggaaaatgc agtgaagtag aagagacagg gatatcccag   120
aaggttatgc aaaacatcaa gagaagatga gaggagtcta tatgtcagaa tacacatttc   180
ccaccttgcc caacagtaga aaaacataag aagagaaaaa cattaaaaaa tgacaaggaa   240
gttaatggaa gtcagcaatg tgatggtgtt tggaggtgga gccttcagaa ggtaattaat   300
gcccttgtaa gaagaggcca gagagcttgc gcaccttctt cctgccatgt gaggagccaa   360
gaagccggct gtctgcaacc tgcaagagga ccctcactag aagctagcca tactggcatc   420
ctcatcttgg ctttccaact tccagaactg tgagaagtat atgttgtggt ttagtcaatg   480
gtctatggta atttttttat agcagtccca gccaagacag tgcctcattt actacatacc   540
atttatatta ttatataggc tcctttcaga aacccatgtt caaataagag ataagatact   600
gaaacacata acaccttcac tagttttag tatacaaata ttgagaaata gtttgttatt    660
aactatctca tccaagaaat gcagattcat gttgtttcta atttttata tataattgac    720 aaaatgaaga aacttaacac catcctagat tttagctgcc caagaatga aaagaatgaa    780 aaaaaatct tgaaaaccc acaagtgata tggatctaat ttatggttaa atagatatag     840
ataacaaaca gaatacgcct gtttaaaact gttaaaatga cattggttct aattatactt   900
```

| | |
|---|---|
| ttatttaaat tgaaagacaa ggcatttata tggtatctct aaccatcaca acttttgtgt | 960 |
| gacaaaaaga aattatcacc aaaatacacc tccttaagta agtgtctgat ttcacacttc | 1020 |
| cagaaaaagt gctctttctg gtcaagccag caagaattga gaaagattaa gaaagtgctt | 1080 |
| caaagatgtt tattaaaaag ttgtcataaa aatgtgaagt agatgtagca tcaagcatac | 1140 |
| caaataaagt aaaactgtca tcaagaagat tcaacagcta tgaaaagagt tcttcaaaat | 1200 |
| atgatatgtt tttctagatg ataataaaat ttatcaattc caaatgtcca cattagtctt | 1260 |
| tcataaagac accaatgagt cacaggaaaa aaattaaaaa taaaaaaacc ctatctcagg | 1320 |
| gaatcatgct aacaacctga tgtgttttct tccacatatt tatgtctgct tataagtatt | 1380 |
| tacaaacata tattcgcata tatgcatttt gaatttttc tgttgctgca cttaaatttt | 1440 |
| tttcataata aaacaagact cctgcaattt gcttttttag gtagactatg tatccctgac | 1500 |
| aaccatccag gtcagcttga tga | 1523 |

```
<210> SEQ ID NO 79
<211> LENGTH: 401
<212> TYPE: DNA
<213> ORGANISM: Homo sapien
<220> FEATURE:
<221> NAME/KEY: misc_feature
<222> LOCATION: (217)..(354)
<223> OTHER INFORMATION: a, c, g or t

<400> SEQUENCE: 79
```

| | |
|---|---|
| caaagaatag ccacaattag ttgaaaaggc tattttaaaa acttttccaa ctgcgtatct | 60 |
| gtgtgaagtc aacttacttc aacaaaaaag tttggatgta gaagcagctg taagaattca | 120 |
| actgtttatt ataacaagat actaaagaga ctgtaaaatg ccaccttct ccttggattg | 180 |
| ttttggaagt tattcttcat aaaaaatgtt aacgtgnnnn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnattatg | 360 |
| atttaaaagt gcattaacct taatctagat aataaaagct t | 401 |

```
<210> SEQ ID NO 80
<211> LENGTH: 586
<212> TYPE: DNA
<213> ORGANISM: Homo sapien

<400> SEQUENCE: 80
```

| | |
|---|---|
| gcacgagggc agtgagtcga gatcgtgcca ctggactcca gcctgggtga cagagcgaga | 60 |
| ctccatttca aaaaaaaaa aaaaaaaaa aaatcacttg tagtcttggt gtggtatcaa | 120 |
| agaatagcca caattagctg aaaaggctat tttaaaaact tttccaactg cgtatctgtg | 180 |
| tgaagtcaac ttacttcaac aaaaaagttt ggatgtagaa gcagctgtaa gaattcaact | 240 |
| gtttattata acaagatact aaagagactg taaaatgcca cccttctcct tggattgttt | 300 |
| tggaagttat tcttcataaa aatgttaac gtgggctggg catggtggct catgcctgta | 360 |
| atcccagcac tctgggaggc tgaggtgggc ggatcacttg agctcaggaa ttcaaggtca | 420 |
| gcctgggcaa catggctaaa ctctgtctct attaagaaaa aaaatgttaa cattatgatt | 480 |
| taaagtgca ttaaccttaa tctagataat aaaagctttt tggggcaacc tccagaactg | 540 |
| tgaaaaataa atttgttatt taaaaaaaaa aaaaaaaag atcggc | 586 |

```
<210> SEQ ID NO 81
```

<211> LENGTH: 309
<212> TYPE: DNA
<213> ORGANISM: Homo sapien

<400> SEQUENCE: 81

| | | |
|---|---|---|
| tggtcgcggc cgaggtacat aagtatggaa caaaaataag tatactttt tgacattcga | 60 |
| ctgtagatac tgcaaatgaa tttacacggg tttaatcaat gtaagataga tatttgtctg | 120 |
| aatattttaa agaagcacct aggtatcaaa aataaaaac aaaaaatata atgaaactcc | 180 |
| aaacatccaa caatctccct taacattctc attctgccaa ggcaaccaca cgttggtgct | 240 |
| tattacacaa tttaagaagg ggaatgttta tttactctat aggaaacaaa tatgaacctt | 300 |
| atctaaggt | 309 |

<210> SEQ ID NO 82
<211> LENGTH: 3982
<212> TYPE: DNA
<213> ORGANISM: Homo sapien

<400> SEQUENCE: 82

| | | |
|---|---|---|
| ggccgccctt tttttttt tttttttt tttttgtaa acaaaattta atacaaccat | 60 |
| atagtcaagt aataatggtt aaaagacatt ttattagata caactttaa aaaattaaac | 120 |
| tatgcaagaa gtatatttaa acaaaacatg taagtaagta ttcacgtgct acaacttaac | 180 |
| taagaacaat taaatacaaa gcattctttc cactatgaag actctggagc ctctaattga | 240 |
| aagcaaatga cctaggtct atactagttg taaagcagat tatactttg ttcaactcta | 300 |
| aatttgtatt gtcttagagc tccaacaact ctcaataaaa atttaaataa agaaaccttg | 360 |
| ggggagggt gatagggaag gggagagtaa gtgcttttc aaaaaggtaa atgaaaaagc | 420 |
| ctgaagaggg aaaaaattgt acataagtat ggaacaaaaa taagtatact tttttgacat | 480 |
| tcgatgtaga tactgcaaat gaatttacac gggtttaatc aatgtaagat agatatttgt | 540 |
| ctgaatatt taaaaagcac ctaggtatca aaaataaaa acaaaaaata taatgaaact | 600 |
| ccaaacatcc aacaatctcc cttaacattc tcattctgcc aagcaaccac acgttggtgc | 660 |
| ttattacaca atttaagaag gggaagttta tttactctat aggaaacaaa tatgaacctt | 720 |
| atctaaggta agcttcattt agattgaaaa aaagttgaa atagcactag agaacttaag | 780 |
| gcacataaac aaattcaggt gcagttattt tgaaaccatt aaaacaaatt ctttctttg | 840 |
| gaacaatata taaataagt tatgaatgtt gctgttttta tcagcactag gaaaatttaa | 900 |
| tatctaaggc aatcacacaa atgtaaaatg ttcatataaa acattaaaaa atgtctaaag | 960 |
| tgtctctgga attattcatt cacactcctg gctcaaatgg tttctggtgc ctagcattag | 1020 |
| atgtgacaat aatgatagct agctagtcaa acctactgcc ttaaagatca accaatttgc | 1080 |
| tccattctgg ttacttggca tggtaaattt atttaactaa aaagaataat ggggtgaggt | 1140 |
| gatgtaaacc tggctttcaa taagatgcac aacaaattct aataaggcca aaactctgtt | 1200 |
| gaggttaact ggtgtcttga gtttactaaa ataaaggcag tccataggaa gcctcaaaga | 1260 |
| gacattatct taccacttgg caccacaaaa acaccaagct ctcctctctg aaaatacagg | 1320 |
| ccggggtgg tggctcacgc ctgtaatccc agcactttgg gaggccgagg cccagaccgc | 1380 |
| gcccccttt cctgccgccc ccttcccgcg ggccggctg caggcccggg atccccgggc | 1440 |
| tcgcgtggcc gccgcagccg aaagggggcgg cccgtcgggc ggccccgctc cccggccctc | 1500 |
| gccgcggccc ctccaactcc gggtgctgcg gggccaagga caacacaaaa ggaaggggg | 1560 |
| ccctgccagc gacgcccctg ccagcccccg agaccccctg cgcgggtcg gcaaagcatc | 1620 |

```
tggacacccc agaagctccg gacgccgaag agagaggccc cacgaaaatt tcaagacacc    1680
tcctggggc tgcaggggcg gccaagtctc cccagcgcca ggtgccccg gccacacggt      1740
tattccctgt tttggtcagt acatcatcca agagtttcct gacaaaagag atgggaagat   1800
ggggaaccgg actactctac ccgagaggcc gcgcgagcgg ggcgagggca agccggccgg   1860
ggcctcgaac aaatcaaatc gaagcaaaga aactgccggc tttcaaaatc ctcctcctcc   1920
gccatcatcc gccgcgagtc atgccagcgt gggtggtggg gcattctctg ggatgaatga   1980
tctggatccc atagccatct gtgtcctgtt tgaggaatgg gaccctcaaa cagagaacag   2040
ccaagatgct caagcagtct gcagatctcc aggggagccc accagcctag tcaacatggc   2100
ctcggaagac attgccaagc tggcagagac acttgccaag actcaggtgg ccggggaca    2160
gctgagtttc aaaggcaaga gcctcaaact caacactgca gaagatgcta agatgtgat    2220
taaagagatt gaagactttg acagcttgga ggctctgcgt ctggaaggca acacagtggg   2280
cgtggaagca gccagggtca tcgccaaggc cttagagaag aagtcggagt tgaagcgctg   2340
ccactggagt gacatgttca cgggaaggct gcggaccgag atcccaccag ccctgatctc   2400
actagggaa ggactcatca cagctggggc tcagctggtg gagctggact taagcgacaa   2460
cgcattcggg cccgacggtg tgcaaggctt cgaggccctg ctcaagagct cagcctgctt   2520
caccctgcag gaactcaagc tcaacaactg tggcatgggc attggcggcg gcaagatcct   2580
ggctgcagct ctgaccgaat gtcaccggaa atccagtgcc caaggcaagc tctggccct    2640
gaaggtcttt gtggctggca gaaaccgtct ggagaatgat ggcgccactg ccttggcaga   2700
agcttttagg ggctggcact caaccaagag acctggggcg tcacgtgccc tctccaagcc   2760
tgttaaccca tccgaaaatg agccagaatt cctgtcgtgc atttctggaa aggacattgc   2820
tgagtccccg atcgtcatcg ggaccctgga ggaggtccac atgccacaga atgggatcaa   2880
ccaccctggc atcactgccc tggccccaggc tttcgctgtc aaccccctgc tgcgggtcat   2940
caacctgaat gacaacacct tcactgagaa gggcgccgtg gccatggccg agaccttgaa   3000
gaccttgcgg caggtggagg tgattaattt tggggactgc ctggtgcgct ccaagggtgc   3060
agttgccatt gcagatgcca tccgcggcgg cctgcccaag ctaaaggagc tgaacttgtc   3120
attctgtgaa atcaagaggg atgctgccct ggctgttgct gaggccatgg cagacaaagc   3180
tgagctggag aagctggacc tgaatggcaa caccctggga gaagaaggct gtgaacagct   3240
tcaggaggtg ctggagggct tcaacatggc caaggtgctg cgtcccctca gtgatgacga   3300
ggacgaggag gaggaggagg aaggagaaga ggaagaagag gaagcagaag aagaggagga   3360
ggaagatgag gaagaggagg aagaagagga ggaggaggag gaagaagagc ctcagcagcg   3420
agggcaggga gagaagtcag ccacgccctc acggaagatt ctggacccta acactgggga   3480
gccagctccc gtgctgtcct ccccacctcc tgcagacgtc tccaccttcc tggcttttcc   3540
ctctccagag aagctgctgc gcctagggcc caagagctcc gtgctgatag cccagcagac   3600
tgacacgtct gaccccgaga aggtggtctc tgccttccta aaggtgtcat ctgtgttcaa   3660
ggacgaagct actgtgagga tggcagtgca ggatgcagta gatgccctga tgcagaaggc   3720
tttcaactcc tcgtccttca actccaacac cttcctcacc aggctgctcg tgcacatggg   3780
tctgctcaag agtgaagaca aggtcaaggc cattgccaac ctgtacgcc cctgatggc    3840
gctgaaccac atggtgcagc aggactattt ccccaaggcc cttgcacccc tgctgctggc   3900
gttcgtgacc aagcccaaca gcgccctgga atcctgctcc ttcgcccgcc acagtctgct   3960
```

```
gcagacgctg tacaaggtct ag                                                  3982
```

<210> SEQ ID NO 83
<211> LENGTH: 607
<212> TYPE: DNA
<213> ORGANISM: Homo sapien

<400> SEQUENCE: 83

```
acctcgaagg gaagcacctc tggcagacaa ccgtcaagag agagacatca tttagtgttc    60
ctgtcttgac tcgcttttga catttgaatt ccagtgctt ggtatatcat ggaggaaaca    120
tccccaaaac gagacatgct agaaaaggct ttattctaaa gctttattc tgaaagccgg    180
cgacaccctg gagggagggg caggtgttgg tgagcctctg cccgtggcct tctctgggga   240
gggccaggct gcttagccca cgtttctctt catctacctt cttgcaccac atgagaacca   300
ggacattgcc tccatgcccg tctctgacaa cattagttct ctaaactctc tagtgtgtcg   360
ccttggaagt ctcgtgcgtg gagtgtaaat ctatatattg ccaggcgagg taacagcagt   420
gccacgcatt ctcataccac ccgcatggga agaatgttcc aatgagagcc tgggtttggg   480
gaagcatcta gttttcaga gctctgctgt ccaccgtgta gggaacacag acagggcctc   540
tcttcaaggt gctgtgacat aatgacacgg taatcgcggt gatggggttg cttcctaagg   600
caaaggt                                                              607
```

<210> SEQ ID NO 84
<211> LENGTH: 1902
<212> TYPE: DNA
<213> ORGANISM: Homo sapien

<400> SEQUENCE: 84

```
ccgggaggtg acctgcgtgt accagctgca gaacggcaca cacgtcgtac gcggcccctc    60
tactgcccgg gcccccggcc ggcggcagtg cagagctgtg aaggccagga ctgcctgtcc   120
atctgggagg cgtctgagtg gtcacagtgc tctgccagct gtggtaaagg ggtgtggaaa   180
cggaccgtgg cgtgcacggc aactcacaag ggaaatgcga cgcatccacg aggccgagag   240
ccgaggaggc ctgcgaggac tactcaggct gctacgagtg gaaaactggt ggactggtct   300
acgtgctcgt cgacctgcgg gaagggcctg cagtcccggg tggtgcggtg catgcacaag   360
gtcacagggc gccacggcag cgagtgcccc gccctctcga agcctgcccc ctacagacag   420
tgctaccagg aggtctgcaa cgacaggatc aacgccaaca ccatcacctc ccccgccctt   480
gctgctctga cctacaaatg cacacgagac cagtggacgg tatattgccg ggtcatccga   540
gaaaagaacc tctgccagga catgcggtgg taccagcgct gctgccagac ctgcagggac   600
ttctatgcaa acaagatgcg ccagccaccg ccgagctcgt gacacgcagt cccaagggtc   660
gctcaaagct cagactcagg tctgaaagcc acccaccgc aagcctacca gccttgtggc   720
cacaccccca cccggctgcc acaagaatcc aactgcatag aacatgagcg tggacttggc   780
gtttgccatt agtgcttccg tacttaatat attgttaaca gccactggct cactttctac   840
agtgaggaga aagtaggcat gagtcacaaa gtaacttcaa tttctaggat ttcaggtacc   900
tcgaagggaa gcacctctgg cagacaaccg tcaagagaga acatcattt agtgttcctg   960
tcttgactcg cttttgacat ttgaatttcc agtgcttggt atatcatgga ggaaacatcc  1020
ccaaaacgag acatgctaga aaaggcttta ttctaaaggc tttattctga agccggcga   1080
cacectggag ggaggggcag gtgttggtga gcctctgccc gtggccttct ctggggaggg  1140
ccgggctgct tagcccacgt ttctcttcat ctaccttctt tgaccacatg agaaccagga  1200
```

| | |
|---|---|
| cattgcctcc atgcccgtct ctgacaacat agtctctaaa tcctaggtgt cgccttggaa | 1260 |
| gtctcgtgcg tggagtgtaa atctatatat tgccaggcga ggtaacagca gtgccacgca | 1320 |
| ttctcatacc acccgcatgg gaagaatgtt ccaagagagc ctgggtttgg gggaagcatc | 1380 |
| taagttttca gagctctggc tgtccaccgt gtagggaaca cagacagggc ctctcttgca | 1440 |
| aggtgctgtg acataatgac acggtaatcg cggtgatggg ttgcttccta aggcaaaggt | 1500 |
| aagcttgggc cagcttcact ggggcggatg ggcacctgcc ccgccttccg cgagcatcca | 1560 |
| ctctggcccg cacttctcta aagctttgta ccttagagta tgctgtacca catcccagtg | 1620 |
| gctttctacc gaccgtggcc atttatctga aggtaagtac gacatttggg acctctgagg | 1680 |
| acacaggcct aggatctgta gagcaaggcc tgactgctct atcctggcac ggagcagcct | 1740 |
| gatatgccgg gaccagggga ggaacgccat ctggctggca ctgtctgcac acccgtccga | 1800 |
| gccttcctgt agccccagac tttgtggtac ccattatcat cacgcctgtc atcattgacc | 1860 |
| catcttcttg gtggggcaag gatgatgcat gtatgaaggt cc | 1902 |

<210> SEQ ID NO 85
<211> LENGTH: 246
<212> TYPE: DNA
<213> ORGANISM: Homo sapien

<400> SEQUENCE: 85

| | |
|---|---|
| gccgggcagg tacaagcaat tgctgtttgg ggacacagcc aacctcatac atatgaacta | 60 |
| atgcatgcca agttttaatt tccttaactg aaaaggctga tgcaaatgac atattgcacc | 120 |
| tggtggcagg cagttacatc tactgctaaa atgacataag atagaagaag ttttctgtag | 180 |
| agaacattgt gtgtcacaaa cagtgacatt ttcaaaagtg cttaattcaa tatgacttcc | 240 |
| cagcgg | 246 |

<210> SEQ ID NO 86
<211> LENGTH: 5119
<212> TYPE: DNA
<213> ORGANISM: Homo sapien

<400> SEQUENCE: 86

| | |
|---|---|
| ggcgcggagc agctccggcg gcgagacggg ggcggcgccg cgcgggtctg gcgggaccgg | 60 |
| tttggaagac tttgccggcc tgcagattgg ccttaagaga aggacggagc cacatactgc | 120 |
| tgacggccca gaactggcag agagaaggtt gccatggctg ctgttgacag tttctacctc | 180 |
| ttgtacaggg aaatcgccag gtcttgcaat tgctatatgg aagctctagc tttggttgga | 240 |
| gcctggtata cggccagaaa aagcatcact gtcatctgtg acttttacag cctgatcagg | 300 |
| ctgcatttta tccccgcct ggggagcaga gcagacttga tcaagcagta tggaagatgg | 360 |
| gccgttgtca gcggtgcaac agatgggatt ggaaaagcct acgctgaaga gttagcaagc | 420 |
| cgaggtctca atataatcct gattagtcgg aacgaggaga agttgcaggt tgttgctaaa | 480 |
| gacatagccg acacgtacaa agtggaaact gatattatag ttgcggactt cagcagcggt | 540 |
| cgtgagatct accttccaat tcgagaagcc ctgaaggaca agacgttgg catcttggta | 600 |
| aataacgtgg gtgtgttta tcctacccg cagtatttca ctcagctgtc cgaggacaag | 660 |
| ctctgggaca tcataaatgt gaacattgcc gccgctagtt tgatggtcca tgttgtgtta | 720 |
| ccgggaatgg tggagagaaa gaaggtgcc atcgtcacga tctcttctgg ctcctgctgc | 780 |
| aaacccactc ctcagctggc tgcatttct gcttctaagg cttatttaga ccacttcagc | 840 |

```
agagccttgc aatatgaata tgcctctaaa ggaatctttg tacagagtct aatccctttc      900
tatgtagcca ccagcatgac agcacccagc aactttctgc acaggtgctc gtggttggtg      960
ccttcgccaa aagtctatgc acatcatgct gtttctactc ttgggatttc caaaaggacc     1020
acaggatatt ggtcccattc tattcagttt cttttttgcac agtatatgcc tgaatggctc    1080
tgggtgtggg gagcaaatat tctcaaccgt tcactacgta aggaagcctt atcctgcaca     1140
gcctgagtct ggatggccac ttgagaagtt ttgccaactc ctgggaacct cgatattctg     1200
acatttggaa aaacacattt aatttatctc ctgtgtttca ttgctgatta ttcagcatac     1260
tgttgattcg tcatttgcaa aacacacata ataccgtcag agtgctgtga aaaaccttaa     1320
gggtgtgtgg atggcacagg atcaataatg cctgaggctg attgacgaca tctacatttc     1380 agtgctttt  ccctaagctg tttgaaagtt acgcttttct gttgttctag agccacagca     1440
gtctaatatt gaaatataat atgatttgtc aggtcttata atttcagatg ttgttttta     1500 agggaaattg accatttcac tagaggagtt gtgctggttt ttaaatgtgc atcaagaaag     1560
actactgaaa agtattattt tgtaactaag attgctggta ctattaggaa aaatctgtgt     1620
gtattgtata gctctagctg tttgactatc tgtaatgaaa atgctgcact tcaactggta     1680
tttcattaga gaaccgtgtg tgtgcgtgtg tgtggtgcct ttgagcaact ttatttatgg     1740
ttaccatatt tttaaaaaga ttttttgtca gggtgactta acatggactc ttataggta     1800 ttaaaacaat ctagattatt ccttttcatc ctaaataagc ctaccaaatt tcatgctgtt     1860
ggtttgccat gaatgatatt acttcctaca ttatatttgt gttttttcaa atctgctatg     1920
gaatgaactt attcctagat ttggatatgt aagagaaacc tgcagtcatc ttttgattta     1980
taaggcaatt cttgtggata aatagtgatt tctcagcctc tgacccattt tataactgaa     2040
atttagccct ttagagcttg ttatatctgg ttttcctacg tttttctatg taatattatt     2100
ccattccagt agcattattg atagaaatag taagtattta tggaatagta aaatatggac     2160
aaattacgtg tgtgacatat ctgtcaaaat aagttagaag cttattcttg gtttgtgtaa     2220
tgaatttatg tattgtagtg aatacctta ctggtgtgaa gataattatg cacaaaccct     2280
cacaatacgc gttaacattg aaacctgtga aatgtcctta ggttgggtca tataaagcca     2340 accattttg aggaccatgt acctagtgct ttgaaaactg taagtcacta tatgaatatg      2400
acaatatgtg cacatttaaa attcagagct cggcattgtg atactgatgc agaagctagt     2460
agattggtta aaagtctgga cttctgtggc attttttcg tgacgtgata atctatcata     2520
agcagaccta agcacagttt tatgaacaca attttgccca tgacattgcc tacaggattt     2580
ccagatgtga cttgcactca gaagatcagt ggtcaacttc agaagttctt ccacgcttag     2640
atcatgtctt cagaacttag atgtgaaaat ctacacactg ggagatgctg tgagccccaa     2700
ggttttgatg gagtttgctt ggaatcctct tgacttcatg ccacattgac gtgaactttg     2760
atgtataata agcagcagca acttcatgtg aaaatatggt caggtagtta tatgtaaggt     2820
tacgtggtcc agtaatgtct tagattgata aattaggtat ggaatccatc agtgttacgt     2880
gatgagaata ggtgaacaca ccttgtcagt gatgatgtaa acttctctcc ttggcaggac     2940
atgggcaaac atgctgattg gtgcaaatgt ggtgccgagc tgtccatagc tgcagtgaaa     3000
gatgaagagc aagaccttct ctaggttttc tagctttcat taaatgtatt ttttccccca     3060
gagctaattt gaaagttgat tggaccactg tggatggggt ctcattaaga atgtgggaaa     3120
taggggccgg gcgcggtggc tcacatctgt aatcccagca ctttgggagt ccaaggaggg     3180
ggatcgcttg agtccaggag tttgagacca gcctggacaa catggtgaaa ccccgtctct     3240
```

-continued

| | |
|---|---|
| acaaaaaata caaaaattag ccatgcatgg tggctcatgc ctgtagtccc agctacttgg | 3300 |
| gaggctgagg caggaggatc acttaagccc agaaggcaga ggttgtagtg agccaagatg | 3360 |
| gtgccactgc actccagcct gggcaacaga aggagactcc gtctcaaaaa aaaaaaaaag | 3420 |
| atggcagcta tataaatgat aaaattaatt acattctctt tcacatgcat gaggtgcaaa | 3480 |
| ctctgtcaca aagtatttta attaccttt accttgtttc atagatcttt atgtgacata | 3540 |
| aaaacagttt ctggcacggt ggctcacgcc tgtaatccta gcactttggg aggctgaggc | 3600 |
| aggtggatca cctgaggtca ggagtttgag accagcctgg ccaatatggt gaaaccccat | 3660 |
| ctctacaaaa tttgcaaaaa gtagatgggt gtggtagtgg gcgcctgtaa tcccagctac | 3720 |
| tcaggaggtt gaggcagaga atcgcttgaa cccgggggt ggaggttgca gtgagctgag | 3780 |
| atcgcaccac tgcactccag catgaaagag cgagactcaa tctcaaaaaa aaaaaagttt | 3840 |
| ctggcacctg aacaggaact ggtttccatc atcaactcag aaagcactaa aatctaggtg | 3900 |
| gtgattcagg gaggagcagg ggaagacagc ctcctatggt ggcatgaata agatgcttcc | 3960 |
| agaactagta gggaaataac taacctcttc aggctttatc aggcctggag gggaaccttg | 4020 |
| ctcatgttag caagaaaggt atcctagaga agccactcaa aaggctccct aatccagcct | 4080 |
| gtctccacat acatactgaa aattcttccc tactctgagg cagggtgtag tggtttaggg | 4140 |
| gtttctccag actggaatcc tacctatctg taccgacaat tgagcaaaca acagttgaga | 4200 |
| gagtccaaaa aaaaaagta ttaaaatgtg attgatgtaa tttaccatgt ttactttatg | 4260 |
| catgcatttt attggggagg ggaggtcaga ataattcacc caaatctagt ggtcttattt | 4320 |
| cataggctaa tctggtttat atttgcatta aagatactgg agggcaatat ttacagagtt | 4380 |
| tagttttct taattaaaaa cagtcctcta ttaatatagt gtgaaatatc tttcaaaatt | 4440 |
| tagagtttag gtttaagatg tctactagat atctttaaga ttttcctgta aactcactgc | 4500 |
| acaaactgga aattactttcc aaaagactta gggaatgcaa atatgttatt cataagatgc | 4560 |
| attgagtatt gtaaataaaa caaaccattt ttgatttgtt taaattgctc gttacagttc | 4620 |
| tcttgtgggg agggactttg tcagtcattt tgcatcttaa gctagactaa acttttttgtt | 4680 |
| gttgttttcc taaaaccata ggtgcaagct ttgccgctgg gaagtcatat tgaattaagc | 4740 |
| acttttgaaa atgtcactgt tgtgacaca caatgttctc tacagaaaac ttcttctatc | 4800 |
| ttatgtcatt ttagcagtag atgtaactgc ctgccaccag gtgcaatatg tcatttgcat | 4860 |
| cagccttttc agttaaggaa attaaaactt ggcatgcatt agttcatatg tatgaggttg | 4920 |
| gctgtgtccc caaacagcaa ttgcttgtac aagatagaag tttgcttctc agctgggcat | 4980 |
| ggtggctcat gcctgtaatc caagctcttt gggaggccaa cgcgggagga ttgtttgagc | 5040 |
| ccaggagttt gaaaccatcc tgagcaatag agagaccccc atctcgacaa aaaaaaaaa | 5100 |
| aaaaaaaaaa aagatcggc | 5119 |

<210> SEQ ID NO 87
<211> LENGTH: 489
<212> TYPE: DNA
<213> ORGANISM: Homo sapien

<400> SEQUENCE: 87

| | |
|---|---|
| actatgtgtt aacataatcc caccttctta gagctttgtt ccttctgaag gtgtatagat | 60 |
| acagcttgtc ttgaaatgtc tttctccaca taatgaagca tgctgaatgc tgggaatctg | 120 |
| gagcagcagc cctgggagcc ctgagttttg aagtgttttg gtttgcttca aaggttagaa | 180 |

| | |
|---|---|
| gaacttgata tgtatggcaa acaactttag aatactagtt actcactaac atgaggcggg | 240 |
| taatgttgct ctagattcta tattccagta aagccagctt ttcttattat tggagtaggc | 300 |
| aaatgaatgg cattagaatt agtgggtggc ttgtaagttg tagttatagg cactttacca | 360 |
| cttcctgcca ttagcaggca tccttgtttt ttcttctttt ccctctttgt tccttctttt | 420 |
| ccctttctcc ttatacattt tctttctcta ctttaattct ccttcctcct tactgtagat | 480 |
| cccaagctt | 489 |

<210> SEQ ID NO 88
<211> LENGTH: 3190
<212> TYPE: DNA
<213> ORGANISM: Homo sapien

<400> SEQUENCE: 88

| | |
|---|---|
| ctctcattag cctgttcaga gtcttggggg aaattgagat ttttgagatt tttttttaaaa | 60 |
| actcaaatat tttactagtt tgcctgccat tttatttctt ttacaaagca gaagcatata | 120 |
| ccaatttatc acagtatttt agtaaatact gcaacattca tccttaaatg ttcaccaaga | 180 |
| aaagcatctt tgtagtagtg ctggaaaact attcagaata tacagataaa aatgctgttc | 240 |
| tttaattgct tacattgctt cttcccataa aaagcaaaaa ggaatcagtg cttgctattg | 300 |
| ctcctttcct tgaagttgta acaattgata catatattat gagttgactg gtcgattctg | 360 |
| tacctggccc atcctttaga atgttcttgt catgtagcag tcctacgtac tcttttcatg | 420 |
| agcagtctgt gatctcactc tgtgagttca gctattactc gctcgtggga gcttaatctt | 480 |
| ttcaaaatga agttgattta aaaagtcttc aggcagagta atcatgttag aggtggtatt | 540 |
| cgatggaaga aagtttagag agttaggagt gggggtagaa ttctagaatt tataagagtc | 600 |
| caggaagcat agcagtcagg ggcaaaaatt agcgtaatat ggagtaggca atagaggagc | 660 |
| tactggagtc agaagtcact gcagagtgca acataggaag atggactcct agcttacatg | 720 |
| agattccctg cagctgtaat atagacaatt cccacatggc tgttctacac agaattacct | 780 |
| gctaagatttt tttgtttatt tttgtttgag tggtatttc actccaattg tataatggaa | 840 |
| atcagtggga aaatagggtt taccttatat tcatgagttc tagtttctac tgttctgcta | 900 |
| tgtgtttcta agcaagagca aaggatactt catacttttt tcgttatatg attgatcttc | 960 |
| aaattgggat ttaccttttt caatatgttt taaagtagtc ttattcctct tttgatttgt | 1020 |
| taaacaagca ttttagttca gctattgaat agccttccaa aaaattaatt cagccttgca | 1080 |
| ggtaagtacc atactaagac tttaacccaa tagtttttaa tcattctgcc tttattccaa | 1140 |
| actgtaaatc tgtacacata agataaaaca tactaagtat tgcataaatt gttaacgtta | 1200 |
| cagtaaattg ttatctgcag ggctgacaga cataatgttg gtgggcaact gtgatcctat | 1260 |
| acatacatat atgcaaaagg ggattttaaa agtgcagatt atagagtaga ttgacaaatt | 1320 |
| ttatttttata ttcagttgtc ctctctgctt ccatctgtgt tgctctctta gttgagagag | 1380 |
| agttagccat ttgacgatttt taagtcagtg ggaacttatt tttagttact caataaaaatt | 1440 |
| aatatttttat ttgtatttta acttacagag taggttggta ataacagctg aactgtgtaa | 1500 |
| cattgttgct tcaaattgaa gtttatatta tgaacattca gaatcaatgc tcatgtagca | 1560 |
| gcatattatt gagctatttt gagtttgaaa tgtggagaaa cgctaaacca tgtactatgt | 1620 |
| gttaacataa tcccacctttc ttagagcttt gttccttctg aaggtgtata gatacagctt | 1680 |
| gtcttgaaat gtctttctcc acataatgaa gcatgctgaa tgctgggaat ctggagcagc | 1740 |
| agccctggga gccctgagtt ttgaagtgtt ttggtttgct tcaaaggtta gaagaacttg | 1800 |

```
atatgtatgg caaacaactt tagaatacta gttactcact aacatgaggc gggtaatgtt    1860
gctctagatt ctatattcca gtaaagccag cttttcttat tattggagta ggcaaatgaa    1920
tggcattaga attagtgggt ggcttgtaag ttgtagttat aggcacttta ccacttcctg    1980
ccattagcag gcatccttgt tttttcttct tttccctctt tgttccttct tttccctttc    2040
tccttataca ttttctttct ctactttaat tctccttcct ccttactgta gatcccaagc    2100
ttctagctta ggtttgcaag tcatattgct tggccctcca cattcactga gaggtgaaga    2160
taggctgacc ccctgtcctc ttacatttga gggatcatag actgctgtgt gaattctgga    2220
aagtctcagg tccctaccag ggcactgaat ggcttctcaa tggctgtaga gacagtacag    2280
ttttccaaag cagcctaatt catctggaca gctaccaggc actttggaaa gttggttcag    2340
ttactactat gaggccataa tatatttgct ggtattaaaa ttcttcagaa ttggaattac    2400
tatttgaaat aatattttgg ttgacttaag ttttgagaga caattctaaa attgatctag    2460
agactcattc aatagcaatg tgacctttta aatacttaca ttaagtaaaa ctgccagtag    2520
attaaatcat atatatatat atatatatat atatatatgt aagagcttcc tctatttact    2580
actgttgaac ttcagtaatt tttagaggct aaataatggt cagaatgttt ttaagtgtgc    2640
tcttttatta catgcttgtg caggttttgt aattcagtac agaaaagttt aaccttgtac    2700 attttgtat gtaaaaagtc ttttaagtag tcttatcctt atttaaataa acagaataaa    2760 attacctga gtaggtctgt tattcttatt aaaatggaaa aatgctctgt aatgacttga    2820
tctgttttta tttgagtgaa caattttgga aagtattctt tatagtacaa ctttctatac    2880
ctggattgat taagatcaga tgtgattcga gtagtccagc catatcttgt agcccttctt    2940
tgaatgagag ggtggctgga gtggtctggt gctgggatat cacggtgcta cagagcctga    3000
catgttgact gtcactacat gttgagggat ggaaatagaa gtctctgaac ttcccatgta    3060
atattaaagc tcttaacaaa atgagacaaa ctagagattc agttgagaga ttttatgtta    3120
gagtgatctg aaaaaaagtt aatttctaaa ctgctatctt aatattatta tatttggaga    3180
ctgatgctgt                                                           3190

<210> SEQ ID NO 89
<211> LENGTH: 520
<212> TYPE: DNA
<213> ORGANISM: Homo sapien

<400> SEQUENCE: 89
actctctctc ccttagagtt tatgagttat tcaaggagga gacttcttaa agacagcaac      60
gcaattcttg taacttgtgt aaatagcccc atctttcaga gtgataccat ttctacattt     120
gataatgcct gtattcctgt aggatgtata tagtttaggg gattttttt tggttggggt      180 tttggttttt tagaaggtca atatgtctgg tttatttat gtgcttgaaa aagatcattt      240 gaaaaaatc aacattacat ttttccaacc acaaaacaaa aagaaaata aacaaaaaa         300 agaaaaaaaa aaagaacgcg tggggtgtac ctcgtggggg tcgtaaggcg ctgtggtccc     360
cggggtggtg gacaattgtg gtctctcgcc cgccgcacac aatttcccca cccacacact     420
cttctaccgc cgacagcaag tggggcggca cgcgagagaa aggaaggaga gagaagagca     480
gaacacgaag agacgacgaa gaagagaaac aaaaacaaca                           520

<210> SEQ ID NO 90
<211> LENGTH: 2395
<212> TYPE: DNA
```

<213> ORGANISM: Homo sapien

<400> SEQUENCE: 90

| | | | | | |
|---|---|---|---|---|---|
| taccgaggag | ggaacaagct | acatgctatt | ttgtttgtag | tattgtggaa | cagtcttgtt | 60 |
| atggagtgcc | agcttagagg | ttgttgcaaa | cttgtctaga | agtgagagca | tggtttttt | 120 |
| tagccctttg | agagtctaca | tctaatgaac | attcttgctc | acccataaat | aacgtcaagc | 180 |
| ctcaatgtca | ccgtcacgtt | gggatactct | ttctcatctg | gcatcctaga | caggacaagg | 240 |
| ttggttacct | ttccttccat | gaaccatgaa | cctgtgacgg | catcattcat | cctgacttca | 300 |
| ccaagctccg | cctgtgggtg | aggccagagc | tcccactggc | aattttaga | agagccagag | 360 |
| gctccctgct | tcctctagaa | ataacagttc | agggtgaagc | atggagggtt | tcagttccca | 420 |
| gacaatggaa | ccatttagag | acaacacagt | tggacatttc | cacttttcc | ttgattcctg | 480 |
| gaagtccagt | gggttctgca | gctgaaaaag | ccctgggtcc | cagcagcaga | gagacaggac | 540 |
| agagggatg | cttgggcggg | gagggacggt | aacctgcaga | acagattcca | tttttataga | 600 |
| acgagtacac | gtttgctaaa | acagtcctgc | tttcccagac | tggattccca | ccacagggac | 660 |
| agtcggaact | caggactagc | tccagcgaca | tctttcctcc | gaattcaagc | cttctatcac | 720 |
| aatgtcaaaa | cagctattta | taaagccatt | tcattgtac | ttgataacag | cacgagtccc | 780 |
| aaaactttta | gaaataaaat | aggacattgg | cttgattgaa | aagagggact | tttttaaaaat | 840 |
| tgttctttcg | tcagaagcct | tttggatgac | ttacaatagc | tctgatgaag | ataccacccc | 900 |
| agcgtcagtc | caataggtca | gtgagtttca | acaggcatcc | atccctccca | tgaagggatt | 960 |
| ctggtgatgg | gaagtttctg | taatgacagg | aaagcattga | ccctcattga | ttgtcaactt | 1020 |
| tggtattagc | catgaaagac | aggatgctca | ttgggtgttc | tgtagagtga | ggaatgctgc | 1080 |
| ctattccctc | ccagaacgtc | tgacccaggg | gtgtgtgttg | aggagccctg | ggggaaatgg | 1140 |
| accaagtttt | cccacagagc | agtattaggc | tgaagagcag | gtgactggta | ggccccagct | 1200 |
| cccatcattc | cctcccaaag | ccattttgtt | cagttgctca | tccacgctgg | attccagaga | 1260 |
| gttttccaat | ttgggaagcc | atgagaaagg | tttttaaatc | ttgggaagat | ggagagaggg | 1320 |
| acataggata | gttgactcca | acatgacagg | aagaggctgg | agattgggaa | ttggccatca | 1380 |
| accaagcctg | tagtagtaaa | gccatggtcc | cgcattggaa | ttacttgggg | aacttataca | 1440 |
| gttctgatac | ccaggctctc | ctagaccagt | tcaaccaatt | ctaggtgggg | gactcaggca | 1500 |
| tcagtgtgtt | tcgtagctcc | ccgggtgttt | tccctgtgca | gccgagcttg | ggaaactgcc | 1560 |
| atgcttttg | gatgtcaagg | cgctgttgga | ggctgggtgt | gacagcacag | agccaggttg | 1620 |
| tcttgtggaa | accacagcca | cgggtttgcc | actggctcag | catggcctca | ctgccagtcc | 1680 |
| cagcctggct | gagggacaag | atggtttctc | ttgggagttc | ctgagtggag | cacccttcca | 1740 |
| ggcttttga | aagccagctg | atctgtggag | ccttgttaag | ggactcaata | cggtgtttgg | 1800 |
| atattgatgt | ttttccttga | gactgtcttg | tccatcaata | aagatggagg | atgtctcctc | 1860 |
| tttgaacccc | gcttccccac | cagtactctc | tctcccttag | agtttatgag | ttattcaagg | 1920 |
| aggagacttc | ttaaagacag | caacgcaatt | cttgtaactt | gtgtaaatag | ccccatcttt | 1980 |
| cagagtgata | ccatttctac | atttgataat | gcctgtattc | ctgtaggatg | tatatagttt | 2040 |
| agggatttt | tttttgttt | ggttttgttt | tttagaagtc | aatatgtctg | gttttattta | 2100 |
| ttgcttgaaa | aagatcattt | gaaaaaaata | aatacatttt | caaccaaaaa | aaaaaaaaa | 2160 |
| aaataaaaaa | aaaaaagaaa | aaaaaaaga | acgcgtgggg | tgtacctcgt | ggggtcgta | 2220 |
| aggcgctgtg | gtccccgggg | tggtggacaa | ttgtggtctc | tcgcccgccg | cacacaattt | 2280 |

```
cccacccac acactcttct accgccgaca gcaagtgggg gcggacgcga gagaaaggaa    2340
ggagagagaa gagcagaaca cgaagagacg acgaagaaga gaaacaaaaa caaca        2395

<210> SEQ ID NO 91
<211> LENGTH: 522
<212> TYPE: DNA
<213> ORGANISM: Homo sapien

<400> SEQUENCE: 91
attttactct agtattaatg tggttttata aatgattata tgccttatat tctgggggga     60
aagaaatgtg aaaatgtgct aacgtagaca gaaacagaat atataagtcg ttttgaatgt   120
tatttctttt ttaaaaaatt tgcttggtgt catatagcca aaactattca tggtgacagt   180
ttcattgcta tactttttat atgatttcag cgaattgaaa acatgtatat aatagcaaaa   240
aactggactt catgctgagt atagatgata catataaaag aagtcaaaat ttggagaaaa   300
aatttaaaaa gataagtaga aaaatgaagt aactgtagaa accatactta ctctttgatc   360
tcaaatgctc aaaaactgaa tgaaaatgtg aatttaggcc gaccaggtag tcttgtcaat   420
aaactaaaag caaaaacagg aaaattgaga aatatgttac aactataaca acacaaaaca   480
gcatagtttt gaaacacttg cagttcttaa atataaaagc tt                     522

<210> SEQ ID NO 92
<211> LENGTH: 1271
<212> TYPE: DNA
<213> ORGANISM: Homo sapien

<400> SEQUENCE: 92
gcaaaacctc attaattgga tgctatcaaa attatgaaag gaaatctgag tgagcacact     60
tgttttgaaa agaaattggt aaatacttct atgatgcagt tttaagttat acaattaact    120
gctatttgga atttaataag tccactataa gcaatgtgcc tgcacaccaa ttaaaggttg    180
gatctgtctc ttcttgacaa ttttttagaa gccattattt cgttaccaaa taaacctgaa    240
gttaagaaat atttatattt acatctattt atatctgttg gagaatattt cataactcag    300
acttggttgt tttacacaga cttctcccca ttatccaaca tagtgagatt tttctatagt    360
tctatatttt actctagtat taatgtggtt ttataaatga ttatatgcct tatattctgg    420
ggggaaagaa atgtgaaaat gtgctaagta gacagaaaca gaatatataa gttgttttga    480
atgttatttc tttttaaaa aatttgcttg gtgtcatata gccaaaacta ttcatggtga    540
cagtttcatt gcttacttt tatatgattt cagcgaattg aaaacatgta taatagaa      600 aaaactggac ttcatgctga gtatagatga tacatataaa agaagtcaaa atttggagaa    660
aaaatttaaa agataagta gaaaaatgaa gtaactgtag aaaccatact tactctttga    720
tctcaaatgc ccaaaaactg aatgaaaatg tgaatttagg ccgaccaggt agtcttgtca    780
ataaactaaa agaaaaacag gaaaattgag aaatatgtta caactataac aacacaaaac    840
agcatagttt tgaaacactt gcagttctta aatataaaag cttttattag ttaattttt    900 aaaaggatct cataggattg acactgaatc aggttgggag gtggaataag ggtgatgca    960 tattcttct gaattactta ttataacatt tctagaatca ttaggtcagt gctactttgt   1020
tgtcgtcaat gtacaataaa ggaatcacaa attgatctta gtgataattt tacagaggca   1080
gacattgcac ataggtatga ctgcaaaat gggtggctaa ctctgggaag atacttgtgt   1140
taaactttat atgacattta ataacccttc atcataaggc aatgttttttt acaaaagat   1200
```

| | |
|---|---|
| tgcacaaaat catgttagtc atttactctg caaaaatggc acattagtgg gggttccaaa | 1260 |
| atccataatg a | 1271 |

<210> SEQ ID NO 93
<211> LENGTH: 679
<212> TYPE: DNA
<213> ORGANISM: Homo sapien

<400> SEQUENCE: 93

| | |
|---|---|
| actgtaactc tttcattgag gggctatgtg atggagacag actaactcat tttgttattt | 60 |
| gccattaaaa ttattttggg tctctggttc caaatggagt ttggagaatg cttgacttgt | 120 |
| tggtctgtgt gaatgtgtat atatatatac ctgaatacag gaacatcgga gacctattca | 180 |
| ctcccacaca ctctgctata gtttgcgtgc ttttgtggac acccctcatg aacaggctgg | 240 |
| cgctctagga cgctctgtgt tcactgatga tgaagaaacc tagaactcca agcctgtttg | 300 |
| taaacacact aaacacagtg gcctagatag aaactgtatc gtagtttaaa atctgcctcg | 360 |
| cgggatgtta ctaaactcgc taatagttta aggttacttt acaatagagc aagttggaca | 420 |
| attttgtggg gttggggaaa tgttagggca aggcctagag gttcattttg aatcttggtt | 480 |
| ggtgacttta gggtagttag aaactttcta cttaatgtac ctttaaaata gtccattttc | 540 |
| tatgttttgt ataatctgaa actgtacatg gaaaataaag tttaaaacca gaaaaaaaa | 600 |
| aagaagaaaa aaaagctggg gggaccgggg ccaaggggc tccgggggga atggtttccg | 660 |
| ccccaatccc caataggaa | 679 |

<210> SEQ ID NO 94
<211> LENGTH: 994
<212> TYPE: DNA
<213> ORGANISM: Homo sapien

<400> SEQUENCE: 94

| | |
|---|---|
| cgtcgacaaa gaaatgacaa aatcagggag aaaacatcca agcttcttac ctgtagatag | 60 |
| aatcagccct cacttggtgc ttattaccag ttattcaaga acaataacaa caacaaaatt | 120 |
| agtagacatc caagaagcac atattaggac caaagatagc atcaactgta tttgaaggaa | 180 |
| ctgtagtttg cgcattttat gacatttttta taaagtactg taattctttc attgaggggc | 240 |
| tatgtgatgg agacagacta actcattttg ttatttgcat taaaattatt ttgggtctct | 300 |
| gttcaaatga gtttggagaa tgcttgactt gttggtctgt gtgaatgtgt atatatatat | 360 |
| acctgaatac aggaacatcg gagacctatt cactcccaca cactctgcta gtttgcgt | 420 |
| gcttttgtgg acacccctca tgaacaggct ggcgctctag gacgctctgt gttcactgat | 480 |
| gatgaagaaa cctagaactc caagcctgtt tgtaaacaca ctaaacacag tggcctagat | 540 |
| agaaactgta tcgtagttta aaatctgcct cgcgggatgt tactaaactc gctaatagtt | 600 |
| taaaggttac ttacaataga gcaagttgga caattttgtg gtgttgggga atgttaggg | 660 |
| caaggcctag aggttcattt tgaatcttgg tttgtgactt tagggtagtt agaaactttc | 720 |
| tacttaatgt acctttaaaa tagtccattt tctatgttttt gtataatctg aaactgtaca | 780 |
| tggaaaataa agtttaaaac cagattgccc agagcaagac tctaatgttc ccaacggtga | 840 |
| tgacatctag ggcagaatgc tgccattttg aggggcaggg ggtcagctga tttctcatca | 900 |
| agataataat gtatggtttt tacactaagc aactgataaa tggacaattt atcactggaa | 960 |
| aaaaaaaaa aaaaaaaaaa aaattggtgc ggcc | 994 |

<210> SEQ ID NO 95
<211> LENGTH: 496
<212> TYPE: DNA
<213> ORGANISM: Homo sapien

<400> SEQUENCE: 95

| | | | | |
|---|---|---|---|---|
| ggtcgcggcg | aggtaccgtc | tgtcctcctg | tttcctttag gtggtagcag | cctctgctga | 60 |
| gtggtttgtg | tgagttcgca | ctgaatccta | ccacaatcct tactcagatg | agggctctga | 120 |
| gattccacct | aacgggagac | gagatggcag | ctgctgacat tctgccctgt | ctgcaagctc | 180 |
| tcctagctct | tccagctctc | ccatctctgc | aaactccgac agcagttgct | cttcctctga | 240 |
| ggaagctgag | cgactgcatc | atccccgac | cacgtcgcct ctgctcagcc | ctcttaatgg | 300 |
| ccgtcattcc | aagggaaagg | caggagccag | gagcctctgg gatgcagccc | cttggttaca | 360 |
| gtgtctgctt | tcagctttgc | ctctgcttct | ccagggtctt tctcaggcag | ttaacccaat | 420 |
| atttatcaac | tctctcccta | ggcccagcac | ttggcagaat ttttttctat | tttgtaaaag | 480 |
| tatgagatat | tccttg | | | 496 |

<210> SEQ ID NO 96
<211> LENGTH: 3175
<212> TYPE: DNA
<213> ORGANISM: Homo sapien

<400> SEQUENCE: 96

| | | | | |
|---|---|---|---|---|
| atggcgaccg | accttcccat | catggcgcgt | ggccccgccc gctccgccgc | gcctgcggga | 60 |
| gggagcagtt | ccgggtgcgg | tgcgcgccag | ggcggggcgg ggggcggcgt | cctggccatg | 120 |
| gccggcctgt | cggacctgga | actcggcgcg | gagctgcagg ccctgggctt | ccagccagga | 180 |
| cccatcaccg | acaccacccg | ggatgtctac | cgcaacaagc tgcgccgcct | gcggggcgag | 240 |
| gcccggctgc | gcgacgagga | gcggctgcgg | aggaggcccc ggccgcgggg | cgaggagcgg | 300 |
| ttacgggaag | aggcccggtt | acgcgaggat | gcgccgctgc gcgcccggcc | cgccgcggcc | 360 |
| tctccgcggg | cggagccctg | gctctcccag | ccggcctcgg gctcggccta | cgcgacccct | 420 |
| ggggcctacg | gtgatatccg | gccctccgcg | gcttcctggg tagggagccg | cggcctcgcc | 480 |
| tatcctgccc | gcccggcgca | actcaggcgc | gcgcgcctcg gtccggggcag | ctccgaggag | 540 |
| gacgaggacg | cccggacgcc | cgacagggcc | acgcagggcc cgggtctcgc | ggcccgccgc | 600 |
| tggtgggcag | cgtctcccgc | cccggcgcgg | ctgccttcct ccctcctcgg | tcccgacccg | 660 |
| cgccggggcc | tgcgggcgac | tcgagcgggc | cctgctggcg cggcgagggc | ccggcctgag | 720 |
| gtggggcgcc | ggctggagcg | ctggctctct | cggcttctgc tctgggccag | cctagggcta | 780 |
| ctgctcgtct | tcctgggcat | cctttgggtg | aagatgggca agccctcagc | gccgcaggag | 840 |
| gcggaggaca | acatgaagtt | attgccagtg | gactgtgaga gaaaaacaga | tgaggtgagt | 900 |
| ttgagtttct | ctggttttta | ttattcttcc | tgaggatatt agcctccatc | aggaggtaaa | 960 |
| cttccccaga | aaagaatag | gatcattttc | agggagtgct tcctgtaatg | taccagagtc | 1020 |
| acattgtgtt | ctgtgatgtt | cttgtcaggc | tcaattgtgg cagtgaagga | atacttgaaa | 1080 |
| tagaattgac | ctcccaaaat | ccaaccctgg | gcttgttatg gacactttcc | catcaaatgt | 1140 |
| agcatcgggg | actttgatct | gcctgagtca | atctagggg atgcagtagg | ttgttgttga | 1200 |
| aggaccctca | agctccctgg | cactgggagg | aagggccggc gtttctaagc | atcaggaggc | 1260 |
| caagttctca | attccacatt | ctctgtctcc | agtggtgcag ctgtggctct | gaaaatgctg | 1320 |
| ttctgatttg | aaacataggg | agtttgtttg | gaacacatct taagtggaat | tagccctctt | 1380 |

-continued

```
agtctacatt tagatttgtt ttatgaagct ctaatattcc ctacaaataa tatttgggga    1440
aggcgagcag ccccatccat ttatgaatca tgaaagcagc attatcaagg agctgggatg    1500
ctgcttctgg tgacagtctg gagaagatat ggggcagtaa attttcaggt cttaaattgt    1560
accaggagga gtcttgtgct gccagagggc atgacttagt agtctaatta agtgtgcaat    1620
gcctggcctc ccaagtcctt agttaacatc tctagtagcc caggggctgg gaaagaaaat    1680
gacgcatggt cctctggcca gccctgcatt gactgtctta ctcatgtaaa tgaggggca     1740 tcctggtgca gataatggct tttatttctc tttggcttcg ggtgtgtcat agttgggggt    1800
gttttattac atccatttat tggattcatc caccaaatat ctttgcttcc caattgtttt    1860
gtaaaaacag attcatagta agtttaatct gccttctatc ataaaaactg tagttgatga    1920
tgagaggaag tggcccagaa acacaggcag ccagagggga aactggaatt tgaagactta    1980
aaacaaaaac aggaaaaaat aactttctgt aagacttctc agtgctgtta gttttgtctt    2040
ttaattagaa aaaagttcca tggtttctat ttcttggtcc ttcacatctc taaatgaatc    2100
agacccacaa gtgaatggca catttgttcc ctggccttct ctgatctgga cacactcagg    2160
ctccacttga gtgagcccag acaggtaccc tccaggtcct agctacagat gcgctccgtg    2220
ggcagacggc attcagcacc tgccagcgag ggcttcagac gcagatatcc ctatttgtaa    2280
ccattcagac cttcatcaga gcatcagaaa gcaggggctg ggccatctca atgcaggctt    2340
tgtggagcta agatttcatg ggcacccctt ggcctttctg gagggtggac acaggaacaa    2400
gcaggtgggg acgtgtttct tggctttggt gaggctcttg ctgaaagtct tattctttgc    2460
atggctccag gcttaccgag atcacagacg ggcatttgaa tttcagattc atgttctttc    2520 cctttcggt cgttgaagac ggtgacactt tgtgttttc tttctgcctt tgtgctgctg     2580
aaaacgtggg gacaggctgg gagtgggtgt gttgtcttaa tcaggccgtc tcgttgtctg    2640
gtaccgtctg tcctcctgtt tcctttaggt ggtagcagcc tctgctgagt ggtttgtgtg    2700
agttcgcact gaatcctacc acaatcctta ctcagatgag ggctctgaga ttccacctaa    2760
cgggagacga gatggcagct gctgacattc tgccctgtct gcaagctctc ctagctcttc    2820
cagctctccc atctctgcaa actccgacag cagttgctct tcctctgagg aagctgagcg    2880
actgcatcat cccccgacca cgtcgcctct gctcagccct cttaatgcc gtcattccaa     2940 gggaaaggca ggagccagga gcctctggga tgcagcccct tggttacagt gtctgctttc    3000
agctttgcct ctgcttctcc agggtctttc tcaggcagtt aacccaatat ttatcaactc    3060
tctccctagg cccagcactt ggcagaattt ttttctattt tgtaaaagta tgagatattc    3120
cttgctgttt agtatttgac agtgtggctg gagaagtaaa gatggacaga ccgga         3175
```

<210> SEQ ID NO 97
<211> LENGTH: 641
<212> TYPE: DNA
<213> ORGANISM: Homo sapien

<400> SEQUENCE: 97

```
acatgcagat gtgcatgtta cagagataaa gtgatcgaga caaggactga ctgggtatag     60
aaggaagaca gactcctgtc ttcactccta aatgcagttc tttggaatca ccctactgtg    120
atgggcgtag tagggagcca tcagctagga agaaacgtgg gagatgtgaa ttccaagagt    180
tgcctggaca gggcaagtca tgttagcgtg ggtcacactt ccaagatatt taaagcaaat    240
acaaaacaga acagaggatt caaaccgcaa gtatgggaga tttaggccct gcagaggcag    300
accattcctt agtatctcac aaagcagagt aatactggag gcagagtagg gggtggttgg    360
```

-continued

```
agagcagtta gtaccaataa caatgaagtc tgtgtttgat ctgatcgata ctttccagtc    420
ccgaatcaaa gatatggaga agcagaagaa ggagggcatt gtttgcaaag aggacaaaaa    480
gcagtccctg tgagaacttc ctatccaggt tccggtggag gaggaggttg ctggtgatct    540
ctgctcctaa cgatgaagac tgggcctatt cacagcagct ctctgccctc agtggtcagg    600
cgtgcaattt tggtctgcgc cacataacca ttctgaagct t                        641
```

<210> SEQ ID NO 98
<211> LENGTH: 2231
<212> TYPE: DNA
<213> ORGANISM: Homo sapien

<400> SEQUENCE: 98

```
tagattctga cttattccat atacttctat tagcctcaga tattttttatt atatagtagt     60 aaatgtaatg acttacagta gtatcatttt cacttacaaa gcacttagga aattaaagga    120
attaactctt gttatcaggt aagagagacc aggatatcca cttgtctcat gactaaagtt    180
tgccttgtaa tttggactaa gggaaagtca ttggttatat gaagtagaca actgtggtta    240
atactgctct tatttacaga gagaaagcgg ttggaagcca agcaacggga agacatctgg    300
gaaggcagag accagtctac agtttgaaca tcactcaatg aaagggataa ttccatgaat    360
cagaaaatgt ttccatagcc ttcagataag atgatccttc cagagctcta tgtacatgca    420
gatgtgcatg ttacagagat aaagtgatcg agacaaggac tgactgggta tagaaggaag    480
acagactcct gtcttcactc ctaaatgcag ttctttggaa tcaccctact gtgatgggcg    540
tagtagggag ccatcagcta ggaagaaacg tgggagatgt gaattccaag agttgcctgg    600
acagggcaag tcatgttagc gtgggtcaca cttccaagat atttaaagca aatacaaaac    660
agaacagagg attcaaaccg caagtatggg agatttaggc cctgcagagg cagaccattc    720
cttagtatct cacaaagcag agtaatactg gaggcagagt aggggtggt tggagagcag    780 ttagtaccaa taacaatgaa gtctgtgttt gatctgatcg atactttcca gtcccgaatc    840
aaagatatgg agaagcagaa gaggagggc attgtttgca aagaggacaa aaagcagtcc    900
ctgtgagaac ttcctatcca ggttccggtg gaggaggagg ttgctggtga tctctgctcc    960
taacgatgaa gactgggcct attcacagca gctctctgcc ctcagtggtc aggcgtgcaa   1020
ttttggtctg cgccacataa ccattctgaa gcttttaggc gttggagagg aagttggggg   1080
agtgttagaa ctgttcccaa ttaatgggag ctctgttgtt gagcgagaag aaaaaaaaga   1140
tgaagaatga gaacgcagac aagttactta agagtgaaaa gcaaatgaag aagtctgaga   1200
aaaagagcaa gcaagagaaa gagaagagca agaagaaaaa aggaggtaaa acagaacagg   1260
atggctatca gaaacccacc aacaaacact tcacgcagag tcccaagaag tcagtggccg   1320
acctgctggg gtcctttgaa ggcaaacgaa gactccttct gatcactgct cccaaggctg   1380
agaacaatat gtatgtgcaa caacgtgatg aatatctgga aagtttctgc aagatggcta   1440
ccaggaaaat ctctgtgatc accatcttcg gccctgtcaa caacagcacc atgaaaatcg   1500
accactttca gctagataat gagaagccca tgcgagtggt ggatgatgaa gacttggtag   1560
accagcgtct catcagcgag ctgaggaaag agtacggaat gacctacaat gacttcttca   1620
tggtgctaac agatgtggat ctgagagtca agcaatacta tgaggtacca ataacaatga   1680
agtctgtgtt tgatctgatc gatactttcc agtcccgaat caaagatatg gagaagcaga   1740
agaaggaggg cattgtttgc aaagaggaca aaaagcagtc cctggagaac ttcctatcca   1800
```

```
ggttccggtg gaggaggagg ttgctggtga tctctgctcc taacgatgaa gactgggcct    1860
attcacagca gctctctgcc ctcagtggtc aggcgtgcac attggtctgg gcgccttacc    1920
ttctgaagct taagcgtgcg cacggactgg gggcccgttc aactggcccc attaagggac    1980
cccgagataa cgagaaacgt acaccccatg gtgaaaaaca ccgcacaaat ccacggaccc    2040
ggagacaacc caggccaggc gcaaaaagca agaccacacg gatatcaccc aaggcagcga    2100
gaagggacca cacacacacc cgcacaacag gacacccaag cggcgccaca acagtcacga    2160
caccacaagg ccacgaagca acacacagaa acatacacag cagcacacgg ccatacaacc    2220
gcccacacag c                                                        2231
```

<210> SEQ ID NO 99
<211> LENGTH: 488
<212> TYPE: DNA
<213> ORGANISM: Homo sapien
<220> FEATURE:
<221> NAME/KEY: misc_feature
<222> LOCATION: (360)..(362)
<223> OTHER INFORMATION: a, c, g or t
<221> NAME/KEY: misc_feature
<222> LOCATION: (372)..(374)
<223> OTHER INFORMATION: a, c, g or t
<221> NAME/KEY: misc_feature
<222> LOCATION: (384)..(384)
<223> OTHER INFORMATION: a, c, g or t
<221> NAME/KEY: misc_feature
<222> LOCATION: (387)..(388)
<223> OTHER INFORMATION: a, c, g or t
<221> NAME/KEY: misc_feature
<222> LOCATION: (424)..(424)
<223> OTHER INFORMATION: a, c, g or t
<221> NAME/KEY: misc_feature
<222> LOCATION: (433)..(433)
<223> OTHER INFORMATION: a, c, g or t
<221> NAME/KEY: misc_feature
<222> LOCATION: (443)..(443)
<223> OTHER INFORMATION: a, c, g or t

<400> SEQUENCE: 99

```
ccgggcaggt acccacccat aaaattatga gtgtaaaagc actttgcaaa ccctgatact      60
ctatgaagaa gtaaaaagta gtgctgtaat tattatcatt attatgtcca atggttgagg     120
tttccgctgc ccacctgtca gctatgtgag gcctaaagag agggagggct aggccattcc     180
tcagcttctg aggttcctgg ccctttttccc cttccatctg tccacagctg actgctaagg    240
ctggatgcgt aggggaaagc agagaaaagg tgatttactg ggacacagag acacaggctg     300
gaacgagcat acgcgatgtg ctcttcctta acaatttctg aaggccatt ttggctgggn      360 nncacagtgg cnnntcacac ctgntannat ccctgcactt tgggaggtaa aggcagagga    420
tttncctggt gtncccaagc agnttacgag tgcctggcca gctggaagcc tactgcactc     480
tgttggcc                                                              488
```

<210> SEQ ID NO 100
<211> LENGTH: 558
<212> TYPE: DNA
<213> ORGANISM: Homo sapien
<220> FEATURE:
<221> NAME/KEY: misc_feature
<222> LOCATION: (430)..(432)
<223> OTHER INFORMATION: a, c, g or t
<221> NAME/KEY: misc_feature
<222> LOCATION: (442)..(444)
<223> OTHER INFORMATION: a, c, g or t
<221> NAME/KEY: misc_feature
<222> LOCATION: (454)..(454)
<223> OTHER INFORMATION: a, c, g or t

```
<221> NAME/KEY: misc_feature
<222> LOCATION: (457)..(458)
<223> OTHER INFORMATION: a, c, g or t
<221> NAME/KEY: misc_feature
<222> LOCATION: (494)..(494)
<223> OTHER INFORMATION: a, c, g or t
<221> NAME/KEY: misc_feature
<222> LOCATION: (503)..(503)
<223> OTHER INFORMATION: a, c, g or t
<221> NAME/KEY: misc_feature
<222> LOCATION: (513)..(513)
<223> OTHER INFORMATION: a, c, g or t

<400> SEQUENCE: 100
gtatgcatgt gctcccataa tcatatactt tcccagcttc tactctgcct gtggtctaat      60
ttcaactcct tcagctgctg tacccaccca taaaattatg agtgtaaaag cactttgcaa     120
accctgatac tctatgaaga agtaaaaagt agtgctgtaa ttattatcat tattatgtcc     180
aatggttgag gtttccgctg cccacctgtc agctatgtga ggcctaaaga gagggagggc     240
taggccattc ctcagcttct gaggttcctg gcccttttcc ccttccatct gtccacagct     300
gactgctaag ctggatgcgt aggggaaagc agagaaaagg tgatttactg ggacacagag     360
acacaggctg gaacgagcat acgcgatgtg ctcttcctta acaatttctg aaggccattt     420
ttggctgggn nncacagtgg cnnntcacac ctgntannat ccctgcactt gggaggtaa      480 aggcagagga tttncctggt gtncccaagc agnttacgag tgcctggcca gctggaagcc     540
tactgcactc tgttggcc                                                   558

<210> SEQ ID NO 101
<211> LENGTH: 799
<212> TYPE: DNA
<213> ORGANISM: Homo sapien

<400> SEQUENCE: 101
tggtcgcggc cgaggtacaa aggctttgag gtccatggac tatacttgtc ccatttatca      60
tcccaggtgg tgcttttgacc ctagggatac cctggctatt aagataaaaa gatttgtgga   120
cattaaaatt atgaatatgt cagtaataat ccagcacaca ttgaaatatt gacacagatt     180
accataattt gtgcaacatc ttataaacaa tgtcatttcc acagtagtct aaggcttcac     240
cagcctggcc cactgtatct agactttagg ttcattttaa ttaattatgc tttccttctc     300
tgtatcattt gggaagttga taaatatcac ttccttagat accttcattc agtgatatat     360
ctggctttta caattaaatt ggaaaaggta agtttctctt tggtgggttg agagttggac     420
catcaattct aatctacaaa aggaaattca tgatttcact ctgacgccta ggatctagcc     480
aaggctggtc tgcagtatca gatgtccaaa ctcatctact attagccata ttttgtgagt     540
cgtttgtcta aactttgtca aaatgccttt gccatgattt tgttgctatc tggatttcaa     600
acatggacag ttaggaagat gtgcattgaa gtaggaaaat tttgttcagc atctgctgtt     660
atttattttt taccacttca aaatggcca ctgtctttttt aacaaacacc aacgacaaca     720
acacacaaaa caaaaaaaaa caccctgcgg cttaccctgg ccctccttttt ccctgttgaa     780 ttgtttccc cccaatcac                                                   799

<210> SEQ ID NO 102
<211> LENGTH: 956
<212> TYPE: DNA
<213> ORGANISM: Homo sapien

<400> SEQUENCE: 102
```

```
atttataagg cccttcaaat ttgtggcttc ctttctcata cttctcaagt ataatgaaag      60
ggggagaaaa accccaccat caacacaaaa gaaggctata aagactgtgc acctttttaac    120 aagtcaattt gtagtcagtc cctgggcctg tcttttttttt tttttaattt tgaagctacc   180
tgaggtttag aattccttca gccctagctg cttttattct gcttttatt taaacaaaaa      240 gaggggagg atctgaagga aactagtttt ctgtacaaag ctttgaggt ccatggacta       300 tacttgtccc atttatcatc ccaggtggtg ctttgaccct gccatacct ggctattaag      360 ataaaaagat tgtggacat taaaattatg aatatgtcag taataatcca gcacacattg      420
aaatattgac acagattacc ataatttgtg caacatctta taaacaatgt catttccata    480
gtagtctaag gcttcaccag cctggcccac tgtatctaga ctttaggttc atttaataa      540 ttatgctttc cttctctgta tcatttggga agttgataaa tatcacttcc ttagatacct    600
tcattcagtg atatatctgg cttttacaat taaattggaa aaggtaagtt tctctttggt    660
gggttgagag ttggaccatc aattctaatc tacaaaagga aattcatgat ttcactctga    720
cgcctaggat ctagccaagg ctggtctgca gtatcagatg tccaaactca tctactatta    780
gccatatttt gtgagtcgtt tgtctaaact ttgtcaaaaa tgcctttgcc atgattttgt    840
tgctatctgg atttcaaaca tggacagtta ggaagatgtg cattgaagta ggaaaatttt    900
gttcagattt gctgttattt attttttaaa ttaaaaatgg aaatgtaaaa aaaaaa         956

<210> SEQ ID NO 103
<211> LENGTH: 488
<212> TYPE: DNA
<213> ORGANISM: Homo sapien

<400> SEQUENCE: 103
acaaccaccc aaagcaccgc cccccccacc catactccgg catgatagac actatagggc      60
aatgttgctc tagatgctgt cgagcggcgc agtgtgatgg ataacttgct cttagaataa    120
gggtaaaaag taaattaaca agtaagtaaa gtatagatag atgttgccac agacatacag    180
gaaaaataaa aagaaaaatt aaaccagaaa ataacacaa aaacattaaa gaggagctga    240
aacaaatcaa aaaagaaag aactaatata gcctagtttt caaagaaaaa cattctaaaa    300
gtttaacatt tcagaacata gaatactatc taagtttacc atacttcaaa aatctatcta    360
aataaatatt gacactatat tacattaaca caacaaacag ctatttttcta agtactagcc    420 aagtatccca tggaaggcaa acgaccctaa gtagttcata ttttacagcc cttgaactta    480
taaagctt                                                              488

<210> SEQ ID NO 104
<211> LENGTH: 386
<212> TYPE: DNA
<213> ORGANISM: Homo sapien

<400> SEQUENCE: 104 aaccctggc caggcccagc tgccacaccc tttctgggag aagcatggcc tacagaatga      60 agaggggac caggaacccc tgtgggagag gcttagacct gaagcagtgc ccactctggc    120
tcctcctgcc ttggctgact gggttcctgg accatgtgca tttcactggg ccatgggatc    180
tacatctcct tgcatcccca gctggtctga tccctgccag gccccttcc ttcctgctca    240 tggtcttcag gtggcctgat catggaaagt aaggagttag gcattacctt ctgggagtga    300
accctgactc catccccta ttgccaccct aaccaatcat gcaaacttct ccctccctgg    360
ggtaattcaa cagttaaaag aagctt                                          386
```

<210> SEQ ID NO 105
<211> LENGTH: 1713
<212> TYPE: DNA
<213> ORGANISM: Homo sapien

<400> SEQUENCE: 105

| | | | | | |
|---|---|---|---|---|---|
| atgccccgcc | ctggacaccc | ccgcccagca | tctgggcctc | cacgcttggg | accgtgggag | 60 |
| cggccaacag | agctatgtct | ggagacatat | gataaaccac | ctcagccccc | accaagccgc | 120 |
| cgcacccgta | gaccagaccc | caaggaccct | ggccaccatg | ggccagagag | cattaccttc | 180 |
| atctctggct | ctgctgagcc | ggcccttgag | tccccacct | gctgcctgct | ctggcgaccc | 240 |
| tgggtgtggg | agtggtgccg | ggctgccttc | tgcttccgcc | gctgccggga | ttgcctccag | 300 |
| cgctgtggag | cctgtgtgcg | gggatgcagc | ccctgcctgt | ctactgagga | ctccactgag | 360 |
| gggactgctg | aagccaactg | gccaaggag | cacaatggag | tgcccccag | ccctgatcgt | 420 |
| gcaccccca | gccggcggga | tgccagcgg | ctcaagtcaa | ccatgggcag | cagcttcagc | 480 |
| taccccgatg | ttaagctcaa | aggcatccct | gtgtatccct | accgagggc | cacctcccca | 540 |
| gcccctgatg | cggactcctg | ctgcaaggag | ccactggccg | atccccacc | catgcgacac | 600 |
| agcctgccca | gcacctttgc | cagtagtcct | cgtggctccg | aggagtacta | ttctttccat | 660 |
| gagtcggacc | tggacctgcc | ggagatgggc | agtggctcca | tgtcgagccg | agaaattgat | 720 |
| gtgctcatct | tcaagaagct | gacagagctg | ttcagcgtac | accagatcga | tgagctggcc | 780 |
| aagtgcacat | cagacactgt | gttcctggag | aagaccagta | agatctcgga | ccttatcagc | 840 |
| agcatcacgc | aggactacca | cctggatgag | caggatgctg | agggccgcct | ggtacgcggc | 900 |
| atcattcgca | ttagtacccg | aaagagccgt | gctcgcccac | agacctcgga | gggtcgttca | 960 |
| actcgggctg | ctgccccaac | cgctgctgcc | cctgacagtg | gccatgagac | catggtgggc | 1020 |
| tcaggtctca | gccaggatga | gctgacagtg | cagatctccc | aggagacgac | tgcagatgcc | 1080 |
| atcgcccgga | agctgaggcc | ttatggagct | ccagggtacc | cagcaagcca | tgactcatcc | 1140 |
| ttccagggca | ccgacacaga | ctcgtcgggg | gcacccttgc | tccaggtgta | ctgctaaccc | 1200 |
| ctgccaggcc | cagctgccac | acccttctg | ggagaagcat | ggcctacaga | atgaagaggg | 1260 |
| ggaccaggaa | cccctgtggg | agaggcttag | acctgaagca | gtgcccactc | tggctcctcc | 1320 |
| tgccttggct | gactgggttc | ctggaccatg | tgcatttcac | tgggccatgg | gatctacatc | 1380 |
| tccttgcatc | cccagctggt | ctgatccctg | ccagggcccc | ttccttcctg | ctcatggtct | 1440 |
| tcaggtggcc | tgatcatgga | agtaaggag | ttaggcatta | ccttctggga | gtgaaccctg | 1500 |
| actccatccc | cctattgcca | ccctaaccaa | tcatgcaaac | ttctccctcc | ctggggtaat | 1560 |
| tcaacagtta | aaagaagctt | atcttaaatg | tattgtattg | ggggtgggc | agggcccact | 1620 |
| ctatgttatg | ttaaggagtt | ggttctggtt | cttggctgat | gttctgtatc | ttaacatgac | 1680 |
| cacagtttgt | aagtacctcg | gccgcgacca | cgc | | | 1713 |

<210> SEQ ID NO 106
<211> LENGTH: 797
<212> TYPE: DNA
<213> ORGANISM: Homo sapien

<400> SEQUENCE: 106

| | | | | | |
|---|---|---|---|---|---|
| aaaaaaaacc | acaaacaaga | gaggattgat | tgataatatg | gggcatgctt | aatctaatca | 60 |
| tgctcgagcg | gcgcagtagt | gatggatcga | gcggcgccgg | gcaggtacct | aacatatagt | 120 |

| | |
|---|---|
| agacagtgga gagtggttct ctttcgttgt ctcagggggca gacagatggg gtgctggagt | 180 |
| cctctatcaa agagtcagag ctctatccca gatgtgtaat gaacgtggtc acagacatat | 240 |
| tgtcccatta ccatttacct tccctataac cactgtgcct ccagccttgt agaatagaca | 300 |
| cataggagcg cagcaatacg tctaaaaata ggagtgagag agggcagggc atgcccgttc | 360 |
| ttgtggtaga agaaaagaat gtcaaagaaa gcagctggga ctaatgaact ttacattagc | 420 |
| catattccat tatttcagct taagtcaaat gtcggtcctc atgaggcaac tggctttgac | 480 |
| aggagctacg ctaatgtgcc acttaccaac ctttaatttc tgggtaaaag cagaaagaga | 540 |
| aaaactaatg gatttttcat tttccagaag agacaagaat caactacact agtagtctgt | 600 |
| cagaacaaaa gaaaacctgc atccaattac aagaattatt actgtctctt taataaataa | 660 |
| ccacattatt taggctgtca aaacacaaaa aaaacaaaaa aacaaaaaca ctcgcggggt | 720 |
| aactacagga gcacaacgtt cccctcgtgt ttaaactttt ttttcgcgcc aaattcccac | 780 |
| cacattagaa caaaggg | 797 |

<210> SEQ ID NO 107
<211> LENGTH: 1386
<212> TYPE: DNA
<213> ORGANISM: Homo sapien

<400> SEQUENCE: 107

| | |
|---|---|
| actgtactcc agcctgcaac agagtgagac actgtcacac aaaaaagaaa gaaatatcac | 60 |
| aatatgtcac aataggccgg gcgcagtggc tcacacctgc agtcccaaag tgctgggagt | 120 |
| ataggtggtg agccaccacg cctggcctaa atgaagtacc acatgaccga ccgaccgacc | 180 |
| tggggaacat agcaagaccc catctctaca aaaatgtaaa aaataaaaat tagccgggtg | 240 |
| tagtggtaca tgcctgtaat cctagatact cgggaggcta aggcagaagg atcacttgag | 300 |
| cccaggagtt cgaggctaca gtgagctgtg atcgtgccac tgcactccat cctgggtggc | 360 |
| agagtgaggc cctgtctcaa aataaataat ccagtccccc ccaagaaagg aatgaagtgc | 420 |
| tataatgaga aaaatcctag tacctaacat atagtagaca gtggagagtg gttctctttc | 480 |
| gtttctcagg ggcagacaga tggggtgctg gagtcctcta tcaaagagtc agagctctat | 540 |
| cccagatgtg taatgaacgt ggtcacagac atattgtccc attaccattt accttcccta | 600 |
| taaccactgt gcctccagcc ttgtagaata gacacatagg agcgcagcaa tacgtctaaa | 660 |
| aataggagtg agagagggca gggcatgccc gttcttgtgg tagaagaaaa gaatgtcaaa | 720 |
| gaaagcagct gggactaatg aactttacat tagccatatt ccattatttc agcttaagtc | 780 |
| aaatgtcggt cctcatgagg caactggctt tgacaggagc tacgctaatt accacttacc | 840 |
| aacctttaat ttctgggtaa aagcaaaaga gaaaaactaa tggattttc attttccaga | 900 |
| gagacaagaa taaataata gtagtctgta gaaaaagaa aacctgcatc aattacaaga | 960 |
| attattaatg tatctttaat aaataaccac attatttagc tgtttaattt cctaaaaaaa | 1020 |
| aaaaaaaaa aaaaaaaaa aaaaaaaaaa aaaaaaaac aaaaaaaaaa aaaaaaaaa | 1080 |
| aaaaaaaaa aaaaaaaaa aaacaaaaaa aggagggggg ggggggcgag aaaaagagcc | 1140 |
| gaggggggag cacagagcgg gccgccgcgc acatatgaaa aaagcgaccc agaagaagaa | 1200 |
| acacaaaacc agcaagcgca aacagaagaa ataagaaaga gaaaaagtta cgagacgaat | 1260 |
| agaaaggaaa taactacagg accaacacgg gacaaaccaa aagcaaataa acaaagaaaa | 1320 |
| taagacagac acaagatgcc aacgagctaa cgcccggaca atggaaacag gtaaacaaca | 1380 |
| taaagc | 1386 |

<210> SEQ ID NO 108
<211> LENGTH: 749
<212> TYPE: DNA
<213> ORGANISM: Homo sapien

<400> SEQUENCE: 108

| | | | | | |
|---|---|---|---|---|---|
| aaagatgatc | atcatatggg | caatgggcct | ctagatgctg | ctcgagcggc | gcagtgtgat | 60 |
| ggatgcgtgg | tcgcggcgag | gtactttctc | caaaattagc | atgcagctat | ttaataggga | 120 |
| atctagattt | caccaagatt | caaatcaaag | caacatttaa | aggaataaga | cctgttcact | 180 |
| aagcattttc | aagggggttc | taaagcattc | aagtgcttaa | aagccataaa | aaatgacttc | 240 |
| ttaattcctg | cctttagtgt | caacttttaa | gttaatacag | gtttcaattg | tggcattaga | 300 |
| aaaaaaaaaa | accttgtgat | gctatggttg | ggggtagtta | gggagagact | acttgaaatt | 360 |
| gtgtgcccct | attttctttc | tgatcctaaa | tcatttggtt | ttataaatca | gctatagcat | 420 |
| cttttctagaa | ttaatcctga | atatgttgaa | tgttaaaata | gagaagttgg | tatatacaca | 480 |
| taattaaaaa | tcaacccttc | tgggcaagat | ttcactttga | aggtgtctgt | ttttaaggga | 540 |
| agggctaaaa | ctttggctgg | atattgtgat | aaaacttgaa | ctctaaaaaa | aaaaacaaaa | 600 |
| aaaaacaaaa | aaaaaaaggc | tggggggggac | ccagggggcc | aaacgggtgg | tcccccggtg | 660 |
| tggaaatttg | tgtttcccgg | ccccccaattc | ccccccaattt | tttccacaac | aaaaggcagc | 720 |
| aaaaacaaac | aaacaccacc | acacaaaaa | | | | 749 |

<210> SEQ ID NO 109
<211> LENGTH: 623
<212> TYPE: DNA
<213> ORGANISM: Homo sapien

<400> SEQUENCE: 109

| | | | | | |
|---|---|---|---|---|---|
| tcgcggccga | ggtacttaat | aatgactgaa | tttcatgttc | ctacagtcat | acatattcat | 60 |
| tagaagttttt | atgttgttgg | tctgatctga | ttcttcttgt | tgtgggtgga | acggcactga | 120 |
| gagaagtata | gttttttaaa | cttgaacatg | ttcagtagtt | acattgcctt | agaaaaccca | 180 |
| gacacatagc | agtggaaatg | aaagaaatgg | catcagaagt | gacttaattt | agcaattgtg | 240 |
| attcctcttg | taaaacaaaa | caaaaaaaca | atgccatatt | tttggagaaa | agttggcaat | 300 |
| atagggtttt | cgttgtctgt | ttcacaagaa | gactcatttg | ttcttttggg | ggaaccagtg | 360 |
| ccttacagat | ttgtatatac | tgtaattatt | caggactagg | gaacaaacaa | ttgtattgta | 420 |
| tttgttacag | attgtatatg | gctttgtttt | aacattcccc | taaataaaat | ggcttcattc | 480 |
| tccccttgga | aaaaaacatg | actgttatgt | tataaaaaaa | acaaaacaaa | aacaaaaaa | 540 |
| aaaacaagcc | ggggagaaaa | caagggaaca | agacgggcc | cgcggggaa | aaaggtaacc | 600 |
| cagggaccaa | aattccacca | aaa | | | | 623 |

<210> SEQ ID NO 110
<211> LENGTH: 1944
<212> TYPE: DNA
<213> ORGANISM: Homo sapien

<400> SEQUENCE: 110

| | | | | | |
|---|---|---|---|---|---|
| gaatttcgta | atccttgaaa | ttgaaaaaaa | aaaaattgtg | tttttaaaga | gtgaaaacag | 60 |
| ttaggaaaca | agtagaactg | taatcagaac | gctgcttcaa | ttgatattaa | aaataacctc | 120 |
| aataataatg | taaaggttcc | tttctcttgt | gtcagttata | ttcttaggga | tagcctagaa | 180 |

-continued

```
ggaatatatg gttagaacta agtgtgacta atcatctgag ccttgaagag aaacttcagt      240
gcctctaaac agatcatcta caaaacaaca ggtaaacatt tatgccagtt aagtgggtca      300 tgttttttgtt tcttgggttt ttcctaaatt taagtgaggt tgggcttacc ttgtagataa     360
aattatgttt tctttttggt aaatacttga atgtggataa cgtcaaatca gaatattttg     420
tgaggaggtg atgatttgaa attaagctag atttctaggg aggtgttggt tccaatgaag      480
gatgggaaga aattaaaata gtcttcaaac ttcttcctta ttatatttgg ttgctttgga      540
aaagattggt cctatcctca atctaattta ttcactatta atattttaaa aacattcctg      600
agatacttaa aaagacccac ttagcgatta tagttgctca atgaaacaag aatttattta     660
tgcatagatt tttctctgta tcttaccaaa atccacttta cttagataac actaaattgt      720
tcttaaagac tactcattc ccaataatcc tttatgattt caaatttct agtggctcag        780 aagtgaattt tattttattt gtctttcact tgaataaatg agaacccaga aattaataat      840
gttgtttatt gcttactgtc aggactattt caaagactaa aagagttc ttctaacccc       900 tccctctcaa aggaatccta aattattagt tgttagataa gttttgtatg ctaagatatt     960
caggtttata gttatgtat gtgtgtatat atataaatat atatgtatat ataaatatta      1020
tgttcagttt ggagtctggc acaactccat tatgtggatt agagagtaag atattatgga      1080
tgataaagta ctaaatgaaa cataatattt atttataaaa gtgtgtagat tgttaaatca     1140
caaaaagagt gctatgacca ttatgtatga ggaaacaggc ctttgacctc ctggaaagca     1200
ctgctcaaaa gtcattagtg cccattttg aattccccaa acagaaagct tcttagaaaa     1260
cacgctgaga ttttattac agggaattct tgacacatt tcaattggtg tgtagtcaag      1320
tatagcaagt acttaataat gactgaattt catgttccta cagtcataca tattcattag      1380
aagttatatg ttgttggtct gatctgattc ttcttgttt gtgggtggaa cggcactgag      1440
agaagtatag ttttttaaac ttgaacatgt tcagtagtta cattgcctta gaaacccag      1500 acacatagca gtggaaatga agaaatggc atcagaagtg acttaattta gcaattgtga      1560
ttcctcttgt aaaacaaaac aaaaaaacaa tgccatatt tttggagaaa agttggcaat      1620
ataggggttt cgttgtctgt ttcacaagaa gactcatttg ttcttttggg ggaaccagtg      1680
ccttacagat tttgtatata ctgtaattat tcaggactag ggaacaaaca attgtattgt     1740
atttgttaca gattgtatat ggctttgttt taacattccc ctaaataaaa tggcttcatt     1800
ctcccctggg aaaaaaacat gactgtttatg ttataaaaaa aacaaacaa aaacaaaaa     1860 aaaaacaagc cggggagaaa acaagggaac aaagacgggc ccgcggggga aaaaggtaac     1920
ccagggacca aaattccacc aaaa                                            1944
```

<210> SEQ ID NO 111
<211> LENGTH: 692
<212> TYPE: DNA
<213> ORGANISM: Homo sapien

<400> SEQUENCE: 111

```
gcgtggtcgc ggcgaggtac caaccccagc acaccccaac agcctttcct cggccccctc      60
ctcaggcctc ctaattactc tttctcagcc tggagtgtgg ggccgttacc gtcctcttcc     120
cccttctcct tccatactgc acttaacctt gctggaagat ttaatgatgg agatttaggg     180
caactgtggc tgcttgggac ccttccctgg gaccaaagga acttaaaacc caataacctga    240 cactggaatg aaatccaagt ttttaaatat caccttttcaa tcactcacag atctcacatc     300
tatcttaaaa tactcagcct cactccttaa ctgagtgctt gcctgagagg gagaaaagtt     360
```

```
ccatttttaaa aacgtattca ctttactgat tactgtgcaa tttgaattaa gtcacgattc      420
tttagtcatg gaggtcgaga atctcagatt caaattgtca gagaccatga tttagaagtc      480
taccaaacac ccagtttcct tccactgttt tagggtaaca ggaaaacatg agattggggt      540
ggtgtccgct attaaatgga accacacatc atgaaattca attctcatgt taagacattc      600
tgtattgtgg gatgtcaaaa gtatttccca aactttcgtt tgacctgcag agctggagat      660
ggcttacctc cctataactt caagtctgtt tc                                    692
```

```
<210> SEQ ID NO 112
<211> LENGTH: 8144
<212> TYPE: DNA
<213> ORGANISM: Homo sapien

<400> SEQUENCE: 112
ggccgctcat ttttttttt tttttttttt tttttttttt tttttttttt tttttttttt       60
tgccacctag agatgataat ttattgtttt accatgactc agaagagaaa caacataaag      120
agaatatttc aaatccccac aatttccttc ctcaacctca ctactcttaa catttcttta      180
tcagacgcca ctggcttcct aaaatggacc actgactatg tatgtgtaca catttcatta      240
tgctgccttt tctcttatga ttaaaacttt agccctcatt cgaggtttcc aatggttact      300
tttagtggag gagttccta gcttttaaaa aaccactttt cctctaagat tccattattt       360
attgaaagaa gtctttctag aaatgttaag gaggatttta aatgaacaca ttcaattaaa      420
aaaaaaatca cgtattgaac atctaccaag catctggact cttcggaacc tagtaaaatg      480
aaaaaatcca gttttaacaa cagtaacttc attctgcggg tatacagaga caagcacgtt      540
tcttcttttg gtctaatta ttctaaacga agaagctggg aactgacaaa acaggacagg       600 ttgttttaa tccagtctac aaataaacaa gacaatgcct gagttagccc tctatataga      660
tttaggctta tgctgacctc gttgtaaaat ctgtatttaa ctaaaagtta ataaaaatac      720
atatgttcat tttaaaataa ttactgattt tgcttggcta tcccaccct tacccccaaa       780 ctcatatatt tttaggacaa gattttcctg cataaccaca acctgtctcc tcccacccca      840
cccccatcat agatgttttc aaataagaac ccctgcgatc agcagaagca tctctaatct      900
aacatgcttt gtccttgcta gggcaggcta aaagctttaa aaagcaaccg gatgctcttc      960
tctggttgag gtgagggaa ggcgctcggg taccaccc agcacacccc aacagccttt        1020
cctcggcccc tcctcaggcc tcctaattac tctttctcag cctggagtgt ggggccgtta     1080
ccgtcctctt cccccttctc cttccatact gcacttaacc ttgctggaag acttaatgat     1140 ggagattag gcaactgtg gctgcttgga cccttcctg gaccaaagga acttaaaacc        1200
caaacctgac actggaatga atccaagtt tttaaatatc acctttcaat cactcacaga      1260
tctcactcta tcttaaaata ctcagcctca ctccttaatg agtgcttgct gaagggagaa     1320
aattccattt taaaaacgta ttcactttac tgattactgt gcaatttgaa ttaagtcacg     1380
attctttagt aaatggaggt gagaatctca gattcaaatt gtcagagacc atgatttaga     1440
agtctaccaa acacccagtt tccttccact gttttagggt aacaggaaaa catgagattg     1500
gggtggtgtc cgctattaaa tggaaccaca catcatgaaa ttcaattctc atgttaagac     1560
attctgtatt gtgggatgtc aaaagtattt cccaaacttt cgtttgacct gcagagttgg    1620
agatggctta cctccctata acttcaagtt tgtttcacaa gctttgaaa agtaaaacag      1680 ataatttcat tttcagataa taaaaaatct gaatagcaaa ataattgctt ttaaatgtag     1740
```

-continued

```
tgtgtccact ctaaaaaaaa aaaccctaaa tctatgttag aaaaacttttt caaataatgc      1800 cttttattaa attctccagt agtagttgaa ataaaaatct accctaattt ctatgaaatg      1860
atctatttat atcactgact tttcttttc tctgattcta tatttcattt aacaatctgc      1920
agactttcac cccatttccc agatgggaaa accctagccc ctcgtatct ctgagaagtt      1980 gctcagagta ggacacagag aaatatggcc cccaccctgg gaagtactgc tgtcactgtt      2040
taagtgtatt tcagttctgt tactccaatt catacacaca gtcttccatg aggatggtag      2100
gatgaacctg gttagctggc tttggataag tagatcagca tgactacctg gaataaaagt      2160
gactgactct aggataaaaa ttaaaaaaag attctttcac agcaacgagt ctttgcaaaa      2220
cctctctcct aataatcaca aaccagggga agaaaagtgg gagcagggaa cacaggaaca      2280
cagccaaagg gaatattgca aaatgcttcc cgagcttcat cagacagact tcttgcaatg      2340
ccacgactgg atgcatctgc acacaattcc gggaaatgcc caccttgctg ttctcctatc      2400
cccaattttc tttctttctt tctttttttt tttcttttt tgagacagag tctctgttac      2460
ccaggctgga gtgcagtggt gcaatctcgg ctcactgcaa cctctgcctc ccagatttag      2520
gtgattctcc tgcctcagcc tcctgagtag ctgggactac aggcgcccac caccacgccc      2580
ggctaatttt tgtatttta gtagagatgg ggtttcacca cattggccag gctggtctca      2640
aactcctgac ctcaagtgat ccgcccacct ctgcctccca aagtgctgag attacaggag      2700
tgagccaccg tgcctggcca gtcctatcct cccccaacc ttttttttt ttttgacatg      2760 gagtctcacg ccatcaccca ggctggagtg cagtggcgcc atcttggctc actgcaacct      2820
ccgcctccca tgttcaagtg atcctcctgc ctcagcctcc tgagtagctg ggactacaga      2880
tgaagacaag cacctgtggt gcccctcact gcaagaagtc agggaggcat tccacagcct      2940
gggtgcccac agtcctgccc tgtaccctct ggggcccttt tggcacggtg gcagcgcttc      3000
cagatttcct ttcagaaaga tgcagtcctt ccgcagctgg gccatgcaga tctcctggca      3060
tccaacttgt tggaaacagt ggccctctgc tcaatgatga gactggggag gggaaacagg      3120
aggacatttc aaggaaagga tggagcgtgg atatgaatgg gaagcgggtg gtgggggagc      3180
tcatcagcat cctcagaggg gctcatgccc acgctgcaac acagaatggg acttgccaga      3240
tgtttgtagt cgactctgag tgccccgtgc tgagaaacct gaaagcacac ccacctatgg      3300
ctgcgcgtgt tgcacgctca aggctgagtt cacatagttc tgtagcctcc tcctacacca      3360
agtcaggtcg gccctgtgtg accagtagaa gagatgggat gtcactttcg agggtgcttc      3420
caggcgaggc tggcctgaat gagaatgagg agcaggacgc tccccaagag attgccttgg      3480
acatcagcct gggccacatc tacaagttca gacccattca gcagctaaat tccaggagca      3540
tcacggagaa tctccggcga gctcagcacc aaggcaggca ctgtgctggc tgtgggccgg      3600
atgctacaga aactgtgtta tcggacacgg gtcctgatct aggccccaag agagagttct      3660
tgtacaagaa agaattgggg ccaggcatgt ttctggcgct gtgtgcccag gcccagccgg      3720
gggcctacac tgatgagaac ctcatgggac tgattgagct gctgtgccgc accagcctgg      3780
acgtggggct ccgcctgctg cccaaagttg acctccagca gcttctcctc ttgctcctgg      3840
agaacatccg ggagtggcca gggaaggcgc ttccttccag gacagatgtc ccacggcttg      3900
cagatggctg ggcccaggag acggtgctag ccctttcctct gagagaaggg gtgcaggctg      3960
ccgccaccgt gccatcctc ctgtacaacc tggaggatgg cttgtcagac catcccctgg      4020
accagggccc cgctgccctg cccggcggcc ctgcagccct gcctcggctc cagctctcac      4080
atcgccaaag aagcccaaga tacaggcacc tggggaaacc gttgacggtt tttgctgttc      4140
```

```
cagttttggc tgcttctcaa gatcacgaag cccagggcac tctgcaaggg tttctgcaag     4200
ttcagcagtt catcgctgga gggcgcttcc ttccaggaca gatgtcccac ggcttgcaga     4260
tggctgggcc ccaggagacg gtgctagccc ttcctctgag agaagggtg caggctgccg      4320 ccaccgcgcc catcctcctg tacaacctgg aggatggctt gtcagaccat cccctggacc     4380
aggggccccg ctgccctgcc cggcggccct gcagccctgc ctcggctcca gctcccacat     4440
cgccaaagaa gcccaagatg caggcacctg gggaaacgtt tcccactgac tggagccccc     4500
cgcccgtgga attcctcaac ccgagggtgc tgcaggccag tcgggaggcc ccggcccaga     4560
ggtgggtggg tgtggtgggc cccagggcc tgaggagact ggctggtgag ctgcccgagg      4620
agttggagca ggaacacctg gacttggacc cgaagagggg cctggccttg ccagagaagc     4680
tgttctggaa cacgtcaggc ctgagccagc aggctgcggc cccagagttt tcctgggggg     4740
gctcaggaag ctacttcaac aacctggact acttactgca ggagaagagg gaacaggccc     4800
tggagcagga gcgagagagg ctgcttctgc aggagtgtct caatctcaac tccttggatc     4860
ttgatgaaga ggaagtgcca ctcacacccg agcacagaaa gaggcaagag agctctctgg     4920
ggcccttcca taagggtacc aatcctattc atgaaggctc caccctcatg cctcatcacc     4980
tcccaaaggc cccacttcct aataccttca ccctggggct ttccttccgg agacaagcag     5040
taaataagat cagtgaagtt gtgctgcaag ggctcctgag aaaggctaac gctgggggca     5100
taaggagtgc tgggaaaggt gtgggctctg atgatgtggg ctctaatcat gtgggctttg     5160
atgatgaagg ctctgatgat gaagggatgc tggtggaaaa gtactcagtg tccctgcaga     5220
ccatcccgcc ggtccatcca ggtgagactg tgtttctgcc caggtgtcac ccctgccat     5280 gcatcctgga ctcctcactc ctgaagccac gcagccacct ggaagggctg ttcctcaggc     5340
agtatgctga gcattgggac ctcaaggatg aggaagatgc agtctctgcc ctagaggagc     5400
ttacagcagc aggaagtttc tgtcatagga cagacccagg gctcaccaag actcaagcag     5460
atgatgaagc ctggggctca ctggcccaat cagcgtattc agactggctg gctgcttatg     5520
aggctcttgg gccagggctg cctgctcagt gggcagctga ctctagctgc tgcaaaatgc     5580 cttttcactca aaggtttttg cttttgccaa tcccctccct cacatgcctt gaaacaagca     5640 cttttcaaaga caaagacata acaacaaaa gggtgcaggc tgagttgcca acttacagtg     5700
tcattgggcc gattcaggtt cttgactgct gcacaaaaga atttgagagc aagtacaaag     5760
caaaagtagg taaagaagtt tattgcaaag cgaagatctc ctgggaggcc ccgtggaga     5820 agaagactga gtgtatccag aaagggaaga caaccaggt gggtgcttgg acgctgctcc     5880
tggtgctgcc ttcaccccag gacgtctcct cccattctgg ccctcgcgct tcactaaccc    5940 ggacacctttt ctgcccccag accgagtgct tcaacttcat ccgcttcctg cagccctaca   6000
atgcctccca cctgtacgtc tgtggcacct acgccttcca gcccaagtgc acctacgtca    6060
acatgctcac cttcactttg gagcatggag agtttgaaga tgggaagggc aagtgtccct     6120
atgacccagc taagggccat gctggccttc ttgtggatgg tgagctgtac tcggccacac    6180
tcaacaactt cctgggcacg gaacccatta tcctgcgtaa catggggccc caccactcca    6240
tgaagacaga gtacctggcc ttttggctca acgaacctca ctttgtaggc tctgcctatg    6300
tacctgagag tgtgggcagc ttcacggggg acgacgacaa ggtctacttc ttcttcaggg    6360
agcgggcagt ggagtccgac tgctatgccg agcaggtggt ggctcgtgtg gcccgtgtct    6420
gcaagggcga tatgggggc gcacggaccc tgcagaggaa gtggaccacg ttcctgaagg     6480
```

-continued

```
cgcggctggc atgctctgcc ccgaactggc agctctactt caaccagctg caggcgatgc      6540
acaccctgca ggacacctcc tggcacaaca ccaccttctt tggggttttt caagcacagt      6600
ggggtgacat gtacctgtcg gccatctgtg agtaccagtt ggaagagatc cagcgggtgt      6660
ttgagggccc ctataaggag taccatgagg aagcccagaa gtgggaccgc tacactgacc      6720
ctgtacccag ccctcggcct ggctcgtgca ttaacaactg gcatcggcgc cacggctaca      6780
ccagctccct ggagctaccc gacaacatcc tcaacttcgt caagaagcac ccgctgatgg      6840
aggagcaggt ggggcctcgg tggagccgcc ccctgctcgt gaagaagggc accaacttca      6900
cccacctggt ggccgaccgg gttacaggac ttgatggagc cacctataca gtgctgttca      6960
ttggcacagg agacggctgg ctgctcaagg ctgtgagcct ggggccctgg gttcacctga      7020
ttgaggagct gcagctgttt gaccaggagc ccatgagaag cctggtgcta tctcagagca      7080
aggtaaagct gctctttgcc ggctcccgct ctcagctggt gcagctgccc gtggccgact      7140
gcatgaagta tcgctcctgt gcagactgtg tcctcgcccg ggaccccttat gcgcctgga      7200 gcgtcaacac cagccgctgt gtggccgtgg gtggccactc tggatctcta ctgatccagc      7260
atgtgatgac ctcggacact tcaggcatct gcaacctccg tggcagtaag aaagtcaggc      7320
ccactcccaa aaacatcacg gtggtggcgg gcacagacct ggtgctgccc tgccacctct      7380
cctccaactt ggcccatgcc cgctggacct ttggggccg ggacctgcct gcggaacagc      7440
ccgggtcctt cctctacgat gcccggctcc aggccctggt tgtgatggct gcccagcccc      7500
gccatgccgg ggcctaccac tgcttttcag aggagcaggg ggcgcggctg gctgctgaag      7560
gctaccttgt ggctgtcgtg gcaggcccgt cggtgacctt ggaggcccgg gcccccctgg      7620
aaaacctggg gctggtgtgg ctggcggtgg tggccctggg ggctgtgtgc ctggtgctgc      7680
tgctgctggt gctgtcattg cgccggcggc tgcgggaaga gctggagaaa ggggccaagg      7740
ctactgagag gaccttggtg taccccctgg agctgcccaa ggagcccacc agtccccct      7800 tccggccctg tcctgaacca gatgagaaac tttgggatcc tgtcggttac tactattcag      7860
atggctccct taagatagta cctgggcatg cccggtgcca gccggtgggg gggccccctt      7920
cgccacctcc aggcatccca ggccagcctc tgccttctcc aactcggctt cacctgggg      7980 gtgggcggaa ctcaaatgcc aatggttacg tgcgcttaca actaggaggg gaggaccggg      8040
gagggctcgg gcaccccctg cctgagctcg cggatgaact gagacgcaaa ctgcagcaac      8100
gccagccact gcccgactcc aaccccgagg agtcatcagt atga                      8144
```

<210> SEQ ID NO 113
<211> LENGTH: 521
<212> TYPE: DNA
<213> ORGANISM: Homo sapien

<400> SEQUENCE: 113

```
gtatatcaat ataggcatgt ctctaatgct gcctcgagcg gcgcagtgta tgatcagcgg        60
cgcccggcag gtaccggact cagcatgctg agcttaaaaa aaatattttt cctaatatgt       120
ccagtttaaa aactctgtca ttaaacacca aaaatattaa agtctaatta atttataact       180
aacgtttgca ttgctgctgc aggaaagaac acaacagccg tcttgccccc atgcctctgc       240
tgagtatgag gggaacgcag ccagaaacgg gcatggcgt taagttggct tcattaaaaa       300
caggacggag tatatctgaa atggatttag gtagcgcaat tcttgtaggt tataattact       360
gattttcctt ttttttttt tttttcccaaa tatggagatt tcattagatg aaaaatgacc       420
cttaatcagg cctacaaggc ctacagaatt cttgggaccc actttctcaa aaaccagtgg       480
```

```
gtctggctcg ctggggcaag gcaattgtta ccattaccag t              521
```

<210> SEQ ID NO 114
<211> LENGTH: 386
<212> TYPE: DNA
<213> ORGANISM: Homo sapien

<400> SEQUENCE: 114

```
acttttttat ggcttacatc tgtgcctggt cggccatcaa gtctgggtgc cactgtttga    60
gatttggggc tgtttcctgc aactgatctc tgctacagat aaggcttccc tcctggaggc   120
caaagccctg gttaacgtta agagctctat gatgatgcaa acttcagagg cgatcaccta   180
acataacaaa aacctcccca gaaccagaac ctgtttttc accaaaaccc ttccgctgct    240
tgaataagaa tgtcttttcc tttcctacaa tttgtgccat ggaaatgtga ataatttttc   300
ttagcgggt aaatcatagt ggttacttga atgccaaaaa gatgctggag gggcaggtgg    360
atatgttgaa aagatataga aagctt                                        386
```

<210> SEQ ID NO 115
<211> LENGTH: 765
<212> TYPE: DNA
<213> ORGANISM: Homo sapien

<400> SEQUENCE: 115

```
ccgacctagt ctccctgatg agaaagtttc tctcagactt ctacccttc caatgtggcc    60
aaagcttttc attccgaaga gtttcctttt ctgagaacgc tcattgtgtc gtttggcttt   120
ccccgtctct gcttgacaca tgaaccaaaa cagaggcagc caaagcaggg aaaaaaaaat   180
cctaggatca gagtccactc tatgcccttt tgagcttcaa aggagaaag agacaaaagc    240
caaaagcaat ggaggtcaag ctgcccggta catgtttctt tacgcctgac ctcctgatgg   300
actcactaga taaaatgctc cttcttgtag ccagcaagca aatgagtact ttttatggc    360
ttacatctgt gcctggtcgg ccatcaagtc tgggtgccac tgtttgagat tggggctgt    420
ttcctgcaac tgatctctgc tacagataag gcttccctcc tgaggccaaa gccctggtta   480
acgttaagag ctctatgatg atgcaaactt cagaggcgat cacctaacat aacaaaaacc   540
tccccagaac cagaacctgt tttttcacca aaacccttcc gctgcttgaa taagaatgtc   600
ttttcctttc ctacaatttg tgccatggaa atgtgaataa ttttcttag cgggtaaat    660
catagtggtt acttgaatgc caaaagatg ctggaggggc aggtggatat gttgaaaga    720
tatagaaagc tttgtaaatt gcttttgaat aaatatgtga ctagt                   765
```

<210> SEQ ID NO 116
<211> LENGTH: 356
<212> TYPE: DNA
<213> ORGANISM: Homo sapien

<400> SEQUENCE: 116

```
acttttttatt caatgtaatc agaagctgtg atgttttgcc tttgtagtcc tgtgctttgt    60
tactgtaatt ttttttttt ttatacaaag cacgtgacgt ggactaatgt aaggcagatg    120
acgtgatctt taagacggct atatatatca gtctcttact ctataaggtt ttaaattaga   180
aaaggcttat atggttaact accttagact atatctacag cagggtctgg tttgccagaa   240
caagtttaaa gtggctgttt attaagttgg ctattttcag aattgaaact ataagaccgc    300
catttgacac tgaaacttgc gtgaatccta aattgcatca attatctatt tgataa        356
```

<210> SEQ ID NO 117
<211> LENGTH: 792
<212> TYPE: DNA
<213> ORGANISM: Homo sapien

<400> SEQUENCE: 117

| | | | | | |
|---|---|---|---|---|---|
| cttctcagtg | ctactagtat | aggcacatac | acatacacag | tctcagcaag | gttataaaga | 60 |
| accctgtcag | gtccacttgc | aacatggcct | tgctacttgg | attagctcct | ttaagcctga | 120 |
| aaataacttt | cctggtcatg | gaagaactgg | acgcatcttt | taacttatga | aatagaagtt | 180 |
| gaacttgaaa | actcttttta | aaaaatcctg | gttttgcagg | acagctacat | aatgaatgta | 240 |
| tatattaaga | ctgtagctga | attgcacatg | aaatcagatt | gccaacttct | tgactttcaa | 300 |
| tgttagacat | ttatccttaa | gttgtgagcg | atatatgtag | catgctgtga | aatgtctgtt | 360 |
| atagctcttt | aattcatcag | tattaataca | gaactatcat | ttgcgtttct | tggtactttt | 420 |
| tattcaatgt | aatcagaagc | tgtgatgttt | tgcctttgta | gtcctgtgct | ttgttactgt | 480 |
| aattttttt | tttttttac | gaagcacgtg | actggactaa | tgtaaggcag | atgacgtgat | 540 |
| ctttaagacg | gctatatata | tcagtctctt | actctataag | gttttaaatt | agaaaaggct | 600 |
| tatatggtta | actaccttag | actatatcta | cagcagggtc | tggtttgcca | gaacaagttt | 660 |
| aaagtggctg | tttattaagt | tggctatttt | cagaattgaa | actataagac | cgccatttga | 720 |
| cactgaaact | tgcgtgaatc | ctaaattgca | tcaattatct | atgtgataca | agcttatcta | 780 |
| gtctcgagtc | ta | | | | | 792 |

<210> SEQ ID NO 118
<211> LENGTH: 517
<212> TYPE: DNA
<213> ORGANISM: Homo sapien

<400> SEQUENCE: 118

| | | | | | |
|---|---|---|---|---|---|
| gaaagtatat | tgacgtaggt | agtggagacg | ccatgagttc | ataatctgtc | cagagtcgca | 60 |
| gtatgatgta | tccggcaccc | gacaggtcaa | gaaagaacta | cttgtttcta | ggaagaacat | 120 |
| atgaagtgct | taatttataa | gcgggctgtc | gaatattatc | caatatagtt | tcttctgaaa | 180 |
| agtgaaaggg | gatcatctat | tgttagatta | gggggtctcg | gaaactttt | gaaaattcga | 240 |
| atcagtggac | caatgtacat | gtgaaaacta | aagagggcag | gggttaaaat | agggcttgaa | 300 |
| tttctcattc | tgtatagacc | agcaaacttc | cctgtgcaag | gcaagtttac | atcacaaatc | 360 |
| caagaatgtt | tgcatcctaa | atgctagttt | gcttcagccc | ctagttaacc | tcaggacttg | 420 |
| gtttgcatat | aaaaggtaga | cagctgatat | gttttcatga | ataaatattg | tcagccagaa | 480 |
| aaggttggtg | tcaggtaatg | catatttttt | taagctt | | | 517 |

<210> SEQ ID NO 119
<211> LENGTH: 730
<212> TYPE: DNA
<213> ORGANISM: Homo sapien

<400> SEQUENCE: 119

| | | | | | |
|---|---|---|---|---|---|
| gggatgatcg | ctcactatag | ggcgctggtc | actagatgca | tgccgagcgg | cgccaggtga | 60 |
| tggatcgagc | ggccgcccgg | gcaggtacat | gttcatgaat | ttgtgctgaa | taattacttg | 120 |
| agtgtgaaat | tgttatgtta | tgcgatatat | agtagtcaaa | tatagaagat | aatgcaaaac | 180 |
| aatttaaagt | gattgtagca | gttcgctgta | ttctacagca | gcaggattgt | aggcagatta | 240 |
| ctgtagttct | cacagcgagc | agcatgtgag | attggccagt | ccgctcaaat | tcgtgccaat | 300 |

```
acttggtata tgctatcttg tcaatttcta gacattctgg agagtgtgta gtacttgttc    360
atcttggaca aattcacttt aatagttatg tatccatttc tctaattttg ataacatttt    420
acataagttt atcgttatga gatatgttct ttattttgaa gtgcttattg tccatttttac   480 attgggtcat ctgttattga attgtaaaca ttccttgaat atttaaatat gagtgcttgg    540
tcagttttgg tcacaaatat cctcgttttt tcacttttg ccctttatt attctgaaaa      600 tgccaagtga ttaaaattaa ttttactatt gtcaaaaaaa aaaacaaaa aaaaaaaagg     660 ccggggtaa ccggggacaa agcggtcccg ggggactgg tttcccgcca acattccaca      720
ttgacgaaac                                                            730

<210> SEQ ID NO 120
<211> LENGTH: 1364
<212> TYPE: DNA
<213> ORGANISM: Homo sapien

<400> SEQUENCE: 120
ctatgattag cttattaggc tttgtggttt atatgcatca gaaagagtaa gacttaattt    60
tgtgtggaac aaatacctg gtgtagcatg tttcattaga atttgtttat agagatattg     120
ccatagaaaa gttattttttt attagtaaag aatgctttgt atttcctttg tggcttctaa   180
gtaccctttt ttggttatta tacctttatc cataagtatc tttaaatatt acaaaaatta   240
catattcttt taaatatttt aaagattat tatattcatt taggttttaa tccacttttta   300 attttttaga tgaaaagtaa gagaaaagta tataaatcat gagcacaaat tgaactaacc   360
aaggtaacaa tcaatctgct caagaaattg agcatcacca ccacctcctc ctgcactgtc   420
caaatcagca ccccagtact ccaaagcaaa tgttactcac tacactgact tctaacacaa   480
tagacttgtt ttgtctgttt tcaactatac aaaaatgaat catagagtat gtgttgtttt   540
gtatctggct cctttcacta aaattttggt ttataaaatt catccatgtg gttgaacaca   600
gttgtagatt gttcatttta attgttttac agtatttatt gtgtgactaa acactactt    660 atttattcta taattgacag actttgggtt gcttttgctt tgggagtata acattttta   720 tatctatgct ttaggtacat gttcatgaat ttgtgctgaa taattacttg agtgtgaaat   780
tgttatgtta tgcgatatat agtagtcaaa tatagaagat aatgcaaaac aatttaaagt   840
gattgtagca gtttgctgta ttctacagca gcagattgta gcagattact gtattctaca   900
gcagcagcat gtgagattgc cagttgctca aattcgtgcc aatacttggt atttttttatc   960 ttttaattt agacattctg gagagtgtgt agtaattttt catcttggaa aattacatta   1020
aattagtatc catttctcta attttgataa cattttcata agtttattgt tattagatat   1080
tttctttatt ttgaagtgct tattgtccat tttacattgg gtcatctgtt attgaattgt   1140
aaacattcct tgaatattta aatatgagtg cttggtcagt ttttgtcaca aatatcctct   1200
tttttcactt tttgcccttt tattattctg aaaatgccaa ttgattaaaa ttaattttac   1260
tattgtcaat aaaaaaaaac aaaaaaaaaa aaggccgggg gtaaccgggg acaaagcggt   1320 cccggggggga ctggtttccc gccaacattc cacattgacg aaac                    1364

<210> SEQ ID NO 121
<211> LENGTH: 578
<212> TYPE: DNA
<213> ORGANISM: Homo sapien

<400> SEQUENCE: 121
```

```
tgatgatata tggggcatgg tcctctagat gctgctcgag cggcgcagtg tgatggatgc    60
gtggtcgcgg cgaggtacca cctgttcatt tggggaactg tgggaaacgg agccaacgga   120
cctaagtgcc ctttgacagt gagtttcata ccatttcagt agtgtatttc tttcttaatc   180
tgaataaacc agtatgatac tctcagacac agaagaataa agggagcgag tcattaacgt   240
tttcttttta aacctttatg atgacttcct tatgaattac tgaacgaaca ctggaatggg   300
actcaggtat cctgaggaca tctctcaact ctggccttag ttcccctct gtaaaattag    360 ggtgccaact aaatgatcta caaggtccct tccagcgccg ccattctgta attacatcat   420
gtgtaactgt attaaacata cacaagtgac tgccaggcat gggaatgtaa cttccgagta   480
aatgctttgg tttgttcaga atacactatg aacttctttc caaagacggg ttgtggtaaa   540
tagtggatat tttgattata agaaatagag tttccttg                           578

<210> SEQ ID NO 122
<211> LENGTH: 1138
<212> TYPE: DNA
<213> ORGANISM: Homo sapien

<400> SEQUENCE: 122
aagaaattcg gcacgaggaa agtgctggga ttacaagcat gagcccagcg cctggctgta    60
tctttcattt tacccaagtc actttaccca agtaagtaat taggggaaag cctgagtctt   120
gtaccacctg ttcatttggg gaactgtggg aaacggagcc aacggaccta agtgcccttt   180
gacagtgagt tcataccat tcagtagtg tatttctttc ttaatctgaa taaaccagaa    240
tgatactctc agcacagaag aataaaggga gcgagtcatt aacgttttct ttttaaacct   300
ttatgatgac ttccttatga attactgaac gaacactgga atgggactca ggtatcctga   360
ggacatctct caactctggc cttagttccc cctctgtaaa attagggtgc caactaaatg   420
atctacaagg tcccttccag cgccgccatt ctgtaattac atcatgtgta actgtattaa   480
acatacacaa gtgactgcca ggcatgggaa tgtaacttcc gagtaaatgc tttggtttgt   540
tcagaataca ctatgaactt ctttccaaag acgggttgtg gtaaatagtg gatattttga   600
ttataagaaa tagagtttcc ttgaagcttt agctggagat acagcaatag tgtggtgttc   660
ctacaaatat cacagtgtat tcaaacatat ttttctatca aaatcatttt ttgtaaaagc   720 tgtgtgttt tatccaactt gtgataataa atgttcttta ttttagaata aaaaaaaaaa    780
aaaaaaaaaa aaagaaaaaa aaaggaaata aaaaaaaaaa acaggagaca agacaacgg    840 cggcacgcaa caaccacatc gcggaaggcg acaagcgaac aacccagccc gagctcgtga   900
aggcgagcca acatgaagga gcgcactatc caagacaggt agctgacata acagaagaga   960
acaaaaacaa gagacaagta gaacaaaaac aaagagaaga caggacacac gagaaaagca  1020
ggtgtaatca gacgaacgac gcgacaaaca gagagacgtg caagcataaa atagcaacaa  1080
ccaagagaca gcgacggaca cacgaagcaa gacgagcgac gccgagcaca gcaggat      1138

<210> SEQ ID NO 123
<211> LENGTH: 963
<212> TYPE: DNA
<213> ORGANISM: Homo sapien

<400> SEQUENCE: 123
tggaagaagg aagggaagag aagaacagag agaggagagc aggagaggag aaagaggaga    60
atgaggatga tatataggggg catgggtctc tagatgctgc tcgagcggcg cagttgtgat   120
ggatcgtggc gcggccgagg tcttaactga taaacagaat atttagaaag gcgagacttg   180
```

```
ggccttacca ttgggtttaa atcataggga cctagggcga gggttcaggg cttctctgga      240
gcagatattg tcaagttcat ggccttaggt agcatgtatc tggtcttaac tctgattgta      300 gcaaagttc tgagaggagc tgagccctgt tgtggcccat aaagaacag ggtcctcagg       360 ccctgaccgc ttcctgtcca catgccccct ccccatcccc agcccagccg agggaatccc      420
gtgggttgct tacctaccta taaggtggtt tataagctgc tgtcctggcc actgcattca      480
aattccaatg tgtacttcat agtgtacaaa tttatatcat tgtgaggtct tttgtctttt      540
attttcttat tctaaaaacg ggaaatatgg cggtactcta ctttaaactt ccaaaaatac      600
cggttattat atgggaaccg ccaaaaaaaa aaacaaaca gaaagacaaa cgaggggat       660 acacaccacg ggcgaaaaag aatacacaca gcggggaaaa aggggaaaca cagcacaaaa      720
accacacaga caagcgcaac aagaccgcgc aacaggacac gacgcaacac gcacgaggcc      780
gagagcgtta tggaacgggg cagcgggacg cgtagaggca gggagcttgc atcaggggag      840
gagagcggac tggagggggg gcggagaagc agggataga aacagagagc gagaaggagg      900
aaaatgcgcc ggggggagaa agaggcgacg tagagagggg accgagggag aaacgcagca      960
acc                                                                   963

<210> SEQ ID NO 124
<211> LENGTH: 986
<212> TYPE: DNA
<213> ORGANISM: Homo sapien

<400> SEQUENCE: 124
gaagatagtc atatagggcg atggtgctct agatgctgtc gagcggcgca gtgtgatgga      60
tcgcccgggc aggtaacgta gaatgttcat tgatcatgca tatttctgtc attgaagtgt     120
atcttttatg tttttaaatg cattcatttt acacttgtgg agtttatcat gactttaaga     180
ggtagaaatg aaaaatgaaa attaaagcta aagccttttt atctattaat gcagatatat     240
tagaataaga atattttggg tttgtgttta ttttttaatg aatttatgtt tacttgatat     300
ggaaaattac gctttatagg tggaaaagta gcaaataaag attaagtaaa agtaagtgaa     360
aatgatgggg aatatagtat tggaattta ttagctagtt aaaacaataa gtatcatcta     420
atttgggtgt ttatttttgca gatgagaaaa cagacctaga accgtggcat gttttgcctg     480
aaacatacag tgagttagag acagggccta agatagcttc tagcatcaga tcaatcccaa     540
gaatccatca gcaacctcag accaacccaa gaagataatt taaatctata ctgcttattg     600
gtcaatatat ttggttctag tattaataaa gaaacaatgt tattaaaata gcatacatag     660
tagtaaaata aaaataccaa aagtgtgttg atttatagct gtttgagatg ataaaagtga     720
agcaaagcct gttaaatcat tggaagactt ggaaacagtt atttttaaagt aaacaattac     780 atgtactaaa aaaaaaaaaa acaacaaaac aaaaaaaaag cgctggggga ccctgggcc      840 aaggcgggtc cccgggggag aaattggttt ccccgcccaa aatcccccc aacagtgcgg      900 agacaagagg gcacagacga cagagcgacg aaggaaacac aaagagcaag cgaaacagaa      960
gagcacaacc agaggcagac aaccag                                          986

<210> SEQ ID NO 125
<211> LENGTH: 986
<212> TYPE: DNA
<213> ORGANISM: Homo sapien

<400> SEQUENCE: 125
```

```
agaaaaaaaa gaagaatgat catataggag aatggggtca ctacatgcag ctcgagcgga    60
cgcagtgtga tggatgcggc gcccgggcag gtactttgtc cctgattaaa taatgtgacg   120
gatagcaatg catcaagtgt ttattatgaa aagagtggaa aagtatatag cttttagcaa   180
aaggtgttgg cccattctaa gaagatgagc gaatatatag aagatacgtg tgggcatttc   240
ttcctgttag gtggagctgt atgctgttga cgtttctccc catactcttc ccactctgtt   300
ttctccccat tatttgaata aagtgactgc tgaagatgac ttggaatcct tatccactta   360
gatttaatgt ttagagaaaa acctgtaggt ggaaagtaag actccttccc tgaattgtca   420
gtttagagca acttgagaga agagtagaca aaaaataaaa tgcacataga aaagagaaa    480 aagggcacaa agggattggc ccaatattga ttcttttttt ataaaacctg cctttggctt   540
agaaggaatg actctagcta caataataca cagtatcgtt caagcaggtt cccttggttg   600
ttgcattaaa tgtaatccac ctttaggtat cttagaacca cagaacaaac actgtgtttg   660
atctagtagg tttctatttt tcctttctct ttacaatgca cataatactt tcctgtattt   720
atatcataac gtgtatagtg taaaatgtga atgactttt tcgtgaatga aaatctaaaa    780
tctttgtaac ttttatatc tgcttttgtt tcaccaaaga aacctaaaat ccttctttta    840
aaacaaaaga aacaaacgac aaaaaaaaaa aaacaaggct gggggtaccc tgggccaaag   900
gcggtccccg ggggaatttg gtccccgccc ccattcccaa cctccgccaa gaacaaggga   960
acagaagaaa aaaaaaaaa aaaaac                                        986

<210> SEQ ID NO 126
<211> LENGTH: 556
<212> TYPE: DNA
<213> ORGANISM: Homo sapien

<400> SEQUENCE: 126
acctattcac cattccaacg tgaagaagct ctgcatgtag aaagaataa ttaacacact     60 tatagtctac tgcccatgta aggatcagct ccggctaaga ggccaaagat gggtgacatc   120
gtcatgctct gccttttatt ttttctttct tacccactta gcttcctaat tggaggaagg   180
aggcgtggta aaggtatatg aagactatgg tttaattaga ccagaaaaca ctgtcataat   240
ctctgggcgt cagtcagaat gtccagtttt gtctttgggc caagataagg gcagtgggat   300
ttatgatgtg ttgtttatag tctgaaacta ctctggtgat caccagggtc agtttcttta   360
atcgatggtt tccaagctgg cctaagtaca tttaagtaga gactgggctg ataaacatga   420
ccagacgaga cataaagacc ctgttgggaa tgacattgaa ctctcaaagt caagatttct   480
tacacaaatc tatcagctgg agaataatga gaggcagctg tggtatatgt gtgcaaataa   540
ggacattatg aagctt                                                  556

<210> SEQ ID NO 127
<211> LENGTH: 1327
<212> TYPE: DNA
<213> ORGANISM: Homo sapien

<400> SEQUENCE: 127
ggaagacctg attgggaata gtcgaaagcc ttgatatgtg caaagaaaga accatttgat    60
caacccagtt cttaatacag gatactaact taaaatatag actcaagtta tacgataatt   120 caaacatttta ttgtatttat actattctat atgtacttt ccaggaacca ggaatacaaa   180
actgacatgt tctctgtaca gaggctcaga ctagtagaga acagttaggt acgccgttaa   240
ttataaacta atatgtatca tcaattatgg gttttatgg gggtttggca ggtggaaggg   300
```

```
accagggaga gatgatgagt gatgatggtt atgtagtctt taggaggatg caattataac    360
attgctcttc ctttcacgca ccacatgatt tagcaagtac ttcatattgg ctccaccatt    420
aacatggtca atggcttctg gatactcaca gttcaggcac agtttctcct gaagattttt    480
tacctctccc atctttaaga aattgtctgg atgtccatga agatgctga cacttgtatt     540 aattcattaa aaacaccac cccctccctg aaataaacta aaagtaatg aattcataga      600 aaaaatttc accaagattg aaactagaga atatacctag acttgcactt tgagctttga     660
gaaatgtgta cctattcacc attccaacgt gaagaagctc tgcagtagga aaaataatta   720
acacacttat agtctactgc ccatgtaagg atcagctccg gctaagaggc caaagatggg   780
tgacatcgtt atgctctgcc tttatttttt ctttcttacc cacttagctt cctaattgga   840
ggaaggaggc gtggtaaagg tatatgaaga ctatggttta attagaccag aaaacactgt   900
cataatctct ggggtcatca gaatgtccag ttttgtcttt gggccaagat aagggcagtg   960
ggatttatga tgtgttgttt atagtctgaa actactctgg tgatcaccag ggtcagtttc  1020
tttaatgatg gtttccaact ggcctaatac attaagtaag actggctgat aacatgacca  1080
gacagacata aagaccctgt tgggaatgac attgaactct caaagtcaag atttcttaca  1140
caaatctatc agctggagaa atgaaggca gtgtggtata tgtgtgcaaa taaggacatt    1200
atgaagctta aatatggaat gtctcttgga cccccgatgt catctgtatt ctcttttct    1260 tcttgtacta tatcctttgc ctgtaaataa aaggtttatt tgaaaaaaaa aaaaaaaaa    1320 gatcggc                                                             1327

<210> SEQ ID NO 128
<211> LENGTH: 472
<212> TYPE: DNA
<213> ORGANISM: Homo sapien

<400> SEQUENCE: 128 acccttatt aagctgtgag cttcttgagg gcaaggactg caattcatta atcattttgg     60
agaaaagtga ataattctga agaattcggt ggttcatgag cttgcctggt atttgtttct   120
ctatggctta tcatctaagt gagataacag atagtagata attgataaat ttaatctgtt   180
acctaattac tgagaggatt cgattcttgc tttatgttat tactgaaaca gactgcccag   240
taatcttctc tagagagcaa ttaggtttgc aatgagttat tttattgaga atgctacttg   300
gaattaaatg tttatagcac tatcttgata taatttaaat ataatttaaa tgtgctgaag   360
tatcttcatt cagataactt gttaccccct aacaaaaggc tgcttgagta ttgtttctct   420
cccatttggc aaaacaccaga tgcagtgatt aataaggtc attatgctac tt           472

<210> SEQ ID NO 129
<211> LENGTH: 1040
<212> TYPE: DNA
<213> ORGANISM: Homo sapien

<400> SEQUENCE: 129
ggggatttag gttattttc actttaaacg ggctattaac ttcacgtgag aaaaaactg       60 tagaaacgtt aactcctgta gaatgatgac tatctgtggt gtagtaagat catacaactt   120
ctctacttgt tactgtgagt tgcttaataa atggcagtac aagtgtcaaa tccataatta   180
gtcaatatca agagctgcat tttggattgc atgtactgtc ccaaatatat gttgtgcaag   240
ttactttgta tcatgttaat ggagaaaaga gtggatatta tgaaatcagc aatataaatc   300
```

| | |
|---|---|
| aaatgtatat gtggtcctgc aatgtaattg aaggtactca gtgttctcag acactcatgc | 360 |
| aatatcttgt gttgctttct cagattttt aggtgtatca tagggatag ctgggaactg | 420 |
| gtagagcaga ggtactaagt tccacctgga aatgctttag agtagctctt tgaatatgtc | 480 |
| tttacttatt atcttacagc gtatgtgtat atgattattt tctagagggt cgtacccttt | 540 |
| attaagctgt gagcttcttg agggcaagga ctgcaattca ttaatcattt tggagaaaag | 600 |
| tgaataattc tgaagaattc ggtggttcat gagcttgcct ggtatttgtt tctctatggc | 660 |
| ttatcatcta agtgagataa cagatagtag ataattgata aatttaatct gttacctaat | 720 |
| tactgagagg attcgattct tgctttatgt tattactgaa acagactgcc cagtaatctt | 780 |
| ctctagagag caattaggtt tgcaatgagt tattttattg agaatgctac ttggaattaa | 840 |
| atgtttatag cactatcttg atataattta aatataattt aaatgtgctg aagtatcttc | 900 |
| attcagataa cttgttaccc cttaacaaaa ggctgcttga gtattgtttc tctcccattt | 960 |
| ggcaaacacc agatgcagtg attaataaag gtcattatgc tacttaaaaa aaataaaaaa | 1020 |
| aaaaaaaaaa aaaggcggcc | 1040 |

<210> SEQ ID NO 130
<211> LENGTH: 242
<212> TYPE: DNA
<213> ORGANISM: Homo sapien

<400> SEQUENCE: 130

| | |
|---|---|
| agttttatc ttttcttgac tttttctcct gaacacttat gtcttagcaa gtggtcaaca | 60 |
| tgaggatttg aacgcctaat tgttggtaaa tggttgaggc atgacaaaaa tattaatatc | 120 |
| cactgtttac catcacgtta tttgaaacaa aagtgaccat gtatactatc ttgcttgaag | 180 |
| aagtctttga cagaaaaagc aatatcatgt catttataaa ttttcttgtt ctaaagaaag | 240 |
| ca | 242 |

<210> SEQ ID NO 131
<211> LENGTH: 1689
<212> TYPE: DNA
<213> ORGANISM: Homo sapien

<400> SEQUENCE: 131

| | |
|---|---|
| gtttgcaggc cagatggtct ctgtggcagc tactcagctc tgcaatttca gtgtgaaaga | 60 |
| agccatagac agtacttgaa tgaaggactg tggctggatt ggcctttag tttgaccccc | 120 |
| tacattaggc cccaaatttt cttaccctga ggtgctgata tctgtatgga tgagttattt | 180 |
| gtcactaaag ttatgagttg tgcctaaaag ttaaaactgt tgactgtatt atgtaatgat | 240 |
| cagtatttca gttgggaaga tattttagag tctagataat tatgtttgta tattgaaaaa | 300 |
| atggtggcca gttttaagt tccttaatag aagagaatta tgtctcagca catataacag | 360 |
| taatgctaat ttattgaaac tactgctgtt agagcacttc ttattcattg tcttttagtg | 420 |
| aaatttatgg cgtaacactt tgtcagagag gaggctatat aattcggagc ggaaattgtc | 480 |
| tataagtagg catttatttc atgattgata tgtcacagaa atcatggtag taaatcacat | 540 |
| tgctatttga atacccctgtt tttgtaagtt tttaaaactc atattctgaa aagatttcat | 600 |
| tctcttagtg ttagcttggg agttagattg ccatgattaa actattattt atccttgtgt | 660 |
| aatatattgt tttaactta acatctgttt ctttttaatc tataatgagc tagttttatg | 720 |
| gaaaatggaa ttcttacta tataaagaat acagagactc attgtattag agaatcaagt | 780 |
| cagccagcta aagtatccta ctgttaaatc cttaaaccta attttggaaa agagaaagtt | 840 |

```
aatcaatgta tttaccttac atgttggaaa gaactatgtt aggtctgatt catgtgaaga      900
agatgttgca aaggatttat ttcacaaatt ttaaaggaga tatgagtaaa gttttttatc      960
ttttcttgac ttttttctcct gaacacttat gtcttagcaa gtggtcaaca tgaggatttg    1020
aacgcctaat tgttggtaaa tggttgaggc atgacaaaaa tattaatatc cactgtttac    1080
catcatgtta tttgaaacaa aagtgaccat gtatactatc ttgcttgaag aagtctttga    1140
cagaaaaagc aatatcatgt catttataaa ttttcttgtt ctaaagaaag cagttatata    1200
tatatataaa ttatgtaaat aaaagttatt ttatatcaaa aaaaaaaaaa aaaaaaaaa     1260 aaaaaaaaaa aaaaaaaaa aaaaaaaaa aagaaaaaaa aaaaaaaaaa agggggggggg     1320 aaaaaaaaaa caggggagaa tataacattt ataaaagcaa aagataaaat gaagagagag    1380
ccagcgtcta tcaaaaaaac agaccgatcg aagaagaaa cagaacaaag aggttaaaat     1440
ctgaggacga gaaccaattt gaccggggat taaaaaagag dacaccaccg cacaagaatt    1500
cccgcagggg aaataaacta ggagttgtac tacgaaccac cctaataacg cagcaagacg    1560
tgccgacatt aaacaataag cggcgaaatc tacaggaga agaataacag gtaccgagga     1620
tacacgatag cagcgagagg agaagagtca acacgacaac gtagaggcag aacacacggc    1680
acagagaac                                                            1689
```

<210> SEQ ID NO 132
<211> LENGTH: 776
<212> TYPE: DNA
<213> ORGANISM: Homo sapien

<400> SEQUENCE: 132

```
atgaaactta ctgagttgaa taacttaata tatttctgtt ttcattccca agggaggcca      60
tgtctggaga tagaccttga atttaataaa ttttaggcac tataccattt cagtggagaa     120
gattgttggg aaatttgggg ggatggatat ataaggggga ggaagtcact ggccagtttg     180
aggtgcttcc attggtctgg gtaactagcc atttcttcct gattgtgcct agtatatccc     240
agacagtttg tttctatgca gaagaatttt atatgaaatt ttcatttctt tgcaaaaact    300
tgttccttct ttcagttcat gacatcatcc atgctaaagt ctgagtcatc tgcttccatt    360
tttgttattc cccacatcca gtcttcagct aagtcctgtc agttctacct caagtctttc    420
ccgtctttct tcctcaccta tgtaatttca gtagtctctc agcttcactt aagctcttac    480
tccagcctac tttatacaca atgttagatt catcttactg aaacatagtt ctgaccatgt    540
attccatgca tgtgttctct ctcccctatt agactgtaag ctccttatgg gcaggatctg    600
tgtctgagtc atctttgtat cttgcctagc acctatcaat aaatacttct gtgaatgaaa    660
aaaaaaaaaa aaaagaaaaa aaaaaagggg ggggggaccc ggggccaagg gggcccgggg    720
gaatgggttc cggcccaatc cccattcccc ggcgccaaaa aagaaaaaag ggaaag        776
```

<210> SEQ ID NO 133
<211> LENGTH: 2910
<212> TYPE: DNA
<213> ORGANISM: Homo sapien

<400> SEQUENCE: 133

```
cgtgtgtgtg gtggtgcgtt gtgtgtgttg tattgtgttg tggtgtgtgg ttgtggaggg      60
gttgtgggag ttgggttagt gagttcggac ggtcggcgta gttgcgtgtt cactgcctgg    120
ggtgttgcgt gcggtttggt ggggtcggca tagtgacgca caggtgttcc ttcgcgagtt    180
```

```
tgcatggtgc gtttcgcagg ccggcgtgga atgcggcgcg gtgttggttt ttgcgcgttg    240
ctttataggc acccttgtta cactaggccg gggttccgtt agctcgggc cctcgtgggg     300 tgtctgggcg gtgcccctgt gtggttgtgt cgtcgagaag tatttattga taggtgctag    360
gcaagataca aagatgactc agacacagat cctgcccata aggagcttac agtctaatag    420
gggagagaga acacatacat ggaatacatg gtcagaacta tgtttcagta agatgaatct    480
aacattgtgt ataaagtagg ctggagtaag aggttaagtg aagctgagag actactgaaa    540
ttacataggt gaggaagaaa gacgggaaag acttgaggta gaactgacag gacttagctg    600
aagactggat gtgggaata acaaaaatgg aagcagatga ctcagacttt agcatggatg     660
atgtcatgaa ctgaaagaag gaacaagttt ttgcaaagaa atgaaaattt catataaaat    720
tcttctgcat agaaacaaac tgtctgggat atactaggca caatcaggaa gaaatggcta    780
gttacccaga ccaatggaag cacctcaaac tggccagtga cttcctcccc cttatatatc    840 catccccca aatttcccaa caattttctc cactgaaatg gtatagtgcc taaaatttat     900
taaattcaag gtctatctcc agacatggcc tcccttggga atgaaaacag aaatatatta    960
agttattcaa ctcagtaagt ttcatctaaa gactctagtt atgagtcact gtaccttctg    1020
gtggaataca gagatgaact ccctagtcct tatcttctag gagcttacag tctagtaaag    1080
tagtaaaaca gataatgtaa ttctaattct agactgaagg ggtaagttat gaactatgag    1140
aaagacaaag tgctctagaa cagtttcaga atgaaggtt ggaacaggac ctcaaacaag     1200
agggaaaatg tggaaagtag atgagaatgg atttgttcct cactccaaat tctggacaga    1260
tcagccccaa aacgggcta ctccccattc ctgttgaaat ttttcttag gaaaaaatat      1320 agctcttgta ctgatctttt aaaaaattac ttacatggca agagatcaga ggaaaggggg    1380
gattgtagat ctcagtggac cttcggggaa gacagaaggc acttgaagcc aaggaatcac    1440
aatgcctggc ttatcgggag gaccctcagt gttttagcaa ggctggagca tcacttccat    1500
gaagagtggg agaaataact caaaagtaat attaagacct tgatataaac atggcattgc    1560
caggcactaa acagggtaca cgcctaagac caaattgctg ccccctagga gcttacagtt    1620
acaacaatac aaggtggaaa aagcaccaca atgtacagaa tgcaaaatgc tgaagtattt    1680
aggagaaatt acagctgagt ttcagctatt aacacattag gatacccaat agctttctga    1740
cagctagtag taaacccatc cctgagggga gcacaagtta atgtccttag acaacaagcc    1800
ctggtagagc tgggccatta aagacagttc taagaaaatt gagaaaacag gggtatgaaa    1860
actacagaag caactgggtg aacatacaaa aagtgatacc ttccctttt ctcctgacaa     1920 actttaacag ggctgccctt cctacagtga atctaaactg atgatcacca tattacttct    1980
aaaagcagat ttgggactct actaaccaat tctctctgat cctttgtaaa atgaaggggt    2040
tgtacaagtc acttcctagt cctttccagc actaacattc tatgattcaa gaattctga    2100 gagtttctct gttccttttg gtaataacca aaatagaaga aaaaaattta agtctgatgc    2160
ttctcactca aaatataat tattttctat ataaatcaca atgatccct atgctatcag      2220 ctaaatttta cttccaccct atccttcttc aaaatccatg aatttttaa aaccacatgt     2280 cctacaagct accttagcat gcaccaaatg atttttcaaa agttttctc atctcctact     2340 cccttatacc aacttcttgg tataatgtca tttaaagggc caaatcagtg tacatccaat    2400
cttcataaca aaattttaaa atttaggaga acaactgaca tcaaagcatg aggacagtga    2460
gtaaccgaag tggttttttgt tgttttctaa tttttttgttt tttagagaca gggtctcact    2520
ctgtcaccca ggttagagtg cagtggtatg atcataactc actgcagcct ccaactcctg    2580
```

| | |
|---|---|
| ggctcaagca atctcctgcc tcagcctcct gagagacgga gactatagga atgcgccacc | 2640 |
| acatctggct cacttttcaa ttatctgtag agacagggtc ttgctatgtt gcgcaagctg | 2700 |
| ctctcaaatt cctggcctcg agcaatcctc tggcctcagc ctcccacagc actgggatta | 2760 |
| caggcatgag ccaccccacc ccaccccaaa gtgattttaa cttcagcaat agttaaaact | 2820 |
| gtttctatcc aggttaaaca ggatttaatc ttccatctaa ttactatcaa aaatataggc | 2880 |
| aaccttcccc aaaagtgggc ttctgaaaac | 2910 |

<210> SEQ ID NO 134
<211> LENGTH: 466
<212> TYPE: DNA
<213> ORGANISM: Homo sapien

<400> SEQUENCE: 134

| | |
|---|---|
| cgtgactaga ctcatatagg cgaatgggcc ctagatcatg ccgagcggcg caggtgatgg | 60 |
| acggcgcccg ggcaggtacc cagtaagttt gatggtttaa attccactaa agaacatatt | 120 |
| cttctaataa ctagcattta ttacatgaaa tttaagagtt taagttccat caaactagcc | 180 |
| ctgtgtaaga ttattatttc ttctctataa cttcaaaata gatatttcat tcaaactgtt | 240 |
| caggtgagaa acataatgg attttttttt tttccctctg gagctgcctg ttcagtgaga | 300 |
| tggaggaggt gggcacattt aaggtcagtt cactaaccta tggttcagag ttctgatcat | 360 |
| atggaagttg ggaaaagaga gcttatcaca ggtttgtatg ctggtgaatg datagtttta | 420 |
| attctcactg tctcaaaaga gaatcagctc tccagcagtt ctagaa | 466 |

<210> SEQ ID NO 135
<211> LENGTH: 3592
<212> TYPE: DNA
<213> ORGANISM: Homo sapien

<400> SEQUENCE: 135

| | |
|---|---|
| tatcaaagaa ccatcaatcc cgtatcatgt tgattgcttt tactgggagc ttttgaaaaa | 60 |
| aagttcaagg gtttcctaat ggtcaaatca tgagctgccc ttgaagtagg atcaaaataa | 120 |
| gattttcatt aaagacctgt attatcccag gatgtatatt atgtatcgct gttttcagag | 180 |
| tgtgggtgaa tatagcagaa atattacagc ggaagtgaca aatttacaac ttttattata | 240 |
| gaaagaaggt gtttctggca atgtaatctt tactgctctc aattaaaaat aattttgagg | 300 |
| cctgaatgat aatcccttga ggacaaatcc aacatgtgct ggtttattct gttaattccc | 360 |
| atttatttgc ctacttcatt tttcttgcac ctcttagaat ctaactatga attgaaaaca | 420 |
| cttaagtaat tctgtttaat caagggattt acactacaaa agaatgctgg cttttttttat | 480 |
| gttgtattcc ttagttgagt tttagaagga atgcttgatg aaacatttta aaataagtca | 540 |
| tgacatgtta gcttgagaat gtattttcat aattgtatac ttgttttttaa ctttaaatgt | 600 |
| aattttaat caggtaaagt ttgacacatg tatagctaca tacacacatt tttaatggtg | 660 |
| ctcatatata ctgtattttt tgttgtttag ttttacttat tgagagtgtc acaacatgaa | 720 |
| tcacataatc atgattttt tttttactt ttactcccca aattattcat gtttcttaga | 780 |
| tcgtagtcat tgagaagtcc caataactct aaactttga gttataacgt agtaaacttc | 840 |
| tctttcatct ttgtgttagc tctgtagtct taacctggat tttaatttt ttgtttccaa | 900 |
| agtcacaatt gaattattct tagatacctt aagccactga attcagttct gtttgactga | 960 |
| aagcaaaaca acgtgacagt ttattttcaa acactaactt cttgatattt tgttatggta | 1020 |

```
tatcttttta ttaaatatttt attttgacta agctttcata aaatatttga agctattta       1080
atcatcaagt atggaaaaca aattactatt gcattttcct atatatgcat atattatgga       1140
ttaaccagaa ttgtatcatt tttggcctaa tgtctggata taaaagataa ttagcctact       1200
atagtattaa taaattttc agttggttg ggcaaattta aacctgaaaa ataggttaaa         1260
aagtagttac aaattaaact tactaattta tacctgatt tttttcttga attaaagtac        1320
attttaaatg agctttataa taccttaaaa agttggttct aatttaaaat atgaaagctc       1380
tggctatcat cctgggatag taatttctaa ttatatagta tttcaaaact atatattttt      1440
tagttccttt gagataacta atttctaatt atatatgttt caaaaccat atcctgtatt       1500
ttttttaaga attgttttat aaataggtca taagatacaa ggtctgcatt agaagaccca     1560
ctcttactag gttccctaag gatctgccat agatttttt tttttttttt ttttttaggg      1620
tagtttaaag caagcactga taccagtggg agttggtctt gatctaggag attctgttaa     1680
gcatccaaaa acaatgccta atttcagttc ttaggttatg gcttgtgact ccagataaaa     1740
gatggagaat acctcatgta ctgtgacttg aaaatgaatt cttaaaattc ttaggctctc     1800
tccatgtatc tttcttaagg aaaagtttct gagtgtgatc tctcttttgc catagtatca     1860
agtggagggt agttcagaaa agttaatagg aaatcttttg tgacagcaga ctataataga      1920
agtttgagta atattttaat aaatttatat aattcaaatg ataaaaatgt atcaatgtta      1980
tccaatgatt tttattaaaa aattaccta ttattagaac tgtgcctatt acataaaaag      2040
tgctcatgta tttgaatttt aaataattta ttaaatcaa gaccaccata agtcattaat      2100
aatttaataa ttgttttaaa tcagtggttt tcaaccctca cttcatatta gaatcatctg     2160
aggacttta atatgaatc cacctcataa caattaagtc taaatttctg aagatggag        2220
ccatgcttgt ttttccaaaa gctctttgag tgattctaat ttgtagtcag agttgaagac     2280
cactgctcta aattagtgca ggaaaatgct tttatttctc ccatgttaac ttttaaaact    2340
agtaatgtac ccagttaagt tttgatggtt taaattccac taaagaacat attcttctaa     2400
taactagcat ttattacatg aaatttaaga gtttaagttc catcaaacta gcccttgtgt     2460
aagattatta tttcttctct ataacttcaa aatagatatt tcattcaaac tgttcaggtg     2520
agaaaacata atggattttt tttttttttcc tctggagctg cctgttcagt gagatggagg    2580
aggtgggcac atttaaggtc agttcactaa cctatggttc agagttctga tcatatggaa    2640
gttgggaaaa gagagcttat cacaggttgg tatgctggtg aatggatagt tttaattctc    2700
actgtctcaa aagagaatca gctctccagc agttctagaa aagcttgaca atccccaagg    2760
ggcaggttac cttactcctt cactgcttct tagaaggtag aattaagttt ctggaattgc    2820
acctacatgt tttcttatta acattcagaa ttgggaatat taattttcc agtgagtagt     2880
tttctgaaat tggtaacttg gagagtaaaa taacgtattt tgcttttcaa ttttgtgttt    2940
gtttactttt atgtaaaaat ttgatatgtg aattacacag ttctaataaa acctcatgcc    3000
ttttcattac atctaatttg aactctcaac ttcatgttac agaatgcttt aaagatgctt    3060
taatgaaaag tattaagaaa atatatgat ttgtatgtca gtttatactt cagaaatcca    3120
tatatttgtc atatttattt ttttagaaac ctcctaattg gataactaga tggtatttaa   3180
aatgaatgcc caaaatatc ttgtaccttt gtccaaaagt ttatctgttg gaagccgcca    3240
gccattcatg tagagagttt ataagaaaat aatttaaaat tgtatgcatt ttatattact    3300
atggtatctg tgtaccatat ttctaagtat tcattattaa attggtactt cttaaaacca    3360
aaaaaaaaaa aaaaaaaaaa aaaagaaaca aaaaaagggg gggggtaaaa acaccggggg    3420
```

```
gcacagtcta cgctccccgt tttggcaagg gggcccaagg ggcggataaa acgaggcggc    3480
gcgggaaagc gggcggacat ccccgggctg tgcggcccct cgggcggcga tggaccccac    3540
agaaacccga gaacaagttg ggaccgcatc ctgcgagttg taaccacccg gt            3592
```

<210> SEQ ID NO 136
<211> LENGTH: 539
<212> TYPE: DNA
<213> ORGANISM: Homo sapien

<400> SEQUENCE: 136

```
gcggcgcccg ggcaggtact aaaatacagc ttgtgccttt taaccctatg ccaactccta    60
aacatataag tagattacag tatacttatc tgatcagagc atgatctgtt tggccacatg    120
caagtgtgag cagaaataga gcagcacgta gaatagtaac ttaaagcaag tcatccttta    180
aaaattctga gctaaaatct atttaccatt gagtaattga attaatccca taggaataag    240
ctccttgtaa gtaaatccat gatatgaatt agaaaaaaaa aacagctgga aattgaagtt    300
tttggatgcc tgtatactgg atatgaaact atttgatttc tagtcttctg tgtttagcag    360
ttgtaatatt ttaatgattt ggcttcatac tcggttaatg gaacataaac atatctttga    420
tacttcttgg tgagtgagag aatgctagat agggtggctt ggttcttggt ttaagttttt    480
tttcctgaat gtagttaatt tatggcatct gtggaataaa actgctaaaa tgacctctc     539
```

<210> SEQ ID NO 137
<211> LENGTH: 2918
<212> TYPE: DNA
<213> ORGANISM: Homo sapien

<400> SEQUENCE: 137

```
tataaaatg ccattgtaac tactgtagag taaagtgtta gctgcgctgc cggaggaaac    60
ggaagaagga gcaagctatg gaggggaaca gggatgaggc tgagaaatgt gtcgagatcg    120
cccgggaggc cctgaacgcc ggcaaccgcg agaaggccca gcgcttcctg cagaaggccg    180
agaagctcta cccactgccc tcggcccgcg cactattgga aataattatg aaaaatggaa    240
gcacggctgg aaatagccct cattgccgaa aaccatcagg tagtggcgat caaagcaagc    300
ctaattgcac aaaggacagc acatctggta gtggtgaagg tggaaaaggc tataccaaag    360
accaagtaga tggagttctc agagctttat ggatattgga acattgatat gggatggtgg    420
acctgtacct aacacacaca caaacaaatg taaaaattac tatgaagtag atggagttac    480
gaaagatgct ggtgatgaag atttgaaaaa agcttataga aagcttgctt tgaagtttca    540
tccagacaaa aaccatgcac ctggagcaac agatgctttt aaaaagattg gaatgcttta    600
tgctgtttta agtaatccag aaaagcgaaa acagtatgac ctcacgggca atgaagaaca    660
agcatgtaac caccaaaaca atggcagatt taatttccat agaggttgtg aagctgatat    720
aactccagaa gacttgttta atatatttt tgggggtgga tttccttcag gtagtgtaca    780 ttcttttca aatggaagag ctggttatag ccaacaacat cagcatcgac atagtggaca    840
tgaaagagaa gaggaaagag gagatggagg ttttctgtg tttatccagc tgatgcccat    900
aattgtattg atcctcgtgt cattattaag ccagttgatg gtctctaatc ctccttattc    960
cttatatccc agatctggaa ctgggcaaac tattaaaatg caaacagaaa acttgggtgt    1020 tgttttattat gtcaacaagg acttcaaaaa tgaatataaa ggaatgttat tacaaaaggt    1080
agaaaagagt gtggaggaag attatgtgac taatattcga ataactgct ggaaagaaag    1140
```

-continued

| | |
|---|---|
| acaacaaaaa acagatatgc agtatgcagc aaaagtatac cgtgatgatc gactccgaag | 1200 |
| gaaggcagat gccttgagca tggacaactg taaagaatta gagcggctta ccagtcttta | 1260 |
| taaaggagga tgaactggaa ttttttattta taccttttag cgtactcttt attttttctg | 1320 |
| taagtaagtt tggtttcatc atgagggatg aaggaaaaga tttgatactg aaaactaaac | 1380 |
| tgaatagttg gttcctgaaa tcttggactg tttatgacct actggctcct ttaaatagta | 1440 |
| actgaaaact aaaatggaat atttагtta acgcttctac aagtattttc attttaaaag | 1500 |
| cttacatgat tcctaactaa agtgtcatga gaaggatta tcacacctgt agcaatttcc | 1560 |
| agttttagtg attctccatt ttttcccttg tcatgtaaat atttatggaa tgatcatttt | 1620 |
| gtgtacatac aggttactgc ttttttattt aaattctttt agtgtttagc tccatgagac | 1680 |
| acttcagttt aaattgatgg aataaatgtt atatgacaca tttacatttt ccttatcaag | 1740 |
| gtgtcaaata tgtggacttt aaacaatgaa acttttcaa aagaaaaaa caaaaacttt | 1800 |
| aactttgtgt aaaatcttat agtattatca gcttagaggg aattgatatt tttaatattg | 1860 |
| ccgttatatt ccaaaatata tattgagata aatgaactgg tgtagaatat cagtttgcta | 1920 |
| tttagttta tgaattacta tacatataca tgcatagaaa tgaaatgcta tactgataaa | 1980 |
| ttttaaagaa aatatgagga aatggctata aatattaaac taaagggtc ttcaacagta | 2040 |
| aagtgcagtt atgtcattta aaattccaat actttaaagg ccaccaaatt ttgatgtata | 2100 |
| tgtccttgaa gggctgctaa aatttatgaa gaggactcac attttcccc atagaaattt | 2160 |
| gcagtttctt ggtgatcatt taagcaggat ccaaagaagt tcctttacaa ataagtaata | 2220 |
| agaaaaatga gtactaaaat acagctttgt gccttttaac cctatgccaa ctcctaaaca | 2280 |
| tataagtaga ttcagtata cttatctgat cagagcatga tctgtttggc cacatgcaag | 2340 |
| tgtgagcaga aatagagcag cacgtagaat agtaacttaa agcaagtcat cctttaaaaa | 2400 |
| ttctgagcta aaatctattt accattgagt aattgaatta atcccatagg aataagctcc | 2460 |
| ttgtaagtaa atccatgata tgaattagaa aaaaaaaca gctggaaatt gaagttttg | 2520 |
| atgcctgtat actggatatg aaactatttg atttctagtc ttctgtgttt agcagttgta | 2580 |
| atatttaat gattttgctt catactcggt taatggaaca taaacatatc tttgatactt | 2640 |
| ctttgtgagt gagagaatgc tagatagggt ggctttgttc tttgtttaag ttttttttcc | 2700 |
| tgaatgtagt taatttatgg catctgttga ataaaactgc taaaatgacc tcttaaaaat | 2760 |
| gttctgttgt atccccttt ccaggtgaat caatagaaat gcctgattga attagtaggt | 2820 |
| taaactaaac aacatactgt cataggaaaa ctggagagct taaccaactt gctcttagaa | 2880 |
| atgttacctt aaaaaaaaaa aaaaaaaat gagcgggc | 2918 |

<210> SEQ ID NO 138
<211> LENGTH: 523
<212> TYPE: DNA
<213> ORGANISM: Homo sapien

<400> SEQUENCE: 138

| | |
|---|---|
| actgtgggtc atttagatga gatgaaaaac ttaattaaat ctgaagtgtc agaggcgctt | 60 |
| agtaagcctt agtaaagttg tgattgaaga aacttaatac aaatgaacta gaggtttgta | 120 |
| atcatgccac tcactaacga ttcttatttc tgtagcagca atcatttttt ctatgtcaag | 180 |
| gtgttaatgt gtgtgtatgt gctttggttg taggaaaact tgcaaaactt ccaacaatcc | 240 |
| ttattttcct actttgagag gctggttcag cagggtgtgt gtgtgtgtgt gtgtgtgtgt | 300 |
| gtgtatgaat gatatattta ttacattatt tagaaagaga atgagtgtgt tatgtgtata | 360 |

-continued

| | |
|---|---|
| atgttatata cacgcaaagt gtatgtttat atttggcaag gaaggtaaga tatctgacac | 420 |
| tcaggcctta accaataggt tgaaagacaa gaccaattga agagttagga aatgtgagta | 480 |
| tgcgtaactt ctgatattcc agctcattgg ttacattgtc tca | 523 |

<210> SEQ ID NO 139
<211> LENGTH: 190
<212> TYPE: DNA
<213> ORGANISM: Homo sapien

<400> SEQUENCE: 139

| | |
|---|---|
| accttagact tggcatttat ttttgataga gcagagataa aatattttga tgaaaggaaa | 60 |
| tcaattttct gtaactgatg atgtgaaaat tttattttct gggaaattat atagccattc | 120 |
| aaaaattcaa agtatgttat tatgattggt tacaagagaa taatgttaca tgtttaattg | 180 |
| taatatttgt | 190 |

<210> SEQ ID NO 140
<211> LENGTH: 3394
<212> TYPE: DNA
<213> ORGANISM: Homo sapien

<400> SEQUENCE: 140

| | |
|---|---|
| cccctgccc gcctctccgc acaatacttg aacattcatc tgtactgaag tgttacttga | 60 |
| accgggggaa tctcggacct gggggagccg gggtgtgagg ggactggacc agcttggact | 120 |
| gagacctgag accgggccgg tgggcgccca tttgggactg cgccaccccc aggcttgttc | 180 |
| ttgtttttact gtattgagcg gcggcacccg ccggacccgc attatggctg ggggcgccag | 240 |
| ccaagaatgg ggaccatggg actcctccag cctggctctt cccactcttt catcgtcatg | 300 |
| gaaacttgta tcccatttgc ccagggaact gccactcctg gttgccatgg aaatagcagc | 360 |
| caacggacac ctcccgatgc cagtgctaag gctggaaatg gccccctctt agttgccatg | 420 |
| ggaacctagt aacagactct gctggccctc cttccctgcc ccttcctcga gcgcggggtg | 480 |
| gggcttcggg accccgggga tgagccgggc caggtcccgc ccctccgcgc aggcctccgg | 540 |
| ggggccgggg cttaccatgt aggggagggg agatctatcc acatacctca ggtggccatg | 600 |
| gtggaggtgc agctggagag tgaccacgag tacccaccag gctgctggt ggccttcagt | 660 |
| gcctgcacca ccgtgctggt ggctgtgcac ctctttgcac tcatggtctc cacgtgtctg | 720 |
| ctgccccaca ttgaagctgt gagcaacatc cacaacctca actctgtcca ccagtcgcca | 780 |
| caccagagac tgcaccgcta cgtggagctg gcctggggct ctccactgc cctgggcacc | 840 |
| tttctcttcc ttgctgaagt tgtcctggtt ggttgggtca agtttgtgcc cattgggct | 900 |
| cccttggaca caccgacccc catggtgccc acatcccggg tgcccgggac tctggcacca | 960 |
| gtggctacct cccttagtcc agcttccaat ctcccacggt cctctgcgtc tgcagcaccg | 1020 |
| tcccaggctg agccagcctg cccaccccgg caagcctgtg gtggtggtgg ggcccatggg | 1080 |
| ccaggctggc aagcagccat ggcctccaca gccatcatgg tacccgtggg gctcgtgttt | 1140 |
| gtggcctttg ccctgcattt ctaccgctcc ttggtggcac acaagacaga ccgctacaag | 1200 |
| caggaactag aggaactgaa tcgcctgcag ggggagctgc aggctgtgtg agactggtgt | 1260 |
| tagccaccgc tcactgcaag cactgcctcc ctccggggtc tgtaagaggc gcaggggcc | 1320 |
| tacagacctc atccccccat cccctggctg gagccacttc cagtggccac tctcaggcag | 1380 |
| agttcagatt cctgcccgca gggtcctctg ggctgggcct tggggcagct cccacattcc | 1440 |

-continued

```
cagggattttt ccccatcagt ctgtcccttg ggttttgcaa gctactctgc acctgggctg    1500
gcctcagttg aaggatcatg cagtagatag aggggaggca gggagagctt gtgggacctt    1560
cagtgctgac tttagccacc atttccattc ctatacagga tgtgaaggtc agaaggcagc    1620
caattgttgg tttaattttt ttttttttt gagacagtct gttgcccagg ctggagtgca    1680
gtggtgccat catagctcac tgtagcctcg accttccggg atcaagcaat cccacttcag    1740
cctcttgaat agctgggact agaagcatgc accaccatgc ccatctaata tttgtatttt    1800
tagtagagac aggatctccc tatgttgtcc agcctagtct caaactcctg ggttcaagca    1860
atcctcccac ctcggcctcc caaagtgctg ggattgcagg catgagccac cgtgcccagc    1920
ctcaaaaata ttttttaaaa gaaaagagaa ataattctt ctgtcaaagg aggttaaatt    1980
ttagttgata gagtacttaa atgcattact ttattaggtt atgtaagtgg tcagtgcatt    2040
ccagtatgtg tcacaacagt gtagttcata ttcatgataa aaatgaaact gtgataagac    2100
atgaaaatta tattattaaa atgttcaatt gtaatggtaa tcatgagtat acttaatttt    2160
atttatgtat agaatatttg tatttatttt ttggacatat atttatcact ttgtcatttt    2220
ttttaaccaa tttgagaaat gttagctgct gaattaattt gttgcccgag ccttcatatt    2280
ttcttctttg ctgccttctc cctgtggcaa tgtactgttc tcacattaag ccttttaaaa    2340
atgttccata ctgtattagc atccttagaa gggacagaac taagaaatac attgctcaaa    2400
taatatttta ctttattgat aatgacaaaa agaatatttt ttaaacccca tcaaaataga    2460
tttcaattga ctgtttcccc tacatctttt gagccacagt cgcccatcga ataagcaaat    2520 ttgttttga gaataaactg gtaaccagtt tgtgatgact ctcagaagcc ttttggctgg    2580
gttacagaag agtttctaag ttcctagaga gccatttaat aattagttgg tgagccagag    2640
gcttgacaga gctgttactt atgtgtgagg gctttattct caggcagtag tttattcatc    2700
atttggtaag ccccctcccca cactcctcta atttaaacaa gtagtgaagg cttatcttaa    2760
actgtgtagt accttagact tggcatttat ttttgataga gcagagataa aatatttga    2820 tggaaggaaa tcaattttct gtaactgatg atgtgaaaat tttattttct gggaaattat    2880
atagccattc aaaaattcaa agtatgttat tatgattggt tacaagagaa taatgttaca    2940
tgtttaattg taatatttgt ctcctatcat tttcttccct ttcagtcata taaatgatt    3000 tacaaaaccc attttgagca ttatcttttg aataatcttc aagaaatacc taatgttttc    3060
attgtcaaag ctgaggtgta gtaccagtga aaatggtagt tattacctcc ttctcttgca    3120
tcatgctttt gtcttcagtg ttgctttgtt ttatccatat aaaagggagc tgttttggag    3180
aattgtaatt ttaatccata tgtgtgcata ttgacacaca atatgtaaat aggtaaatag    3240
atagaaatat tggttctccc atgatttcat atttcatata ggtgagttga atggattgtg    3300
ttccaaaaat ttgtcttaaa tgttctggat tgtgtgtgtg tgcccttaaa atcaaatact    3360
atcacagctt agaaatgact ttaactctca attt                                3394
```

<210> SEQ ID NO 141
<211> LENGTH: 467
<212> TYPE: DNA
<213> ORGANISM: Homo sapien

<400> SEQUENCE: 141

```
acaggttttt atgtaatgcg atttaaaatt tttaaaaaca tgggcttcat gaaaacacca      60
ttgttactaa cttgggctta gatgggaatc taatgtgaat agttcaagtt atgggacttg     120
tctaaatgtg tctatactct aaacctgggg gaaggtggtg tggaacattg acttgactac     180
```

-continued

```
agtcgaatac atgttgggaa tcattcccaa tcataagaca tcgtcgtttc tgtaggatga       240
ctgcatatgt tcagagtagc tttttgaatt tggttccctt agctttaggg atgtgatgtt       300
atagtccaaa atgtttacaa gaaaacctaa gtcttcaaaa gcacaacttt tgttgcttag       360
gactttgcat caactgttgt tccagacctc acttcaactt cttggtctct gaactggttt       420
tagctagcat gcatgagaga cagttttcat gtataatgtt tctgctc                    467
```

<210> SEQ ID NO 142
<211> LENGTH: 4106
<212> TYPE: DNA
<213> ORGANISM: Homo sapien

<400> SEQUENCE: 142

```
ttttttata attaggataa tgcctttatt aacgagaatg aaacgttcat tcctccttcc        60
actccttctc gtggttttct ggacacagct cacctgatcc tagaaacgtg tcagtctgct      120
tgtggcttcc ctccttgatg actcacgctg tgtgatgtct tgagaagtat ctatccactt      180
catgtgaatg agcactccaa tatcagccaa catcaatcat tcttacctaa agaataataa      240
gaaaaagtta atataaaaga caagggtata aaataaaggt ttgaaaatgc tagtcaactt      300
caaaatttaa agagtaaaaa tccagagata aagattgggg gtaagttaca gcataaaaaa      360
ataggaagaa acttcatggt gggggggaaa tctaaaatta ttcttacata aaataagtag      420
acacctgaat tagaatgaaa actgtatttt ctttaaaatg taaaagcctg actctcagtt      480
tcaccagtct gagcacaagt ttgactgcaa cccaaaatat actatccctt atgtgaaggt      540
atgtgacaac gttgacctca ccaaatgagt tttaacatca gctcttttt catatgaaag       600 cacatacccct gctccccatt caagtatgtc ttccattgtc aggcaggctg accaccttca      660
gcaggagtcc tccaagagtg cccaactccc cttcccacag tacacaacgc tgtagttgtt      720
gtcctgcaat cctttgtatt tacctcattc tttcccatct aagtcctcac tgagttttaa      780
agttagggct ggaaaagcta tgccttactg ggacagcaag gaaccaattt ttttctgagg      840
gagaagacat tcaccttcac tatatgcctg gcagggccac agtgcacaaa acaaagatca      900
gccttcattc aagttccagg ttttttcttcc tccctgaatg attactgcaa agggtatatg      960
aagtaagagt tccctgttgc acatgtacca tccataaggg atactatatc gttttgcatt     1020 cttccccccca ttctccacat tgtcctatct taagtccaag ccctttttcac tctcaaaaaa     1080 aaaaaaaaaa tattttttttc agcactggtg ttcaaaagca acgttttttat ggttaatggt     1140 ttaccagcaa ctgttgagat ttccagttga gtcttaaaaa ttgccaatca ttatctagca     1200
gcaatgacag atgattagga gcagtcaaat cctctgaatt cttttccctaa taggcagcca     1260 tttgagaact gcactagctg acatcactaa acattatca gctaaagcca aaaccaaata      1320
aaggcccaga ccaacatcct ggctctctaa acctgtcca aaatcattaa gtgaaaggca      1380
gtaaatgcag gactgtggat catgtcactg cagctgacaa tgattaacaa taggagacat     1440
gcaaccccca ttaaggttaa aagtccaaaa ctagtcacac gcatctcttt attggggaaa     1500
agtgagacta ttatgcattc ttggtaggtt tgcaaccttg catgaagagc acccattgca     1560 tttcttcat ctttcagaaa gcaccggtat ctgttccaag ggcctaacag tacgaaaata      1620
cattctggca tcacacctct gaacccaaga ctgttctcat taaaaataat tttggtttgt     1680
aacaaaatta tgaaatacaa tgcaagcacc tcggtatagc attattactg aaaccactta     1740
attcccagct ttttgagttt tttaaaaaaa cccactgcac taagattcac aattcattgc     1800
```

-continued

```
tacatacaaa ttaaagctag taagaacaca ctaacgtcac aagtttctca ttctaaagtg       1860
caaaagccta atcatctgaa agtgaacagg gtaaggcaaa attaaccccc caccccaata       1920
aagttcctga agtccatata ttatatacca agtacattct ctaaaaattg ttactgactg       1980
gtaagaaata gacctgagtt tttatttcta acacccaatc actaaaccac ggcagcaagc       2040
actggccacc gatttaatgg attacgacac aggaaacccc atcagggttc tatgtaattt       2100
agtgatactc atgtcactaa tattgagcat tatacttgat ctgcattata ttgttgatat       2160
gcagaggcta aactagtcat catttgctct ttcatctatc agtagagtcc aaagttgttt       2220
gcttgaatgg actacatgtt aaagtacaag tctgtcccca ccttgtgaat tgcttgccaa       2280
cgagcaagct ttttcttgat acacagaaga aaagtctcat agtcatgaag ttttcatcag       2340
catttatgca aagtaaacca ctttccagtt acagagcaga acattatac atgaaaactg        2400 tctctcatgc atgctagcta aaaccagttc agagaccaag aagttgaagt gaggtctgga       2460
acaacagttg atgcaaagtc ctaagcaaca aaagttgtgc ttttgaagac ttaggttttc       2520
ttgtaaacat tttggactat aacatcacat ccctaaagct aagggaacca aattcaaaaa       2580
gctactctga acatatgcag tcatcctaca gaaacgacga tgtcttatga ttgggaatga       2640
ttcccaacat gtattcgact gtagtcaagt caatgttcca caccaccttc ccccaggttt       2700
agagtataga cacatttaga caagtcccat aacttgaact attcacatta gattcccatc       2760
taagcccaag ttagtaacaa tggtgttttc atgaagccca tgttttttaaa aattttaaat      2820 cgcattacaa aaaaacctgt acttttagtt caactcaact tgtagaatta ccaagattgc       2880
ataatgaaat tactgatatt gccgatctat gggcaggtca gtttgctaca atagagacta       2940
attatcacat gctatacggt ccatgtcaag gtgctaaaag caccctagtt cccaagtata       3000
gtttagttcc ctctccccca caccactgat gtgttccatg ttatcttcag ttacaatgca       3060
actaaaggaa accacaactg agtcagatat accaaagaat caagttgcac tttttatctg       3120
agaactgcaa cagcactgaa ttctgcctga caaattacag ctctaacccc acacccacac       3180
agttttgatg taagctagct ttaccataca agtgttaggt gctgcactgt aatttcatgt       3240
cagaaatgtg atgccagaat gcccacggaa taaaagtaca tacaagtcac caagttagat       3300
tatatgcttg ttacctacct gtatgcagtc ggcaatgaga atcttggagc aagcaggaat       3360
actacatccg ggtcctaatg tccattgcca tttgcggtac tacgttcctc acagttacgc       3420
actgcagaaa tgctggctaa atgcagttat gtagcaggcc actactttaa tagtgcataa       3480
ttgcagtcca agaacaccag aaaacattcc gccacaactt agtggcttgc ccaagaaaag       3540
ccaagtatct aaatttttaat ctgccataat atgccactta aaaattgcac aggcgtaaca      3600
ttacaatttc cccatttttt agctgtttat attagtggta caatacatct ataaagagtg       3660
gtgggttagg tctgtaattt gtcaggcaga attcagtgct gttgcagttc tcagataaaa       3720
agtgcaaact tgattctttg gtatatctga ctcagttgtg tggtgtcctt tagttgcatt       3780
gtaactgaag ataacatgga acacatcagt ggtgtggggt taggtctgta atttgtcagg       3840
cagagtgagg tttgttgtgg agctggcaga tccaaagttg gaggtgaaat ggtataaaaa       3900
tggtcaagaa attcgaccca gtaccaaata catctttgaa cacaaaggat gccagagaat       3960
cctgtttatc aataactgtc agatgacaga tgattcagag tattatgtga cagccggtga       4020
tgcgaaatgt tccactgagc tcttcgtaag agagcctcca tttatggtgc cgagcagctg       4080
gatagaaacc cccgctgatt gttgtt                                            4106
```

<210> SEQ ID NO 143
<211> LENGTH: 192
<212> TYPE: DNA
<213> ORGANISM: Homo sapien

<400> SEQUENCE: 143

| | | | | | |
|---|---|---|---|---|---|
| gcgtggcgcg | gccgaggtac | tgtctctaca | gccattgaga | agccattcag | tgccctggta | 60 |
| gggacctgag | actttccaga | attcacacag | cagtctatga | tccctcaaat | gtaagaggac | 120 |
| aggggtcag | cctatcttca | cctctcagtg | aatgtggagg | ccaagcaat | atgacttgca | 180 |
| aacctaagct | ag | | | | | 192 |

<210> SEQ ID NO 144
<211> LENGTH: 2641
<212> TYPE: DNA
<213> ORGANISM: Homo sapien

<400> SEQUENCE: 144

| | | | | | |
|---|---|---|---|---|---|
| tttttttttt | tcttttcca | agttatttaa | tttacagcat | cagtctccaa | atataataat | 60 |
| attaagatag | cagtttagaa | attaactttt | tttcagatca | ctctaacata | aaatctctca | 120 |
| actgaatctc | tagtttgtct | cattttgtta | agagctttaa | tattacatgg | gaagttcaga | 180 |
| gacttctatt | tccatccctc | aacatgtagt | gacagtcaac | atgtcaggct | ctgtagcacc | 240 |
| gtgatatccc | agcaccagac | cactccagcc | accctctcat | tcaaagaagg | gctacaagat | 300 |
| atggctggac | tactcgaatc | acatctgatc | ttaatcaatc | caggtataga | aagttgtact | 360 |
| ataaagaata | ctttccaaaa | ttgttcactc | aaataaaaac | agatcaagtc | attacagagc | 420 |
| attttttccat | tttaataaga | ataacagacc | tactcaaggt | aatttttattc | tgtttattta | 480 |
| aataaggata | agactactta | aaagactttt | tacatacaaa | aatgtacaag | gttaaacttt | 540 |
| tctgtactga | attacaaaac | ctgcacaagc | atgtaataaa | agagcacact | taaaaacatt | 600 |
| ctgaccatta | tttagcctct | aaaaattact | gaagttcaac | agtagtaaat | agaggaagct | 660 |
| cttacatata | tatatatata | tatatatata | tatatgattt | aatctactgg | cagttttact | 720 |
| taatgtaagt | atttaaaagg | tcacattgct | attgaatgag | tctctagatc | aattttagaa | 780 |
| ttgtctctca | aaacttaagt | caaccaaaat | attatttcaa | atagtaattc | caattctgaa | 840 |
| gaattttaat | accagcaaat | atattatggc | ctcatagtag | taactgaacc | aacttttccaa | 900 |
| agtgcctggt | agctgtccag | atgaattagg | ctgctttgga | aaactgtact | gtctctacag | 960 |
| ccattgagaa | gccattcagt | gccctggtag | ggacctgaga | ctttccagaa | ttcacacagc | 1020 |
| agtctatgat | ccctcaaatg | taagaggaca | ggggtcagc | ctatcttcac | ctctcagtga | 1080 |
| atgtggaggg | ccaagcaata | tgacttgcaa | acctaagcta | gaagcttggg | atctacagta | 1140 |
| aggaggaagg | agaattaaag | tagagaaaga | aaatgtataa | ggagaaaggg | aaaagaagga | 1200 |
| acaaagaggg | aaaagaagaa | aaaacaagga | tgcctgctaa | tggcaggaag | tggtaaagtg | 1260 |
| cctataacta | caacttacaa | gccacccact | aattctaatg | ccattcattt | gcctactcca | 1320 |
| ataataagaa | aagctggctt | tactggaata | tagaatctag | agcaacatta | cccgcctcat | 1380 |
| gttagtgagt | aactagtatt | ctaaagttgt | ttgccataca | tatcaagttc | ttctaacctt | 1440 |
| tgaagcaaac | caaacacttt | caaaactcag | ggctcccagg | gctgctgctc | cagattccca | 1500 |
| gcattcagca | tgcttcatta | tgtggagaaa | gacatttcaa | gacaagctgt | atctatacac | 1560 |
| cttcagaagg | aacaaagctc | taagaaggtg | ggattatgtt | aacacatagt | acatggttta | 1620 |
| gcgtttctcc | acatttcaaa | ctcaaaatag | ctcaataata | tgctgctaca | tgagcattga | 1680 |

-continued

```
ttctgaatgt tcataatata aacttcaatt tgaagcaaca atgttacaca gttcagctgt    1740
tattaccaac ctactctgta agttaaaata caaataaaat attaatttta ttgagtaact    1800
aaaaataagt tcccactgac ttaaaatcgt caaatggcta actctctctc aactaagaga    1860
gcaacacaga tggaagcaga gaggacaact gaatataaaa taaaatttgt caatctactc    1920
tataatctgc acttttaaaa tccccttttg catatatgta tgtataggat cacagttgcc    1980
caccaacatt atgtctgtca gccctgcaga taacaattta ctgtaacgtt aacaatttat    2040
gcaatactta gtatgtttta tcttatgtgt acagatttac agtttggaat aaaggcagaa    2100
tgattaaaaa ctattgggtt aaagtcttag tatggtactt acctgcaagg ctgaattaat    2160
tttttggaag gctattcaat agctgaacta aaatgcttgt ttaacaaatc aaaagaggaa    2220
taagactact ttaaaacata ttgaaaaagg taaatcccaa tttgaagatc aatcatataa    2280
cgaaaaaagt atgaagtatc ctttgctctt gcttagaaac acatagcaga acagtagaaa    2340
ctagaactca tgaatataag gtaaacccta ttttcccact gatttccatt atacaattgg    2400
agtgaaaata ccactcaaac aaaaataaac aaaaaatctt agcaggtaat tctgtgtaga    2460
acagccatgt gggaattgtc tatattcag ctgcagggaa tctcatgtaa gctaggagtc    2520
catcttccta tgttgcactc tgcagtgact tctgactccc agtagctcct ctattgccta    2580
ctccatatta cgctaatttt tgcccccctga ctgctatgct tcctgggact cttattaaat    2640
t                                                                   2641
```

<210> SEQ ID NO 145
<211> LENGTH: 490
<212> TYPE: DNA
<213> ORGANISM: Homo sapien

<400> SEQUENCE: 145

```
acatatattt aaagggaaga tggatacaat ttgtttttat tatataaatc taggtaaggt      60
gaaatgcttt tgtcaacaaa atacagtgt agtgaatttt atatttgtcg cttgattagg     120
taaactgaaa actaacaata gaatatttat tttactgcat tgaaatacca tgaactttca     180
gacttgttag ttctacaagc agttgtgcta ccttaatttt gtgtttccag aaataaaaat     240
taaccttagt tatgctgtca ttttaactta ataaaaaaag tataattcat aaaactttg     300 gctttataag ataattataa aattatatat ttttttctgt ttttgtgggg ttgggaaaac     360
attttcttat ttctattcac tcttcaaatg caggtctcat aatatgtgtc aatgatataa     420
gatgatggaa gactttgtaa taaaaacata tgtcattatc ttcaatttgt tccatacata     480
atttaatgtg                                                           490
```

<210> SEQ ID NO 146
<211> LENGTH: 3361
<212> TYPE: DNA
<213> ORGANISM: Homo sapien

<400> SEQUENCE: 146

```
tgatgtgatt tgttcaagaa cctgtattct attccttact gagtgtccct tctttacata      60
gtgtttgctg aattaagccg attgggggc agtggcgcta actggtggaa aaaggaaagt    120
atatatgtta gagttttgaa tgagggataa atagaaagca gaatgaatta atggaaaaga    180
actcggctgt taggccattc tctaaattct agtttagcca aaagtttatg tgtggtttgg    240
ggcttcattt atttatctca tgagtaaaat gggataatac ctaacaggca ggctctggaa    300
gttggatatc acatacacac acacacacac agacacacac acacacgatc aatcatgtag    360
```

-continued

```
ctcatattag atgttcaata ataacagct actacagatg cctatcagtt gagtaagtag      420
ttcattaaat tgagctccca aaggtctctt ctcttcacat ccatatccgt ttctgcagca      480
atcaaataga tacatgattg ttttctgta agaaattact gcaaagagaa tctttttctc      540
ctactaactg ttccttctac ctggtatagg agataaatgt acgtttctta attagctgac      600
tttttagtgt gtcatttctg aaggaaaaat aaattaacct taaagtggca tgtaggtcca      660
attcagtttt cctacatgtt ccaaaatttt atttaaatta ctgtgtccaa aattatgagg      720
acagtgtcat tcattcacca tagtttatat ttttagttat atatcaaact tccttggcac      780
ctaggataag aacatttctt ttgaagttat ccaattttt tttattttta cttgacttga       840
aggaaagttg gaaatatgg tggaaaaaat cttccgcatt aaaaggggga aaaacacaa        900 ccatttacga tctcagtcag cagatttact ctactcaagg aaaaaaaaaa acaatcttat      960
tggaagcaga tgttgacact gtgtcagtta ttgaagacgg aaggagttca cttgagccat     1020
tgcagttaca aaggggtatt gatggcagtt tggattcctg attgatcacc tttgcagcca     1080
agggaaagac agcagaaact gtatgggatc agaaatgaaa tcagcctgcc agtttaatgg     1140
agaggctcct agaaactcat ttttttttctt tcctgtaaga taaaagacat ctttcagaat    1200
aagaaaggct tgtttgagag agaaattaca gtttattctc tgaaaatatt taaaggccaa     1260
agtgcccttt aaatctatta ttaaagcatt gaaactgtta taaaatcat tatagaaaaa      1320 ttaggtaaaa atttttagcct aactttcaac atccattcaa aaacgaatgt tgaaaacaaa    1380 catataaccct ataaaaaagt gaatggctct ggcaagtggg ggcatgggtg gagtccataa    1440
ggaaacctca gtctcaataa cttcaaaatg ttacttttca tggtaacttg gtcatggaga     1500
ttggtcacag cacagacatt tagaattttt tagcaggttt ttttttttctt ttgaatcttg    1560 tagtgctctc tgggaattgc accatgtaca cttttacaac ctacagaaat cgtcattatt     1620
gttaaagtat ctcaacttt ctatttcttt tattgtctat tgtgctttt ttgtttaaaa       1680 atacttttat agttttaaag tattggtcaa agtagtattc tcttgaagtt ctagtcaatt     1740
taatttgatc caataagttt ttctgaatct ccttttttaag ttccaagaaa ttctattata    1800
aataagtgta cttttaccaa ttccattgta taagcaaaca gacacctttt agaaaaggat     1860
aagtaatcat caatttgttt ttttttaaaaa aaaaacaatt tctagactac taaatttggc    1920
ataagaataa ttcttttaaa atgcaacata ctttaattag ttttttttggt atatgcataa    1980 gatgtgaact ttcctattga tatcacttta tattaataga gatgtacatt tctttctatg    2040
ccgtggctag agcaaaagtt aataatgatt atttacacaa ttgatttaat ttcttaggat    2100
atgtataata ttggatatta tatctgattt aaaaatacta ttccatacat tttttttttc    2160
aggagataaa acatagggaa aggttttcat gtgaattctt tgtatcactt tgaagtacat    2220
atatttaaag ggaagatgga tacaatttgt ttttattata taaatctagg taaggtgaaa   2280
tgcttttgtc aacaaaaata cagtgtagtg aattttatat ttgtcacttg attaggtaaa    2340
ctgaaaacta acaatagaaa tattatttta ctgcattgaa ataccatgaa ctttcagact   2400
tgttagttct acaagcagtt gtgctacctt aattttgtgt ttccagaaat aaaaattaac   2460
cttagttatg ctgtcatttt taactaataa aaaagtata attcataaaa cttttggctt    2520
tataagataa ttataaaatt atatatttt ttctgttttt gtgggttgg gaaaacattt    2580 tcttatttct attcactctt caatgcagg tctcataata tgtgtcaatg atataagatg    2640
atggaagact ttgtaataaa aacatatgtc attatcttca atttgttcaa taaataattt   2700
```

```
aatgtgaatt gaatgtttgt attttaacat agcatttgga tttggtctgc atttcttgag    2760
aatttaaagc tcttttgtt tcctccttat tcaattaagc atcttataaa tattttggaa    2820
attacaacat cttaggtgtt attaattaag aagttaattt ctagggccaa gaagtctata    2880
tgttacagca aggaatagat tataaaatac atgtttataa tggaaaagaa aatgaaatgg    2940
ggtatattaa ttacataaca gcaagagtct tgagaatttt ataatacaat gcttctaagg    3000
atattggttg accaaggtgt attttattgt ttttacattt gttgacaggg actctgccat    3060
aagtagtatg aaaaaacaaa caaaaacttt tctacgattc attaacattg aaaagagaat    3120
tccaagacct tgtattctga agaaagctag agttctctca cgtgggcctt caattttctt    3180
attacacgta tctttaatgt gaaagtacta aagtctgaaa atcagcattt aaataataga    3240 cttttccagca ttacagatga aataaatttgg cgcaggcttt ttaactgtct accatattta    3300
gaatgtggtg tcaaaatgag attttttagaa ctgctgtaaa atattactac attactacaa    3360
c                                                                        3361

<210> SEQ ID NO 147
<211> LENGTH: 271
<212> TYPE: DNA
<213> ORGANISM: Homo sapien

<400> SEQUENCE: 147
caggagctgg gcaagcaacg aaggtaagag tcgtagagac ttcggtaaac tggagcacat      60
gattcctggg aaggcaggcc tagtgtaaac aatttatttt tctagaaaag acagaagttt     120
agagtatatg aaatctaatt tttaagtatg gttggcaact aattgactat cgtctaccat     180
aaggttatat gataattatt agggcaggag agtgaatgca tcttaatatg catggcagaa     240
ctgtgtgttt ccttccatct ggattttcat a                                    271

<210> SEQ ID NO 148
<211> LENGTH: 1148
<212> TYPE: DNA
<213> ORGANISM: Homo sapien

<400> SEQUENCE: 148
ggtgaattca ccttatttc agttggtaga gtatggaaaa atgtatcact tatttgaaat       60
acctgaatgg aaacccagcc tctactactg taacttaaca ctgggcagtt acttgttctt     120
cctgagcctc aaattttctt tctctgtaag aatgggaatt aatgcccacc tacgggttgc     180
aagtgcttac aggagctggg caagcaacga aggtaagagt tgtagagact tcggtaaact     240
ggagcacatg attcctggga agcaggccta gtgtaaacaa tttattttc tagaaaagac     300 agaagtttag agtatatgaa atctaatttt taagtattgg ttggcaacta attgactatc     360
gtctaccata aggttatatg ataattatta gggcaggaga gtgaatgcat cttaatatgc     420
atggcagaac tgtgtgtttc cttccatctg gattttcata aagctttctg atttatcagt     480
aacgatctga aaaatgtact gtggcatgta acatctttta ttcattttat taggcattag     540
aggaagaata ttctgtagtc ctgctttatt ctgccatctt tacctggaaa tccattttta     600
taaaattttt gtaataaaaa ttcacttgat cacttgcctg cttttctttta aacagtgcca    660 agcgtaatgc cccttgataa tttacatata tgtgaacgtg gctgtgatag ctgctgatgt    720
tcacacatag gccatcttac atgtaatgat tccatgtttg gacttaaaca gcttcacaca    780
tttattgtac agtaggtgt cacatgcttt tactttttat tttataatct gtatttctgt     840
gaggtagaca ttattggctc catgttatat acattgatag cccggagcta gagattgaac    900
```

```
ccaggccatc ctcccactg cctttcatca tcaacacaac caccaccaac agtattttaa    960
aagtgttaaa tattggcaga cgtgtcattg ttctgagcac taggactagg gcttatgcgg   1020
ctgtctgagg aattccctgt acaaggaaac atcatatacc aaaaagttac tcatggaagg   1080
agtttggaga tgatgagcta aaagtattac acatggacta ttgtaaaaaa aaaaaaaaaa   1140
gcaagctt                                                            1148
```

<210> SEQ ID NO 149
<211> LENGTH: 1139
<212> TYPE: DNA
<213> ORGANISM: Homo sapien

<400> SEQUENCE: 149

```
cgaggtaccc attataatta ctaaactgtg aagtcactat tattagtatc tgaccagcta     60
tacaaaacat catcaatttt acttttgaca caaaaggtag taaaaatcgc aaacgataaa    120
gaagacacta ctcattaaaa gtcatgttta ctaatccagc accataattc cagtctcaga    180
acctcccatg cagattggaa agggattatg ggaacgaggt gagtatgtag acatgtcgg    240
cgctagtaac atcaaattga cggccccata tttgctcgct tcacaagaca aaaacacag    300
ggtcctccca agtaagcag aagatgacat gacggcatgg agacgaaaaa caaaacgcta    360
gcgcgctaaa tcaatggtca atagctgcaa aaccatctga tgacaactag ggtaacttcc    420
cgtgtcaacc aaaaattcac aaacaagtaa gcactacctg tagaacagac acgaagtcac    480
gcaaacctac actttgagca cgcctgacca gagatccgag cacactcccc gacccaccaa    540
cacacagcag gccacgcggt agagagaaca agaatacaaa ggacaagcga gtagctgtag    600
aagcgatgag agagagcgta cgtagagatg ggggaggaac accacgtagg agcagaactg    660
ctgcactgcg tgcacacgcg acgcgaacag acgaaactac acgaagacaa aaggaaaagg    720
aaaggatggg accagagggg agagccaagc atgagagaca caccaaaagg cacccgcacg    780
ctgcatggcg aagcgagaag aacagcagat aaccacaaaa aaaagcacac acggtgggac    840
atacacacca gaggggagc atcagacaca gggacaaacc actaaagcag agaacatgg    900
cgcgaaagga ctgaactaaa cagcacaaac acgcaacgag cagcgaacag ccgatcatag    960
gcgtgacacc cgactacagc aaaagaaacg gagaagttat cgacacaagg gatgacaagg   1020
aaacaggcta atggcccaag gagaggaaca ataagatgga tgagcacagt agggcgaaca   1080
agggataacc caagtgaaga aacagtgaag agaggaatg cacacaataa gaacgcaaa    1139
```

<210> SEQ ID NO 150
<211> LENGTH: 267
<212> TYPE: DNA
<213> ORGANISM: Homo sapien

<400> SEQUENCE: 150

```
actgtagcag tgagctcaag tgttgggtgt atcagctcaa acaccatgt gatgccaatc     60
atctccacag gagcaatttg tttaccaaga atctaagaat taaatcttag aatgtattaa    120
tgttaaattt ctgtgagatt atattgtagt cacgtagaat gtcctgactt gtaggaatac    180
ccactaagga aatcagaaat cacggtagag cgtcagcaat ttactctcaa atggttcaga    240
gaaagaaagt tctttgtagt aaagctt                                       267
```

<210> SEQ ID NO 151
<211> LENGTH: 300
<212> TYPE: DNA

<213> ORGANISM: Homo sapien

<400> SEQUENCE: 151

| | | | | | |
|---|---|---|---|---|---|
| gccgcccggg | caggtacttg | ttttccatgt | gtttgctttt | atccactggc | attttagct | 60 |
| ccttgaagac | atatcatgtg | tgagataact | tccttcacat | ctcccatggt | ccctagcaaa | 120 |
| atgctaggcc | tgtagtagtc | aaggtgctca | gtaaatattt | gtttgggtgg | tttgtgagcc | 180 |
| ttgctgccaa | gtcctgcctt | tgggtcgaca | tagtatggaa | gtatttgaga | gagagaacct | 240 |
| ttccactccc | actgccagga | ttttgtattg | ccatcgggtg | ccaaataaat | gctcatattt | 300 |

<210> SEQ ID NO 152
<211> LENGTH: 956
<212> TYPE: DNA
<213> ORGANISM: Homo sapien

<400> SEQUENCE: 152

| | | | | | |
|---|---|---|---|---|---|
| tgccagattg | gttttaata | taatcctgtt | cacccccctg | cttagaccct | tctgctttct | 60 |
| attacccctc | atttaagatg | taaactcttc | accttggttt | atgagaactg | gttctggcat | 120 |
| tcacctggaa | cctcattaaa | tggtgatttc | ttgctaagct | ccagcccgag | tggtctcctc | 180 |
| tcagcttcta | attttgtgct | ctttcctgcc | cttttcctgg | gccttctcag | ctctccaccc | 240 |
| ccaccactct | tgactcaggt | ggtgtccttc | ttcctcaagt | cttgacaatt | cccgggccct | 300 |
| tcagtccctg | agcagtctac | ttctgtgtct | gtcaccacat | cttgtctttt | ccctcattg | 360 |
| catttattgc | agtttatata | tatgctactt | ttacttgttc | atttctgtct | ccctaccag | 420 |
| gctgtaaatg | agggcagaaa | ccttgtttgt | tttattcacc | atcatgtacc | aagtgcttgg | 480 |
| cacatagtgg | gccttcatta | aatgtttgtt | gaataaaaga | gggaagaagg | caagccaacc | 540 |
| ttagctacaa | tcctaccttt | tgataaaatg | ttccttttga | caatatacac | ggattattat | 600 |
| ttgtactttg | ttttttccatg | tgttttgctt | ttatccactg | gcattttag | ctccttgaag | 660 |
| acatatcatg | tgtgagataa | cttccttcac | atctcccatg | gtccctagca | aaatgctagg | 720 |
| cctgtagtag | tcaaggtgct | caataaatat | ttgtttgggt | ggtttgtgag | ccttgctgcc | 780 |
| aagtcctgcc | tttgggtcga | catagtatgg | aagtatttga | gagagagaac | ctttccactc | 840 |
| ccactgccag | gattttgtat | tgccatcggg | tgccaaataa | atgctcatat | ttattactga | 900 |
| aaaaaaaaaa | aaaaaaaaaa | aaaaaaaaaa | aaaaaaaaaa | aaaaaatga | gcggcc | 956 |

<210> SEQ ID NO 153
<211> LENGTH: 784
<212> TYPE: DNA
<213> ORGANISM: Homo sapien

<400> SEQUENCE: 153

| | | | | | |
|---|---|---|---|---|---|
| acctggcaca | aagcaaacaa | taaatattat | tgttattgtt | gttataattg | taaaatgaat | 60 |
| gacttcaaaa | acatagtccc | agtttggagg | gattttgtga | tgcagaatat | ctaagtcata | 120 |
| gaaatagaag | acaggtggaa | taagtatatg | ttcagagttt | ttagatgtgt | tgagtagaga | 180 |
| cggtaataat | ggaagcatta | aatacaaatg | aaaatcacac | cagatatccc | tgaaattcaa | 240 |
| gcaaagaaag | ttcatcatgt | attcttgggc | agcaagagaa | aggactaggg | ttatggcaat | 300 |
| gtgtggaaaa | gttgaggctt | gctaagggtt | gagatctgtt | ggtagccctg | atcacatgg | 360 |
| ggtcagcacc | aggcagtgcc | tctgaaagcg | gagagaggtc | ctggacttcc | cttgtgtata | 420 |
| acagttccta | gtgtccaaca | atgaggaaac | ggtgaagcat | ggttacaaaa | ctgtgacaaa | 480 |
| aatatttaca | tctagcactg | ttaccactca | catgccaaac | attggctgca | cacgtgcagc | 540 |

```
cttatttgta attaacatca aaagactaga tctgaagcct tccataaatg agagaccatt    600
catatggcat tcctggaaca aaacactgca caggtaccaa ggctctccac tccctgacgg    660
gttggtgctg aacagtcagg gattgtcttg actagacttc tgatgcttct gcatcttctt    720
tcctcttccc ggaattccaa ataaccaatt cataccattg tatttatgct tcgggtaacc    780
tagt                                                                  784
```

<210> SEQ ID NO 154
<211> LENGTH: 2184
<212> TYPE: DNA
<213> ORGANISM: Homo sapien
<220> FEATURE:
<221> NAME/KEY: misc_feature
<222> LOCATION: (1930)..(1930)
<223> OTHER INFORMATION: a, c, g or t

<400> SEQUENCE: 154

```
gaaaaataca ttcccggtgt tagtagttct tcatttcctg tctccaacag aaaattcact     60
cattttagaa ctagtgtaat tcttgataat aaaataagag ttttgattaa gaacagcata    120
gagcttcaaa atgcaaagtg aatgattagt aaaattatgt ctcattttat tttttcagca    180
cccataccac aattaatatt aggctggatt gccatgggaa acattttttg cattaatgc     240 agcaacataa tactcacttt aggtattact acatagttga aggatttaac tgaatgtatg    300
gatcaaattt atttatttga catattcgaa gctgtggttt aataggaatt tgagaaaggt    360
gtaagaaata ggataaaaag aaggtcagca ccatgtacca ggaatagctt tacttttccat   420 acatagaaat ataaatttag tggtatccta tattacttta gtgtcgtacg ctttgtaaga    480
cttaaatatt ttattctatt gattccacta cttttggtatg ttaagacatt tctttaaaga   540
tgaccaacaa tatccttatt ttaggtgcca ctagcagatg taagcgtata cttagttgcc    600
gttagatgtg acagaatgag ataatttatg taaagcagta gagtacctgg cacaaagcaa    660
acaataaata ttattgttat tgttgttata attgtaaaat gaatgacttc aaaaacatag    720
tcccagtttg gagggatttg tgatgcagaa tatctaagtc atagaaatag aagacaggtg    780
gaataagtat atgttcagag ttttagatg tgttgagtag agacggtaat aatggaagca    840
ttaaatacaa atgaaaatca caccagatat ccctgaaatt caagcaaaga aagttcatca    900
tgtattcttg ggcagcaaga gaaaggacta gggttatggc aatgtgtgga aaagttgagg    960
cttgctaagg gttgagatct gttggtagcc ctggatcaca tggggtcagc accaggcagt   1020
gcctctgaaa gcggagagag gtcctggact tcccttgtgt ataacagttc ctagtgtcca   1080
acaatgagga aacggtgaag catggttaca aaactgtgac aaaaatattt acatctagca   1140
ctgttaccac tcacatgcca acattggct gcacacgtgc agccttattt gtaattaaca    1200
tcaaaagact agatctgaag ccttccataa atgagaggcc attcatatgg cattcctgga    1260
acaaaacact gcacaggtac cagcctctcc actcctgacc gggttggtgc tgaacagtca   1320
gggattgttc ttgaactaga cttctgatgc ttccttgcaat cttctttcat ctttccctga   1380
aatacacaaa ataaacaaat acaataacaa atagtaatta aatgactttc aggataacat   1440
ctagttgttc agacttcacc cttcacaggt gtgtgtgtat gtgtgtttat gtctgtatat   1500
tgaagcaatt tgaatttatt tactgtatat tttctgagta aaagactgaa atgaactact   1560
tggttcagat catggtgtcc attggtgaca ttgtttggag gcataatatt ctttatatgg   1620
aaaatccttt aattccacag ttagttacct cagattcaga atatgaatac tgtttataat   1680
```

| | |
|---|---|
| acgcttttgt aggaatgaat tcgaaaggta gttgtcagta aacaaaagca caacaaacta | 1740 |
| atctcagagt ctgccctgat ggctgtgata gggacagaaa gctaaaccct actgctgacg | 1800 |
| cgccccgcac attgggcgca gaatttccca agaaaacggg gcaaatcacc gccacggtcc | 1860 |
| taactctgaa ctctatacgg gccatctcgc ctaaaccact acaaggcacg cacgggaaag | 1920 |
| gactctccgn tcgcgactcg caagcctacg gcccccgaac gacaggcgca ccacgacacc | 1980 |
| accggcgcgt ctacgagaca tgatcagcgt caagggcacc tgaaaaaacg atgccccaac | 2040 |
| tagtgcggcc cgcaaccagg cagacactaa gcttgatagc acagcgactg caccaagagc | 2100 |
| taatcacgca cacaaccaaa gacagaaact acccactcta tcactacacg gacgacacta | 2160 |
| gaaacaaccct gcaattgtta ctgc | 2184 |

<210> SEQ ID NO 155
<211> LENGTH: 418
<212> TYPE: DNA
<213> ORGANISM: Homo sapien

<400> SEQUENCE: 155

| | |
|---|---|
| actgtgctta ttaatctact tactaaattt tcacattgac atttttgggg atgatactac | 60 |
| catatacgaa atggaaaatg taatatgctc agtgcttctg taaaatgcag caatactggt | 120 |
| attactttac atcagtaggc atctttgaca tgagcatata aatattttgt tgactcagca | 180 |
| aaggtgacac tttgtggact aaagtatccc attatatata atgttttttg aaatgttgga | 240 |
| aattttgggg aattatcaaa tgtatagaag ttgcatgaag gttatagaga ggtgtaactg | 300 |
| tttgttaact attacatgga tttcatacta ggcagtgaca actaacatgt tacttcaact | 360 |
| aaaagtgtat aatgggttgt cttttttattt atgaaacata acaagtaatt ttacttac | 418 |

<210> SEQ ID NO 156
<211> LENGTH: 941
<212> TYPE: DNA
<213> ORGANISM: Homo sapien

<400> SEQUENCE: 156

| | |
|---|---|
| tgagtttttt tcttgaacat acagaagtac taaatactgc ttgcagtata atattgatat | 60 |
| tggaagctgc agtttccaga ataagtggag taataactaa acagacattt aattttattt | 120 |
| caatatctat ggaaaaaaca cttgattaaa tctccctgta ttttatgttg tctctattac | 180 |
| agaatcactt gtctgtttgt tgtgtgccac ttactgacaa aactttaaac agtacttgat | 240 |
| gccagctctc tactctgtgg ctgcgggacc tgtttctttt aggtacttgt gcttattaat | 300 |
| ctacttacta aattttcaca ttgacatttt tggggatgat actaccatat acgaaatgga | 360 |
| aaatgtaata tgctcagtgc ttctgtaaaa tgcagcaata ctggtattac tttacatcag | 420 |
| taggcatctt tgacatgagc atataaatat tttgttgact cagcaaaggt gacactttgt | 480 |
| gactaaagta tcccattata tataatgttt tttgaaatgt tggaaatttt ggggaattat | 540 |
| caaatgtata gaagttgcat gaaggttata gagaggtgta actgtttgtt aactattaca | 600 |
| tggatttcat actaggcagt gacaactaac atgttacttc aactaaaagt gtataatggg | 660 |
| ttgtcttttt atttatgaaa ataaagtaa ttttacttac aatttcattg agatcttttg | 720 |
| tttttcgaca atatttttta tacttactaa gccagtagca gttaaaacag tgcaaaatta | 780 |
| ttcttcacag taatgttttta aaatgacaga taaccaggca tggtggctta cgcctataat | 840 |
| cctagcattt taggaggctt gggcaggaag attgcttgag cccaggagtt gagaccagcc | 900 |
| tggacaacgt ggtgaaaccc tgtctctgta aaaaaaaaaa a | 941 |

<210> SEQ ID NO 157
<211> LENGTH: 740
<212> TYPE: DNA
<213> ORGANISM: Homo sapien

<400> SEQUENCE: 157

| | | | | | |
|---|---|---|---|---|---|
| acttaagcaa | atactgagta | gtgttttaaa | ttcagaaata | gagcttctat | tatgaacaca | 60 |
| tgagaatgat | tttttctct | taatcattat | taaggaaata | ttttaatttc | atggtcatat | 120 |
| aatggtgata | agtaatacct | gattgtttcc | ttttctgttc | tagtaactca | gaggagatac | 180 |
| gtgttttatt | tgtgatagca | aattcctaaa | tgaacattag | gcaagtggta | tcattatcag | 240 |
| gccagctgca | gcctcttgcc | ttgacctgca | ttcctagaat | ttctttgttg | ctgtaattct | 300 |
| tgattaagtg | accttgactt | tcattttgta | attttgctaa | tcatcagcaa | attcacttgc | 360 |
| atgacgttac | tgccaaatat | gaaggcagtt | gaattattat | gagtgattgt | ggcagaggtt | 420 |
| tgtgccatgg | tgaaaacttt | gatgtttgtc | tgtgttcatt | ggatccatct | ttttaaatga | 480 |
| cattaccatg | agtctgttgt | caaacctaaa | tatctttgtt | tgaatttaa | atgggactct | 540 |
| atattgttgt | agttcaggtc | ttcattgact | aagagattga | gagaaatctg | acataagaaa | 600 |
| atattgtttt | cactgcagga | ataaagagga | agtaacagtg | aaaaaaaaaa | caaaaaaaaa | 660 |
| aaaaaaacaa | aaaagggcgg | ggggaacagg | gcaaagggt | cccgggggga | aaatgttccg | 720 |
| ggccaaatca | caaaaaaaaa | | | | | 740 |

<210> SEQ ID NO 158
<211> LENGTH: 1888
<212> TYPE: DNA
<213> ORGANISM: Homo sapien

<400> SEQUENCE: 158

| | | | | | |
|---|---|---|---|---|---|
| aaggatcctt | aattaaatta | atcccccccc | ccgaaccgtt | cgctaactga | aatgatggcg | 60 |
| actggaacgc | cagagtctca | agcgcggttc | ggtcagtccg | tgaagggct | tctcacggag | 120 |
| aaggtgacca | cctgtggtac | tgacgtaatc | gcgctcacca | agcaggtgct | gaaaggctcc | 180 |
| cggagctccg | agctgctagg | tcaggcagct | cgaaacatgg | tactccagga | agatgccatc | 240 |
| ttgcactcag | aagatagttt | aaggaagatg | gcaataataa | caacacatct | tcaataccag | 300 |
| caagaagcta | ttcagaagaa | tgttgaacag | tcatcggatc | tacaggacca | gttgaatcat | 360 |
| ctgttgaaat | agaatgacat | gtaagagtgc | tgtaggactc | ctttgcctaa | tgctgaggag | 420 |
| taaatacctt | acacagctgt | cctctgggtt | tggttttcta | ttttcttctc | caaaagttaa | 480 |
| gttagaaaag | ttctgtgtta | gggccgggcg | cggtagctca | cgcctgtaat | cccagcactt | 540 |
| tgggaggccg | aggcgggtgg | atcacgaggt | caggagttcg | agaccagcct | ggccaagatg | 600 |
| gtgaaacccc | gtctctacta | aaaatacaaa | aattagctg | gcgtggtgg | cgggcgcctg | 660 |
| taatcccagc | tactcgggaa | gctgaggcaa | gagaatcgct | tgaacccagg | aggtggaggt | 720 |
| tgcagtgagc | caagatcgcg | ccactgcact | ccagcctggg | cgacagagtg | agattccatc | 780 |
| tccaaaaaaa | aaaaaaagaa | aaaaaaaag | aaagttctg | tgttgatgta | cagtttctcc | 840 |
| taagaagaag | cgaggtggtt | gaattttgga | agcacttctt | gaatcggatt | aacccatgct | 900 |
| cttattgaat | tttttcatct | gctctgttta | gtttgatatt | aaagcaaaat | taagaggtct | 960 |
| tagttttttcc | tatagaactt | ttaatatgtc | aaaagctata | ttgtctaaat | ttcagtactt | 1020 |
| aagcaaatac | tgagtagtgt | tttaaattca | gaaatagagc | ttctattatg | aacacatgag | 1080 |

```
aatgattttt ttctcttaat cattattaag gaaatatttt aatttcatgg tcatataatg   1140
gtgataagta atacctgatt gtttcctttt ctgttctagt aactcagagg agatacgtgt   1200
tttatttgtg atagcaaatt cctaaatgaa cattaggcaa gtggtatcat tatcaggcca   1260
gctgcagcct cttgccttga cctgcattcc tagaatttct ttgttgctgt aattcttgat   1320
taagtgacct tgactttcat tttgtaattt tgctaatcat cagcaaattc acttgcatga   1380
cgttactgcc aaatatgaag gcagttgaat tattatgagt gattgtggca gaggtttgtg   1440
ccatggtgaa aactttgatg tttgtctgtg ttcattggat ccatcttttt aaatgacatt   1500
accatgagtc tgttgtcaaa cctaaatatc tttgtttgaa tttaaaatgg gactctatat   1560
tgttgtagtt caggtcttca ttgactaaga gattgagaga atctgacat  aagaaaatat   1620 tgttttcact gcaggaataa agaggaagta acagtgaatc caatatagtt catattgtta   1680
ttgtccaatc atcaagttaa ctaagcatta tcagattacg tttatttctc atacatatgg   1740
atattaactt aaggtaaaaa agctggatgt gaaggatctg aaaaggcatt aatttatgta   1800
ctaattctat aaacatgtat taataattgc agtattatta aatacagatg gactcaaaaa   1860
aaaaaaaaaa aaaaaaaaaa tatgcggc                                     1888

<210> SEQ ID NO 159
<211> LENGTH: 417
<212> TYPE: DNA
<213> ORGANISM: Homo sapien

<400> SEQUENCE: 159
ccgcccgggc aggtacatac atattctccg ttttgtgctt gcttttgcat cgggtcataa     60
gggtaaaagc agttagttgt attgtggagt tttgcatggg tgcagttaac aatggatgtt    120
tcatcagctg agtttaattt agtattctct cttcattcta tttggtcttg aaataaattc    180
ttttgcattc atttaaatat taggattgat caggaaatag tgtttgtaat ctacacgttt    240
atttgagcct ttaaaaatat ttctgaacag agatttaagc tctgtcagta ttttcattta    300
ctgatagcat ttatatttta aatatggcat tgtatatttc attattatcc ttcataacag    360
aattataatg agaatatgaa tttgttattt ttcttgttgg tagatgtgaa aatggtg       417

<210> SEQ ID NO 160
<211> LENGTH: 1545
<212> TYPE: DNA
<213> ORGANISM: Homo sapien

<400> SEQUENCE: 160
tccttctctt catgtacatg tctgtgcaca tgcacgcaca aatacatttg taatctcact     60 cattacctttt acatttttgtt tatcagtatt taaacagctg aactgcaatc atgacctaga   120
atatggctta tgttatgggc aggtctgttt gaggactgct tggaagagtc agaggcagag    180
gaatttgcta ttgtaagcaa aggtgacatt gctgagccat caggaagcgc tgtggctatt    240
tctggaaaca aagatgtcat attaaaattg gataagtgag agttggtcat gtgcattggt    300
ggcatatctg ggagaagagg aaaacttggt tgagcaaacc caacaggtct gggaggagat    360
tacaaatgta tttgtgcgtg catgtgcaca gacatgtaca tgaagagaag gattgtgtgt    420
gtgtgtctgt ataatcagtt ttcagttatc ttcatgaatg tagggaagcc atgtcagatg    480
cagatactgg gttgtcagat aaacaagtta tctttcgttt tcaactgcat ggtgtacttt    540
tttattttcc atagtagatt tacatttcca agttgatatt tcctaaatat ctaattagct    600 ggaaatttggg ggagatcatc ttgtcatgta ctgggtagta ggagggagcc tagactttaa   660
```

```
acttgattgt tgataactta tggaatatgt aggtaagttg ctactgaata aatataggca    720
gcttgataaa acacagtggc tcataatcaa gtgctggcta atgtcagcat ctagaacagc    780
ttcttaccta tgacagatgt tgaactgatg ttgagtttaa tgtccgtagt taaagtcaag    840
cagttagcaa ataaataaaa gcaatcagcc tttattctca aagtttggtt tagatacagg    900
cttctttcta aattataaca atgcataaat tatctgaatt ttatgtcttg ttcttcaaat    960
tagggagctg tgttacccct taatgtgcca agattattta aagcaaaggt cttccttaga   1020
caattattta gccgtaaata tagaaagcta aaaagttaag tacatacata ttctccgttt   1080
tgtgcttgca ttttgcatcg ggtcataagg gtaaaagcag ttagttgtat tgtggagttt   1140
tgcatgggtg cagttaacaa tggatgtttc atcagctgag tttaatttag tattctctct   1200
tcattctatt tatttggtct tgaaataaat tctttttgcat tcatttaaat attaggattg   1260
atcaggaaat agtgtttgta atctacacgt ttatttgagc cttactttaa aaatatttct   1320
gaacagagat ttaagctctg tcagtatttt catttactga tagcatttat attttaaata   1380
tggcattgta tatttcatta ttatccttca taacagaatt ataatgagaa tatgaatttg   1440
ttatttttct tgttggtaga tgtgaaatgg tgcttcaaaa aatatatagt ctttctgtaa   1500
aaaaaaaaaa aaaaaaaaaa ttctgcggcg caagaattct tgtta                  1545

<210> SEQ ID NO 161
<211> LENGTH: 196
<212> TYPE: DNA
<213> ORGANISM: Homo sapien

<400> SEQUENCE: 161
acagtatgtg gcccatgggg tgggggaacc ctgctcttaa ggttcccaat tatcagctct     60
gaggtagttc aagcaacaga gccccttgac gatgttcagg gagatagtcc cgatatccca    120 aggggggccaa ttagattcta atggtgttaa aacacatctt aaggtttatt gtaaaaatat    180
ctactctcct aagctt                                                    196

<210> SEQ ID NO 162
<211> LENGTH: 1128
<212> TYPE: DNA
<213> ORGANISM: Homo sapien

<400> SEQUENCE: 162
tacattgatt gtacacttta tttctattat tattacactg taatatgtaa tgaaagaatc     60
atacactgaa ccataattca gaatcagtgg gagccctgag cttgttttcc tgcaactaga    120
cggtcccatc tgggggtgat gggagacggt aacagatcat caggaattag attctcataa    180
ggagcgtgaa acctagatcc ctcacgtgca cagttcacga tagggctcat gctcctctga    240
gaatctactg ctgtgctgag ctgacaggag gtggagctga ggccgtaatg ctcactcgcc    300
caccacgccc ctcctgctgt gtgacccggg tcctgatgga ccatggacca gtaccagtat    360
gtggcccagg ggttggggaa ccctgctctt aaggttccca attatcagct ctgaggtagt    420
tcaagcaaca gagccccttg acgatgttca gggagatagt cccgatatcc taagggggcc    480
aattagattc taatggtgtt aaaacacatc ttaattttta ttgtaaaaat atctactctc    540
ctaagcttag aacaatattg agaagaaatg aagtggatgt tggaagccct gggggtggg    600 ccttcacagt ggggaaggct gtgggtggag agccagggca tcgggtaggt gaaggccagg    660
gatgccactc agcatcctgt agggcccggt atagcccgca gcagcacaga atgatcccaa    720
```

| | |
|---|---|
| ggctaagaaa cctctatcta gaatgctctt gaatgttcta gaaccgaggt tctttctttt | 780 |
| cttttctttt cttttttcaag acaggaaagt gcttatcaca agaacccccc gatctcgact | 840 |
| ggggaagggt tggcagttga ctctctggcc agcactatgt gtagcacgca tcactagagg | 900 |
| tgtgaaggcc ccacagaggc tctggtgtgt ggctttgttt tgaccaaggc gtgcaggcag | 960 |
| tggtcctacg gcagggctgg cccgcgcctc gcctcagtgc cctcagcgcc ttctgtcttc | 1020 |
| tggctggatt cagagtcccg ggggaaagag actgaccttc tcgacttgcc ctcaggttga | 1080 |
| ttacgaagcc tcagagccct tgttcaaggc agtcctggag gacacgac | 1128 |

<210> SEQ ID NO 163
<211> LENGTH: 870
<212> TYPE: DNA
<213> ORGANISM: Homo sapien

<400> SEQUENCE: 163

| | |
|---|---|
| tacgcattta ttttagact gaacctaaag taggttgttc ttttaacaaa gggtttaatt | 60 |
| cgggtgggga atataacata tcaaaataca tgaaccaatg gaaagttact tctagaaaag | 120 |
| caaagaaatt gggtatcatt tttgtttctt gggaagctaa ttttgttgaa tgtttagaat | 180 |
| tgagcaaaga tgtaaatttt tgaagggcag tttagaaaaa ttaacttgtg aatgaactta | 240 |
| agatgtctgt actctatatg tgatgctgtg cagttgtttt tatatggaaa gatgtcaact | 300 |
| atagccataa ccaataaaat aaaaactgat gaggcatgca gctttcagca catctttat | 360 |
| acatgaagaa attaatttgt gttgctatgg tgttgaaata ccaagatgt tctgtatcta | 420 |
| tgtaaacatg attcctttaa taaatgtatt ttattattaa caaacacaaa aaaaaaacaa | 480 |
| aaaaaaaag cgggggcgcc accggggcca agcggcccgg ggggcagggt ttcccgccca | 540 |
| aattcccccca ataatgaaac caagaggtca agcaccaaga ctatataaac cgctttatat | 600 |
| acgagagtgt atatcatgga catcttagga ggagtgagac aaaggggtgg ggcggaggac | 660 |
| tcaatgatga agactgcaga cggagggtga ggagggaggg cagcgcagac aggcgaggcg | 720 |
| aaggagagtg agaaagtagt ggagttatca gcgaggagct ttcacgggta ggaggaggga | 780 |
| agatagttgt ggaggaggaa cgacgcgtgg agcgggggtgt aggggaggca agatagtggt | 840 |
| gtaggagacc gattgacgag gggcagggga | 870 |

<210> SEQ ID NO 164
<211> LENGTH: 1186
<212> TYPE: DNA
<213> ORGANISM: Homo sapien

<400> SEQUENCE: 164

| | |
|---|---|
| catcacttaa cgccgggatt atacacattc tagaaatgat ggtgggaatg atttgccttt | 60 |
| aaaagcctac aaattaaaag gggaaagatg ctaagctaga tgctggtttt ctgtaaagat | 120 |
| gaatttgtag gcttttaaag gcaaatcatt cccaccatca cttaacgccg ggattataca | 180 |
| cattctagaa atgattctga gaggagtgta tagtatggtg cctatctaca ctcacatgat | 240 |
| attcttattc acgtttttttt taaccataag tggcaaatat tttaaaatat ttgaaaaaca | 300 |
| ctccagaatc tagtacgctt tattttttaga ctgaacctaa agtaggttgt tcttttaaca | 360 |
| aagggtttaa ttcgggtggg gaatataaca tatcaaaata catgaacaaa tggaaagtta | 420 |
| cttctagaaa agcaaagaaa ttgggtatca ttttttgtttc ttgggaagct aattttgttg | 480 |
| aatgtttaga attgagcaaa gatgtaaatt tttgaagggc agtttagaaa aattaacttt | 540 |
| gtgaatgaac ttaagatgtc tgtactctat atgtgatgct gtgcagtttg tttttatatg | 600 |

-continued

```
gaaagatgtc aactatagcc ataaccaata aaataaaaac tgatgaggca tgcagctttc      660
agcacatttt ttatacatga agaaattaat tttgggttgc tatggtgttg aaaaatccaa      720
gatgttttgg atttatgtaa acatgattcc tttaataaat tgtattttat tattaacaaa      780
cacaaaaaaa aaacaaaaaa aaaagcggg ggcgccaccg gggccaagcg gcccgggggg       840 cagggttttcc cgcccaaatt cccccaataa tgaaaccaag aggtcaagca ccaagactat     900
ataaaccgct ttatatacga gagtgtatat catggacatc ttaggaggag tgagacaaag      960
gggtggggcg gaggactcaa tgatgaagac tgcagacgga gggtgaggag ggagggcagc    1020
gcagacaggc gaggcgaagg agagtgagaa agtagtggag ttatcagcga ggagctttca    1080
cgggtaggag gagggaagat agttgtggag gaggaacgac gcgtggagcg gggtgtaggg    1140
gaggcaagat agtggtgtag gagaccgatt gacgaggggc agggga                     1186
```

<210> SEQ ID NO 165
<211> LENGTH: 96
<212> TYPE: PRT
<213> ORGANISM: Homo sapien

<400> SEQUENCE: 165

Met Ala Phe Ile Leu Ala Arg Thr Val Gln Ile Val Thr Arg Lys Ile
1               5                   10                  15

Arg Asp Gly Lys Tyr Glu Gln Leu Tyr Phe Asn Arg Cys Arg Lys Gln
                20                  25                  30

Ile Phe Phe Thr Val Glu Ile Trp Leu Leu Asn Leu Trp Gly Leu His
            35                  40                  45

Thr Ser His Leu Glu Thr Arg Leu Gly Gln Leu His Val Glu Arg Asn
        50                  55                  60

Asn Leu Leu Pro Asp His Ile Ser Thr Leu Lys Glu Val Phe Ile Thr
65                  70                  75                  80

Arg Leu Phe Phe Leu Lys Thr Pro Asn Arg Pro Arg Val Thr Lys Asn
                85                  90                  95

<210> SEQ ID NO 166
<211> LENGTH: 54
<212> TYPE: PRT
<213> ORGANISM: Homo sapien

<400> SEQUENCE: 166

Met Cys Arg Val Pro Ser Pro Lys Val Asn Leu Glu Pro Leu Asp Asn
1               5                   10                  15

Thr Asn Lys Asn Ile Tyr Phe Thr Ser Val Ile Tyr Leu Glu Asn Val
                20                  25                  30

Leu Ser Ile Leu His Ile Phe Leu Ile Lys Ser Thr Gly Asp His Cys
            35                  40                  45

Glu Val Asp Ile Leu Phe
        50

<210> SEQ ID NO 167
<211> LENGTH: 50
<212> TYPE: PRT
<213> ORGANISM: Homo sapien

<400> SEQUENCE: 167

Met Val Phe Tyr Tyr Tyr Tyr Gly Phe Lys Lys Ser Asn Phe Ile
1               5                   10                  15

Ser Phe Cys Lys Glu Leu Ser Asn Ile Leu Tyr Arg Phe Cys Glu Arg

```
                    20                  25                  30
Thr Tyr Phe Leu Thr Val Ile Phe Ile Ser Phe Lys Ile Phe Val Ser
            35                  40                  45

His Leu
    50

<210> SEQ ID NO 168
<211> LENGTH: 229
<212> TYPE: PRT
<213> ORGANISM: Homo sapien

<400> SEQUENCE: 168

Met Ala Glu Met Glu Ser Ser Leu Glu Ala Ser Phe Ser Ser Ser
1               5                   10                  15

Gly Ala Val Ser Gly Ala Ser Gly Phe Leu Pro Pro Ala Arg Ser Arg
            20                  25                  30

Ile Phe Lys Ile Ile Val Ile Gly Asp Ser Asn Val Gly Lys Thr Cys
        35                  40                  45

Leu Thr Tyr Arg Phe Cys Ala Gly Arg Phe Pro Asp Arg Thr Glu Ala
    50                  55                  60

Thr Ile Gly Val Asp Phe Arg Glu Arg Ala Val Glu Ile Asp Gly Glu
65                  70                  75                  80

Arg Ile Lys Ile Gln Leu Trp Asp Thr Ala Gly Gln Glu Arg Phe Arg
                85                  90                  95

Lys Ser Met Val Gln His Tyr Tyr Arg Asn Val His Ala Val Val Phe
            100                 105                 110

Val Tyr Asp Met Thr Asn Met Ala Ser Phe His Ser Leu Pro Ser Trp
        115                 120                 125

Ile Glu Glu Cys Lys Gln His Leu Leu Ala Asn Asp Ile Pro Arg Ile
    130                 135                 140

Leu Val Gly Asn Lys Cys Asp Leu Arg Ser Ala Ile Gln Val Pro Thr
145                 150                 155                 160

Asp Leu Ala Gln Lys Phe Ala Asp Thr His Ser Met Pro Leu Phe Glu
                165                 170                 175

Thr Ser Ala Lys Asn Pro Asn Asp Asn Asp His Val Glu Ala Ile Phe
            180                 185                 190

Met Thr Leu Ala His Lys Leu Lys Ser His Lys Pro Leu Met Leu Ser
        195                 200                 205

Gln Pro Pro Asp Asn Gly Ile Ile Leu Lys Pro Glu Pro Lys Pro Ala
    210                 215                 220

Met Thr Cys Trp Cys
225

<210> SEQ ID NO 169
<211> LENGTH: 56
<212> TYPE: PRT
<213> ORGANISM: Homo sapien

<400> SEQUENCE: 169

Met Tyr Leu Lys Glu Lys Tyr Pro Asp Leu Lys Pro Thr Ala Asp Val
1               5                   10                  15

Ala Asn Phe His Thr Thr Ala Gly His Gly Ser Leu Leu Thr Thr His
            20                  25                  30

Cys His Leu Arg Leu Cys Leu Cys Phe Ile Gln Arg Glu Arg Gly Gly
        35                  40                  45

Leu Lys Gly Met Leu Pro Gly Gly
```

```
                           50                  55

<210> SEQ ID NO 170
<211> LENGTH: 34
<212> TYPE: PRT
<213> ORGANISM: Homo sapien

<400> SEQUENCE: 170

Met Thr Ser Val Tyr Ala Thr Leu Gly Ser Leu Pro Asp Tyr Lys Val
1               5                   10                  15

Pro Phe Met Gly Cys Thr Met Phe Thr Leu Val Ser Gln Glu Asn Ser
            20                  25                  30

Ser Ala

<210> SEQ ID NO 171
<211> LENGTH: 77
<212> TYPE: PRT
<213> ORGANISM: Homo sapien

<400> SEQUENCE: 171

Met Val Tyr Asn Leu Tyr Ser Phe Gly Leu Lys Val Thr Thr Arg Arg
1               5                   10                  15

Ile Arg Glu Ser Pro Gln Asn Pro Gly Ala Gly Leu Leu Ser Ile Leu
            20                  25                  30

Leu Ile Thr Leu Val Phe Ser Ser Val Asn Lys Ile Ile Leu Leu Phe
        35                  40                  45

Gln Lys Lys Lys Gln Lys Lys Gly Val Gly Tyr Pro Gly Pro Lys Ala
    50                  55                  60

Phe Pro Gly Trp Asn Leu Phe Pro Pro Ile Lys Pro Lys
65                  70                  75

<210> SEQ ID NO 172
<211> LENGTH: 43
<212> TYPE: PRT
<213> ORGANISM: Homo sapien

<400> SEQUENCE: 172

Met Gln Glu Phe Thr Trp Leu Phe Glu Lys Glu Asn Phe Lys Val Ser
1               5                   10                  15

Gly Trp Thr Glu Ser His Glu Ala Arg Ser Leu Leu Thr Ala Arg Ser
            20                  25                  30

Leu Glu Lys Gln Val Ser Gly Ser Phe Thr Ser
        35                  40

<210> SEQ ID NO 173
<211> LENGTH: 39
<212> TYPE: PRT
<213> ORGANISM: Homo sapien

<400> SEQUENCE: 173

Met Thr Gln Leu Tyr Met Thr Leu Ser Ser Tyr Gln His Tyr His Asn
1               5                   10                  15

Ser Asn Ile Asn Asn Tyr Asn Lys Ser His Tyr Tyr Ser Leu Glu Ala
            20                  25                  30

Leu Val Gln Asn Arg Phe Tyr
        35

<210> SEQ ID NO 174
<211> LENGTH: 48
<212> TYPE: PRT
```

<213> ORGANISM: Homo sapien

<400> SEQUENCE: 174

Met Leu Lys Gly His Tyr Gln Tyr Gly Met Glu Asp Leu Ser Phe His
1               5                   10                  15

Thr Phe Ser Ser Ser Phe Leu Asn Phe Leu Leu Phe Leu Leu Ser
            20                  25                  30

Cys Met Val Ala Pro Phe Pro Phe Leu Leu Ser Val Pro Ser Lys Gln
        35                  40                  45

<210> SEQ ID NO 175
<211> LENGTH: 108
<212> TYPE: PRT
<213> ORGANISM: Homo sapien

<400> SEQUENCE: 175

Phe Leu Lys Arg Gln Ser Ile Ser Leu Leu Pro Gln Leu Glu Cys Ser
1               5                   10                  15

Gly Thr Ile Ile Val His His Thr Leu Glu Leu Leu Gly Lys Gly Ser
            20                  25                  30

Ser Leu Ala Ser Ala Ser Gln Val Ala Arg Tyr Thr Gly Met Cys Tyr
        35                  40                  45

His Ala Trp Leu Ile Lys Lys Ile Phe Leu Glu Met Arg Ser Cys Cys
    50                  55                  60

Val Ala Gln Ala Gly Leu Lys Leu Leu Gly Ser Asn Pro Pro Thr
65                  70                  75                  80

Leu Ala Ser Gln Ser Ala Gly Ile Thr Gly Val Ser His Ser Thr Ala
                85                  90                  95

Pro Tyr Leu Gln Ile Leu Asn Gln Ala Ile Ala Ile
            100                 105

<210> SEQ ID NO 176
<211> LENGTH: 48
<212> TYPE: PRT
<213> ORGANISM: Homo sapien

<400> SEQUENCE: 176

Met Val His Ile Thr Phe Ile Gln His Leu Leu Glu Pro Arg His Cys
1               5                   10                  15

Asn Tyr Met Phe Phe Leu Val Thr Tyr Phe Val Arg Ser Cys Phe Leu
            20                  25                  30

Ala Thr Ser Asp Tyr Ser Lys His Arg Lys Phe Asn Lys Thr Ile Phe
        35                  40                  45

<210> SEQ ID NO 177
<211> LENGTH: 302
<212> TYPE: PRT
<213> ORGANISM: Homo sapien

<400> SEQUENCE: 177

Trp Ser Ala Asn Asn Trp Glu Ile His Thr His Thr Lys Asn Leu Asn
1               5                   10                  15

Pro Tyr Leu Thr Pro Asp Thr Lys Ala Thr Phe Lys Ala Ile Ile Gly
            20                  25                  30

Leu Thr Ala Arg Ala Lys Thr Met Gln Leu Pro Glu Ser Phe Cys Gln
        35                  40                  45

Lys Glu Asn Thr Gly Glu Asn Leu Ser Asp Leu Gly Val Gly Lys Asp
    50                  55                  60

```
Phe Leu Arg His Lys Lys His Glu Val Ala Arg Gly Lys Ile Ala Lys
 65                  70                  75                  80

Leu Asp Phe Ile Gln Val Lys Asn Phe Ala Ser Leu Lys Asp Thr Phe
                 85                  90                  95

Lys Lys Met Lys Lys Tyr Ala Leu Gly Trp Glu Lys Ile Phe Ala Glu
            100                 105                 110

Arg Val Ser Asp Arg Gly Cys Val Ser Arg Arg Tyr Lys Glu Leu Ala
        115                 120                 125

Thr Gln Glu Leu Lys Asp Asn Pro Ile Arg Lys Gly Gly Asn Asn Leu
    130                 135                 140

Asn Lys Val His Gln Arg Ile Ala Met Ala Asn Lys His Met Lys Arg
145                 150                 155                 160

Cys Pro Lys Ser Ala Val Ile Arg Glu Ile Ala Ile Ala Thr Ile Met
                165                 170                 175

Arg Tyr His Cys Ile Leu Pro Arg Met Ala Val Met Asn Ala Asp Ala
            180                 185                 190

Ser His Gly Asp Lys Asn Gly Gly Ser Ser Gly Thr Leu Ile His Ala
        195                 200                 205

Arg Ala Glu Cys Glu Met Asp Gln Leu Leu Trp Lys Thr Ile Gly Gln
    210                 215                 220

Phe Leu Ser Lys Val Asn Val Lys Met Pro Tyr Asp Ser Ser Ile Pro
225                 230                 235                 240

Phe Leu Ile Ile Gln Glu Lys Ala Asn Cys Ile Ser Thr Lys Lys Thr
                245                 250                 255

Cys Thr Gln Thr Phe Thr Ala Ala Ile Tyr Leu Leu Val Ile Ala Lys
            260                 265                 270

Asn Cys Lys Gln Leu Pro Tyr Pro Ser Ser Val Trp Ile Asn Lys Ile
        275                 280                 285

Trp Cys Ile Tyr Thr Met Glu Tyr Tyr Ser Ala Ile Lys Arg
    290                 295                 300

<210> SEQ ID NO 178
<211> LENGTH: 47
<212> TYPE: PRT
<213> ORGANISM: Homo sapien

<400> SEQUENCE: 178

Met Leu Thr Leu Thr Phe Cys Ile Tyr Arg His Phe Leu Tyr Phe Leu
 1               5                  10                  15

His Phe Ser Tyr Val Asn Pro Pro His Ser Pro His Ile Ile Ile His
             20                  25                  30

Tyr Asp His Glu Gly Phe Ile Pro Gly Tyr Ser Leu Ile Glu Asn
         35                  40                  45

<210> SEQ ID NO 179
<211> LENGTH: 85
<212> TYPE: PRT
<213> ORGANISM: Homo sapien

<400> SEQUENCE: 179

Met Gly Gly Asn Gly Ser Thr Cys Lys Pro Asp Thr Glu Arg Gln Gly
 1               5                  10                  15

Thr Leu Ser Thr Ala Ala Pro Thr Thr Ser Pro Ala Pro Cys Leu Ser
             20                  25                  30

Asn His His Asn Lys Lys His Leu Ile Leu Ala Phe Cys Ala Gly Val
         35                  40                  45
```

```
Leu Leu Thr Leu Leu Leu Ile Ala Phe Ile Phe Leu Ile Ile Lys Ser
    50                  55                  60

Tyr Arg Lys Tyr His Ser Lys Pro Gln Ala Pro Asp Pro His Ser Asp
65                  70                  75                  80

Pro Pro Ala Lys Leu
            85

<210> SEQ ID NO 180
<211> LENGTH: 102
<212> TYPE: PRT
<213> ORGANISM: Homo sapien

<400> SEQUENCE: 180

Asn Gly Ser Thr Cys Lys Pro Asp Thr Glu Arg Gln Gly Thr Leu Ser
1               5                   10                  15

Thr Ala Ala Pro Thr Thr Ser Pro Ala Pro Cys Leu Ser Asn His His
            20                  25                  30

Asn Lys Lys His Leu Ile Leu Ala Phe Cys Ala Gly Val Leu Leu Thr
        35                  40                  45

Leu Leu Leu Ile Ala Phe Ile Phe Leu Ile Ile Lys Ser Tyr Arg Lys
    50                  55                  60

Tyr His Ser Lys Pro Gln Ala Pro Asp Pro His Ser Asp Pro Pro Ala
65                  70                  75                  80

Lys Leu Ser Ser Ile Pro Gly Glu Ser Leu Thr Tyr Ala Ser Thr Thr
                85                  90                  95

Phe Lys Leu Ser Glu Asp
            100

<210> SEQ ID NO 181
<211> LENGTH: 56
<212> TYPE: PRT
<213> ORGANISM: Homo sapien

<400> SEQUENCE: 181

Met Trp Ala Asp Ile Tyr Lys Asp Val Arg Arg Val Ala Gln Ser Val
1               5                   10                  15

Phe Phe Phe Val Phe Phe Ser Thr Gln Ala Leu Ile His Phe Ser Asp
            20                  25                  30

Val Phe Pro Lys Asn Glu Thr Tyr Ile Phe Pro Gln Pro Val Leu Arg
        35                  40                  45

Ser Ser Lys Cys Leu Thr Lys Lys
    50                  55

<210> SEQ ID NO 182
<211> LENGTH: 742
<212> TYPE: PRT
<213> ORGANISM: Homo sapien

<400> SEQUENCE: 182

Gly Lys Pro Phe Cys Asn Asn Glu Thr Phe Gly Gln Tyr Pro Leu Gln
1               5                   10                  15

Val Asn Gly Tyr Arg Asn Leu Asp Glu Cys Leu Glu Gly Ala Met Val
            20                  25                  30

Glu Gly Asp Val Glu Leu Leu Pro Ser Asp His Ser Val Lys Tyr Gly
        35                  40                  45

Gln Glu Arg Trp Phe Thr Lys Leu Pro Pro Val Leu Thr Glu Phe Leu
    50                  55                  60

Ser Arg Phe Glu Phe Asn Gln Ser Leu Gly Gln Pro Glu Lys Ile His
```

-continued

```
            65                  70                  75                  80
Asn Lys Leu Glu Phe Pro Gln Ile Ile Tyr Met Asp Arg Tyr Met Tyr
                    85                  90                  95
Arg Ser Lys Glu Leu Ile Arg Asn Lys Arg Glu Cys Ile Arg Lys Leu
                100                 105                 110
Lys Glu Glu Ile Lys Ile Leu Gln Gln Lys Leu Glu Arg Tyr Val Lys
                115                 120                 125
Tyr Gly Ser Gly Pro Ala Arg Phe Pro Leu Pro Asp Met Leu Lys Tyr
            130                 135                 140
Val Ile Glu Phe Ala Ser Thr Lys Pro Ala Ser Glu Ser Cys Pro Pro
145                 150                 155                 160
Glu Ser Asp Thr His Met Thr Leu Pro Leu Ser Ser Val His Cys Ser
                165                 170                 175
Val Ser Asp Gln Thr Ser Lys Glu Ser Thr Ser Thr Glu Ser Ser Ser
                180                 185                 190
Gln Asp Val Glu Ser Thr Phe Ser Ser Pro Glu Asp Ser Leu Pro Lys
                195                 200                 205
Ser Lys Pro Leu Thr Ser Ser Arg Ser Ser Met Glu Met Pro Ser Gln
210                 215                 220
Pro Ala Pro Arg Thr Val Thr Asp Glu Glu Ile Asn Phe Val Lys Thr
225                 230                 235                 240
Cys Leu Gln Arg Trp Arg Ser Glu Ile Glu Gln Asp Ile Gln Asp Leu
                245                 250                 255
Lys Thr Cys Ile Ala Ser Thr Thr Gln Thr Ile Glu Gln Met Tyr Cys
                260                 265                 270
Asp Pro Leu Leu Arg Gln Val Pro Tyr Arg Leu His Ala Val Leu Val
                275                 280                 285
His Glu Gly Gln Ala Asn Ala Gly His Tyr Trp Ala Tyr Ile Tyr Asn
            290                 295                 300
Gln Pro Arg Gln Ser Trp Leu Lys Tyr Asn Asp Ile Ser Val Thr Glu
305                 310                 315                 320
Ser Ser Trp Glu Glu Val Glu Arg Asp Ser Tyr Gly Gly Leu Arg Asn
                325                 330                 335
Val Ser Ala Tyr Cys Leu Met Tyr Ile Asn Asp Lys Leu Pro Tyr Phe
                340                 345                 350
Asn Ala Glu Ala Ala Pro Thr Glu Ser Asp Gln Met Ser Glu Val Glu
            355                 360                 365
Ala Leu Ser Val Glu Leu Lys His Tyr Ile Gln Glu Asp Asn Trp Arg
            370                 375                 380
Phe Glu Gln Glu Val Glu Glu Trp Glu Glu Glu Gln Ser Cys Lys Ile
385                 390                 395                 400
Pro Gln Met Glu Ser Ser Thr Asn Ser Ser Ser Gln Asp Tyr Ser Thr
                405                 410                 415
Ser Gln Glu Pro Ser Val Ala Ser Ser His Gly Val Arg Cys Leu Ser
                420                 425                 430
Ser Glu His Ala Val Ile Val Lys Glu Gln Thr Ala Gln Ala Ile Ala
                435                 440                 445
Asn Thr Ala Arg Ala Tyr Glu Lys Ser Gly Val Glu Ala Leu Ser
            450                 455                 460
Glu Ala Phe His Glu Glu Tyr Ser Arg Leu Tyr Gln Leu Ala Lys Glu
465                 470                 475                 480
Thr Pro Thr Ser His Ser Asp Pro Arg Leu Gln His Val Leu Val Tyr
                485                 490                 495
```

```
Phe Phe Gln Asn Glu Ala Pro Lys Arg Val Glu Arg Thr Leu Leu
            500                 505                 510
Glu Gln Phe Ala Asp Lys Asn Leu Ser Tyr Asp Glu Arg Ser Ile Ser
        515                 520                 525
Ile Met Lys Val Ala Gln Ala Lys Leu Lys Glu Ile Gly Pro Asp Asp
    530                 535                 540
Met Asn Met Glu Glu Tyr Lys Lys Trp His Glu Asp Tyr Ser Leu Phe
545                 550                 555                 560
Arg Lys Val Ser Val Tyr Leu Leu Thr Gly Leu Glu Leu Tyr Gln Lys
                565                 570                 575
Gly Lys Tyr Gln Glu Ala Leu Ser Tyr Leu Val Tyr Ala Tyr Gln Ser
            580                 585                 590
Asn Ala Ala Leu Leu Met Lys Gly Pro Arg Arg Gly Val Lys Glu Ser
        595                 600                 605
Val Ile Ala Leu Tyr Arg Arg Lys Cys Leu Leu Glu Leu Asn Ala Lys
    610                 615                 620
Ala Ala Ser Leu Phe Glu Thr Asn Asp Asp His Ser Val Thr Glu Gly
625                 630                 635                 640
Ile Asn Val Met Asn Glu Leu Ile Ile Pro Cys Ile His Leu Ile Ile
                645                 650                 655
Asn Asn Asp Ile Ser Lys Asp Asp Leu Asp Ala Ile Glu Val Met Arg
            660                 665                 670
Asn His Trp Cys Ser Tyr Leu Gly Gln Asp Ile Ala Glu Asn Leu Gln
        675                 680                 685
Leu Cys Leu Gly Glu Phe Leu Pro Arg Leu Leu Asp Pro Ser Ala Glu
    690                 695                 700
Ile Ile Val Leu Lys Glu Pro Pro Thr Ile Arg Pro Asn Ser Pro Tyr
705                 710                 715                 720
Asp Leu Cys Ser Arg Phe Ala Ala Val Met Glu Ser Ile Gln Gly Val
                725                 730                 735
Ser Thr Val Thr Val Lys
            740

<210> SEQ ID NO 183
<211> LENGTH: 50
<212> TYPE: PRT
<213> ORGANISM: Homo sapien

<400> SEQUENCE: 183

Met Met Tyr Val Cys Ile Phe His Tyr Ile Phe Leu Phe Phe Tyr Asn
1               5                   10                  15
Trp Val Leu Asn Ile Phe Gly Arg Lys Ile Ile Ile Leu Ser Leu Leu
            20                  25                  30
Lys Ile Asn Met His Asn Leu Pro Leu Tyr Ile Ala Tyr Asn Ile Leu
        35                  40                  45
Met Met
    50

<210> SEQ ID NO 184
<211> LENGTH: 1518
<212> TYPE: PRT
<213> ORGANISM: Homo sapien

<400> SEQUENCE: 184

Met Cys Lys Lys Leu Ser Gly Asn His Leu Asn Pro Glu Pro Asn Gln
1               5                   10                  15
```

```
Pro Ala Pro Ser Val Asp Leu Asp Phe Leu Glu Asp Asp Ile Leu Gly
            20                  25                  30

Ser Pro Ala Thr Gly Gly Gly Gly Gly Ser Gly Gly Ala Asp Gln
        35                  40                  45

Pro Cys Asp Ile Leu Gln Gln Ser Leu Gln Glu Ala Asn Ile Thr Glu
            50                  55                  60

Gln Thr Leu Glu Ala Glu Ala Glu Leu Asp Leu Gly Pro Phe Gln Leu
65                  70                  75                  80

Pro Thr Leu Gln Pro Ala Asp Gly Gly Ala Gly Pro Thr Gly Ala Gly
                85                  90                  95

Gly Ala Ala Ala Val Ala Ala Gly Pro Gln Ala Leu Phe Pro Gly Ser
            100                 105                 110

Thr Asp Leu Leu Gly Leu Gln Gly Pro Pro Thr Val Leu Thr His Gln
            115                 120                 125

Ala Leu Val Pro Pro Gln Asp Val Val Asn Lys Ala Leu Ser Val Gln
        130                 135                 140

Pro Phe Leu Gln Pro Val Gly Leu Gly Asn Val Thr Leu Gln Pro Ile
145                 150                 155                 160

Pro Gly Leu Gln Gly Leu Pro Asn Gly Ser Pro Gly Gly Ala Thr Ala
                165                 170                 175

Ala Thr Leu Gly Leu Ala Pro Ile Gln Val Val Gly Gln Pro Val Met
            180                 185                 190

Ala Leu Asn Thr Pro Thr Ser Gln Leu Leu Ala Lys Gln Val Pro Val
            195                 200                 205

Ser Gly Tyr Leu Ala Ser Ala Ala Gly Pro Ser Glu Pro Val Thr Leu
        210                 215                 220

Ala Ser Ala Gly Val Ser Pro Gln Gly Ala Gly Leu Val Ile Gln Lys
225                 230                 235                 240

Asn Leu Ser Ala Ala Val Ala Thr Thr Leu Asn Gly Asn Ser Val Phe
                245                 250                 255

Gly Gly Ala Gly Ala Ala Ser Ala Pro Thr Gly Thr Pro Ser Gly Gln
            260                 265                 270

Pro Leu Ala Val Ala Pro Gly Leu Gly Ser Ser Pro Leu Val Pro Ala
            275                 280                 285

Pro Asn Val Ile Leu His Arg Thr Pro Thr Pro Ile Gln Pro Lys Pro
290                 295                 300

Ala Gly Val Leu Pro Pro Lys Leu Tyr Gln Leu Thr Pro Lys Pro Phe
305                 310                 315                 320

Ala Pro Ala Gly Ala Thr Leu Thr Ile Gln Gly Glu Pro Gly Ala Leu
                325                 330                 335

Pro Gln Gln Pro Lys Ala Pro Gln Asn Leu Thr Phe Met Ala Ala Gly
            340                 345                 350

Lys Ala Gly Gln Asn Val Val Leu Ser Gly Phe Pro Ala Pro Ala Leu
            355                 360                 365

Gln Ala Asn Val Phe Lys Gln Pro Ala Thr Thr Thr Gly Ala Ala
        370                 375                 380

Pro Pro Gln Pro Pro Gly Ala Leu Ser Lys Pro Met Ser Val His Leu
385                 390                 395                 400

Leu Asn Gln Gly Ser Ser Ile Val Ile Pro Ala Gln His Met Leu Pro
                405                 410                 415

Gly Gln Asn Gln Phe Leu Leu Pro Gly Ala Pro Ala Val Gln Leu Pro
            420                 425                 430
```

-continued

```
Gln Gln Leu Ser Ala Leu Pro Ala Asn Val Gly Gly Gln Ile Leu Ala
        435                 440                 445
Ala Ala Ala Pro His Thr Gly Gly Gln Leu Ile Ala Asn Pro Ile Leu
    450                 455                 460
Thr Asn Gln Asn Leu Ala Gly Pro Leu Ser Leu Gly Pro Val Leu Ala
465                 470                 475                 480
Pro His Ser Gly Ala His Ser Ala His Ile Leu Ser Ala Ala Pro Ile
                485                 490                 495
Gln Val Gly Gln Pro Ala Leu Phe Gln Met Pro Val Ser Leu Ala Ala
            500                 505                 510
Gly Ser Leu Pro Thr Gln Ser Gln Pro Ala Pro Ala Gly Pro Ala Ala
        515                 520                 525
Thr Thr Val Leu Gln Gly Val Thr Leu Pro Pro Ser Ala Val Ala Met
    530                 535                 540
Leu Asn Thr Pro Asp Gly Leu Val Gln Pro Ala Thr Pro Ala Ala Ala
545                 550                 555                 560
Thr Gly Glu Ala Ala Pro Val Leu Thr Val Gln Pro Ala Pro Gln Ala
                565                 570                 575
Pro Pro Ala Val Ser Thr Pro Leu Pro Leu Gly Leu Gln Gln Pro Gln
            580                 585                 590
Ala Gln Gln Pro Pro Gln Ala Pro Thr Pro Gln Ala Ala Ala Pro Pro
        595                 600                 605
Gln Ala Thr Thr Pro Gln Pro Ser Pro Gly Leu Ala Ser Ser Pro Glu
    610                 615                 620
Lys Ile Val Leu Gly Gln Pro Pro Ser Ala Thr Pro Thr Ala Ile Leu
625                 630                 635                 640
Thr Gln Asp Ser Leu Gln Met Phe Leu Pro Gln Glu Arg Ser Gln Gln
                645                 650                 655
Pro Leu Ser Ala Glu Gly Pro His Leu Ser Val Pro Ala Ser Val Ile
            660                 665                 670
Val Ser Ala Pro Pro Ala Gln Asp Pro Ala Pro Ala Thr Pro Val
        675                 680                 685
Ala Lys Gly Ala Gly Leu Gly Pro Gln Ala Pro Asp Ser Gln Ala Ser
    690                 695                 700
Pro Ala Pro Ala Pro Gln Ile Pro Ala Ala Pro Leu Lys Gly Pro
705                 710                 715                 720
Gly Pro Ser Ser Pro Ser Leu Pro His Gln Ala Pro Leu Gly Asp
                725                 730                 735
Ser Pro His Leu Pro Ser Pro His Pro Thr Arg Pro Pro Ser Arg Pro
            740                 745                 750
Pro Ser Arg Pro Gln Ser Val Ser Arg Pro Pro Ser Glu Pro Pro Leu
        755                 760                 765
His Pro Cys Pro Pro Gln Ala Pro Thr Leu Pro Gly Ile Phe
    770                 775                 780
Val Ile Gln Asn Gln Leu Gly Val Pro Pro Ala Ser Asn Pro Ala
785                 790                 795                 800
Pro Thr Ala Pro Gly Pro Pro Gln Pro Leu Arg Pro Gln Ser Gln
                805                 810                 815
Pro Pro Glu Gly Pro Leu Pro Ala Pro His Leu Pro Pro Ser Ser
            820                 825                 830
Thr Ser Ser Ala Val Ala Ser Ser Glu Thr Ser Ser Arg Leu Pro
        835                 840                 845
Ala Pro Thr Pro Ser Asp Phe Gln Leu Gln Phe Pro Pro Ser Gln Gly
```

-continued

```
            850                 855                 860
Pro His Lys Ser Pro Thr Pro Pro Thr Leu His Leu Val Pro Glu
865                 870                 875                 880

Pro Ala Ala Pro Pro Pro Pro Pro Arg Thr Phe Gln Met Val Thr
                885                 890                 895

Thr Pro Phe Pro Ala Leu Pro Gln Pro Lys Ala Leu Leu Glu Arg Phe
            900                 905                 910

His Gln Val Pro Ser Gly Ile Ile Leu Gln Asn Lys Ala Gly Gly Ala
                915                 920                 925

Pro Ala Ala Pro Gln Thr Ser Thr Ser Leu Gly Pro Leu Thr Ser Pro
930                 935                 940

Ala Ala Ser Val Leu Val Ser Gly Gln Ala Pro Ser Gly Thr Pro Thr
945                 950                 955                 960

Ala Pro Ser His Ala Pro Ala Pro Ala Pro Met Ala Ala Thr Gly Leu
                965                 970                 975

Pro Pro Leu Leu Pro Ala Glu Asn Lys Ala Phe Ala Ser Asn Leu Pro
                980                 985                 990

Thr Leu Asn Val Ala Lys Ala Ala  Ser Ser Gly Pro Gly  Lys Pro Ser
                995                 1000                1005

Gly Leu  Gln Tyr Glu Ser Lys  Leu Ser Gly Leu Lys  Lys Pro Pro
    1010                1015                1020

Thr Leu  Gln Pro Ser Lys Glu  Ala Cys Phe Leu Glu  His Leu His
    1025                1030                1035

Lys His  Gln Gly Ser Val Leu  His Pro Asp Tyr Lys  Thr Ala Phe
    1040                1045                1050

Pro Ser  Phe Glu Asp Ala Leu  His Arg Leu Leu Pro  Tyr His Val
    1055                1060                1065

Tyr Gln  Gly Ala Leu Pro Ser  Pro Ser Asp Tyr His  Lys Val Asp
    1070                1075                1080

Glu Glu  Phe Glu Thr Val Ser  Thr Gln Leu Leu Lys  Arg Thr Gln
    1085                1090                1095

Ala Met  Leu Asn Lys Tyr Arg  Leu Leu Leu Leu Glu  Glu Ser Arg
    1100                1105                1110

Arg Val  Ser Pro Ser Ala Glu  Met Val Met Ile Asp  Arg Met Phe
    1115                1120                1125

Ile Gln  Glu Glu Lys Thr Thr  Leu Ala Leu Asp Lys  Gln Leu Ala
    1130                1135                1140

Lys Glu  Lys Pro Asp Glu Tyr  Val Ser Ser Ser Arg  Ser Leu Gly
    1145                1150                1155

Leu Pro  Ile Ala Ala Ser Ser  Glu Gly His Arg Leu  Pro Gly His
    1160                1165                1170

Gly Pro  Leu Ser Ser Ser Ala  Pro Gly Ala Ser Thr  Gln Pro Pro
    1175                1180                1185

Pro His  Leu Pro Thr Lys Leu  Val Ile Arg His Gly  Gly Ala Gly
    1190                1195                1200

Gly Ser  Pro Ser Val Thr Trp  Ala Arg Ala Ser Ser  Ser Leu Ser
    1205                1210                1215

Ser Ser  Ser Ser Ser Ser Ser  Ala Ala Ser Ser Leu  Asp Ala Asp
    1220                1225                1230

Glu Asp  Gly Pro Met Pro Ser  Arg Asn Arg Pro Pro  Ile Lys Thr
    1235                1240                1245

Tyr Glu  Ala Arg Ser Arg Ile  Gly Leu Lys Leu Lys  Ile Lys Gln
    1250                1255                1260
```

-continued

```
Glu Ala Gly Leu Ser Lys Val Val His Asn Thr Ala Leu Asp Pro
    1265                1270                1275

Val His Gln Pro Pro Pro Pro Ala Thr Leu Lys Val Ala Glu
    1280                1285                1290

Pro Pro Pro Arg Pro Pro Pro Pro Pro Thr Gly Gln Met
    1295                1300                1305

Asn Gly Thr Val Asp His Pro Pro Ala Ala Pro Glu Arg Lys
    1310                1315                1320

Pro Leu Gly Thr Ala Pro His Cys Pro Arg Leu Pro Leu Arg Lys
    1325                1330                1335

Thr Tyr Arg Glu Asn Val Gly Gly Pro Gly Ala Pro Glu Gly Thr
    1340                1345                1350

Pro Ala Gly Arg Ala Arg Gly Gly Ser Pro Ala Pro Leu Pro Ala
    1355                1360                1365

Lys Val Asp Glu Ala Thr Ser Gly Leu Ile Arg Glu Leu Ala Ala
    1370                1375                1380

Val Glu Asp Glu Leu Tyr Gln Arg Met Leu Lys Gly Pro Pro Pro
    1385                1390                1395

Glu Pro Ala Ala Ser Ala Ala Gln Gly Thr Gly Asp Pro Asp Trp
    1400                1405                1410

Glu Ala Pro Gly Leu Pro Pro Ala Lys Arg Arg Lys Ser Glu Ser
    1415                1420                1425

Pro Asp Val Asp Gln Ala Ser Phe Ser Ser Asp Ser Pro Gln Asp
    1430                1435                1440

Asp Thr Leu Thr Glu His Leu Gln Ser Ala Ile Asp Ser Ile Leu
    1445                1450                1455

Asn Leu Gln Gln Ala Pro Gly Arg Thr Pro Ala Pro Ser Tyr Pro
    1460                1465                1470

His Ala Ala Ser Ala Gly Thr Pro Ala Ser Pro Pro Leu His
    1475                1480                1485

Arg Pro Glu Ala Tyr Pro Pro Ser Ser His Asn Gly Gly Leu Gly
    1490                1495                1500

Ala Arg Thr Leu Thr Arg Gly Leu Gly Ala Arg Thr Leu Thr Arg
    1505                1510                1515
```

<210> SEQ ID NO 185
<211> LENGTH: 42
<212> TYPE: PRT
<213> ORGANISM: Homo sapien

<400> SEQUENCE: 185

```
Met Lys His Gly Ser Phe Tyr Phe Thr Val Ser Asn Leu Ile Ala Ser
1               5                   10                  15

His Leu Lys Ser Ala Lys Ile Glu Leu Pro Lys Lys Cys Tyr Met Pro
                20                  25                  30

Lys Gly Ala His Asn Tyr Leu Met Ala Asn
            35                  40
```

<210> SEQ ID NO 186
<211> LENGTH: 96
<212> TYPE: PRT
<213> ORGANISM: Homo sapien

<400> SEQUENCE: 186

```
Met Met Leu Gly Gln Asp Ser Ile Leu Asn Gln Ser Asn Ser Ile Phe
1               5                   10                  15
```

```
Gly Cys Ile Phe Tyr Thr Leu Gln Leu Leu Gly Cys Leu Arg Thr
            20                  25                  30

Arg Trp Ala Ser Val Leu Ile Leu Ser Ser Leu Val Ser Leu Ala
            35                  40                  45

Gly Ser Val Tyr Leu Ala Trp Ile Leu Phe Phe Val Leu Tyr Asp Phe
 50                      55                  60

Cys Ile Val Cys Ile Thr Thr Tyr Ala Ile Asn Val Ser Leu Met Trp
 65                  70                  75                  80

Leu Ser Phe Arg Lys Val Gln Glu Pro Gln Gly Lys Ala Lys Arg His
                85                  90                  95
```

<210> SEQ ID NO 187
<211> LENGTH: 105
<212> TYPE: PRT
<213> ORGANISM: Homo sapien

<400> SEQUENCE: 187

```
Trp Gly Arg Gly Ile Gly Leu Val Glu His Val Leu Gly Gln Asp Ser
 1               5                  10                  15

Ile Leu Asn Gln Ser Asn Ser Ile Phe Gly Cys Ile Phe Tyr Thr Leu
            20                  25                  30

Gln Leu Leu Gly Cys Leu Arg Thr Arg Trp Ala Ser Val Leu Met
            35                  40                  45

Leu Leu Ser Ser Leu Val Ser Leu Ala Gly Ser Val Tyr Leu Ala Trp
 50                      55                  60

Ile Leu Phe Phe Val Leu Tyr Asp Phe Cys Ile Val Cys Ile Thr Thr
 65                  70                  75                  80

Tyr Ala Ile Asn Val Ser Leu Met Trp Leu Ser Phe Arg Lys Val Gln
                85                  90                  95

Glu Pro Gln Gly Lys Ala Lys Arg His
                100                 105
```

<210> SEQ ID NO 188
<211> LENGTH: 59
<212> TYPE: PRT
<213> ORGANISM: Homo sapien

<400> SEQUENCE: 188

```
Met Gly Lys Lys Ala His Arg His Leu Gln Phe Thr Ser Phe Lys Phe
 1               5                  10                  15

Leu Lys Thr Pro Gln Lys Lys Pro Phe Leu Pro Gly Lys Ala His
            20                  25                  30

Glu Ile Asn Tyr Arg Ile Glu Leu Tyr Asn Ser Thr Ser Thr Ser Leu
            35                  40                  45

Thr Leu Met Cys Phe Ala Lys Asn Leu Glu Lys
 50                      55
```

<210> SEQ ID NO 189
<211> LENGTH: 400
<212> TYPE: PRT
<213> ORGANISM: Homo sapien

<400> SEQUENCE: 189

```
Met Ala Trp Arg Arg Arg Glu Ala Gly Val Gly Ala Arg Gly Val Leu
 1               5                  10                  15

Ala Leu Ala Leu Leu Ala Leu Ala Leu Cys Val Pro Gly Ala Arg Gly
            20                  25                  30
```

Arg Ala Leu Glu Trp Phe Ser Ala Val Val Asn Ile Glu Tyr Val Asp
        35                  40                  45

Pro Gln Thr Asn Leu Thr Val Trp Ser Val Ser Glu Ser Gly Arg Phe
    50                  55                  60

Gly Asp Ser Ser Pro Lys Glu Gly Ala His Gly Leu Val Gly Val Pro
65                  70                  75                  80

Trp Ala Pro Gly Gly Asp Leu Glu Gly Cys Ala Pro Asp Thr Arg Phe
                85                  90                  95

Phe Val Pro Glu Pro Gly Gly Arg Gly Ala Ala Pro Trp Val Ala Leu
                100                 105                 110

Val Ala Arg Gly Gly Cys Thr Phe Lys Asp Lys Val Leu Val Ala Ala
            115                 120                 125

Arg Arg Asn Ala Ser Ala Val Val Leu Tyr Asn Glu Glu Arg Tyr Gly
        130                 135                 140

Asn Ile Thr Leu Pro Met Ser His Ala Gly Thr Gly Asn Ile Val Val
145                 150                 155                 160

Ile Met Ile Ser Tyr Pro Lys Gly Arg Glu Ile Leu Glu Leu Val Gln
                165                 170                 175

Lys Gly Ile Pro Val Thr Met Thr Ile Gly Val Gly Thr Arg His Val
                180                 185                 190

Gln Glu Phe Ile Ser Gly Gln Ser Val Val Phe Val Ala Ile Ala Phe
            195                 200                 205

Ile Thr Met Met Ile Ile Ser Leu Ala Trp Leu Ile Phe Tyr Tyr Ile
        210                 215                 220

Gln Arg Phe Leu Tyr Thr Gly Ser Gln Ile Gly Ser Gln Ser His Arg
225                 230                 235                 240

Lys Glu Thr Lys Lys Val Ile Gly Gln Leu Leu Leu His Thr Val Lys
                245                 250                 255

His Gly Glu Lys Gly Ile Asp Val Asp Ala Glu Asn Cys Ala Val Cys
                260                 265                 270

Ile Glu Asn Phe Lys Val Lys Asp Ile Ile Arg Ile Leu Pro Cys Lys
            275                 280                 285

His Ile Phe His Arg Ile Cys Ile Asp Pro Trp Leu Leu Asp His Arg
        290                 295                 300

Thr Cys Pro Met Cys Lys Leu Asp Val Ile Lys Ala Leu Gly Tyr Trp
305                 310                 315                 320

Gly Glu Pro Gly Asp Val Gln Glu Met Pro Ala Pro Glu Ser Pro Pro
                325                 330                 335

Gly Arg Asp Pro Ala Ala Asn Leu Ser Leu Ala Leu Pro Asp Asp Asp
            340                 345                 350

Gly Ser Asp Glu Ser Ser Pro Pro Ser Ala Ser Pro Ala Glu Ser Glu
        355                 360                 365

Pro Gln Cys Asp Pro Ser Phe Lys Gly Asp Ala Gly Glu Asn Thr Ala
    370                 375                 380

Leu Leu Glu Ala Gly Arg Ser Asp Ser Arg His Gly Gly Pro Ile Ser
385                 390                 395                 400

<210> SEQ ID NO 190
<211> LENGTH: 46
<212> TYPE: PRT
<213> ORGANISM: Homo sapien

<400> SEQUENCE: 190

Met Gly Glu Leu Gly Pro Gly Lys Lys Phe Pro Pro Gly Thr Pro Leu
1               5                   10                  15

```
Trp Pro Arg Val Pro Gln Ala Phe Phe Phe Phe Leu Phe Phe
            20                  25                  30

Phe Phe Gln Cys Ile Ser Ser Met Phe Leu Leu Gly Lys Asn
        35                  40                  45
```

<210> SEQ ID NO 191
<211> LENGTH: 37
<212> TYPE: PRT
<213> ORGANISM: Homo sapien

<400> SEQUENCE: 191

```
Met Asn Ile Pro Thr Asn Ala Tyr Asp Leu Gly Tyr Gln Cys Ile Leu
1               5                   10                  15

Ser His Leu Gly Phe Cys Phe Cys Leu Ser Val Tyr Trp Lys Leu Val
            20                  25                  30

Pro Arg Arg Asp His
            35
```

<210> SEQ ID NO 192
<211> LENGTH: 60
<212> TYPE: PRT
<213> ORGANISM: Homo sapien

<400> SEQUENCE: 192

```
Met Val Pro Phe Lys Glu Lys Asn Thr Lys Gln Gln Lys Thr Thr Ala
1               5                   10                  15

Gln Asp Gly Lys His Arg Asp Lys Pro Arg Thr Thr Gly Glu Asn Lys
            20                  25                  30

Lys Asn Arg Thr Glu Ile Gln Gln Lys Asn Pro Lys Gln Arg Glu Thr
            35                  40                  45

Gln Pro Gln Gln Arg Gly Glu Lys Lys Ala Lys
        50                  55                  60
```

<210> SEQ ID NO 193
<211> LENGTH: 81
<212> TYPE: PRT
<213> ORGANISM: Homo sapien

<400> SEQUENCE: 193

```
Met Lys Ile Cys Lys Arg Leu Phe Tyr Val Val Ala Leu Ile Pro Tyr
1               5                   10                  15

Thr Gln Gln Leu Pro Val Leu Gly Thr Phe Gln Ile Ser Asp Leu Arg
            20                  25                  30

Glu Gln Thr Val Phe Ser Ala Ser Tyr Gly Ala Met Gln Ala Leu Pro
            35                  40                  45

Arg Pro Trp Leu Ser Pro Lys Ser His Val Leu Ser Val Leu His Leu
        50                  55                  60

Lys Arg Val Arg Glu Arg Arg Gly Gly Glu Lys Gly Ala Ser Gly Ala
65                  70                  75                  80

Arg
```

<210> SEQ ID NO 194
<211> LENGTH: 80
<212> TYPE: PRT
<213> ORGANISM: Homo sapien

<400> SEQUENCE: 194

```
Met Gly Met Gln Val Pro Cys Ile Ser Trp Tyr Leu Ser Ala Phe Pro
1               5                   10                  15
```

```
Leu Ala Ala Pro Pro Thr Arg Gly Arg Phe Leu Leu Asp Cys Lys Cys
            20                  25                  30

Leu Phe Ser Leu Asp Ser Ala Leu Thr Ala Pro Pro Gly Arg Pro
        35                  40                  45

Ser Arg Thr Ser Ser Ser Gly Ser Ser Ser Ser Asp Pro Ile Gly Thr
 50                  55                  60

Pro Asp Leu Asn Leu Phe Pro Gly Ser Arg Ala Cys Ser Pro Ser Gln
 65                  70                  75                  80
```

<210> SEQ ID NO 195
<211> LENGTH: 101
<212> TYPE: PRT
<213> ORGANISM: Homo sapien

<400> SEQUENCE: 195

```
Phe Leu Phe Phe Phe Phe Leu Arg Gln Asn Leu Ala Leu Val Thr
 1               5                  10                  15

Gln Ala Gly Val Gln Trp Tyr Asp Leu Ser Ser Leu Gln Pro Gln Arg
            20                  25                  30

Pro Gly Phe Lys Arg Phe Ser Cys Leu Ser Trp Asp His Arg Arg Pro
        35                  40                  45

Pro Pro Cys Leu Ala Asn Phe Gly Ile Val Val Glu Met Gly Phe His
 50                  55                  60

His Val Gly Gln Ala Gly Leu Glu Leu Leu Thr Ser Ser Asp Pro Pro
 65                  70                  75                  80

Thr Ser Ala Ser Gln Thr Ala Gly Ile Thr Gly Met Ser His Leu Ala
            85                  90                  95

Arg Leu Thr Arg Ser
            100
```

<210> SEQ ID NO 196
<211> LENGTH: 16
<212> TYPE: PRT
<213> ORGANISM: Homo sapien

<400> SEQUENCE: 196

```
Met Pro His Val Val Leu Lys Thr Leu Pro Ser Leu Pro Ala Pro Pro
 1               5                  10                  15
```

<210> SEQ ID NO 197
<211> LENGTH: 78
<212> TYPE: PRT
<213> ORGANISM: Homo sapien

<400> SEQUENCE: 197

```
Met Glu Val Ile Ser Ser Phe Leu Gly Ser Lys Leu Lys Gly Gly Gly
 1               5                  10                  15

Ser Phe Val Asn Thr Thr Asn Tyr Ile Arg Lys Ala Ser Pro Ile Pro
            20                  25                  30

His Ser Lys Ser Ile Thr Ala Leu Glu Met Ser Asn Asn Asp Leu Ser
        35                  40                  45

Cys Ser Arg Leu Lys Gln Arg Pro Cys His Met Ile Val Leu Gly Leu
 50                  55                  60

Asn Val Cys Gly Pro Val Leu Tyr Thr Leu Val Pro Asp Pro
 65                  70                  75
```

<210> SEQ ID NO 198
<211> LENGTH: 928

-continued

```
<212> TYPE: PRT
<213> ORGANISM: Homo sapien

<400> SEQUENCE: 198

Asn Leu Cys Ser Leu Ile Ile Pro Leu Arg Glu Val Thr Ile Val Glu
1               5                   10                  15

Lys Ala Asp Ser Ser Val Leu Pro Ser Pro Leu Ser Ile Ser Thr
            20                  25                  30

Arg Asn Arg Met Thr Phe Leu Phe Ala Asn Leu Lys Asp Arg Asp Phe
            35                  40                  45

Leu Val Gln Arg Ile Ser Asp Phe Leu Gln Gln Thr Thr Ser Lys Ile
50                  55                  60

Tyr Ser Asp Lys Glu Phe Ala Gly Ser Tyr Asn Ser Ser Asp Asp Glu
65                  70                  75                  80

Val Tyr Ser Arg Pro Ser Ser Leu Val Ser Ser Pro Gln Arg Ser
                85                  90                  95

Thr Ser Ser Asp Ala Asp Gly Glu Arg Gln Phe Asn Leu Asn Gly Asn
                100                 105                 110

Ser Val Pro Thr Ala Thr Gln Thr Leu Met Thr Met Tyr Arg Arg Arg
            115                 120                 125

Ser Pro Glu Glu Phe Asn Pro Lys Leu Ala Lys Glu Phe Leu Lys Glu
            130                 135                 140

Gln Ala Trp Lys Ile His Phe Ala Glu Tyr Gly Gln Gly Ile Cys Met
145                 150                 155                 160

Tyr Arg Thr Glu Lys Thr Arg Glu Leu Val Leu Lys Gly Ile Pro Glu
                165                 170                 175

Ser Met Arg Gly Glu Leu Trp Leu Leu Ser Gly Ala Ile Asn Glu
            180                 185                 190

Lys Ala Thr His Pro Gly Tyr Tyr Glu Asp Leu Val Glu Lys Ser Met
            195                 200                 205

Gly Lys Tyr Asn Leu Ala Thr Glu Glu Ile Glu Arg Asp Leu His Arg
210                 215                 220

Ser Leu Pro Glu His Pro Ala Phe Gln Asn Glu Met Gly Ile Ala Ala
225                 230                 235                 240

Leu Arg Arg Val Leu Thr Ala Tyr Ala Phe Arg Asn Pro Asn Ile Gly
                245                 250                 255

Tyr Cys Gln Ala Met Asn Ile Val Thr Ser Val Leu Leu Tyr Ala
            260                 265                 270

Lys Glu Glu Glu Ala Phe Trp Leu Leu Ala Leu Cys Glu Arg Met
            275                 280                 285

Leu Pro Asp Tyr Tyr Asn Thr Arg Val Val Gly Ala Leu Val Asp Gln
290                 295                 300

Gly Val Phe Glu Glu Leu Ala Arg Asp Tyr Val Pro Gln Leu Tyr Asp
305                 310                 315                 320

Cys Met Gln Asp Leu Gly Val Ile Ser Thr Ile Ser Leu Ser Trp Phe
                325                 330                 335

Leu Thr Leu Phe Leu Ser Val Met Pro Phe Glu Ser Ala Val Val Val
            340                 345                 350

Val Asp Cys Phe Phe Tyr Glu Gly Ile Lys Val Ile Phe Gln Leu Ala
            355                 360                 365

Leu Ala Val Leu Asp Ala Asn Val Asp Lys Leu Leu Asn Cys Lys Asp
370                 375                 380

Asp Gly Glu Ala Met Thr Val Leu Gly Arg Tyr Leu Asp Ser Val Thr
385                 390                 395                 400
```

```
Asn Lys Asp Ser Thr Leu Pro Pro Ile Pro His Leu His Ser Leu Leu
                405                 410                 415
Ser Asp Asp Val Glu Pro Tyr Pro Glu Val Asp Ile Phe Arg Leu Ile
                420                 425                 430
Arg Thr Ser Tyr Glu Lys Phe Gly Thr Ile Arg Ala Asp Leu Ile Glu
                435                 440                 445
Gln Met Arg Phe Lys Gln Arg Leu Lys Val Ile Gln Thr Leu Glu Asp
            450                 455                 460
Thr Thr Lys Arg Asn Val Val Arg Thr Ile Val Thr Glu Thr Ser Phe
465                 470                 475                 480
Thr Ile Asp Glu Leu Glu Leu Tyr Ala Leu Phe Lys Val Ser Cys
                485                 490                 495
Lys Ala Glu His Leu Thr Ser Cys Tyr Trp Gly Gly Ser Ser Asn Ala
                500                 505                 510
Leu Asp Arg His Asp Pro Ser Leu Pro Tyr Leu Glu Gln Tyr Arg Ile
                515                 520                 525
Asp Phe Glu Gln Phe Lys Gly Met Phe Ala Leu Leu Phe Pro Trp Ala
            530                 535                 540
Cys Gly Thr His Ser Asp Val Leu Ala Ser Arg Leu Phe Gln Leu Leu
545                 550                 555                 560
Asp Glu Asn Gly Asp Ser Leu Ile Asn Phe Arg Glu Phe Val Ser Gly
                565                 570                 575
Leu Ser Ala Ala Cys His Gly Asp Leu Thr Glu Lys Leu Lys Leu Leu
                580                 585                 590
Tyr Lys Met His Val Leu Pro Glu Pro Ser Ser Asp Gln Asp Glu Pro
            595                 600                 605
Asp Ser Ala Phe Glu Ala Thr Gln Tyr Phe Phe Glu Asp Ile Thr Pro
            610                 615                 620
Glu Cys Thr His Val Val Gly Leu Asp Ser Arg Ser Lys Gln Gly Ala
625                 630                 635                 640
Asp Asp Gly Phe Val Thr Val Ser Leu Lys Pro Asp Lys Gly Lys Arg
                645                 650                 655
Ala Asn Ser Gln Glu Asn Arg Asn Tyr Leu Arg Leu Trp Thr Pro Glu
            660                 665                 670
Asn Lys Ser Lys Ser Lys Asn Ala Lys Asp Leu Pro Lys Leu Asn Gln
                675                 680                 685
Gly Gln Phe Ile Glu Leu Cys Lys Thr Met Tyr Asn Met Phe Ser Glu
            690                 695                 700
Asp Pro Asn Glu Gln Glu Leu Tyr His Ala Thr Ala Ala Val Thr Ser
705                 710                 715                 720
Leu Leu Leu Glu Ile Gly Glu Val Gly Lys Leu Phe Val Ala Gln Pro
                725                 730                 735
Ala Lys Glu Gly Gly Ser Gly Gly Ser Gly Pro Ser Cys His Gln Gly
            740                 745                 750
Ile Pro Gly Val Leu Phe Pro Lys Lys Gly Pro Gly Gln Pro Tyr Val
            755                 760                 765
Val Glu Ser Val Glu Pro Leu Pro Ala Ser Leu Ala Pro Asp Ser Glu
            770                 775                 780
Glu His Ser Leu Gly Gly Gln Met Glu Asp Ile Lys Leu Glu Asp Ser
785                 790                 795                 800
Ser Pro Arg Asp Asn Gly Ala Cys Ser Ser Met Leu Ile Ser Asp Asp
                805                 810                 815
```

```
Asp Thr Lys Asp Asp Ser Ser Met Ser Ser Tyr Ser Val Leu Ser Ala
            820                 825                 830

Gly Ser His Glu Glu Asp Lys Leu His Cys Glu Asp Ile Gly Glu Asp
            835                 840                 845

Thr Val Leu Val Arg Ser Gly Gln Gly Thr Ala Ala Leu Pro Arg Ser
            850                 855                 860

Thr Ser Leu Asp Arg Asp Trp Ala Ile Thr Phe Glu Gln Phe Leu Ala
865                 870                 875                 880

Ser Leu Leu Thr Glu Pro Ala Leu Val Lys Tyr Phe Asp Lys Pro Val
            885                 890                 895

Cys Met Met Ala Arg Ile Thr Ser Ala Lys Asn Ile Arg Met Met Gly
            900                 905                 910

Lys Pro Leu Thr Ser Ala Ser Asp Tyr Glu Ile Ser Ala Met Ser Gly
            915                 920                 925

<210> SEQ ID NO 199
<211> LENGTH: 27
<212> TYPE: PRT
<213> ORGANISM: Homo sapien

<400> SEQUENCE: 199

Met His Val Glu Arg Arg Ser Val Met Asp Ala Trp Ser Arg Arg Gly
1               5                   10                  15

Ala Gly Lys Tyr Thr Asp Ile Lys Asp Gln Ile
            20                  25

<210> SEQ ID NO 200
<211> LENGTH: 318
<212> TYPE: PRT
<213> ORGANISM: Homo sapien

<400> SEQUENCE: 200

Met Asn Arg Phe Gly Thr Arg Leu Val Gly Ala Thr Ala Thr Ser Ser
1               5                   10                  15

Pro Pro Pro Lys Ala Arg Ser Asn Glu Asn Leu Asp Lys Ile Asp Met
            20                  25                  30

Ser Leu Asp Asp Ile Ile Lys Leu Asn Arg Lys Glu Gly Lys Lys Gln
            35                  40                  45

Asn Phe Pro Arg Leu Asn Arg Arg Leu Leu Gln Gln Ser Gly Ala Gln
        50                  55                  60

Gln Phe Arg Met Arg Val Arg Trp Gly Ile Gln Gln Asn Ser Gly Phe
65                  70                  75                  80

Gly Lys Thr Ser Leu Asn His Arg Gly Arg Val Met Pro Gly Lys Arg
            85                  90                  95

Arg Pro Asn Gly Val Ile Thr Gly Leu Ala Ala Arg Lys Thr Thr Gly
            100                 105                 110

Ile Arg Lys Gly Ile Ser Pro Met Asn Arg Pro Pro Leu Ser Asp Lys
            115                 120                 125

Asn Ile Glu Gln Tyr Phe Pro Val Leu Lys Arg Lys Ala Asn Leu Leu
        130                 135                 140

Arg Gln Asn Glu Gly Gln Arg Lys Pro Val Ala Val Leu Lys Arg Pro
145                 150                 155                 160

Ser Gln Leu Ser Arg Lys Asn Asn Ile Pro Ala Asn Phe Thr Arg Ser
            165                 170                 175

Gly Asn Lys Leu Asn His Gln Lys Asp Thr Arg Gln Ala Thr Phe Leu
            180                 185                 190
```

```
Phe Arg Arg Gly Leu Lys Val Gln Ala Gln Leu Asn Thr Glu Gln Leu
            195                 200                 205

Leu Asp Asp Val Val Ala Lys Arg Thr Arg Gln Trp Arg Thr Ser Thr
210                 215                 220

Thr Asn Gly Gly Ile Leu Thr Val Ser Ile Asp Asn Pro Gly Ala Val
225                 230                 235                 240

Gln Cys Pro Val Thr Gln Lys Pro Arg Leu Thr Arg Thr Ala Val Pro
            245                 250                 255

Ser Phe Leu Thr Lys Arg Glu Gln Ser Asp Val Lys Val Pro Lys
            260                 265                 270

Gly Val Pro Leu Gln Phe Asp Ile Asn Ser Val Gly Lys Gln Thr Gly
            275                 280                 285

Met Thr Leu Asn Glu Arg Phe Gly Ile Leu Lys Glu Gln Arg Ala Thr
            290                 295                 300

Leu Thr Tyr Asn Lys Gly Gly Ser Arg Phe Val Thr Val Gly
305                 310                 315
```

<210> SEQ ID NO 201
<211> LENGTH: 102
<212> TYPE: PRT
<213> ORGANISM: Homo sapien

<400> SEQUENCE: 201

```
Met Ile Lys Lys Arg Leu Ile Gly Ile Phe Val Asn Phe Arg Lys Gly
1               5                   10                  15

Ile Phe Val Asn Leu Tyr Gly Gln Ser Ile Thr Thr Asn Lys His Thr
            20                  25                  30

Asn Thr Gln Gln Arg Thr Ala Phe Gly Glu Lys Pro His Gly Ala Lys
        35                  40                  45

Glu Arg Lys Gly Pro Pro Gly Gly Glu Thr Ser Gly Asp Thr Thr Pro
    50                  55                  60

Gly Thr Asn Asn His His Gln Gln Lys Leu Ser Ala Lys Gln Thr Lys
65                  70                  75                  80

Lys Asn Lys Thr Gln Thr Lys Asn Lys Arg Thr Arg Asn Glu Asp Thr
            85                  90                  95

Lys Lys Asn Asn Lys Gln
            100
```

<210> SEQ ID NO 202
<211> LENGTH: 107
<212> TYPE: PRT
<213> ORGANISM: Homo sapien

<400> SEQUENCE: 202

```
Met Glu Thr Gln Pro Leu Leu Tyr Leu Thr Leu Gly Ser Tyr Leu
1               5                   10                  15

Phe Phe Leu Ser Pro Gln Ile Phe Leu Ser Leu Leu Glu Trp Asp Leu
            20                  25                  30

Cys His Leu Arg Gly Cys Ser Ala Tyr Arg Gly Trp Ala Ala Thr Glu
        35                  40                  45

Val Glu Leu Leu Arg Pro Arg Leu Arg Gly Leu Val Ala Arg Gln Pro
    50                  55                  60

Cys Thr Ile Phe Phe Ser Thr Pro Ser Leu Val Phe Asn Ser Leu Val
65                  70                  75                  80

Gly Gly Leu Ala Ala Pro Ser Phe Ile Arg Arg Glu Ala Asn Gly Arg
            85                  90                  95
```

```
Gly Pro Gly Gln Trp Arg Val Val Pro His Lys
            100                 105
```

```
<210> SEQ ID NO 203
<211> LENGTH: 93
<212> TYPE: PRT
<213> ORGANISM: Homo sapien

<400> SEQUENCE: 203

Met Cys His Ile Gly Pro Leu Pro Ala Val Ala Lys Ala Ser Cys Phe
1               5                   10                  15

Ser Pro Thr Glu Glu Thr Val Leu Cys His Asp Asp Arg Ala Leu Leu
            20                  25                  30

Gly Leu Val Phe Leu Val Phe Pro Phe Trp Gln Cys Gly Leu Gln Glu
        35                  40                  45

Leu Asp Val Tyr Ala Gln Gly Ile Glu Phe Thr Leu Lys Leu Gly Asn
    50                  55                  60

Gly Val Phe Asn Leu Cys Ser Cys Leu Phe Ile Leu Leu Phe Ile Phe
65                  70                  75                  80

Cys His Pro Ala Leu Tyr Trp Ala Asn Asn Glu Ile Lys
                85                  90
```

```
<210> SEQ ID NO 204
<211> LENGTH: 54
<212> TYPE: PRT
<213> ORGANISM: Homo sapien

<400> SEQUENCE: 204

Met Val Pro Ile Leu Gly Gly Gly Lys Leu Ser Val Arg Leu Phe
1               5                   10                  15

Gln Cys Gly Asn Thr Lys Tyr Asp Thr Arg Val Ile Ala Met Met Pro
            20                  25                  30

Gly Gly Thr Arg Pro Glu Ala Val Phe Ser Cys Phe Ser Leu Leu Ser
        35                  40                  45

Gly Ile Thr Thr Glu Leu
    50
```

```
<210> SEQ ID NO 205
<211> LENGTH: 82
<212> TYPE: PRT
<213> ORGANISM: Homo sapien

<400> SEQUENCE: 205

Met Thr Phe Ser Met Val His Asp Leu Leu Arg Ala Asp Ala Asn Ser
1               5                   10                  15

Gly Lys Leu Phe Phe Met Ile Ser Lys Asp Leu Gly Tyr Val Asn Glu
            20                  25                  30

Met Ile Lys Arg His Phe Ser Glu Phe Ala Arg Arg Arg Leu Lys Asn
        35                  40                  45

Gln Asn Lys Asp Pro Thr Ala Phe His Val Ala Thr Cys Ser Pro Leu
    50                  55                  60

His His Asn Ser Lys Pro Thr Gly Glu Leu Ser Leu Lys Tyr Thr Phe
65                  70                  75                  80

Gln Met
```

```
<210> SEQ ID NO 206
<211> LENGTH: 116
<212> TYPE: PRT
<213> ORGANISM: Homo sapien
```

```
<400> SEQUENCE: 206

Leu Tyr Ile Ile Ser Leu Ile Tyr Phe Asn Met Asp Phe Leu Phe Leu
1               5                   10                  15

Phe Ser Ala Asp Gly Val Leu Val Cys His Pro Gly Trp Ser Ala Val
            20                  25                  30

Ala Arg Ser Arg Leu Thr Thr Thr Ser Ala Ser Gln Val Gln Ala Ile
        35                  40                  45

Leu Leu Ala Ser Ala Ser Gln Phe Thr Gly Ile Thr Gly Thr Cys His
    50                  55                  60

His Ala Gln Leu Ile Phe Val Phe Leu Val Glu Met Gly Phe His His
65                  70                  75                  80

Val Asp Gln Ala Asp Phe Glu Leu Leu Thr Ser Gly Asp Ser Pro Ala
                85                  90                  95

Ser Pro Ser His Ser Ala Gly Ile Ile Gly Met Ser His Cys Pro Arg
            100                 105                 110

Pro Asp Phe Phe
        115

<210> SEQ ID NO 207
<211> LENGTH: 52
<212> TYPE: PRT
<213> ORGANISM: Homo sapien

<400> SEQUENCE: 207

Met Ile Ile Ser Lys Met Ser Thr Pro Leu Pro Lys Lys Leu Leu Lys
1               5                   10                  15

Tyr Leu Tyr Leu Cys Asn Gly Thr His Asp Ser His Gly Pro Arg Ile
            20                  25                  30

Lys Ser Gln Phe Ile Leu Arg Ile Asn Leu Ser Lys Asn Met Ser Ser
        35                  40                  45

Asn Ser His Lys
    50

<210> SEQ ID NO 208
<211> LENGTH: 54
<212> TYPE: PRT
<213> ORGANISM: Homo sapien

<400> SEQUENCE: 208

Met Ala Leu Ser Leu Tyr Cys Phe Phe Asn Lys Asn Phe Phe Ser Ile
1               5                   10                  15

Ile Leu Leu Gln Cys Tyr Ser Glu Gln Val Leu Cys Gln Ile Ser Cys
            20                  25                  30

Ile Met Phe Val Trp Lys Ile Lys Phe Tyr Ser Cys Met Val Arg Leu
        35                  40                  45

Phe Gln Leu Leu Ile Leu
    50

<210> SEQ ID NO 209
<211> LENGTH: 82
<212> TYPE: PRT
<213> ORGANISM: Homo sapien

<400> SEQUENCE: 209

Met Ser Arg Leu Met Leu Tyr Gly Cys Leu Pro Met Ser Gly Ile Val
1               5                   10                  15

Ser Arg Tyr Pro Ser Pro Cys Val Pro Arg Glu Leu Trp Gly Asn Trp
```

-continued

```
                20                  25                  30
Ser Pro Glu Lys Pro Thr Cys His Thr His Gly Lys His Pro Met Cys
        35                  40                  45

His Trp Ser Thr Pro Gln Ala Cys Tyr Val Phe Ile Ile Phe Asp Val
 50                  55                  60

Phe Met Phe Leu Leu Leu Ile Leu Lys Glu Asn Thr Leu Leu Phe
 65                  70                  75                  80

Ser Asn

<210> SEQ ID NO 210
<211> LENGTH: 59
<212> TYPE: PRT
<213> ORGANISM: Homo sapien

<400> SEQUENCE: 210

Met Glu Pro Ser Asp Leu Lys Ser Arg Gln Lys Ser Leu Leu Arg Pro
 1               5                  10                  15

Val Leu Ala His Pro Ser Pro Arg Thr Cys Gln Ile Arg Cys Ile Arg
                20                  25                  30

Gln Val Glu Thr Leu Pro Val Asn Ser Gly His Lys Gln Gly Glu Gly
        35                  40                  45

Arg Thr Asn Gln Pro Pro Ser Ser Tyr Leu Tyr
        50                  55

<210> SEQ ID NO 211
<211> LENGTH: 112
<212> TYPE: PRT
<213> ORGANISM: Homo sapien

<400> SEQUENCE: 211

Met Gly Ile Ile Leu Asn Trp Leu Asn Gln Trp Ala Gln Ile Thr Tyr
 1               5                  10                  15

Leu Pro Ser Leu Leu Cys Asp Ser Pro Ala Val Thr His Thr Ile His
                20                  25                  30

Ile Leu Cys Thr Ser Asn Glu Gln Thr Trp Phe Pro Cys Phe Leu Asp
        35                  40                  45

Ile Ser Met Thr Val Ser His Thr Asn Tyr Trp Val Arg Phe Phe Ser
 50                  55                  60

Cys Tyr Arg Pro Thr Ser Cys Leu Cys Val Val Leu Gln Lys Leu
 65                  70                  75                  80

Ser Ile Pro Thr Pro Leu Leu Cys His Leu Gln Glu Ser Gly Ile Val
                85                  90                  95

Arg Ser Gln Leu Arg Lys Val Leu Val Pro Leu Thr Gly His Ile Leu
                100                 105                 110

<210> SEQ ID NO 212
<211> LENGTH: 56
<212> TYPE: PRT
<213> ORGANISM: Homo sapien

<400> SEQUENCE: 212

Met Pro Pro Arg Gly Ser Gln Ala Val Ser Ser Gly Arg Ala Ile
 1               5                  10                  15

Asn Leu Ser Ser Gly Gln Glu Lys Thr Asp His Trp Ser Pro Lys Met
                20                  25                  30

Leu Asp Ser Ile Ala Arg Ser His Leu Asn Asn Ser Asp Cys Ser Phe
        35                  40                  45
```

```
Thr Gln Val Val Gln Asn Leu
    50                  55

<210> SEQ ID NO 213
<211> LENGTH: 118
<212> TYPE: PRT
<213> ORGANISM: Homo sapien

<400> SEQUENCE: 213

Glu Arg Gln Gly Thr Leu Ser Thr Ala Ala Pro Thr Thr Ser Pro Ala
1               5                   10                  15

Pro Cys Leu Ser Asn His His Asn Lys Lys His Leu Ile Leu Ala Phe
            20                  25                  30

Cys Ala Gly Val Leu Leu Thr Leu Leu Leu Ile Ala Phe Ile Phe Leu
        35                  40                  45

Ile Ile Lys Ser Tyr Arg Lys Tyr His Ser Lys Pro Gln Ala Pro Asp
    50                  55                  60

Pro His Ser Asp Pro Pro Ala Lys Leu Ser Ile Pro Gly Glu Ser
65                  70                  75                  80

Leu Thr Tyr Ala Ser Thr Thr Phe Lys Leu Ser Glu Glu Lys Ser Asn
                85                  90                  95

His Leu Ala Glu Asn His Ser Ala Asp Phe Asp Pro Ile Val Tyr Ala
            100                 105                 110

Gln Ile Lys Val Thr Asn
        115

<210> SEQ ID NO 214
<211> LENGTH: 51
<212> TYPE: PRT
<213> ORGANISM: Homo sapien

<400> SEQUENCE: 214

Met Ala Leu Glu Phe Lys Phe Cys Arg Lys Trp Ile Ala Ile Asn Asn
1               5                   10                  15

Pro Met Lys Met Gly His Ile Leu Pro Leu Ile Glu Ser Gln Ser Thr
            20                  25                  30

Arg Thr Asn Arg Ile Ser His Leu Ser Ile Phe Arg Tyr Gly Arg Gln
        35                  40                  45

Gln Lys Gln
    50

<210> SEQ ID NO 215
<211> LENGTH: 55
<212> TYPE: PRT
<213> ORGANISM: Homo sapien

<400> SEQUENCE: 215

Met Thr Cys Phe Arg Glu Cys Leu Leu Val Tyr Leu Tyr Ser Ile Cys
1               5                   10                  15

Leu Leu Asn Ser Leu His Lys Leu Glu Leu Leu Ser Arg Arg Leu Arg
            20                  25                  30

Glu Cys Lys Tyr Val Thr His Lys Met His Trp Ser Met Val Asn Lys
        35                  40                  45

Thr Asn His Phe Gly Leu Val
    50                  55

<210> SEQ ID NO 216
<211> LENGTH: 129
<212> TYPE: PRT
```

-continued

<213> ORGANISM: Homo sapien

<400> SEQUENCE: 216

Met Val Ser Arg Pro His Asn Pro Pro Lys Lys Tyr Ala Ala Ser Lys
1               5                   10                  15

Thr Cys Cys Asp Asp Glu Ala Arg Thr Ser Thr Thr Arg Arg His
            20                  25                  30

Glu Ala Pro Gln Asn Gly Glu Arg Arg Lys Thr Arg Thr Arg Lys Thr
        35                  40                  45

Arg Asn Glu Glu Thr Glu Arg Thr Pro His Arg Arg Gln Thr Arg Asp
50                  55                  60

Arg Lys Lys Gln Glu Thr Met Val Pro His Arg Ala Glu Thr Arg Ser
65                  70                  75                  80

Ala Ala Gln Arg Glu Gln Ser Thr Glu Ala Asn Ser Arg Ser Thr Gln
                85                  90                  95

Ser Lys Ala Pro Gln Leu Arg Thr Pro Thr Thr Gln Glu Ala Glu Arg
            100                 105                 110

Glu Ser Asn Thr His Thr His Ala Thr Gln Ala Thr Glu Arg Arg Thr
        115                 120                 125

Arg

<210> SEQ ID NO 217
<211> LENGTH: 58
<212> TYPE: PRT
<213> ORGANISM: Homo sapien

<400> SEQUENCE: 217

Met Gly Ala Asn Pro Pro Phe His Pro Gly Ser Pro Leu Val Pro Pro
1               5                   10                  15

Arg Val Ser Pro Gln Leu Ser Phe Phe Cys Phe Val Phe Phe Pro
            20                  25                  30

Phe Val Phe Phe Phe Cys Phe Phe Arg Phe Phe Ile Ile Leu Phe Thr
        35                  40                  45

Arg Tyr Thr Gly Leu Lys Lys Ile Ile Ser
    50                  55

<210> SEQ ID NO 218
<211> LENGTH: 116
<212> TYPE: PRT
<213> ORGANISM: Homo sapien

<400> SEQUENCE: 218

Met Thr Gln Leu Arg His Gln Gln Lys Lys Lys Lys Ala Gly Arg
1               5                   10                  15

Thr Gln Gly Gln Ser Gly Ser Arg Cys Arg Met Val Ile Pro Pro Thr
            20                  25                  30

Phe Pro His Asn Thr Ala Thr Thr His Thr His His His Thr
        35                  40                  45

Ala His Pro Ser Ala His Thr His Thr Asn Arg Ser Ala Gly Arg
    50                  55                  60

Asp Arg Pro Arg Lys Gln Thr Glu Pro Ala Gln Thr Ser Lys His His
65                  70                  75                  80

Thr Asn Gly Gln His Asp Thr Thr Ala Gln Gly Thr His Lys His Asp
                85                  90                  95

Ser Thr Trp Pro Thr Pro Pro Arg Ser Tyr Pro His Gly Arg Arg
            100                 105                 110

Ser Pro Pro Thr
        115

<210> SEQ ID NO 219
<211> LENGTH: 600
<212> TYPE: PRT
<213> ORGANISM: Homo sapien

<400> SEQUENCE: 219

Met Gly Lys Lys Leu Asp Leu Ser Lys Leu Thr Asp Glu Glu Ala Gln
1               5                   10                  15

His Val Leu Glu Val Val Gln Arg Asp Phe Asp Leu Arg Arg Lys Glu
            20                  25                  30

Glu Glu Arg Leu Glu Ala Leu Lys Gly Lys Ile Lys Lys Glu Ser Ser
        35                  40                  45

Lys Arg Glu Leu Leu Ser Asp Thr Ala His Leu Asn Glu Thr His Cys
50                  55                  60

Ala Arg Cys Leu Gln Pro Tyr Gln Leu Leu Val Asn Ser Lys Arg Gln
65                  70                  75                  80

Cys Leu Glu Cys Gly Leu Phe Thr Cys Lys Ser Cys Gly Arg Val His
                85                  90                  95

Pro Glu Glu Gln Gly Trp Ile Cys Asp Pro Cys His Leu Ala Arg Val
            100                 105                 110

Val Lys Ile Gly Ser Leu Glu Trp Tyr Tyr Glu His Val Lys Ala Arg
        115                 120                 125

Phe Lys Arg Phe Gly Ser Ala Lys Val Ile Arg Ser Leu His Gly Arg
130                 135                 140

Leu Gln Gly Gly Ala Gly Pro Glu Leu Ile Ser Glu Glu Arg Ser Gly
145                 150                 155                 160

Asp Ser Asp Gln Thr Asp Glu Asp Gly Glu Pro Gly Ser Glu Ala Gln
                165                 170                 175

Ala Gln Ala Gln Pro Phe Gly Ser Lys Lys Lys Arg Leu Leu Ser Val
            180                 185                 190

His Asp Phe Asp Phe Glu Gly Asp Ser Asp Asp Ser Thr Gln Pro Gln
        195                 200                 205

Gly His Ser Leu His Leu Ser Ser Val Pro Glu Ala Arg Asp Ser Pro
    210                 215                 220

Gln Ser Leu Thr Asp Glu Ser Cys Ser Glu Lys Ala Ala Pro His Lys
225                 230                 235                 240

Ala Glu Gly Leu Glu Glu Ala Asp Thr Gly Ala Ser Gly Cys His Ser
                245                 250                 255

His Pro Glu Glu Gln Pro Thr Ser Ile Ser Pro Ser Arg His Gly Ala
            260                 265                 270

Leu Ala Glu Leu Cys Pro Pro Gly Gly Ser His Arg Met Ala Leu Gly
        275                 280                 285

Thr Ala Ala Leu Gly Ser Asn Val Ile Arg Asn Glu Gln Leu Pro
    290                 295                 300

Leu Gln Tyr Leu Ala Asp Val Asp Thr Ser Asp Glu Glu Ser Ile Arg
305                 310                 315                 320

Ala His Val Met Ala Ser His His Ser Lys Arg Arg Gly Arg Ala Ser
                325                 330                 335

Ser Glu Ser Gln Ile Phe Glu Leu Asn Lys Arg Ile Ser Ala Val Glu
            340                 345                 350

Cys Leu Leu Thr Tyr Leu Glu Asn Thr Val Val Pro Pro Leu Ala Lys
        355                 360                 365

```
Gly Leu Gly Ala Gly Val Arg Thr Glu Ala Asp Val Glu Glu Ala
            370                 375                 380

Leu Arg Arg Lys Leu Glu Glu Leu Thr Ser Asn Val Ser Asp Gln Glu
385                 390                 395                 400

Thr Ser Ser Glu Glu Glu Ala Lys Asp Glu Lys Ala Glu Pro Asn
                405                 410                 415

Arg Asp Lys Ser Val Gly Pro Leu Pro Gln Ala Asp Pro Glu Val Gly
            420                 425                 430

Thr Ala Ala His Gln Thr Asn Arg Gln Glu Lys Ser Pro Gln Asp Pro
            435                 440                 445

Gly Asp Pro Val Gln Tyr Asn Arg Thr Thr Asp Glu Glu Leu Ser Glu
            450                 455                 460

Leu Glu Asp Arg Val Ala Val Thr Ala Ser Glu Val Gln Gln Ala Glu
465                 470                 475                 480

Ser Glu Val Ser Asp Ile Glu Ser Arg Ile Ala Ala Leu Arg Ala Ala
                485                 490                 495

Gly Leu Thr Val Lys Pro Ser Gly Lys Pro Arg Arg Lys Ser Asn Leu
            500                 505                 510

Pro Ile Phe Leu Pro Arg Val Ala Gly Lys Leu Gly Lys Arg Pro Glu
            515                 520                 525

Asp Pro Asn Ala Asp Pro Ser Ser Glu Ala Lys Ala Met Ala Val Pro
            530                 535                 540

Tyr Leu Leu Arg Arg Lys Phe Ser Asn Ser Leu Lys Ser Gln Gly Lys
545                 550                 555                 560

Asp Asp Asp Ser Phe Asp Arg Lys Ser Val Tyr Arg Gly Ser Leu Thr
                565                 570                 575

Gln Arg Asn Pro Asn Ala Arg Lys Gly Met Ala Ser His Thr Phe Ala
            580                 585                 590

Lys Pro Val Val Ala His Gln Ser
            595                 600

<210> SEQ ID NO 220
<211> LENGTH: 48
<212> TYPE: PRT
<213> ORGANISM: Homo sapien

<400> SEQUENCE: 220

Met Met Ile Leu Ser Gln Lys Gly Leu Phe Thr Val Tyr Val Asp Ile
1               5                   10                  15

Lys Leu Thr Val Cys Ile Tyr Lys Cys Arg Cys Ala Glu Ala Ile Tyr
                20                  25                  30

Thr Lys Thr Gly Ile Leu Thr Ser Asp Arg Tyr Val Arg Asn Ala Glu
            35                  40                  45

<210> SEQ ID NO 221
<211> LENGTH: 58
<212> TYPE: PRT
<213> ORGANISM: Homo sapien

<400> SEQUENCE: 221

Met Val Ile Phe Tyr Ser Ser Pro Ser Gln Asp Ser Ala Leu Ile Tyr
1               5                   10                  15

Tyr Ile Pro Phe Ile Leu Leu Tyr Arg Leu Leu Ser Glu Thr His Val
                20                  25                  30

Gln Ile Arg Asp Lys Ile Leu Lys His Ile Thr Pro Ser Leu Val Phe
            35                  40                  45
```

-continued

```
Ser Ile Gln Ile Leu Arg Asn Ser Cys Tyr
    50                  55

<210> SEQ ID NO 222
<211> LENGTH: 38
<212> TYPE: PRT
<213> ORGANISM: Homo sapien

<400> SEQUENCE: 222

Met Arg Met Leu Arg Glu Ile Val Gly Cys Leu Glu Phe His Tyr Ile
1               5                   10                  15

Phe Cys Phe Tyr Phe Leu Ile Pro Arg Cys Phe Lys Ile Phe Arg
                20                  25                  30

Gln Ile Ser Ile Leu His
        35

<210> SEQ ID NO 223
<211> LENGTH: 61
<212> TYPE: PRT
<213> ORGANISM: Homo sapien

<400> SEQUENCE: 223

Met Trp Cys Lys Lys Val Asp Glu Glu Lys Arg Gly Leu Ser Ser Leu
1               5                   10                  15

Ala Leu Pro Arg Glu Gly His Gly Gln Arg Leu Thr Asn Thr Cys Pro
                20                  25                  30

Ser Leu Gln Gly Val Ala Gly Phe Gln Asn Lys Ala Phe Arg Ile Lys
        35                  40                  45

Pro Phe Leu Ala Cys Leu Val Leu Gly Met Phe Pro Pro
    50                  55                  60

<210> SEQ ID NO 224
<211> LENGTH: 41
<212> TYPE: PRT
<213> ORGANISM: Homo sapien

<400> SEQUENCE: 224

Met Ser Leu Phe Val Thr His Asn Val Leu Tyr Arg Lys Leu Leu Leu
1               5                   10                  15

Ser Tyr Val Ile Leu Ala Val Asp Val Thr Ala Cys His Gln Val Gln
                20                  25                  30

Tyr Val Ile Cys Ile Ser Leu Phe Ser
        35                  40

<210> SEQ ID NO 225
<211> LENGTH: 318
<212> TYPE: PRT
<213> ORGANISM: Homo sapien

<400> SEQUENCE: 225

Met Glu Ala Leu Ala Leu Val Gly Ala Trp Tyr Thr Ala Arg Lys Ser
1               5                   10                  15

Ile Thr Val Ile Cys Asp Phe Tyr Ser Leu Ile Arg Leu His Phe Ile
                20                  25                  30

Pro Arg Leu Gly Ser Arg Ala Asp Leu Ile Lys Gln Tyr Gly Arg Trp
        35                  40                  45

Ala Val Val Ser Gly Ala Thr Asp Gly Ile Gly Lys Ala Tyr Ala Glu
    50                  55                  60

Glu Leu Ala Ser Arg Gly Leu Asn Ile Ile Leu Ile Ser Arg Asn Glu
```

-continued

```
                65                  70                  75                  80
Glu Lys Leu Gln Val Val Ala Lys Asp Ile Ala Asp Thr Tyr Lys Val
                    85                  90                  95

Glu Thr Asp Ile Ile Val Ala Asp Phe Ser Ser Gly Arg Glu Ile Tyr
                100                 105                 110

Leu Pro Ile Arg Glu Ala Leu Lys Asp Lys Asp Val Gly Ile Leu Val
                115                 120                 125

Asn Asn Val Gly Val Phe Tyr Pro Tyr Pro Gln Tyr Phe Thr Gln Leu
            130                 135                 140

Ser Glu Asp Lys Leu Trp Asp Ile Ile Asn Val Asn Ile Ala Ala Ala
145                 150                 155                 160

Ser Leu Met Val His Val Val Leu Pro Gly Met Val Glu Arg Lys Lys
                    165                 170                 175

Gly Ala Ile Val Thr Ile Ser Ser Gly Ser Cys Cys Lys Pro Thr Pro
                180                 185                 190

Gln Leu Ala Ala Phe Ser Ala Ser Lys Ala Tyr Leu Asp His Phe Ser
                195                 200                 205

Arg Ala Leu Gln Tyr Glu Tyr Ala Ser Lys Gly Ile Phe Val Gln Ser
            210                 215                 220

Leu Ile Pro Phe Tyr Val Ala Thr Ser Met Thr Ala Pro Ser Asn Phe
225                 230                 235                 240

Leu His Arg Cys Ser Trp Leu Val Pro Ser Pro Lys Val Tyr Ala His
                    245                 250                 255

His Ala Val Ser Thr Leu Gly Ile Ser Lys Arg Thr Thr Gly Tyr Trp
                260                 265                 270

Ser His Ser Ile Gln Phe Leu Phe Ala Gln Tyr Met Pro Glu Trp Leu
            275                 280                 285

Trp Val Trp Gly Ala Asn Ile Leu Asn Arg Ser Leu Arg Lys Glu Ala
            290                 295                 300

Leu Ser Cys Thr Ala Arg Lys Glu Ala Leu Ser Cys Thr Ala
305                 310                 315
```

<210> SEQ ID NO 226
<211> LENGTH: 37
<212> TYPE: PRT
<213> ORGANISM: Homo sapien

<400> SEQUENCE: 226

```
Met Ala Gly Ser Gly Lys Val Pro Ile Thr Thr Thr Tyr Lys Pro Pro
1               5                   10                  15

Thr Asn Ser Asn Ala Ile His Leu Pro Thr Pro Ile Ile Arg Lys Ala
            20                  25                  30

Gly Phe Thr Gly Ile
        35
```

<210> SEQ ID NO 227
<211> LENGTH: 87
<212> TYPE: PRT
<213> ORGANISM: Homo sapien

<400> SEQUENCE: 227

```
Met Phe Leu Phe Leu Phe Phe Val Ser Ser Cys Ser Ala Leu Leu
1               5                   10                  15

Ser Pro Ser Phe Leu Ser Arg Pro Pro Leu Ala Val Gly Gly Arg
            20                  25                  30

Arg Val Cys Gly Trp Gly Asn Cys Val Arg Arg Ala Arg Asp His Asn
```

```
                        35                  40                  45
Cys Pro Pro Arg Gly Pro Gln Arg Leu Thr Thr Pro Thr Arg Tyr
 50                  55                  60

Thr Pro Arg Val Leu Phe Phe Leu Phe Leu Phe Tyr Phe Leu Phe
 65                  70                  75                  80

Cys Phe Val Val Gly Lys Met
                 85

<210> SEQ ID NO 228
<211> LENGTH: 30
<212> TYPE: PRT
<213> ORGANISM: Homo sapien

<400> SEQUENCE: 228

Met Asn Ser Phe Gly Tyr Met Thr Pro Ser Lys Phe Lys Lys Glu
 1               5                  10                  15

Ile Thr Phe Lys Thr Thr Tyr Ile Phe Cys Phe Cys Leu Arg
                 20                  25                  30

<210> SEQ ID NO 229
<211> LENGTH: 52
<212> TYPE: PRT
<213> ORGANISM: Homo sapien

<400> SEQUENCE: 229

Met Arg Gly Val His Lys Ser Thr Gln Thr Ile Ala Glu Cys Val Gly
 1               5                  10                  15

Val Asn Arg Ser Pro Met Phe Leu Tyr Ser Gly Ile Tyr Ile Tyr Thr
                 20                  25                  30

Phe Thr Gln Thr Asn Lys Ser Ser Ile Leu Gln Thr Pro Phe Gly Thr
                 35                  40                  45

Arg Asp Pro Lys
     50

<210> SEQ ID NO 230
<211> LENGTH: 125
<212> TYPE: PRT
<213> ORGANISM: Homo sapien

<400> SEQUENCE: 230

Met Arg Ala Leu Arg Phe His Leu Thr Gly Asp Glu Met Ala Ala Ala
 1               5                  10                  15

Asp Ile Leu Pro Cys Leu Gln Ala Leu Leu Ala Leu Pro Ala Leu Pro
                 20                  25                  30

Ser Leu Gln Thr Pro Thr Ala Val Ala Leu Pro Leu Arg Lys Leu Ser
                 35                  40                  45

Asp Cys Ile Ile Pro Arg Pro Arg Leu Cys Ser Ala Leu Leu Met
 50                  55                  60

Ala Val Ile Pro Arg Glu Arg Gln Glu Pro Gly Ala Ser Gly Met Gln
 65                  70                  75                  80

Pro Leu Gly Tyr Ser Val Cys Phe Gln Leu Cys Leu Cys Phe Ser Arg
                 85                  90                  95

Val Phe Leu Arg Gln Leu Thr Gln Tyr Leu Ser Thr Leu Ser Leu Gly
                100                 105                 110

Pro Ala Leu Gly Arg Ile Phe Phe Tyr Phe Val Lys Val
                115                 120                 125

<210> SEQ ID NO 231
```

```
<211> LENGTH: 273
<212> TYPE: PRT
<213> ORGANISM: Homo sapien

<400> SEQUENCE: 231

Arg Gly Pro Ala Arg Ser Ala Ala Pro Ala Gly Gly Ser Ser Ser Gly
1               5                   10                  15

Cys Gly Ala Ala Pro Gly Ala Gly Gly Arg Arg Pro Gly His Gly
            20                  25                  30

Arg Pro Val Gly Pro Gly Thr Ala Ala Gly Ala Ala Gly Pro Gly Leu
        35                  40                  45

Pro Ala Arg Thr His His Arg His His Pro Gly Cys Leu Pro Gln Gln
    50                  55                  60

Ala Ala Pro Pro Ala Gly Arg Gly Pro Ala Ala Arg Gly Ala Ala
65                  70                  75                  80

Ala Gly Gly Pro Ala Ala Gly Arg Gly Ala Val Thr Gly Arg Gly
                85                  90                  95

Pro Val Thr Arg Gly Cys Ala Ala Arg Pro Ala Arg Arg Gly Leu
            100                 105                 110

Ser Ala Gly Gly Ala Leu Ala Leu Pro Ala Gly Leu Gly Leu Gly Leu
            115                 120                 125

Arg Asp Pro Gly Ala Tyr Gly Asp Ile Arg Pro Ser Ala Ala Ser Trp
130                 135                 140

Val Gly Ser Arg Gly Leu Ala Tyr Pro Pro Ala Arg Arg Asn Ser Gly
145                 150                 155                 160

Ala Ala Pro Arg Ser Gly Ala Ala Pro Gly Gly Arg Gly Arg Pro Asp
                165                 170                 175

Ala Arg Gln Gly His Ala Gly Pro Gly Ser Arg Gly Pro Pro Leu Val
            180                 185                 190

Gly Ser Val Ser Arg Pro Gly Ala Ala Ala Phe Leu Pro Pro Arg Ser
        195                 200                 205

Arg Pro Ala Pro Gly Pro Ala Gly Asp Ser Ser Gly Pro Cys Trp Arg
    210                 215                 220

Gly Glu Gly Pro Ala Ala Gly Gly Ala Pro Gly Ala Leu Ala Leu
225                 230                 235                 240

Ser Ala Ser Ala Leu Gly Gln Pro Arg Ala Thr Ala Arg Leu Pro Gly
                245                 250                 255

His Pro Leu Gly Glu Asp Gly Gln Ala Leu Ser Ala Ala Gly Gly Gly
            260                 265                 270

Gly

<210> SEQ ID NO 232
<211> LENGTH: 104
<212> TYPE: PRT
<213> ORGANISM: Homo sapien

<400> SEQUENCE: 232

Met Pro Ser Phe Phe Cys Phe Ser Ile Ser Leu Ile Arg Asp Trp Lys
1               5                   10                  15

Val Ser Ile Arg Ser Asn Thr Asp Phe Ile Val Ile Gly Thr Asn Cys
            20                  25                  30

Ser Pro Thr Thr Pro Tyr Ser Ala Ser Ser Ile Thr Leu Leu Cys Glu
        35                  40                  45

Ile Leu Arg Asn Gly Leu Pro Leu Gln Gly Leu Asn Leu Pro Tyr Leu
    50                  55                  60
```

```
Arg Phe Glu Ser Ser Val Leu Phe Cys Ile Cys Phe Lys Tyr Leu Gly
 65                  70                  75                  80

Ser Val Thr His Ala Asn Met Thr Cys Pro Val Gln Ala Thr Leu Gly
                 85                  90                  95

Ile His Ile Ser His Val Ser Ser
                100

<210> SEQ ID NO 233
<211> LENGTH: 260
<212> TYPE: PRT
<213> ORGANISM: Homo sapien

<400> SEQUENCE: 233

Glu Lys Lys Lys Met Lys Asn Glu Asn Ala Asp Lys Leu Leu Lys
  1               5                  10                  15

Ser Glu Lys Gln Met Lys Lys Ser Glu Lys Ser Lys Gln Glu Lys
                 20                  25                  30

Glu Lys Ser Lys Lys Lys Gly Gly Lys Thr Glu Gln Asp Gly Tyr
             35                  40                  45

Gln Lys Pro Thr Asn Lys His Phe Thr Gln Ser Pro Lys Lys Ser Val
 50                  55                  60

Ala Asp Leu Leu Gly Ser Phe Glu Gly Lys Arg Arg Leu Leu Leu Ile
 65                  70                  75                  80

Thr Ala Pro Lys Ala Glu Asn Asn Met Tyr Val Gln Gln Arg Asp Glu
                 85                  90                  95

Tyr Leu Glu Ser Phe Cys Lys Met Ala Thr Arg Lys Ile Ser Val Ile
            100                 105                 110

Thr Ile Phe Gly Pro Val Asn Asn Ser Thr Met Lys Ile Asp His Phe
        115                 120                 125

Gln Leu Asp Asn Glu Lys Pro Met Arg Val Val Asp Glu Asp Leu
130                 135                 140

Val Asp Gln Arg Leu Ile Ser Glu Leu Arg Lys Glu Tyr Gly Met Thr
145                 150                 155                 160

Tyr Asn Asp Phe Phe Met Val Leu Thr Asp Val Asp Leu Arg Val Lys
                165                 170                 175

Gln Tyr Tyr Glu Val Pro Ile Thr Met Lys Ser Val Phe Asp Leu Ile
            180                 185                 190

Asp Thr Phe Gln Ser Arg Ile Lys Asp Met Glu Lys Gln Lys Lys Glu
        195                 200                 205

Gly Ile Val Cys Lys Glu Asp Lys Lys Gln Ser Leu Glu Asn Phe Leu
    210                 215                 220

Ser Arg Phe Arg Trp Arg Arg Leu Leu Val Ile Ser Ala Pro Asn
225                 230                 235                 240

Asp Glu Asp Trp Ala Tyr Ser Gln Gln Leu Ser Ala Leu Ser Gly Gln
                245                 250                 255

Ala Cys Thr Leu
            260

<210> SEQ ID NO 234
<211> LENGTH: 72
<212> TYPE: PRT
<213> ORGANISM: Homo sapien

<400> SEQUENCE: 234

Met Glu Gly Glu Lys Gly Gln Glu Pro Gln Lys Leu Arg Asn Gly Leu
  1               5                  10                  15
```

```
Ala Leu Pro Leu Phe Arg Pro His Ile Ala Asp Arg Trp Ala Ala Glu
            20                  25                  30

Thr Ser Thr Ile Gly His Asn Asn Asp Asn Asn Tyr Ser Thr Thr Phe
        35                  40                  45

Tyr Phe Phe Ile Glu Tyr Gln Gly Leu Gln Ser Ala Phe Thr Leu Ile
    50                  55                  60

Ile Leu Trp Val Gly Thr Cys Pro
65                  70

<210> SEQ ID NO 235
<211> LENGTH: 52
<212> TYPE: PRT
<213> ORGANISM: Homo sapien

<400> SEQUENCE: 235

Met Thr Leu Phe Ile Arg Cys Cys Thr Asn Tyr Gly Asn Leu Cys Gln
1               5                   10                  15

Tyr Phe Asn Val Cys Trp Ile Ile Thr Asp Ile Phe Ile Ile Leu Met
            20                  25                  30

Ser Thr Asn Leu Phe Ile Leu Ile Ala Arg Val Ser Leu Gly Ser Lys
        35                  40                  45

His His Leu Gly
        50

<210> SEQ ID NO 236
<211> LENGTH: 75
<212> TYPE: PRT
<213> ORGANISM: Homo sapien

<400> SEQUENCE: 236

Met Phe Leu Cys Tyr Phe Ser Gly Leu Ile Phe Leu Phe Ile Phe Pro
1               5                   10                  15

Val Cys Leu Trp Gln His Leu Ser Ile Leu Tyr Leu Leu Val Asn Leu
            20                  25                  30

Leu Phe Thr Leu Ile Leu Arg Ala Ser Tyr Pro Ser His Cys Ala Ala
        35                  40                  45

Arg Gln His Leu Glu Gln His Cys Pro Ile Val Ser Ile Met Pro Glu
    50                  55                  60

Tyr Gly Trp Gly Arg Cys Phe Gly Trp Leu
65                  70                  75

<210> SEQ ID NO 237
<211> LENGTH: 75
<212> TYPE: PRT
<213> ORGANISM: Homo sapien

<400> SEQUENCE: 237

Met Ala Tyr Arg Met Lys Arg Gly Thr Arg Asn Pro Cys Gly Arg Gly
1               5                   10                  15

Leu Asp Leu Lys Gln Cys Pro Leu Trp Leu Leu Pro Trp Leu Thr
            20                  25                  30

Gly Phe Leu Asp His Val His Phe Thr Gly Pro Trp Asp Leu His Leu
        35                  40                  45

Leu Ala Ser Pro Ala Gly Leu Ile Pro Ala Arg Ala Pro Ser Phe Leu
    50                  55                  60

Leu Met Val Phe Arg Trp Pro Asp His Gly Lys
65                  70                  75
```

```
<210> SEQ ID NO 238
<211> LENGTH: 212
<212> TYPE: PRT
<213> ORGANISM: Homo sapien

<400> SEQUENCE: 238

Ser Pro His Gln Ala Ala Pro Val Asp Gln Thr Pro Arg Thr Leu
1               5                   10                  15

Ala Thr Met Gly Gln Arg Ala Leu Pro Ser Ser Leu Ala Leu Leu Ser
            20                  25                  30

Arg Pro Leu Ser Pro Pro Ala Ala Cys Ser Gly Asp Pro Gly Cys
            35                  40                  45

Gly Ser Gly Ala Gly Leu Pro Ser Ala Ser Ala Ala Gly Ile Ala
        50                  55                  60

Ser Ser Ala Val Glu Pro Val Cys Gly Asp Ala Ala Pro Ala Cys Leu
65                  70                  75                  80

Leu Arg Thr Pro Leu Arg Gly Leu Leu Lys Pro Thr Gly Pro Arg Ser
                85                  90                  95

Thr Met Glu Cys Pro Pro Ala Leu Ile Val His Pro Ala Gly Gly
            100                 105                 110

Met Ala Ser Gly Ser Ser Gln Pro Trp Ala Ala Ser Ala Thr Pro
            115                 120                 125

Met Leu Ser Ser Lys Ala Ser Leu Cys Ile Pro Thr Arg Gly Pro Pro
        130                 135                 140

Pro Gln Pro Leu Met Arg Thr Pro Ala Ala Arg Ser His Trp Pro Ile
145                 150                 155                 160

Pro His Pro Cys Asp Thr Ala Cys Pro Ala Pro Leu Pro Val Val Leu
                165                 170                 175

Val Ala Pro Arg Ser Thr Ile Leu Ser Met Ser Arg Thr Trp Thr Cys
                180                 185                 190

Arg Arg Trp Ala Val Ala Pro Cys Arg Ala Glu Lys Leu Met Cys Ser
            195                 200                 205

Ser Ser Arg Ser
    210

<210> SEQ ID NO 239
<211> LENGTH: 62
<212> TYPE: PRT
<213> ORGANISM: Homo sapien

<400> SEQUENCE: 239

Met Asn Phe Thr Leu Ala Ile Phe His Tyr Phe Ser Leu Ser Gln Met
1               5                   10                  15

Ser Val Leu Met Arg Gln Leu Ala Leu Thr Gly Ala Thr Leu Met Cys
            20                  25                  30

His Leu Pro Thr Phe Asn Phe Trp Val Lys Ala Glu Arg Glu Lys Leu
        35                  40                  45

Met Asp Phe Ser Phe Ser Arg Arg Asp Lys Asn Gln Leu His
    50                  55                  60

<210> SEQ ID NO 240
<211> LENGTH: 128
<212> TYPE: PRT
<213> ORGANISM: Homo sapien

<400> SEQUENCE: 240

Cys Leu Ile Ser Ala Lys Lys Lys Lys Lys Lys Lys Lys Lys Lys
1               5                   10                  15
```

```
Lys Lys Lys Asn Lys Lys Lys Lys Lys Lys Lys Lys Lys
             20              25              30

Lys Lys Thr Lys Lys Arg Arg Gly Gly Arg Glu Lys Glu Pro Arg
         35              40              45

Gly Glu His Arg Ala Gly Arg Arg Ala His Met Lys Lys Ala Thr Gln
         50              55              60

Lys Lys Lys His Lys Thr Ser Lys Arg Lys Gln Lys Lys Ala Glu Arg
65              70              75              80

Glu Lys Val Thr Arg Arg Ile Glu Arg Lys Ala Leu Gln Asp Gln His
                 85              90              95

Gly Thr Asn Gln Lys Gln Ile Asn Lys Glu Asn Lys Thr Asp Thr Arg
                100             105             110

Cys Gln Arg Ala Asn Ala Arg Thr Met Glu Thr Gly Lys Gln His Lys
                115             120             125

<210> SEQ ID NO 241
<211> LENGTH: 41
<212> TYPE: PRT
<213> ORGANISM: Homo sapien

<400> SEQUENCE: 241

Met Leu Leu Glu Arg Arg Ser Val Met Asp Ala Trp Ser Arg Arg Gly
1               5                   10                  15

Thr Phe Ser Lys Ile Ser Met Gln Leu Phe Asn Arg Glu Ser Arg Phe
            20                  25                  30

His Gln Asp Ser Asn Gln Ser Asn Ile
        35                  40

<210> SEQ ID NO 242
<211> LENGTH: 42
<212> TYPE: PRT
<213> ORGANISM: Homo sapien

<400> SEQUENCE: 242

Met Pro Tyr Phe Trp Arg Lys Val Gly Asn Ile Gly Val Ser Leu Ser
1               5                   10                  15

Val Ser Gln Glu Asp Ser Phe Val Leu Leu Gly Glu Pro Val Pro Tyr
            20                  25                  30

Arg Phe Val Tyr Thr Val Ile Ile Gln Asp
        35                  40

<210> SEQ ID NO 243
<211> LENGTH: 45
<212> TYPE: PRT
<213> ORGANISM: Homo sapien

<400> SEQUENCE: 243

Met Glu Pro His Ile Met Lys Phe Asn Ser His Val Lys Thr Phe Cys
1               5                   10                  15

Ile Val Gly Cys Gln Lys Tyr Phe Pro Asn Phe Arg Leu Thr Cys Arg
            20                  25                  30

Ala Gly Asp Gly Leu Pro Pro Tyr Asn Phe Lys Ser Val
        35                  40                  45

<210> SEQ ID NO 244
<211> LENGTH: 785
<212> TYPE: PRT
<213> ORGANISM: Homo sapien
```

<400> SEQUENCE: 244

```
Lys Ala Lys Ile Ser Trp Glu Ala Pro Val Glu Lys Thr Glu Cys
1               5                   10                  15

Ile Gln Lys Gly Lys Asn Asn Gln Val Gly Ala Trp Thr Leu Leu
            20                  25                  30

Val Leu Pro Ser Pro Gln Asp Val Ser Ser His Ser Gly Pro Arg Ala
        35                  40                  45

Leu Thr Asn Arg Thr Pro Phe Cys Pro Gln Thr Glu Cys Phe Asn Phe
    50                  55                  60

Ile Arg Phe Leu Gln Pro Tyr Asn Ala Ser His Leu Tyr Val Cys Gly
65                  70                  75                  80

Thr Tyr Ala Phe Gln Pro Lys Cys Thr Tyr Val Asn Met Leu Thr Phe
                85                  90                  95

Thr Leu Glu His Gly Glu Phe Glu Asp Gly Lys Gly Lys Cys Pro Tyr
                100                 105                 110

Asp Pro Ala Lys Gly His Ala Gly Leu Leu Val Asp Gly Glu Leu Tyr
            115                 120                 125

Ser Ala Thr Leu Asn Asn Phe Leu Gly Thr Glu Pro Ile Ile Leu Arg
130                 135                 140

Asn Met Gly Pro His His Ser Met Lys Thr Glu Tyr Leu Ala Phe Trp
145                 150                 155                 160

Leu Asn Glu Pro His Phe Val Gly Ser Ala Tyr Val Pro Glu Ser Val
                165                 170                 175

Gly Ser Phe Thr Gly Asp Asp Lys Val Tyr Phe Phe Arg Glu
            180                 185                 190

Arg Ala Val Glu Ser Asp Cys Tyr Ala Glu Gln Val Val Ala Arg Val
            195                 200                 205

Ala Arg Val Cys Lys Gly Asp Met Gly Gly Ala Arg Thr Leu Gln Arg
210                 215                 220

Lys Trp Thr Thr Phe Leu Lys Ala Arg Leu Ala Cys Ser Ala Pro Asn
225                 230                 235                 240

Trp Gln Leu Tyr Phe Asn Gln Leu Gln Ala Met His Thr Leu Gln Asp
                245                 250                 255

Thr Ser Trp His Asn Thr Thr Phe Phe Gly Val Phe Gln Ala Gln Trp
            260                 265                 270

Gly Asp Met Tyr Leu Ser Ala Ile Cys Glu Tyr Gln Leu Glu Glu Ile
            275                 280                 285

Gln Arg Val Phe Glu Gly Pro Tyr Lys Glu Tyr His Glu Glu Ala Gln
290                 295                 300

Lys Trp Asp Arg Tyr Thr Asp Pro Val Pro Ser Pro Arg Pro Gly Ser
305                 310                 315                 320

Cys Ile Asn Asn Trp His Arg Arg His Gly Tyr Thr Ser Ser Leu Glu
                325                 330                 335

Leu Pro Asp Asn Ile Leu Asn Phe Val Lys Lys His Pro Leu Met Glu
            340                 345                 350

Glu Gln Val Gly Pro Arg Trp Ser Arg Pro Leu Leu Val Lys Lys Gly
            355                 360                 365

Thr Asn Phe Thr His Leu Val Ala Asp Arg Val Thr Gly Leu Asp Gly
370                 375                 380

Ala Thr Tyr Thr Val Leu Phe Ile Gly Thr Asp Gly Trp Leu Leu
385                 390                 395                 400

Lys Ala Val Ser Leu Gly Pro Trp Val His Leu Ile Glu Glu Leu Gln
                405                 410                 415
```

```
Leu Phe Asp Gln Glu Pro Met Arg Ser Leu Val Leu Ser Gln Ser Lys
            420                 425                 430
Val Lys Leu Leu Phe Ala Gly Ser Arg Ser Gln Leu Val Gln Leu Pro
        435                 440                 445
Val Ala Asp Cys Met Lys Tyr Arg Ser Cys Ala Asp Cys Val Leu Ala
    450                 455                 460
Arg Asp Pro Tyr Cys Ala Trp Ser Val Asn Thr Ser Arg Cys Val Ala
465                 470                 475                 480
Val Gly Gly His Ser Gly Ser Leu Leu Ile Gln His Val Met Thr Ser
                485                 490                 495
Asp Thr Ser Gly Ile Cys Asn Leu Arg Gly Ser Lys Lys Val Arg Pro
            500                 505                 510
Thr Pro Lys Asn Ile Thr Val Val Ala Gly Thr Asp Leu Val Leu Pro
        515                 520                 525
Cys His Leu Ser Ser Asn Leu Ala His Ala Arg Trp Thr Phe Gly Gly
    530                 535                 540
Arg Asp Leu Pro Ala Glu Gln Pro Gly Ser Phe Leu Tyr Asp Ala Arg
545                 550                 555                 560
Leu Gln Ala Leu Val Val Met Ala Ala Gln Pro Arg His Ala Gly Ala
                565                 570                 575
Tyr His Cys Phe Ser Glu Glu Gln Gly Ala Arg Leu Ala Ala Glu Gly
            580                 585                 590
Tyr Leu Val Ala Val Val Ala Gly Pro Ser Val Thr Leu Glu Ala Arg
        595                 600                 605
Ala Pro Leu Glu Asn Leu Gly Leu Val Trp Leu Ala Val Val Ala Leu
    610                 615                 620
Gly Ala Val Cys Leu Val Leu Leu Leu Val Leu Ser Leu Arg Arg
625                 630                 635                 640
Arg Leu Arg Glu Glu Leu Glu Lys Gly Ala Lys Ala Thr Glu Arg Thr
                645                 650                 655
Leu Val Tyr Pro Leu Glu Leu Pro Lys Glu Pro Thr Ser Pro Pro Phe
            660                 665                 670
Arg Pro Cys Pro Glu Pro Asp Glu Lys Leu Trp Asp Pro Val Gly Tyr
        675                 680                 685
Tyr Tyr Ser Asp Gly Ser Leu Lys Ile Val Pro Gly His Ala Arg Cys
    690                 695                 700
Gln Pro Gly Gly Gly Pro Pro Ser Pro Pro Gly Ile Pro Gly Gln
705                 710                 715                 720
Pro Leu Pro Ser Pro Thr Arg Leu His Leu Gly Gly Arg Asn Ser
                725                 730                 735
Asn Ala Asn Gly Tyr Val Arg Leu Gln Leu Gly Gly Glu Asp Arg Gly
            740                 745                 750
Gly Leu Gly His Pro Leu Pro Glu Leu Ala Asp Glu Leu Arg Arg Lys
        755                 760                 765
Leu Gln Gln Arg Gln Pro Leu Pro Asp Ser Asn Pro Glu Glu Ser Ser
    770                 775                 780
Val
785

<210> SEQ ID NO 245
<211> LENGTH: 43
<212> TYPE: PRT
<213> ORGANISM: Homo sapien
```

```
-continued
```

<400> SEQUENCE: 245

Met Pro Leu Leu Ser Met Arg Gly Thr Gln Pro Glu Thr Gly His Gly
1               5                   10                  15

Val Lys Leu Ala Ser Leu Lys Thr Gly Arg Ser Ile Ser Glu Met Asp
            20                  25                  30

Leu Gly Ser Ala Ile Leu Val Gly Tyr Asn Tyr
        35                  40

<210> SEQ ID NO 246
<211> LENGTH: 38
<212> TYPE: PRT
<213> ORGANISM: Homo sapien

<400> SEQUENCE: 246

Met Ala Gln Ile Val Gly Lys Glu Lys Thr Phe Leu Phe Lys Gln Arg
1               5                   10                  15

Lys Gly Phe Gly Glu Lys Thr Gly Ser Gly Ser Gly Glu Val Phe Val
            20                  25                  30

Met Leu Gly Asp Arg Leu
        35

<210> SEQ ID NO 247
<211> LENGTH: 31
<212> TYPE: PRT
<213> ORGANISM: Homo sapien

<400> SEQUENCE: 247

Met Phe Cys Leu Cys Ser Pro Val Leu Cys Tyr Cys Asn Phe Phe Phe
1               5                   10                  15

Phe Tyr Thr Lys His Val Thr Trp Thr Asn Val Arg Gln Met Thr
            20                  25                  30

<210> SEQ ID NO 248
<211> LENGTH: 50
<212> TYPE: PRT
<213> ORGANISM: Homo sapien

<400> SEQUENCE: 248

Met Arg Asn Ser Ser Pro Ile Leu Thr Pro Ala Leu Phe Ser Phe His
1               5                   10                  15

Met Tyr Ile Gly Pro Leu Ile Arg Ile Phe Lys Lys Phe Pro Arg Pro
            20                  25                  30

Pro Asn Leu Thr Ile Asp Asp Pro Leu Ser Leu Phe Arg Arg Asn Tyr
        35                  40                  45

Ile Gly
    50

<210> SEQ ID NO 249
<211> LENGTH: 77
<212> TYPE: PRT
<213> ORGANISM: Homo sapien

<400> SEQUENCE: 249

Met Leu Leu Ala Val Arg Thr Thr Val Ile Cys Leu Gln Ser Cys Cys
1               5                   10                  15

Cys Arg Ile Gln Arg Thr Ala Thr Ile Thr Leu Asn Cys Phe Ala Leu
            20                  25                  30

Ser Ser Ile Phe Asp Tyr Tyr Ile Ser His Asn Ile Thr Ile Ser His
        35                  40                  45

-continued

Ser Ser Asn Tyr Ser Ala Gln Ile His Glu His Val Pro Ala Arg Ala
            50                  55                  60

Ala Ala Arg Ser Ile Thr Trp Arg Arg Ser Ala Cys Ile
 65                  70                  75

<210> SEQ ID NO 250
<211> LENGTH: 70
<212> TYPE: PRT
<213> ORGANISM: Homo sapien

<400> SEQUENCE: 250

Met Pro Gly Ser His Leu Cys Met Phe Asn Thr Val Thr His Asp Val
  1               5                  10                  15

Ile Thr Glu Trp Arg Arg Trp Lys Gly Pro Cys Arg Ser Phe Ser Trp
             20                  25                  30

His Pro Asn Phe Thr Glu Gly Glu Leu Arg Pro Glu Leu Arg Asp Val
                35                  40                  45

Leu Arg Ile Pro Glu Ser His Ser Ser Val Arg Ser Val Ile His Lys
            50                  55                  60

Glu Val Ile Ile Lys Val
 65                  70

<210> SEQ ID NO 251
<211> LENGTH: 117
<212> TYPE: PRT
<213> ORGANISM: Homo sapien

<400> SEQUENCE: 251

Met Gly Thr Ala Lys Lys Lys Gln Thr Glu Arg Gln Thr Arg Gly
  1               5                  10                  15

Ile His Thr Thr Gly Glu Lys Glu Tyr Thr Gln Arg Gly Lys Arg Gly
             20                  25                  30

Asn Thr Ala Gln Lys Pro His Arg Gln Ala Gln Asp Arg Ala Thr
                35                  40                  45

Gly His Asp Ala Thr Arg Thr Arg Pro Arg Ala Leu Trp Asn Gly Ala
            50                  55                  60

Ala Gly Arg Val Glu Ala Gly Ser Leu His Gln Gly Arg Arg Ala Asp
 65                  70                  75                  80

Trp Arg Gly Gly Gly Glu Ala Gly Asp Arg Asn Arg Glu Arg Glu Gly
                 85                  90                  95

Gly Lys Cys Ala Gly Gly Arg Lys Arg Arg Arg Glu Gly Thr Glu
                100                 105                 110

Gly Glu Thr Gln Gln
            115

<210> SEQ ID NO 252
<211> LENGTH: 66
<212> TYPE: PRT
<213> ORGANISM: Homo sapien

<400> SEQUENCE: 252

Met Val Val Cys Leu Trp Leu Cys Ser Ser Val Ser Leu Ala Leu Cys
  1               5                  10                  15

Val Ser Phe Val Ala Leu Ser Ser Val Pro Ser Cys Leu Arg Thr Val
             20                  25                  30

Gly Gly Asp Phe Gly Arg Gly Asn Gln Phe Leu Pro Arg Gly Pro Ala
                35                  40                  45

Leu Ala Gln Gly Ser Pro Ser Ala Phe Phe Leu Phe Cys Cys Phe Phe

```
            50                  55                  60
Phe Phe
 65
```

<210> SEQ ID NO 253
<211> LENGTH: 31
<212> TYPE: PRT
<213> ORGANISM: Homo sapien

<400> SEQUENCE: 253

```
Met Leu Glu Ala Ile Leu Gly Pro Val Ser Asn Ser Leu Tyr Val Ser
 1               5                  10                  15

Gly Lys Thr Cys His Gly Ser Arg Ser Val Phe Ser Ser Ala Lys
            20                  25                  30
```

<210> SEQ ID NO 254
<211> LENGTH: 37
<212> TYPE: PRT
<213> ORGANISM: Homo sapien

<400> SEQUENCE: 254

```
Met Thr Leu Ala Thr Ile Ile His Ser Ile Val Gln Ala Gly Ser Leu
 1               5                  10                  15

Gly Cys Cys Ile Lys Cys Asn Pro Pro Leu Gly Ile Leu Glu Pro Gln
            20                  25                  30

Asn Lys His Cys Val
         35
```

<210> SEQ ID NO 255
<211> LENGTH: 45
<212> TYPE: PRT
<213> ORGANISM: Homo sapien

<400> SEQUENCE: 255

```
Met Tyr Leu Gly Gln Leu Gly Asn His Arg Leu Lys Lys Leu Thr Leu
 1               5                  10                  15

Val Ile Thr Arg Val Val Ser Asp Tyr Lys Gln His Ile Ile Asn Pro
            20                  25                  30

Thr Ala Leu Ile Leu Ala Gln Arg Gln Asn Trp Thr Phe
         35                  40                  45
```

<210> SEQ ID NO 256
<211> LENGTH: 32
<212> TYPE: PRT
<213> ORGANISM: Homo sapien

<400> SEQUENCE: 256

```
Met Asn His Arg Ile Leu Gln Asn Tyr Ser Leu Phe Ser Lys Met Ile
 1               5                  10                  15

Asn Glu Leu Gln Ser Leu Pro Ser Arg Ser Ser Gln Leu Asn Lys Gly
            20                  25                  30
```

<210> SEQ ID NO 257
<211> LENGTH: 31
<212> TYPE: PRT
<213> ORGANISM: Homo sapien

<400> SEQUENCE: 257

```
Met Ile Leu Leu Phe Leu Ser Lys Thr Ser Ser Ser Lys Ile Val Tyr
 1               5                  10                  15

Met Val Thr Phe Val Ser Asn Asn Val Met Val Asn Ser Gly Tyr
```

20                  25                  30

<210> SEQ ID NO 258
<211> LENGTH: 62
<212> TYPE: PRT
<213> ORGANISM: Homo sapien

<400> SEQUENCE: 258

Met Thr Ser Ser Met Leu Lys Ser Glu Ser Ala Ser Ile Phe Val
1               5                   10                  15

Ile Pro His Ile Gln Ser Ser Ala Lys Ser Cys Gln Phe Tyr Leu Lys
            20                  25                  30

Ser Phe Pro Ser Phe Phe Leu Thr Tyr Val Ile Ser Val Val Ser Gln
        35                  40                  45

Leu His Leu Ser Ser Tyr Ser Ser Leu Leu Tyr Thr Gln Cys
    50                  55                  60

<210> SEQ ID NO 259
<211> LENGTH: 103
<212> TYPE: PRT
<213> ORGANISM: Homo sapien

<400> SEQUENCE: 259

Phe Phe Val Phe Ala Arg Gln Gly Leu Thr Leu Ser Pro Arg Leu Glu
1               5                   10                  15

Cys Ser Gly Met Ile Ile Thr His Cys Ser Leu Gln Leu Leu Gly Ser
            20                  25                  30

Ser Asn Ser Pro Ala Ser Ala Ser Ala Glu Thr Glu Thr Ile Gly Met
        35                  40                  45

Arg His His Ile Trp Leu Thr Phe Gln Leu Ser Val Glu Thr Gly Ser
    50                  55                  60

Cys Tyr Val Ala Gln Ala Ala Leu Lys Phe Leu Ala Ser Ser Asn Pro
65                  70                  75                  80

Leu Ala Ser Ala Ser His Ser Thr Gly Ile Thr Gly Met Ser His Pro
                85                  90                  95

Thr Pro Pro Gln Ser Asp Phe
            100

<210> SEQ ID NO 260
<211> LENGTH: 42
<212> TYPE: PRT
<213> ORGANISM: Homo sapien

<400> SEQUENCE: 260

Met Val Gln Ser Ser Asp His Met Glu Val Gly Lys Arg Glu Leu Ile
1               5                   10                  15

Thr Gly Leu Tyr Ala Gly Glu Trp Ile Val Leu Ile Leu Thr Val Ser
            20                  25                  30

Lys Glu Asn Gln Leu Ser Ser Ser Arg
        35                  40

<210> SEQ ID NO 261
<211> LENGTH: 26
<212> TYPE: PRT
<213> ORGANISM: Homo sapien

<400> SEQUENCE: 261

Met Thr Cys Phe Lys Leu Leu Phe Tyr Val Leu Leu Tyr Phe Cys Ser
1               5                   10                  15

His Leu His Val Ala Lys Gln Ile Met Leu
            20                  25

<210> SEQ ID NO 262
<211> LENGTH: 397
<212> TYPE: PRT
<213> ORGANISM: Homo sapien

<400> SEQUENCE: 262

Met Glu Gly Asn Arg Asp Glu Ala Glu Lys Cys Val Glu Ile Ala Arg
1               5                   10                  15

Glu Ala Leu Asn Ala Gly Asn Arg Glu Lys Ala Gln Arg Phe Leu Gln
            20                  25                  30

Lys Ala Glu Lys Leu Tyr Pro Leu Pro Ser Ala Arg Ala Leu Leu Glu
        35                  40                  45

Ile Ile Met Lys Asn Gly Ser Thr Ala Gly Asn Ser Pro His Cys Arg
    50                  55                  60

Lys Pro Ser Gly Ser Gly Asp Gln Ser Lys Pro Asn Cys Thr Lys Asp
65                  70                  75                  80

Ser Thr Ser Gly Ser Gly Glu Gly Gly Lys Gly Tyr Thr Lys Asp Gln
                85                  90                  95

Val Asp Gly Val Leu Arg Ala Leu Trp Ile Leu Glu His Ala Tyr Gly
            100                 105                 110

Met Val Asp Leu Tyr Leu Thr His Thr Thr Asn Lys Cys Lys Asn Tyr
        115                 120                 125

Tyr Glu Val Asp Gly Val Thr Lys Asp Ala Gly Asp Glu Asp Leu Lys
    130                 135                 140

Lys Ala Tyr Arg Lys Leu Ala Leu Lys Phe His Pro Asp Lys Asn His
145                 150                 155                 160

Ala Pro Gly Ala Thr Asp Ala Phe Lys Lys Ile Gly Asn Ala Tyr Ala
                165                 170                 175

Val Leu Ser Asn Pro Glu Lys Arg Lys Gln Tyr Asp Leu Thr Gly Asn
            180                 185                 190

Glu Glu Gln Ala Cys Asn His Gln Asn Asn Gly Arg Phe Asn Phe His
        195                 200                 205

Arg Gly Cys Glu Ala Asp Ile Thr Pro Glu Asp Leu Phe Asn Ile Phe
    210                 215                 220

Phe Gly Gly Gly Phe Pro Ser Gly Ser Val His Ser Phe Ser Asn Gly
225                 230                 235                 240

Arg Ala Gly Tyr Ser Gln Gln His Gln His Arg His Ser Gly His Glu
                245                 250                 255

Arg Glu Glu Arg Gly Asp Gly Gly Phe Ser Val Phe Ile Gln Leu
            260                 265                 270

Met Pro Ile Ile Val Leu Ile Leu Val Ser Leu Leu Ser Gln Leu Met
    275                 280                 285

Val Ser Asn Pro Pro Tyr Ser Leu Tyr Pro Arg Ser Gly Thr Gly Gln
    290                 295                 300

Thr Ile Lys Met Gln Thr Glu Asn Leu Gly Val Val Tyr Tyr Val Asn
305                 310                 315                 320

Lys Asp Phe Lys Asn Glu Tyr Lys Gly Met Leu Leu Gln Lys Val Glu
                325                 330                 335

Lys Ser Val Glu Glu Asp Tyr Val Thr Asn Ile Arg Asn Asn Cys Trp
            340                 345                 350

Lys Glu Arg Gln Gln Lys Thr Asp Met Gln Tyr Ala Ala Lys Val Tyr
        355                 360                 365

```
Arg Asp Asp Arg Leu Arg Arg Lys Ala Asp Ala Leu Ser Met Asp Asn
        370                 375                 380

Cys Lys Glu Leu Glu Arg Leu Thr Ser Leu Tyr Lys Gly
385                 390                 395
```

<210> SEQ ID NO 263
<211> LENGTH: 54
<212> TYPE: PRT
<213> ORGANISM: Homo sapien

<400> SEQUENCE: 263

```
Met Cys Phe Gly Cys Arg Lys Thr Cys Lys Thr Ser Asn Asn Pro Tyr
1               5                   10                  15

Phe Pro Thr Leu Arg Gly Trp Phe Ser Arg Val Cys Val Cys Val Cys
            20                  25                  30

Val Cys Val Cys Met Asn Asp Ile Phe Ile Thr Leu Phe Arg Lys Arg
        35                  40                  45

Met Ser Val Leu Cys Val
    50
```

<210> SEQ ID NO 264
<211> LENGTH: 31
<212> TYPE: PRT
<213> ORGANISM: Homo sapien

<400> SEQUENCE: 264

```
Met Lys Gly Asn Gln Phe Ser Val Thr Asp Asp Val Lys Ile Leu Phe
1               5                   10                  15

Ser Gly Lys Leu Tyr Ser His Ser Lys Ile Gln Ser Met Leu Leu
            20                  25                  30
```

<210> SEQ ID NO 265
<211> LENGTH: 219
<212> TYPE: PRT
<213> ORGANISM: Homo sapien

<400> SEQUENCE: 265

```
Val Ala Met Val Glu Val Gln Leu Glu Ser Asp His Glu Tyr Pro Pro
1               5                   10                  15

Gly Leu Leu Val Ala Phe Ser Ala Cys Thr Thr Val Leu Val Ala Val
            20                  25                  30

His Leu Phe Ala Leu Met Val Ser Thr Cys Leu Leu Pro His Ile Glu
        35                  40                  45

Ala Val Ser Asn Ile His Asn Leu Asn Ser Val His Gln Ser Pro His
    50                  55                  60

Gln Arg Leu His Arg Tyr Val Glu Leu Ala Trp Gly Phe Ser Thr Ala
65                  70                  75                  80

Leu Gly Thr Phe Leu Phe Leu Ala Glu Val Val Leu Val Gly Trp Val
            85                  90                  95

Lys Phe Val Pro Ile Gly Ala Pro Leu Asp Thr Pro Thr Pro Met Val
            100                 105                 110

Pro Thr Ser Arg Val Pro Gly Thr Leu Ala Pro Val Ala Thr Ser Leu
        115                 120                 125

Ser Pro Ala Ser Asn Leu Pro Arg Ser Ser Ala Ser Ala Ala Pro Ser
    130                 135                 140

Gln Ala Glu Pro Ala Cys Pro Pro Arg Gln Ala Cys Gly Gly Gly Gly
145                 150                 155                 160
```

```
Ala His Gly Pro Gly Trp Gln Ala Ala Met Ala Ser Thr Ala Ile Met
            165                 170                 175

Val Pro Val Gly Leu Val Phe Val Ala Phe Ala Leu His Phe Tyr Arg
            180                 185                 190

Ser Leu Val Ala His Lys Thr Asp Arg Tyr Lys Gln Glu Leu Glu Glu
            195                 200                 205

Leu Asn Arg Leu Gln Gly Glu Leu Gln Ala Val
        210                 215

<210> SEQ ID NO 266
<211> LENGTH: 33
<212> TYPE: PRT
<213> ORGANISM: Homo sapien

<400> SEQUENCE: 266

Met Phe Thr Arg Lys Pro Lys Ser Ser Lys Ala Gln Leu Leu Leu Leu
1               5                   10                  15

Arg Thr Leu His Gln Leu Leu Phe Gln Thr Ser Leu Gln Leu Leu Gly
            20                  25                  30

Leu

<210> SEQ ID NO 267
<211> LENGTH: 88
<212> TYPE: PRT
<213> ORGANISM: Homo sapien

<400> SEQUENCE: 267

Gly Arg Val Arg Phe Val Val Glu Leu Ala Asp Pro Lys Leu Glu Val
1               5                   10                  15

Lys Trp Tyr Lys Asn Gly Gln Glu Ile Arg Pro Ser Thr Lys Tyr Ile
            20                  25                  30

Phe Glu His Lys Gly Cys Gln Arg Ile Leu Phe Ile Asn Asn Cys Gln
            35                  40                  45

Met Thr Asp Asp Ser Glu Tyr Tyr Val Thr Ala Gly Asp Ala Lys Cys
        50                  55                  60

Ser Thr Glu Leu Phe Val Arg Glu Pro Pro Phe Met Val Pro Ser Ser
65                  70                  75                  80

Trp Ile Glu Thr Pro Ala Asp Cys
                85

<210> SEQ ID NO 268
<211> LENGTH: 11
<212> TYPE: PRT
<213> ORGANISM: Homo sapien

<400> SEQUENCE: 268

Met Trp Arg Ala Lys Gln Tyr Asp Leu Gln Thr
1               5                   10

<210> SEQ ID NO 269
<211> LENGTH: 32
<212> TYPE: PRT
<213> ORGANISM: Homo sapien

<400> SEQUENCE: 269

Met Glu Gln Ile Glu Asp Asn Asp Ile Cys Phe Tyr Tyr Lys Val Phe
1               5                   10                  15

His His Leu Ile Ser Leu Thr His Ile Met Arg Pro Ala Phe Glu Glu
            20                  25                  30
```

<210> SEQ ID NO 270
<211> LENGTH: 19
<212> TYPE: PRT
<213> ORGANISM: Homo sapien

<400> SEQUENCE: 270

Met His Ile Lys Met His Ser Leu Ser Cys Pro Asn Asn Tyr His Ile
1               5                   10                  15

Thr Leu Trp

<210> SEQ ID NO 271
<211> LENGTH: 173
<212> TYPE: PRT
<213> ORGANISM: Homo sapien

<400> SEQUENCE: 271

Met Ile Gly Cys Ser Leu Leu Val Ala Cys Leu Cys Cys Leu Val Gln
1               5                   10                  15

Ser Phe Arg Ala Met Phe Ser Cys Phe Ser Gly Leu Ser Leu Cys Leu
                20                  25                  30

Met Leu Pro Leu Trp Cys Val Cys Pro Thr Val Cys Ala Phe Phe Cys
            35                  40                  45

Gly Tyr Leu Leu Phe Phe Ser Leu Arg His Ala Ala Cys Gly Cys Leu
        50                  55                  60

Leu Val Cys Leu Ser Cys Leu Ala Leu Pro Ser Gly Pro Ile Leu Ser
65                  70                  75                  80

Phe Ser Phe Cys Leu Arg Val Val Ser Ser Val Arg Val Ala Cys Ala
                85                  90                  95

Arg Ser Ala Ala Val Leu Leu Leu Arg Gly Val Pro Pro Ser Leu
                100                 105                 110

Arg Thr Leu Ser Leu Ile Ala Ser Thr Ala Thr Arg Leu Ser Phe Val
            115                 120                 125

Phe Leu Phe Ser Leu Pro Arg Gly Leu Leu Cys Val Gly Gly Ser Gly
        130                 135                 140

Ser Val Leu Gly Ser Leu Val Arg Arg Ala Gln Ser Val Gly Leu Arg
145                 150                 155                 160

Asp Phe Val Ser Val Leu Gln Val Val Leu Thr Cys Leu
                165                 170

<210> SEQ ID NO 272
<211> LENGTH: 20
<212> TYPE: PRT
<213> ORGANISM: Homo sapien

<400> SEQUENCE: 272

Met Ile Gly Ile Thr Trp Cys Phe Glu Leu Ile His Pro Thr Leu Glu
1               5                   10                  15

Leu Thr Ala Thr
            20

<210> SEQ ID NO 273
<211> LENGTH: 85
<212> TYPE: PRT
<213> ORGANISM: Homo sapien

<400> SEQUENCE: 273

Met Ser Ile Tyr Leu Ala Pro Asp Gly Asn Thr Lys Ser Trp Gln Trp
1               5                   10                  15

```
Glu Trp Lys Gly Ser Leu Ser Gln Ile Leu Pro Tyr Tyr Val Asp Pro
             20                  25                  30

Lys Ala Gly Leu Gly Ser Lys Ala His Lys Pro Pro Lys Gln Ile Phe
         35                  40                  45

Thr Glu His Leu Asp Tyr Tyr Arg Pro Ser Ile Leu Leu Gly Thr Met
     50                  55                  60

Gly Asp Val Lys Glu Val Ile Ser His Met Ile Cys Leu Gln Gly Ala
 65                  70                  75                  80

Lys Asn Ala Ser Gly
             85

<210> SEQ ID NO 274
<211> LENGTH: 86
<212> TYPE: PRT
<213> ORGANISM: Homo sapien

<400> SEQUENCE: 274

Met Met Asn Phe Leu Cys Leu Asn Phe Arg Asp Ile Trp Cys Asp Phe
 1               5                  10                  15

His Leu Tyr Leu Met Leu Pro Leu Leu Pro Ser Leu Leu Asn Thr Ser
             20                  25                  30

Lys Asn Ser Glu His Ile Leu Ile Pro Pro Val Phe Tyr Phe Tyr Asp
         35                  40                  45

Leu Asp Ile Leu His His Lys Ile Pro Pro Asn Trp Asp Tyr Val Phe
     50                  55                  60

Glu Val Ile His Phe Thr Ile Thr Thr Ile Thr Ile Ile Phe Ile
 65                  70                  75                  80

Val Cys Phe Val Pro Gly
             85

<210> SEQ ID NO 275
<211> LENGTH: 36
<212> TYPE: PRT
<213> ORGANISM: Homo sapien

<400> SEQUENCE: 275

Met Phe Phe Glu Met Leu Glu Ile Leu Gly Asn Tyr Gln Met Tyr Arg
 1               5                  10                  15

Ser Cys Met Lys Val Ile Glu Arg Cys Asn Cys Leu Leu Thr Ile Thr
             20                  25                  30

Trp Ile Ser Tyr
         35

<210> SEQ ID NO 276
<211> LENGTH: 35
<212> TYPE: PRT
<213> ORGANISM: Homo sapien

<400> SEQUENCE: 276

Met Ala Gln Thr Ser Ala Thr Ile Thr His Asn Asn Ser Thr Ala Phe
 1               5                  10                  15

Ile Phe Gly Ser Asn Val Met Gln Val Asn Leu Leu Met Ile Ser Lys
             20                  25                  30

Ile Thr Lys
         35

<210> SEQ ID NO 277
<211> LENGTH: 105
<212> TYPE: PRT
```

<213> ORGANISM: Homo sapien

<400> SEQUENCE: 277

Met Ala Thr Gly Thr Pro Glu Ser Gln Ala Arg Phe Gly Gln Ser Val
1               5                   10                  15

Lys Gly Leu Leu Thr Glu Lys Val Thr Thr Cys Gly Thr Asp Val Ile
            20                  25                  30

Ala Leu Thr Lys Gln Val Leu Lys Gly Ser Arg Ser Ser Glu Leu Leu
        35                  40                  45

Gly Gln Ala Ala Arg Asn Met Val Leu Gln Glu Asp Ala Ile Leu His
    50                  55                  60

Ser Glu Asp Ser Leu Arg Lys Met Ala Ile Ile Thr Thr His Leu Gln
65                  70                  75                  80

Tyr Gln Gln Glu Ala Ile Gln Lys Asn Val Glu Gln Ser Ser Asp Leu
                85                  90                  95

Gln Asp Gln Leu Asn His Leu Leu Lys
            100                 105

<210> SEQ ID NO 278
<211> LENGTH: 41
<212> TYPE: PRT
<213> ORGANISM: Homo sapien

<400> SEQUENCE: 278

Met Lys His Pro Leu Leu Thr Ala Pro Met Gln Asn Ser Thr Ile Gln
1               5                   10                  15

Leu Thr Ala Phe Thr Leu Met Thr Arg Cys Lys Ser Lys His Lys Thr
            20                  25                  30

Glu Asn Met Tyr Val Pro Ala Arg Ala
            35                  40

<210> SEQ ID NO 279
<211> LENGTH: 35
<212> TYPE: PRT
<213> ORGANISM: Homo sapien

<400> SEQUENCE: 279

Met Phe Arg Glu Ile Val Pro Ile Ser Gln Gly Gly Gln Leu Asp Ser
1               5                   10                  15

Asn Gly Val Lys Thr His Leu Lys Val Tyr Cys Lys Asn Ile Tyr Ser
            20                  25                  30

Pro Lys Leu
        35

<210> SEQ ID NO 280
<211> LENGTH: 83
<212> TYPE: PRT
<213> ORGANISM: Homo sapien

<400> SEQUENCE: 280

Met Ser Met Ile Tyr Thr Leu Val Tyr Lys Ala Val Tyr Ile Val Leu
1               5                   10                  15

Val Leu Asp Leu Leu Val Ser Leu Leu Gly Glu Phe Gly Arg Glu Thr
            20                  25                  30

Leu Pro Pro Gly Pro Leu Gly Pro Gly Ala Pro Ala Phe Phe Phe
        35                  40                  45

-continued

```
Cys Phe Phe Phe Val Phe Val Asn Asn Lys Ile His Leu Leu Lys Glu
    50              55              60
Ser Cys Leu His Arg Tyr Arg Thr Ser Trp Ile Phe Gln His His Ser
65              70              75              80
Asn Thr Asn
```